United States Patent
Dai et al.

(10) Patent No.: US 11,396,517 B1
(45) Date of Patent: Jul. 26, 2022

(54) EXO-AZA SPIRO INHIBITORS OF MENIN-MLL INTERACTION

(71) Applicant: Janssen Pharmaceutica NV, Beerse (BE)

(72) Inventors: Xuedong Dai, Shanghai (CN); Olivier Alexis Georges Querolle, Issy-les Moulineaux (FR); Daniel Jason Krosky, Raritan, NJ (US); Wei Cai, Shanghai (CN); Liqiang Fu, Shanghai (CN); Linglong Kong, Shanghai (CN); Yingtao Liu, Shanghai (CN); Zhao-Kui Wan, Shanghai (CN); Barbara Morschhäuser Geb. Herkert, Beerse (BE); Vineet Pande, Beerse (BE); James Patrick Edwards, Raritan, NJ (US); Aaron Nathaniel Patrick, Raritan, NJ (US); Patrick René Angibaud, Issy-les Moulineaux (FR); Virginie Sophie Poncelet, Issy-les Moulineaux (FR)

(73) Assignee: Janssen Pharmaceutica NV, Beerse (BE)

( * ) Notice: Subject to any disclaimer, the term of this patent is extended or adjusted under 35 U.S.C. 154(b) by 36 days.

(21) Appl. No.: 16/955,142

(22) PCT Filed: Dec. 19, 2018

(86) PCT No.: PCT/CN2018/121960
§ 371 (c)(1),
(2) Date: Jun. 18, 2020

(87) PCT Pub. No.: WO2019/120209
PCT Pub. Date: Jun. 27, 2019

(30) Foreign Application Priority Data

Dec. 20, 2017 (WO) ................ PCT/CN2017/117536
Dec. 19, 2018 (WO) ................ PCT/CN2018/121960

(51) Int. Cl.
*C07D 495/04* (2006.01)
*A61P 35/00* (2006.01)
*C07D 519/00* (2006.01)

(52) U.S. Cl.
CPC ............ *C07D 495/04* (2013.01); *A61P 35/00* (2018.01); *C07D 519/00* (2013.01)

(58) Field of Classification Search
CPC ...... C07D 495/04; C07D 519/00; A61P 35/00
See application file for complete search history.

(56) References Cited

U.S. PATENT DOCUMENTS

| | | |
|---|---|---|
| 2004/0043959 A1 | 3/2004 | Bloom et al. |
| 2006/0074102 A1 | 4/2006 | Cusack et al. |
| 2010/0331348 A1 | 12/2010 | Selles et al. |
| 2013/0310333 A1 | 11/2013 | Chesworth et al. |
| 2013/0310334 A1 | 11/2013 | Chesworth et al. |
| 2014/0221345 A1 | 8/2014 | Duncan et al. |
| 2014/0228343 A1 | 8/2014 | Duncan et al. |
| 2014/0275070 A1 | 9/2014 | Grembecka et al. |
| 2014/0329794 A1 | 11/2014 | Duncan et al. |
| 2016/0244475 A1 | 8/2016 | Tatlock et al. |
| 2017/0198006 A1 | 7/2017 | Duncan et al. |
| 2017/0355711 A1 | 12/2017 | Tabar et al. |
| 2018/0105531 A1 | 4/2018 | Grembecka et al. |
| 2018/0243328 A1 | 8/2018 | Wu et al. |
| 2019/0010167 A1 | 1/2019 | Claremon et al. |

FOREIGN PATENT DOCUMENTS

| | | |
|---|---|---|
| CN | 101048412 A | 10/2007 |
| CN | 101107253 A | 1/2008 |
| CN | 102149718 A | 8/2011 |
| CN | 103664991 A | 3/2014 |
| CN | 105188705 A | 12/2015 |
| CN | 105732636 A | 7/2016 |
| JP | 2007-537296 A | 12/2007 |
| JP | 2010-532777 A | 10/2010 |

(Continued)

OTHER PUBLICATIONS

Provisional application for Claremon US 2019/0010167—Jan. 8, 2017 (filed Dec. 22, 2015).

(Continued)

*Primary Examiner* — John M Mauro
(74) *Attorney, Agent, or Firm* — BakerHostetler

(57) ABSTRACT

Provided are compounds of Formula (I), pharmaceutical compositions comprising such compounds, and their use as menin/MLL protein/protein interaction inhibitors, useful for treating diseases such as cancer, myelodysplastic syndrome (MDS) and diabetes.

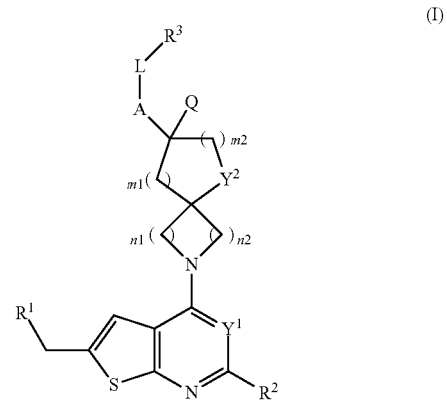

13 Claims, No Drawings

Specification includes a Sequence Listing.

(56) References Cited

FOREIGN PATENT DOCUMENTS

| | | |
|---|---|---|
| JP | 2011-026305 A | 2/2011 |
| JP | 2013-503906 A | 2/2013 |
| JP | 2016-512514 A | 4/2016 |
| JP | 2018-538330 A | 12/2018 |
| JP | 2019-532100 A | 11/2019 |
| WO | 96/40686 A1 | 12/1996 |
| WO | 03/70739 | 8/2003 |
| WO | 03/74083 | 9/2003 |
| WO | 2004/014850 A2 | 2/2004 |
| WO | 2004/056800 A1 | 7/2004 |
| WO | 2010/041366 A1 | 4/2010 |
| WO | 2011/029054 A1 | 3/2011 |
| WO | 2012/075500 A2 | 6/2012 |
| WO | 2012/082436 A2 | 6/2012 |
| WO | 2013/018404 A1 | 2/2013 |
| WO | 2014/035140 A2 | 3/2014 |
| WO | 2014/100695 A1 | 6/2014 |
| WO | 2014/164543 A1 | 10/2014 |
| WO | 2015/191701 A1 | 12/2015 |
| WO | 2016/040330 A1 | 3/2016 |
| WO | 2016/081732 A1 | 5/2016 |
| WO | 2016/195776 A1 | 12/2016 |
| WO | 2016/197027 A1 | 12/2016 |
| WO | 2017/112768 A1 | 6/2017 |
| WO | 2017/161002 A1 | 9/2017 |
| WO | 2017/161028 A1 | 9/2017 |
| WO | 2017/192543 A1 | 11/2017 |
| WO | 2017/207387 A1 | 12/2017 |
| WO | 2017/214367 A1 | 12/2017 |
| WO | 2018/024602 A1 | 2/2018 |
| WO | 2018/047598 A1 | 3/2018 |
| WO | 2018/050684 A1 | 3/2018 |
| WO | 2018/050686 A1 | 3/2018 |
| WO | 2018/053267 A1 | 3/2018 |
| WO | 2018/109088 A1 | 6/2018 |
| WO | 2018/175746 A1 | 9/2018 |

OTHER PUBLICATIONS

International Application No. PCT/EP2017/073004, Written Opinion of the International Searching Authority, dated March 8, 2019, 4 pages Acute Leukemia, Merck Manual (Online Edition) 6 pages, pp. 1-6 (2013).

Borkin et al., "Pharmacologic Inhibition of the Menin-MLL Interaction Blocks Progression of MLL Leukemia In Vivo.", Cancer Cell, Apr. 13, 2015, pp. 589-602, vol. 27.

Borkin et al., "Property Focused Structure-Based Optimization of Small Molecule Inhibitors of the Protein-Protein Interaction between Menin and Mixed Lineage Leukemia (MLL).", J. Med. Chem., 2016, pp. 892-913, vol. 59.

Cermakova et al., "Validation and Structural Characterization of the LEDGF/p75- MLL Interface as a New Target for theTreatment of MLL-Dependent Leukemia", Cancer Res., Sep. 15, 2014, pp. 5139-5151, vol. 74(18).

Charron et al., "Recent developments in radiolabelled peptides for PET imaging of cancer ", Tetrahedron Letters, 2016, pp. 4119-4127, vol. 57.

Chen et al., "The tumor suppressor menin regulates hematopoiesis and myeloid transformation by influencing Hox gene expression.", PNAS, Jan. 24, 2006, pp. 1018-1023, vol. 103(4).

Cierpicki, T. and Grembecka, J., "Challenges and opportunities in targeting the menin-MLL interaction ", Future Med. Chem., 2 014, pp. 447-462, vol. 6(4).

European Search Report EP17150502 completed Mar. 7, 2017.
European Search Report EP18201390 completed Nov. 14, 2018.

Gennaro, A.R., Remington's 181h ed., Mack Publishing Company, (1990) see especially Part 8: Pharmaceutical preparations and their Manufacture, pp. 1435-1712.

Greene, T.W., et al., "Greene's Protective Groups in Organic Synthesis", 4th ed., (2007), Wilev-Interscience, Hoboken, New JerseY.

Grembecka et al., "Menin-MLL Inhibitors Reverse Oncogenic Activity of MLL Fusion Proteins in Leukemia.", Nat. Chem. Bio, published on-line on Jan. 29, 2012, DOI: 10.1038/NCHEMBI0.773; Mar. 2012, pp. 277-284, vol. 8.

Gura, "Systems for identifying new drugs are often faulty.", Science, 278(5340): 1041-2.

He et al., "High-Affinity Small-Molecule Inhibitors of the Menin-Mixed Lineage Leukemia (MLL) Interaction Closely Mimic a Natural Protein-Protein Interaction ", J. Med. Chem., 2014, 1543-1556, vol. 57.

International Search Report PCT/CN2017/117536 dated Jul. 31, 2018.

International Search Report PCT/EP2017/073001 dated Nov. 6, 2017.

International Search Report PCT/EP2017/073004 dated Nov. 28, 2017.

International Search Report PCT/EP2017/082826 dated Feb. 14, 2018.

Johnson et al., "Relationships between drug activity in NCI preclinical in vitro and vivo models and early clinical trials.", Br J Cancer 84(10): 1424-31.

Li et al., "Distinct pathways regulated by menin and by MLL1 in hematopoietic stem cells and developing B cells.", Blood, Sep. 19, 2013, pp. 2039-2046, vol. 122(12).

Malik et al., "Targeting the MLL complex in castration resistant prostate cancer.", Nat. Med., Apr. 2015, DD. 344-352, vol. 21(4).

Marschalek, R., "Mechanisms of leukemogenesis by MLL fusion proteins ", British J. of Haematology, 2010, pp. 141-154, vol. 152.

Meyer et al., "The MLL recombinome of acute leukemias in 2013.", Leukemia, 2013, pp. 2165-2176, vol. 27.

Mishra et al., "The Histone Methyltransferase Activity of MLL1 Is Dispensable for Hematopoiesis and Leukemogenesis.", Cell Rep., May 22, 2014, pp. 1239-1247, vol. 7(4).

Pantel et al., "Molecular imaging to guide systemic cancer therapy: Illustrative examples of PET imaging cancer biomarkers.", Cancer Letters, 2017, pp. 25-31, vol. 387.

Pearce et al., "Failure modes in anticancer drug discovery and development.", Cancer Drug Design and Discovery Edited by Stephen Neidle, Chapter 18, pp. 424-435 (2008).

Ren et al., "Design and synthesis of benzylpiperidine inhibitors targeting the menin-MLL1 interface ", Bioorganic & Medicinal Chemistry Letters, 2016, pp. 4472 4476, vol. 26.

Shah, S.K., et al., "Synthesis and evaluation of CCR5 antagonists containing modified 4-piperidinyl-2-phenyl-1-(phenylsulfonylamino)-butane", Bioorganic & Medicinal Chemistry Letters, 2005, pp. 977-982, vol. 15.

Simone, Introduction, Omenn, Cancer Prevention, Part XIV, Oncology, Cecil Textbook of Medecine, 20lh Edition, vol. 1, pp. 1004-1010.

Thiel et al., "Menin as a Hub Controlling Mixed Lineage Leukemia.", Bioessays, Sep. 2012, pp. 771-780, vol. 34(9).

Tomizawa et al., "Repetitive Cycles of High-Dose Cytarabine Are Effective for Childhood Acute Myeloid Leukemia: Long-Term Outcome of the Children With AML Treated on Two Consecutive Trials of Tokyo Children's Cancer Study Group.", Pediatr. Blood Cancer, 2007, pp. 127-132, vol. 49.

Written Opinion PCT/EP2017/073001 dated Nov. 6, 2017.
Written Opinion PCT/EP2017/073004 dated Nov. 28, 2017.
Written Opinion PCT/EP2017/082826, dated Feb. 14, 2018.

Yokoyama et al., "The Menin Tumor Suppressor Protein Is an Essential Oncogenic Cofactor for MLL-Associated Leukemogenesis.", Cell, Oct. 21, 2005, pp. 207-218, vol. 123.

Yokoyama, A. and Cleary, M., "Menin Critically Links MLL Proteins with LEDGF on Cancer-Associated Target Genes.", Cancer Cell, Jul. 2008, pp. 36-46, vol. 14.

EXO-AZA SPIRO INHIBITORS OF MENIN-MLL INTERACTION

CROSS-REFERENCE TO RELATED APPLICATIONS

This application is the National Stage of International Patent Application No. PCT/CN2018/121960, filed Dec. 19, 2018, which claims the benefit of International Application No. PCT/CN2017/117536, filed Dec. 20, 2017 and International Application No. PCT/CN2018/091521, filed Jun. 15, 2018, the contents of which are incorporated herein by reference.

SEQUENCE LISTING

The instant application contains a Sequence Listing which is being submitted herewith electronically in ASCII format and is hereby incorporated by reference in its entirety. Said ASCII copy, created on Jul. 9, 2020, is named 103693_003042_SL.txt and is 6,350 bytes in size.

FIELD OF THE INVENTION

The present invention relates to pharmaceutical agents useful for therapy and/or prophylaxis in a mammal, pharmaceutical composition comprising such compounds, and their use as menin/MLL protein/protein interaction inhibitors, useful for treating diseases such as cancer, myelodysplastic syndrome (MDS) and diabetes.

BACKGROUND OF THE INVENTION

Chromosomal rearrangements affecting the mixed lineage leukemia gene (MLL; MLL1; KMT2A) result in aggressive acute leukemias across all age groups and still represent mostly incurable diseases emphasizing the urgent need for novel therapeutic approaches. Acute leukemias harboring these chromosomal translocations of MLL represent as lymphoid, myeloid or biphenotypic disease and constitute 5 to 10% of acute leukemias in adults and approximately 70% in infants (Marschalek, Br J Haematol 2011. 152(2), 141-54; Tomizawa et al, Pediatr Blood Cancer 2007. 49(2), 127-32). MLL is a histone methyltransferase that methylates histone H3 on lysine 4 (H3K4) and functions in multiprotein complexes. Use of inducible loss-of-function alleles of Mll1 demonstrated that Mll plays an essential role in sustaining hematopoietic stem cells (HSCs) and developing B cells although its histone methyltransferase activity is dispensable for hematopoiesis (Mishra et al., Cell Rep 2011. 7(4), 1239-47). Fusion of MLL with more than 60 different partners has been reported to date and has been associated with leukemia formation/progression (Meyer et al., Leukemia 2013. 27, 2165-2176). Interestingly, the SET (Su(var) 3-9, enhancer of zeste, and trithorax) domain of MLL is not retained in chimeric proteins but is replaced by the fusion partner (Thiel et al., Bioessays 2012. 34, 771-80). Recruitment of chromatin modifying enzymes like Dot1L and/or the pTEFb complex by the fusion partner leads to enhanced transcription and transcriptional elongation of MLL target genes including HOXA genes (e.g. HOXA9) and the HOX cofactor MEIS1 as the most prominent ones. Aberrant expression of these genes in turn blocks hematopoietic differentiation and enhances proliferation.

Menin which is encoded by the Multiple Endocrine Neoplasia type 1 (MEN1) gene is expressed ubiquitously and is predominantly localized in the nucleus. It has been shown to interact with numerous proteins and is, therefore, involved in a variety of cellular processes. The best understood function of menin is its role as an oncogenic cofactor of MLL fusion proteins. Menin interacts with two motifs within the N-terminal fragment of MLL, that is retained in all fusion proteins, MBM1 (menin-binding motif 1) and MB M2 (Thiel et al., Bioessays 2012. 34, 771-80). Menin/MLL interaction leads to the formation of a new interaction surface for lens epithelium-derived growth factor (LEDGF). Although MLL directly binds to LEDGF, menin is obligatory for the stable interaction between MLL, and LEDGF and the gene specific chromatin recruitment of the MLL complex via the PWWP domain of LEDGF (Cermakova et al., Cancer Res 2014. 15, 5139-51; Yokoyama & Cleary, Cancer Cell 2008. 8, 36-46). Furthermore, numerous genetic studies have shown that menin is strictly required for oncogenic transformation by MlX fusion proteins suggesting the menin/MLL, interaction as an attractive therapeutic target. For example, conditional deletion of Men1 prevents leukomogenesis in bone marrow progenitor cells ectopically expressing MLL fusions (Chen et al., Proc Natl Acad Sci 2006. 103, 1018-23). Similarly, genetic disruption of menin/MLL fusion interaction by loss-of-function mutations abrogates the oncogenic properties of the MLL fusion proteins, blocks the development of leukemia in vivo and releases the differentiation block of MLL-transformed leukemic blasts. These studies also showed that menin is required for the maintenance of HOX gene expression by MlX fusion proteins (Yokoyama et al., Cell 2005. 123, 207-18). In addition, small molecule inhibitors of menin/MLL interaction have been developed suggesting druggability of this protein/protein interaction and have also demonstrated efficacy in preclinical models of AML (Borkin et al., Cancer Cell 2015. 27, 589-602; Cierpicki and Grembecka, Future Med Chem 2014. 6, 447-462). Together with the observation that menin is not a requisite cofactor of MLL1 during normal hematopoiesis (Li et al., Blood 2013. 122, 2039-2046), these data validate the disruption of menin/MLL interaction as a promising new therapeutic approach for the treatment of MlX rearranged leukemia and other cancers with an active HOX/MEIS1 gene signature. For example, an internal partial tandem duplication (PTD) within the 5'region of the MLL gene represents another major aberration that is found predominantly in de novo and secondary AML as well as myeloid dysplasia syndromes. Although the molecular mechanism and the biological function of MLL-PTD is not well understood, new therapeutic targeting strategies affecting the menin/MLL interaction might also prove effective in the treatment of MLL-PTD-related leukemias. Furthermore, castration-resistant prostate cancer has been shown to be dependent on the menin/MLL interaction (Malik et al., Nat Med 2015. 21, 344-52).

Several references describe inhibitors targeting the menin-MLL interaction: WO2011029054, J Med Chem 2016, 59, 892-913 describe the preparation of thienopyrimidine and benzodiazepine derivatives; WO2014164543 describes thienopyrimidine and thienopyridine derivatives; *Nature Chemical Biology* March 2012, 8, 277-284 and Ren, J; et al. *Bioorg Med Chem Lett* (2016), 26(18), 4472-4476 describe thienopyrimidine derivatives; *J Med Chem* 2014, 57, 1543-1556 describes hydroxy- and aminomethylpiperidine derivatives; *Future Med Chem*, 2014, 6, 447-462 reviews small molecule and peptidomimetic compounds; WO2016/195776 describes furo[2,3-d]pyrimidine, 9H-purine, [1,3]oxazolo[5,4-d]pyrimidine, [1,3]oxazolo[4,5-d]pyrimidine, [1,3]thiazolo[5,4-d]pyrimidine, thieno[2,3-b]pyridine and thieno[2,3-d]pyrimidine derivatives; and WO2016/

197027 describes 5,6,7,8-tetrahydropyrido[3,4-d]pyrimidine, 5,6,7,8-tetrahydropyrido]4,3-d]pyrimidine, pyrido[2,3-d]pyrimidine and quinoline derivatives; and WO2016040330 describes thienopyrimidine and thienopyridine compounds. WO2017192543 describes piperidines as Menin inhibitors. WO2017112768, WO2017207387, WO2017214367, WO2018053267 and WO2018024602 describe inhibitors of the menin-MLL interaction. WO2017161002 and WO2017161028 describe inhibitors of menin-MLL. WO2018050686, WO2018050684 and WO2018109088 describe inhibitors of the menin-MLL interaction.

DESCRIPTION OF THE INVENTION

The present invention concerns novel compounds of Formula (I),

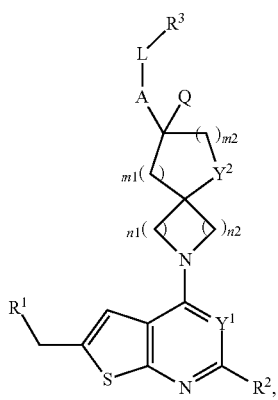

(I)

and the tautomers and the stereoisomeric forms thereof, wherein $R^1$ is selected from the group consisting of $CH_3$, $CH_2F$, $CHF_2$ and $CF_3$;

$Y^1$ is N or $CR^y$;

when $Y^1$ represents N, $R^2$ is selected from the group consisting of hydrogen, $CH_3$, —$OCH_3$, —$NH_2$, and —NH—$CH_3$;

when $Y^1$ represents $CR^y$, $R^2$ is hydrogen;

$R^y$ is selected from the group consisting of hydrogen, cyano, and $C_{1-4}$alkyl optionally substituted with hydroxy, —O—$C_{1-4}$alkyl, or —O—$C_{3-6}$cycloalkyl;

$Y^2$ is $CH_2$ or O;

A is a covalent bond or —$CR^{15a}R^{15b}$—;

$R^{15a}$ and $R^{15b}$ are each independently selected from the group consisting of hydrogen or $C_{1-4}$alkyl;

Q is hydrogen or $C_{1-4}$alkyl optionally substituted with phenyl;

-L-$R^3$ is selected from (a), (b), (c), (d), (e), or (f):

(a) -L-$R^3$ is —$NR^4R^{14}$, wherein $R^4$ is selected from the group consisting of hydrogen; cyclopropyl; $C_{1-4}$alkyl optionally substituted with a substituent selected from the group consisting of fluoro and —CN; and $C_{2-4}$alkyl substituted with a substituent selected from the group consisting of —$OR^{3a}$ and —$NR^{4a}R^{4aa}$;

$R^{14}$ is selected from the group consisting of $C_{1-6}$alkyl optionally substituted with one, two or three fluoro substituents; and $C_{2-6}$alkyl substituted with a substituent selected from the group consisting of —$OR^{1a}$ and —$NR^{2a}R^{2aa}$, wherein $R^{1a}$, $R^{2a}$, $R^{2aa}$, $R^{3a}$, $R^{4a}$, and $R^{4aa}$ are each independently selected from the group consisting of hydrogen, $C_{1-4}$alkyl and cyclopropyl;

or (b) L is selected from the group consisting of —N($R^B$)—, —N($R^B$)—$CR^{1B}R^{1BB}$—, and —($NR^B$)—$CHR^{1B}$—$CHR^{2B}$—; and $R^3$ is selected from the group consisting of Ar; $Het^1$; $Het^2$; $Het^3$; $R^{17}$; and a 7- to 10-membered saturated spirocarbobicyclic system; wherein $R^B$ is selected from the group consisting of hydrogen; cyclopropyl; $C_{1-4}$alkyl optionally substituted with a substituent selected from the group consisting of fluoro and —CN; and $C_{2-4}$alkyl substituted with a substituent selected from the group consisting of —$OR^{1b}$ and —$NR^{2b}R^{2bb}$; provided that when $R^3$ is $R^{17}$, $R^B$ is hydrogen;

wherein $R^{1b}$, $R^{2b}$, and $R^{2bb}$ are each independently selected from the group consisting of hydrogen, $C_{1-4}$alkyl and cyclopropyl;

$R^{1B}$ is selected from the group consisting of hydrogen; halo; $C_{3-6}$cycloalkyl; $C_{1-4}$alkyl optionally substituted with a substituent selected from the group consisting of fluoro, hydroxy, and —CN; $C_{2-4}$alkyl substituted with a substituent selected from the group consisting of —$OR^{4B}$ and —$NR^{5B}R^{5BB}$; and C-linked 4- to 7-membered non-aromatic heterocyclyl containing at least one nitrogen, oxygen or sulfur atom; and $R^{1BB}$ is selected from the group consisting of hydrogen and methyl; or $R^{1B}$ and $R^{1BB}$ together with the carbon to which they are attached form a $C_{3-6}$cycloalkyl or a C-linked 4- to 7-membered non-aromatic heterocyclyl containing at least one nitrogen, oxygen or sulfur atom;

$R^{2B}$ is selected from the group consisting of hydrogen; —$OR^{6B}$; —$NR^{7B}R^{7BB}$; $CF_3$, $C_{1-4}$alkyl optionally substituted with a substituent selected from the group consisting of fluoro, —CN, —$OR^{4B}$, and —$NR^{5B}R^{5BB}$; and C-linked 4- to 7-membered non-aromatic heterocyclyl containing at least one nitrogen, oxygen or sulfur atom; wherein $R^{4B}$, $R^{5B}$, $R^{5BB}$, $R^{6B}$, $R^{7B}$, and $R^{7BB}$ are each independently selected from the group consisting of hydrogen; $C_{1-4}$alkyl optionally substituted with a substituent selected from the group consisting of fluoro, —CN and —C(=O)$NR^{9B}R^{9BB}$; and $C_{2-4}$alkyl substituted with a substituent selected from the group consisting of —$OR^{10B}$ and —$NR^{11B}R^{11BB}$; wherein $R^{9B}$, $R^{9BB}$, $R^{10B}$, $R^{11B}$ and $R^{11BB}$ are each independently selected from the group consisting of hydrogen; $C_{1-4}$alkyl; and C-linked 4- to 7-membered non-aromatic heterocyclyl containing at least one nitrogen, oxygen or sulfur atom;

or (c) -L-$R^3$ is selected from the group consisting of —N($R^C$)—$COR^{5C}$; and —N($R^C$)—$SO_2$—$R^{13C}$ wherein $R^C$ is selected from the group consisting of hydrogen; cyclopropyl; $C_{1-4}$alkyl optionally substituted with a substituent selected from the group consisting of fluoro and —CN; and $C_{2-4}$alkyl substituted with a substituent selected from the group consisting of —$OR^{1c}$ and —$NR^{2c}R^{2cc}$;

$R^{5C}$ and $R^{13C}$ are each independently selected from the group consisting of hydrogen; Ar; $Het^1$; $Het^2$; $Het^3$; $R^{17}$; a 7- to 10-membered saturated spirocarbobicyclic system; and $C_{1-4}$alkyl optionally substituted with —$NR^{2c}R^{2cc}$, Ar, $Het^1$ or $Het^2$; wherein $R^{1c}$, $R^{2c}$, and $R^{2cc}$ are each independently selected from the group consisting of hydrogen and $C_{1-4}$alkyl;

or (d) L is selected from —N($R^D$)—C$R^{1D}R^{1DD}$— and —N($R^D$)—C$R^{1D}R^{1DD}$—C$R^{2D}R^{2DD}$—; wherein $R^D$ is selected from the group consisting of hydrogen; $C_{1-4}$alkyl optionally substituted with a substituent selected from the group consisting of fluoro and —CN; and $C_{2-4}$alkyl substituted with a substituent selected from —O$R^{1d}$ and —N$R^{2d}R^{2dd}$; wherein $R^{1d}$, $R^{2d}$ and $R^{2dd}$ are each independently selected from the group consisting of hydrogen and $C_{1-4}$alkyl;

$R^{1D}$, $R^{1DD}$, $R^{2D}$ and $R^{2DD}$ are each independently selected from the group consisting of hydrogen and $C_{1-4}$alkyl; and $R^3$ is selected from the group consisting of

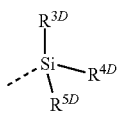

and

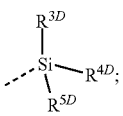

wherein $R^{3D}$, $R^{4D}$, and $R^{5D}$ are each independently selected from the group consisting of $C_{1-6}$alkyl optionally substituted with a —OH, —O$C_{1-6}$alkyl, or a —NH$_2$ substituent;

or (e) -L-$R^3$ is

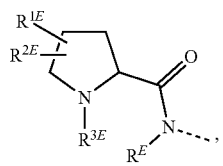

wherein $R^E$ is selected from the group consisting of hydrogen and $C_{1-4}$alkyl;

$R^{1E}$ is selected from the group consisting of hydrogen, fluoro and $C_{1-4}$alkyl; and $R^{2E}$ is selected from the group consisting of fluoro, —O$C_{1-4}$alkyl, and $C_{1-4}$alkyl optionally substituted with 1, 2 or 3 fluoro substituents; or $R^{1E}$ and $R^{2E}$ are bound to the same carbon atom and together form a $C_{3-5}$cycloalkyl or a C-linked 4- to 6-membered heterocyclyl containing an oxygen atom; and $R^{3E}$ is selected from the group consisting of hydrogen; $C_{1-4}$alkyl optionally substituted with a fluoro or a —CN substituent; and $C_{2-4}$alkyl substituted with a substituent selected from the group consisting of —O$R^{4E}$ and —N$R^{5E}R^{5EE}$; wherein $R^{4E}$, $R^{5E}$ and $R^{5EE}$ are each independently selected from the group consisting of hydrogen; $C_{1-4}$alkyl optionally substituted with a substituent selected from the group consisting of fluoro, —CN, and —C(=O)N$R^{6E}R^{6EE}$; $C_{2-4}$alkyl substituted with a substituent selected from the group consisting of —O$R^{7E}$ and —N$R^{8E}R^{8EE}$; and C-linked 4- to 7-membered non-aromatic heterocyclyl containing at least one nitrogen, oxygen or sulfur atom; wherein $R^{6E}$, $R^{6EE}$, $R^{7E}$, $R^{8E}$ and $R^{8EE}$ are each independently selected from the group consisting of hydrogen and $C_{1-4}$alkyl;

or (f) -L-$R^3$ is a radical

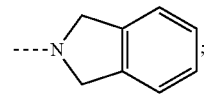

Ar is phenyl optionally substituted with one, two, or three substituents each independently selected from the group consisting of halo, —CN, —O$R^4$, —N$R^5R^{5'}$, —C(=O)N$R^5R^{5'}$, Het$^4$, —O-Het$^4$, —N$R^5$—Het$^4$, —C(=O)—Het$^4$, —S(=O)$_2$—Het$^4$, —S(=O)$_2$—N$R^5R^{5'}$, —S(=O)$_2$—$C_{1-4}$alkyl, $R^{14}$, CF$_3$, $C_{3-5}$cycloalkyl optionally substituted with —CN, and $C_{1-4}$alkyl optionally substituted with one or two substituents each independently selected from the group consisting of fluoro, Het$^4$, —CN, —O$R^6$, —N$R^7R^{7'}$, —S(=O)$_2$—$C_{1-4}$alkyl and —C(=O)N$R^8R^{8'}$;

Het$^1$ is a monocyclic heteroaryl selected from the group consisting of pyridyl, 2-, 4-, 5- or 6-pyrimidinyl, pyrazinyl, pyridazinyl, furanyl, thienyl, pyrrolyl, pyrazolyl, imidazolyl, 4- or 5-thiazolyl, isothiazolyl, and isoxazolyl; each of which may be optionally substituted with one, two, or three substituents each independently selected from the group consisting of halo, —CN, —O$R^4$, —N$R^5R^{5'}$, —C(=O)N$R^5R^{5'}$, —C(=O)—Het$^4$, and $C_{1-4}$alkyl optionally substituted with a substituent selected from the group consisting of fluoro, —CN, —O$R^6$, Het$^2$, —N$R^7R^{7'}$, and —C(=O)N$R^8R^{8'}$; and Het$^2$ is a non-aromatic heterocyclyl optionally substituted with one, two, or three substituents each independently selected from the group consisting of halo, —CN, —C(=O)—$C_{1-6}$alkyl, —C(=O)Ar, —C(=O)Het$^1$, —C(=O)Het$^2$, —O$R^4$, —N$R^5R^{5'}$, and $C_{1-4}$alkyl optionally substituted with a substituent selected from the group consisting of fluoro, —CN, —O$R^6$, —N$R^7R^{7'}$, $R^{12}$ and —C(=O)N$R^8R^{8'}$;

wherein $R^{12}$ is C-linked 4- to 7-membered non-aromatic heterocyclyl containing at least one nitrogen, oxygen or sulfur atom;

$R^4$, $R^5$, $R^{5'}$, $R^6$, $R^7$, $R^{7'}$, $R^8$ and $R^{8'}$ are each independently selected from the group consisting of hydrogen; —C(=O)—$C_{1-4}$alkyl; —S(=O)$_2$—$C_{1-4}$alkyl;

$C_{1-4}$alkyl optionally substituted with a substituent selected from the group consisting of fluoro, —CN, —C(=O)—$C_{1-4}$alkyl, —S(=O)$_2$—$C_{1-4}$alkyl, $R^{11'''}$, $R^{16}$ and —C(=O)N$R^9R^{9'}$;

$C_{1-4}$alkyl substituted with three fluoro atoms; and $C_{2-4}$alkyl substituted with a substituent selected from the group consisting of —O$R^{10}$ and —N$R^{11}R^{11'}$; wherein $R^9$, $R^{9'}$, $R^{10}$, $R^{11}$, $R^{11'}$ and $R^{11''}$ are each independently selected from the group consisting of hydrogen; $C_{1-4}$alkyl; —S(=O)$_2$—$C_{1-4}$alkyl; and C-linked 4- to 7-membered non-aromatic heterocyclyl containing at least one nitrogen, oxygen or sulfur atom, wherein said heterocyclyl is optionally substituted with one, two, or three substituents each independently selected from the group consisting of —S(═O)$_2$—C$_{1-4}$alkyl, halo, cyano, and C$_{1-4}$alkyl optionally substituted with —O—C$_{1-4}$alkyl;

R$^{16}$ is N-linked 4- to 7-membered non-aromatic heterocyclyl containing at least one N-atom and optionally one additional heteroatom selected from nitrogen, oxygen and sulfur, wherein said heterocyclyl is optionally substituted with one, two, or three substituents each independently selected from the group consisting of —S(═O)$_2$—C$_{1-4}$alkyl, halo, cyano, and C$_{1-4}$alkyl optionally substituted with —O—C$_{1-4}$alkyl;

R$^{14}$ is a 5-membered monocyclic heteroaryl containing at least one nitrogen atom, and optionally 1, 2 or 3 additional heteroatoms each independently selected from nitrogen, oxygen and sulfur;

Het$^3$ is selected from the group consisting of formula (b-1) and (b-2):

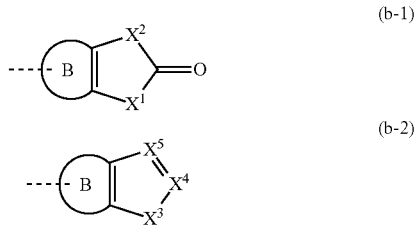

Ring B is phenyl;
X$^1$ represents CH$_2$, O or NH;
X$^2$ represents NH or O;
X$^3$ represents NH or O;
X$^4$ represents CH or N;
X$^5$ represents CH or N;

wherein one C-atom or one N-atom in the 5-membered ring of (b-1) or (b-2), including suitable C-atoms and N-atoms in the definition of X$^1$, X$^2$, X$^3$, X$^4$ and X$^5$, might be substituted with one or where possible two C$_{1-4}$alkyl groups optionally substituted with one, two or three substituents each independently selected from the group consisting of halo, cyano, —C(═O)NR$^5$R$^{5'}$, and Het$^4$;

Het$^4$ is a 4- to 7-membered non-aromatic heterocyclyl containing at least one nitrogen, oxygen or sulfur atom, wherein said heterocyclyl is optionally substituted with one, two, or three substituents each independently selected from the group consisting of halo, —CN, oxo, —C(═O)NR$^5$R$^{5'}$, —O—C$_{1-4}$alkyl, —S(═O)$_2$—C$_{1-4}$alkyl, and C$_{1-4}$alkyl optionally substituted with —O—C$_{1-4}$alkyl;

R$^{17}$ is C$_{3-6}$cycloalkyl optionally substituted with one or more substituents selected from the group consisting of halo, —CN, —OR$^4$, —NR$^5$R$^{5'}$, —C(═O)NR$^5$R$^{5'}$, and C$_{1-4}$alkyl optionally substituted with a substituent selected from the group consisting of fluoro, —CN, —OR$^6$, —NR$^7$R$^{7'}$, and —C(═O)NR$^8$R$^{8'}$;

n1, n2, and m1 are each independently selected from 1 and 2;

m2 is 0 or 1;

and the pharmaceutically acceptable salts and the solvates thereof.

The present invention also relates to a pharmaceutical composition comprising a therapeutically effective amount of a compound of Formula (I), a pharmaceutically acceptable salt, or a solvate thereof, and a pharmaceutically acceptable carrier or excipient.

Additionally, the invention relates to a compound of Formula (I), a pharmaceutically acceptable salt, or a solvate thereof, for use as a medicament, and to a compound of Formula (I), a pharmaceutically acceptable salt, or a solvate thereof, for use in the treatment or in the prevention of cancer, myelodysplastic syndrome (MDS) and diabetes.

In a particular embodiment, the invention relates to a compound of Formula (I), a pharmaceutically acceptable salt, or a solvate thereof, for use in the treatment or in the prevention of cancer.

In a specific embodiment said cancer is selected from leukemias, myeloma or a solid tumor cancer (e.g. prostate cancer, lung cancer, breast cancer, pancreatic cancer, colon cancer, liver cancer, melanoma and glioblastoma, etc.). In some embodiments, the leukemias include acute leukemias, chronic leukemias, myeloid leukemias, myelogeneous leukemias, lymphoblastic leukemias, lymphocytic leukemias, Acute myelogenous leukemias (AML), Chronic myelogenous leukemias (CML), Acute lymphoblastic leukemias (ALL), Chronic lymphocytic leukemias (CLL), T cell prolymphocytic leukemias (T-PLL), Large granular lymphocytic leukemia, Hairy cell leukemia (HCL), MLL-rearranged leukemias, MLL-PTD leukemias, MLL amplified leukemias, MLL-positive leukemias, leukemias exhibiting HOX/MEIS1 gene expression signatures etc.

The invention also relates to the use of a compound of Formula (I), a pharmaceutically acceptable salt, or a solvate thereof, in combination with an additional pharmaceutical agent for use in the treatment or prevention of cancer, myelodysplastic syndrome (MDS) and diabetes.

Furthermore, the invention relates to a process for preparing a pharmaceutical composition according to the invention, characterized in that a pharmaceutically acceptable carrier is intimately mixed with a therapeutically effective amount of a compound of Formula (I), a pharmaceutically acceptable salt, or a solvate thereof. The invention also relates to a product comprising a compound of Formula (I), a pharmaceutically acceptable salt, or a solvate thereof, and an additional pharmaceutical agent, as a combined preparation for simultaneous, separate or sequential use in the treatment or prevention of cancer, myelodysplastic syndrome (MDS) and diabetes.

Additionally, the invention relates to a method of treating or preventing a cell proliferative disease in a warm-blooded animal which comprises administering to the said animal an effective amount of a compound of Formula (I), a pharmaceutically acceptable salt, or a solvate thereof, as defined herein, or a pharmaceutical composition or combination as defined herein.

DETAILED DESCRIPTION OF THE INVENTION

The term 'halo' or 'halogen' as used herein represents fluoro, chloro, bromo and iodo.

The prefix 'C$_{x-y}$' (where x and y are integers) as used herein refers to the number of carbon atoms in a given group. Thus, a C$_{1-6}$alkyl group contains from 1 to 6 carbon atoms, and so on.

The term 'C$_{1-4}$alkyl' as used herein as a group or part of a group represents a straight or branched chain saturated hydrocarbon radical having from 1 to 4 carbon atoms, such as methyl, ethyl, n-propyl, isopropyl, n-butyl, s-butyl, t-butyl and the like.

The term 'C$_{2-4}$alkyl' as used herein as a group or part of a group represents a straight or branched chain saturated hydrocarbon radical having from 2 to 4 carbon atoms, such as ethyl, n-propyl, isopropyl, n-butyl, s-butyl, t-butyl and the like.

The term '$C_{1-6}$alkyl' as used herein as a group or part of a group represents a straight or branched chain saturated hydrocarbon radical having from 1 to 6 carbon atoms such as the groups defined for $C_{1-4}$alkyl and n-pentyl, n-hexyl, 2-methylbutyl and the like.

The term '$C_{2-6}$alkyl' as used herein as a group or part of a group represents a straight or branched chain saturated hydrocarbon radical having from 2 to 6 carbon atoms such as the groups defined for $C_{2-4}$alkyl and n-pentyl, n-hexyl, 2-methylbutyl and the like.

The term '$C_{3-5}$cycloalkyl' as used herein as a group or part of a group defines a saturated, cyclic hydrocarbon radical having from 3 to 5 carbon atoms, such as cyclopropyl, cyclobutyl and cyclopentyl. The term '$C_{3-6}$cycloalkyl' as used herein as a group or part of a group defines a saturated, cyclic hydrocarbon radical having from 3 to 6 carbon atoms, such as cyclopropyl, cyclobutyl, cyclopentyl and cyclohexyl.

It will be clear for the skilled person that $S(=O)_2$, $(SO_2)$ or $SO_2$ represents a sulfonyl moiety.

It will be clear for the skilled person that CO or $C(=O)$ represents a carbonyl moiety.

It will be clear for the skilled person that —$N(R^B)$— or —$(NR^B)$— represents

As used herein 'spirocarbobicyclic' systems are cyclic carbon systems wherein two cycles are joined at a single atom. Examples of 7- to 10-membered saturated spirocarbobicyclic systems include, but are not limited to

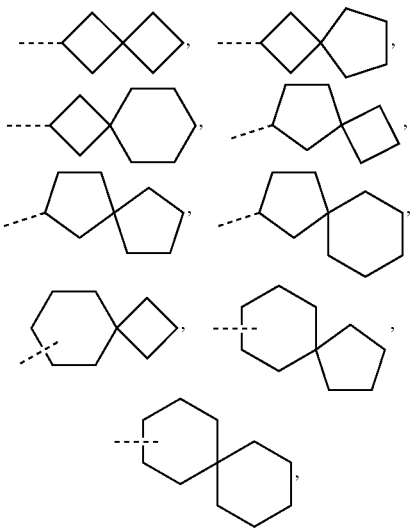

and the like.

In general, whenever the term 'substituted' is used in the present invention, it is meant, unless otherwise indicated or clear from the context, to indicate that one or more hydrogens, in particular from 1 to 4 hydrogens, more in particular from 1 to 3 hydrogens, preferably 1 or 2 hydrogens, more preferably 1 hydrogen, on the atom or radical indicated in the expression using 'substituted' are replaced with a selection from the indicated group, provided that the normal valency is not exceeded, and that the substitution results in a chemically stable compound, i.e. a compound that is sufficiently robust to survive isolation to a useful degree of purity from a reaction mixture.

Whenever one C-atom or one N-atom in the 5-membered ring of (b-1) or (b-2) is substituted with one or where possible two substituents, those substituents may replace any hydrogen atom bound to a carbon or nitrogen atom, including NH, CH and $CH_2$ groups in the definition of $X^1$, $X^2$, $X^3$, $X^4$ and $X^5$.

It will be clear for the skilled person that when e.g. L is —$N(R^B)$—$CR^{1B}R^{1BB}$— in option (b) of -L-$R^3$, this means that the nitrogen atom substituted with $R^B$ is attached to variable A. This is similar for other definitions of L such as for example —$(NR^B)$—$CHR^{1B}$—$CHR^{2B}$— (nitrogen atom substituted with $R^B$ attached to variable A), —$N(R^D)$—$CR^{1D}R^{1DD}$— (nitrogen atom substituted with $R^D$ attached to variable A), —$N(R^D)$—$CR^{1D}R^{1DD}$—$CR^{2D}R^{2DD}$— (nitrogen atom substituted with $R^D$ attached to variable A), or other similar definitions of L in the scope.

It will be clear for the skilled person that when A is a covalent bond, Formula (I) is limited to Formula (I-x) wherein all variables are as defined herein:

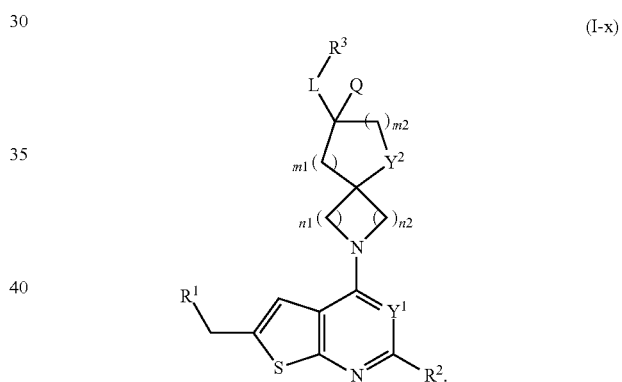

(I-x)

Combinations of substituents and/or variables are permissible only if such combinations result in chemically stable compounds. 'Stable compound' is meant to indicate a compound that is sufficiently robust to survive isolation to a useful degree of purity from a reaction mixture.

The skilled person will understand that when an atom or radical is substituted with 'a substituent', it is meant that the atom or radical referred to is substituted with one substituent selected from the indicated group.

The skilled person will understand that the term 'optionally substituted' means that the atom or radical indicated in the expression using 'optionally substituted' may or may not be substituted (this means substituted or unsubstituted respectively).

When two or more substituents are present on a moiety they may, where possible and unless otherwise indicated or clear from the context, replace hydrogens on the same atom or they may replace hydrogen atoms on different atoms in the moiety.

It will be clear for the skilled person that, unless otherwise is indicated or is clear from the context, a substituent on a heterocyclyl group may replace any hydrogen atom on a ring carbon atom or on a ring heteroatom (e.g. a hydrogen on a nitrogen atom may be replaced by a substituent).

Within the context of this invention 'saturated' means 'fully saturated', if not otherwise specified.

A 'non-aromatic group' embraces unsaturated ring systems without aromatic character, partially saturated and fully saturated carbocyclic and heterocyclic ring systems. The term 'partially saturated' refers to rings wherein the ring structure(s) contain(s) at least one multiple bond e.g. a C=C, N=C bond. The term 'fully saturated' refers to rings where there are no multiple bonds between ring atoms. Thus, a 'non-aromatic heterocyclyl' is a non-aromatic monocyclic or bicyclic system, unless otherwise specified, having for example, 3 to 12 ring members, more usually 5 to 10 ring members. Examples of monocyclic groups are groups containing 4 to 7 ring members, more usually, 5 or 6 ring members. Examples of bicyclic groups are those containing 7 to 12, 8 to 12, more usually 9 or 10 ring members.

The skilled person will understand that a 'non-aromatic heterocyclyl' contains at least one heteroatom such as N, O or S, if not otherwise specified or is clear from the context.

Non-limiting examples of monocyclic heterocyclyl systems containing at least one heteroatom selected from nitrogen, oxygen or sulfur (N, O, S) include, but are not limited to 4- to 7-membered heterocyclyl systems such as azetidinyl, oxetanyl, pyrrolidinyl, tetrahydrofuranyl, piperidinyl, piperazinyl, pyranyl, dihydropyranyl, tetrahydropyranyl, morpholinyl, thiomorpholinyl, and tetrahydro-2H-thiopyranyl 1,1-dioxide, in particular azetidinyl, oxetanyl, pyrrolidinyl, tetrahydrofuranyl, piperidinyl, piperazinyl, pyranyl, dihydropyranyl, tetrahydropyranyl, morpholinyl, and thiomorpholinyl.

Non-limiting examples of bicyclic heterocyclyl systems containing at least one heteroatom selected from nitrogen, oxygen or sulfur (N, O, S) include, but are not limited to octahydro-1H-indolyl, indolinyl,

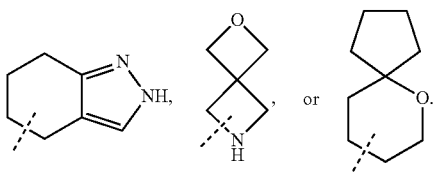

Unless otherwise specified, each can be bound to the remainder of the molecule of Formula (I) through any available ring carbon atom (C-linked) or nitrogen atom (N-linked), and may optionally be substituted, where possible, on carbon and/or nitrogen atoms according to the embodiments. E.g. $Het^2$ and $Het^4$ can be C-linked or N-linked to the remainder of the molecule of Formula (I).

The term 'C-linked 4- to 7-membered heterocyclyl containing at least one nitrogen, oxygen or sulphur atom' as used herein alone or as part of another group, defines a saturated, cyclic hydrocarbon radical containing at least one nitrogen, oxygen or sulphur atom having from 4 to 7 ring members, as defined above, bound through an available carbon atom. It will be clear that similar the term 'C-linked 4- to 6-membered heterocyclyl containing an oxygen atom' as used herein alone or as part of another group, defines a saturated, cyclic hydrocarbon radical containing one oxygen atom having from 4 to 6 ring members, as defined above, bound through an available carbon atom (such as for example oxetanyl, tetrahydrofuranyl, and tetrahydropyranyl).

Similar, it will be clear that the term 'C-linked 4- to 7-membered non-aromatic heterocyclyl containing at least one nitrogen, oxygen or sulphur atom' as used herein alone or as part of another group, defines a non-aromatic, cyclic hydrocarbon radical containing at least one nitrogen, oxygen or sulphur atom having from 4 to 7 ring members, as defined above, bound through an available carbon atom. It will be clear that similar the term 'C-linked 4- to 6-membered non-aromatic heterocyclyl containing an oxygen atom' as used herein alone or as part of another group, defines a non-aromatic, cyclic hydrocarbon radical containing one oxygen atom having from 4 to 6 ring members, as defined above, bound through an available carbon atom (such as for example oxetanyl, tetrahydrofuranyl, piperidinyl and tetrahydropyranyl).

Similar, it will be clear that the term 'N-linked 4- to 7-membered non-aromatic heterocyclyl containing at least one N-atom and optionally one additional heteroatom selected from nitrogen, oxygen and sulfur' as used herein alone or as part of another group, defines a non-aromatic, cyclic hydrocarbon radical containing at least one N-atom and optionally one additional heteroatom selected from nitrogen, oxygen and sulfur, having from 4 to 7 ring members, as defined above, bound through an available N-atom. It should be understood that 5-membered monocyclic heteroaryl groups (as in the definition of $R^{14}$) are aromatic and may be attached to the remainder of the molecule of Formula (I) through any available ring carbon or nitrogen atom as appropriate, if not otherwise specified. Preferably via a carbon atom. Non-limiting examples of 5-membered monocyclic heteroaryl containing at least one nitrogen atom, and optionally 1, 2 or 3 additional heteroatoms each independently selected from nitrogen, oxygen and sulfur include, but are not limited to pyrazolyl, imidazolyl, triazolyl, oxazolyl, isothiazolyl or thiazolyl.

Whenever substituents are represented by chemical structure, '- - -' represents the bond of attachment to the remainder of the molecule of Formula (I).

Lines (such as '- - -') drawn into ring systems indicate that the bond may be attached to any of the suitable ring atoms.

For example when $Het^3$ is (b-1) wherein Ring B is phenyl

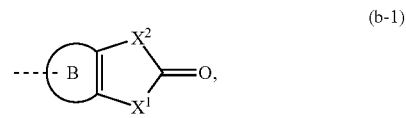
(b-1)

this covers any one of the following ring systems

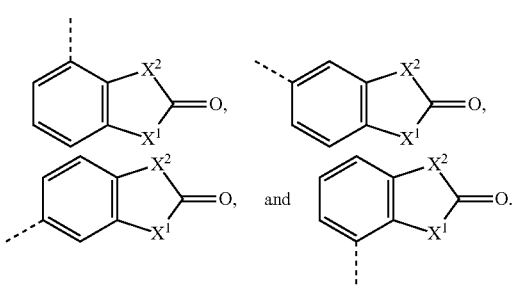

For example when Het³ is (b-2) wherein Ring B is phenyl

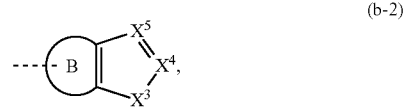

this covers any one of the following ring systems

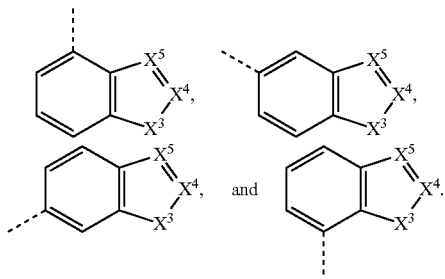

Het¹, Het² and Het⁴ may be attached to the remainder of the molecule of Formula (I) through any available ring carbon or nitrogen atom as appropriate, if not otherwise specified.

It will be clear that a saturated cyclic moiety may, where possible, have substituents on both carbon and nitrogen atoms, unless otherwise is indicated or is clear from the context.

When any variable occurs more than one time in any constituent, each definition is independent.

When any variable occurs more than one time in any formula (e.g. Formula (I)), each definition is independent.

The term "subject" as used herein, refers to an animal, preferably a mammal (e.g. cat, dog, primate or human), more preferably a human, who is or has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medicinal doctor or other clinician, which includes alleviation or reversal of the symptoms of the disease or disorder being treated.

The term "composition" is intended to encompass a product comprising the specified ingredients in the specified amounts, as well as any product which results, directly or indirectly, from combinations of the specified ingredients in the specified amounts.

The term "treatment", as used herein, is intended to refer to all processes wherein there may be a slowing, interrupting, arresting or stopping of the progression of a disease, but does not necessarily indicate a total elimination of all symptoms.

The term "compound(s) of the (present) invention" or "compound(s) according to the (present) invention" as used herein, is meant to include the compounds of Formula (I) and the pharmaceutically acceptable salts, and the solvates thereof.

As used herein, any chemical formula with bonds shown only as solid lines and not as solid wedged or hashed wedged bonds, or otherwise indicated as having a particular configuration (e.g. R, S) around one or more atoms, contemplates each possible stereoisomer, or mixture of two or more stereoisomers.

Hereinbefore and hereinafter, the term "compound(s) of Formula (I)" is meant to include the tautomers thereof and the stereoisomeric forms thereof.

The terms "stereoisomers", "stereoisomeric forms" or "stereochemically isomeric forms" hereinbefore or hereinafter are used interchangeably.

The invention includes all stereoisomers of the compounds of the invention either as a pure stereoisomer or as a mixture of two or more stereoisomers.

Enantiomers are stereoisomers that are non-superimposable mirror images of each other. A 1:1 mixture of a pair of enantiomers is a racemate or racemic mixture.

Atropisomers (or atropoisomers) are stereoisomers which have a particular spatial configuration, resulting from a restricted rotation about a single bond, due to large steric hindrance. All atropisomeric forms of the compounds of Formula (I) are intended to be included within the scope of the present invention.

Diastereomers (or diastereoisomers) are stereoisomers that are not enantiomers, i.e. they are not related as mirror images. If a compound contains a double bond, the substituents may be in the E or the Z configuration.

Substituents on bivalent cyclic saturated or partially saturated radicals may have either the cis- or trans-configuration; for example if a compound contains a disubstituted cycloalkyl group, the substituents may be in the cis or trans configuration.

Therefore, the invention includes enantiomers, atropisomers, diastereomers, racemates, E isomers, Z isomers, cis isomers, trans isomers and mixtures thereof, whenever chemically possible.

The meaning of all those terms, i.e. enantiomers, atropisomers, diastereomers, racemates, E isomers, Z isomers, cis isomers, trans isomers and mixtures thereof are known to the skilled person.

The absolute configuration is specified according to the Cahn-Ingold-Prelog system. The configuration at an asymmetric atom is specified by either R or S. Resolved stereoisomers whose absolute configuration is not known can be designated by (+) or (−) depending on the direction in which they rotate plane polarized light. For instance, resolved enantiomers whose absolute configuration is not known can be designated by (+) or (−) depending on the direction in which they rotate plane polarized light.

When a specific stereoisomer is identified, this means that said stereoisomer is substantially free, i.e. associated with less than 50%, preferably less than 20%, more preferably less than 10%, even more preferably less than 5%, in particular less than 2% and most preferably less than 1%, of the other stereoisomers. Thus, when a compound of Formula (I) is for instance specified as (R), this means that the compound is substantially free of the (X) isomer; when a compound of Formula (I) is for instance specified as E, this means that the compound is substantially free of the Z isomer; when a compound of Formula (I) is for instance specified as cis, this means that the compound is substantially free of the trans isomer.

Some of the compounds according to Formula (I) may also exist in their tautomeric form. Such forms in so far as they may exist, although not explicitly indicated in the above Formula (I) are intended to be included within the scope of the present invention. It follows that a single compound may exist in both stereoisomeric and tautomeric form.

Pharmaceutically acceptable salts include acid addition salts and base addition salts. Such salts may be formed by conventional means, for example by reaction of a free acid or a free base form with one or more equivalents of an appropriate base or acid, optionally in a solvent, or in a medium in which the salt is insoluble, followed by removal of said solvent, or said medium, using standard techniques (e.g. in vacuo, by freeze-drying or by filtration). Salts may also be prepared by exchanging a counter-ion of a compound of the invention in the form of a salt with another counter-ion, for example using a suitable ion exchange resin.

The pharmaceutically acceptable salts as mentioned hereinabove or hereinafter are meant to comprise the therapeutically active non-toxic acid and base salt forms which the compounds of Formula (I) and solvates thereof, are able to form.

Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic, tartaric, citric, methanesulfonic, ethanesulfonic, benzenesulfonic, p-toluene-sulfonic, cyclamic, salicylic, p-aminosalicylic, pamoic and the like acids. Conversely said salt forms can be converted by treatment with an appropriate base into the free base form.

The compounds of Formula (I) and solvates thereof containing an acidic proton may also be converted into their non-toxic metal or amine salt forms by treatment with appropriate organic and inorganic bases.

Appropriate base salt forms comprise, for example, the ammonium salts, the alkali and earth alkaline metal salts, e.g. the lithium, sodium, potassium, cesium, magnesium, calcium salts and the like, salts with organic bases, e.g. primary, secondary and tertiary aliphatic and aromatic amines such as methylamine, ethylamine, propylamine, isopropylamine, the four butyl amine isomers, dimethylamine, diethyl amine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquinoline; the benzathine, N-methyl-D-glucamine, hydrabamine salts, and salts with amino acids such as, for example, arginine, lysine and the like. Conversely the salt form can be converted by treatment with acid into the free acid form.

The term solvate comprises the solvent addition forms as well as the salts thereof, which the compounds of Formula (I) are able to form. Examples of such solvent addition forms are e.g. hydrates, alcoholates and the like.

The compounds of the invention as prepared in the processes described below may be synthesized in the form of mixtures of enantiomers, in particular racemic mixtures of enantiomers, that can be separated from one another following art-known resolution procedures. A manner of separating the enantiomeric forms of the compounds of Formula (I), and pharmaceutically acceptable salts, and solvates thereof, involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound would be synthesized by stereospecific methods of preparation. These methods will advantageously employ enantiomerically pure starting materials.

The present invention also embraces isotopically-labeled compounds of the presen t invention which are identical to those recited herein, but for the fact that one or more atoms are replaced by an atom having an atomic mass or mass number different from the atomic mass or mass number usually found in nature (or the most abundant one found in nature).

All isotopes and isotopic mixtures of any particular atom or element as specified herein are contemplated within the scope of the compounds of the invention, either naturally occurring or synthetically produced, either with natural abundance or in an isotopically enriched form. Exemplary isotopes that can be incorporated into compounds of the invention include isotopes of hydrogen, carbon, nitrogen, oxygen, phosphorus, sulfur, fluorine, chlorine and iodine, such as $^{2}H$, $^{3}H$, $^{11}C$, $^{13}C$, $^{14}C$, $^{13}N$, $^{15}O$, $^{17}O$, $^{18}O$, $^{32}P$, $^{33}P$, $^{35}S$, $^{18}F$, $^{36}Cl$, $^{122}I$, $^{123}I$, $^{125}I$, $^{131}I$, $^{75}Br$, $^{76}Br$, $^{77}Br$ and $^{82}Br$. Preferably, the radioactive isotope is selected from the group of $^{2}H$, $^{3}H$, $^{11}C$ and $^{18}F$. More preferably, the radioactive isotope is $^{2}H$. In particular, deuterated compounds are intended to be included within the scope of the present invention.

Certain isotopically-labeled compounds of the present invention (e.g., those labeled with $^{3}H$ and $^{14}C$) may be useful for example in substrate tissue distribution assays. Tritiated ($^{3}H$) and carbon-14 ($^{14}C$) isotopes are useful for their ease of preparation and detectability. Further, substitution with heavier isotopes such as deuterium (i.e., $^{2}H$) may afford certain therapeutic advantages resulting from greater metabolic stability (e.g., increased in vivo half-life or reduced dosage requirements) and hence may be preferred in some circumstances. Thus, in a particular embodiment of the present invention, $R^2$ is selected from hydrogen or deuterium, in particular deuterium. Positron emitting isotopes such as $^{15}O$, $^{13}N$, $^{11}C$ and $^{18}F$ are useful for positron emission tomography (PET) studies. PET imaging in cancer finds utility in helping locate and identify tumours, stage the disease and determine suitable treatment. Human cancer cells overexpress many receptors or proteins that are potential disease-specific molecular targets. Radiolabelled tracers that bind with high affinity and specificity to such receptors or proteins on tumour cells have great potential for diagnostic imaging and targeted radionuclide therapy (Charron, Carlie L. et al. Tetrahedron Lett. 2016, 57(37), 4119-4127). Additionally, target-specific PET radiotracers may be used as biomarkers to examine and evaluate pathology, by for example, measuring target expression and treatment response (Austin R. et al. Cancer Letters (2016), doi: 10.1016/j.canlet.2016.05.008).

The present invention relates in particular to compounds of Formula (I) as defined herein, and the tautomers and the stereoisomeric forms thereof, wherein $R^1$ is selected from the group consisting of $CH_3$, $CH_2F$, $CHF_2$ and $CF_3$;

$Y^1$ is N or $CR^y$;

when $Y^1$ represents N, $R^2$ is selected from the group consisting of hydrogen, $CH_3$—$OCH_3$, —$NH_2$, and —NH—$CH_3$;

when $Y^1$ represents $CR^y$, $R^2$ is hydrogen;

$R^y$ is selected from the group consisting of hydrogen, cyano, and $C_{1-4}$alkyl optionally substituted with hydroxy, —O—$C_{1-4}$alkyl, or —O—$C_{3-6}$cycloalkyl;

$Y^2$ is $CH_2$ or O;

A is a covalent bond or —$CR^{15a}R^{15b}$—;

$R^{15a}$ and $R^{15b}$ are each independently selected from the group consisting of hydrogen or $C_{1-4}$alkyl;

Q is hydrogen or $C_{1-4}$alkyl optionally substituted with phenyl;

-L-$R^3$ is selected from (a), (b), (c), (d), (e), or (f):

(a) -L-$R^3$ is —$NR^4R^{14}$, wherein

R$^A$ is selected from the group consisting of hydrogen; cyclopropyl; C$_{1-4}$alkyl optionally substituted with a substituent selected from the group consisting of fluoro and —CN; and C$_{2-4}$alkyl substituted with a substituent selected from the group consisting of —OR$^{3a}$ and —NR$^{4a}$R$^{4aa}$;

R$^{1A}$ is selected from the group consisting of C$_{1-6}$alkyl optionally substituted with one, two or three fluoro substituents; and C$_{2-6}$alkyl substituted with a substituent selected from the group consisting of —OR$^{1a}$ and —NR$^{2a}$R$^{2aa}$, wherein R$^{1a}$, R$^{2a}$, R$^{2aa}$, R$^{3a}$, R$^{4a}$, and R$^{4aa}$ are each independently selected from the group consisting of hydrogen, C$_{1-4}$alkyl and cyclopropyl;

or (b) L is selected from the group consisting of —N(R$^B$)—, —N(R$^B$)—CR$^{1B}$R$^{1BB}$—, and —(NR$^B$)—CHR$^{1B}$—CHR$^{2B}$—; and R$^3$ is selected from the group consisting of Ar; Het$^1$; Het$^2$; Het$^3$; R$^{17}$; and a 7- to 10-membered saturated spirocarbobicyclic system; wherein R$^B$ is selected from the group consisting of hydrogen; cyclopropyl; C$_{1-4}$alkyl optionally substituted with a substituent selected from the group consisting of fluoro and —CN; and C$_{2-4}$alkyl substituted with a substituent selected from the group consisting of —OR$^{1b}$ and —NR$^{2b}$R$^{2bb}$; provided that when R$^3$ is R$^{17}$, R$^B$ is hydrogen;

wherein
R$^{1b}$, R$^{2b}$, and R$^{2bb}$ are each independently selected from the group consisting of hydrogen, C$_{1-4}$alkyl and cyclopropyl;

R$^{1B}$ is selected from the group consisting of hydrogen; halo; C$_{3-6}$cycloalkyl; C$_{1-4}$alkyl optionally substituted with a substituent selected from the group consisting of fluoro, hydroxy, and —CN; C$_{2-4}$alkyl substituted with a substituent selected from the group consisting of —OR$^{4B}$ and —NR$^{5B}$R$^{5BB}$; and C-linked 4- to 7-membered non-aromatic heterocyclyl containing at least one nitrogen, oxygen or sulfur atom; and R$^{1BB}$ is selected from the group consisting of hydrogen and methyl; or R$^{1B}$ and R$^{1BB}$ together with the carbon to which they are attached form a C$_{3-6}$cycloalkyl or a C-linked 4- to 7-membered non-aromatic heterocyclyl containing at least one nitrogen, oxygen or sulfur atom;

R$^{2B}$ is selected from the group consisting of hydrogen; —OR$^{6B}$; —NR$^{7B}$R$^{7BB}$; CF$_3$, C$_{1-4}$alkyl optionally substituted with a substituent selected from the group consisting of fluoro, —CN, —OR$^{4B}$, and —NR$^{5B}$R$^{5BB}$; and C-linked 4- to 7-membered non-aromatic heterocyclyl containing at least one nitrogen, oxygen or sulfur atom; wherein R$^{4B}$, R$^{5B}$, R$^{5BB}$, R$^{6B}$, R$^{7B}$, and R$^{7BB}$ are each independently selected from the group consisting of hydrogen; C$_{1-4}$alkyl optionally substituted with a substituent selected from the group consisting of fluoro, —CN and —C(=O)NR$^{9B}$R$^{9BB}$; and C$_{2-4}$alkyl substituted with a substituent selected from the group consisting of —OR$^{10B}$ and —NR$^{11B}$R$^{11BB}$; wherein R$^{9B}$, R$^{9BB}$, R$^{10B}$, R$^{11B}$ and R$^{11BB}$ are each independently selected from the group consisting of hydrogen; C$_{1-4}$alkyl; and C-linked 4- to 7-membered non-aromatic heterocyclyl containing at least one nitrogen, oxygen or sulfur atom;

or (c) -L-R$^3$ is selected from the group consisting of —N(R$^C$)—COR$^{5C}$; and —N(R$^C$)—SO$_2$—R$^{13C}$ wherein R$^C$ is selected from the group consisting of hydrogen; cyclopropyl; C$_{1-4}$alkyl optionally substituted with a substituent selected from the group consisting of fluoro and —CN; and C$_{2-4}$alkyl substituted with a substituent selected from the group consisting of —OR$^{1c}$ and —NR$^{2c}$R$^{2cc}$;

R$^{5C}$ and R$^{13C}$ are each independently selected from the group consisting of hydrogen; Ar; Het$^1$; Het$^2$; Het$^3$; R$^{17}$; a 7- to 10-membered saturated spirocarbobicyclic system; and C$_{1-4}$alkyl optionally substituted with —NR$^{2c}$R$^{2cc}$, Ar, Het$^1$ or Het$^2$; wherein R$^{1c}$, R$^{2c}$, and R$^{2cc}$ are each independently selected from the group consisting of hydrogen and C$_{1-4}$alkyl;

or (d) L is selected from —N(R$^D$)—CR$^{1D}$R$^{1DD}$— and —N(R$^D$)—CR$^{1D}$R$^{1DD}$—CR$^{2D}$R$^{2DD}$—; wherein R$^D$ is selected from the group consisting of hydrogen; C$_{1-4}$alkyl optionally substituted with a substituent selected from the group consisting of fluoro and —CN; and C$_{2-4}$alkyl substituted with a substituent selected from —OR$^{1d}$ and —NR$^{2d}$R$^{2dd}$; wherein R$^{1d}$, R$^{2d}$ and R$^{2dd}$ are each independently selected from the group consisting of hydrogen and C$_{1-4}$alkyl;

R$^{1D}$, R$^{1DD}$, R$^{2D}$ and R$^{2DD}$ are each independently selected from the group consisting of hydrogen and C$_{1-4}$alkyl; and R$^3$ is selected from the group consisting of

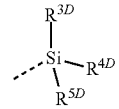

and

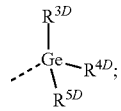

wherein
R$^{3D}$, R$^{4D}$, and R$^{5D}$ are each independently selected from the group consisting of C$_{1-6}$alkyl optionally substituted with a —OH, —OC$_{1-6}$alkyl, or a —NH$_2$ substituent;

or (e) -L-R$^3$ is

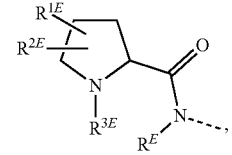

wherein
R$^E$ is selected from the group consisting of hydrogen and C$_{1-4}$alkyl;

R$^{1E}$ is selected from the group consisting of hydrogen, fluoro and C$_{1-4}$alkyl; and R$^{2E}$ is selected from the group consisting of fluoro, —OC$_{1-4}$alkyl, and C$_{1-4}$alkyl optionally substituted with 1, 2 or 3 fluoro substituents; or R$^{1E}$ and R$^{2E}$ are bound to the same carbon atom and together form a C$_{3-5}$cycloalkyl or a C-linked 4- to 6-membered heterocyclyl containing an oxygen atom; and R³ᴱ is selected from the group consisting of hydrogen; C₁₋₄alkyl optionally substituted with a fluoro or a —CN substituent; and C₂₋₄alkyl substituted with a substituent selected from the group consisting of —OR⁴ᴱ and —NR⁵ᴱR⁵ᴱᴱ; wherein R⁴ᴱ, R⁵ᴱ and R⁵ᴱᴱ are each independently selected from the group consisting of hydrogen; C₁₋₄alkyl optionally substituted with a substituent selected from the group consisting of fluoro, —CN, and —C(=O)NR⁶ᴱR⁶ᴱᴱ; C₂₋₄alkyl substituted with a substituent selected from the group consisting of —OR⁷ᴱ and —NR⁸ᴱR⁸ᴱᴱ; and C-linked 4- to 7-membered non-aromatic heterocyclyl containing at least one nitrogen, oxygen or sulfur atom; wherein R⁶ᴱ, R⁶ᴱᴱ, R⁷ᴱ, R⁸ᴱ and R⁸ᴱᴱ are each independently selected from the group consisting of hydrogen and C₁₋₄alkyl;

or (f) -L-R³ is a radical

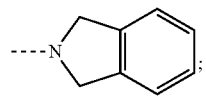

Ar is phenyl optionally substituted with one, two, or three substituents each independently selected from the group consisting of halo, —CN, —OR⁴, —NR⁵R⁵', —C(=O)NR⁵R⁵', Het⁴, —O-Het⁴, —NR⁵—Het⁴, —C(=O)—Het⁴, —S(=O)₂—Het⁴, —S(=O)₂—NR⁵R⁵', —S(=O)₂—C₁₋₄alkyl, R¹⁴, CF₃, C₃₋₅cycloalkyl optionally substituted with —CN, and C₁₋₄alkyl optionally substituted with one or two substituents each independently selected from the group consisting of fluoro, Het⁴, —CN, —OR⁶, —NR⁷R⁷', —S(=O)₂—C₁₋₄alkyl and —C(=O)NR⁸R⁸';

Het¹ is a monocyclic heteroaryl selected from the group consisting of pyridyl, 2-, 4-, 5- or 6-pyrimidinyl, pyrazinyl, pyridazinyl, furanyl, thienyl, pyrrolyl, pyrazolyl, imidazolyl, 4- or 5-thiazolyl, isothiazolyl, and isoxazolyl; each of which may be optionally substituted with one, two, or three substituents each independently selected from the group consisting of halo, —CN, —OR⁴, —NR⁵R⁵', —C(=O)NR⁵R⁵', —C(=O)—Het⁴, and C₁₋₄alkyl optionally substituted with a substituent selected from the group consisting of fluoro, —CN, —OR⁶, Het², —NR⁷R⁷', and —C(=O)NR⁸R⁸'; and Het² is a non-aromatic heterocyclyl optionally substituted with one, two, or three substituents each independently selected from the group consisting of halo, —CN, —C(=O)—C₁₋₆alkyl, —C(=O)Ar, —C(=O)Het¹, —C(=O)Het², —OR⁴, —NR⁵R⁵', and C₁₋₄alkyl optionally substituted with a substituent selected from the group consisting of fluoro, —CN, —OR⁶, —NR⁷R⁷', R¹² and —C(=O)NR⁸R⁸';

wherein

R¹² is C-linked 4- to 7-membered non-aromatic heterocyclyl containing at least one nitrogen, oxygen or sulfur atom;

R⁴, R⁵, R⁵', R⁶, R⁷, R⁷', R⁸ and R⁸' are each independently selected from the group consisting of hydrogen; —C(=O)—C₁₋₄alkyl; —S(=O)₂—C₁₋₄alkyl; C₁₋₄alkyl optionally substituted with a substituent selected from the group consisting of fluoro, —C(=O)—C₁₋₄alkyl, —S(=O)₂—C₁₋₄alkyl, R¹¹'', R¹⁶ and —C(=O)NR⁹R⁹'; and C₂₋₄alkyl substituted with a substituent selected from the group consisting of —OR¹⁰ and —NR¹¹R¹¹'; wherein R⁹, R⁹', R¹⁰, R¹¹, R¹¹' and R¹¹'' are each independently selected from the group consisting of hydrogen; C₁₋₄alkyl; —S(=O)₂—C₁₋₄alkyl; and C-linked 4- to 7-membered non-aromatic heterocyclyl containing at least one nitrogen, oxygen or sulfur atom, wherein said heterocyclyl is optionally substituted with one, two, or three substituents each independently selected from the group consisting of —S(=O)₂—C₁₋₄alkyl, halo, cyano, and C₁₋₄alkyl optionally substituted with —O—C₁₋₄alkyl;

R¹⁶ is N-linked 4- to 7-membered non-aromatic heterocyclyl containing at least one N-atom and optionally one additional heteroatom selected from nitrogen, oxygen and sulfur, wherein said heterocyclyl is optionally substituted with one, two, or three substituents each independently selected from the group consisting of —S(=O)₂—C₁₋₄alkyl, halo, cyano, and C₁₋₄alkyl optionally substituted with —O—C₁₋₄alkyl;

R¹⁴ is a 5-membered monocyclic heteroaryl containing at least one nitrogen atom, and optionally 1, 2 or 3 additional heteroatoms each independently selected from nitrogen, oxygen and sulfur;

Het³ is selected from the group consisting of formula (b-1) and (b-2):

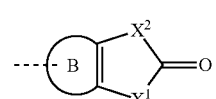 (b-1)

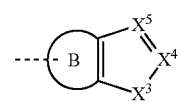 (b-2)

Ring B is phenyl;
X¹ represents CH₂, O or NH;
X² represents NH or O;
X³ represents NH or O;
X⁴ represents CH or N;
X⁵ represents CH or N;
wherein one C-atom or one N-atom in the 5-membered ring of (b-1) or (b-2), including suitable C-atoms and N-atoms in the definition of X¹, X², X³, X⁴ and X⁵, might be substituted with one or where possible two C₁₋₄alkyl groups optionally substituted with one, two or three substituents each independently selected from the group consisting of halo, cyano, —C(=O)NR⁵R⁵', and Het⁴;

Het⁴ is a 4- to 7-membered non-aromatic heterocyclyl containing at least one nitrogen, oxygen or sulfur atom, wherein said heterocyclyl is optionally substituted with one, two, or three substituents each independently selected from the group consisting of halo, —CN, oxo, —C(=O)NR⁵R⁵', —O—C₁₋₄alkyl, —S(=O)₂—C₁₋₄alkyl, and C₁₋₄alkyl optionally substituted with —O—C₁₋₄alkyl;

R¹⁷ is C₃₋₆cycloalkyl optionally substituted with one or more substituents selected from the group consisting of halo, —CN, —OR⁴, —NR⁵R⁵', —C(=O)NR⁵R⁵', and C₁₋₄alkyl optionally substituted with a substituent selected from the group consisting of fluoro, —CN, —OR⁶, —NR⁷R⁷', and —C(=O)NR⁸R⁸';

n1, n2, and m1 are each independently selected from 1 and 2;

m2 is 0 or 1;

and the pharmaceutically acceptable salts and the solvates thereof.

The present invention relates in particular to compounds of Formula (I) as defined herein, and the tautomers and the stereoisomeric forms thereof, wherein $R^1$ is $CF_3$;
$Y^1$ is N;
when $Y^1$ represents N, $R^2$ is selected from the group consisting of hydrogen, $CH_3$—$OCH_3$, —$NH_2$, and —NH—$CH_3$;
$Y^2$ is $CH_2$;
A is a covalent bond or —$CR^{15a}R^{15b}$—;
$R^{15a}$ and $R^{15b}$ are hydrogen;
Q is hydrogen;
-L-$R^3$ is selected from (a), (b), (c), (d), (e), or (f):
(a) -L-$R^3$ is —$NR^AR^{14}$, wherein
$R^A$ is selected from the group consisting of hydrogen and $C_{1-4}$alkyl;
$R^{14}$ is $C_{1-6}$alkyl;
or
(b) L is selected from the group consisting of —$N(R^B)$—, and —$N(R^B)$—$CR^{1B}R^{1BB}$; and $R^3$ is selected from the group consisting of Ar; $Het^1$; $Het^2$; $Het^3$; and $R^{17}$; in particular $R^3$ is selected from the group consisting of Ar; $Het^1$; $Het^3$; and $R^{17}$; wherein
$R^B$ is selected from the group consisting of hydrogen and $C_{1-4}$alkyl;
$R^{1B}$ is selected from the group consisting of hydrogen and $C_{1-4}$alkyl; and
$R^{1BB}$ is selected from the group consisting of hydrogen and methyl; or $R^{1B}$ and $R^{1BB}$ together with the carbon to which they are attached form a $C_{3-6}$cycloalkyl;
or
(c) -L-$R^3$ is selected from the group consisting of —$N(R^C)$—$COR^{5C}$; and —$N(R^C)$—$SO_2$—$R^{13C}$ wherein
$R^C$ is selected from the group consisting of hydrogen and $C_{1-4}$alkyl;
$R^{5C}$ and $R^{13C}$ are each independently selected from the group consisting of Ar; and $C_{1-4}$alkyl optionally substituted with $Het^2$;
Ar is phenyl optionally substituted with one, two, or three substituents each independently selected from the group consisting of halo, —CN, —$OR^4$, —$NR^5R^{5'}$, —C(=O)$NR^5R^{5'}$, $Het^4$, —O-$Het^4$, —C(=O)—$Het^4$, —S(=O)$_2$-$Het^4$, —S(=O)$_2$—$NR^5R^{5'}$, —S(=O)$_2$—$C_{1-4}$alkyl, $R^{14}$, $CF_3$, $C_{3-5}$cycloalkyl optionally substituted with —CN, and $C_{1-4}$alkyl optionally substituted with one or two substituents each independently selected from the group consisting of $Het^4$, —CN, —$OR^6$, —$NR^7R^{7'}$, —S(=O)$_2$—$C_{1-4}$alkyl and —C(=O)$NR^8R^{8'}$;
$Het^1$ is a monocyclic heteroaryl selected from the group consisting of pyridyl, 2-, 4-, 5- or 6-pyrimidinyl, pyrazinyl, pyridazinyl, pyrazolyl, and imidazolyl; each of which may be optionally substituted with one, two, or three substituents each independently selected from the group consisting of —CN, —$OR^4$, —C(=O)$NR^5R^{5'}$, —C(=O)—$Het^4$, and $C_{1-4}$alkyl optionally substituted with —C(=O)$NR^8R^{8'}$; and
$Het^2$ is a non-aromatic heterocyclyl;
wherein
$R^4$, $R^5$, $R^{5'}$, $R^6$, $R^7$, $R^{7'}$, $R^8$ and $R^{8'}$ are each independently selected from the group consisting of hydrogen; —C(=O)—$C_{1-4}$alkyl; —S(=O)$_2$—$C_{1-4}$alkyl; $C_{1-4}$alkyl optionally substituted with a substituent selected from the group consisting of —CN, $R^{11''}$, and $R^{16}$;
$C_{1-4}$alkyl substituted with three fluoro atoms; and $C_{2-4}$alkyl substituted with a substituent selected from the group consisting of —$OR^{10}$ and —$NR^{11}R^{11'}$; wherein $R^{10}$, $R^{11}$, $R^{11'}$ and $R^{11''}$ are each independently selected from the group consisting of hydrogen; $C_{1-4}$alkyl; —S(=O)$_2$—$C_{1-4}$alkyl; and C-linked 4- to 7-membered non-aromatic heterocyclyl containing at least one nitrogen, oxygen or sulfur atom, wherein said heterocyclyl is optionally substituted with one, two, or three substituents each independently selected from the group consisting of —S(=O)$_2$—$C_{1-4}$alkyl and $C_{1-4}$alkyl;
$R^{16}$ is N-linked 4- to 7-membered non-aromatic heterocyclyl containing at least one N-atom and optionally one additional heteroatom selected from nitrogen, oxygen and sulfur, wherein said heterocyclyl is optionally substituted with one, two, or three substituents each independently selected from the group consisting of —S(=O)$_2$—$C_{1-4}$alkyl;
$R^{14}$ is a 5-membered monocyclic heteroaryl containing at least one nitrogen atom, and optionally 1, 2 or 3 additional heteroatoms each independently selected from nitrogen, oxygen and sulfur;
$Het^3$ is selected from the group consisting of formula (b-1) and (b-2):

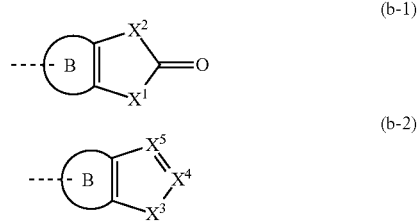

Ring B is phenyl;
$X^1$ represents $CH_2$, O or NH;
$X^2$ represents NH or O;
$X^3$ represents NH or O;
$X^4$ represents CH or N;
$X^5$ represents CH or N;
wherein one C-atom or one N-atom in the 5-membered ring of (b-1) or (b-2), including suitable C-atoms and N-atoms in the definition of $X^1$, $X^2$, $X^3$, $X^4$ and $X^5$, might be substituted with one or where possible two $C_{1-4}$alkyl groups optionally substituted with one, two or three substituents each independently selected from the group consisting of halo, cyano, —C(=O)$NR^5R^{5'}$, and $Het^4$;
$Het^4$ is a 4- to 7-membered non-aromatic heterocyclyl containing at least one nitrogen, oxygen or sulfur atom, wherein said heterocyclyl is optionally substituted with one, two, or three substituents each independently selected from the group consisting of —CN, oxo, —C(=O)$NR^5R^{5'}$, —O—$C_{1-4}$alkyl, —S(=O)$_2$—$C_{1-4}$alkyl, and $C_{1-4}$alkyl optionally substituted with —O—$C_{1-4}$alkyl;
$R^{17}$ is $C_{3-6}$cycloalkyl optionally substituted with one or more substituents selected from the group consisting of —$NR^5R^{5'}$;
n1, n2, and m1 are each independently selected from 1 and 2;
m2 is 0 or 1;
and the pharmaceutically acceptable salts and the solvates thereof.

The present invention relates in particular to compounds of Formula (I) as defined herein, and the tautomers and the stereoisomeric forms thereof wherein $R^1$ is selected from the group consisting of $CH_3$, $CH_2F$, $CHF_2$ and $CF_3$;

$Y^1$ is N or $CR^y$;

when $Y^1$ represents N, $R^2$ is selected from the group consisting of hydrogen, $CH_3$—$OCH_3$, —$NH_2$, and —NH—$CH_3$;

when $Y^1$ represents $CR^y$, $R^2$ is hydrogen;

$R^y$ is selected from the group consisting of hydrogen, cyano, and $C_{1-4}$alkyl optionally substituted with hydroxy, —O—$C_{1-4}$alkyl, or —O—$C_{3-6}$cycloalkyl;

$Y^2$ is $CH_2$ or O;

A is a covalent bond;

Q is hydrogen or $C_{1-4}$alkyl optionally substituted with phenyl;

-L-$R^3$ is selected from (a), (b), (c), (d), (e), or (f):

(a) -L-$R^3$ is —$NR^4R^{14}$, wherein $R^4$ is selected from the group consisting of hydrogen; cyclopropyl; $C_{1-4}$alkyl optionally substituted with a substituent selected from the group consisting of fluoro and —CN; and $C_{2-4}$alkyl substituted with a substituent selected from the group consisting of —$OR^{3a}$ and —$NR^{4a}R^{4aa}$;

$R^{14}$ is selected from the group consisting of $C_{1-6}$alkyl optionally substituted with one, two or three fluoro substituents; and $C_{2-6}$alkyl substituted with a substituent selected from the group consisting of —$OR^{1a}$ and —$NR^{2a}R^{2aa}$, wherein $R^{1a}$, $R^{2a}$, $R^{2aa}$, $R^{3a}$, $R^{4a}$, and $R^{4aa}$ are each independently selected from the group consisting of hydrogen, $C_{1-4}$alkyl and cyclopropyl;

or (b) L is selected from the group consisting of —$N(R^B)$—, —$N(R^B)$—$CR^{1B}R^{1BB}$—, and —$(NR^B)$—$CHR^{1B}$—$CHR^{2B}$—; and $R^3$ is selected from the group consisting of Ar; $Het^1$; $Het^2$; $Het^3$; $R^{17}$; and a 7- to 10-membered saturated spirocarbobicyclic system; wherein $R^B$ is selected from the group consisting of hydrogen; cyclopropyl; $C_{1-4}$alkyl optionally substituted with a substituent selected from the group consisting of fluoro and —CN; and $C_{2-4}$alkyl substituted with a substituent selected from the group consisting of —$OR^{1b}$ and —$NR^{2b}R^{2bb}$; provided that when $R^3$ is $R^{17}$, $R^B$ is hydrogen;

wherein $R^{1b}$, $R^{2b}$, and $R^{2bb}$ are each independently selected from the group consisting of hydrogen, $C_{1-4}$alkyl and cyclopropyl;

$R^{1B}$ is selected from the group consisting of hydrogen; halo; $C_{3-6}$cycloalkyl; $C_{1-4}$alkyl optionally substituted with a substituent selected from the group consisting of fluoro, hydroxy, and —CN; $C_{2-4}$alkyl substituted with a substituent selected from the group consisting of —$OR^{4B}$ and —$NR^{5B}R^{5BB}$; and C-linked 4- to 7-membered non-aromatic heterocyclyl containing at least one nitrogen, oxygen or sulfur atom; and $R^{1BB}$ is selected from the group consisting of hydrogen and methyl; or $R^{1B}$ and $R^{1BB}$ together with the carbon to which they are attached form a $C_{3-6}$cycloalkyl or a C-linked 4- to 7-membered non-aromatic heterocyclyl containing at least one nitrogen, oxygen or sulfur atom;

$R^{2B}$ is selected from the group consisting of hydrogen; —$OR^{6B}$; —$NR^{7B}R^{7BB}$; $CF_3$, $C_{1-4}$alkyl optionally substituted with a substituent selected from the group consisting of fluoro, —CN, —$OR^{4B}$, and —$NR^{5B}R^{5BB}$; and C-linked 4- to 7-membered non-aromatic heterocyclyl containing at least one nitrogen, oxygen or sulfur atom; wherein $R^{4B}$, $R^{5B}$, $R^{5BB}$, $R^{6B}$, $R^{7B}$, and $R^{7BB}$ are each independently selected from the group consisting of hydrogen; $C_{1-4}$alkyl optionally substituted with a substituent selected from the group consisting of fluoro, —CN and —C(=O)$NR^{9B}R^{9BB}$; and $C_{2-4}$alkyl substituted with a substituent selected from the group consisting of —$OR^{10B}$ and —$NR^{11B}R^{11BB}$; wherein $R^{9B}$, $R^{9BB}$, $R^{10B}$, $R^{11B}$ and $R^{11BB}$ are each independently selected from the group consisting of hydrogen; $C_{1-4}$alkyl; and C-linked 4- to 7-membered non-aromatic heterocyclyl containing at least one nitrogen, oxygen or sulfur atom;

or (c) -L-$R^3$ is selected from the group consisting of —$N(R^C)$—$COR^{5C}$; and —$N(R^C)$—$SO_2$—$R^{13C}$ wherein $R^C$ is selected from the group consisting of hydrogen; cyclopropyl; $C_{1-4}$alkyl optionally substituted with a substituent selected from the group consisting of fluoro and —CN; and $C_{2-4}$alkyl substituted with a substituent selected from the group consisting of —$OR^{1c}$ and —$NR^{2c}R^{2cc}$;

$R^{5C}$ and $R^{13C}$ are each independently selected from the group consisting of hydrogen; Ar; $Het^1$; $Het^2$; $Het^3$; $R^{17}$; a 7- to 10-membered saturated spirocarbobicyclic system; and $C_{1-4}$alkyl optionally substituted with —$NR^{2c}R^{2cc}$, Ar, $Het^1$ or $Het^2$; wherein $R^{1c}$, $R^{2c}$, and $R^{2cc}$ are each independently selected from the group consisting of hydrogen and $C_{1-4}$alkyl;

or (d) L is selected from —$N(R^D)$—$CR^{1D}R^{1DD}$— and —$N(R^D)$—$CR^{1D}R^{1DD}$—$CR^{2D}R^{2DD}$—; wherein $R^D$ is selected from the group consisting of hydrogen; $C_{1-4}$alkyl optionally substituted with a substituent selected from the group consisting of fluoro and —CN; and $C_{2-4}$alkyl substituted with a substituent selected from —$OR^{1d}$ and —$NR^{2d}R^{2dd}$; wherein $R^{1d}$, $R^{2d}$ and $R^{2dd}$ are each independently selected from the group consisting of hydrogen and $C_{1-4}$alkyl;

$R^{1D}$, $R^{1DD}$, $R^{2D}$ and $R^{2DD}$ are each independently selected from the group consisting of hydrogen and $C_{1-4}$alkyl; and $R^3$ is selected from the group consisting of

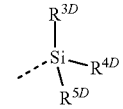

and

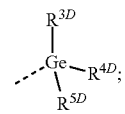

wherein $R^{3D}$, $R^{4D}$, and $R^{5D}$ are each independently selected from the group consisting of $C_{1-6}$alkyl optionally substituted with a —OH, —$OC_{1-6}$alkyl, or a —$NH_2$ substituent;

or
(e) -L-R³ is

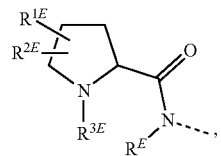

wherein
R^E is selected from the group consisting of hydrogen and C_{1-4}alkyl;
R^{1E} is selected from the group consisting of hydrogen, fluoro and C_{1-4}alkyl; and
R^{2E} is selected from the group consisting of fluoro, —OC_{1-4}alkyl, and C_{1-4}alkyl optionally substituted with 1, 2 or 3 fluoro substituents; or R^{1E} and R^{2E} are bound to the same carbon atom and together form a C_{3-5}cycloalkyl or a C-linked 4- to 6-membered heterocyclyl containing an oxygen atom; and
R^{3E} is selected from the group consisting of hydrogen; C_{1-4}alkyl optionally substituted with a fluoro or a —CN substituent; and C_{2-4}alkyl substituted with a substituent selected from the group consisting of —OR^{4E} and —NR^{5E}R^{5EE}; wherein
R^{4E}, R^{5E} and R^{5EE} are each independently selected from the group consisting of hydrogen; C_{1-4}alkyl optionally substituted with a substituent selected from the group consisting of fluoro, —CN, and —C(=O)NR^{6E}R^{6EE}; C_{2-4}alkyl substituted with a substituent selected from the group consisting of —OR^{7E} and —NR^{8E}R^{8EE}; and C-linked 4- to 7-membered non-aromatic heterocyclyl containing at least one nitrogen, oxygen or sulfur atom; wherein R^{6E}, R^{6EE}, R^{7E}, R^{8E} and R^{8EE} are each independently selected from the group consisting of hydrogen and C_{1-4}alkyl;
or
(f) -L-R³ is a radical

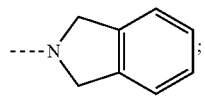

Ar is phenyl optionally substituted with one, two, or three substituents each independently selected from the group consisting of halo, —CN, —OR⁴, —NR⁵R⁵', —C(=O)NR⁵R⁵', Het⁴, —O-Het⁴, —NR⁵—Het⁴, —C(=O)—Het⁴, —S(=O)_2—Het⁴, —S(=O)_2—NR⁵R⁵', —S(=O)_2—C_{1-4}alkyl, R^{14}, CF_3, C_{3-5}cycloalkyl optionally substituted with —CN, and C_{1-4}alkyl optionally substituted with one or two substituents each independently selected from the group consisting of fluoro, Het⁴, —CN, —OR⁶, —NR⁷R⁷', —S(=O)_2—C_{1-4}alkyl and —C(=O)NR⁸R⁸';
Het¹ is a monocyclic heteroaryl selected from the group consisting of pyridyl, 2-, 4-, 5- or 6-pyrimidinyl, pyrazinyl, pyridazinyl, furanyl, thienyl, pyrrolyl, pyrazolyl, imidazolyl, 4- or 5-thiazolyl, isothiazolyl, and isoxazolyl; each of which may be optionally substituted with one, two, or three substituents each independently selected from the group consisting of halo, —CN, —OR⁴, —NR⁵R⁵', —C(=O)NR⁵R⁵', —C(=O)—Het⁴, and C_{1-4}alkyl optionally substituted with a substituent selected from the group consisting of fluoro, —CN, —OR⁶, Het², —NR⁷R⁷', and —C(=O)NR⁸R⁸'; and
Het² is a non-aromatic heterocyclyl optionally substituted with one, two, or three substituents each independently selected from the group consisting of halo, —CN, —C(=O)—C_{1-6}alkyl, —C(=O)Ar, —C(=O)Het¹, —C(=O)Het², —OR⁴, —NR⁵R⁵', and C_{1-4}alkyl optionally substituted with a substituent selected from the group consisting of fluoro, —CN, —OR⁶, —NR⁷R⁷', R^{12} and —C(=O)NR⁸R⁸';
wherein
R^{12} is C-linked 4- to 7-membered non-aromatic heterocyclyl containing at least one nitrogen, oxygen or sulfur atom;
R⁴, R⁵, R⁵', R⁶, R⁷, R⁷', R⁸ and R⁸' are each independently selected from the group consisting of hydrogen; —C(=O)—C_{1-4}alkyl; —S(=O)_2—C_{1-4}alkyl; C_{1-4}alkyl optionally substituted with a substituent selected from the group consisting of fluoro, —C(=O)—C_{1-4}alkyl, —S(=O)_2—C_{1-4}alkyl, R^{11''}, R^{16} and —C(=O)NR⁹R⁹'; and C_{2-4}alkyl substituted with a substituent selected from the group consisting of —OR^{10} and —NR^{11}R^{11'}; wherein
R⁹, R⁹', R^{10}, R^{11}, R^{11'} and R^{11''} are each independently selected from the group consisting of hydrogen; C_{1-4}alkyl; —S(=O)_2—C_{1-4}alkyl; and C-linked 4- to 7-membered non-aromatic heterocyclyl containing at least one nitrogen, oxygen or sulfur atom, wherein said heterocyclyl is optionally substituted with one, two, or three substituents each independently selected from the group consisting of —S(=O)_2—C_{1-4}alkyl, halo, cyano, and C_{1-4}alkyl optionally substituted with —O—C_{1-4}alkyl;
R^{16} is N-linked 4- to 7-membered non-aromatic heterocyclyl containing at least one N-atom and optionally one additional heteroatom selected from nitrogen, oxygen and sulfur, wherein said heterocyclyl is optionally substituted with one, two, or three substituents each independently selected from the group consisting of —S(=O)_2—C_{1-4}alkyl, halo, cyano, and C_{1-4}alkyl optionally substituted with —O—C_{1-4}alkyl;
R^{14} is a 5-membered monocyclic heteroaryl containing at least one nitrogen atom, and optionally 1, 2 or 3 additional heteroatoms each independently selected from nitrogen, oxygen and sulfur;
Het³ is selected from the group consisting of formula (b-1) and (b-2):

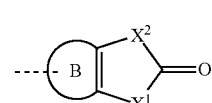

(b-1)

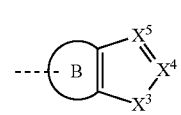

(b-2)

Ring B is phenyl;
X¹ represents CH_2, O or NH;
X² represents NH or O;
X³ represents NH or O;
X⁴ represents CH or N;
X⁵ represents CH or N;

wherein one C-atom or one N-atom in the 5-membered ring of (b-1) or (b-2), including suitable C-atoms and N-atoms in the definition of $X^1$, $X^2$, $X^3$, $X^4$ and $X^5$, might be substituted with one or where possible two $C_{1-4}$alkyl groups optionally substituted with one, two or three substituents each independently selected from the group consisting of halo, cyano, —C(=O)NR$^5$R$^{5'}$, and Het$^4$;

Het$^4$ is a 4- to 7-membered non-aromatic heterocyclyl containing at least one nitrogen, oxygen or sulfur atom, wherein said heterocyclyl is optionally substituted with one, two, or three substituents each independently selected from the group consisting of halo, —CN, oxo, —C(=O)NR$^5$R$^{5'}$, —O—$C_{1-4}$alkyl, —S(=O)$_2$—$C_{1-4}$alkyl, and $C_{1-4}$alkyl optionally substituted with —O—$C_{1-4}$alkyl;

$R^{17}$ is $C_{3-6}$cycloalkyl optionally substituted with one or more substituents selected from the group consisting of halo, —CN, —OR$^4$, —NR$^5$R$^{5'}$, —C(=O)NR$^5$R$^{5'}$, and $C_{1-4}$alkyl optionally substituted with a substituent selected from the group consisting of fluoro, —CN, —OR$^6$, —NR$^7$R$^{7'}$, and —C(=O)NR$^8$R$^{8'}$;

n1, n2, and m1 are each independently selected from 1 and 2;

m2 is 0 or 1;

and the pharmaceutically acceptable salts and the solvates thereof.

The present invention relates in particular to compounds of Formula (I) as defined herein, and the tautomers and the stereoisomeric forms thereof, wherein $R^1$ is selected from the group consisting of $CH_3$, $CH_2F$, $CHF_2$ and $CF_3$;

$Y^1$ is N or $CR^y$;

when $Y^1$ represents N, $R^2$ is selected from the group consisting of hydrogen, $CH_3$—OCH$_3$, —NH$_2$, and —NH—CH$_3$;

when $Y^1$ represents $CR^y$, $R^2$ is hydrogen;

$R^y$ is selected from the group consisting of hydrogen, cyano, and $C_{1-4}$alkyl optionally substituted with hydroxy, —O—$C_{1-4}$alkyl, or —O—$C_{3-6}$cycloalkyl;

$Y^2$ is $CH_2$ or O;

A is —$CR^{15a}R^{15b}$—;

$R^{15a}$ and $R^{15b}$ are each independently selected from the group consisting of hydrogen or $C_{1-4}$alkyl;

Q is hydrogen or $C_{1-4}$alkyl optionally substituted with phenyl;

-L-$R^3$ is selected from (a), (b), (c), (d), (e), or (f):

(a) -L-$R^3$ is —NR$^4$R$^{14}$, wherein $R^4$ is selected from the group consisting of hydrogen; cyclopropyl; $C_{1-4}$alkyl optionally substituted with a substituent selected from the group consisting of fluoro and —CN; and $C_{2-4}$alkyl substituted with a substituent selected from the group consisting of —OR$^{3a}$ and —NR$^{4a}$R$^{4aa}$;

$R^{14}$ is selected from the group consisting of $C_{1-6}$alkyl optionally substituted with one, two or three fluoro substituents; and $C_{2-6}$alkyl substituted with a substituent selected from the group consisting of —OR$^{1a}$ and —NR$^{2a}$R$^{2aa}$, wherein $R^{1a}$, $R^{2a}$, $R^{2aa}$, $R^{3a}$, $R^{4a}$, and $R^{4aa}$ are each independently selected from the group consisting of hydrogen, $C_{1-4}$alkyl and cyclopropyl;

or (b) L is selected from the group consisting of —N(R$^B$)—, —N(R$^B$)—CR$^{1B}$R$^{1BB}$—, and —(NR$^B$)—CHR$^{1B}$—CHR$^{2B}$—; and $R^3$ is selected from the group consisting of Ar; Het$^1$; Het$^2$; Het$^3$; $R^{17}$; and a 7- to 10-membered saturated spirocarbobicyclic system; wherein $R^B$ is selected from the group consisting of hydrogen; cyclopropyl; $C_{1-4}$alkyl optionally substituted with a substituent selected from the group consisting of fluoro and —CN; and $C_{2-4}$alkyl substituted with a substituent selected from the group consisting of —OR$^{1b}$ and —NR$^{2b}$R$^{2bb}$; provided that when $R^3$ is $R^{17}$, $R^B$ is hydrogen;

wherein $R^{1b}$, $R^{2b}$, and $R^{2bb}$ are each independently selected from the group consisting of hydrogen, $C_{1-4}$alkyl and cyclopropyl;

$R^{1B}$ is selected from the group consisting of hydrogen; halo; $C_{3-6}$cycloalkyl; $C_{1-4}$alkyl optionally substituted with a substituent selected from the group consisting of fluoro, hydroxy, and —CN; $C_{2-4}$alkyl substituted with a substituent selected from the group consisting of —OR$^{4B}$ and —NR$^{5B}$R$^{5BB}$; and C-linked 4- to 7-membered non-aromatic heterocyclyl containing at least one nitrogen, oxygen or sulfur atom; and $R^{1BB}$ is selected from the group consisting of hydrogen and methyl; or $R^{1B}$ and $R^{1BB}$ together with the carbon to which they are attached form a $C_{3-6}$cycloalkyl or a C-linked 4- to 7-membered non-aromatic heterocyclyl containing at least one nitrogen, oxygen or sulfur atom;

$R^{2B}$ is selected from the group consisting of hydrogen; —OR$^{6B}$; —NR$^{7B}$R$^{7BB}$; $CF_3$, $C_{1-4}$alkyl optionally substituted with a substituent selected from the group consisting of fluoro, —CN, —OR$^{4B}$, and —NR$^{5B}$R$^{5BB}$; and C-linked 4- to 7-membered non-aromatic heterocyclyl containing at least one nitrogen, oxygen or sulfur atom; wherein $R^{4B}$, $R^{5B}$, $R^{5BB}$, $R^{6B}$, $R^{7B}$, and $R^{7BB}$ are each independently selected from the group consisting of hydrogen; $C_{1-4}$alkyl optionally substituted with a substituent selected from the group consisting of fluoro, —CN and —C(=O)NR$^{9B}$R$^{9BB}$; and $C_{2-4}$alkyl substituted with a substituent selected from the group consisting of —OR$^{10B}$ and —NR$^{11B}$R$^{11BB}$; wherein $R^{9B}$, $R^{9BB}$, $R^{10B}$, $R^{11B}$ and $R^{11BB}$ are each independently selected from the group consisting of hydrogen; $C_{1-4}$alkyl; and C-linked 4- to 7-membered non-aromatic heterocyclyl containing at least one nitrogen, oxygen or sulfur atom;

or (c) -L-$R^3$ is selected from the group consisting of —N(R$^C$)—COR$^{5C}$; and —N(R$^C$)—SO$_2$—R$^{13C}$ wherein $R^C$ is selected from the group consisting of hydrogen; cyclopropyl; $C_{1-4}$alkyl optionally substituted with a substituent selected from the group consisting of fluoro and —CN; and $C_{2-4}$alkyl substituted with a substituent selected from the group consisting of —OR$^{1c}$ and —NR$^{2c}$R$^{2cc}$;

$R^{5C}$ and $R^{13C}$ are each independently selected from the group consisting of hydrogen; Ar; Het$^1$; Het$^2$; Het$^3$; $R^{17}$; a 7- to 10-membered saturated spirocarbobicyclic system; and $C_{1-4}$alkyl optionally substituted with —NR$^{2c}$R$^{2cc}$, Ar, Het$^1$ or Het$^2$; wherein $R^{1c}$, $R^{2c}$, and $R^{2cc}$ are each independently selected from the group consisting of hydrogen and $C_{1-4}$alkyl;

or (d) L is selected from —N(R$^D$)—CR$^{1D}$R$^{1DD}$— and —N(R$^D$)—CR$^{1D}$R$^{1DD}$—CR$^{2D}$R$^{2DD}$—; wherein $R^D$ is selected from the group consisting of hydrogen; $C_{1-4}$alkyl optionally substituted with a substituent selected from the group consisting of fluoro and —CN; and $C_{2-4}$alkyl substituted with a substituent selected from —OR$^{1d}$ and —NR$^{2d}$R$^{2dd}$; wherein $R^{1d}$, $R^{2d}$ and $R^{2dd}$ are each independently selected from the group consisting of hydrogen and $C_{1-4}$alkyl;

$R^{1D}$, $R^{1DD}$, $R^{2D}$ and $R^{2DD}$ are each independently selected from the group consisting of hydrogen and $C_{1-4}$alkyl; and $R^3$ is selected from the group consisting of

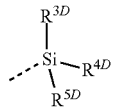

and

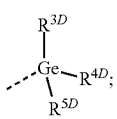

wherein $R^{3D}$, $R^{4D}$, and $R^{5D}$ are each independently selected from the group consisting of $C_{1-6}$alkyl optionally substituted with a —OH, —$OC_{1-6}$alkyl, or a —$NH_2$ substituent;

or (e) -L-$R^3$ is

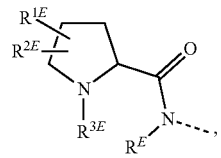

wherein $R^E$ is selected from the group consisting of hydrogen and $C_{1-4}$alkyl;

$R^{1E}$ is selected from the group consisting of hydrogen, fluoro and $C_{1-4}$alkyl; and $R^{2E}$ is selected from the group consisting of fluoro, —$OC_{1-4}$alkyl, and $C_{1-4}$alkyl optionally substituted with 1, 2 or 3 fluoro substituents; or $R^{1E}$ and $R^{2E}$ are bound to the same carbon atom and together form a $C_{3-5}$cycloalkyl or a C-linked 4- to 6-membered heterocyclyl containing an oxygen atom; and $R^{3E}$ is selected from the group consisting of hydrogen; $C_{1-4}$alkyl optionally substituted with a fluoro or a —CN substituent; and $C_{2-4}$alkyl substituted with a substituent selected from the group consisting of —$OR^{4E}$ and —$NR^{5E}R^{5EE}$; wherein $R^{4E}$, $R^{5E}$ and $R^{5EE}$ are each independently selected from the group consisting of hydrogen; $C_{1-4}$alkyl optionally substituted with a substituent selected from the group consisting of fluoro, —CN, and —C(=O)$NR^{6E}R^{6EE}$; $C_{2-4}$alkyl substituted with a substituent selected from the group consisting of —$OR^{7E}$ and —$NR^{8E}R^{8EE}$; and C-linked 4- to 7-membered non-aromatic heterocyclyl containing at least one nitrogen, oxygen or sulfur atom; wherein $R^{6E}$, $R^{6EE}$, $R^{7E}$, $R^{8E}$ and $R^{8EE}$ are each independently selected from the group consisting of hydrogen and $C_{1-4}$alkyl;

or (f) -L-$R^3$ is a radical

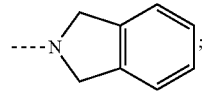;

Ar is phenyl optionally substituted with one, two, or three substituents each independently selected from the group consisting of halo, —CN, —$OR^4$, —$NR^5R^{5'}$, —C(=O)$NR^5R^{5'}$, $Het^4$, —O-$Het^4$, —$NR^5$—$Het^4$, —C(=O)—$Het^4$, —S(=O)$_2$—$Het^4$, —S(=O)$_2$—$NR^5R^{5'}$, —S(=O)$_2$—$C_{1-4}$alkyl, $R^{14}$, $CF_3$, $C_{3-5}$cycloalkyl optionally substituted with —CN, and $C_{1-4}$alkyl optionally substituted with one or two substituents each independently selected from the group consisting of fluoro, $Het^4$, —CN, —$OR^6$, —$NR^7R^{7'}$, —S(=O)$_2$—$C_{1-4}$alkyl and —C(=O)$NR^8R^{8'}$;

$Het^1$ is a monocyclic heteroaryl selected from the group consisting of pyridyl, 2-, 4-, 5- or 6-pyrimidinyl, pyrazinyl, pyridazinyl, furanyl, thienyl, pyrrolyl, pyrazolyl, imidazolyl, 4- or 5-thiazolyl, isothiazolyl, and isoxazolyl; each of which may be optionally substituted with one, two, or three substituents each independently selected from the group consisting of halo, —CN, —$OR^4$, —$NR^5R^{5'}$, —C(=O)$NR^5R^{5'}$, —C(=O)—$Het^4$, and $C_{1-4}$alkyl optionally substituted with a substituent selected from the group consisting of fluoro, —CN, —$OR^6$, $Het^2$, —$NR^7R^{7'}$, and —C(=O)$NR^8R^{8'}$; and $Het^2$ is a non-aromatic heterocyclyl optionally substituted with one, two, or three substituents each independently selected from the group consisting of halo, —CN, —C(=O)—$C_{1-6}$alkyl, —C(=O)Ar, —C(=O)$Het^1$, —C(=O)$Het^2$, —$OR^4$, —$NR^5R^{5'}$, and $C_{1-4}$alkyl optionally substituted with a substituent selected from the group consisting of fluoro, —CN, —$OR^6$, —$NR^7R^{7'}$, $R^{12}$ and —C(=O)$NR^8R^{8'}$;

wherein $R^{12}$ is C-linked 4- to 7-membered non-aromatic heterocyclyl containing at least one nitrogen, oxygen or sulfur atom;

$R^4$, $R^5$, $R^{5'}$, $R^6$, $R^7$, $R^{7'}$, $R^8$ and $R^{8'}$ are each independently selected from the group consisting of hydrogen; —C(=O)—$C_{1-4}$alkyl; —S(=O)$_2$—$C_{1-4}$alkyl; $C_{1-4}$alkyl optionally substituted with a substituent selected from the group consisting of fluoro, —C(=O)—$C_{1-4}$alkyl, —S(=O)$_2$—$C_{1-4}$alkyl, $R^{11'}$, $R^{16}$ and —C(=O)$NR^9R^{9'}$; and $C_{2-4}$alkyl substituted with a substituent selected from the group consisting of —$OR^{10}$ and —$NR^{11}R^{11'}$; wherein $R^9$, $R^{9'}$, $R^{10}$, $R^{11}$, $R^{11'}$ and $R^{11''}$ are each independently selected from the group consisting of hydrogen; $C_{1-4}$alkyl; —S(=O)$_2$—$C_{1-4}$alkyl; and C-linked 4- to 7-membered non-aromatic heterocyclyl containing at least one nitrogen, oxygen or sulfur atom, wherein said heterocyclyl is optionally substituted with one, two, or three substituents each independently selected from the group consisting of —S(=O)$_2$—$C_{1-4}$alkyl, halo, cyano, and $C_{1-4}$alkyl optionally substituted with —O—$C_{1-4}$alkyl;

$R^{16}$ is N-linked 4- to 7-membered non-aromatic heterocyclyl containing at least one N-atom and optionally one additional heteroatom selected from nitrogen, oxygen and sulfur, wherein said heterocyclyl is optionally substituted with one, two, or three substituents each independently selected from the group consisting of —S(=O)$_2$—$C_{1-4}$alkyl, halo, cyano, and $C_{1-4}$alkyl optionally substituted with —O—$C_{1-4}$alkyl;

R¹⁴ is a 5-membered monocyclic heteroaryl containing at least one nitrogen atom, and optionally 1, 2 or 3 additional heteroatoms each independently selected from nitrogen, oxygen and sulfur;

Het³ is selected from the group consisting of formula (b-1) and (b-2):

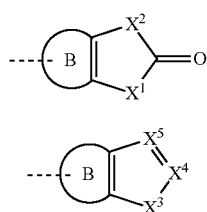

Ring B is phenyl;
X¹ represents CH₂, O or NH;
X² represents NH or O;
X³ represents NH or O;
X⁴ represents CH or N;
X⁵ represents CH or N;
wherein one C-atom or one N-atom in the 5-membered ring of (b-1) or (b-2), including suitable C-atoms and N-atoms in the definition of X¹, X², X³, X⁴ and X⁵, might be substituted with one or where possible two $C_{1-4}$alkyl groups optionally substituted with one, two or three substituents each independently selected from the group consisting of halo, cyano, —C(=O)NR⁵R⁵', and Het⁴;

Het⁴ is a 4- to 7-membered non-aromatic heterocyclyl containing at least one nitrogen, oxygen or sulfur atom, wherein said heterocyclyl is optionally substituted with one, two, or three substituents each independently selected from the group consisting of halo, —CN, oxo, —C(=O)NR⁵R⁵', —O—$C_{1-4}$alkyl, —S(=O)₂—$C_{1-4}$alkyl, and $C_{1-4}$alkyl optionally substituted with —O—$C_{1-4}$alkyl;

R¹⁷ is $C_{3-6}$cycloalkyl optionally substituted with one or more substituents selected from the group consisting of halo, —CN, —OR⁴, —NR⁵R⁵', —C(=O)NR⁵R⁵', and $C_{1-4}$alkyl optionally substituted with a substituent selected from the group consisting of fluoro, —CN, —OR⁶, —NR⁷R⁷', and —C(=O)NR⁸R⁸';

n1, n2, and m1 are each independently selected from 1 and 2;

m2 is 0 or 1; and the pharmaceutically acceptable salts and the solvates thereof.

The present invention relates in particular to compounds of Formula (I) as defined herein, and the tautomers and the stereoisomeric forms thereof, wherein R¹ is selected from the group consisting of CH₃, CH₂F, CHF₂ and CF₃;
Y¹ is N;
R² is selected from the group consisting of hydrogen, CH₃—OCH₃, —NH₂, and —NH—CH₃;
Y² is CH₂;
A is a covalent bond or —CR¹⁵ᵃR¹⁵ᵇ—;
R¹⁵ᵃ and R¹⁵ᵇ are each independently selected from the group consisting of hydrogen or $C_{1-4}$alkyl;
Q is hydrogen;
-L-R³ is selected from (a), (b), or (c):
(a) -L-R³ is —NR⁴R¹⁴, wherein
R⁴ is selected from the group consisting of hydrogen; cyclopropyl; $C_{1-4}$alkyl optionally substituted with a substituent selected from the group consisting of fluoro and —CN; and $C_{2-4}$alkyl substituted with a substituent selected from the group consisting of —OR³ᵃ and —NR⁴ᵃR⁴ᵃᵃ;

R¹⁴ is selected from the group consisting of $C_{1-6}$alkyl optionally substituted with one, two or three fluoro substituents; and $C_{2-6}$alkyl substituted with a substituent selected from the group consisting of —OR¹ᵃ and —NR²ᵃR²ᵃᵃ,
wherein R¹ᵃ, R²ᵃ, R²ᵃᵃ, R³ᵃ, R⁴ᵃ, and R⁴ᵃᵃ are each independently selected from the group consisting of hydrogen, $C_{1-4}$alkyl and cyclopropyl;
or
(b) L is selected from the group consisting of —N(Rᴮ)—, —N(Rᴮ)—CR¹ᴮR¹ᴮᴮ—, and —(NRᴮ)—CHR¹ᴮ—CHR²ᴮ—; and R³ is selected from the group consisting of Ar; Het¹; Het²; Het³; R¹⁷; and a 7- to 10-membered saturated spirocarbobicyclic system; wherein Rᴮ is selected from the group consisting of hydrogen; cyclopropyl; $C_{1-4}$alkyl optionally substituted with a substituent selected from the group consisting of fluoro and —CN; and $C_{2-4}$alkyl substituted with a substituent selected from the group consisting of —OR¹ᵇ and —NR²ᵇR²ᵇᵇ; provided that when R³ is R¹⁷, Rᴮ is hydrogen;
wherein
R¹ᵇ, R²ᵇ, and R²ᵇᵇ are each independently selected from the group consisting of hydrogen, $C_{1-4}$alkyl and cyclopropyl;

R¹ᴮ is selected from the group consisting of hydrogen; halo; $C_{3-6}$cycloalkyl; $C_{1-4}$alkyl optionally substituted with a substituent selected from the group consisting of fluoro, hydroxy, and —CN; $C_{2-4}$alkyl substituted with a substituent selected from the group consisting of —OR⁴ᴮ and —NR⁵ᴮR⁵ᴮᴮ; and C-linked 4- to 7-membered non-aromatic heterocyclyl containing at least one nitrogen, oxygen or sulfur atom; and R¹ᴮᴮ is selected from the group consisting of hydrogen and methyl; or R¹ᴮ and R¹ᴮᴮ together with the carbon to which they are attached form a $C_{3-6}$cycloalkyl or a C-linked 4- to 7-membered non-aromatic heterocyclyl containing at least one nitrogen, oxygen or sulfur atom;

R²ᴮ is selected from the group consisting of hydrogen; —OR⁶ᴮ; —NR⁷ᴮR⁷ᴮᴮ; CF₃, $C_{1-4}$alkyl optionally substituted with a substituent selected from the group consisting of fluoro, —CN, —OR⁴ᴮ, and —NR⁵ᴮR⁵ᴮᴮ; and C-linked 4- to 7-membered non-aromatic heterocyclyl containing at least one nitrogen, oxygen or sulfur atom; wherein R⁴ᴮ, R⁵ᴮ, R⁵ᴮᴮ, R⁶ᴮ, R⁷ᴮ, and R⁷ᴮᴮ are each independently selected from the group consisting of hydrogen; $C_{1-4}$alkyl optionally substituted with a substituent selected from the group consisting of fluoro, —CN and
—C(=O)NR⁹ᴮR⁹ᴮᴮ; and $C_{2-4}$alkyl substituted with a substituent selected from the group consisting of —OR¹⁰ᴮ and —NR¹¹ᴮR¹¹ᴮᴮ; wherein
R⁹ᴮ, R⁹ᴮᴮ, R¹⁰ᴮ, R¹¹ᴮ and R¹¹ᴮᴮ are each independently selected from the group consisting of hydrogen; $C_{1-4}$alkyl; and C-linked 4- to 7-membered non-aromatic heterocyclyl containing at least one nitrogen, oxygen or sulfur atom;
or
(c) -L-R³ is selected from the group consisting of —N(Rᶜ)—COR⁵ᶜ; and —N(Rᶜ)—SO₂—R¹³ᶜ wherein
Rᶜ is selected from the group consisting of hydrogen; cyclopropyl; $C_{1-4}$alkyl optionally substituted with a substituent selected from the group consisting of fluoro and —CN; and $C_{2-4}$alkyl substituted with a substituent selected from the group consisting of —OR¹ᶜ and —NR²ᶜR²ᶜᶜ;

$R^{5C}$ and $R^{13C}$ are each independently selected from the group consisting of hydrogen; Ar; Het$^1$; Het$^2$; Het$^3$; $R^{17}$; a 7- to 10-membered saturated spirocarbobicyclic system; and C$_{1-4}$alkyl optionally substituted with —NR$^{2c}$R$^{2cc}$, Ar, Het$^1$ or Het$^2$; wherein $R^{1c}$, $R^{2c}$, and $R^{2cc}$ are each independently selected from the group consisting of hydrogen and C$_{1-4}$alkyl;

Ar is phenyl optionally substituted with one, two, or three substituents each independently selected from the group consisting of halo, —CN, —OR$^4$, —NR$^5$R$^{5'}$, —C(=O)NR$^5$R$^{5'}$, Het$^4$, —O-Het$^4$, —NR$^5$—Het$^4$, —C(=O)—Het$^4$, —S(=O)$_2$—Het$^4$, —S(=O)$_2$—NR$^5$R$^{5'}$, —S(=O)$_2$—C$_{1-4}$alkyl, $R^{14}$, CF$_3$, C$_{3-5}$cycloalkyl optionally substituted with —CN, and C$_{1-4}$alkyl optionally substituted with one or two substituents each independently selected from the group consisting of fluoro, Het$^4$, —CN, —OR$^6$, —NR$^7$R$^{7'}$, —S(=O)$_2$—C$_{1-4}$alkyl and —C(=O)NR$^8$R$^{8'}$;

Het$^1$ is a monocyclic heteroaryl selected from the group consisting of pyridyl, 2-, 4-, 5- or 6-pyrimidinyl, pyrazinyl, pyridazinyl, furanyl, thienyl, pyrrolyl, pyrazolyl, imidazolyl, 4- or 5-thiazolyl, isothiazolyl, and isoxazolyl; each of which may be optionally substituted with one, two, or three substituents each independently selected from the group consisting of halo, —CN, —OR$^4$, —NR$^5$R$^{5'}$, —C(=O)NR$^5$R$^{5'}$, —C(=O)—Het$^4$, and C$_{1-4}$alkyl optionally substituted with a substituent selected from the group consisting of fluoro, —CN, —OR$^6$, Het$^2$, —NR$^7$R$^{7'}$, and —C(=O)NR$^8$R$^{8'}$; and Het$^2$ is a non-aromatic heterocyclyl optionally substituted with one, two, or three substituents each independently selected from the group consisting of halo, —CN, —C(=O)—C$_{1-6}$alkyl, —C(=O)Ar, —C(=O)Het$^1$, —C(=O)Het$^2$, —OR$^4$, —NR$^5$R$^{5'}$, and C$_{1-4}$alkyl optionally substituted with a substituent selected from the group consisting of fluoro, —CN, —OR$^6$, —NR$^7$R$^{7'}$, $R^{12}$ and —C(=O)NR$^8$R$^{8'}$;

wherein $R^{12}$ is C-linked 4- to 7-membered non-aromatic heterocyclyl containing at least one nitrogen, oxygen or sulfur atom;

$R^4$, $R^5$, $R^{5'}$, $R^6$, $R^7$, $R^{7'}$, $R^8$ and $R^{8'}$ are each independently selected from the group consisting of hydrogen; —C(=O)—C$_{1-4}$alkyl; —S(=O)$_2$—C$_{1-4}$alkyl; C$_{1-4}$alkyl optionally substituted with a substituent selected from the group consisting of fluoro, —C(=O)—C$_{1-4}$alkyl, —S(=O)$_2$—C$_{1-4}$alkyl, $R^{11}$, $R^{16}$ and —C(=O)NR$^9$R$^{9'}$; and C$_{2-4}$alkyl substituted with a substituent selected from the group consisting of —OR$^{10}$ and —NR$^{11}$R$^{11'}$; wherein $R^9$, $R^{9'}$, $R^{10}$, $R^{11}$, $R^{11'}$ and $R^{11''}$ are each independently selected from the group consisting of hydrogen; C$_{1-4}$alkyl; —S(=O)$_2$—C$_{1-4}$alkyl; and C-linked 4- to 7-membered non-aromatic heterocyclyl containing at least one nitrogen, oxygen or sulfur atom, wherein said heterocyclyl is optionally substituted with one, two, or three substituents each independently selected from the group consisting of —S(=O)$_2$—C$_{1-4}$alkyl, halo, cyano, and C$_{1-4}$alkyl optionally substituted with —O—C$_{1-4}$alkyl;

$R^{16}$ is N-linked 4- to 7-membered non-aromatic heterocyclyl containing at least one N-atom and optionally one additional heteroatom selected from nitrogen, oxygen and sulfur, wherein said heterocyclyl is optionally substituted with one, two, or three substituents each independently selected from the group consisting of —S(=O)$_2$—C$_{1-4}$alkyl, halo, cyano, and C$_{1-4}$alkyl optionally substituted with —O—C$_{1-4}$alkyl;

$R^{14}$ is a 5-membered monocyclic heteroaryl containing at least one nitrogen atom, and optionally 1, 2 or 3 additional heteroatoms each independently selected from nitrogen, oxygen and sulfur;

Het$^3$ is selected from the group consisting of formula (b-1) and (b-2):

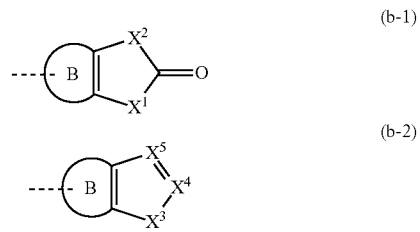

Ring B is phenyl;
$X^1$ represents CH$_2$, O or NH;
$X^2$ represents NH or O;
$X^3$ represents NH or O;
$X^4$ represents CH or N;
$X^5$ represents CH or N;

wherein one C-atom or one N-atom in the 5-membered ring of (b-1) or (b-2), including suitable C-atoms and N-atoms in the definition of $X^1$, $X^2$, $X^3$, $X^4$ and $X^5$, might be substituted with one or where possible two C$_{1-4}$alkyl groups optionally substituted with one, two or three substituents each independently selected from the group consisting of halo, cyano, —C(=O)NR$^5$R$^{5'}$, and Het$^4$;

Het$^4$ is a 4- to 7-membered non-aromatic heterocyclyl containing at least one nitrogen, oxygen or sulfur atom, wherein said heterocyclyl is optionally substituted with one, two, or three substituents each independently selected from the group consisting of halo, —CN, oxo, —C(=O)NR$^5$R$^{5'}$, —O—C$_{1-4}$alkyl, —S(=O)$_2$—C$_{1-4}$alkyl, and C$_{1-4}$alkyl optionally substituted with —O—C$_{1-4}$alkyl;

$R^{17}$ is C$_{3-6}$cycloalkyl optionally substituted with one or more substituents selected from the group consisting of halo, —CN, —OR$^4$, —NR$^5$R$^{5'}$, —C(=O)NR$^5$R$^{5'}$, and C$_{1-4}$alkyl optionally substituted with a substituent selected from the group consisting of fluoro, —CN, —OR$^6$, —NR$^7$R$^{7'}$, and —C(=O)NR$^8$R$^{8'}$;

n1, n2, and m1 are each independently selected from 1 and 2;

m2 is 0 or 1;

and the pharmaceutically acceptable salts and the solvates thereof.

The present invention relates in particular to compounds of Formula (I) as defined herein, and the tautomers and the stereoisomeric forms thereof, wherein $R^1$ is selected from the group consisting of CH$_3$, CH$_2$F, CHF$_2$ and CF$_3$;

$Y^1$ is N;

$R^2$ is selected from the group consisting of hydrogen, CH$_3$—OCH$_3$, —NH$_2$, and —NH—CH$_3$;

$Y^2$ is CH$_2$;

A is a covalent bond;

Q is hydrogen;

-L-R$^3$ is selected from (a), (b), or (c):

(a) -L-R$^3$ is —NR$^4$R$^{1A}$, wherein $R^4$ is selected from the group consisting of hydrogen; cyclopropyl; C$_{1-4}$alkyl optionally substituted with a substituent selected from the group consisting of fluoro and —CN; and $C_{2-4}$alkyl substituted with a substituent selected from the group consisting of —OR$^{3a}$ and —NR$^{4a}$R$^{4aa}$;

R$^{1A}$ is selected from the group consisting of $C_{1-6}$alkyl optionally substituted with one, two or three fluoro substituents; and $C_{2-6}$alkyl substituted with a substituent selected from the group consisting of —OR$^{1a}$ and —NR$^{2a}$R$^{2aa}$, wherein R$^{1a}$, R$^{2a}$, R$^{2aa}$, R$^{3a}$, R$^{4a}$, and R$^{4aa}$ are each independently selected from the group consisting of hydrogen, $C_{1-4}$alkyl and cyclopropyl;

or (b) L is selected from the group consisting of —N(R$^B$)—, —N(R$^B$)—CR$^{1B}$R$^{1BB}$—, and —(NR$^B$)—CHR$^{1B}$—CHR$^{2B}$—; and R$^3$ is selected from the group consisting of Ar; Het$^1$; Het$^2$; Het$^3$; R$^{17}$; and a 7- to 10-membered saturated spirocarbobicyclic system; wherein R$^B$ is selected from the group consisting of hydrogen; cyclopropyl; $C_{1-4}$alkyl optionally substituted with a substituent selected from the group consisting of fluoro and —CN; and $C_{2-4}$alkyl substituted with a substituent selected from the group consisting of —OR$^{1b}$ and —NR$^{2b}$R$^{2bb}$; provided that when R$^3$ is R$^{17}$, R$^B$ is hydrogen;

wherein

R$^{1b}$, R$^{2b}$, and R$^{2bb}$ are each independently selected from the group consisting of hydrogen, $C_{1-4}$alkyl and cyclopropyl;

R$^{1B}$ is selected from the group consisting of hydrogen; halo; $C_{3-6}$cycloalkyl; $C_{1-4}$alkyl optionally substituted with a substituent selected from the group consisting of fluoro, hydroxy, and —CN; $C_{2-4}$alkyl substituted with a substituent selected from the group consisting of —OR$^{4B}$ and —NR$^{5B}$R$^{5BB}$; and C-linked 4- to 7-membered non-aromatic heterocyclyl containing at least one nitrogen, oxygen or sulfur atom; and R$^{1BB}$ is selected from the group consisting of hydrogen and methyl; or R$^{1B}$ and R$^{1BB}$ together with the carbon to which they are attached form a $C_{3-6}$cycloalkyl or a C-linked 4- to 7-membered non-aromatic heterocyclyl containing at least one nitrogen, oxygen or sulfur atom;

R$^{2B}$ is selected from the group consisting of hydrogen; —OR$^{6B}$; —NR$^{7B}$R$^{7BB}$; CF$_3$, $C_{1-4}$alkyl optionally substituted with a substituent selected from the group consisting of fluoro, —CN, —OR$^{4B}$, and —NR$^{5B}$R$^{5BB}$; and C-linked 4- to 7-membered non-aromatic heterocyclyl containing at least one nitrogen, oxygen or sulfur atom; wherein R$^{4B}$, R$^{5B}$, R$^{5BB}$, R$^{6B}$, R$^{7B}$, and R$^{7BB}$ are each independently selected from the group consisting of hydrogen; $C_{1-4}$alkyl optionally substituted with a substituent selected from the group consisting of fluoro, —CN and —C(=O)NR$^{9B}$R$^{9BB}$; and $C_{2-4}$alkyl substituted with a substituent selected from the group consisting of —OR$^{10B}$ and —NR$^{11B}$R$^{11BB}$; wherein R$^{9B}$, R$^{9BB}$, R$^{10B}$, R$^{11B}$ and R$^{11BB}$ are each independently selected from the group consisting of hydrogen; $C_{1-4}$alkyl; and C-linked 4- to 7-membered non-aromatic heterocyclyl containing at least one nitrogen, oxygen or sulfur atom;

or (c) -L-R$^3$ is selected from the group consisting of —N(R$^C$)—COR$^{5C}$; and —N(R$^C$)—SO$_2$—R$^{13C}$ wherein R$^C$ is selected from the group consisting of hydrogen; cyclopropyl; $C_{1-4}$alkyl optionally substituted with a substituent selected from the group consisting of fluoro and —CN; and $C_{2-4}$alkyl substituted with a substituent selected from the group consisting of —OR$^{1c}$ and —NR$^{2c}$R$^{2cc}$;

R$^{5C}$ and R$^{13C}$ are each independently selected from the group consisting of hydrogen; Ar; Het$^1$; Het$^2$; Het$^3$; R$^{17}$; a 7- to 10-membered saturated spirocarbobicyclic system; and $C_{1-4}$alkyl optionally substituted with —NR$^{2c}$R$^{2cc}$, Ar, Het$^1$ or Het$^2$; wherein R$^{1c}$, R$^{2c}$, and R$^{2cc}$ are each independently selected from the group consisting of hydrogen and $C_{1-4}$alkyl;

Ar is phenyl optionally substituted with one, two, or three substituents each independently selected from the group consisting of halo, —CN, —OR$^4$, —NR$^5$R$^{5'}$, —C(=O)NR$^5$R$^{5'}$, Het$^4$, —O-Het$^4$, —NR$^5$—Het$^4$, —C(=O)—Het$^4$, —S(=O)$_2$—Het$^4$, —S(=O)$_2$—NR$^5$R$^{5'}$, —S(=O)$_2$—$C_{1-4}$alkyl, R$^{14}$, CF$_3$, $C_{3-5}$cycloalkyl optionally substituted with —CN, and $C_{1-4}$alkyl optionally substituted with one or two substituents each independently selected from the group consisting of fluoro, Het$^4$, —CN, —OR$^6$, —NR$^7$R$^{7'}$, —S(=O)$_2$—$C_{1-4}$alkyl and —C(=O)NR$^8$R$^{8'}$;

Het$^1$ is a monocyclic heteroaryl selected from the group consisting of pyridyl, 2-, 4-, 5- or 6-pyrimidinyl, pyrazinyl, pyridazinyl, furanyl, thienyl, pyrrolyl, pyrazolyl, imidazolyl, 4- or 5-thiazolyl, isothiazolyl, and isoxazolyl; each of which may be optionally substituted with one, two, or three substituents each independently selected from the group consisting of halo, —CN, —OR$^4$, —NR$^5$R$^{5'}$, —C(=O)NR$^5$R$^{5'}$, —C(=O)—Het$^4$, and $C_{1-4}$alkyl optionally substituted with a substituent selected from the group consisting of fluoro, —CN, —OR$^6$, Het$^2$, —NR$^7$R$^{7'}$, and —C(=O)NR$^8$R$^{8'}$; and Het$^2$ is a non-aromatic heterocyclyl optionally substituted with one, two, or three substituents each independently selected from the group consisting of halo, —CN, —C(=O)—$C_{1-6}$alkyl, —C(=O)Ar, —C(=O)Het$^1$, —C(=O)Het$^2$, —OR$^4$, —NR$^5$R$^{5'}$, and $C_{1-4}$alkyl optionally substituted with a substituent selected from the group consisting of fluoro, —CN, —OR$^6$, —NR$^7$R$^{7'}$, R$^{12}$ and —C(=O)NR$^8$R$^{8'}$;

wherein

R$^{12}$ is C-linked 4- to 7-membered non-aromatic heterocyclyl containing at least one nitrogen, oxygen or sulfur atom;

R$^4$, R$^5$, R$^{5'}$, R$^6$, R$^7$, R$^{7'}$, R$^8$ and R$^{8'}$ are each independently selected from the group consisting of hydrogen; —C(=O)—$C_{1-4}$alkyl; —S(=O)$_2$—$C_{1-4}$alkyl; $C_{1-4}$alkyl optionally substituted with a substituent selected from the group consisting of fluoro, —C(=O)—$C_{1-4}$alkyl, —S(=O)$_2$—$C_{1-4}$alkyl, R$^{11''}$, R$^{16}$ and —C(=O)NR$^9$R$^{9'}$; and $C_{2-4}$alkyl substituted with a substituent selected from the group consisting of —OR$^{10}$ and —NR$^{11}$R$^{11'}$; wherein R$^9$, R$^{9'}$, R$^{10}$, R$^{11}$, R$^{11'}$ and R$^{11''}$ are each independently selected from the group consisting of hydrogen; $C_{1-4}$alkyl; —S(=O)$_2$—$C_{1-4}$alkyl; and C-linked 4- to 7-membered non-aromatic heterocyclyl containing at least one nitrogen, oxygen or sulfur atom, wherein said heterocyclyl is optionally substituted with one, two, or three substituents each independently selected from the group consisting of —S(=O)$_2$—$C_{1-4}$alkyl, halo, cyano, and $C_{1-4}$alkyl optionally substituted with —O—$C_{1-4}$alkyl;

R$^{16}$ is N-linked 4- to 7-membered non-aromatic heterocyclyl containing at least one N-atom and optionally one additional heteroatom selected from nitrogen, oxygen and sulfur, wherein said heterocyclyl is optionally substituted with one, two, or three substituents each independently selected from the group consisting of —S(=O)$_2$—$C_{1-4}$alkyl, halo, cyano, and $C_{1-4}$alkyl optionally substituted with —O—$C_{1-4}$alkyl;

R$^{14}$ is a 5-membered monocyclic heteroaryl containing at least one nitrogen atom, and optionally 1, 2 or 3 additional heteroatoms each independently selected from nitrogen, oxygen and sulfur;

Het$^3$ is selected from the group consisting of formula (b-1) and (b-2):

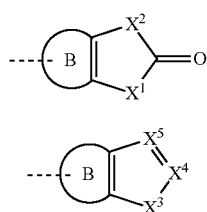

Ring B is phenyl;
X$^1$ represents CH$_2$, O or NH;
X$^2$ represents NH or O;
X$^3$ represents NH or O;
X$^4$ represents CH or N;
X$^5$ represents CH or N;
wherein one C-atom or one N-atom in the 5-membered ring of (b-1) or (b-2), including suitable C-atoms and N-atoms in the definition of X$^1$, X$^2$, X$^3$, X$^4$ and X$^5$, might be substituted with one or where possible two C$_{1-4}$alkyl groups optionally substituted with one, two or three substituents each independently selected from the group consisting of halo, cyano, —C(=O)NR$^5$R$^{5'}$, and Het$^4$;

Het$^4$ is a 4- to 7-membered non-aromatic heterocyclyl containing at least one nitrogen, oxygen or sulfur atom, wherein said heterocyclyl is optionally substituted with one, two, or three substituents each independently selected from the group consisting of halo, —CN, oxo, —C(=O)NR$^5$R$^{5'}$, —O—C$_{1-4}$alkyl, —S(=O)$_2$—C$_{1-4}$alkyl, and C$_{1-4}$alkyl optionally substituted with —O—C$_{1-4}$alkyl;

R$^{17}$ is C$_{3-6}$cycloalkyl optionally substituted with one or more substituents selected from the group consisting of halo, —CN, —OR$^4$, —NR$^5$R$^{5'}$, —C(=O)NR$^5$R$^{5'}$, and C$_{1-4}$alkyl optionally substituted with a substituent selected from the group consisting of fluoro, —CN, —OR$^6$, —NR$^7$R$^{7'}$, and —C(=O)NR$^8$R$^{8'}$;

n1, n2, and m1 are each independently selected from 1 and 2;
m2 is 0 or 1;
and the pharmaceutically acceptable salts and the solvates thereof.

The present invention relates in particular to compounds of Formula (I) as defined herein, and the tautomers and the stereoisomeric forms thereof, wherein
R$^1$ is selected from the group consisting of CF$_3$;
Y$^1$ is N;
R$^2$ is selected from the group consisting of hydrogen, —OCH$_3$, —NH$_2$, and —NH—CH$_3$;
Y$^2$ is CH$_2$;
A is a covalent bond or —CR$^{15a}$R$^{15b}$—;
R$^{15a}$ and R$^{15b}$ are hydrogen;
Q is hydrogen;
-L-R$^3$ is selected from (a), (b), or (c):
(a) -L-R$^3$ is —NR$^A$R$^{14}$, wherein
R$^A$ is selected from the group consisting of hydrogen; or C$_{1-4}$alkyl;
R$^{14}$ is C$_{1-6}$alkyl;
or (b) L is selected from the group consisting of —N(R$^B$)—, and —N(R$^B$)—CR$^{1B}$R$^{1BB}$—; and R$^3$ is selected from the group consisting of Ar; Het$^1$; Het$^2$; Het$^3$; and R$^{17}$; wherein
R$^B$ is hydrogen;
R$^{1B}$ is selected from the group consisting of hydrogen; and C$_{1-4}$alkyl; and
R$^{1BB}$ is selected from the group consisting of hydrogen and methyl; or R$^{1B}$ and R$^{1BB}$ together with the carbon to which they are attached form a C$_{3-6}$cycloalkyl;
or
(c) -L-R$^3$ is selected from the group consisting of —N(R$^C$)—COR$^{5C}$; and —N(R$^C$)—SO$_2$—R$^{13C}$ wherein
R$^C$ is selected from the group consisting of hydrogen; and C$_{1-4}$alkyl;
R$^{5C}$ and R$^{13C}$ are each independently selected from the group consisting of hydrogen; Ar; Het$^3$; and C$_{1-4}$alkyl optionally substituted with Het$^2$;

Ar is phenyl optionally substituted with one, two, or three substituents each independently selected from the group consisting of halo, —CN, —OR$^4$, —NR$^5$R$^{5'}$, —C(=O)NR$^5$R$^{5'}$, Het$^4$, —O-Het$^4$, —NR$^5$—Het$^4$, —C(=O)—Het$^4$, —S(=O)$_2$—Het$^4$, —S(=O)$_2$—NR$^5$R$^{5'}$, —S(=O)$_2$—C$_{1-4}$alkyl, R$^{14}$, CF$_3$, C$_{3-5}$cycloalkyl optionally substituted with —CN, and C$_{1-4}$alkyl optionally substituted with one or two substituents each independently selected from the group consisting of Het$^4$, —CN, —OR$^6$, —S(=O)$_2$—C$_{1-4}$alkyl and —C(=O)NR$^8$R$^{8'}$;

Het$^1$ is a monocyclic heteroaryl selected from the group consisting of pyridyl, 2-pyrimidinyl, pyrazinyl, pyridazinyl, and pyrazolyl; each of which may be optionally substituted with one, two, or three substituents each independently selected from the group consisting of —CN, —OR$^4$, —C(=O)NR$^5$R$^{5'}$, —C(=O)—Het$^4$, and C$_{1-4}$alkyl; and Het$^2$ is a non-aromatic heterocyclyl optionally substituted with one, two, or three substituents each independently selected from the group consisting of C$_{1-4}$alkyl optionally substituted with a substituent selected from the group consisting of fluoro; wherein
R$^4$, R$^5$, R$^{5'}$, R$^6$, R$^8$ and R$^{8'}$ are each independently selected from the group consisting of hydrogen; —C(=O)—C$_{1-4}$alkyl; —S(=O)$_2$—C$_{1-4}$alkyl; C$_{1-4}$alkyl optionally substituted with a substituent selected from the group consisting of —S(=O)$_2$—C$_{1-4}$alkyl, and R$^{16}$; and C$_{2-4}$alkyl substituted with a substituent selected from the group consisting of —OR$^{10}$ and —NR$^{11}$R$^{11'}$; wherein
R$^{10}$, R$^{11}$, and R$^{11'}$ are each independently selected from the group consisting of hydrogen; C$_{1-4}$alkyl; —S(=O)$_2$—C$_{1-4}$alkyl; and C-linked 4- to 7-membered non-aromatic heterocyclyl containing at least one nitrogen, oxygen or sulfur atom, wherein said heterocyclyl is optionally substituted with one, two, or three —S(=O)$_2$—C$_{1-4}$alkyl substituents;
R$^{16}$ is N-linked 4- to 7-membered non-aromatic heterocyclyl containing at least one N-atom and optionally one additional heteroatom selected from nitrogen, oxygen and sulfur, wherein said heterocyclyl is optionally substituted with one, two, or three —S(=O)$_2$—C$_{1-4}$alkyl substituents;
R$^{14}$ is a 5-membered monocyclic heteroaryl containing at least one nitrogen atom, and optionally 1, 2 or 3 additional heteroatoms each independently selected from nitrogen, oxygen and sulfur;
Het$^3$ is selected from the group consisting of formula (b-1) and (b-2):

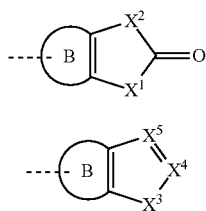

Ring B is phenyl;
X$^1$ represents CH$_2$, O or NH;
X$^2$ represents NH or O;
X$^3$ represents NH or O;
X$^4$ represents CH or N;
X$^5$ represents CH or N;
wherein one C-atom or one N-atom in the 5-membered ring of (b-1) or (b-2), including suitable C-atoms and N-atoms in the definition of X$^1$, X$^2$, X$^3$, X$^4$ and X$^5$, might be substituted with one or where possible two C$_{1-4}$alkyl groups optionally substituted with one, two or three substituents each independently selected from the group consisting of halo, cyano, —C(=O)NR$^5$R$^{5'}$, and Het$^4$;

Het$^4$ is a 4- to 7-membered non-aromatic heterocyclyl containing at least one nitrogen, oxygen or sulfur atom, wherein said heterocyclyl is optionally substituted with one, two, or three substituents each independently selected from the group consisting of —CN, oxo, —C(=O)NR$^5$R$^{5'}$, —O—C$_{1-4}$alkyl, —S(=O)$_2$—C$_{1-4}$alkyl, and C$_{1-4}$alkyl optionally substituted with —O—C$_{1-4}$alkyl;

R$^{17}$ is C$_{3-6}$cycloalkyl optionally substituted with one or more —NR$^5$R$^5$ substituents;

n1, n2, and m1 are each independently selected from 1 and 2;

m2 is 0 or 1;

and the pharmaceutically acceptable salts and the solvates thereof.

The present invention relates in particular to compounds of Formula (I) as defined herein, and the tautomers and the stereoisomeric forms thereof, wherein R$^1$ is selected from the group consisting of CF$_3$;
Y$^1$ is N;
R$^2$ is selected from the group consisting of hydrogen, —OCH$_3$, and —NH—CH$_3$;
Y$^2$ is CH$_2$;
A is a covalent bond or —CR$^{15a}$R$^{15b}$—;
R$^{15a}$ and R$^{15b}$ are hydrogen;
Q is hydrogen;
-L-R$^3$ is selected from (a), (b), or (c):
(a) -L-R$^3$ is —NR$^A$R$^{1A}$, wherein
R$^A$ is C$_{1-4}$alkyl;
R$^{1A}$ is C$_{1-6}$alkyl;
or
(b) L is selected from the group consisting of —N(R$^B$)—, and —N(R$^B$)—CR$^{1B}$R$^{1BB}$—; and R$^3$ is selected from the group consisting of Ar; Het$^1$; Het$^3$; and R$^{17}$; wherein
R$^B$ is hydrogen;
R$^{1B}$ is hydrogen; and
R$^{1BB}$ is selected from the group consisting of hydrogen and methyl;
or
(c) -L-R$^3$ is selected from the group consisting of —N(R$^C$)—COR$^{5C}$; and —N(R$^C$)—SO$_2$—R$^{13C}$ wherein
R$^C$ is selected from the group consisting of hydrogen; and C$_{1-4}$alkyl;

R$^{5C}$ and R$^{13C}$ are each independently selected from the group consisting of hydrogen; Ar; Het$^3$; and C$_{1-4}$alkyl optionally substituted with Het$^2$;

Ar is phenyl optionally substituted with one, two, or three substituents each independently selected from the group consisting of halo, —CN, —OR$^4$, —NR$^5$R$^{5'}$, —C(=O)NR$^5$R$^{5'}$, Het$^4$, —O-Het$^4$, —NR$^5$—Het$^4$, —C(=O)—Het$^4$, R$^{14}$, CF$_3$, and C$_{1-4}$alkyl optionally substituted with one or two —CN substituents;

Het$^1$ is a monocyclic heteroaryl selected from the group consisting of pyridyl, and pyrazolyl; each of which may be optionally substituted with one, two, or three substituents each independently selected from the group consisting of —C(=O)NR$^5$R$^{5'}$, and C$_{1-4}$alkyl; and Het$^2$ is a non-aromatic heterocyclyl;
wherein
R$^4$, R$^5$, and R$^5$ are each independently selected from the group consisting of hydrogen; —S(=O)$_2$—C$_{1-4}$alkyl; C$_{1-4}$alkyl optionally substituted with a R$^{16}$ substituent; and C$_{2-4}$alkyl substituted with a substituent selected from the group consisting of —OR$^{10}$ and —NR$^{11}$R$^{11'}$;
wherein
R$^{10}$, R$^{11}$, and R$^{11}$ are each independently selected from the group consisting of hydrogen; and C$_{1-4}$alkyl;
R$^{16}$ is N-linked 4- to 7-membered non-aromatic heterocyclyl containing at least one N-atom and optionally one additional heteroatom selected from nitrogen, oxygen and sulfur;
R$^{14}$ is a 5-membered monocyclic heteroaryl containing at least one nitrogen atom, and optionally 1, 2 or 3 additional heteroatoms each independently selected from nitrogen, oxygen and sulfur;

Het$^3$ is selected from the group consisting of formula (b-1) and (b-2):

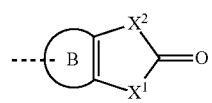

Ring B is phenyl;
X$^1$ represents O or NH;
X$^2$ represents NH;
X$^3$ represents NH;
X$^4$ represents N;
X$^5$ represents CH;
wherein one C-atom or one N-atom in the 5-membered ring of (b-1) or (b-2), including suitable C-atoms and N-atoms in the definition of X$^1$, X$^2$, X$^3$, X$^4$ and X$^5$, might be substituted with one or where possible two C$_{1-4}$alkyl groups optionally substituted with one, two or three cyano substituents;

Het$^4$ is a 4- to 7-membered non-aromatic heterocyclyl containing at least one nitrogen, oxygen or sulfur atom, wherein said heterocyclyl is optionally substituted with one, two, or three C$_{1-4}$alkyl substituents;

R$^{17}$ is C$_{3-6}$cycloalkyl optionally substituted with one or more —NR$^5$R$^5$ substituents;

n1, n2, and m1 are each independently selected from 1 and 2;

m2 is 0 or 1;
and the pharmaceutically acceptable salts and the solvates thereof.

The present invention relates in particular to compounds of Formula (I) as defined herein, and the tautomers and the stereoisomeric forms thereof wherein
$R^1$ is $CF_3$;
$Y^1$ is N;
$R^2$ is selected from the group consisting of hydrogen, —$OCH_3$, and —NH—$CH_3$;
$Y^2$ is $CH_2$;
A is a covalent bond;
Q is hydrogen;
-L-$R^3$ is selected from (a), (b), or (c):
(a) -L-$R^3$ is —$NR^AR^{1A}$, wherein
$R^A$ is $C_{1-4}$alkyl;
$R^{1A}$ is $C_{1-6}$alkyl;
or
(b) L is selected from the group consisting of —$N(R^B)$—, and —$N(R^B)$—$CR^{1B}R^{1BB}$—; and $R^3$ is selected from the group consisting of Ar; Het$^3$; and $R^{17}$; wherein
$R^B$ is hydrogen;
$R^{1B}$ is hydrogen; and
$R^{1BB}$ is selected from the group consisting of hydrogen and methyl;
or
(c) -L-$R^3$ is selected from the group consisting of —$N(R^C)$—$COR^{5C}$; and —$N(R^C)$—$SO_2$—$R^{13C}$ wherein
$R^C$ is selected from the group consisting of hydrogen; and $C_{1-4}$alkyl;
$R^{5C}$ and $R^{13C}$ are each independently selected from the group consisting of hydrogen; Ar; Het$^3$; and $C_{1-4}$alkyl optionally substituted with Het$^2$;
Ar is phenyl optionally substituted with one, two, or three substituents each independently selected from the group consisting of halo, —CN, —$OR^4$, —$NR^5R^{5'}$, —C(=O)$NR^5R^{5'}$, Het$^4$, —O-Het$^4$, —$NR^5$—Het$^4$, $R^{14}$, $CF_3$, and $C_{1-4}$alkyl optionally substituted with one or two —CN substituents;
wherein
$R^4$, $R^5$, and $R^5$ are each independently selected from the group consisting of hydrogen; —S(=O)$_2$—$C_{1-4}$alkyl; and $C_{2-4}$alkyl substituted with a substituent selected from the group consisting of —$OR^{10}$, —$NR^{11}R^{11'}$ and $R^{16}$;
wherein
$R^{10}$, $R^{11}$, and $R^{11}$ are each independently selected from the group consisting of hydrogen; and $C_{1-4}$alkyl;
$R^{16}$ is N-linked 4- to 7-membered non-aromatic heterocyclyl containing at least one N-atom and optionally one additional heteroatom selected from nitrogen, oxygen and sulfur;
$R^{14}$ is a 5-membered monocyclic heteroaryl containing at least one nitrogen atom, and optionally 1, 2 or 3 additional heteroatoms each independently selected from nitrogen, oxygen and sulfur;
Het$^3$ is selected from the group consisting of formula (b-1):

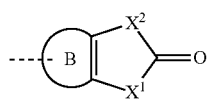

Ring B is phenyl;
$X^1$ represents O or NH;
$X^2$ represents NH;
wherein one N-atom in the 5-membered ring of (b-1), including suitable N-atoms in the definition of $X^1$ and $X^2$, might be substituted with one $C_{1-4}$alkyl group;
Het$^4$ is a 4- to 7-membered non-aromatic heterocyclyl containing at least one nitrogen, oxygen or sulfur atom, wherein said heterocyclyl is optionally substituted with one, two, or three $C_{1-4}$alkyl substituents;
$R^{17}$ is $C_{3-6}$cycloalkyl optionally substituted with one or more —$NR^5R^5$ substituents;
n1, n2, and m1 are each independently selected from 1 and 2;
m2 is 0 or 1;
and the pharmaceutically acceptable salts and the solvates thereof.

The present invention relates in particular to compounds of Formula (I) as defined herein, and the tautomers and the stereoisomeric forms thereof, wherein
$R^1$ is $CF_3$;
$Y^1$ is N;
$R^2$ is selected from the group consisting of hydrogen, —$OCH_3$, and —NH—$CH_3$;
$Y^2$ is $CH_2$;
A is a covalent bond;
Q is hydrogen;
-L-$R^3$ is (b):
(b) L is selected from the group consisting of —$N(R^B)$—, and —$N(R^B)$—$CR^{1B}R^{1BB}$—; and $R^3$ is selected from the group consisting of Ar and Het$^3$; wherein
$R^B$ is hydrogen;
$R^{1B}$ is hydrogen; and
$R^{1BB}$ is selected from the group consisting of hydrogen;
Ar is phenyl optionally substituted with one, two, or three substituents each independently selected from the group consisting of halo, —$OR^4$, —C(=O)$NR^5R^{5'}$, Het$^4$, —O-Het$^4$, —$NR^5$—Het$^4$, $R^{14}$, and $C_{1-4}$alkyl optionally substituted with one or two —CN substituents;
wherein
$R^4$, $R^5$, and $R^5$ are each independently selected from the group consisting of hydrogen; —S(=O)$_2$—$C_{1-4}$alkyl; and $C_{2-4}$alkyl substituted with a substituent selected from the group consisting of —$OR^{10}$, —$NR^{11}R^{11'}$ and $R^{16}$;
wherein
$R^{10}$, $R^{11}$, and $R^{11}$ are each independently selected from the group consisting of hydrogen; and $C_{1-4}$alkyl;
wherein $R^{16}$ is N-linked 4- to 7-membered non-aromatic heterocyclyl containing at least one N-atom and optionally one additional heteroatom selected from nitrogen, oxygen and sulfur;
$R^{14}$ is a 5-membered monocyclic heteroaryl containing at least one nitrogen atom, and optionally 1, 2 or 3 additional heteroatoms each independently selected from nitrogen, oxygen and sulfur;
Het$^3$ is selected from the group consisting of formula (b-1):

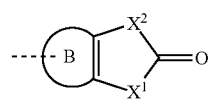

Ring B is phenyl;

$X^1$ represents O or NH;

$X^2$ represents NH;

wherein one N-atom in the 5-membered ring of (b-1), including suitable N-atoms in the definition of $X^1$ and $X^2$, might be substituted with one $C_{1-4}$alkyl group;

$Het^4$ is a 4- to 7-membered non-aromatic heterocyclyl containing at least one nitrogen, oxygen or sulfur atom, wherein said heterocyclyl is substituted with one, two, or three $C_{1-4}$alkyl substituents;

n1, n2, and m1 are each independently selected from 1 and 2;

m2 is 0 or 1;

and the pharmaceutically acceptable salts and the solvates thereof.

The present invention relates in particular to compounds of Formula (I) as defined herein, and the tautomers and the stereoisomeric forms thereof, wherein $R^1$ is selected from the group consisting of $CH_3$, $CH_2F$, $CHF_2$ and $CF_3$;

$Y^1$ is N or $CR^y$;

when $Y^1$ represents N, $R^2$ is selected from the group consisting of hydrogen, $CH_3$—$OCH_3$, —$NH_2$, and —NH—$CH_3$;

when $Y^1$ represents $CR^y$, $R^2$ is hydrogen;

$R^y$ is selected from the group consisting of hydrogen, cyano, and $C_{1-4}$alkyl optionally substituted with hydroxy, —O—$C_{1-4}$alkyl, or —O—$C_{3-6}$cycloalkyl;

$Y^2$ is $CH_2$ or O;

A is a covalent bond or —$CR^{15a}R^{15b}$—;

$R^{15a}$ and $R^{15b}$ are each independently selected from the group consisting of hydrogen or $C_{1-4}$alkyl;

Q is hydrogen or $C_{1-4}$alkyl optionally substituted with phenyl;

-L-$R^3$ is selected from (a), (b), (c), (d), (e), or (f):

(a) -L-$R^3$ is —$NR^AR^{14}$, wherein $R^A$ is selected from the group consisting of hydrogen; cyclopropyl; $C_{1-4}$alkyl optionally substituted with a substituent selected from the group consisting of fluoro and —CN; and $C_{2-4}$alkyl substituted with a substituent selected from the group consisting of —$OR^{3a}$ and —$NR^{4a}R^{4aa}$;

$R^{14}$ is selected from the group consisting of $C_{1-6}$alkyl optionally substituted with one, two or three fluoro substituents; and $C_{2-6}$alkyl substituted with a substituent selected from the group consisting of —$OR^{1a}$ and —$NR^{2a}R^{2aa}$, wherein $R^{1a}$, $R^{2a}$, $R^{2aa}$, $R^{3a}$, $R^{4a}$, and $R^{4aa}$ are each independently selected from the group consisting of hydrogen, $C_{1-4}$alkyl and cyclopropyl;

or (b) L is selected from the group consisting of —$N(R^B)$—, —$N(R^B)$—$CR^{1B}R^{1BB}$—, and —$(NR^B)$—$CHR^{1B}$—$CHR^{2B}$—; and $R^3$ is selected from the group consisting of Ar; $Het^1$; $Het^2$; $Het^3$; and a 7- to 10-membered saturated spirocarbobicyclic system; wherein $R^B$ is selected from the group consisting of hydrogen; cyclopropyl; $C_{1-4}$alkyl optionally substituted with a substituent selected from the group consisting of fluoro and —CN; and $C_{2-4}$alkyl substituted with a substituent selected from the group consisting of —$OR^{1b}$ and —$NR^{2b}R^{2bb}$;

wherein $R^{1b}$, $R^{2b}$, and $R^{2bb}$ are each independently selected from the group consisting of hydrogen, $C_{1-4}$alkyl and cyclopropyl;

$R^{1B}$ is selected from the group consisting of hydrogen; halo; $C_{3-6}$cycloalkyl; $C_{1-4}$alkyl optionally substituted with a substituent selected from the group consisting of fluoro, hydroxy, and —CN; $C_{2-4}$alkyl substituted with a substituent selected from the group consisting of —$OR^{4B}$ and —$NR^{5B}R^{5BB}$; and C-linked 4- to 7-membered non-aromatic heterocyclyl containing at least one nitrogen, oxygen or sulfur atom; and $R^{1BB}$ is selected from the group consisting of hydrogen and methyl; or $R^{1B}$ and $R^{1BB}$ together with the carbon to which they are attached form a $C_{3-6}$cycloalkyl or a C-linked 4- to 7-membered non-aromatic heterocyclyl containing at least one nitrogen, oxygen or sulfur atom;

$R^{2B}$ is selected from the group consisting of hydrogen; —$OR^{6B}$; —$NR^{7B}R^{7BB}$; $CF_3$, $C_{1-4}$alkyl optionally substituted with a substituent selected from the group consisting of fluoro, —CN, —$OR^{4B}$, and —$NR^{5B}R^{5BB}$; and C-linked 4- to 7-membered non-aromatic heterocyclyl containing at least one nitrogen, oxygen or sulfur atom; wherein $R^{4B}$, $R^{5B}$, $R^{5BB}$, $R^{6B}$, $R^{7B}$, and $R^{7BB}$ are each independently selected from the group consisting of hydrogen; $C_{1-4}$alkyl optionally substituted with a substituent selected from the group consisting of fluoro, —CN and —C(=O)$NR^{9B}R^{9BB}$; and $C_{2-4}$alkyl substituted with a substituent selected from the group consisting of —$OR^{10B}$ and —$NR^{11B}R^{11BB}$; wherein $R^{9B}$, $R^{9BB}$, $R^{10B}$, $R^{11B}$ and $R^{11BB}$ are each independently selected from the group consisting of hydrogen; $C_{1-4}$alkyl; and C-linked 4- to 7-membered non-aromatic heterocyclyl containing at least one nitrogen, oxygen or sulfur atom;

or (c) -L-$R^3$ is selected from the group consisting of —$N(R^C)$—$COR^{5C}$; and —$N(R^C)$—$SO_2$—$R^{13C}$ wherein $R^C$ is selected from the group consisting of hydrogen; cyclopropyl; $C_{1-4}$alkyl optionally substituted with a substituent selected from the group consisting of fluoro and —CN; and $C_{2-4}$alkyl substituted with a substituent selected from the group consisting of —$OR^{1c}$ and —$NR^{2c}R^{2cc}$;

$R^{5C}$ and $R^{13C}$ are each independently selected from the group consisting of hydrogen; Ar; $Het^1$; $Het^2$; $Het^3$; a 7- to 10-membered saturated spirocarbobicyclic system; and $C_{1-4}$alkyl optionally substituted with —$NR^{2c}R^{2cc}$, Ar, $Het^1$ or $Het^2$; wherein $R^{1c}$, $R^{2c}$, and $R^{2cc}$ are each independently selected from the group consisting of hydrogen and $C_{1-4}$alkyl;

or (d) L is selected from —$N(R^D)$—$CR^{1D}R^{1DD}$— and —$N(R^D)$—$CR^{1D}R^{1DD}$—$CR^{2D}R^{2DD}$—; wherein $R^D$ is selected from the group consisting of hydrogen; $C_{1-4}$alkyl optionally substituted with a substituent selected from the group consisting of fluoro and —CN; and $C_{2-4}$alkyl substituted with a substituent selected from —$OR^{1d}$ and —$NR^{2d}R^{2dd}$; wherein $R^{1d}$, $R^{2d}$ and $R^{2dd}$ are each independently selected from the group consisting of hydrogen and $C_{1-4}$alkyl;

$R^{1D}$, $R^{1DD}$, $R^{2D}$ and $R^{2DD}$ are each independently selected from the group consisting of hydrogen and $C_{1-4}$alkyl; and $R^3$ is selected from the group consisting of

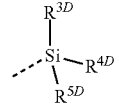

and

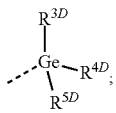

wherein
R$^{3D}$, R$^{4D}$, and R$^{5D}$ are each independently selected from the group consisting of C$_{1-6}$alkyl optionally substituted with a —OH, —OC$_{1-6}$alkyl, or a —NH$_2$ substituent;
or
(e) -L-R$^3$ is

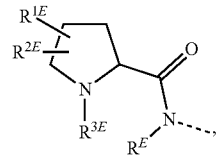

wherein
R$^E$ is selected from the group consisting of hydrogen and C$_{1-4}$alkyl;
R$^{1E}$ is selected from the group consisting of hydrogen, fluoro and C$_{1-4}$alkyl; and
R$^{2E}$ is selected from the group consisting of fluoro, —OC$_{1-4}$alkyl, and C$_{1-4}$alkyl optionally substituted with 1, 2 or 3 fluoro substituents; or R$^{1E}$ and R$^{2E}$ are bound to the same carbon atom and together form a C$_{3-5}$cycloalkyl or a C-linked 4- to 6-membered heterocyclyl containing an oxygen atom; and
R$^{3E}$ is selected from the group consisting of hydrogen; C$_{1-4}$alkyl optionally substituted with a fluoro or a —CN substituent; and C$_{2-4}$alkyl substituted with a substituent selected from the group consisting of —OR$^{4E}$ and —NR$^{5E}$R$^{5EE}$; wherein
R$^{4E}$, R$^{5E}$ and R$^{5EE}$ are each independently selected from the group consisting of hydrogen; C$_{1-4}$alkyl optionally substituted with a substituent selected from the group consisting of fluoro, —CN, and —C(=O)NR$^{6E}$R$^{6EE}$; C$_{2-4}$alkyl substituted with a substituent selected from the group consisting of —OR$^{7E}$ and —NR$^{8E}$R$^{8EE}$; and C-linked 4- to 7-membered non-aromatic heterocyclyl containing at least one nitrogen, oxygen or sulfur atom; wherein R$^{6E}$, R$^{6EE}$, R$^{7E}$, R$^{8E}$ and R$^{8EE}$ are each independently selected from the group consisting of hydrogen and C$_{1-4}$alkyl;
or
(f) -L-R$^3$ is a radical

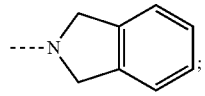

Ar is phenyl optionally substituted with one, two, or three substituents each independently selected from the group consisting of halo, —CN, —OR$^4$, —NR$^5$R$^{5'}$, —C(=O)NR$^5$R$^{5'}$, —S(=O)$_2$—NR$^5$R$^{5'}$, —S(=O)$_2$—C$_{1-4}$alkyl, R$^{14}$, CF$_3$, C$_{3-5}$cycloalkyl optionally substituted with —CN, and C$_{1-4}$alkyl optionally substituted with one or two substituents each independently selected from the group consisting of fluoro, —CN, —OR$^6$, —NR$^7$R$^{7'}$, —S(=O)$_2$—C$_{1-4}$alkyl and —C(=O)NR$^8$R$^{8'}$;

Het$^1$ is a monocyclic heteroaryl selected from the group consisting of pyridyl, 2-, 4-, 5- or 6-pyrimidinyl, pyrazinyl, pyridazinyl, furanyl, thienyl, pyrrolyl, pyrazolyl, imidazolyl, 4- or 5-thiazolyl, isothiazolyl, and isoxazolyl; each of which may be optionally substituted with one, two, or three substituents each independently selected from the group consisting of halo, —CN, —OR$^4$, —NR$^5$R$^{5'}$, —C(=O)NR$^5$R$^{5'}$, and C$_{1-4}$alkyl optionally substituted with a substituent selected from the group consisting of fluoro, —CN, —OR$^6$, Het$^2$, —NR$^7$R$^{7'}$, and —C(=O)NR$^8$R$^{8'}$; and Het$^2$ is a non-aromatic heterocyclyl optionally substituted with one, two, or three substituents each independently selected from the group consisting of halo, —CN, —C(=O)—C$_{1-6}$alkyl, —C(=O)Ar, —C(=O)Het$^1$, —C(=O)Het$^2$, —OR$^4$, —NR$^5$R$^{5'}$, and C$_{1-4}$alkyl optionally substituted with a substituent selected from the group consisting of fluoro, —CN, —OR$^6$, —NR$^7$R$^{7'}$, R$^{12}$ and —C(=O)NR$^8$R$^{8'}$;
wherein
R$^{12}$ is C-linked 4- to 7-membered non-aromatic heterocyclyl containing at least one nitrogen, oxygen or sulfur atom;
R$^4$, R$^5$, R$^{5'}$, R$^6$, R$^7$, R$^{7'}$, R$^8$ and R$^{8'}$ are each independently selected from the group consisting of hydrogen; —C(=O)—C$_{1-4}$alkyl; —S(=O)$_2$—C$_{1-4}$alkyl; C$_{1-4}$alkyl optionally substituted with a substituent selected from the group consisting of fluoro, —C(=O)—C$_{1-4}$alkyl, —S(=O)$_2$—C$_{1-4}$alkyl, R$^{11'}$, R$^{16}$ and —C(=O)NR$^9$R$^{9'}$; and C$_{2-4}$alkyl substituted with a substituent selected from the group consisting of —OR$^{10}$ and —NR$^{11}$R$^{11'}$; wherein
R$^9$, R$^{9'}$, R$^{10}$, R$^{11}$, R$^{11'}$ and R$^{11''}$ are each independently selected from the group consisting of hydrogen; C$_{1-4}$alkyl; —S(=O)$_2$—C$_{1-4}$alkyl; and C-linked 4- to 7-membered non-aromatic heterocyclyl containing at least one nitrogen, oxygen or sulfur atom, wherein said heterocyclyl is optionally substituted with one, two, or three substituents each independently selected from the group consisting of —S(=O)$_2$—C$_{1-4}$alkyl, halo, cyano, and C$_{1-4}$alkyl optionally substituted with —O—C$_{1-4}$alkyl;
R$^{16}$ is N-linked 4- to 7-membered non-aromatic heterocyclyl containing at least one N-atom and optionally one additional heteroatom selected from nitrogen, oxygen and sulfur, wherein said heterocyclyl is optionally substituted with one, two, or three substituents each independently selected from the group consisting of —S(=O)$_2$—C$_{1-4}$alkyl, halo, cyano, and C$_{1-4}$alkyl optionally substituted with —O—C$_{1-4}$alkyl;
R$^{14}$ is a 5-membered monocyclic heteroaryl containing at least one nitrogen atom, and optionally 1, 2 or 3 additional heteroatoms each independently selected from nitrogen, oxygen and sulfur;
Het$^3$ is selected from the group consisting of formula (b-1) and (b-2):

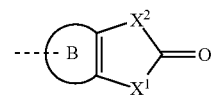

(b-1)

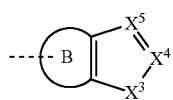

(b-2)

Ring B is phenyl;
$X^1$ represents $CH_2$, O or NH;
$X^2$ represents NH or O;
$X^3$ represents NH or O;
$X^4$ represents CH or N;
$X^5$ represents CH or N;
wherein one C-atom or one N-atom in the 5-membered ring of (b-1) or (b-2), including suitable C-atoms and N-atoms in the definition of $X^1$, $X^2$, $X^3$, $X^4$ and $X^5$, might be substituted with one or where possible two $C_{1-4}$alkyl groups optionally substituted with one, two or three substituents each independently selected from the group consisting of halo, cyano, and —C(=O)$NR^5R^5$;
n1, n2, and m1 are each independently selected from 1 and 2;
m2 is 0 or 1;
and the pharmaceutically acceptable salts and the solvates thereof.

The present invention relates in particular to compounds of Formula (I) as defined herein, and the tautomers and the stereoisomeric forms thereof, wherein
$R^1$ is selected from the group consisting of $CH_3$, $CH_2F$, $CHF_2$ and $CF_3$;
$Y^1$ is N or $CR^y$;
when $Y^1$ represents N, $R^2$ is selected from the group consisting of hydrogen, $CH_3$, —$OCH_3$, —$NH_2$, and —NH—$CH_3$;
when $Y^1$ represents $CR^y$, $R^2$ is hydrogen;
$R^y$ is selected from the group consisting of hydrogen, cyano, and $C_{1-4}$alkyl optionally substituted with hydroxy, —O—$C_{1-4}$alkyl, or —O—$C_{3-6}$cycloalkyl;
$Y^2$ is $CH_2$ or O;
A is a covalent bond or —$CR^{15a}R^{15b}$—;
$R^{15a}$ and $R^{15b}$ are each independently selected from the group consisting of hydrogen or $C_{1-4}$alkyl;
Q is hydrogen or $C_{1-4}$alkyl optionally substituted with phenyl;
-L-$R^3$ is selected from (a), (b), (c), (d), (e), or (f):
(a) -L-$R^3$ is —$NR^4R^{14}$, wherein
$R^4$ is selected from the group consisting of hydrogen; cyclopropyl; $C_{1-4}$alkyl optionally substituted with a substituent selected from the group consisting of fluoro and —CN; and $C_{2-4}$alkyl substituted with a substituent selected from the group consisting of —$OR^{3a}$ and —$NR^{4a}R^{4aa}$;
$R^{14}$ is selected from the group consisting of $C_{1-6}$alkyl optionally substituted with one, two or three fluoro substituents; and $C_{2-6}$alkyl substituted with a substituent selected from the group consisting of —$OR^{1a}$ and —$NR^{2a}R^{2aa}$,
wherein $R^{1a}$, $R^{2a}$, $R^{2aa}$, $R^{3a}$, $R^{4a}$, and $R^{4aa}$ are each independently selected from the group consisting of hydrogen, $C_{1-4}$alkyl and cyclopropyl;
or
(b) L is selected from the group consisting of —N($R^B$)—, —N($R^B$)—$CR^{1B}R^{1BB}$—, and —(N$R^B$)—$CHR^{1B}$—$CHR^{2B}$—; and $R^3$ is selected from the group consisting of Ar; $Het^1$; $Het^2$; $Het^3$; and a 7- to 10-membered saturated spirocarbobicyclic system; wherein
$R^B$ is selected from the group consisting of hydrogen; cyclopropyl; $C_{1-4}$alkyl optionally substituted with a substituent selected from the group consisting of fluoro and —CN; and $C_{2-4}$alkyl substituted with a substituent selected from the group consisting of —$OR^{1b}$ and —$NR^{2b}R^{2bb}$; wherein
$R^{1b}$, $R^{2b}$, and $R^{2bb}$ are each independently selected from the group consisting of hydrogen, $C_{1-4}$alkyl and cyclopropyl;
$R^{1B}$ is selected from the group consisting of hydrogen; halo; $C_{3-6}$cycloalkyl; $C_{1-4}$alkyl optionally substituted with a substituent selected from the group consisting of fluoro, hydroxy, and —CN; $C_{2-4}$alkyl substituted with a substituent selected from the group consisting of —$OR^{4B}$ and —$NR^{5B}R^{5BB}$; and C-linked 4- to 7-membered non-aromatic heterocyclyl containing at least one nitrogen, oxygen or sulfur atom; and
$R^{1BB}$ is selected from the group consisting of hydrogen and methyl; or $R^{1B}$ and $R^{1BB}$ together with the carbon to which they are attached form a $C_{3-6}$cycloalkyl or a C-linked 4- to 7-membered non-aromatic heterocyclyl containing at least one nitrogen, oxygen or sulfur atom;
$R^{2B}$ is selected from the group consisting of hydrogen; —$OR^{6B}$; —$NR^{7B}R^{7BB}$; $CF_3$, $C_{1-4}$alkyl optionally substituted with a substituent selected from the group consisting of fluoro, —CN, —$OR^{4B}$, and —$NR^{5B}R^{5BB}$; and C-linked 4- to 7-membered non-aromatic heterocyclyl containing at least one nitrogen, oxygen or sulfur atom; wherein
$R^{4B}$, $R^{5B}$, $R^{5BB}$, $R^{6B}$, $R^{7B}$, and $R^{7BB}$ are each independently selected from the group consisting of hydrogen; $C_{1-4}$alkyl optionally substituted with a substituent selected from the group consisting of fluoro, —CN and —C(=O)$NR^{9B}R^{9BB}$; and $C_{2-4}$alkyl substituted with a substituent selected from the group consisting of —$OR^{10B}$ and —$NR^{11B}R^{11BB}$; wherein
$R^{9B}$, $R^{9BB}$, $R^{10B}$, $R^{11B}$ and $R^{11BB}$ are each independently selected from the group consisting of hydrogen; $C_{1-4}$alkyl; and C-linked 4- to 7-membered non-aromatic heterocyclyl containing at least one nitrogen, oxygen or sulfur atom;
or
(c) -L-$R^3$ is selected from the group consisting of —N($R^C$)—$COR^{5C}$; and —N($R^C$)—$SO_2$—$R^{13C}$ wherein
$R^C$ is selected from the group consisting of hydrogen; cyclopropyl; $C_{1-4}$alkyl optionally substituted with a substituent selected from the group consisting of fluoro and —CN; and $C_{2-4}$alkyl substituted with a substituent selected from the group consisting of —$OR^{1c}$ and —$NR^{2c}R^{2cc}$;
$R^{5C}$ and $R^{13C}$ are each independently selected from the group consisting of hydrogen; Ar; $Het^1$; $Het^2$; $Het^3$; a 7- to 10-membered saturated spirocarbobicyclic system; and $C_{1-4}$alkyl optionally substituted with —$NR^{2c}R^{2cc}$, Ar, $Het^1$ or $Het^2$; wherein
$R^{1c}$, $R^{2c}$, and $R^{2cc}$ are each independently selected from the group consisting of hydrogen and $C_{1-4}$alkyl;
or
(d) L is selected from —N($R^D$)—$CR^{1D}R^{1DD}$— and —N($R^D$)—$CR^{1D}R^{1DD}$—$CR^{2D}R^{2DD}$—; wherein
$R^D$ is selected from the group consisting of hydrogen; $C_{1-4}$alkyl optionally substituted with a substituent selected from the group consisting of fluoro and —CN; and $C_{2-4}$alkyl substituted with a substituent selected from —$OR^{1d}$ and —$NR^{2d}R^{2dd}$; wherein
$R^{1d}$, $R^{2d}$ and $R^{2dd}$ are each independently selected from the group consisting of hydrogen and $C_{1-4}$alkyl;
$R^{1D}$, $R^{1DD}$, $R^{2D}$ and $R^{2DD}$ are each independently selected from the group consisting of hydrogen and $C_{1-4}$alkyl; and R³ is selected from the group consisting of

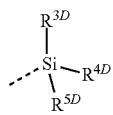

and

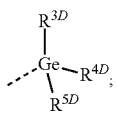

wherein R$^{3D}$, R$^{4D}$, and R$^{5D}$ are each independently selected from the group consisting of C$_{1-6}$alkyl optionally substituted with a —OH, —OC$_{1-6}$alkyl, or a —NH$_2$ substituent;
or
(e) -L-R³ is

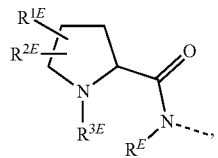

wherein
R$^E$ is selected from the group consisting of hydrogen and C$_{1-4}$alkyl;
R$^{1E}$ is selected from the group consisting of hydrogen, fluoro and C$_{1-4}$alkyl; and
R$^{2E}$ is selected from the group consisting of fluoro, —OC$_{1-4}$alkyl, and C$_{1-4}$alkyl optionally substituted with 1, 2 or 3 fluoro substituents; or R$^{1E}$ and R$^{2E}$ are bound to the same carbon atom and together form a C$_{3-5}$cycloalkyl or a C-linked 4- to 6-membered heterocyclyl containing an oxygen atom; and
R$^{3E}$ is selected from the group consisting of hydrogen; C$_{1-4}$alkyl optionally substituted with a fluoro or a —CN substituent; and C$_{2-4}$alkyl substituted with a substituent selected from the group consisting of —OR$^{4E}$ and —NR$^{5E}$R$^{5EE}$; wherein
R$^{4E}$, R$^{5E}$ and R$^{5EE}$ are each independently selected from the group consisting of hydrogen; C$_{1-4}$alkyl optionally substituted with a substituent selected from the group consisting of fluoro, —CN, and —C(=O)NR$^{6E}$R$^{6EE}$; C$_{2-4}$alkyl substituted with a substituent selected from the group consisting of —OR$^{7E}$ and —NR$^{8E}$R$^{8EE}$; and C-linked 4- to 7-membered non-aromatic heterocyclyl containing at least one nitrogen, oxygen or sulfur atom; wherein R$^{6E}$, R$^{6EE}$, R$^{7E}$, R$^{8E}$ and R$^{8EE}$ are each independently selected from the group consisting of hydrogen and C$_{1-4}$alkyl;
or
(f) -L-R³ is a radical

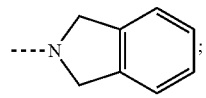

Ar is phenyl optionally substituted with one, two, or three substituents each independently selected from the group consisting of halo, —CN, —OR$^4$, —NR$^5$R$^{5'}$, —C(=O)NR$^5$R$^{5'}$, —S(=O)$_2$—NR$^5$R$^{5'}$, R$^{14}$, CF$_3$, and C$_{1-4}$alkyl optionally substituted with a substituent selected from the group consisting of fluoro, —CN, —OR$^6$, —NR$^7$R$^{7'}$, and —C(=O)NR$^8$R$^{8'}$;

Het$^1$ is a monocyclic heteroaryl selected from the group consisting of pyridyl, 4-, 5- or 6-pyrimidinyl, pyrazinyl, pyridazinyl, furanyl, thienyl, pyrrolyl, pyrazolyl, imidazolyl, 4- or 5-thiazolyl, isothiazolyl, and isoxazolyl; each of which may be optionally substituted with one, two, or three substituents each independently selected from the group consisting of halo, —CN, —OR$^4$, —NR$^5$R$^{5'}$, and C$_{1-4}$alkyl optionally substituted with a substituent selected from the group consisting of fluoro, —CN, —OR$^6$, Het$^2$, —NR$^7$R$^{7'}$, and —C(=O)NR$^8$R$^{8'}$; and Het$^2$ is a non-aromatic heterocyclyl optionally substituted with one, two, or three substituents each independently selected from the group consisting of halo, —CN, —C(=O)—C$_{1-6}$alkyl, —C(=O)Ar, —C(=O)Het$^1$, —C(=O)Het$^2$, —OR$^4$, —NR$^5$R$^{5'}$, and C$_{1-4}$alkyl optionally substituted with a substituent selected from the group consisting of fluoro, —CN, —OR$^6$, —NR$^7$R$^{7'}$, R$^{12}$ and —C(=O)NR$^8$R$^{8'}$;
wherein
R$^{12}$ is C-linked 4- to 7-membered non-aromatic heterocyclyl containing at least one nitrogen, oxygen or sulfur atom;
R$^4$, R$^5$, R$^{5'}$, R$^6$, R$^7$, R$^{7'}$, R$^8$ and R$^{8'}$ are each independently selected from the group consisting of hydrogen; —S(=O)$_2$—C$_{1-4}$alkyl; C$_{1-4}$alkyl optionally substituted with a substituent selected from the group consisting of fluoro, —C(=O)—C$_{1-4}$alkyl, —S(=O)$_2$—C$_{1-4}$alkyl, R$^{11''}$ and —C(=O)NR$^9$R$^{9'}$; and C$_{2-4}$alkyl substituted with a substituent selected from the group consisting of —OR$^{10}$ and —NR$^{11}$R$^{11'}$; wherein
R$^9$, R$^{9'}$, R$^{10}$, R$^{11}$, R$^{11'}$ and R$^{11''}$ are each independently selected from the group consisting of hydrogen; C$_{1-4}$alkyl; and C-linked 4- to 7-membered non-aromatic heterocyclyl containing at least one nitrogen, oxygen or sulfur atom;
R$^{14}$ is a 5-membered monocyclic heteroaryl containing at least one nitrogen atom, and optionally 1, 2 or 3 additional heteroatoms each independently selected from nitrogen, oxygen and sulfur;
Het$^3$ is selected from the group consisting of formula (b-1) and (b-2):

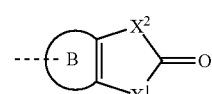

(b-1)

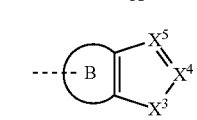

(b-2)

Ring B is phenyl;
X$^1$ represents CH$_2$, O or NH;
X$^2$ represents NH or O;
X$^3$ represents NH or O;
X$^4$ represents CH or N;
X$^5$ represents CH or N;

wherein one C-atom or one N-atom in the 5-membered ring of (b-1) or (b-2), including suitable C-atoms and N-atoms in the definition of $X^1$, $X^2$, $X^3$, $X^4$ and $X^5$, might be substituted with one or where possible two $C_{1-4}$alkyl groups optionally substituted with one, two or three halo atoms;

n1, n2, and m1 are each independently selected from 1 and 2;

m2 is 0 or 1;

and the pharmaceutically acceptable salts and the solvates thereof.

The present invention relates in particular to compounds of Formula (I) as defined herein, and the tautomers and the stereoisomeric forms thereof, wherein $R^1$ is selected from the group consisting of $CH_3$, $CH_2F$, $CHF_2$ and $CF_3$;

$Y^1$ is N or $CR^y$;

when $Y^1$ represents N, $R^2$ is selected from the group consisting of hydrogen, $CH_3$, —$OCH_3$, —$NH_2$, and —NH—$CH_3$;

when $Y^1$ represents $CR^y$, $R^2$ is hydrogen;

$R^y$ is selected from the group consisting of hydrogen, cyano, and $C_{1-4}$alkyl optionally substituted with hydroxy, —O—$C_{1-4}$alkyl, or —O—$C_{3-6}$cycloalkyl;

$Y^2$ is $CH_2$ or O;

A is a covalent bond;

Q is hydrogen or $C_{1-4}$alkyl optionally substituted with phenyl;

-L-$R^3$ is selected from (a), (b), (c), (d), (e), or (f):

(a) -L-$R^3$ is —$NR^AR^{1A}$, wherein $R^A$ is selected from the group consisting of hydrogen; cyclopropyl; $C_{1-4}$alkyl optionally substituted with a substituent selected from the group consisting of fluoro and —CN; and $C_{2-4}$alkyl substituted with a substituent selected from the group consisting of —$OR^{3a}$ and —$NR^{4a}R^{4aa}$;

$R^{1A}$ is selected from the group consisting of $C_{1-6}$alkyl optionally substituted with one, two or three fluoro substituents; and $C_{2-6}$alkyl substituted with a substituent selected from the group consisting of —$OR^{1a}$ and —$NR^{2a}R^{2aa}$, wherein $R^{1a}$, $R^{2a}$, $R^{2aa}$, $R^{3a}$, $R^{4a}$, and $R^{4aa}$ are each independently selected from the group consisting of hydrogen, $C_{1-4}$alkyl and cyclopropyl;

or (b) L is selected from the group consisting of —N($R^B$)—, —N($R^B$)—$CR^{1B}R^{1BB}$—, and —(N$R^B$)—$CHR^{1B}$—$CHR^{2B}$—; and $R^3$ is selected from the group consisting of Ar; $Het^1$; $Het^2$; $Het^3$; and a 7- to 10-membered saturated spirocarbobicyclic system; wherein $R^B$ is selected from the group consisting of hydrogen; cyclopropyl; $C_{1-4}$alkyl optionally substituted with a substituent selected from the group consisting of fluoro and —CN; and $C_{2-4}$alkyl substituted with a substituent selected from the group consisting of —$OR^{1b}$ and —$NR^{2b}R^{2bb}$; wherein $R^{1b}$, $R^{2b}$, and $R^{2bb}$ are each independently selected from the group consisting of hydrogen, $C_{1-4}$alkyl and cyclopropyl;

$R^{1B}$ is selected from the group consisting of hydrogen; halo; $C_{3-6}$cycloalkyl; $C_{1-4}$alkyl optionally substituted with a substituent selected from the group consisting of fluoro, hydroxy, and —CN; $C_{2-4}$alkyl substituted with a substituent selected from the group consisting of —$OR^{4B}$ and —$NR^{5B}R^{5BB}$; and C-linked 4- to 7-membered non-aromatic heterocyclyl containing at least one nitrogen, oxygen or sulfur atom; and $R^{1BB}$ is selected from the group consisting of hydrogen and methyl; or $R^{1B}$ and $R^{1BB}$ together with the carbon to which they are attached form a $C_{3-6}$cycloalkyl or a C-linked 4- to 7-membered non-aromatic heterocyclyl containing at least one nitrogen, oxygen or sulfur atom;

$R^{2B}$ is selected from the group consisting of hydrogen; —$OR^{6B}$; —$NR^{7B}R^{7BB}$; $CF_3$, $C_{1-4}$alkyl optionally substituted with a substituent selected from the group consisting of fluoro, —CN, —$OR^{4B}$, and —$NR^{5B}R^{5BB}$; and C-linked 4- to 7-membered non-aromatic heterocyclyl containing at least one nitrogen, oxygen or sulfur atom; wherein $R^{4B}$, $R^{5B}$, $R^{5BB}$, $R^{6B}$, $R^{7B}$, and $R^{7BB}$ are each independently selected from the group consisting of hydrogen; $C_{1-4}$alkyl optionally substituted with a substituent selected from the group consisting of fluoro, —CN and —C(=O)$NR^{9B}R^{9BB}$; and $C_{2-4}$alkyl substituted with a substituent selected from the group consisting of —$OR^{10B}$ and —$NR^{11B}R^{11BB}$; wherein $R^{9B}$, $R^{9BB}$, $R^{10B}$, $R^{11B}$ and $R^{11BB}$ are each independently selected from the group consisting of hydrogen; $C_{1-4}$alkyl; and C-linked 4- to 7-membered non-aromatic heterocyclyl containing at least one nitrogen, oxygen or sulfur atom;

or (c) -L-$R^3$ is selected from the group consisting of —N($R^C$)—$COR^{5C}$; and —N($R^C$)—$SO_2$—$R^{13C}$ wherein $R^C$ is selected from the group consisting of hydrogen; cyclopropyl; $C_{1-4}$alkyl optionally substituted with a substituent selected from the group consisting of fluoro and —CN; and $C_{2-4}$alkyl substituted with a substituent selected from the group consisting of —$OR^{1c}$ and —$NR^{2c}R^{2cc}$;

$R^{5C}$ and $R^{13C}$ are each independently selected from the group consisting of hydrogen; Ar; $Het^1$; $Het^2$; $Het^3$; a 7- to 10-membered saturated spirocarbobicyclic system; and $C_{1-4}$alkyl optionally substituted with —$NR^{2c}R^{2cc}$, Ar, $Het^1$ or $Het^2$; wherein $R^{1c}$, $R^{2c}$, and $R^{2cc}$ are each independently selected from the group consisting of hydrogen and $C_{1-4}$alkyl;

or (d) L is selected from —N($R^D$)—$CR^{1D}R^{1DD}$— and —N($R^D$)—$CR^{1D}R^{1DD}$—$CR^{2D}R^{2DD}$—; wherein $R^D$ is selected from the group consisting of hydrogen; $C_{1-4}$alkyl optionally substituted with a substituent selected from the group consisting of fluoro and —CN; and $C_{2-4}$alkyl substituted with a substituent selected from —$OR^{1d}$ and —$NR^{2d}R^{2dd}$; wherein $R^{1d}$, $R^{2d}$ and $R^{2dd}$ are each independently selected from the group consisting of hydrogen and $C_{1-4}$alkyl;

$R^{1D}$, $R^{1DD}$, $R^{2D}$ and $R^{2DD}$ are each independently selected from the group consisting of hydrogen and $C_{1-4}$alkyl; and $R^3$ is selected from the group consisting of

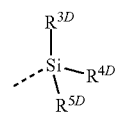

and

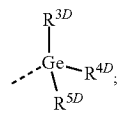

wherein
R$^{3D}$, R$^{4D}$, and R$^{5D}$ are each independently selected from the group consisting of C$_{1-6}$alkyl optionally substituted with a —OH, —OC$_{1-6}$alkyl, or a —NH$_2$ substituent;
or
(e) -L-R$^3$ is

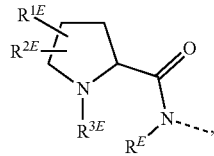

wherein
R$^E$ is selected from the group consisting of hydrogen and C$_{1-4}$alkyl;
R$^{1E}$ is selected from the group consisting of hydrogen, fluoro and C$_{1-4}$alkyl; and
R$^{2E}$ is selected from the group consisting of fluoro, —OC$_{1-4}$alkyl, and C$_{1-4}$alkyl optionally substituted with 1, 2 or 3 fluoro substituents; or R$^{1E}$ and R$^{2E}$ are bound to the same carbon atom and together form a C$_{3-5}$cycloalkyl or a C-linked 4- to 6-membered heterocyclyl containing an oxygen atom; and
R$^{3E}$ is selected from the group consisting of hydrogen; C$_{1-4}$alkyl optionally substituted with a fluoro or a —CN substituent; and C$_{2-4}$alkyl substituted with a substituent selected from the group consisting of —OR$^{4E}$ and —NR$^{5E}$R$^{5EE}$; wherein
R$^{4E}$, R$^{5E}$ and R$^{5EE}$ are each independently selected from the group consisting of hydrogen; C$_{1-4}$alkyl optionally substituted with a substituent selected from the group consisting of fluoro, —CN, and —C(=O)NR$^{6E}$R$^{6EE}$; C$_{2-4}$alkyl substituted with a substituent selected from the group consisting of —OR$^{7E}$ and —NR$^{8E}$R$^{8EE}$; and C-linked 4- to 7-membered non-aromatic heterocyclyl containing at least one nitrogen, oxygen or sulfur atom; wherein R$^{6E}$, R$^{6EE}$, R$^{7E}$, R$^{8E}$ and R$^{8EE}$ are each independently selected from the group consisting of hydrogen and C$_{1-4}$alkyl;
or
(f) -L-R$^3$ is a radical

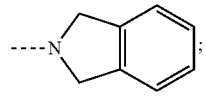

Ar is phenyl optionally substituted with one, two, or three substituents each independently selected from the group consisting of halo, —CN, —OR$^4$, —NR$^5$R$^{5'}$, —C(=O)NR$^5$R$^{5'}$, —S(=O)$_2$—NR$^5$R$^{5'}$, R$^{14}$, CF$_3$, and C$_{1-4}$alkyl optionally substituted with a substituent selected from the group consisting of fluoro, —CN, —OR$^6$, —NR$^7$R$^{7'}$, and —C(=O)NR$^8$R$^{8'}$;
Het$^1$ is a monocyclic heteroaryl selected from the group consisting of pyridyl, 4-, 5- or 6-pyrimidinyl, pyrazinyl, pyridazinyl, furanyl, thienyl, pyrrolyl, pyrazolyl, imidazolyl, 4- or 5-thiazolyl, isothiazolyl, and isoxazolyl; each of which may be optionally substituted with one, two, or three substituents each independently selected from the group consisting of halo, —CN, —OR$^4$, —NR$^5$R$^{5'}$, and C$_{1-4}$alkyl optionally substituted with a substituent selected from the group consisting of fluoro, —CN, —OR$^6$, Het$^2$, —NR$^7$R$^{7'}$, and —C(=O)NR$^8$R$^{8'}$; and
Het$^2$ is a non-aromatic heterocyclyl optionally substituted with one, two, or three substituents each independently selected from the group consisting of halo, —CN, —C(=O)—C$_{1-6}$alkyl, —C(=O)Ar, —C(=O)Het$^1$, —C(=O)Het$^2$, —OR$^4$, —NR$^5$R$^{5'}$, and C$_{1-4}$alkyl optionally substituted with a substituent selected from the group consisting of fluoro, —CN, —OR$^6$, —NR$^7$R$^{7'}$, R$^{12}$ and —C(=O)NR$^8$R$^{8'}$;
wherein
R$^{12}$ is C-linked 4- to 7-membered non-aromatic heterocyclyl containing at least one nitrogen, oxygen or sulfur atom;
R$^4$, R$^5$, R$^{5'}$, R$^6$, R$^7$, R$^{7'}$, R$^8$ and R$^{8'}$ are each independently selected from the group consisting of hydrogen; —S(=O)$_2$—C$_{1-4}$alkyl; C$_{1-4}$alkyl optionally substituted with a substituent selected from the group consisting of fluoro, —C(=O)—C$_{1-4}$alkyl, —S(=O)$_2$—C$_{1-4}$alkyl, R$^{11'''}$ and —C(=O)NR$^9$R$^{9'}$; and C$_{2-4}$alkyl substituted with a substituent selected from the group consisting of —OR$^{10}$ and —NR$^{11}$R$^{11'}$; wherein
R$^9$, R$^{9'}$, R$^{10}$, R$^{11}$, R$^{11'}$ and R$^{11'''}$ are each independently selected from the group consisting of hydrogen; C$_{1-4}$alkyl; and C-linked 4- to 7-membered non-aromatic heterocyclyl containing at least one nitrogen, oxygen or sulfur atom;
R$^{14}$ is a 5-membered monocyclic heteroaryl containing at least one nitrogen atom, and optionally 1, 2 or 3 additional heteroatoms each independently selected from nitrogen, oxygen and sulfur;
Het$^3$ is selected from the group consisting of formula (b-1) and (b-2):

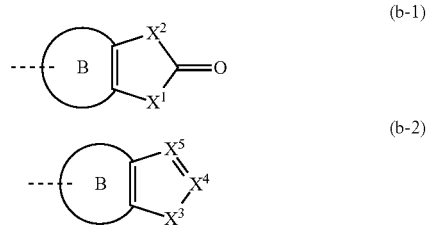

Ring B is phenyl;
X$^1$ represents CH$_2$, O or NH;
X$^2$ represents NH or O;
X$^3$ represents NH or O;
X$^4$ represents CH or N;
X$^5$ represents CH or N;
wherein one C-atom or one N-atom in the 5-membered ring of (b-1) or (b-2), including suitable C-atoms and N-atoms in the definition of X$^1$, X$^2$, X$^3$, X$^4$ and X$^5$, might be substituted with one or where possible two C$_{1-4}$alkyl groups optionally substituted with one, two or three halo atoms;
n1, n2, and m1 are each independently selected from 1 and 2;
m2 is 0 or 1; and the pharmaceutically acceptable salts and the solvates thereof.

The present invention relates in particular to compounds of Formula (I) as defined herein, and the tautomers and the stereoisomeric forms thereof, wherein $R^1$ is selected from the group consisting of $CH_3$, $CH_2F$, $CHF_2$ and $CF_3$;

$Y^1$ is N or $CR^y$;

when $Y^1$ represents N, $R^2$ is selected from the group consisting of hydrogen, $CH_3$, —$OCH_3$, —$NH_2$, and —NH—$CH_3$;

when $Y^1$ represents $CR^y$, $R^2$ is hydrogen;

$R^y$ is selected from the group consisting of hydrogen, cyano, and $C_{1-4}$alkyl optionally substituted with hydroxy, —O—$C_{1-4}$alkyl, or —O—$C_{3-6}$cycloalkyl;

$Y^2$ is $CH_2$ or O;

A is —$CR^{15a}R^{15b}$—;

$R^{15a}$ and $R^{15b}$ are each independently selected from the group consisting of hydrogen or $C_{1-4}$alkyl; in particular $R^{15a}$ and $R^{15b}$ are hydrogen;

Q is hydrogen or $C_{1-4}$alkyl optionally substituted with phenyl;

-L-$R^3$ is selected from (a), (b), (c), (d), (e), or (f):

(a) -L-$R^3$ is —$NR^AR^{1A}$, wherein $R^A$ is selected from the group consisting of hydrogen; cyclopropyl; $C_{1-4}$alkyl optionally substituted with a substituent selected from the group consisting of fluoro and —CN; and $C_{2-4}$alkyl substituted with a substituent selected from the group consisting of —$OR^{3a}$ and —$NR^{4a}R^{4aa}$;

$R^{1A}$ is selected from the group consisting of $C_{1-6}$alkyl optionally substituted with one, two or three fluoro substituents; and $C_{2-6}$alkyl substituted with a substituent selected from the group consisting of —$OR^{1a}$ and —$NR^{2a}R^{2aa}$, wherein $R^{1a}$, $R^{2a}$, $R^{2aa}$, $R^{3a}$, $R^{4a}$, and $R^{4aa}$ are each independently selected from the group consisting of hydrogen, $C_{1-4}$alkyl and cyclopropyl;

or (b) L is selected from the group consisting of —N($R^B$)—, —N($R^B$)—$CR^{1B}R^{1BB}$—, and —(N$R^B$)—$CHR^{1B}$—$CHR^{2B}$—; and $R^3$ is selected from the group consisting of Ar; $Het^1$; $Het^2$; $Het^3$; and a 7- to 10-membered saturated spirocarbobicyclic system; wherein $R^B$ is selected from the group consisting of hydrogen; cyclopropyl; $C_{1-4}$alkyl optionally substituted with a substituent selected from the group consisting of fluoro and —CN; and $C_{2-4}$alkyl substituted with a substituent selected from the group consisting of —$OR^{1b}$ and —$NR^{2b}R^{2bb}$; wherein $R^{1b}$, $R^{2b}$, and $R^{2bb}$ are each independently selected from the group consisting of hydrogen, $C_{1-4}$alkyl and cyclopropyl;

$R^{1B}$ is selected from the group consisting of hydrogen; halo; $C_{3-6}$cycloalkyl; $C_{1-4}$alkyl optionally substituted with a substituent selected from the group consisting of fluoro, hydroxy, and —CN; $C_{2-4}$alkyl substituted with a substituent selected from the group consisting of —$OR^{4B}$ and —$NR^{5B}R^{5BB}$; and C-linked 4- to 7-membered non-aromatic heterocyclyl containing at least one nitrogen, oxygen or sulfur atom; and $R^{1BB}$ is selected from the group consisting of hydrogen and methyl; or $R^{1B}$ and $R^{1BB}$ together with the carbon to which they are attached form a $C_{3-6}$cycloalkyl or a C-linked 4- to 7-membered non-aromatic heterocyclyl containing at least one nitrogen, oxygen or sulfur atom;

$R^{2B}$ is selected from the group consisting of hydrogen; —$OR^{6B}$; —$NR^{7B}R^{7BB}$; $CF_3$, $C_{1-4}$alkyl optionally substituted with a substituent selected from the group consisting of fluoro, —CN, —$OR^{4B}$, and —$NR^{5B}R^{5BB}$; and C-linked 4- to 7-membered non-aromatic heterocyclyl containing at least one nitrogen, oxygen or sulfur atom; wherein $R^{4B}$, $R^{5B}$, $R^{5BB}$, $R^{6B}$, $R^{7B}$, and $R^{7BB}$ are each independently selected from the group consisting of hydrogen; $C_{1-4}$alkyl optionally substituted with a substituent selected from the group consisting of fluoro, —CN and —C(=O)$NR^{9B}R^{9BB}$; and $C_{2-4}$alkyl substituted with a substituent selected from the group consisting of —$OR^{10B}$ and —$NR^{11B}R^{11BB}$; wherein $R^{9B}$, $R^{9BB}$, $R^{10B}$, $R^{11B}$ and $R^{11BB}$ are each independently selected from the group consisting of hydrogen; $C_{1-4}$alkyl; and C-linked 4- to 7-membered non-aromatic heterocyclyl containing at least one nitrogen, oxygen or sulfur atom;

or (c) -L-$R^3$ is selected from the group consisting of —N($R^C$)—$COR^{5C}$; and —N($R^C$)—$SO_2$—$R^{13C}$ wherein $R^C$ is selected from the group consisting of hydrogen; cyclopropyl; $C_{1-4}$alkyl optionally substituted with a substituent selected from the group consisting of fluoro and —CN; and $C_{2-4}$alkyl substituted with a substituent selected from the group consisting of —$OR^{1c}$ and —$NR^{2c}R^{2cc}$;

$R^{5C}$ and $R^{13C}$ are each independently selected from the group consisting of hydrogen; Ar; $Het^1$; $Het^2$; $Het^3$; a 7- to 10-membered saturated spirocarbobicyclic system; and $C_{1-4}$alkyl optionally substituted with —$NR^{2c}R^{2cc}$, Ar, $Het^1$ or $Het^2$; wherein $R^{1c}$, $R^{2c}$, and $R^{2cc}$ are each independently selected from the group consisting of hydrogen and $C_{1-4}$alkyl;

or (d) L is selected from —N($R^D$)—$CR^{1D}R^{1DD}$— and —N($R^D$)—$CR^{1D}R^{1DD}$—$CR^{2D}R^{2DD}$—; wherein $R^D$ is selected from the group consisting of hydrogen; $C_{1-4}$alkyl optionally substituted with a substituent selected from the group consisting of fluoro and —CN; and $C_{2-4}$alkyl substituted with a substituent selected from —$OR^{1d}$ and —$NR^{2d}R^{2dd}$; wherein $R^{1d}$, $R^{2d}$ and $R^{2dd}$ are each independently selected from the group consisting of hydrogen and $C_{1-4}$alkyl;

$R^{1D}$, $R^{1DD}$, $R^{2D}$ and $R^{2DD}$ are each independently selected from the group consisting of hydrogen and $C_{1-4}$alkyl; and $R^3$ is selected from the group consisting of

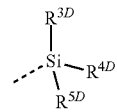

and

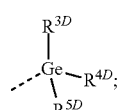

wherein $R^{3D}$, $R^{4D}$, and $R^{5D}$ are each independently selected from the group consisting of $C_{1-6}$alkyl optionally substituted with a —OH, —$OC_{1-6}$alkyl, or a —$NH_2$ substituent;

or (e) -L-R³ is

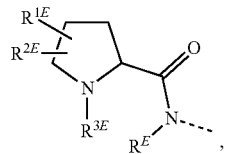

wherein
R$^E$ is selected from the group consisting of hydrogen and C$_{1-4}$alkyl;
R$^{1E}$ is selected from the group consisting of hydrogen, fluoro and C$_{1-4}$alkyl; and
R$^{2E}$ is selected from the group consisting of fluoro, —OC$_{1-4}$alkyl, and C$_{1-4}$alkyl optionally substituted with 1, 2 or 3 fluoro substituents; or R$^{1E}$ and R$^{2E}$ are bound to the same carbon atom and together form a C$_{3-5}$cycloalkyl or a C-linked 4- to 6-membered heterocyclyl containing an oxygen atom; and
R$^{3E}$ is selected from the group consisting of hydrogen; C$_{1-4}$alkyl optionally substituted with a fluoro or a —CN substituent; and C$_{2-4}$alkyl substituted with a substituent selected from the group consisting of —OR$^{4E}$ and —NR$^{5E}$R$^{5EE}$; wherein
R$^{4E}$, R$^{5E}$ and R$^{5EE}$ are each independently selected from the group consisting of hydrogen; C$_{1-4}$alkyl optionally substituted with a substituent selected from the group consisting of fluoro, —CN, and —C(=O)NR$^{6E}$R$^{6EE}$; C$_{2-4}$alkyl substituted with a substituent selected from the group consisting of —OR$^{7E}$ and —NR$^{8E}$R$^{8EE}$; and C-linked 4- to 7-membered non-aromatic heterocyclyl containing at least one nitrogen, oxygen or sulfur atom; wherein R$^{6E}$, R$^{6EE}$, R$^{7E}$, R$^{8E}$ and R$^{8EE}$ are each independently selected from the group consisting of hydrogen and C$_{1-4}$alkyl;

or (f) -L-R³ is a radical

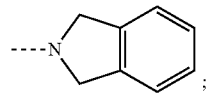

Ar is phenyl optionally substituted with one, two, or three substituents each independently selected from the group consisting of halo, —CN, —OR⁴, —NR⁵R⁵', —C(=O)NR⁵R⁵', —S(=O)₂—NR⁵R⁵', R¹⁴, CF₃, and C$_{1-4}$alkyl optionally substituted with a substituent selected from the group consisting of fluoro, —CN, —OR⁶, —NR⁷R⁷', and —C(=O)NR⁸R⁸';

Het¹ is a monocyclic heteroaryl selected from the group consisting of pyridyl, 4-, 5- or 6-pyrimidinyl, pyrazinyl, pyridazinyl, furanyl, thienyl, pyrrolyl, pyrazolyl, imidazolyl, 4- or 5-thiazolyl, isothiazolyl, and isoxazolyl; each of which may be optionally substituted with one, two, or three substituents each independently selected from the group consisting of halo, —CN, —OR⁴, —NR⁵R⁵', and C$_{1-4}$alkyl optionally substituted with a substituent selected from the group consisting of fluoro, —CN, —OR⁶, Het², —NR⁷R⁷', and —C(=O)NR⁸R⁸'; and Het² is a non-aromatic heterocyclyl optionally substituted with one, two, or three substituents each independently selected from the group consisting of halo, —CN, —C(=O)—C$_{1-6}$alkyl, —C(=O)Ar, —C(=O)Het¹, —C(=O)Het², —OR⁴, —NR⁵R⁵', and C$_{1-4}$alkyl optionally substituted with a substituent selected from the group consisting of fluoro, —CN, —OR⁶, —NR⁷R⁷', R¹² and —C(=O)NR⁸R⁸';
wherein
R¹² is C-linked 4- to 7-membered non-aromatic heterocyclyl containing at least one nitrogen, oxygen or sulfur atom;
R⁴, R⁵, R⁵', R⁶, R⁷, R⁷', R⁸ and R⁸' are each independently selected from the group consisting of hydrogen; —S(=O)₂—C$_{1-4}$alkyl; C$_{1-4}$alkyl optionally substituted with a substituent selected from the group consisting of fluoro, —C(=O)—C$_{1-4}$alkyl, —S(=O)₂—C$_{1-4}$alkyl, R¹¹'' and —C(=O)NR⁹R⁹'; and C$_{2-4}$alkyl substituted with a substituent selected from the group consisting of —OR¹⁰ and —NR¹¹R¹¹'; wherein
R⁹, R⁹', R¹⁰, R¹¹, R¹¹' and R¹¹'' are each independently selected from the group consisting of hydrogen; C$_{1-4}$alkyl; and C-linked 4- to 7-membered non-aromatic heterocyclyl containing at least one nitrogen, oxygen or sulfur atom;
R¹⁴ is a 5-membered monocyclic heteroaryl containing at least one nitrogen atom, and optionally 1, 2 or 3 additional heteroatoms each independently selected from nitrogen, oxygen and sulfur;

Het³ is selected from the group consisting of formula (b-1) and (b-2):

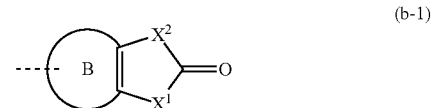

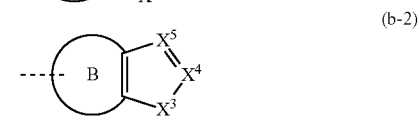

Ring B is phenyl;
X¹ represents CH₂, O or NH;
X² represents NH or O;
X³ represents NH or O;
X⁴ represents CH or N;
X⁵ represents CH or N;
wherein one C-atom or one N-atom in the 5-membered ring of (b-1) or (b-2), including suitable C-atoms and N-atoms in the definition of X¹, X², X³, X⁴ and X⁵, might be substituted with one or where possible two C$_{1-4}$alkyl groups optionally substituted with one, two or three halo atoms;
n1, n2, and m1 are each independently selected from 1 and 2;
m2 is 0 or 1;
and the pharmaceutically acceptable salts and the solvates thereof.

The present invention relates in particular to compounds of Formula (I) as defined herein, and the tautomers and the stereoisomeric forms thereof, wherein
R¹ is CF₃;
Y¹ is N;
R² is selected from the group consisting of hydrogen, CH₃ and —NH₂;
Y² is CH₂;
A is a covalent bond or —CR$^{15a}$R$^{15b}$—;

$R^{15a}$ and $R^{15b}$ are hydrogen;

Q is hydrogen;

-L-$R^3$ is selected from (a), (b), (c):

(a) -L-$R^3$ is —$NR^AR^{14}$, wherein
$R^A$ is hydrogen;
$R^{14}$ is $C_{1-6}$alkyl;

or (b) L is selected from the group consisting of —$N(R^B)$—, and —$N(R^B)$—$CR^{1B}R^{1BB}$—; and $R^3$ is selected from the group consisting of Ar; Het$^1$; and Het$^3$; wherein
$R^B$ is hydrogen;
$R^{1B}$ is selected from the group consisting of hydrogen and $C_{1-4}$alkyl; and
$R^{1BB}$ is selected from the group consisting of hydrogen and methyl; or $R^{1B}$ and $R^{1BB}$ together with the carbon to which they are attached form a $C_{3-6}$cycloalkyl;

or (c) -L-$R^3$ is selected from the group consisting of —$N(R^C)$—$COR^{5C}$; and —$N(R^C)$—$SO_2$—$R^{13C}$ wherein
$R^C$ is selected from the group consisting of hydrogen and $C_{1-4}$alkyl;
$R^{5C}$ and $R^{13C}$ are each independently selected from the group consisting of Ar; Het; and $C_{1-4}$alkyl optionally substituted with Het$^2$;

Ar is phenyl optionally substituted with one, two, or three substituents each independently selected from the group consisting of halo, —CN, —$NR^5R^{5'}$, —$C(=O)NR^5R^{5'}$, $R^{14}$, $CF_3$, and $C_{1-4}$alkyl optionally substituted with a —CN substituent;

Het$^1$ is pyrazolyl optionally substituted with one, two, or three $C_{1-4}$alkyl substituents; and Het$^2$ is a non-aromatic heterocyclyl;

wherein
$R^5$ and $R^{5'}$ are each independently selected from the group consisting of hydrogen; —$S(=O)_2$—$C_{1-4}$alkyl; and $C_{1-4}$alkyl;
$R^{14}$ is pyrazolyl, in particular pyrazolyl attached to the remainder of the molecule via a C-atom;

Het$^3$ is selected from the group consisting of formula (b-1) and (b-2):

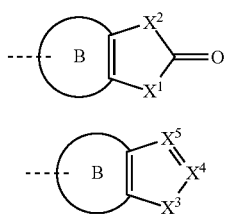

Ring B is phenyl;
$X^1$ represents O or NH;
$X^2$ represents NH;
$X^3$ represents NH or O;
$X^4$ represents CH or N;
$X^5$ represents CH or N;
wherein one C-atom or one N-atom in the 5-membered ring of (b-1) or (b-2), including suitable C-atoms and N-atoms in the definition of $X^1$, $X^2$, $X^3$, $X^4$ and $X^5$, might be substituted with one or where possible two $C_{1-4}$alkyl groups optionally substituted with one, two or three halo atoms;

n1, n2, and m1 are each independently selected from 1 and 2;

m2 is 0 or 1;

and the pharmaceutically acceptable salts and the solvates thereof.

The present invention relates in particular to compounds of Formula (I) as defined herein, and the tautomers and the stereoisomeric forms thereof, wherein $R^1$ is $CF_3$;
$Y^1$ is N;
$R^2$ is hydrogen;
$Y^2$ is $CH_2$;
A is a covalent bond or —$CR^{15a}R^{15b}$—;
$R^{15a}$ and $R^{15b}$ are hydrogen;
Q is hydrogen;

-L-$R^3$ is selected from (a), (b), (c):

(a) -L-$R^3$ is —$NR^AR^{14}$, wherein
$R^A$ is hydrogen;
$R^{14}$ is $C_{1-6}$alkyl;

or (b) L is selected from the group consisting of —$N(R^B)$—, and —$N(R^B)$—$CR^{1B}R^{1BB}$—; and $R^3$ is selected from the group consisting of Ar; Het$^1$; and Het$^3$; wherein
$R^B$ is hydrogen;
$R^{1B}$ is hydrogen; and
$R^{1BB}$ is selected from the group consisting of hydrogen and methyl;

or (c) -L-$R^3$ is selected from the group consisting of —$N(R^C)$—$COR^{5C}$; and —$N(R^C)$—$SO_2$—$R^{13C}$ wherein
$R^C$ is selected from the group consisting of hydrogen and $C_{1-4}$alkyl;
$R^{5C}$ and $R^{13C}$ are each independently selected from the group consisting of Ar; Het; and $C_{1-4}$alkyl optionally substituted with Het$^2$;

Ar is phenyl optionally substituted with one, two, or three substituents each independently selected from the group consisting of halo, —CN, —$NR^5R^{5'}$, —$C(=O)NR^5R^{5'}$, $R^{14}$, $CF_3$, and $C_{1-4}$alkyl optionally substituted with a —CN substituent;

Het$^1$ is pyrazolyl optionally substituted with one, two, or three $C_{1-4}$alkyl substituents; and Het$^2$ is a non-aromatic heterocyclyl;

wherein
$R^5$ and $R^{5'}$ are each independently selected from the group consisting of hydrogen; —$S(=O)_2$—$C_{1-4}$alkyl; and $C_{1-4}$alkyl;
$R^{14}$ is pyrazolyl, in particular pyrazolyl attached to the remainder of the molecule via a C-atom;

Het$^3$ is selected from the group consisting of formula (b-1) and (b-2):

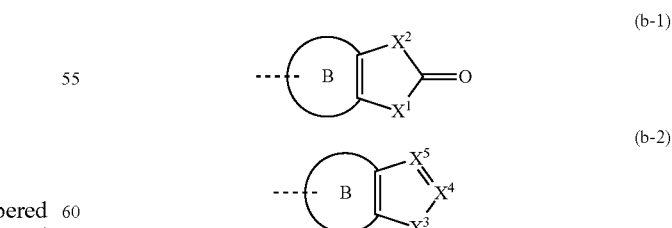

Ring B is phenyl;
$X^1$ represents O or NH;
$X^2$ represents NH;
$X^3$ represents NH;
$X^4$ represents N;

$X^5$ represents CH;

n1, n2, and m1 are each independently selected from 1 and 2;

m2 is 0 or 1;

and the pharmaceutically acceptable salts and the solvates thereof.

The present invention relates in particular to compounds of Formula (I) as defined herein, and the tautomers and the stereoisomeric forms thereof, wherein $R^1$ is $CF_3$;

$Y^1$ is N;

$R^2$ is hydrogen;

$Y^2$ is $CH_2$;

A is a covalent bond;

Q is hydrogen;

-L-$R^3$ is (b):

(b) L is selected from the group consisting of —N($R^B$)—, and —N($R^B$)—$CR^{1B}R^{1BB}$—; and $R^3$ is selected from the group consisting of Ar and $Het^3$; wherein $R^B$ is hydrogen;

$R^{1B}$ is hydrogen; and $R^{1BB}$ is hydrogen;

Ar is phenyl optionally substituted with a $C_{1-4}$alkyl optionally substituted with a —CN substituent;

$Het^3$ is (b-1):

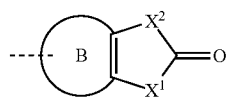

Ring B is phenyl;

$X^1$ represents O;

$X^2$ represents NH;

n1 is 1;

n2 and m1 are each independently selected from 1 and 2;

m2 is 0 or 1;

and the pharmaceutically acceptable salts and the solvates thereof.

The present invention relates in particular to compounds of Formula (I) as defined herein, and the tautomers and the stereoisomeric forms thereof, wherein $R^1$ is $CF_3$;

$Y^1$ is $CR^y$;

$R^2$ is selected from the group consisting of hydrogen, —$OCH_3$, and —NH—$CH_3$;

$R^y$ is hydrogen;

$Y^2$ is $CH_2$;

A is a covalent bond;

Q is hydrogen;

-L-$R^3$ is (b):

(b) L is selected from the group consisting of —N($R^B$)—, and —N($R^B$)—$CR^{1B}R^{1BB}$—; and $R^3$ is selected from the group consisting of Ar; $Het^1$; and $Het^3$; wherein $R^B$ is hydrogen;

$R^{1B}$ is hydrogen; and $R^{1BB}$ is hydrogen;

Ar is phenyl optionally substituted with one, two, or three substituents each independently selected from the group consisting of halo, —$OR^4$, —C(=O)$NR^5R^{5'}$, $Het^4$, —O-$Het^4$, —$NR^5$—$Het^4$, and $C_{1-4}$alkyl optionally substituted with one or two —CN substituents;

$Het^1$ is pyridyl, which may be optionally substituted with one, two, or three —C(=O)$NR^5R^5$ substituents;

wherein $R^4$, $R^5$, and $R^{5'}$ are each independently selected from the group consisting of hydrogen; $C_{1-4}$alkyl substituted with a $R^{16}$ substituent; and $C_{2-4}$alkyl substituted with a substituent selected from the group consisting of —$OR^{10}$ and —$NR^{11}R^{11'}$; wherein $R^{10}$, $R^{11}$, and $R^{11'}$ are each independently selected from the group consisting of hydrogen; and $C_{1-4}$alkyl;

$R^{16}$ is N-linked 4- to 7-membered non-aromatic heterocyclyl containing at least one N-atom and optionally one additional heteroatom selected from nitrogen, oxygen and sulfur;

$R^{14}$ is a 5-membered monocyclic heteroaryl containing at least one nitrogen atom, and optionally 1, 2 or 3 additional heteroatoms each independently selected from nitrogen, oxygen and sulfur;

$Het^3$ is selected from the group consisting of formula (b-1):

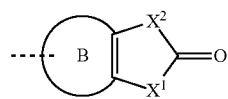

Ring B is phenyl;

$X^1$ represents O or NH;

$X^2$ represents NH;

wherein one C-atom or one N-atom in the 5-membered ring of (b-1), including suitable C-atoms and N-atoms in the definition of $X^1$ and $X^2$, might be substituted with one or where possible two $C_{1-4}$alkyl groups optionally substituted with one, two or three cyano substituents;

$Het^4$ is a 4- to 7-membered non-aromatic heterocyclyl containing at least one nitrogen, oxygen or sulfur atom, wherein said heterocyclyl is optionally substituted with one, two, or three $C_{1-4}$alkyl substituents;

n1, n2, and m1 are each independently selected from 1 and 2;

m2 is 0 or 1;

and the pharmaceutically acceptable salts and the solvates thereof.

Another embodiment of the present invention relates to those compounds of Formula (I) and the pharmaceutically acceptable salts, and the solvates thereof, or any subgroup thereof as mentioned in any of the other embodiments wherein $R^1$ is $CF_3$;

$R^2$ is hydrogen;

$Y^1$ is N;

$Y^2$ is $CH_2$.

Another embodiment of the present invention relates to those compounds of Formula (I) and the pharmaceutically acceptable salts, and the solvates thereof, or any subgroup thereof as mentioned in any of the other embodiments wherein $R^1$ is $CF_3$;

$R^2$ is hydrogen;

$Y^1$ is N.

Another embodiment of the present invention relates to those compounds of Formula (I) and the pharmaceutically acceptable salts, and the solvates thereof, or any subgroup thereof as mentioned in any of the other embodiments wherein A is a covalent bond.

Another embodiment of the present invention relates to those compounds of Formula (I) and the pharmaceutically acceptable salts, and the solvates thereof, or any subgroup thereof as mentioned in any of the other embodiments wherein A is —$CR^{15a}R^{15b}$—.

Another embodiment of the present invention relates to those compounds of Formula (I) and the pharmaceutically acceptable salts, and the solvates thereof, or any subgroup thereof as mentioned in any of the other embodiments wherein A is —$CR^{15a}R^{15b}$—; $R^{15a}$ and $R^{15b}$ are hydrogen.

Another embodiment of the present invention relates to those compounds of Formula (I) and the pharmaceutically acceptable salts, and the solvates thereof, or any subgroup thereof as mentioned in any of the other embodiments wherein $R^{15a}$ and $R^{15b}$ are hydrogen.

In an embodiment, the present invention relates to those compounds of Formula (I) and the pharmaceutically acceptable salts, and the solvates thereof, or any subgroup thereof as mentioned in any of the other embodiments, wherein
-L-$R^3$ is selected from (a), (b), (c), (d), or (e).

In an embodiment, the present invention relates to those compounds of Formula (I) and the pharmaceutically acceptable salts, and the solvates thereof, or any subgroup thereof as mentioned in any of the other embodiments, wherein -L-$R^3$ is (a).

In an embodiment, the present invention relates to those compounds of Formula (I) and the pharmaceutically acceptable salts, and the solvates thereof, or any subgroup thereof as mentioned in any of the other embodiments, wherein -L-$R^3$ is (b).

In an embodiment, the present invention relates to those compounds of Formula (I) and the pharmaceutically acceptable salts, and the solvates thereof, or any subgroup thereof as mentioned in any of the other embodiments, wherein -L-$R^3$ is (c).

In an embodiment, the present invention relates to those compounds of Formula (I) and the pharmaceutically acceptable salts, and the solvates thereof, or any subgroup thereof as mentioned in any of the other embodiments, wherein-L-$R^3$ is (d).

In an embodiment, the present invention relates to those compounds of Formula (I) and the pharmaceutically acceptable salts, and the solvates thereof, or any subgroup thereof as mentioned in any of the other embodiments, wherein -L-$R^3$ is (e).

In an embodiment, the present invention relates to those compounds of Formula (I) and the pharmaceutically acceptable salts, and the solvates thereof, or any subgroup thereof as mentioned in any of the other embodiments, wherein -L-$R^3$ is (f).

In an embodiment, the present invention relates to those compounds of Formula (I) and the pharmaceutically acceptable salts, and the solvates thereof, or any subgroup thereof as mentioned in any of the other embodiments, wherein -L-$R^3$ is (b);
$R^3$ is selected from the group consisting of Ar; $Het^3$; $R^{17}$; and a 7- to 10-membered saturated spirocarbobicyclic system;
Ar is phenyl optionally substituted with one, two, or three substituents each independently selected from the group consisting of halo, —CN, —$OR^4$, —$NR^5R^{5'}$, —C(=O)$NR^5R^{5'}$, $Het^4$, —O-$Het^4$, —$NR^5$—$Het^4$, —C(=O)—$Het^4$, —S(=O)$_2$—$Het^4$, —S(=O)$_2$—$NR^5R^{5'}$, —S(=O)$_2$—$C_{1-4}$alkyl, $R^{14}$, $CF_3$, and $C_{1-4}$alkyl optionally substituted with one or two substituents each independently selected from the group consisting of fluoro, —CN, —$OR^6$, —$NR^7R^{7'}$, —S(=O)$_2$—$C_{1-4}$alkyl and —C(=O)$NR^8R^{8'}$;
$R^4$, $R^5$, $R^{5'}$, $R^6$, $R^7$, $R^{7'}$, $R^8$ and $R^{8'}$ are each independently selected from the group consisting of hydrogen; —C(=O)—$C_{1-4}$alkyl; —S(=O)$_2$—$C_{1-4}$alkyl; $C_{1-4}$alkyl optionally substituted with a substituent selected from the group consisting of fluoro, —C(=O)—$C_{1-4}$alkyl, —S(=O)$_2$—$C_{1-4}$alkyl, $R^{11'}$, and —C(=O)$NR^9R^{9'}$; and $C_{2-4}$alkyl substituted with a substituent selected from the group consisting of —$OR^{10}$, —$NR^{11}R^{11'}$ and $R^{16}$; wherein
$R^9$, $R^{9'}$, $R^{10}$, $R^{11}$, $R^{11'}$ and $R^{11''}$ are each independently selected from the group consisting of hydrogen; $C_{1-4}$alkyl; and —S(=O)$_2$—$C_{1-4}$alkyl;
$R^{16}$ is N-linked 4- to 7-membered non-aromatic heterocyclyl containing at least one N-atom and optionally one additional heteroatom selected from nitrogen, oxygen and sulfur;
$R^{14}$ is a 5-membered monocyclic heteroaryl containing at least one nitrogen atom, and optionally 1, 2 or 3 additional heteroatoms each independently selected from nitrogen, oxygen and sulfur;
$Het^3$ is selected from the group consisting of formula (b-1):

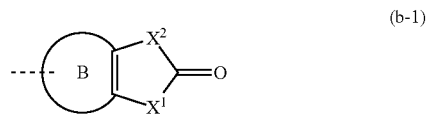

Ring B is phenyl;
$X^1$ represents O or NH;
$X^2$ represents NH;
wherein one N-atom in the 5-membered ring of (b-1) or (b-2), including suitable N-atoms in the definition of $X^1$ and $X^2$, might be substituted with one or where possible two $C_{1-4}$alkyl groups;
$Het^4$ is a 4- to 7-membered non-aromatic heterocyclyl containing at least one nitrogen, oxygen or sulfur atom, wherein said heterocyclyl is optionally substituted with one, two, or three $C_{1-4}$alkyl substituents;
$R^{17}$ is $C_{3-6}$cycloalkyl optionally substituted with one or more substituents selected from the group consisting of halo, —CN, —$OR^4$, —$NR^5R^{5'}$, —C(=O)$NR^5R^{5'}$, and $C_{1-4}$alkyl optionally substituted with a substituent selected from the group consisting of fluoro, —CN, —$OR^6$, —$NR^7R^{7'}$, and —C(=O)$NR^8R^{8'}$.

In an embodiment, the present invention relates to those compounds of Formula (I) and the pharmaceutically acceptable salts, and the solvates thereof, or any subgroup thereof as mentioned in any of the other embodiments, wherein -L-$R^3$ is (b);
$R^3$ is selected from the group consisting of Ar; $Het^3$; $R^{17}$; and a 7- to 10-membered saturated spirocarbobicyclic system;
Ar is phenyl optionally substituted with one, two, or three substituents each independently selected from the group consisting of halo, —CN, —$OR^4$, —$NR^5R^{5'}$, —C(=O) $NR^5R^{5'}$, $Het^4$, —O-$Het^4$, —$NR^5$—$Het^4$, —C(=O)—$Het^4$, —S(=O)$_2$—$Het^4$, —S(=O)$_2$—$NR^5R^{5'}$, —S(=O)$_2$—$C_{1-4}$ alkyl, $R^{14}$, $CF_3$, and $C_{1-4}$alkyl optionally substituted with one or two substituents each independently selected from the group consisting of fluoro, —CN, —$OR^6$, —$NR^7R^{7'}$, —S(=O)$_2$—$C_{1-4}$alkyl and —C(=O)$NR^8R^{8'}$;
$R^4$, $R^5$, $R^{5'}$, $R^6$, $R^7$, $R^{7'}$, $R^8$ and $R^{8'}$ are each independently selected from the group consisting of hydrogen; —C(=O)—$C_{1-4}$alkyl; —S(=O)$_2$—$C_{1-4}$alkyl; $C_{1-4}$alkyl optionally substituted with a substituent selected from the group consisting of fluoro, —C(=O)—$C_{1-4}$alkyl, —S(=O)$_2$—$C_{1-4}$alkyl, $R^{11''}$, and —C(=O)

$NR^9R^{9'}$; and $C_{2-4}$alkyl substituted with a substituent selected from the group consisting of —$OR^{10}$, —$NR^{11}R^{11'}$ and $R^{16}$;
wherein
$R^9$, $R^{9'}$, $R^{10}$, $R^{11}$, $R^{11'}$ and $R^{11''}$ are each independently selected from the group consisting of hydrogen; $C_{1-4}$alkyl; and —$S(=O)_2$—$C_{1-4}$alkyl;
$R^{16}$ is N-linked 4- to 7-membered non-aromatic heterocyclyl containing at least one N-atom and optionally one additional heteroatom selected from nitrogen, oxygen and sulfur;
$R^{14}$ is a 5-membered monocyclic heteroaryl containing at least one nitrogen atom, and optionally 1, 2 or 3 additional heteroatoms each independently selected from nitrogen, oxygen and sulfur;
Het³ is selected from the group consisting of formula (b-1):

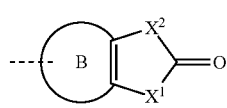

Ring B is phenyl;
$X^1$ represents O or NH;
$X^2$ represents NH; wherein one N-atom in the 5-membered ring of (b-1) or (b-2), including suitable N-atoms in the definition of $X^1$ and $X^2$, might be substituted with one or where possible two $C_{1-4}$alkyl groups;
Het⁴ is a 4- to 7-membered non-aromatic heterocyclyl containing at least one nitrogen, oxygen or sulfur atom, wherein said heterocyclyl is substituted with one, two, or three $C_{1-4}$alkyl substituents;
$R^{17}$ is $C_{3-6}$cycloalkyl optionally substituted with one or more substituents selected from the group consisting of halo, —CN, —$OR^4$, —$NR^5R^{5'}$, —$C(=O)NR^5R^{5'}$, and $C_{1-4}$alkyl optionally substituted with a substituent selected from the group consisting of fluoro, —CN, —$OR^6$, —$NR^7R^{7'}$, and —$C(=O)NR^8R^{8'}$.

In an embodiment, the present invention relates to those compounds of Formula (I) and the pharmaceutically acceptable salts, and the solvates thereof, or any subgroup thereof as mentioned in any of the other embodiments, wherein -L-$R^3$ is (b); $R^3$ is selected from the group consisting of Ar; and a 7- to 10-membered saturated spirocarbobicyclic system.

In an embodiment, the present invention relates to those compounds of Formula (I) and the pharmaceutically acceptable salts, and the solvates thereof, or any subgroup thereof as mentioned in any of the other embodiments, wherein -L-$R^3$ is (b); $R^3$ is Ar.

In an embodiment, the present invention relates to those compounds of Formula (I) and the pharmaceutically acceptable salts, and the solvates thereof, or any subgroup thereof as mentioned in any of the other embodiments, wherein -L-$R^3$ is (b); $R^3$ is Ar;
Ar is phenyl optionally substituted with one, two, or three substituents each independently selected from the group consisting of halo, —CN, —$OR^4$, —$NR^5R^{5'}$, —$C(=O)NR^5R^{5'}$, —$S(=O)_2$—$NR^5R^{5'}$, —$S(=O)_2$—$C_{1-4}$alkyl, $CF_3$, and $C_{1-4}$alkyl optionally substituted with one or two substituents each independently selected from the group consisting of fluoro, —CN, —$OR^6$, —$NR^7R^{7'}$, —$S(=O)_2$—$C_{1-4}$ alkyl and —$C(=O)NR^8R^{8'}$.

In an embodiment, the present invention relates to those compounds of Formula (I) and the pharmaceutically acceptable salts, and the solvates thereof, or any subgroup thereof as mentioned in any of the other embodiments, wherein -L-$R^3$ is (b);
$R^3$ is Ar;
Ar is phenyl optionally substituted with one, two, or three substituents each independently selected from the group consisting of halo, —CN, —$OR^4$, —$NR^5R^{5'}$, —$C(=O)NR^5R^{5'}$, —$S(=O)_2$—$NR^5R^{5'}$, —$S(=O)_2$—$C_{1-4}$alkyl, $CF_3$, and
$C_{1-4}$alkyl optionally substituted with one or two substituents each independently selected from the group consisting of fluoro, —CN, —$OR^6$, —$NR^7R^{7'}$, —$S(=O)_2$—$C_{1-4}$alkyl and —$C(=O)NR^8R^{8'}$;
$R^4$, $R^5$, $R^{5'}$, $R^6$, $R^7$, $R^{7'}$, $R^8$ and $R^{8'}$ are each independently selected from the group consisting of hydrogen; —$C(=O)$—$C_{1-4}$alkyl; —$S(=O)_2$—$C_{1-4}$alkyl; $C_{1-4}$alkyl optionally substituted with a substituent selected from the group consisting of fluoro, —$C(=O)$—$C_{1-4}$alkyl, —$S(=O)_2$—$C_{1-4}$alkyl, $R^{11'}$, and —$C(=O)NR^9R^{9'}$; and $C_{2-4}$alkyl substituted with a substituent selected from the group consisting of —$OR^{10}$ and —$NR^{11}R^{11'}$; wherein
$R^9$, $R^{9'}$, $R^{10}$, $R^{11}$, $R^{11'}$ and $R^{11''}$ are each independently selected from the group consisting of hydrogen; $C_{1-4}$alkyl; and —$S(=O)_2$—$C_{1-4}$alkyl.

In an embodiment, the present invention relates to those compounds of Formula (I) and the pharmaceutically acceptable salts, and the solvates thereof, or any subgroup thereof as mentioned in any of the other embodiments, wherein n1 is 2, n2 is 1, m1 is 1, and m2 is 0.

In an embodiment, the present invention relates to those compounds of Formula (I) and the pharmaceutically acceptable salts, and the solvates thereof, or any subgroup thereof as mentioned in any of the other embodiments, wherein n1 is 1, n2 is 1, m1 is 1, and m2 is 1.

In an embodiment, the present invention relates to those compounds of Formula (I) and the pharmaceutically acceptable salts, and the solvates thereof, or any subgroup thereof as mentioned in any of the other embodiments, wherein Het² is morpholinyl, in particular 1-morpholinyl.

In an embodiment, the present invention relates to those compounds of Formula (I) and the pharmaceutically acceptable salts, and the solvates thereof, or any subgroup thereof as mentioned in any of the other embodiments, wherein Het² is morpholinyl, in particular 1-morpholinyl;
optionally substituted as defined in any of the other embodiments.

In an embodiment, the present invention relates to those compounds of Formula (I) and the pharmaceutically acceptable salts, and the solvates thereof, or any subgroup thereof as mentioned in any of the other embodiments, wherein Het² is a monocyclic non-aromatic heterocyclyl.

In an embodiment, the present invention relates to those compounds of Formula (I) and the pharmaceutically acceptable salts, and the solvates thereof, or any subgroup thereof as mentioned in any of the other embodiments, wherein Het² is a monocyclic non-aromatic heterocyclyl optionally substituted as defined in any of the other embodiments.

In an embodiment, the present invention relates to those compounds of Formula (I) and the pharmaceutically acceptable salts, and the solvates thereof, or any subgroup thereof as mentioned in any of the other embodiments, wherein Het² is a bicyclic non-aromatic heterocyclyl.

In an embodiment, the present invention relates to those compounds of Formula (I) and the pharmaceutically acceptable salts, and the solvates thereof, or any subgroup thereof as mentioned in any of the other embodiments, wherein Het$^2$ is a bicyclic non-aromatic heterocyclyl optionally substituted as defined in any of the other embodiments.

In an embodiment, the present invention relates to those compounds of Formula (I) and the pharmaceutically acceptable salts, and the solvates thereof, or any subgroup thereof as mentioned in any of the other embodiments, wherein Het$^3$ is selected from

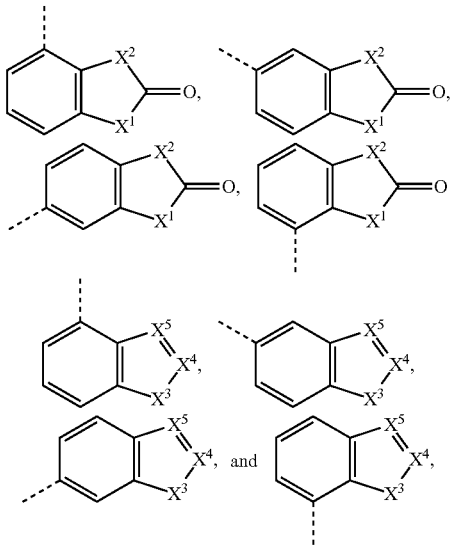

wherein $X^1$, $X^2$, $X^3$, $X^4$ and $X^5$ are defined as in any of the other embodiments, and which might be substituted as defined in any of the other embodiments.

In an embodiment, the present invention relates to those compounds of Formula (I) and the pharmaceutically acceptable salts, and the solvates thereof, or any subgroup thereof as mentioned in any of the other embodiments, wherein Het$^3$ is selected from

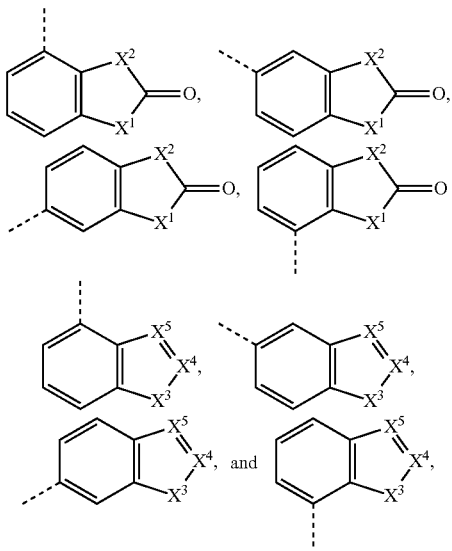

$X^1$ represents CH$_2$, O or NH;
$X^2$ represents NH or O;
$X^3$ represents NH or O;
$X^4$ represents CH or N;
$X^5$ represents CH or N;

wherein one C-atom or one N-atom in the 5-membered ring, including suitable C-atoms and N-atoms in the definition of $X^1$, $X^2$, $X^3$, $X^4$ and $X^5$, might be substituted with one or where possible two $C_{1-4}$alkyl groups optionally substituted with one, two or three substituents each independently selected from the group consisting of halo, cyano, —C(=O)NR$^5$R$^{5'}$, and Het$^4$.

In an embodiment, the present invention relates to those compounds of Formula (I) and the pharmaceutically acceptable salts, and the solvates thereof, or any subgroup thereof as mentioned in any of the other embodiments, wherein Het$^3$ is selected from

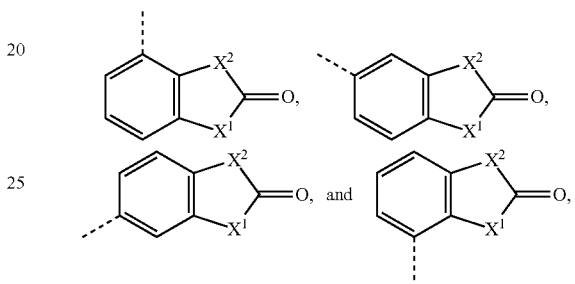

wherein $X^1$ and $X^2$ are defined as in any of the other embodiments, and which might be substituted as defined in any of the other embodiments.

In an embodiment, the present invention relates to those compounds of Formula (I) and the pharmaceutically acceptable salts, and the solvates thereof, or any subgroup thereof as mentioned in any of the other embodiments, wherein Het$^3$ is selected from

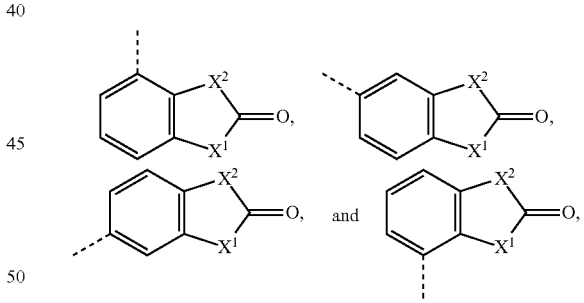

$X^1$ represents CH$_2$, O or NH;
$X^2$ represents NH or O;

wherein one C-atom or one N-atom in the 5-membered ring, including suitable C-atoms and N-atoms in the definition of $X^1$ and $X^2$, might be substituted with one or where possible two $C_{1-4}$alkyl groups optionally substituted with one, two or three substituents each independently selected from the group consisting of halo, cyano, —C(=O)NR$^5$R$^{5'}$, and Het$^4$.

In an embodiment, the present invention relates to those compounds of Formula (I) and the pharmaceutically acceptable salts, and the solvates thereof, or any subgroup thereof as mentioned in any of the other embodiments, wherein Het$^3$ is selected from

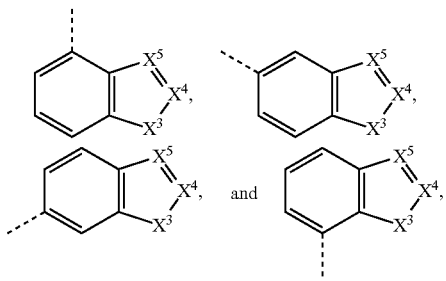

wherein $X^3$, $X^4$ and $X^5$ are defined as in any of the other embodiments, and which might be substituted as defined in any of the other embodiments.

In an embodiment, the present invention relates to those compounds of Formula (I) and the pharmaceutically acceptable salts, and the solvates thereof, or any subgroup thereof as mentioned in any of the other embodiments, wherein $Het^3$ is selected from

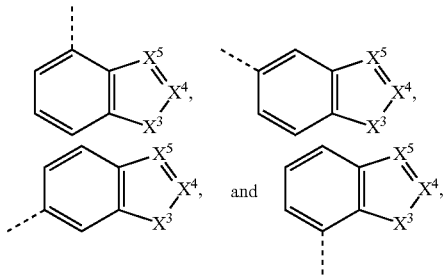

$X^3$ represents NH or O;
$X^4$ represents CH or N;
$X^5$ represents CH or N;
wherein one C-atom or one N-atom in the 5-membered ring, including suitable C-atoms and N-atoms in the definition of $X^3$, $X^4$ and $X^5$, might be substituted with one or where possible two $C_{1-4}$alkyl groups optionally substituted with one, two or three substituents each independently selected from the group consisting of halo, cyano, —C(=O)$NR^5R^{5'}$, and $Het^4$.

In an embodiment, the present invention relates to those compounds of Formula (I) and the pharmaceutically acceptable salts, and the solvates thereof, or any subgroup thereof as mentioned in any of the other embodiments, wherein $Het^4$ is always substituted.

In an embodiment, the present invention relates to those compounds of Formula (I) and the pharmaceutically acceptable salts, and the solvates thereof, or any subgroup thereof as mentioned in any of the other embodiments, wherein $Het^4$ is a 4- to 7-membered non-aromatic heterocyclyl containing at least one nitrogen, oxygen or sulfur atom, wherein said heterocyclyl is substituted with one, two, or three $C_{1-4}$alkyl substituents.

In an embodiment, the present invention relates to those compounds of Formula (I) and the pharmaceutically acceptable salts, and the solvates thereof, or any subgroup thereof as mentioned in any of the other embodiments, wherein $Het^4$ is morpholinyl, imidazolidinyl, piperidinyl, morpholinyl, or oxazolidinyl; in particular 1-morpholinyl, 1-imidazolidinyl, 1-piperidinyl, 1-morpholinyl or 3-oxazolidinyl.

In an embodiment, the present invention relates to those compounds of Formula (I) and the pharmaceutically acceptable salts, and the solvates thereof, or any subgroup thereof as mentioned in any of the other embodiments, wherein $Het^4$ is morpholinyl, imidazolidinyl, piperidinyl, morpholinyl, or oxazolidinyl; in particular 1-morpholinyl, 1-imidazolidinyl, 1-piperidinyl, 1-morpholinyl or 3-oxazolidinyl; each of which may be optionally substituted as defined in any of the other embodiments.

In an embodiment, the present invention relates to those compounds of Formula (I) and the pharmaceutically acceptable salts, and the solvates thereof, or any subgroup thereof as mentioned in any of the other embodiments, wherein $Het^4$ is morpholinyl, imidazolidinyl, piperidinyl, morpholinyl, or oxazolidinyl; in particular 1-morpholinyl, 1-imidazolidinyl, 1-piperidinyl, 1-morpholinyl or 3-oxazolidinyl; each of which is substituted with one, two, or three substituents each independently selected from the group consisting of halo, —CN, oxo, —C(=O)$NR^5R^{5'}$, —O—$C_{1-4}$alkyl, —S(=O)$_2$—$C_{1-4}$alkyl, and $C_{1-4}$alkyl optionally substituted with —O—$C_{1-4}$alkyl.

In an embodiment, the present invention relates to those compounds of Formula (I) and the pharmaceutically acceptable salts, and the solvates thereof, or any subgroup thereof as mentioned in any of the other embodiments, wherein Ar is phenyl optionally substituted with one, two, or three substituents each independently selected from the group consisting of halo, —CN, —$OR^4$, —$NR^5R^{5'}$, —C(=O)$NR^5R^{5'}$, —S(=O)$_2$—$NR^5R^{5'}$, —S(=O)$_2$—$C_{1-4}$alkyl, $R^{14}$, $CF_3$, $C_{3-5}$cycloalkyl optionally substituted with —CN, and $C_{1-4}$alkyl optionally substituted with one or two substituents each independently selected from the group consisting of fluoro, —CN, —$OR^6$, —$NR^7R^{7'}$, —S(=O)$_2$—$C_{1-4}$alkyl and —C(=O)$NR^8R^{8'}$;

$Het^1$ is a monocyclic heteroaryl selected from the group consisting of pyridyl, 2-, 4-, 5- or 6-pyrimidinyl, pyrazinyl, pyridazinyl, furanyl, thienyl, pyrrolyl, pyrazolyl, imidazolyl, 4- or 5-thiazolyl, isothiazolyl, and isoxazolyl; each of which may be optionally substituted with one, two, or three substituents each independently selected from the group consisting of halo, —CN, —$OR^4$, —$NR^5R^{5'}$, —C(=O)$NR^5R^{5'}$, and $C_{1-4}$alkyl optionally substituted with a substituent selected from the group consisting of fluoro, —CN, —$OR^6$, $Het^2$, —$NR^7R^{7'}$, and —C(=O)$NR^8R^{8'}$.

In an embodiment, the present invention relates to those compounds of Formula (I) and the pharmaceutically acceptable salts, and the solvates thereof, or any subgroup thereof as mentioned in any of the other embodiments, wherein Q is hydrogen.

In an embodiment, the present invention relates to those compounds of Formula (I) and the pharmaceutically acceptable salts, and the solvates thereof, or any subgroup thereof as mentioned in any of the other embodiments, wherein Q is hydrogen when A is —$CR^{15a}R^{15b}$—;
Q is hydrogen or $C_{1-4}$alkyl optionally substituted with phenyl, when A is a covalent bond.

In an embodiment, the present invention relates to those compounds of Formula (I) and the pharmaceutically acceptable salts, and the solvates thereof, or any subgroup thereof as mentioned in any of the other embodiments, wherein $Het^1$ is a monocyclic heteroaryl selected from the group consisting of pyridyl, 2-, 4-, 5- or 6-pyrimidinyl, pyrazinyl, pyridazinyl, furanyl, thienyl, pyrrolyl, pyrazolyl, imidazolyl, 4- or 5-thiazolyl, isothiazolyl, and isoxazolyl; each of which may be optionally substituted with one, two, or three substituents each independently selected from the group consisting of halo, —CN, —$OR^4$, —$NR^5R^{5'}$, —C(=O)$NR^5R^{5'}$, —C(=O)—$Het^4$, and $C_{1-4}$alkyl optionally substituted with a substituent selected from the group consisting of fluoro, —CN, —OR$^6$, Het$^{2a}$, —NR$^7$R$^{7'}$, and —C(=O)NR$^8$R$^{8'}$; and Het$^2$ is a non-aromatic heterocyclyl optionally substituted with one, two, or three substituents each independently selected from the group consisting of halo, —CN, —C(=O)—C$_{1-6}$alkyl, —C(=O)Ar, —C(=O)Het$^{1a}$, —C(=O)Het$^{2a}$, —OR$^4$, —NR$^5$R$^{5'}$, and C$_{1-4}$alkyl optionally substituted with a substituent selected from the group consisting of fluoro, —CN, —OR$^6$, —NR$^7$R$^{7'}$, R$^{12}$ and —C(=O)NR$^8$R$^{8'}$;

Het$^{1a}$ is a monocyclic heteroaryl selected from the group consisting of pyridyl, 2-, 4-, 5- or 6-pyrimidinyl, pyrazinyl, pyridazinyl, furanyl, thienyl, pyrrolyl, pyrazolyl, imidazolyl, 4- or 5-thiazolyl, isothiazolyl, and isoxazolyl;

Het$^{2a}$ is a non-aromatic heterocyclyl.

In an embodiment, the present invention relates to those compounds of Formula (I) and the pharmaceutically acceptable salts, and the solvates thereof, or any subgroup thereof as mentioned in any of the other embodiments, wherein Het$^1$ is a monocyclic heteroaryl selected from the group consisting of pyridyl, 2-, 4-, 5- or 6-pyrimidinyl, pyrazinyl, pyridazinyl, furanyl, thienyl, pyrrolyl, pyrazolyl, imidazolyl, 4- or 5-thiazolyl, isothiazolyl, and isoxazolyl; each of which may be optionally substituted with one, two, or three substituents each independently selected from the group consisting of halo, —CN, —OR$^4$, —NR$^5$R$^{5'}$, —C(=O)NR$^5$R$^{5'}$, —C(=O)—Het$^4$, and C$_{1-4}$alkyl optionally substituted with a substituent selected from the group consisting of fluoro, —CN, —OR$^6$, —NR$^7$R$^{7'}$, and —C(=O)NR$^8$R$^{8'}$; and Het$^2$ is a non-aromatic heterocyclyl optionally substituted with one, two, or three substituents each independently selected from the group consisting of halo, —CN, —C(=O)—C$_{1-6}$alkyl, —C(=O)Ar, —OR$^4$, —NR$^5$R$^{5'}$, and C$_{1-4}$alkyl optionally substituted with a substituent selected from the group consisting of fluoro, —CN, —OR$^6$, —NR$^7$R$^{7'}$, R$^{12}$ and —C(=O)NR$^8$R$^{8'}$.

In an embodiment, the present invention relates to those compounds of Formula (I) and the pharmaceutically acceptable salts, and the solvates thereof, or any subgroup thereof as mentioned in any of the other embodiments, wherein Q is hydrogen when R$^{15a}$ and R$^{15b}$ are C$_{1-4}$alkyl.

In an embodiment, the present invention relates to those compounds of Formula (I) and the pharmaceutically acceptable salts, and the solvates thereof, or any subgroup thereof as mentioned in any of the other embodiments, wherein when -L-R$^3$ is (b); R$^3$ is selected from the group consisting of Ar; Het$^1$; Het$^3$; R$^{17}$; and a 7- to 10-membered saturated spirocarbobicyclic system.

In an embodiment, the present invention relates to those compounds of Formula (I) and the pharmaceutically acceptable salts, and the solvates thereof, or any subgroup thereof as mentioned in any of the other embodiments, wherein when -L-R$^3$ is (b); R$^3$ is selected from the group consisting of Ar; Het$^1$; Het$^2$; Het$^3$; and a 7- to 10-membered saturated spirocarbobicyclic system.

In an embodiment, the present invention relates to those compounds of Formula (I) and the pharmaceutically acceptable salts, and the solvates thereof, or any subgroup thereof as mentioned in any of the other embodiments, wherein when -L-R$^3$ is (b); R$^3$ is selected from the group consisting of Ar; Het$^1$; Het$^3$; and a 7- to 10-membered saturated spirocarbobicyclic system.

In an embodiment, the present invention relates to those compounds of Formula (I) and the pharmaceutically acceptable salts, and the solvates thereof, or any subgroup thereof as mentioned in any of the other embodiments, wherein when -L-R$^3$ is (b); R$^3$ is selected from the group consisting of Ar; Het$^1$; Het$^2$; and a 7- to 10-membered saturated spirocarbobicyclic system.

In an embodiment, the present invention relates to those compounds of Formula (I) and the pharmaceutically acceptable salts, and the solvates thereof, or any subgroup thereof as mentioned in any of the other embodiments, wherein -L-R$^3$ is (b); and R$^3$ is selected from the group consisting of Ar; Het$^1$; Het$^3$; R$^{17}$; and a 7- to 10-membered saturated spirocarbobicyclic system.

In an embodiment, the present invention relates to those compounds of Formula (I) and the pharmaceutically acceptable salts, and the solvates thereof, or any subgroup thereof as mentioned in any of the other embodiments, wherein -L-R$^3$ is (b); R$^3$ is selected from the group consisting of Ar; Het$^1$; Het$^2$; Het$^3$; and a 7- to 10-membered saturated spirocarbobicyclic system.

In an embodiment, the present invention relates to those compounds of Formula (I) and the pharmaceutically acceptable salts, and the solvates thereof, or any subgroup thereof as mentioned in any of the other embodiments, wherein -L-R$^3$ is (b); and R$^3$ is selected from the group consisting of Ar; Het$^1$; Het$^3$; and a 7- to 10-membered saturated spirocarbobicyclic system.

In an embodiment, the present invention relates to those compounds of Formula (I) and the pharmaceutically acceptable salts, and the solvates thereof, or any subgroup thereof as mentioned in any of the other embodiments, wherein R$^{14}$ is a 5-membered monocyclic heteroaryl containing at least one nitrogen atom, and optionally 1 additional heteroatom selected from nitrogen, oxygen and sulfur.

In an embodiment, the present invention relates to those compounds of Formula (I) and the pharmaceutically acceptable salts, and the solvates thereof, or any subgroup thereof as mentioned in any of the other embodiments, wherein X$^1$ represents O or NH;
X$^2$ represents NH;
X$^3$ represents NH;
X$^4$ represents N;
X$^5$ represents CH.

In an embodiment, the present invention relates to those compounds of Formula (I) and the pharmaceutically acceptable salts, and the solvates thereof, or any subgroup thereof as mentioned in any of the other embodiments, wherein X$^1$ represents O or NH.

In an embodiment, the present invention relates to those compounds of Formula (I) and the pharmaceutically acceptable salts, and the solvates thereof, or any subgroup thereof as mentioned in any of the other embodiments, wherein A is a covalent bond;

-L-R$^3$ is selected from (a), (b), or (c).

In an embodiment, the present invention relates to those compounds of Formula (I) and the pharmaceutically acceptable salts, and the solvates thereof, or any subgroup thereof as mentioned in any of the other embodiments, wherein A is —CR$^{15a}$R$^{15b}$—;

R$^{15a}$ and R$^{15b}$ are each independently selected from the group consisting of hydrogen or C$_{1-4}$alkyl;

-L-R$^3$ is selected from (a), (b), or (c).

In an embodiment, the present invention relates to those compounds of Formula (I) and the pharmaceutically acceptable salts, and the solvates thereof, or any subgroup thereof as mentioned in any of the other embodiments, wherein A is restricted to a covalent bond, hereby named compounds of Formula (I-x):

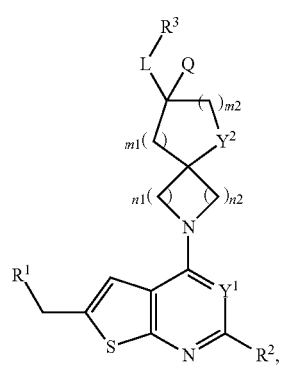
(I-x)

wherein all variables are as defined for the compounds of Formula (I) or any subgroup thereof as mentioned in any of the other embodiments.

In an embodiment, the present invention relates to those compounds of Formula (I) and the pharmaceutically acceptable salts, and the solvates thereof, or any subgroup thereof as mentioned in any of the other embodiments, wherein A is restricted to —CR$^{15a}$R$^{15b}$—, hereby named compounds of Formula (I-xx):

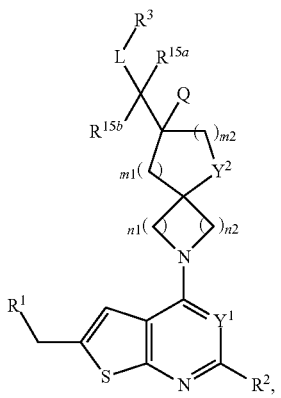
(I-xx)

wherein all variables are as defined for the compounds of Formula (I) or any subgroup thereof as mentioned in any of the other embodiments.

In an embodiment, the present invention relates to those compounds of Formula (I) and the pharmaceutically acceptable salts, and the solvates thereof, or any subgroup thereof as mentioned in any of the other embodiments, wherein the compounds of Formula (I) are restricted to compounds of Formula (I-y):

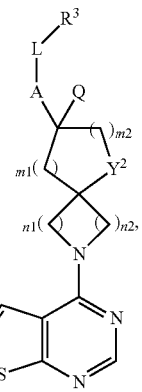
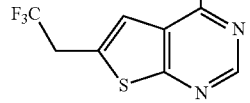
(I-y)

wherein all variables are as defined for the compounds of Formula (I) or any subgroup thereof as mentioned in any of the other embodiments.

In an embodiment, the present invention relates to those compounds of Formula (I) and the pharmaceutically acceptable salts, and the solvates thereof, or any subgroup thereof as mentioned in any of the other embodiments, wherein the compounds of Formula (I) are restricted to compounds of Formula (I-z):

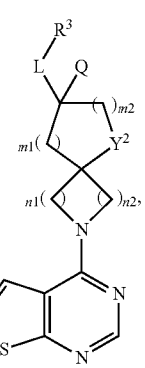
(I-z)

wherein all variables are as defined for the compounds of Formula (I) or any subgroup thereof as mentioned in any of the other embodiments.

In an embodiment the compound of Formula (I) is selected from the group consisting of any of the exemplified compounds, tautomers and stereoisomeric forms thereof, and the free bases, any pharmaceutically acceptable addition salts, and the solvates thereof.

All possible combinations of the above indicated embodiments are considered to be embraced within the scope of the invention.

Methods for the Preparation of Compounds of Formula (I)

In this section, as in all other sections unless the context indicates otherwise, references to Formula (I) also include all other sub-groups and examples thereof as defined herein.

The general preparation of some typical examples of the compounds of Formula (I) is described hereunder and in the specific examples, and are generally prepared from starting materials which are either commercially available or prepared by standard synthetic processes commonly used by those skilled in the art. The following schemes are only meant to represent examples of the invention and are in no way meant to be a limit of the invention.

Alternatively, compounds of the present invention may also be prepared by analogous reaction protocols as described in the general schemes below, combined with standard synthetic processes commonly used by those skilled in the art of organic chemistry.

The skilled person will realize that in the reactions described in the Schemes, although this is not always explicitly shown, it may be necessary to protect reactive functional groups (for example hydroxy, amino, or carboxy groups) where these are desired in the final product, to avoid their unwanted participation in the reactions. For example in Scheme 1, the NH moiety on intermediate (III) can be protected with a tert-butoxycarbonyl protecting group. In general, conventional protecting groups can be used in accordance with standard practice. The protecting groups may be removed at a convenient subsequent stage using methods known from the art. This is illustrated in the specific examples.

The skilled person will realize that in the reactions described in the Schemes, it may be advisable or necessary to perform the reaction under an inert atmosphere, such as for example under $N_2$-gas atmosphere.

It will be apparent for the skilled person that it may be necessary to cool the reaction mixture before reaction work-up (refers to the series of manipulations required to isolate and purify the product(s) of a chemical reaction such as for example quenching, column chromatography, extraction).

The skilled person will realize that heating the reaction mixture under stirring may enhance the reaction outcome. In some reactions microwave heating may be used instead of conventional heating to shorten the overall reaction time.

The skilled person will realize that another sequence of the chemical reactions shown in the Schemes below, may also result in the desired compound of Formula (I).

The skilled person will realize that intermediates and final compounds shown in the Schemes below may be further functionalized according to methods well-known by the person skilled in the art. The intermediates and compounds described herein can be isolated in free form or as a salt.

Schemes 1-16 relate in particular to compounds/intermediates wherein variable 'A' is a covalent bond.

Scheme 1

In general, compounds of Formula (I) wherein $R^2$ is restricted to H or Me (methyl) and $Y^1$ is restricted to N and C—CN, wherein $R^{1A}$ is selected from the group consisting of $C_{0-5}$alkyl optionally substituted with one, two or three fluoro substituents; and $C_{1-5}$alkyl substituted with a substituent selected from the group consisting of —$OR^{1a}$ and —$NR^{2a}R^{2aa}$, and wherein all other variables are defined according to the scope of the present invention, hereby named compounds of Formula (I-a) can be prepared according to the following reaction Scheme 1. In Scheme 1, $LG^1$ and $LG^2$ each represent a suitable leaving group, such as for example halo (a suitable halogen) or methanesulfonyl; $PG^1$ represents a suitable protecting group, such as for example tert-butyloxycarbonyl; $R^{1A}$-$PG^2$ represents an $R^{1A}$ as defined in Formula (I) with an appropriate protecting group, such as for example tert-butyloxycarbonyl, all other variables in Scheme 1 are defined according to the scope of the present invention.

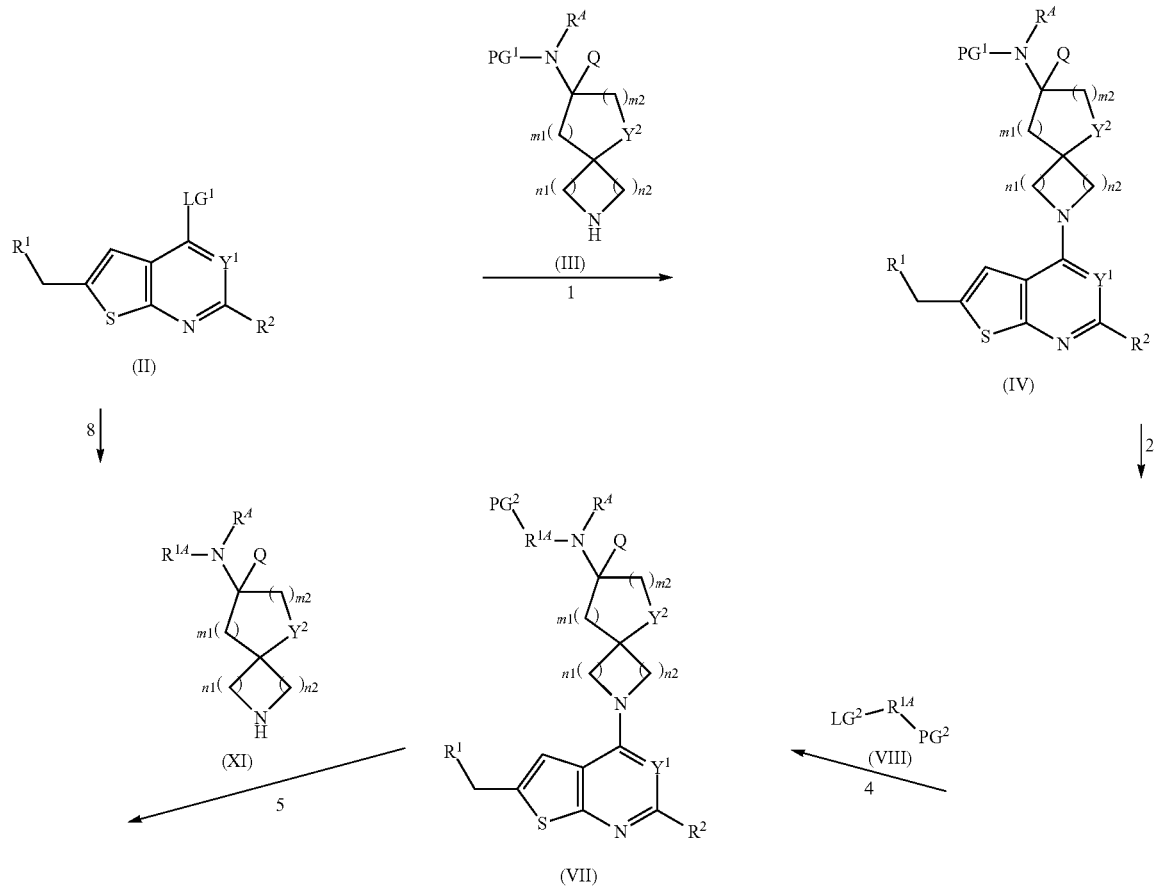

-continued

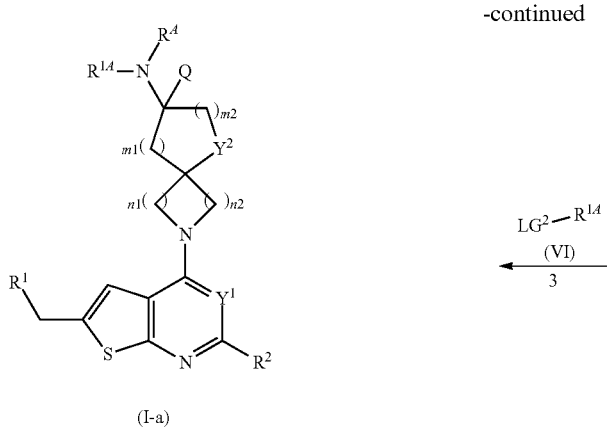

(I-a)

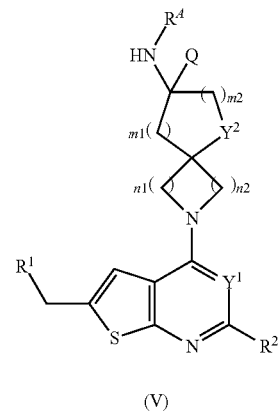

(V)

In Scheme 1, the following reaction conditions apply:

1: at a suitable temperature such as ranged from rt to 90° C., in the presence of a suitable base such as for example diisopropylethylamine or triethylamine, in a suitable solvent such as for example acetonitrile or isopropanol or ethanol (EtOH) or dichloromethane (DCM);

2: when $PG^1$ is tert-butyloxycarbonyl, at a suitable temperature range such as for example from 0° C. to room temperature, in the presence of suitable cleavage conditions, such as for example an acid such as HCl or trifluoroacetic acid in a suitable solvent such as acetonitrile or DCM or methanol (MeOH); Alternatively, at a suitable temperature such as for example room temperature in a suitable solvent such as acetic acid 3: at a suitable temperature such as for example room temperature or 90° C., in the presence of a suitable base such as for example potassium carbonate or 1,8-Diazabicyclo [5.4.0]undec-7-ene, in a suitable solvent such as for example acetonitrile or dimethyl sulfoxide (DMSO);

4: at a suitable temperature such as for example room temperature or 90° C., in the presence of a suitable base such as for example potassium carbonate or 1,8-Diazabicyclo [5.4.0]undec-7-ene, in a suitable solvent such as for example acetonitrile or DMSO;

5: at a suitable reaction temperature range such as for example from 0° C. to room temperature, in the presence of suitable cleavage conditions, such as for example an acid such as HCl or trifluoroactic acid in a suitable solvent such as acetonitrile or DCM when $PG^2$ is tert-butyloxycarbonyl.

6: at a suitable temperature, for example room temperature, in the presence of a suitable reducing agent, such as for example sodium triacetoxyborohydride ($NaBH(OAc)_3$), decaborane, or sodium borohydride in a suitable solvent such as DCM, DCE, Methanol or tetrahydropyran, with or without a suitable acid such as for example acetic acid;

8: at a suitable temperature such as for example at 90° C., in the presence of a suitable base such as for example diisopropylethylamine or triethylamine, in a suitable solvent such as for example acetonitrile or isopropanol or DCM. In step 8, reagents of Formula (XI) are either commercially available, prepared according to scheme 3 by methods known to the skilled person from commercially available starting materials, e.g. by appropriate protection/deprotection steps and functional group interconversion, from starting materials, such as 2-Azaspiro[4.5]decane-2-carboxylic acid, 8-amino-, 1,1-dimethylethyl ester (CAS [1363381-61-6]).

Scheme 2

Intermediates of Formula (II), wherein $R^2$ is methyl and $Y^1$ is N, hereby named intermediate of Formula (XIII) can be prepared according to the following reaction Scheme 2, wherein $LG^1$ represents a suitable leaving group, such as for example halo or methanesulfonyl. All other variables in Scheme 2 are defined according to the scope of the present invention.

In Scheme 2, the following reaction conditions apply:

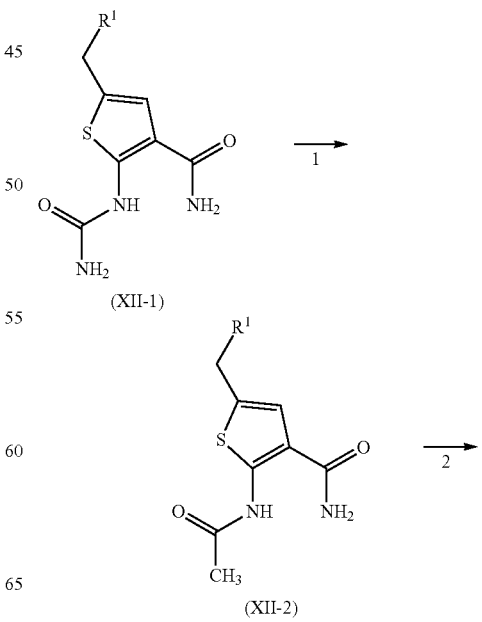

-continued

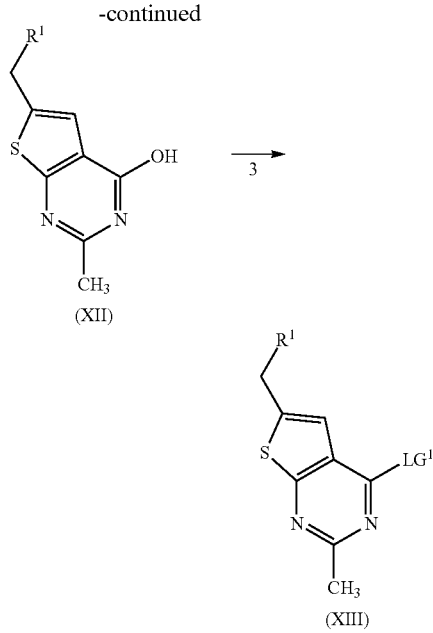

1: at a suitable temperature such as for example at reflux temperature, in the presence of acetic anhydride and a suitable base such as for example trimethylamine, in a suitable solvent such as for example toluene;

2: at a suitable temperature such as for example at reflux temperature, in the presence of a suitable base such as potassium hydroxide, in a suitable solvent such as for example EtOH;

3: under suitable reaction conditions to form a leaving group, such as for example, chloro, for example by reaction with phosphoryl trichloride at a suitable temperature such as 110° C.

Scheme 3

Intermediates of Formula (III) and (XI), wherein $PG^3$ is a suitable protective group, orthogonal to $PG^1$, such as for example a benzyloxycarbonyl, can be prepared according to the following reaction Scheme 3. All other variables in Scheme 3 are defined as above or according to the scope of the present invention.

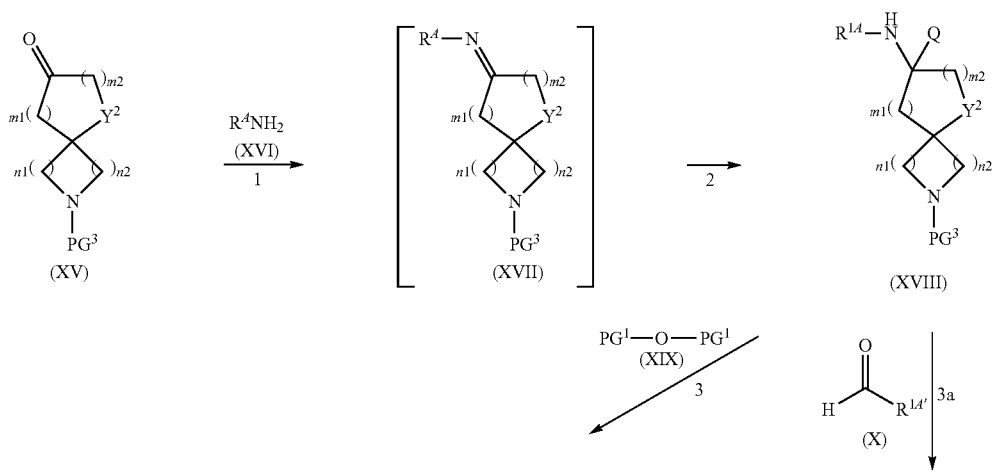

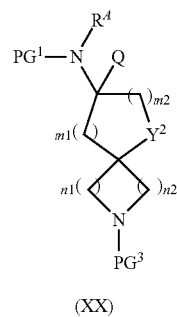

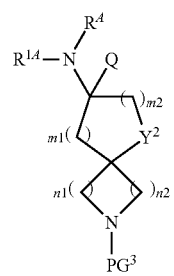

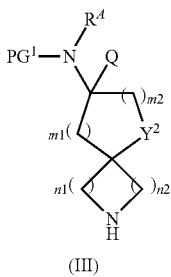

(III)

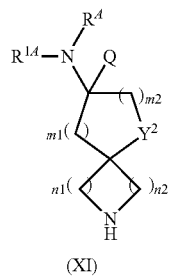

(XI)

In Scheme 3, the following reaction conditions apply:

1: at a suitable temperature for example 80° C., in a suitable solvent such as EtOH or tetrahydrofuran (THF);

2: in case Q is different than hydrogen, at a suitable temperature such as for example 0° C., in the presence of a suitable organolithium (Q-Li) or Grignard (Q-Mg-halo) reagents that are either commercially available or can be prepared by methods known to the skilled person, in a suitable solvent such as for example THF;

Alternatively, in case Q is a hydrogen, at a suitable temperature such as for example room temperature, in the presence of a suitable reducing agent such as for example sodium triacetoxyborohydride, in a suitable solvent such as for example THF or MeOH; In case Q is a hydrogen, step 1 and 2 can be performed at the same time;

3a: at a suitable temperature, for example room temperature, in the presence of a suitable reducing agent, such as for example sodium triacetoxyborohydride (NaBH(OAc)$_3$), decaborane, or sodium borohydride in a suitable solvent such as DCM, DCE, Methanol or tetrahydropyran, with or without a suitable acid such as for example acetic acid;

3: at a suitable temperature such as room temperature, in the presence of a suitable base such as for example diisopropylamine, in a suitable solvent such as DCM;

4: at a suitable temperature such as for example room temperature, in the presence of a suitable catalyst such as for example palladium on carbon (Pd/C), in the presence of a suitable atmosphere of hydrogen, in a suitable solvent such as for example EtOH or a mixture of EtOH and THF;

Scheme 4

Alternatively, when Q is restricted to hydrogen, intermediates of formula (III) and (XI), hereby named intermediate of Formula (IIIa) and (XIa) can also be prepared according to scheme 4.

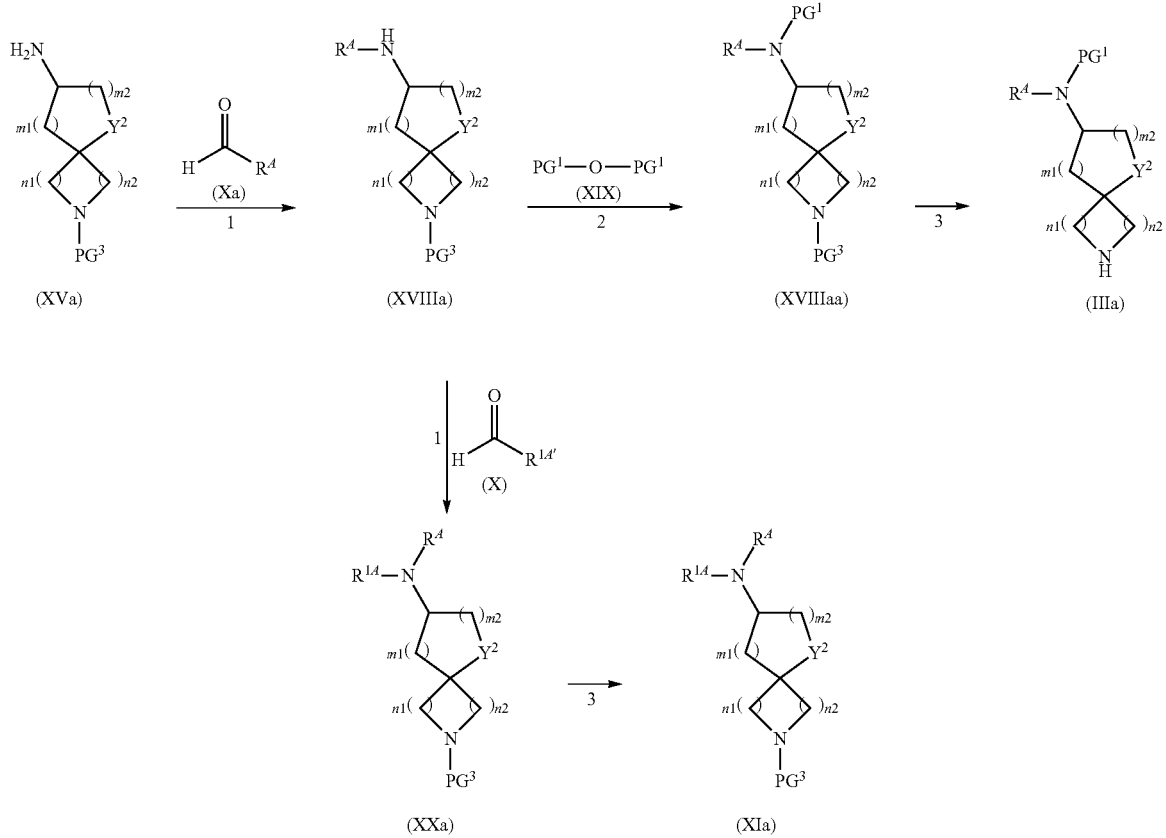

In Scheme 4, the following reaction conditions apply:

1: at a suitable temperature, for example room temperature, in the presence of a suitable reducing agent, such as for example sodium triacetoxyborohydride (NaBH(OAc)$_3$), decaborane or sodium borohydride in a suitable solvent such as for example DCM, DCE, methanol or tetrahydropyran, with or without a suitable acid such as for example acetic acid;

2: at a suitable temperature such as room temperature, in the presence of a suitable base such as for example diisopropylamine, in a suitable solvent such as DCM;

3: at a suitable temperature such as for example room temperature, in the presence of a suitable catalyst such as for example Pd/C, in the presence of a suitable atmosphere of hydrogen, in a suitable solvent such as for example EtOH or a mixture of EtOH and THF;

Scheme 5

Intermediates of Formula (II), wherein $R^2$ is H, and $Y^1$ is C—CN, hereby named intermediate of Formula (XXVIII) can be prepared according to the following reaction Scheme 5.

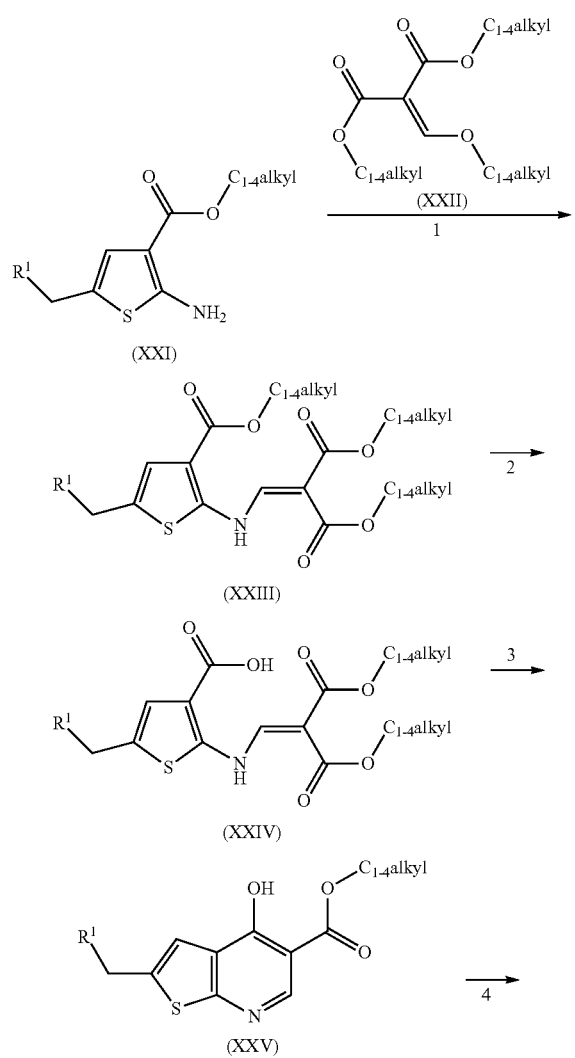

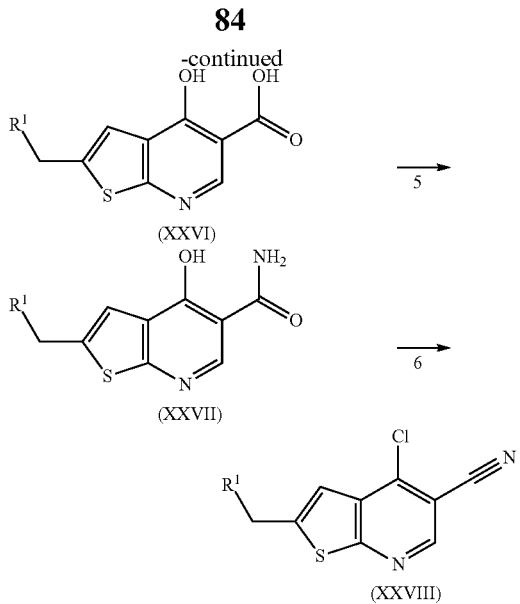

In Scheme 5, the following reaction conditions apply:

1: at a suitable temperature such as for example 135° C.;

2: at a suitable temperature such as for example 40° C., in the presence of a suitable base such as for example lithium hydroxide, in a suitable solvent such as for example a mixture of THF and water;

3: at a suitable temperature such as for example 135%, in a suitable acid such polyphosphoric acid (PPA);

4: at a suitable temperature such as for example 40° C., in the presence of a suitable base such as for example sodium hydroxide, in a suitable solvent such as for example a mixture of MeOH and water;

5: a) at a suitable temperature such as for example 70° C., in the presence of a suitable chlorinating reagent such as for example oxalyl chloride, a catalytic amount of dimethylformamide, in a suitable solvent such as for example chloroform;

b) at a suitable temperature such as for example 25° C., in the presence of ammoniac, in a suitable solvent such as for example DCM;

6: at a suitable temperature such as for example 0° C., in the presence of a suitable reagent such as for example trifluoroacetic anhydride, a suitable base such as for example triethylamine, in a suitable solvent such as for example DCM;

Scheme 6

In general, compounds of Formula (I) wherein $R^2$ is restricted to H or Me, and $Y^1$ is restricted to N and C—CN, wherein $R^{1A'}$ is selected from the group consisting of $C_{0-5}$alkyl optionally substituted with one, two or three fluoro substituents; and $C_{1-5}$alkyl substituted with a substituent selected from the group consisting of —$OR^{1a}$ and —$NR^{2a}R^{2aa}$, and wherein all other variables are defined according to the scope of the present invention, hereby named compounds of Formula (Ib), (Ica) and (Icb), can be prepared according to the following reaction Scheme 1. In Scheme 6, $LG^2$ each represent a suitable leaving group, such as for example halo or methanesulfonyl; $PG^1$ represents a suitable protecting group, such as for example tert-butyloxycarbonyl; All other variables in Scheme 1 are defined according to the scope of the present invention.

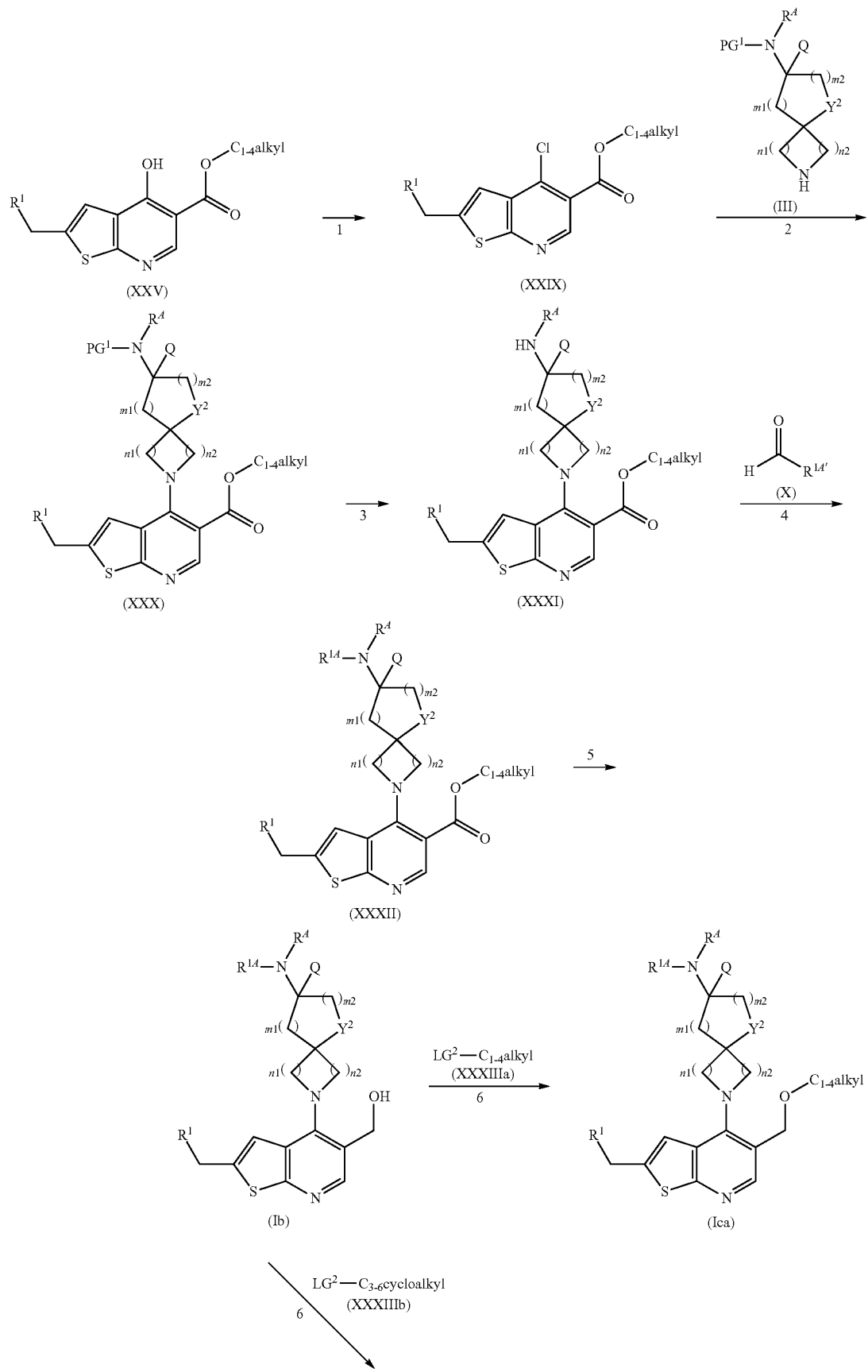

-continued

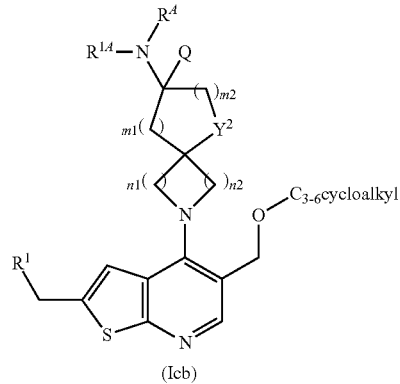

(Icb)

In Scheme 6, the following reaction conditions apply.

1: at a suitable temperature such as for example 70° C., in the presence of a suitable chlorinating reagent such as for example oxalyl chloride, a catalytic amount of dimethylformamide, in a suitable solvent such as for example chloroform;

2: at a suitable temperature such as ranged from rt to 90° C., in the presence of a suitable base such as for example diisopropylethylamine or triethylamine, in a suitable solvent such as for example acetonitrile or isopropanol or EtOH or DCM;

3: at a suitable temperature such as for example room temperature, in the presence of a suitable acid such as for example trifluoroacetic acid, in a suitable solvent such as for example DCM;

4: at a suitable temperature, for example room temperature, in the presence of a suitable reducing agent, such as for example NaBH(OAc)$_3$, decaborane or sodium borohydride in a suitable solvent such as DCM, DCE, methanol or tetrahydropyran, with or without a suitable acid such as for example acetic acid;

5: at a suitable temperature such as for example −78° C., in the presence of a suitable reducing agent such as for example diisobutylaluminium hydride, in a suitable solvent such as for example DCM;

6: at a suitable temperature such as for example 0° C., in the presence of a suitable deprotonating agent such as for example sodium hydride, in a suitable solvent such as for example THF or dimethylformamide;

Scheme 7

In general, compounds of Formula (I) wherein $R^2$ is restricted to H or Me and $Y^1$ is restricted to N and C—CN, and wherein all other variables are defined according to the scope of the present invention, hereby named compounds of Formula (Id), (Ie) and (If) can be prepared according to the following reaction Scheme 7. In Scheme 7, $LG^2$ represent a suitable leaving group, such as for example halo or methanesulfonyl;

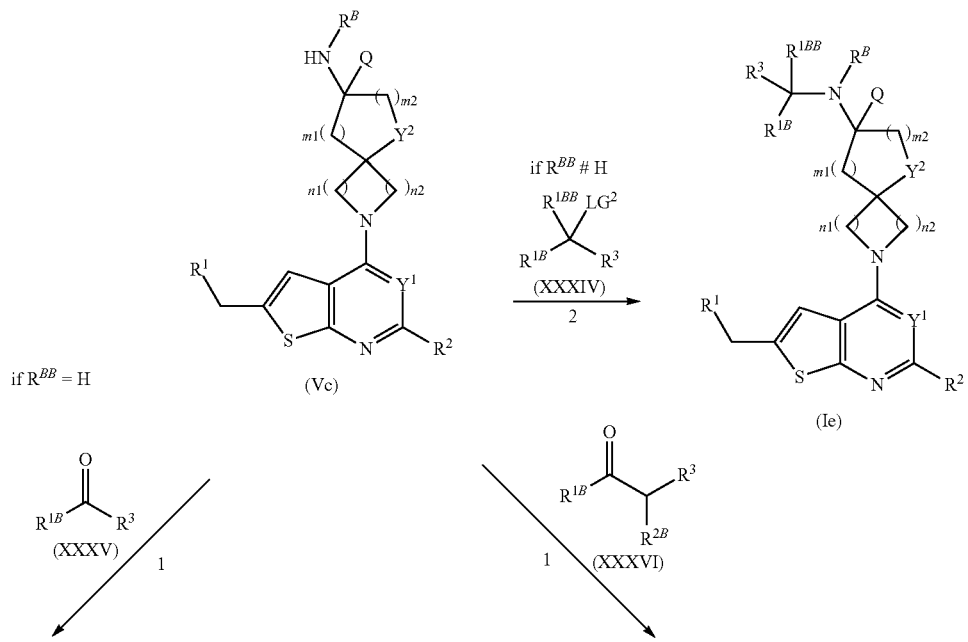

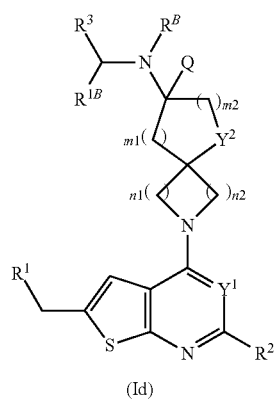

(Id)

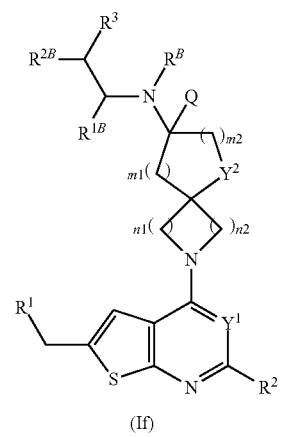

(If)

Someone skilled in the art will recognize that intermediate (Vc) can be prepared following a similar pathway than the one use for the preparation of intermediate (V) and reported in scheme 1.

In Scheme 7, the following reaction conditions apply:

1: at a suitable temperature, for example room temperature, in the presence of a suitable reducing agent, such as for example NaBH(OAc)$_3$, decaborane or sodium borohydride in a suitable solvent such as DCM, DCE, methanol or tetrahydropyran, with or without a suitable acid such as for example acetic acid;

Or alternatively and successively a) at a suitable temperature such as for example room temperature or 45° C., in the presence of titanium (IV) ethoxide or titanium (IV) isopropoxide, in a suitable solvent such as for example tetrahydropyrane, DCE or a mixture of DCE and MeOH;

b) at a suitable temperature such as for example room temperature, in the presence of a suitable reducting agent such as for example sodium borohydride, sodium triacetoxyborohydride or sodium cyanoborohydride, in a suitable solvent such as for example tetrahydropyrane, DCE or a mixture of DCE and MeOH; Steps a and b can be performed as a one-pot procedure.

2: at a suitable temperature such as for example room temperature or 90° C., in the presence of a suitable base such as for example potassium carbonate or 1,8-Diazabicyclo [5.4.0]undec-7-ene, in a suitable solvent such as for example acetonitrile or DMSO.

Scheme 8

In general, compounds of Formula (I) wherein R$^2$ is restricted to H or Me and Y$^1$ is restricted to N and C—CN, Q is restricted to hydrogen, and wherein all other variables are defined according to the scope of the present invention, hereby named compounds of Formula (Ih) and (Ii) can be prepared according to the following reaction Scheme 8.

In Scheme 8, LG$^1$ represent a suitable leaving group, such as for example halo or methanesulfonyl;

In Scheme 8, the following reaction conditions apply:

1: at a suitable temperature such as ranged from rt to 90° C., in the presence of a suitable base such as for example diisopropylethylamine or triethylamine, in a suitable solvent such as for example acetonitrile or isopropanol or EtOH or DCM;

2: at a suitable temperature, for example room temperature, in the presence of a suitable reducing agent, such as for example NaBH(OAc)$_3$, decaboraneor sodium borohydride in a suitable solvent such as DCM, DCE, methanol or tetrahydropyran, with or without a suitable acid such as for example acetic acid;

Or alternatively and successively a) at a suitable temperature such as for example room temperature or 45° C., in the presence of titanium (IV) ethoxide or titanium (IV) isopropoxide, in a suitable solvent such as for example tetrahydropyrane, DCE or a mixture of DCE and MeOH;

b) at a suitable temperature such as for example room temperature, in the presence of a suitable reducting agent such as for example sodium borohydride, sodium triacetoxyborohydride or sodium cyanoborohydride, in a suitable solvent such as for example tetrahydropyrane, DCE or a mixture of DCE and MeOH;

Steps a and b can be performed as a one-pot procedure.

Scheme 9

In general, compounds of Formula (I) wherein R$^2$ is restricted to H or Me, Y$^1$ is restricted to N and C—CN, R$^{3aa}$ is restricted to Ar; Het$^1$ or Het$^3$, R$^{3b}$ is restricted to Het$^2$ and R$^{17}$ and R$^{3c}$ is restricted to Het$^1$ hereby named compounds of Formula (Ij), (Ik) and (Ika) can be prepared according to the following reaction Scheme 9. In Scheme 9, halo represent a suitable halogen atom such as for example chloro, bromo or iodo, halo1 represent a suitable halogen atom such as for example chloro or fluoro and all other variables are defined according to the scope of the present invention,

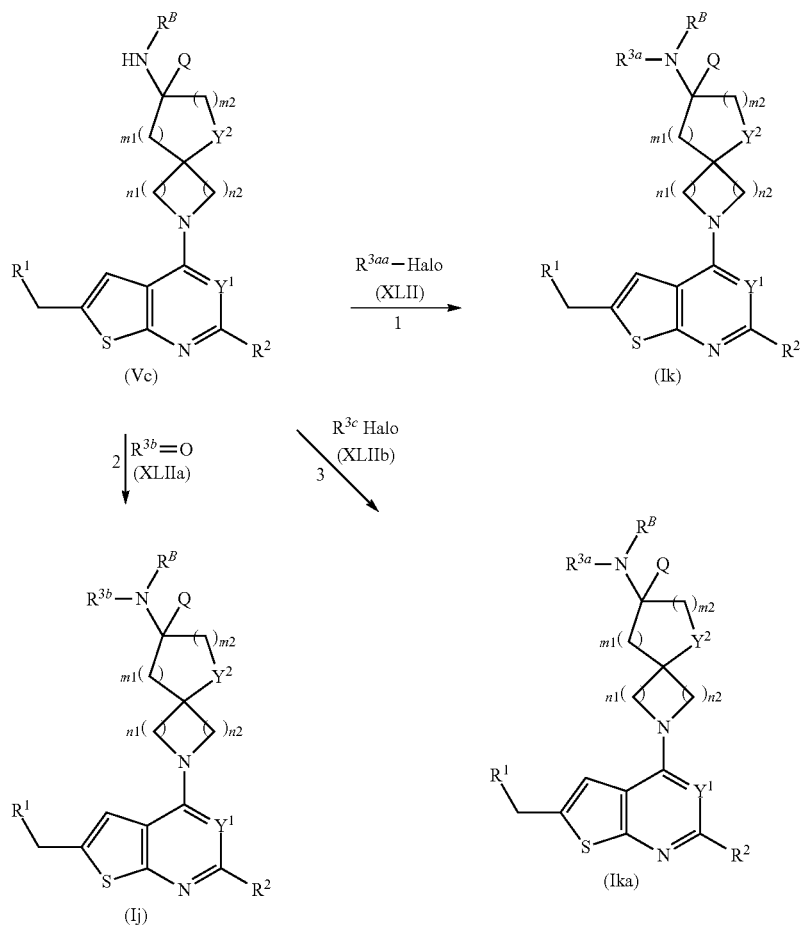

In Scheme 9, the following reaction conditions apply:

1: under microwave irradiation, at a suitable temperature such as for example 130° C., in the presence of a suitable catalyst such as for example Tris(dibenzylideneacetone)-dipalladium(0), a suitable ligand such as for example 2-(Dicyclohexylphosphino)3,6-dimethoxy-2',4',6'-triisopropyl-1,1'-biphenyl, a suitable base such as for example sodium tert-butylate, in a suitable solvent such as for example dioxane;

2: at a suitable temperature, for example room temperature, in the presence of a suitable reducing agent, such as for example $NaBH(OAc)_3$, decaborane or sodium borohydride in a suitable solvent such as DCM, DCE, methanol or tetrahydropyran, with or without a suitable acid such as for example acetic acid;

Or alternatively and successively
  a) at a suitable temperature such as for example room temperature or 45° C., in the presence of titanium (IV) ethoxide or titanium (IV) isopropoxide, in a suitable solvent such as for example tetrahydropyrane, DCE or a mixture of DCE and MeOH;
  b) at a suitable temperature such as for example room temperature, in the presence of a suitable reducing agent such as for example sodium borohydride, sodium triacetoxyborohydride or sodium cyanoborohydride, in a suitable solvent such as for example tetrahydropyrane, DCE or a mixture of DCE and MeOH;

Steps a and b can be performed as a one-pot procedure.

3: at a suitable temperature such as for example 100° C., in the presence of a suitable base such as for example diisopropylethylamine, in a suitable solvent such as for example isopropanol.

Scheme 10

In general, compounds of Formula (I) wherein $R^2$ is restricted to H or Me, $Y^1$ is restricted to N and C—CN, and Q is restricted to hydrogen, hereby named compounds of Formula (Im) can be prepared according to the following reaction Scheme 10. In Scheme 10, all other variables are defined according to above or according to the scope of the present invention,

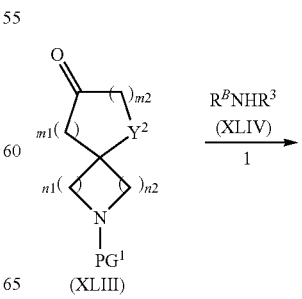

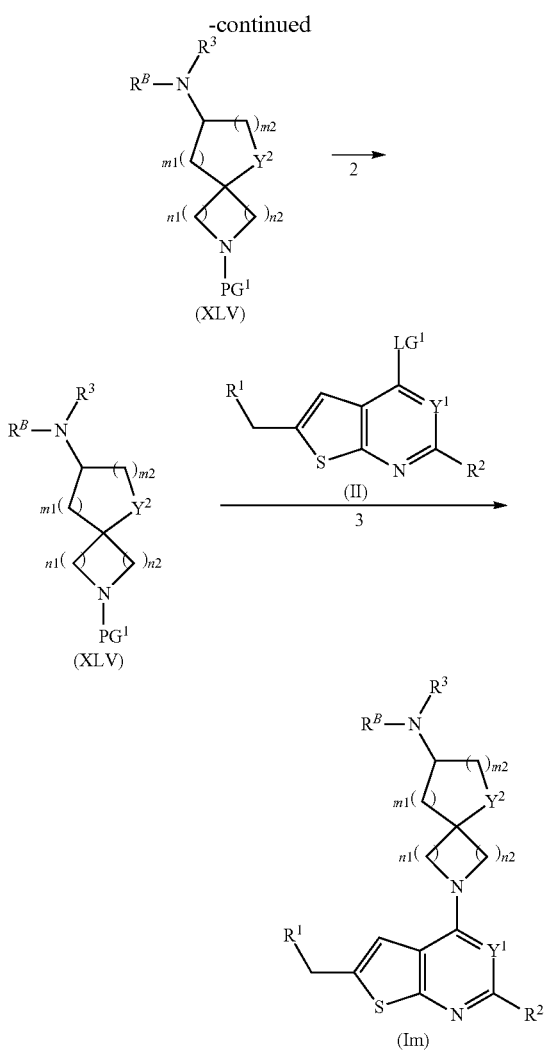

(XLV)

(XLV)

(Im)

In Scheme 10, the following reaction conditions apply:

1: at a suitable temperature, for example room temperature, in the presence of a suitable reducing agent, such as for example NaBH(OAc)$_3$, decaborane or sodium borohydride in a suitable solvent such as DCM, DCE, methanol or tetrahydropyran, with or without a suitable acid such as for example acetic acid;

Or alternatively and successively a) at a suitable temperature such as for example room temperature or 45° C., in the presence of titanium (IV) ethoxide or titanium (IV) isopropoxide, in a suitable solvent such as for example tetrahydropyrane, DCE or a mixture of DCE and MeOH;

b) at a suitable temperature such as for example room temperature, in the presence of a suitable reducing agent such as for example sodium borohydride, sodium triacetoxyborohydride or sodium cyanoborohydride, in a suitable solvent such as for example tetrahydropyrane, DCE or a mixture of DCE and MeOH;

Steps a and b can be performed as a one-pot procedure.

2: at a suitable temperature range such as for example from 0° C. to room temperature, in the presence of suitable cleavage conditions, such as for example an acid such as HCl or trifluoroacetic acid in a suitable solvent such as acetonitrile or DCM or MeOH or ethyl acetate;

3: at a suitable temperature such as ranged from rt to 90° C., in the presence of a suitable base such as for example diisopropylethylamine or triethylamine, in a suitable solvent such as for example acetonitrile or isopropanol or EtOH or DCM.

Scheme 11

In general, compounds of Formula (I) wherein $R^2$ is restricted to NH$_2$, and $Y^1$ is restricted to N, hereby named compounds of Formula (In) can be prepared according to the following reaction Scheme 11. In Scheme 11, all other variables are defined according to above or according to the scope of the present invention,

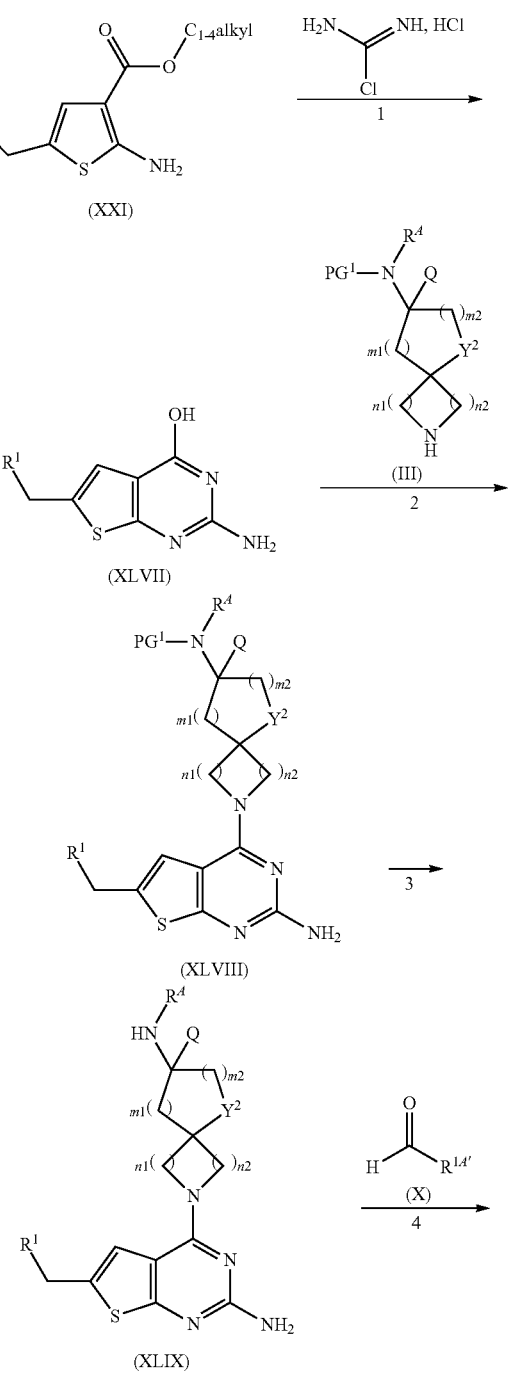

-continued

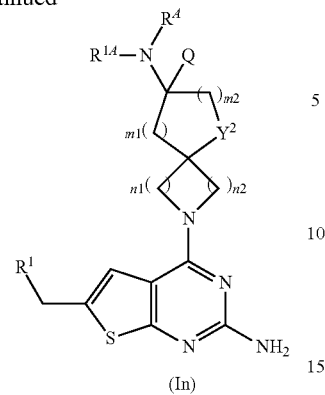

(In)

In Scheme 11, the following reaction conditions apply:

1: under microwave irradiation, at a suitable temperature such as for example 160° C., in a suitable solvent such as for example diglyme;

2: at a suitable temperature such as for example 40° C., in the presence of a suitable coupling agent such as for example (Benzotriazol-1-yloxy)tris(dimethyl-amino)phosphonium hexafluorophosphate (BOP), a suitable base such as for example 1,8-Diazabicyclo[5.4.0]undec-7-ene (DBU), in a suitable solvent such as for example DMF;

3: when $PG^1$ is tert-butyloxycarbonyl, at a suitable temperature range such as for example from 0° C. to room temperature, in the presence of suitable cleavage conditions, such as for example an acid such as HCl or trifluoroacetic acid in a suitable solvent such as acetonitrile or DCM or MeOH;

Alternatively, at a suitable temperature such as for example room temperature in a suitable solvent such as acetic acid 4: at a suitable temperature, for example room temperature, in the presence of a suitable reducing agent, such as for example $NaBH(OAc)_3$ or sodium borohydride in a suitable solvent such as DCM, DCE or tetrahydropyran, with or without a suitable acid such as for example acetic acid.

Scheme 12

In general, compounds of Formula (I) wherein $R^2$ is restricted to NHMe, and $Y^1$ is restricted to N, hereby named compounds of Formula (Jo) can be prepared according to the following reaction Scheme 12. In Scheme 12, all other variables are defined according to above or according to the scope of the present invention,

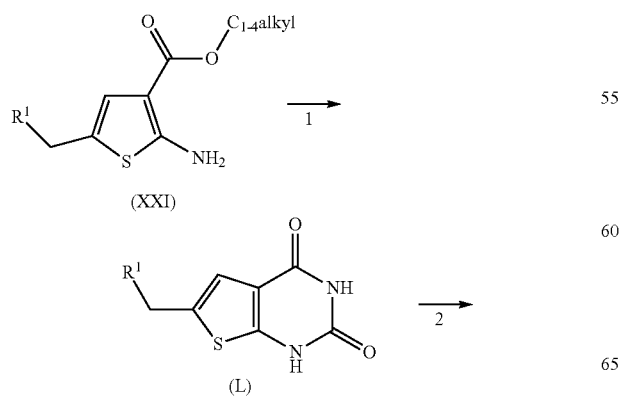

-continued

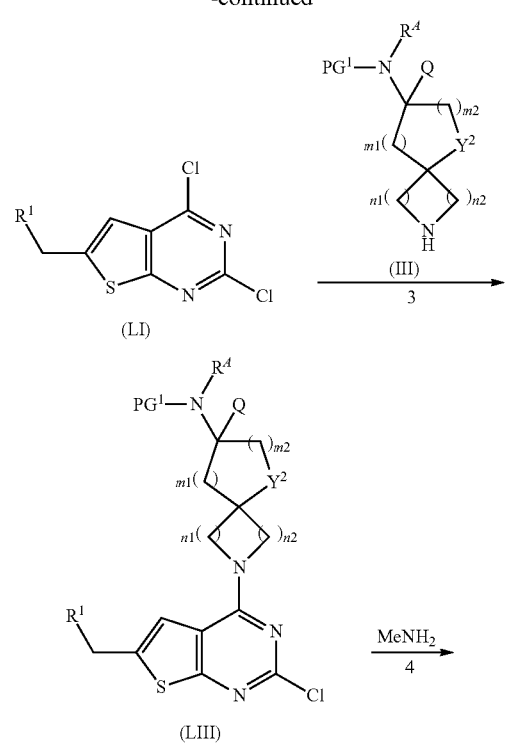

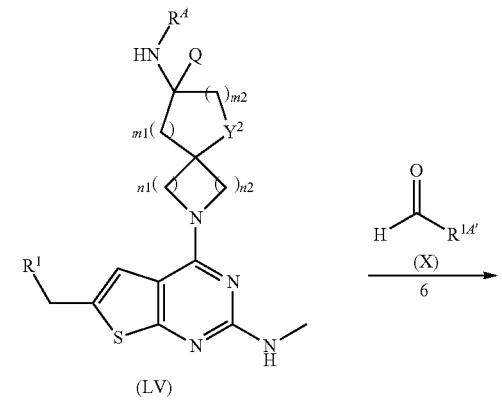

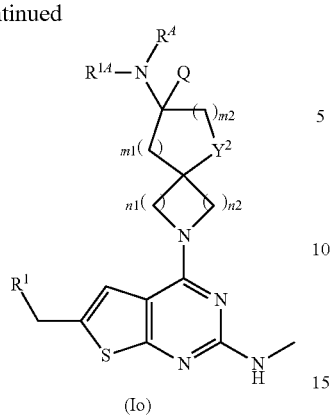

(Io)

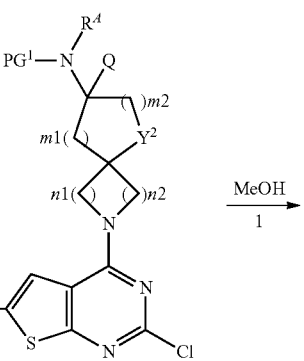

(LIII)

In Scheme 12, the following reaction conditions apply:

1: at a suitable temperature ranged from −60° C. to 180° C., in the presence of a suitable reagent such as for example sulfuryl chloride isocyanate or urea;

2: at a suitable temperature such as 115° C., in a suitable chlorinating reagent such as for example phosphonyltrichloride;

3: at a suitable temperature such as ranged from rt to 90° C., in the presence of a suitable base such as for example diisopropylethylamine or triethylamine, in a suitable solvent such as for example acetonitrile or isopropanol or EtOH or DCM;

4: under microwave irradiation or not, at a suitable temperature such as for example 100° C., in a suitable solvent such as for example THF or dimethylformamide;

5: when PG$^1$ is tert-butyloxycarbonyl, at a suitable temperature range such as for example from 0° C. to room temperature, in the presence of suitable cleavage conditions, such as for example an acid such as HCl or trifluoroacetic acid in a suitable solvent such as acetonitrile or DCM or MeOH;

Alternatively, at a suitable temperature such as for example room temperature in a suitable solvent such as acetic acid 6: at a suitable temperature, for example room temperature, in the presence of a suitable reducing agent, such as for example NaBH(OAc)$_3$ or sodium borohydride in a suitable solvent such as DCM, DCE or tetrahydropyran, with or without a suitable acid such as for example acetic acid;

Scheme 13

In general, compounds of Formula (I) wherein R$^2$ is restricted to OMe, and Y$^1$ is restricted to N, wherein R$^{14'}$ is selected from the group consisting of C$_{0-5}$alkyl optionally substituted with one, two or three fluoro substituents; and C$_{1-5}$alkyl substituted with a substituent selected from the group consisting of —OR$^{1a}$ and —NR$^{2a}$R$^{2aa}$ hereby named compounds of Formula (Ip) can be prepared according to the following reaction Scheme 13. In Scheme 13, all other variables are defined according to above or according to the scope of the present invention,

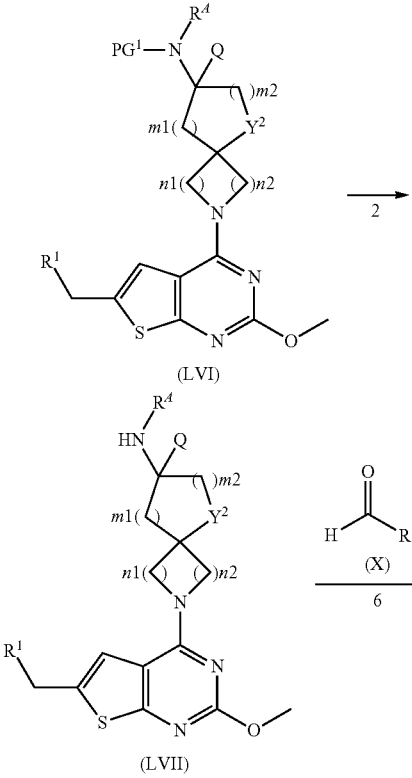

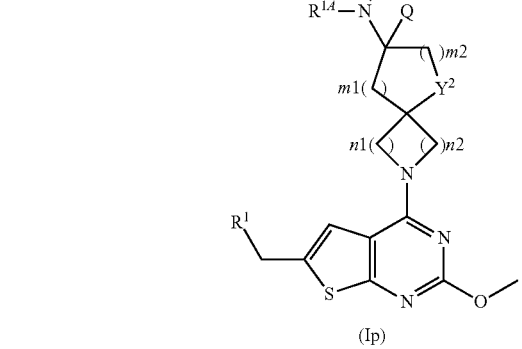

(Ip)

In Scheme 13, the following reaction conditions apply:

1: at a suitable temperature such as for example 100° C. or 110° C., in the presence of a suitable catalyst such as for example palladium acetate, a suitable ligand such as for example 2,2'-Bis(diphenylphosphino)-1,1'-binaphthyl, a suitable base such as for example cesium carbonate, in a suitable solvent such as for example toluene;

2: when PG$^1$ is tert-butyloxycarbonyl, at a suitable temperature range such as for example from 0° C. to room temperature, in the presence of suitable cleavage conditions, such as for example an acid such as HCl or trifluoroacetic acid in a suitable solvent such as acetonitrile or DCM or MeOH;

Alternatively, at a suitable temperature such as for example room temperature in a suitable solvent such as acetic acid 3: at a suitable temperature, for example room temperature, in the presence of a suitable reducing agent, such as for example NaBH(OAc)$_3$ or sodium borohydride in a suitable solvent such as DCM, DCE or tetrahydropyran, with or without a suitable acid such as for example acetic acid.

Scheme 14

In general, compounds of Formula (I) wherein R$^2$ is restricted to H or Me, and Y$^1$ is restricted to N and C—CN, and wherein R$^3$ is restricted to

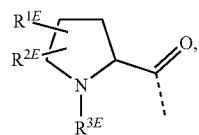

hereby named compounds of Formula (Iq) can be prepared according to the following reaction Scheme 14. In Scheme 14, all other variables are defined according to above or according to the scope of the present invention.

Someone skilled in the art will recognize that intermediate (Va) can be prepared following a similar pathway than the one use for the preparation of intermediate V and reported in scheme 1.

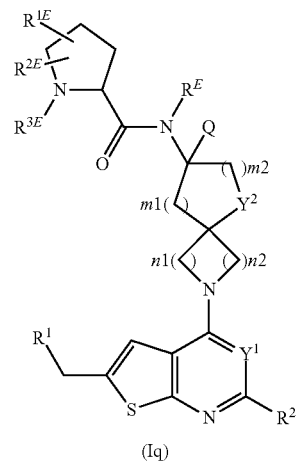

(Iq)

In Scheme 14, the following reaction conditions apply:

1: at a suitable temperature, such as for example room temperature, in the presence of a suitable acid coupling agent, such as for example 1-[bis(dimethylamino)methylene]-1H-benzotriazoliumhexafluorophosphate(1-)3-oxide (HBTU) or 1-[Bis(dimethyl-amino)methylene]-1H-1,2,3-triazolo[4,5-b]pyridinium 3-oxide hexafluorophosphate (HATU), in the presence of a suitable base such as for example N-ethyl-N-(1-methyl-ethyl)-2-propanamine (DIPEA), in a suitable solvent such as N,N-dimethylformamide (DMF).

Scheme 15

In general, compounds of Formula (I) wherein R$^2$ is restricted to H or Me, and Y$^1$ is restricted to N and C—CN, hereby named compounds of Formula (Ir) can be prepared according to the following reaction Scheme 15. In Scheme 15, all other variables are defined according to above or according to the scope of the present invention,

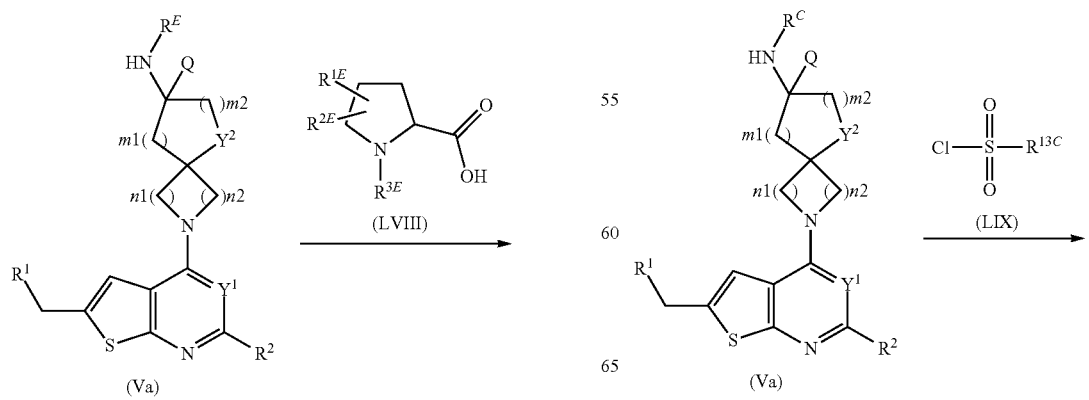

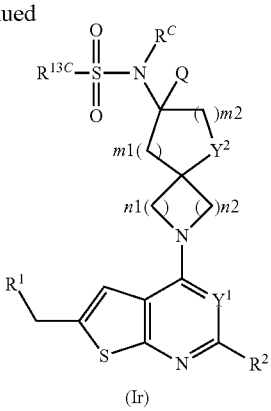

(Ir)

In Scheme 15, the following reaction conditions apply:

1: at a suitable temperature, for example room temperature, in the presence of a suitable base such as for example potassium carbonate or triethylamine, in a suitable solvent such as for example acetonitrile or DCM.

Someone skilled in the art will recognize that intermediate (Vb) can be prepared following a similar pathway than the one use for the preparation of intermediate V and reported in scheme 1.

Scheme 16

In general, compounds of Formula (I) wherein $R^2$ is restricted to H or Me, and $Y^1$ is restricted to N and C—CN, hereby named compounds of Formula (Is) can be prepared according to the following reaction Scheme 16. In Scheme 16, all other variables are defined according to above or according to the scope of the present invention.

In Scheme 16, the following reaction conditions apply:

1: in case of (LXa), at a suitable temperature, in the presence of a suitable base such as for example triethylamine, in a suitable solvent such as for example DCM, in case of (LXb), at a suitable temperature, such as for example room temperature, in the presence of a suitable acid coupling agent, such as for example 1-[bis(dimethyl-amino)methylene]-1H-benzotriazoliumhexafluorophosphate(1-)3-oxide (HBTU) or 1-[Bis(dimethylamino)methylene]-1H-1,2,3-triazolo[4,5-b]pyridinium 3-oxide hexafluorophosphate (HATU) or N-(3-Dimethylaminopropyl)-N'-ethylcarbodiimide hydrochloride (EDCI), optionally in the presence of a suitable reagent such as for example 1-Hydroxybenzotriazole, in the presence of a suitable base such as for example N-ethyl-N-(1-methylethyl)-2-propanamine (DIPEA) or triethylamine, in a suitable solvent such as N,N-dimethylformamide (DMF) or DCM.

Someone skilled in the art will recognize that conversion depicted in scheme 15 and 16 can be applied to other intermediates as for example intermediates (LVII) depicted in scheme 13.

Schemes 17-19 relate in particular to compounds/intermediates wherein variable 'A' is —$CR^{15a}R^{15b}$—.

Scheme 17

In general, compounds of Formula (I) wherein Q, $R^{15a}$ and $R^{15b}$ are restricted to H, and $Y^1$ is restricted to N and C—CN, hereby named compounds of Formula (It) can be prepared according to the following reaction Scheme 17. In Scheme 17, all other variables are defined according to above or according to the scope of the present invention,

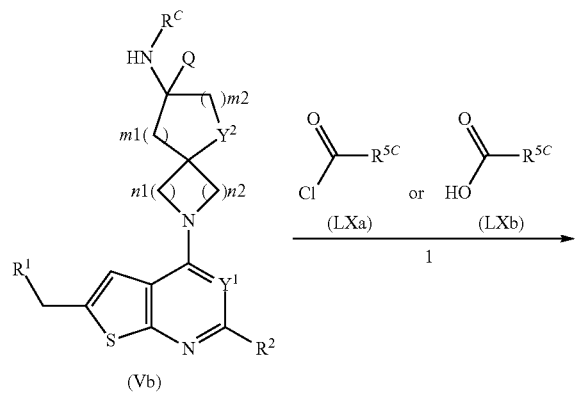

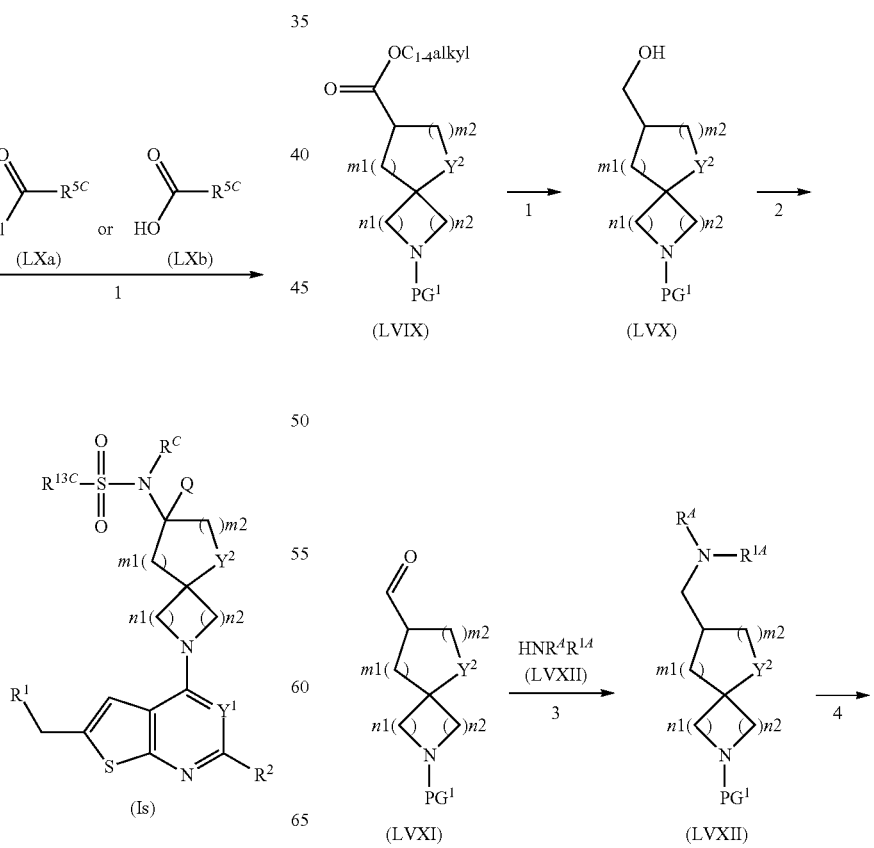

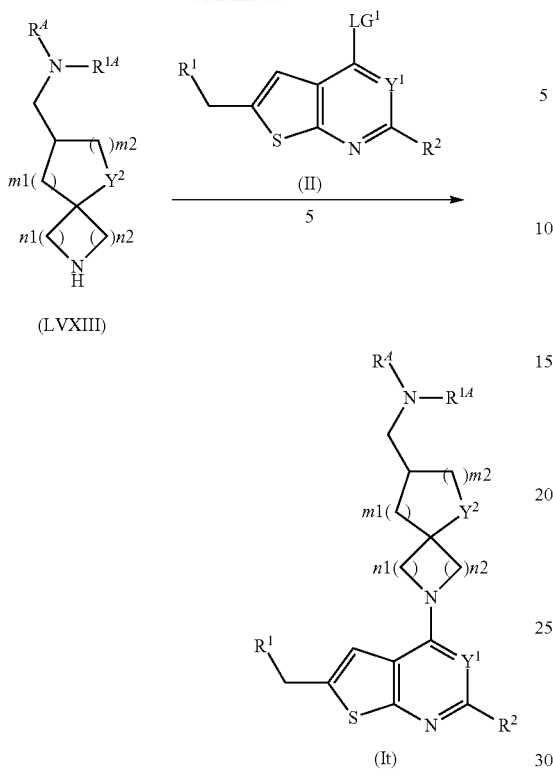

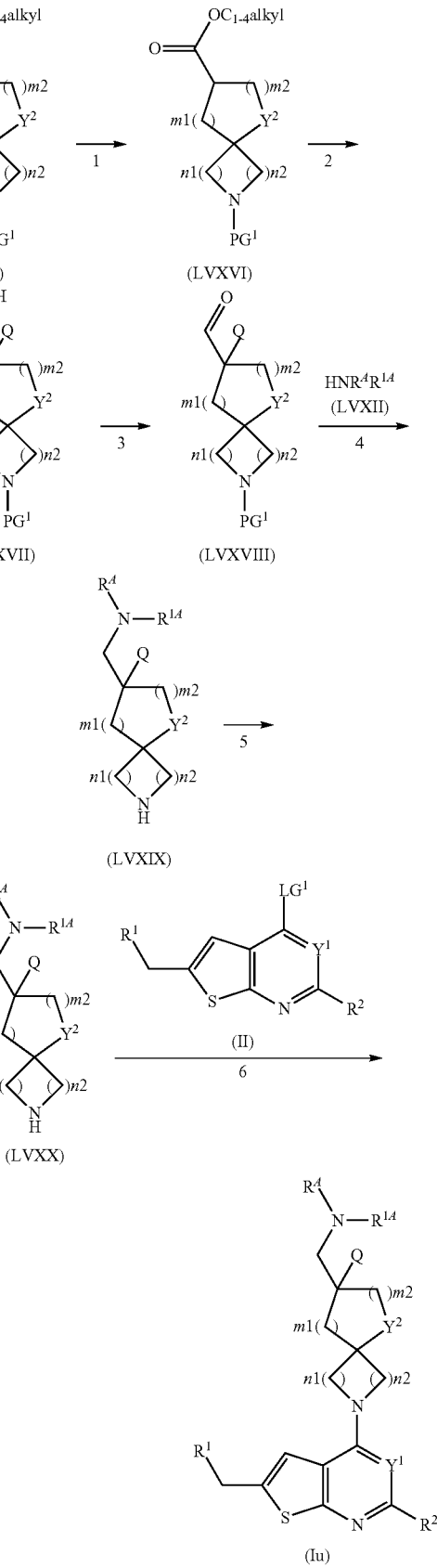

In Scheme 17, the following reaction conditions apply:

1: at a suitable temperature such as ranged between 0° C. and room temperature, in the presence of a suitable reducing agent such as for example lithium aluminium hydride, in a suitable solvent such as for example tetrahydrofuran;

2: at a suitable temperature such as for example −78° C., in the presence of suitable reagents such as for example oxalylchloride, dimethylsulfoxide, in the presence of a suitable base such as for example triethylamine, in a suitable solvent such as for example dichloromethane;

3: at a suitable temperature such as for example room temperature, in the presence of a suitable reducing agent such as for example sodium cyanoborohydride, with or without a suitable acid such as for example acetic acid, in a suitable solvent such as for example methanol;

4: at a suitable temperature such as for example room temperature, in the presence of a suitable acid such as for example trifluoroacetic acid, in a suitable solvent such as for example dichloromethane or ethyl acetate;

5: at a suitable temperature such as ranged from rt to 90° C., in the presence of a suitable base such as for example diisopropylethylamine or triethylamine, in a suitable solvent such as for example acetonitrile or isopropanol or ethanol (EtOH) or dichloromethane (DCM).

Scheme 18

In general, compounds of Formula (I) wherein $R^{15a}$ and $R^{15b}$ are restricted to H, and $Y^1$ is restricted to N and C—CN, hereby named compounds of Formula (Iu) can be prepared according to the following reaction Scheme 18. In Scheme 18, all other variables are defined according to above or according to the scope of the present invention, In Scheme 18, the following reaction conditions apply:

1: at a suitable temperature ranged from −78° C. to room temperature, in the presence of a suitable deprotonating agent such as for example sodium hydride or lithium diisopropylamide, in a suitable solvent such as for example tetrahydrofuran;

2: at a suitable temperature such as ranged between 0° C. and room temperature, in the presence of a suitable reducing agent such as for example lithium aluminium hydride, in a suitable solvent such as for example tetrahydrofuran;

3: at a suitable temperature such as for example −78° C., in the presence of suitable reagents such as for example oxalylchloride, dimethylsulfoxide, in the presence of a suitable base such as for example triethylamine, in a suitable solvent such as for example dichloromethane;

4: at a suitable temperature such as for example room temperature, in the presence of a suitable reducing agent such as for example sodium cyanoborohydride, with or without a suitable acid such as for example acetic acid, in a suitable solvent such as for example methanol;

5: at a suitable temperature such as for example room temperature, in the presence of a suitable acid such as for example trifluoroacetic acid, in a suitable solvent such as for example dichloromethane or ethyl acetate;

6: at a suitable temperature such as ranged from rt to 90° C., in the presence of a suitable base such as for example diisopropylethylamine or triethylamine, in a suitable solvent such as for example acetonitrile or isopropanol or ethanol (EtOH) or dichloromethane (DCM).

Scheme 19

In general, compounds of Formula (I) wherein Q is restricted to H and $Y^1$ is restricted to N and C—CN, hereby named compounds of Formula (Iv) can be prepared according to the following reaction Scheme 19. In Scheme 19, halo is a suitable halogen, $LG^3$ is a suitable leaving group, such as for example methanesulfonyl or 4-toluenesulfonyl, and all other variables are defined according to above or according to the scope of the present invention,

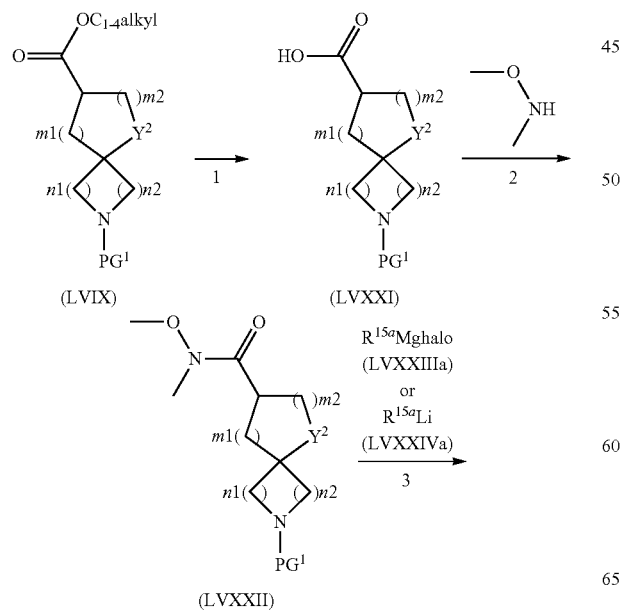

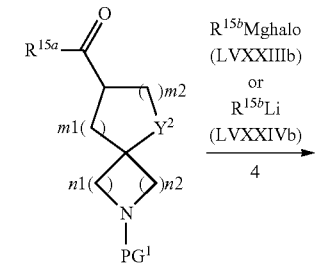

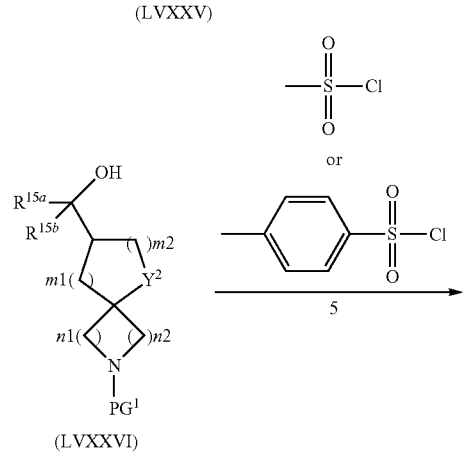

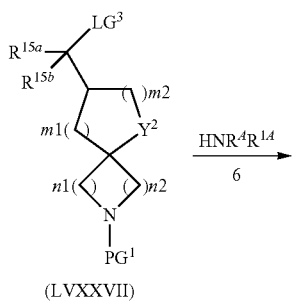

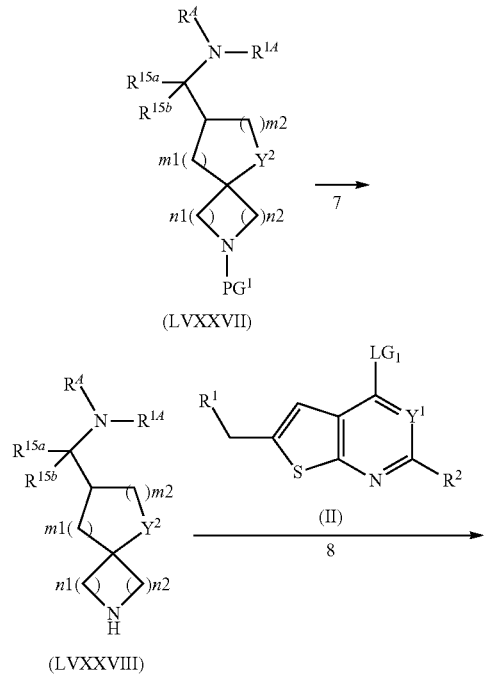

-continued

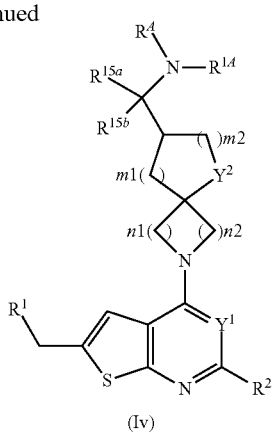

(Iv)

In Scheme 19, the following reaction conditions apply:

1: at a suitable temperature ranged for example between room temperature and 60° C., in the presence of a suitable base such as for example lithium hydroxide or sodium hydroxide; in a suitable solvent such as for example a mixture of tetrahydrofurane and water;

2: at a suitable temperature, such as for example room temperature, in the presence of a suitable acid coupling agent, such as for example 1-[bis(dimethylamino)methylene]-1H-benzotriazoliumhexafluorophosphate(1-)3-oxide (HBTU) or 1-[Bis(dimethylamino)methylene]-1H-1,2,3-triazolo[4,5-b]pyridinium 3-oxide hexafluorophosphate (HATU), in the presence of a suitable base such as for example N-ethyl-N-(1-methylethyl)-2-propanamine (DIPEA), in a suitable solvent such as N,N-dimethylformamide (DMF);

3: at a suitable temperature such as for example −78° C., 0° C. or room temperature, in a suitable solvent such as for example tetrahydrofuran;

4: at a suitable temperature such as for example −78° C., 0° C. or room temperature, in a suitable solvent such as for example tetrahydrofuran;

5: at a suitable temperature such as for example room temperature, in the presence of a suitable base such as for example triethylamine or diispropylamine, in a suitable solvent such as for example tetrahydrofuran or dichloromethane;

6: at a suitable temperature such as for example room temperature, in the presence of a suitable reducing agent such as for example sodium cyanoborohydride, with or without a suitable acid such as for example acetic acid, in a suitable solvent such as for example methanol;

7: at a suitable temperature such as for example room temperature, in the presence of a suitable acid such as for example trifluoroacetic acid, in a suitable solvent such as for example dichloromethane or ethyl acetate;

8: at a suitable temperature such as ranged from rt to 90° C., in the presence of a suitable base such as for example diisopropylethylamine or triethylamine, in a suitable solvent such as for example acetonitrile or isopropanol or ethanol (EtOH) or dichloromethane (DCM).

A skilled person will realize that the chemistry of Schemes 1 to 16 can also be applied to the intermediates depicted in Schemes 17 to 19.

It will be appreciated that where appropriate functional groups exist, compounds of various formulae or any intermediates used in their preparation may be further derivatised by one or more standard synthetic methods employing condensation, substitution, oxidation, reduction, or cleavage reactions. Particular substitution approaches include conventional alkylation, arylation, heteroarylation, acylation, sulfonylation, halogenation, nitration, formylation and coupling procedures.

The compounds of Formula (I) may be synthesized in the form of racemic mixtures of enantiomers which can be separated from one another following art-known resolution procedures. The racemic compounds of Formula (I) containing a basic nitrogen atom may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of Formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically.

In the preparation of compounds of the present invention, protection of remote functionality (e.g., primary or secondary amine) of intermediates may be necessary. The need for such protection will vary depending on the nature of the remote functionality and the conditions of the preparation methods. Suitable amino-protecting groups (NH-Pg) include acetyl, trifluoroacetyl, t-butoxycarbonyl (Boc), benzyloxycarbonyl (CBz) and 9-fluorenylmethyleneoxycarbonyl (Fmoc). The need for such protection is readily determined by one skilled in the art. For a general description of protecting groups and their use, see T. W. Greene and P. G. M. Wuts, Protective Groups in Organic Synthesis, 4th ed., Wiley, Hoboken, N.J., 2007.

Pharmacology

It has been found that the compounds of the present invention block the interaction of menin with MLL proteins and oncogenic MLL fusion proteins. Therefore the compounds according to the present invention and the pharmaceutical compositions comprising such compounds may be useful for the treatment or prevention, in particular treatment, of diseases such as cancer, myelodysplastic syndrome (MDS) and diabetes.

In particular, the compounds according to the present invention and the pharmaceutical compositions thereof may be useful in the treatment or prevention of cancer. According to one embodiment, cancers that may benefit from a treatment with menin/MLL inhibitors of the invention comprise leukemias, myeloma or a solid tumor cancer (e.g. prostate cancer, lung cancer, breast cancer, pancreatic cancer, colon cancer, liver cancer, melanoma and glioblastoma, etc.). In some embodiments, the leukemias include acute leukemias, chronic leukemias, myeloid leukemias, myelogeneous leukemias, lymphoblastic leukemias, lymphocytic leukemias, Acute myelogeneous leukemias (AML), Chronic myelogenous leukemias (CML), Acute lymphoblastic leukemias (ALL), Chronic lymphocytic leukemias (CLL), T cell prolymphocytic leukemias (T-PLL), Large granular lymphocytic leukemia, Hairy cell leukemia (HCL), MlLL-rearranged leukemias, MlLL-PTD leukemias, MlLL amplified leukemias, MlLL-positive leukemias, leukemias exphibiting HOX/MEIS1 gene expression signatures etc.

Hence, the invention relates to compounds of Formula (I), the tautomers and the stereoisomeric forms thereof, and the pharmaceutically acceptable salts, and the solvates thereof, for use as a medicament.

The invention also relates to the use of a compound of Formula (I), a tautomer or a stereoisomeric form thereof, or a pharmaceutically acceptable salt, or a solvate thereof, or a pharmaceutical composition according to the invention, for the manufacture of a medicament.

The present invention also relates to a compound of Formula (I), a tautomer or a stereoisomeric form thereof, or a pharmaceutically acceptable salt, or a solvate thereof, or a pharmaceutical composition according to the invention, for use in the treatment, prevention, amelioration, control or reduction of the risk of disorders associated with the interaction of menin with MLL proteins and oncogenic MLL fusion proteins in a mammal, including a human, the treatment or prevention of which is affected or facilitated by blocking the interaction of menin with MILL proteins and oncogenic MLL fusion proteins.

Also, the present invention relates to the use of a compound of Formula (I), a tautomer or a stereoisomeric form thereof, or a pharmaceutically acceptable salt, or a solvate thereof, or a pharmaceutical composition according to the invention, for the manufacture of a medicament for treating, preventing, ameliorating, controlling or reducing the risk of disorders associated with the interaction of menin with MLL proteins and oncogenic MILL fusion proteins in a mammal, including a human, the treatment or prevention of which is affected or facilitated by blocking the interaction of menin with MLL proteins and oncogenic MLL fusion proteins.

The invention also relates to a compound of Formula (I), a tautomer or a stereoisomeric form thereof, or a pharmaceutically acceptable salt, or a solvate thereof, for use in the treatment or prevention of any one of the diseases mentioned hereinbefore.

The invention also relates to a compound of Formula (I), a tautomer or a stereoisomeric form thereof, or a pharmaceutically acceptable salt, or a solvate thereof, for use in treating or preventing any one of the diseases mentioned hereinbefore.

The invention also relates to the use of a compound of Formula (I), a tautomer or a stereoisomeric form thereof, or a pharmaceutically acceptable salt, or a solvate thereof, for the manufacture of a medicament for the treatment or prevention of any one of the disease conditions mentioned hereinbefore.

The compounds of the present invention can be administered to mammals, preferably humans, for the treatment or prevention of any one of the diseases mentioned hereinbefore.

In view of the utility of the compounds of Formula (I), the tautomers and the stereoisomeric forms thereof and the pharmaceutically acceptable salts, and the solvates thereof, there is provided a method of treating warm-blooded animals, including humans, suffering from any one of the diseases mentioned hereinbefore.

Said method comprises the administration, i.e. the systemic or topical administration, preferably oral administration, of a therapeutically effective amount of a compound of Formula (I), a tautomer or a stereoisomeric form thereof, or a pharmaceutically acceptable salt, or a solvate thereof, to warm-blooded animals, including humans.

Therefore, the invention also relates to a method for the treatment or prevention of any one of the diseases mentioned hereinbefore comprising administering a therapeutically effective amount of compound according to the invention to a patient in need thereof.

One skilled in the art will recognize that a therapeutically effective amount of the compounds of the present invention is the amount sufficient to have therapeutic activity and that this amount varies inter alias, depending on the type of disease, the concentration of the compound in the therapeutic formulation, and the condition of the patient. Generally, the amount of a compound of the present invention to be administered as a therapeutic agent for treating the disorders referred to herein will be determined on a case by case by an attending physician.

Those of skill in the treatment of such diseases could determine the effective therapeutic daily amount from the test results presented hereinafter. An effective therapeutic daily amount would be from about 0.005 mg/kg to 100 mg/kg, in particular 0.005 mg/kg to 50 mg/kg, in particular 0.01 mg/kg to 50 mg/kg body weight, more in particular from 0.01 mg/kg to 25 mg/kg body weight, preferably from about 0.01 mg/kg to about 15 mg/kg, more preferably from about 0.01 mg/kg to about 10 mg/kg, even more preferably from about 0.01 mg/kg to about 1 mg/kg, most preferably from about 0.05 mg/kg to about 1 mg/kg body weight. A particular effective therapeutic daily amount might be 1 mg/kg body weight, 2 mg/kg body weight, 4 mg/kg body weigth, or 8 mg/kg body weight. The amount of a compound according to the present invention, also referred to herein as the active ingredient, which is required to achieve a therapeutically effect may vary on case-by-case basis, for example with the particular compound, the route of administration, the age and condition of the recipient, and the particular disorder or disease being treated. A method of treatment may also include administering the active ingredient on a regimen of between one and four intakes per day. In these methods of treatment the compounds according to the invention are preferably formulated prior to administration. As described herein below, suitable pharmaceutical formulations are prepared by known procedures using well known and readily available ingredients.

The present invention also provides compositions for preventing or treating the disorders referred to herein. Said compositions comprising a therapeutically effective amount of a compound of Formula (I), a tautomer or a stereoisomeric form thereof, or a pharmaceutically acceptable salt, or a solvate thereof, and a pharmaceutically acceptable carrier or diluent.

While it is possible for the active ingredient to be administered alone, it is preferable to present it as a pharmaceutical composition. Accordingly, the present invention further provides a pharmaceutical composition comprising a compound according to the present invention, together with a pharmaceutically acceptable carrier or diluent. The carrier or diluent must be "acceptable" in the sense of being compatible with the other ingredients of the composition and not deleterious to the recipients thereof.

The pharmaceutical compositions of this invention may be prepared by any methods well known in the art of pharmacy, for example, using methods such as those described in Gennaro et al. Remington's Pharmaceutical Sciences (18$^{th}$ ed., Mack Publishing Company, 1990, see especially Part 8: Pharmaceutical preparations and their Manufacture). A therapeutically effective amount of the particular compound, in base form or salt form, as the active ingredient is combined in intimate admixture with a pharmaceutically acceptable carrier, which may take a wide variety of forms depending on the form of preparation desired for administration. These pharmaceutical compositions are desirably in unitary dosage form suitable, preferably, for systemic administration such as oral, percutaneous or parenteral administration; or topical administration such as via inhalation, a nose spray, eye drops or via a cream, gel, shampoo or the like. For example, in preparing the compositions in oral dosage form, any of the usual pharmaceutical media tray be employed, such as, for example, water, glycols, oils, alcohols and the like in the case of oral liquid preparations such as suspensions, syrups, elixirs and solutions: or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wettable agent, optionally combined with suitable additives of any nature in minor proportions, which additives do not cause any significant deleterious effects on the skin. Said additives may facilitate the administration to the skin and/or may be helpful for preparing the desired compositions. These compositions may be administered in various ways, e.g., as a transdermal patch, as a spot-on or as an ointment.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfils and the like, and segregated multiples thereof.

The present compounds can be used for systemic administration such as oral, percutaneous or parenteral administration; or topical administration such as via inhalation, a nose spray, eye drops or via a cream, gel, shampoo or the like. The compounds are preferably orally administered. The exact dosage and frequency of administration depends on the particular compound of Formula (I) used, the particular condition being treated, the severity of the condition being treated, the age, weight, sex, extent of disorder and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention.

The compounds of the present invention may be administered alone or in combination with one or more additional therapeutic agents. Combination therapy includes administration of a single pharmaceutical dosage formulation which contains a compound according to the present invention and one or more additional therapeutic agents, as well as administration of the compound according to the present invention and each additional therapeutic agent in its own separate pharmaceutical dosage formulation. For example, a compound according to the present invention and a therapeutic agent may be administered to the patient together in a single oral dosage composition such as a tablet or capsule, or each agent may be administered in separate oral dosage formulations.

Therefore, an embodiment of the present invention relates to a product containing as first active ingredient a compound according to the invention and as further active ingredient one or more anticancer agent, as a combined preparation for simultaneous, separate or sequential use in the treatment of patients suffering from cancer.

The one or more other medicinal agents and the compound according to the present invention may be administered simultaneously (e.g. in separate or unitary compositions) or sequentially in either order. In the latter case, the two or more compounds will be administered within a period and in an amount and manner that is sufficient to ensure that an advantageous or synergistic effect is achieved. It will be appreciated that the preferred method and order of administration and the respective dosage amounts and regimes for each component of the combination will depend on the particular other medicinal agent and compound of the present invention being administered, their route of administration, the particular condition, in particular tumour, being treated and the particular host being treated. The optimum method and order of administration and the dosage amounts and regime can be readily determined by those skilled in the art using conventional methods and in view of the information set out herein.

The weight ratio of the compound according to the present invention and the one or more other anticancer agent(s) when given as a combination may be determined by the person skilled in the art. Said ratio and the exact dosage and frequency of administration depends on the particular compound according to the invention and the other anticancer agent(s) used, the particular condition being treated, the severity of the condition being treated, the age, weight, gender, diet, time of administration and general physical condition of the particular patient, the mode of administration as well as other medication the individual may be taking, as is well known to those skilled in the art. Furthermore, it is evident that the effective daily amount may be lowered or increased depending on the response of the treated subject and/or depending on the evaluation of the physician prescribing the compounds of the instant invention. A particular weight ratio for the present compound of Formula (I) and another anticancer agent may range from 1/10 to 10/1, more in particular from 1/5 to 5/1, even more in particular from 1/3 to 3/1.

The following examples further illustrate the present invention.

EXAMPLES

Several methods for preparing the compounds of this invention are illustrated in the following examples. Unless otherwise noted, all starting materials were obtained from commercial suppliers and used without further purification, or alternatively can be synthesized by a skilled person by using well-known methods.

Hereinafter, the terms: 'ACN', 'MeCN' or 'AcCN' means acetonitrile, 'DCM' means dichloromethane, 'DEA' means diethylamine, 'DIPEA' or 'DIEA' means N,N-diisopropylethylamine, 'h' means hours(s), 'min' means minute(s), 'DMF' means dimethylformamide, 'TEA or 'Et$_3$N' means triethyl amine 'EtOAc' or 'EA' means ethyl acetate, 'EtOH' means ethanol, 'HPLC' means High-performance Liquid Chromatography, 'Prep-HPLC' means preparative HPLC, 'Prep-TLC' means preparative TLC, 'iPrOH', 'IPA', '$^i$PA', 'i-PrOH' or 'iPrOH' means isopropyl alcohol, 'LC/MS' means Liquid Chromatography/Mass Spectrometry, 'MeOH' means methanol, 'MeNH₂' means methylamine, 'NMR' means Nuclear Magnetic Resonance, 'rt' or 'RT' means room temperature, 'SFC' means supercritical fluid chromatography, 'AcOH' means acetic acid, 'BOC' or 'Boc' means tert-butyloxycarbonyl, 'EDCI' or 'EDCi' means 1-(3-Dimethylaminopropyl)-3-ethylcarbodiimide hydrochloride, 'eq.' means equivalent(s), 'HOBT' or 'HOBt' means N-Hydroxybenzotrizole monohydrate, 'iPrNH₂' means isopropylamine, 'PE' means petroleum ether, 'NaBH(OAc)₃' means sodium triacetoxyborohydride, '$R_t$' means retention time, 'SFC' means supercritical fluid chromatography, 'T' means temperature, 'FA' means formic acid, 'TFA' means trifluoroacetic acid, 'TFAA' means trifluoroacetic anhydride, 'THF' means tetrahydrofuran, 'BrettPhos' means 2-(Dicyclohexylphosphino)3,6-dimethoxy-2',4',6'-triisopropyl-1,1'-biphenyl, 'ⁱBuONa' or 't-BuONa' means sodium tert-butoxide, 'Ts' means tosyl; 'Pd₂(dba)₃' means tris(dibenzylideneacetone)dipalladium(0), 'TLC' means thin layer chromatography, 'prep-TLC' means preparative TLC, 'DCE' means dichloroethane, 'Et₂O' means diethyl ether, 'HBTU' means 1-[bis(dimethylamino)-methylene]-1H-benzotriazoliumhexafluorophosphate(1-)3-oxide, 'SFC' means Supercritical Fluid Chromatography, '(Boc)₂O' means tert-butoxycarbonyl anhydride, 'ee' means enantiomeric excess, 'Pd₂(dba)₃' means Tris(dibenzylideneacetone)dipalladium, 'Pd(dppf)Cl₂' means [1,1'-Bis(diphenyl-phosphino)ferrocene]dichloropalladium(II), 'Pd(OAc)₂' means palladium(II) acetate, 'BINAP' means [1,1'-binaphthalene]-2,2'-diylbis[diphenylphosphine] (racemic), 'Ti(i-PrO)₄' means titanium isopropoxide, 'DMA' means N,N-dimethylacetamide, '18-Crown-6' means 1,4,7,10,13,16-hexaoxacyclooctadecane, 'CDI' means 1,1'-carbonyldiimidazole, 'HATU' means 1-[bis(dimethylamino)methylene]-1H-[1,2,3]triazolo[4,5-b]pyridin-1-ium 3-oxide hexafluorophosphate, 'DMSO' means dimethyl sulfoxide, 'FCC' means flash column chromatography, 'DBU' means 1,8-Diazabicyclo[5.4.0]undec-7-ene, 'NMP' means 1-methyl-2-pyrrolidinone, 'MW' means microwave or molecular weight (clear from context), 'T₃P' means propylphosphonic anhydride, 'DME' means 1,2-dimethoxyethane, 'Dess-Martin periodinane' or 'DMP' means 1,1,1-Triacetoxy-1,1-dihydro-1,2-benziodoxol-3(1H)-one, 'BPR' means backpressure, 'DIBAL-H' means Di-isobutylaluminiumhydride, 'psi' means pound-force per square inch, 'v/v' means volume per volume, 'conc.' means concentrated, 'Ph₃P' means triphenylphosphine, 'DEAD' means diethyl azodicarboxylate, 'DEGDME' means di-ethylene glycol dimethyl ether, 'BOP' means benzotriazole-1-yl-N-oxy-tris(pyrrolidino)phosphonium hexafluorophosphate, 'Hep' means n-heptane, 'MsCl' means mesyl chloride, 'Zn(OAc)₂.2H₂O' means zinc acetate dihydrate, 'TMSCN' means trimethylsilyl cyanide, 'Hantzsch ester' means diethyl 1,4-dihydro-2,6-dimethyl-3,5-pyridinedicarboxylate.

As understood by a person skilled in the art, compounds synthesized using the protocols as indicated may exist as a solvate e.g. hydrate, and/or contain residual solvent or minor impurities. Compounds isolated as a salt form, may be integer stoichiometric i.e. mono- or di-salts, or of intermediate stoichiometry. When an intermediate or compound in the experimental part below is indicated as 'HCl salt', 'formate salt' or 'TFA salt' without indication of the number of equivalents of HCl, formate or TFA, this means that the number of equivalents of HCl, formate or TFA was not determined.

The stereochemical configuration for centers in some compounds may be designated "R" or "S" when the mixture(s) was separated; for some compounds, the stereochemical configuration at indicated centers has been designated as "*R" (first eluted from the column in case the column conditions are described in the synthesis protocol and when only one stereocenter present or indicated) or "*S" (second eluted from the column in case the column conditions are described in the synthesis protocol and when only one stereocenter present or indicated) when the absolute stereochemistry is undetermined (even if the bonds are drawn stereo specifically) although the compound itself has been isolated as a single stereoisomer and is enantiomerically pure. For example, it will be clear that Compound 46

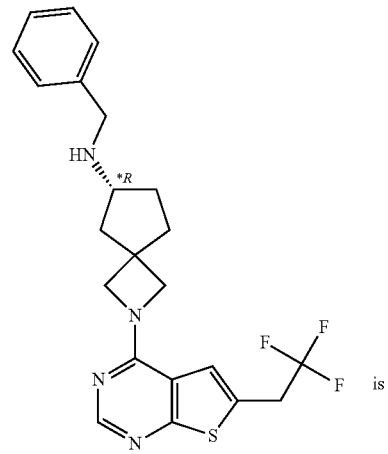

is

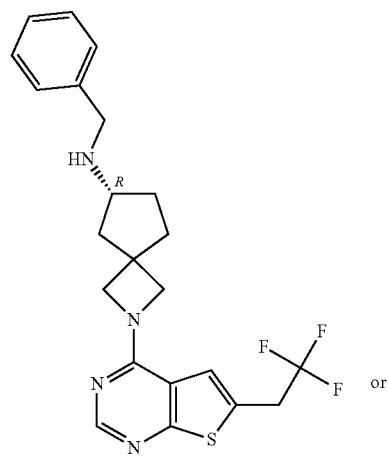

or

-continued

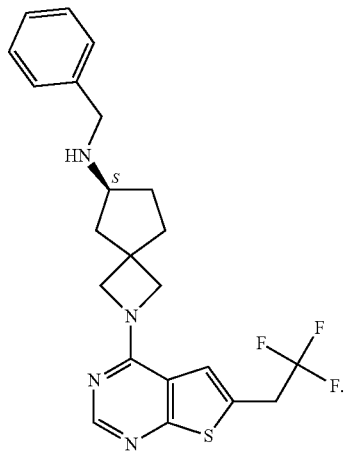

this means that the compound is

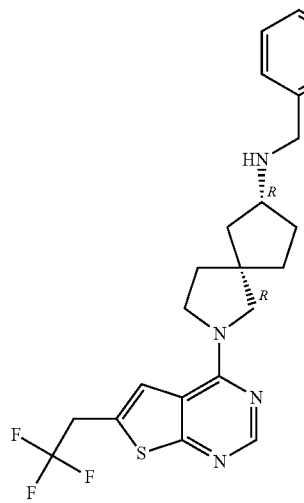

or

For compounds wherein the stereochemical configuration of two stereocentres is indicated by * (e.g. *R or *S), the absolute stereochemistry of the stereocentres is undetermined (even if the bonds are drawn stereospecifically), although the compound itself has been isolated as a single stereoisomer and is enantiomerically pure. In this case, the configuration of the first stereocentre is independent of the configuration of the second stereocentre in the same compound.

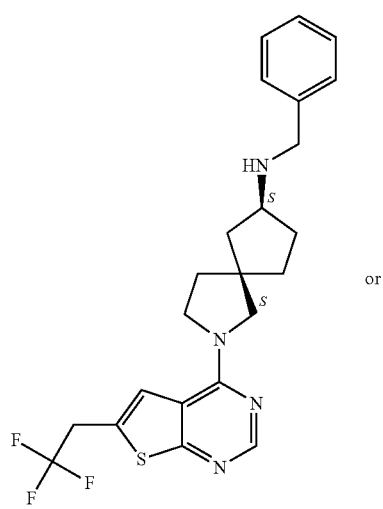

or

For example, for Compound 3

Compound 3

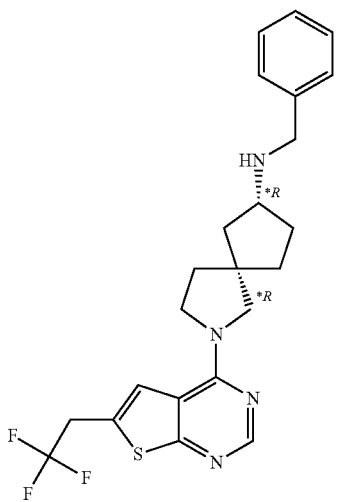

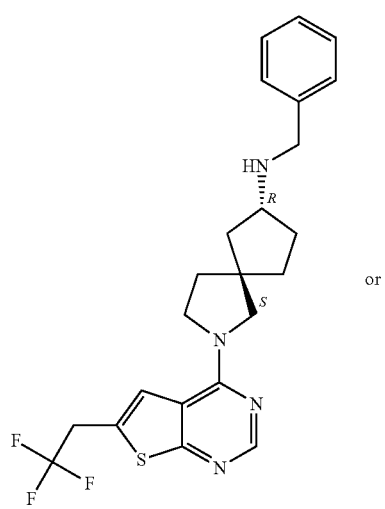

or

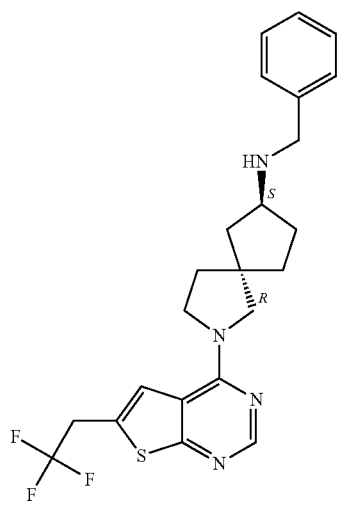

As mentioned above, substituents on bivalent cyclic saturated or partially saturated radicals may have either the cis- or trans-configuration; for example if a compound contains a disubstituted cycloalkyl group, the substituents may be in the cis or trans configuration.

For some compounds of Formula (I), the ring containing $Y^2$ is cyclobutyl ($Y^2$ is $CH_2$, m1 is 1, m2 is 0) or cyclohexyl ($Y^2$ is $CH_2$, m1 is 2, m2 is 1). The stereochemical configuration of the spiro moiety of such compounds may be indicated as 'cis or trans' or 'trans or cis'. This means that the absolute stereochemical configuration of the spiro moiety is undetermined, although the compound itself has been isolated as a single isomer.

For example, the compound below

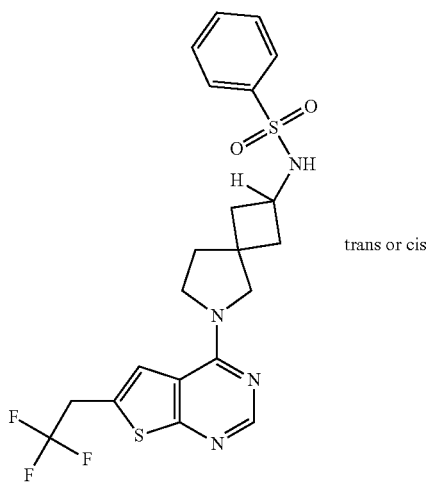

is

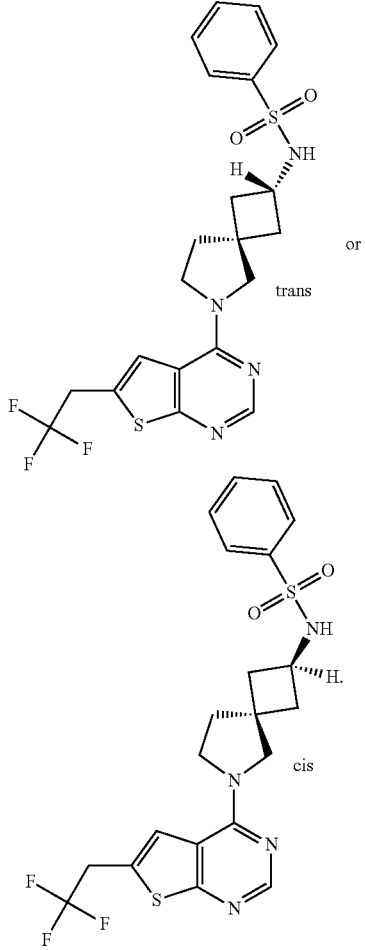

The paragraphs above about stereochemical configurations, also apply to intermediates. The term "enantiomerically pure" as used herein means that the product contains at least 80% by weight of one enantiomer and 20% by weight or less of the other enantiomer. Preferably the product contains at least 90% by weight of one enantiomer and 10% by weight or less of the other enantiomer. In the most preferred embodiment the term "enantiomerically pure" means that the composition contains at least 99% by weight of one enantiomer and 1% or less of the other enantiomer.

A skilled person will realize that, even where not mentioned explicitly in the experimental protocols below, typically after a column chromatography purification, the desired fractions were collected and the solvent was evaporated.

In case no stereochemistry is indicated in the spirocycle represented by L1, this means it is a mixture of stereoisomers, unless otherwise is indicated or is clear from the context.

When a stereocentre is indicated with 'RS' this means that a racemic mixture (or racemate) was obtained at the indicated centre, unless otherwise indicated. In the context of this experimental part 'racemic mixture' (or 'racemate') means a mixture in a ratio as determined via the Analytical Chiral-HPLC methods described herein, typically in a range of 40/60 to 60/40 ratio, preferably in a range of 45/55 to 55/45 ratio, more preferably in a range from 48/52 to 52/48 ratio, most preferably 50/50 ratio.

Purities mentioned in the experimental part below, are based on the result of HPLC (254 nm or 214 nm).

A. PREPARATION OF THE INTERMEDIATES

For intermediates that were used in a next reaction step as a crude or as a partially purified intermediate, in some cases no mol amounts are mentioned for such intermediate in the next reaction step or alternatively estimated mol amounts or theoretical mol amounts for such intermediate are indicated in the reaction protocols described below.

Example A1

Preparation of Intermediate 1

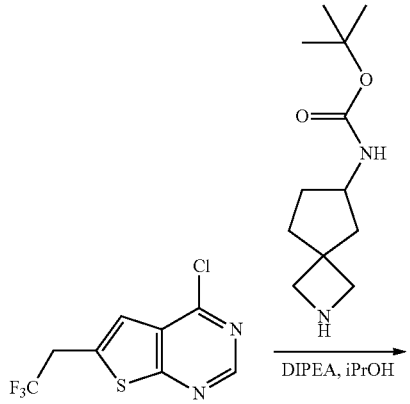

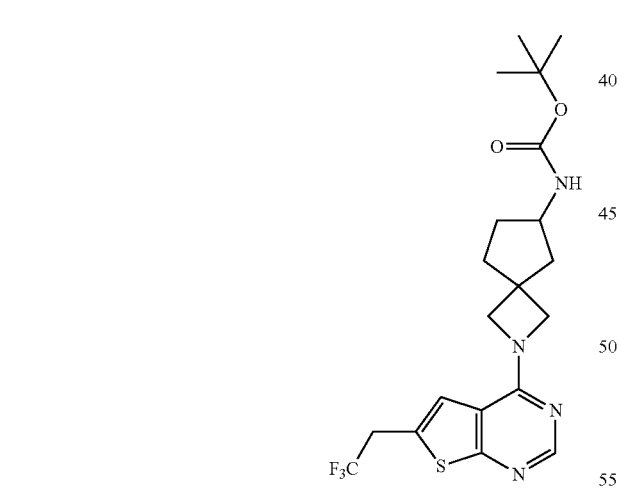

To a solution of tert-butyl (2-azaspiro[3.4]octan-6-yl)carbamate (2.70 g, 11.9 mmol) in isopropanol (20 mL) was added DIPEA (4.60 g, 35.8 mmol) and 4-chloro-6-(2,2,2-trifluoroethyl)thieno[2,3-d]pyrimidine (3.00 g, 11.9 mmol). After stirring at room temperature for 5 h, the reaction mixture was diluted with water (50 mL) and extracted with EtOAc (50 mL×3). The organic phase was washed with brine, dried over $Na_2SO_4$ and concentrated. The crude product was purified with column chromatography to give intermediate 1 (4.30 g).

Preparation of Intermediate 2

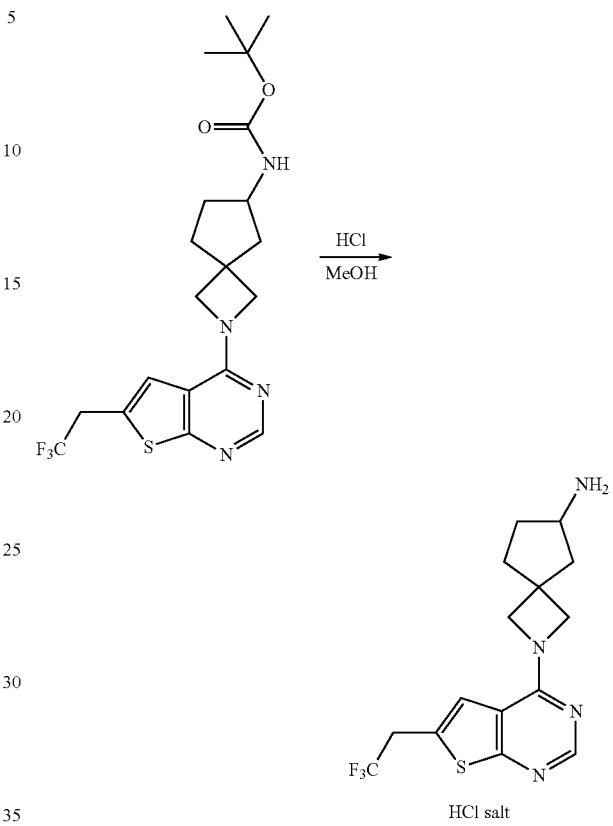

To a solution of intermediate 1 (4.60 g, 10.4 mmol) in MeOH (10 mL) was added conc. HCl (5.0 mL). After stirring at room temperature for 1 h, the mixture was concentrated to give intermediate 2 (3.0 g) as a HCl salt, which was used directly in the next step without further purification.

The intermediates in the table below were prepared by an analogous reaction protocol as described for the preparation of intermediate 2 starting from the respective starting materials.

| Intermediate number | Structure |
| --- | --- |
| Intermediate 3 (TFA was used to deprotect the Boc group) | (structure shown: 2-azaspiro[3.3]heptane with pyrrolidine ring fused to thieno[2,3-d]pyrimidine bearing CF$_2$F substituent, NH$_2$, TFA salt) |

| Intermediate number | Structure |
|---|---|
| Intermediate 3a | ![Intermediate 3a structure] NH₂, HCl salt |

| Intermediate number | Structure |
|---|---|
| Intermediate 5 | ![Intermediate 5 structure] |

Alternative Preparation of Intermediate 4

Intermediate 16 (215 mg; 1.33 mmol), 4-chloro-6-(2,2,2-trifluoroethyl)thieno[2,3-d]-pyrimidine (269 mg; 1.07 mmol) and DIPEA (516.5 mg; 4.0 mmol) were diluted in isopropanol (10 mL). The reaction was stirred for 12 h at 80° C. The solvent was removed to afford a yellow solid which was purified by column chromatography over silica gel (gradient eluent: DCM/MeOH from 100/0 to 10:1) to afford 200 mg (43%) of intermediate 4 as a yellow solid.

Intermediate 5 was also prepared alternatively by an analogous reaction protocol as the alternative preparation of intermediate 4, starting from the respective starting materials.

| Intermediate number | Structure |
|---|---|
| Intermediate 5 (from 6-azaspiro[3.4]octan-2-one (CAS[1803350-94-8]) and 4-chloro-6-(2,2,2-trifluoroethyl)thieno[2,3-d]pyrimidine ) | ![structure] |

Example A2

Preparation of Intermediate 4

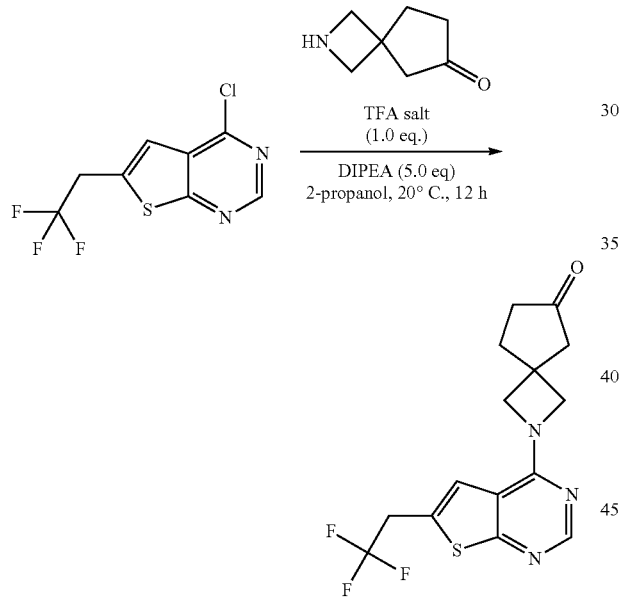

2-Azaspiro[3.4]octan-6-one trifluoroacetate (intermediate 16b) (180 mg), DIPEA (486 mg, 3.76 mmol) and 2-propanol (5 mL) were added to a 50 mL round-bottomed flask. The reaction mixture was treated with 4-chloro-6-(2,2,2-trifluoroethyl)thieno[2,3-d]-pyrimidine (190 mg, 0.752 mmol) before stirring at 20° C. for 12 h. The mixture was then poured into water (10 mL) and extracted with ethyl acetate (10 mL×2). The organic extracts were washed with brine (10 mL), dried over anhydrous Na₂SO₄, filtered and concentrated under reduced pressure to afford the crude product which was purified by flash column chromatography (eluent: petroleum ether:ethyl acetate from 1:0 to 0:1) to afford intermediate 4 (140 mg, 49.1% yield) as yellow oil.

The intermediate in the table below was prepared by an analogous reaction protocol as described above for the preparation of intermediate 4 starting from the respective starting materials.

Preparation of Intermediate 16

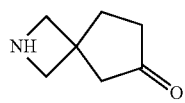

2-Boc-6-oxo-2-azaspiro[3.4]octane (300 mg, 1.33 mmol) was added to 4N HCl in dioxane (4 mL). The reaction was stirred for 1 h at room temperature. The solvent was evaporated till dryness yielding 280 mg of intermediate 16 of HCl salt.

The skilled person will understand that the TFA salt of intermediate 16 can also be obtained in an analogous way (TFA salt is intermediate 16b).

Example A3

Preparation of Intermediate 6

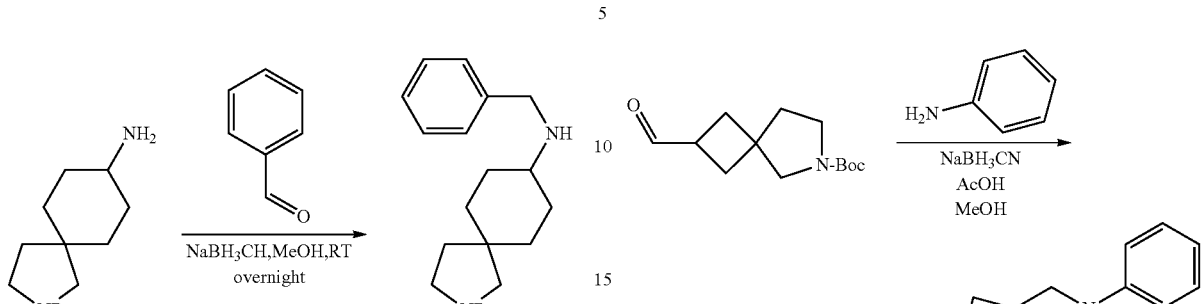

To a solution of tert-butyl 8-amino-2-azaspiro[4.5]decane-2-carboxylate (300 mg, 1.18 mmol) in MeOH (10 mL) was added benzaldehyde (125 mg, 1.18 mmol) and the mixture was stirred at room temperature for 2 h. NaBH$_3$CN (148 mg, 2.36 mmol) was then added into the mixture and stirred overnight at room temperature. The mixture was concentrated, diluted with EtOAc and H$_2$O, separated and extracted twice with EtOAc. The combined extracts ware concentrated in vacuo to afford intermediate 6 (360 mg, 88.6% yield), which was used as such in the next step without further purification.

Preparation of Intermediate 7

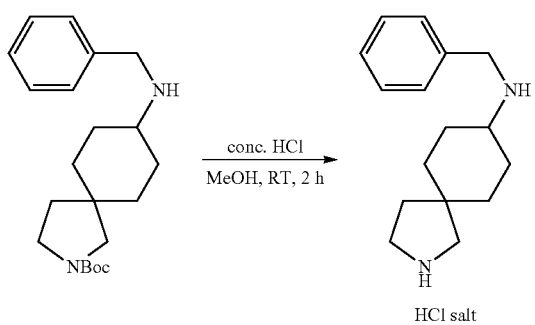 [SMILES: CC(C)(C)OC(=O)N1CCC2(CCC(NCc3ccccc3)CC2)C1 ; c1ccc(CNC2CCC3(CCNC3)CC2)cc1]

To a solution of intermediate 6 (360 mg, 1.05 mmol) in MeOH (5 mL) was added conc. HCl (3 mL). After stirring at room temperature for 1 h, the mixture was concentrated, diluted with EtOAc and washed with H$_2$O, combined the extracts and concentrated to give intermediate 7 as HCl salt (216 mg), which was used as such in the next step without further purification.

The intermediate in the table below was prepared by an analogous reaction protocol as described for the preparation of intermediate 7 starting from the respective starting materials.

| Intermediate number | Structure |
|---|---|
| Intermediate 8 | 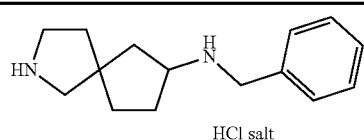 HCl salt |

Example A4

Preparation of Intermediate 9

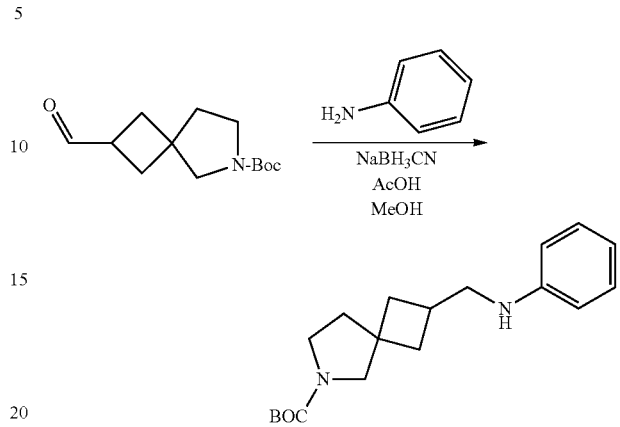

To a solution of tert-butyl 2-formyl-6-azaspiro[3.4]octane-6-carboxylate (200 mg, 0.836 mmol) and aniline (78 mg, 0.836 mmol) in MeOH (5 mL) were added CH$_3$COOH (5 mg) and NaBH$_3$CN (158 mg, 2.51 mmol) at 0° C. The mixture was stirred at room temperature overnight. The reaction was diluted with NH$_4$Cl solution, extracted with EA, washed with brine, dried over Na$_2$SO$_4$, filtered and concentrated.

The residue was purified by column chromatography (PE/EA=10/1) to afford intermediate 9 (230 mg, 76% yield).

Preparation of Intermediate 10

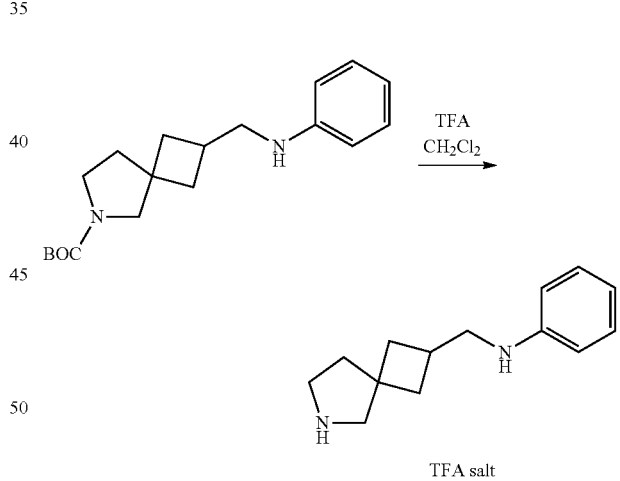

To a solution of intermediate 9 (230 mg, 0.727 mmol) in DCM (3 mL) was added TFA (1 mL). The resulting mixture was stirred at room temperature for 1.5 h, and then the mixture was concentrated to give intermediate 10 as a TFA salt (157 mg, crude), which was used as such in the next step without further purification.

The intermediates in the table below were prepared by an analogous reaction protocol as described for the preparation of intermediate 10, starting from the respective starting materials. For intermediates 11-12-13, HCl was used to deprotect the Boc group. The starting materials of intermediates 11, 12 and 13 were prepared via analogous reaction protocols as used for intermediate 9.

Intermediate 11

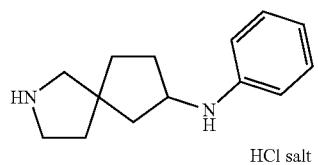 [SMILES: c1ccc(NC2CCC3(CCNC3)C2)cc1]

HCl salt

Intermediate 12

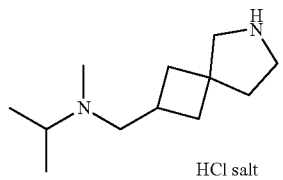

HCl salt

Intermediate 13

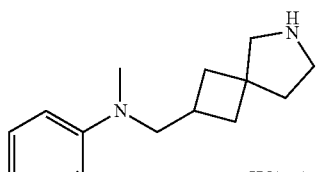

HCl salt

Example A5

Preparation of Intermediate 14

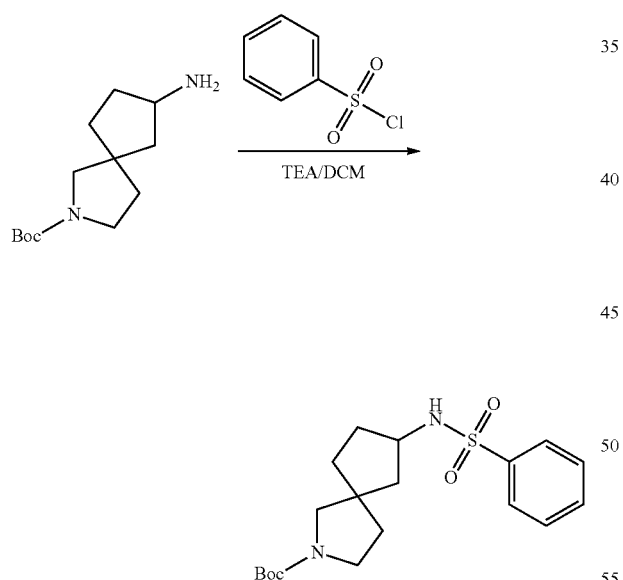

To a solution of tert-butyl 7-amino-2-azaspiro[4.4]nonane-2-carboxylate (50.0 mg, 0.208 mmol) and TEA (63.0 mg, 0.624 mmol) in DCM (20 mL) was added benzenesulfonyl chloride (48.0 mg, 0.271 mmol). After stirring at 0° C. for 5 h, the reaction mixture was added water (20 mL) and extracted with EtOAc (50 mL×3). The organic phase was washed with brine, dried over $Na_2SO_4$ and concentrated to give crude intermediate 14 (60 mg), which was used as such in the next step without further purification.

Preparation of Intermediate 15

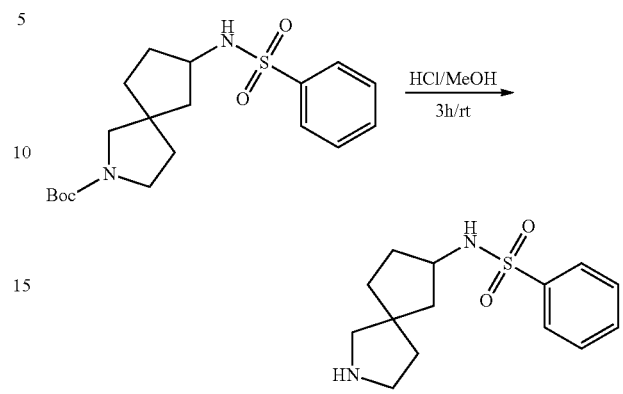

To a solution of crude intermediate 14 (60 mg) in MeOH (5 mL) was added conc. HCl (3 mL). After stirring at room temperature for 1 h, the mixture was concentrated to give intermediate 15 (35 mg), which was used as such in the next step without further purification.

Example A6

Preparation of Intermediate 17

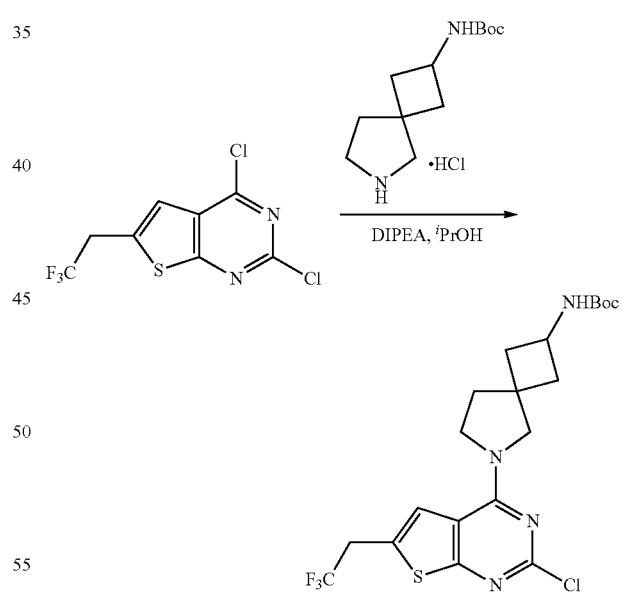

A mixture of 2,4-dichloro-6-(2,2,2-trifluoroethyl)thieno [2,3-d]pyrimidine and tert-butyl 6-azaspiro[3.4]octan-2-yl-carbamate hydrochloride (2.63 g, 10 mmol) and DIPEA (3.87 g, 30 mmol) in isopropanol (30 mL) was stirred at room temperature for 2 hours. After the reaction was completed, the reaction mixture was concentrated under reduced pressure. The residue was purified by silica gel column chromatography (Petroleum ether/EtOAc=1/1) to give intermediate 17 (4.7 g, 100% yield) as a light orange solid.

Preparation of Intermediate 18

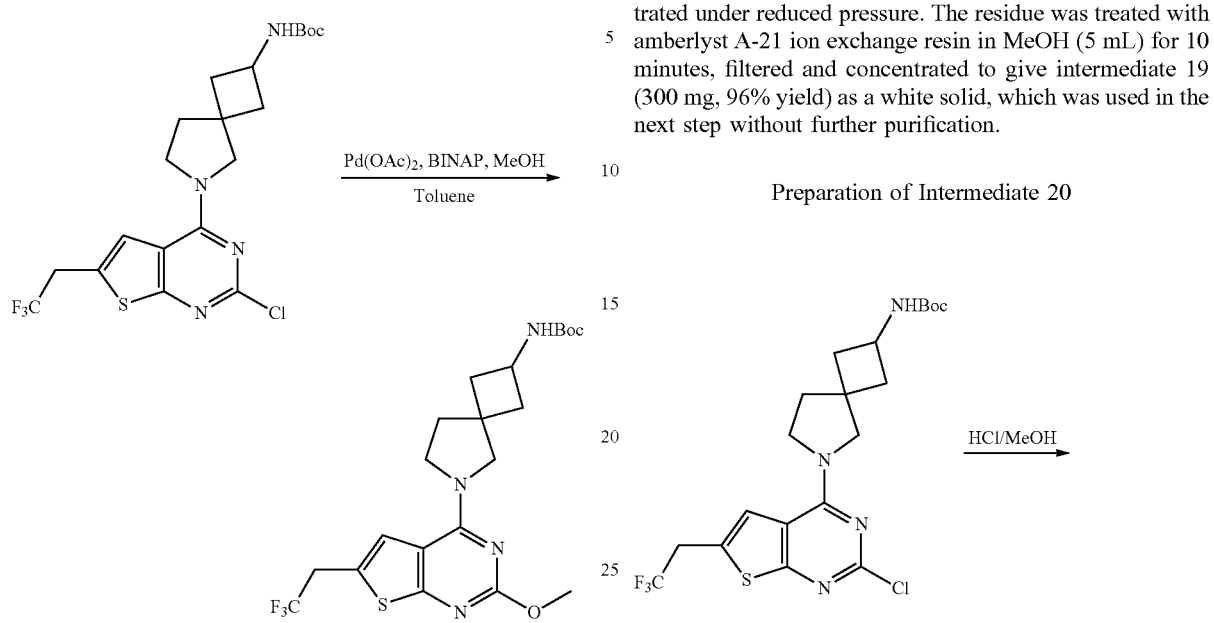

To a mixture of intermediate 17 (954 mg, 2.0 mmol), Pd(OAc)$_2$ (56.0 mg, 0.20 mmol), BINAP (150 mg, 0.24 mmol) and Cs$_2$CO$_3$ (978 mg, 3.0 mmol) in toluene (20 mL) was added MeOH (384 mg. 12 mmol). After being stirred at 110° C. overnight under Ar, the mixture was diluted with H$_2$O (20 mL) and extracted with EtOAc (20 mL×3). The combined organic layers were washed with brine (40 mL), dried over Na$_2$SO$_4$, filtered and concentrated under reduced pressure. The residue was purified by silica gel column chromatography (Petroleum ether/EtOAc=3/1) to give intermediate 18 (810 mg, 86% yield) as a yellow solid.

TFA (2 mL) was added to a mixture of intermediate 18 (tert-butyl (6-(2-methoxy-6-(2,2,2-trifluoroethyl)thieno[2,3-d]pyrimidin-4-yl)-6-azaspiro[3.4]octan-2-yl)carbamate) (400 mg, 0.88 mmol) in DCM (2 mL). After being stirred at room temperature for 2 h, the reaction mixture was concentrated under reduced pressure. The residue was treated with amberlyst A-21 ion exchange resin in MeOH (5 mL) for 10 minutes, filtered and concentrated to give intermediate 19 (300 mg, 96% yield) as a white solid, which was used in the next step without further purification.

Preparation of Intermediate 20

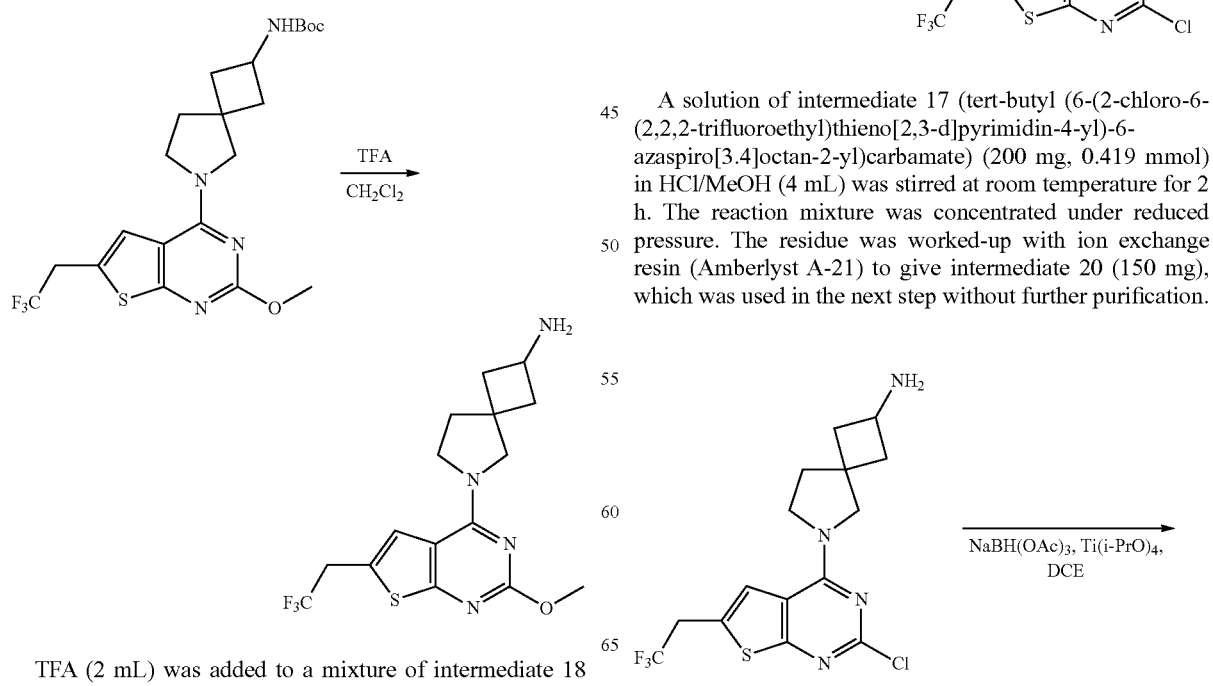

A solution of intermediate 17 (tert-butyl (6-(2-chloro-6-(2,2,2-trifluoroethyl)thieno[2,3-d]pyrimidin-4-yl)-6-azaspiro[3.4]octan-2-yl)carbamate) (200 mg, 0.419 mmol) in HCl/MeOH (4 mL) was stirred at room temperature for 2 h. The reaction mixture was concentrated under reduced pressure. The residue was worked-up with ion exchange resin (Amberlyst A-21) to give intermediate 20 (150 mg), which was used in the next step without further purification.

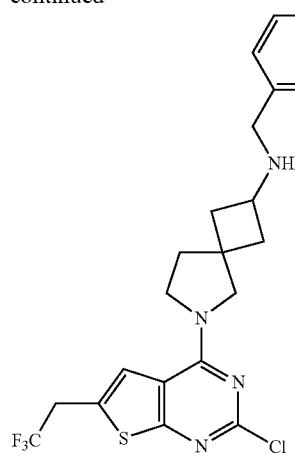

To a solution of intermediate 20 (6-(2-chloro-6-(2,2,2-trifluoroethyl)thieno[2,3-d]-pyrimidin-4-yl)-6-azaspiro[3.4]octan-2-amine) (169 mg, 0.448 mmol), benzaldehyde (95 mg, 0.895 mmol) and Titanium tetraisopropanolate (127 mg, 0.448 mmol) in DCE (5 mL) was added NaBH(OAc)$_3$ (285 mg, 1.34 mmol) in portions at room temperature. After being stirred at room temperature overnight, the reaction mixture was quenched with aqueous NaHCO$_3$ and extracted with DCM (20 mL×3). The combined organic layers were washed with brine and dried over Na$_2$SO$_4$, filtered and concentrated under reduced pressure. The residue was purified by silica gel column chromatography (PE/EtOAc=3:1~1:1) to give intermediate 21 (250 mg) as a white solid.

Example A7

Preparation of Intermediate 22

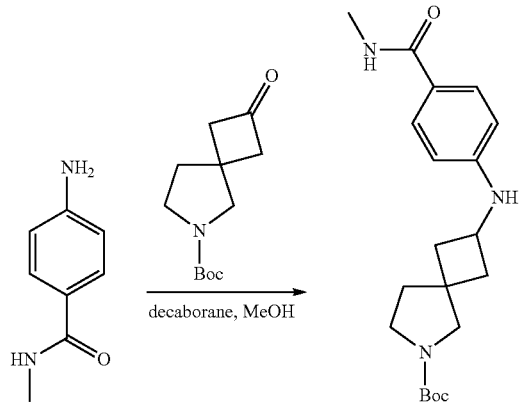 [SMILES: CNC(=O)c1ccc(N)cc1 ; CC(C)(C)OC(=O)N1CCC2(CC(=O)C2)C1 ; CNC(=O)c1ccc(NC2CC3(CCN(C(=O)OC(C)(C)C)C3)C2)cc1]

To a solution of 4-amino-N-methylbenzamide (150 mg, 1.00 mmol) in MeOH (4 mL) was added tert-butyl 2-oxo-6-azaspiro[3.4]octane-6-carboxylate (292 mg, 1.3 mmol) and decaborane (42.7 mg, 0.35 mmol). After being stirred at room temperature overnight, the resulting mixture was concentrated under reduced pressure to give intermediate 22 (350 mg, crude, 95% yield), which was used in the next step without further purification.

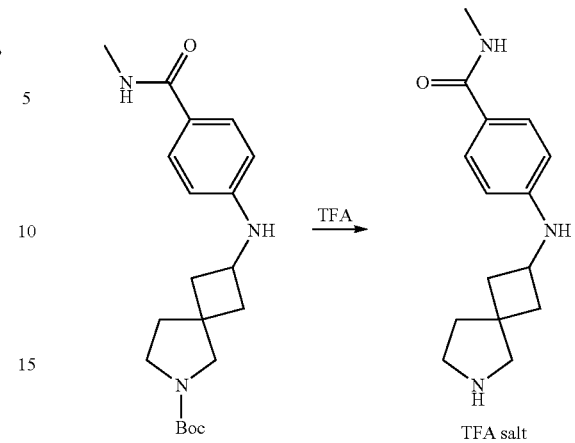

To a solution of intermediate 22 (tert-butyl 2-((4-(methylcarbamoyl)phenyl)amino)-6-azaspiro[3.4]octane-6-carboxylate) (350 mg, crude) in DCM (10 mL) was added TFA (2 mL). After being stirred at room temperature for 3 h, the resulting mixture was concentrated under reduced pressure to yield intermediate 23 (250 mg, crude TFA salt, 98% yield), which was used in the next step without further purification.

Preparation of Intermediate 24

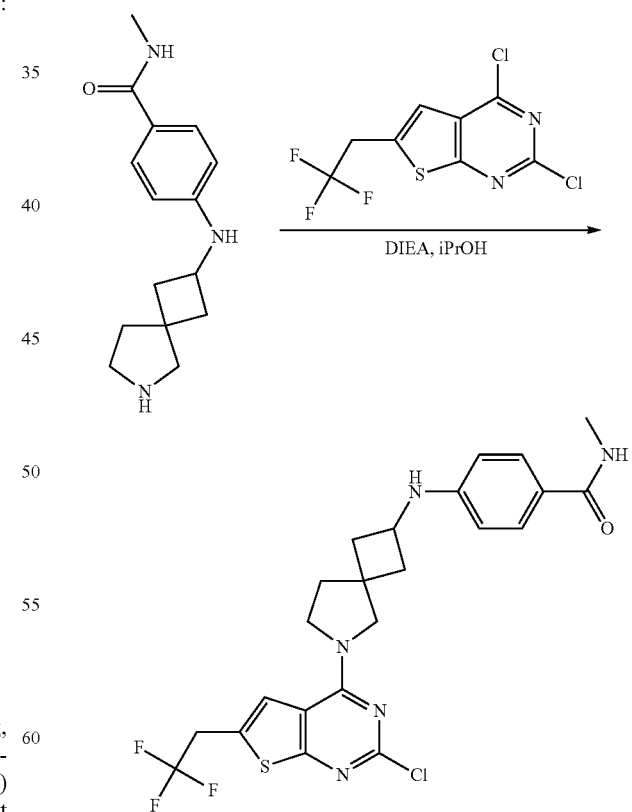

To a mixture of 2,4-dichloro-6-(2,2,2-trifluoroethyl)thieno[2,3-d]pyrimidine (300 mg, 1.04 mmol) and intermediate 23 (250 mg, crude) in $^i$PrOH (5 mL) was added DIPEA (404 mg, 3.12 mmol). After being stirred at room temperature overnight, the resulting mixture was concentrated under reduced pressure. The residue was purified by prep-TLC (DCM:MeOH=20:1) to give intermediate 24 (200 mg, 39% yield over 3 steps).

Example A8

Preparation of Intermediate 25

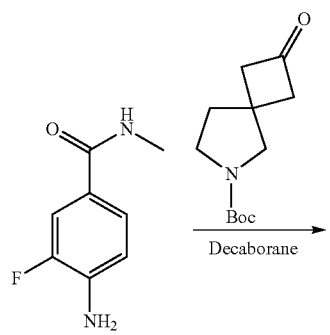

To a solution of methyl 4-amino-3-fluoro-N-methylbenzamide (200 mg, 1.19 mmol) and tert-butyl 2-oxo-6-azaspiro[3.4]octane-6-carboxylate (268 mg, 1.19 mmol) in MeOH (10 mL) was added decaborane (44 mg, 0.357 mmol). After being stirred at room temperature for 3 days, the mixture was diluted with water (20 mL) and extracted with EtOAc (50 mL×3). The organic phase was washed with brine, dried over Na$_2$SO$_4$, filtered and concentrated under reduced pressure. The residue was purified by silica gel column chromatography (PE/EA=5/1) to give intermediate 25 (400 mg, 89% yield) as a white solid.

Preparation of Intermediate 26

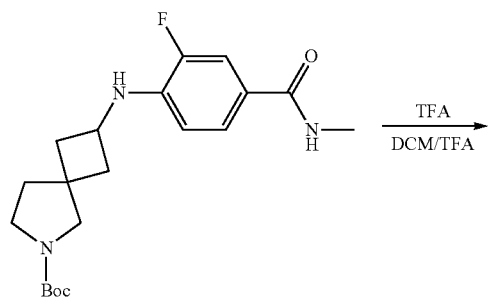

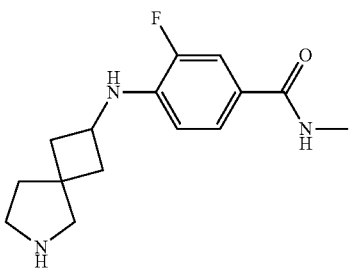

To a solution of intermediate 25 (tert-butyl 2-((2-fluoro-4-(methylcarbamoyl)phenyl)-amino)-6-azaspiro[3.4]octane-6-carboxylate) (400 mg, 1.06 mmol) in DCM (5 mL) was added TFA (2 ml). After being stirred at room temperature for 3 h, the mixture was adjusted pH>7 with NaHCO$_3$ and extracted with ethyl acetate (100 mL×3). The combined organic layers were washed with brine (50 mL×2) and dried over Na$_2$SO$_4$, filtered and concentrated under reduced pressure. The residue was purified by silica gel column chromatography (PE:EA=10:1) to afford intermediate 26 (200 mg, 68% yield) as oil.

Example A9

Preparation of Intermediate 27

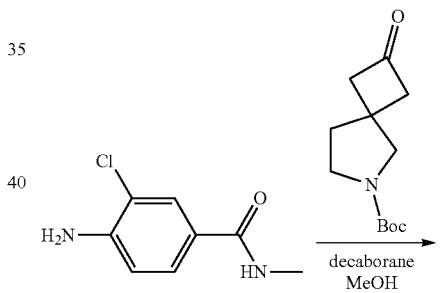

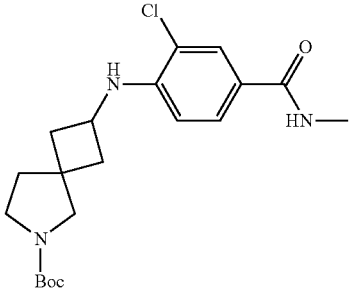

To a solution of 4-amino-3-chloro-N-methylbenzamide (485 mg, 2.635 mmol) and tert-butyl 2-oxo-6-azaspiro[3.4] octane-6-carboxylate (592 mg, 2.635 mmol) in MeOH (10 mL) was added decaborane (112 mg, 0.922 mmol). After being stirred at room temperature for 12 h, the mixture was diluted with water (20 mL) and extracted with EtOAc (50 mL×3). The organic phase was washed with brine, dried over Na$_2$SO$_4$, filtered and concentrated to give crude intermediate 27 as yellow oil.

Preparation of Intermediate 28

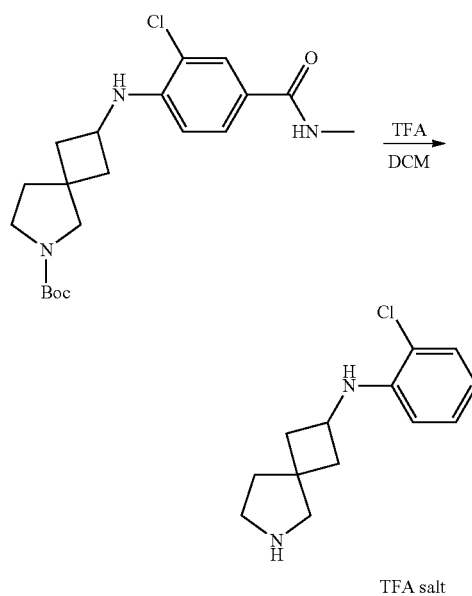

TFA salt

To a solution of intermediate 27 (tert-butyl 2-((2-chloro-4-(methylcarbamoyl)phenyl)-amino)-6-azaspiro[3.4]octane-6-carboxylate) (350 mg, 0.890 mmol) in CH$_2$Cl$_2$ (5 mL) was added TFA (5 mL). After being stirred at room temperature for 3 h, the mixture was concentrated under reduced pressure to give intermediate 28 (260 mg, crude), which was used in the next step without further purification.

Example A10

Preparation of Intermediate 29

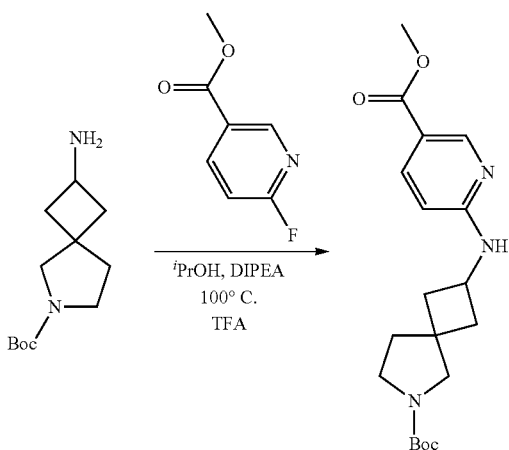 [SMILES: CC(C)(C)OC(=O)N1CCC2(CC(N)C2)C1 ; COC(=O)c1ccc(F)nc1 ; COC(=O)c1ccc(NC2CC3(CCN(C(=O)OC(C)(C)C)C3)C2)nc1]

To a solution of tert-butyl 2-amino-6-azaspiro[3.4]octane-6-carboxylate (200 mg, 0.88 mmol) and methyl 6-fluoronicotinate (178 mg, 1.15 mmol) in i-PrOH (2 mL) was added DIPEA (342 mg, 2.65 mmol). After being stirred at 100° C. for 12 h, the mixture was diluted with water (20 mL) and extracted with EtOAc (50 mL×3). The combined organic phase was washed with brine and dried over Na$_2$SO$_4$, filtered and concentrated under reduced pressure. The residue was purified by prep-TLC (DCM:MeOH=30:1) to give intermediate 29 (220 mg, 69% yield).

Preparation of Intermediate 30

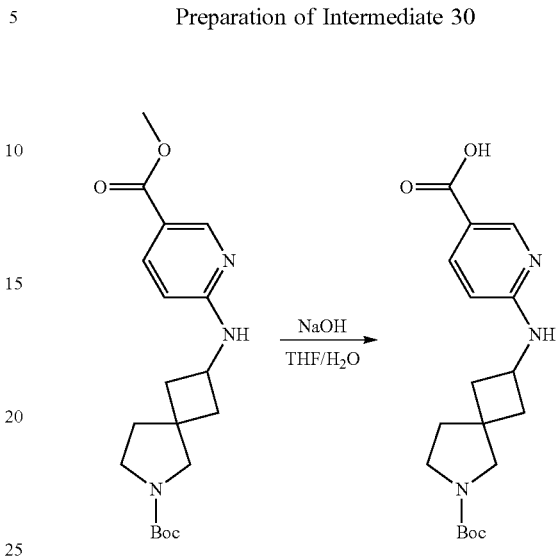

To a solution of intermediate 29 (tert-butyl 2-((5-(methoxycarbonyl)pyridin-2-yl)-amino)-6-azaspiro[3.4]octane-6-carboxylate) (200 mg, 0.55 mmol) in THF (4 mL) was added aq. NaOH (2N, 2 mL). After being stirred at 80° C. for 2 h, the resulting mixture was cooled to room temperature, adjusted pH~4 with 1N HCl and extracted with EtOAc (50 mL×3). The organic phase was washed with brine, dried over Na$_2$SO$_4$, filtered and concentrated to yield intermediate 30 (150 mg, 78% yield).

Preparation of Intermediate 31

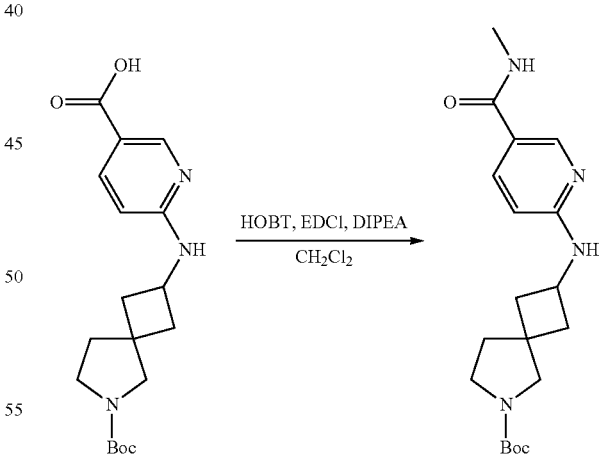

A solution of intermediate 30 (6-(((6-(tert-butoxycarbonyl)-6-azaspiro[3.4]octan-2-yl)-amino)nicotinic acid) (100 mg, 0.288 mmol), CH$_3$NH$_2$.HCl (29 mg, 0.432 mmol), HOBT (78 mg, 0.576 mmol), EDCI (110 mg, 0.576 mmol) and DIPEA (111 mg, 0.864 mmol) in DCM (5 mL) was stirred at room temperature for 12 h. The mixture was diluted with water (20 mL) and extracted with EtOAc (50 mL×3). The organic phase was washed with brine, dried over Na$_2$SO$_4$, filtered and concentrated. The crude was purified by prep-TLC (DCM:MeOH=20:1) to give intermediate 31 (100 mg, 97% yield).

Preparation of Intermediate 32

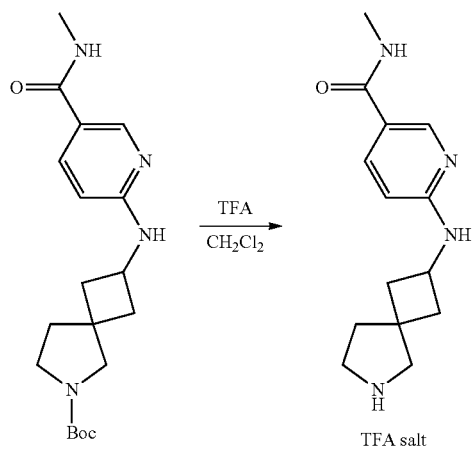

A solution of intermediate 31 (tert-butyl 2-((5-(methylcarbamoyl)pyridin-2-yl)amino)-6-azaspiro[3.4]octane-6-carboxylate) (100 mg, 0.277 mmol) and TFA (2 mL) in DCM (4 mL) was stirred at room temperature for 12 h. The mixture was concentrated under reduced pressure to give intermediate 32 (100 mg, crude TFA salt), which was used in the next step without further purification.

Example A11

Preparation of Intermediate 33

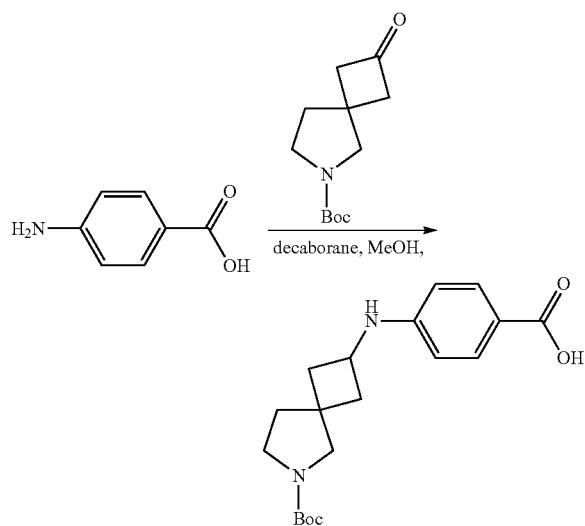

To a solution of tert-butyl 2-oxo-6-azaspiro[3.4]octane-6-carboxylate (2.00 g, 8.89 mmol) in MeOH (20 mL) were added 4-aminobenzoic acid (1.20 g, 8.89 mmol) and decaborane (380 mg, 3.11 mmol). After being stirred at room temperature overnight, the mixture was concentrated under reduced pressure to yield intermediate 33 (3.10 g, 100% yield) as colorless oil, which was used in the next step directly without further purification.

Preparation of Intermediate 34

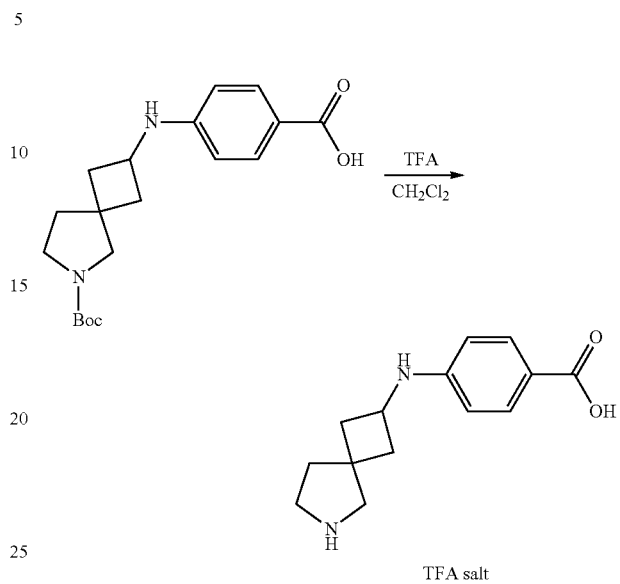

To a solution of intermediate 33 (4-((6-(tert-butoxycarbonyl)-6-azaspiro[3.4]octan-2-yl)amino)benzoic acid) (3.10 g, 8.89 mmol) in DCM (20 mL) was added TFA (10 mL). After being stirred at room temperature for 1 hour, the mixture was concentrated under reduced pressure to yield intermediate 34 (2.20 g, TFA salt) as brown oil, which was used in the next step directly without further purification.

Preparation of Intermediate 35

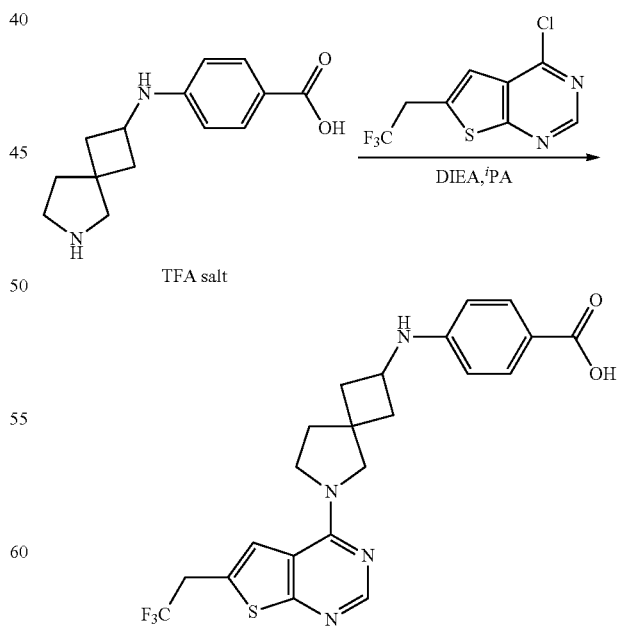

To a solution of intermediate 34 (4-((6-azaspiro[3.4]octan-2-yl)amino)benzoic acid TFA salt (2.20 g, 8.89 mmol) in i-PrOH (20 mL) were added 4-chloro-6-(2,2,2-trifluoroethyl)thieno[2,3-d]pyrimidine (2.20 g, 8.89 mmol) and DIPEA (5.70 g, 44.45 mmol) dropwise. The resulting mixture was stirred at room temperature overnight. The reaction mixture was concentrated under reduced pressure. The resulting yellow oil was diluted in aqueous NH₄Cl while being stirred overnight. The suspension was filtered and dried under reduced pressure. The residue was purified with silica gel column chromatography eluted with DCM/MeOH (30/1 to 20/1) to yield intermediate 35 (2.30 g, 56% yield) as a yellow solid.

Example A12

Preparation of Intermediate 36

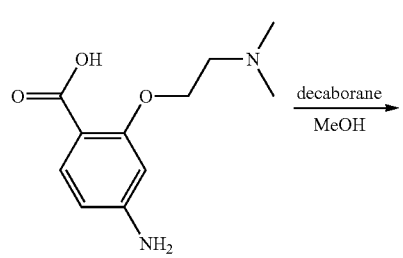

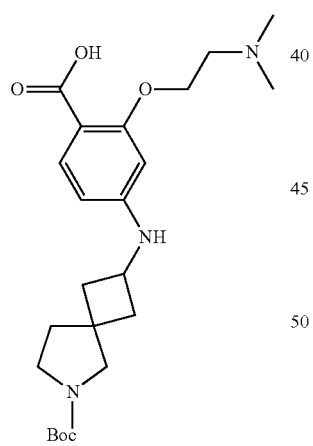

To a solution of 4-amino-2-(2-(dimethylamino)ethoxy) benzoic acid (450 mg, crude) in MeOH (5 ml) was added tert-butyl 2-oxo-6-azaspiro[3.4]octane-6-carboxylate (398 mg, 1.77 mmol) and decaborane (75.58 mg, 0.62 mmol). After being stirred at room temperature for 12 h, the mixture was concentrated, diluted with water (30 mL) and extracted with ethyl acetate (30 mL×3). The combined organic layers were washed with brine, dried over Na₂SO₄, filtered and concentrated under reduced pressure to give intermediate 36 (800 mg, crude) as a yellow solid, which was used in the next step without further purification.

Preparation of Intermediate 37

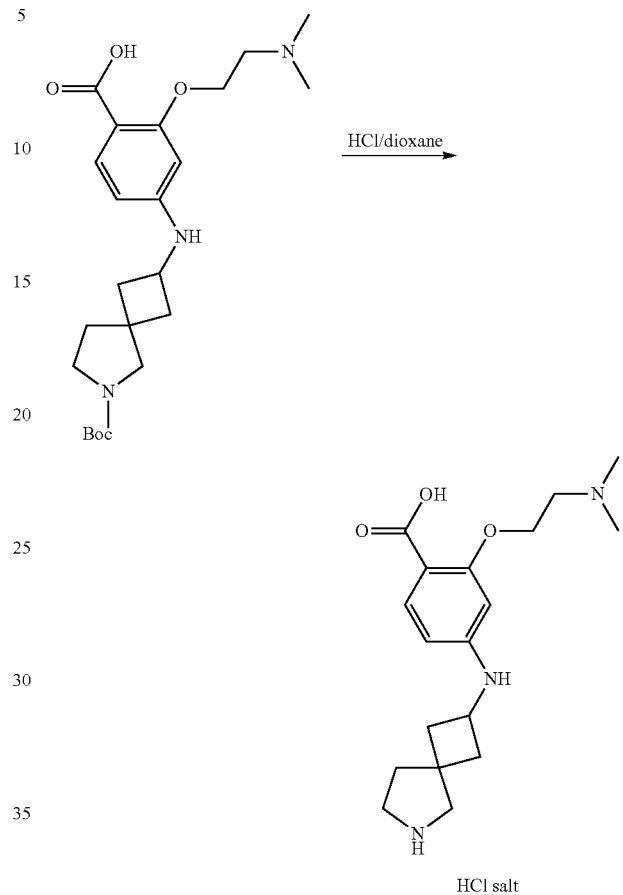

To a solution of intermediate 36 (4-((6-(tert-butoxycarbonyl)-6-azaspiro[3.4]octan-2-yl)amino)-2-(2-(dimethylamino)ethoxy)benzoic acid) (800 mg, crude) in MeOH (5 ml) was added HCl/dioxane (10 ml, 4 M). After being stirred at room temperature for 3 h, the mixture was concentrated under reduced pressure to give intermediate 37 (700 mg, crude HCl salt) as a yellow solid, which was used in the next step without further purification.

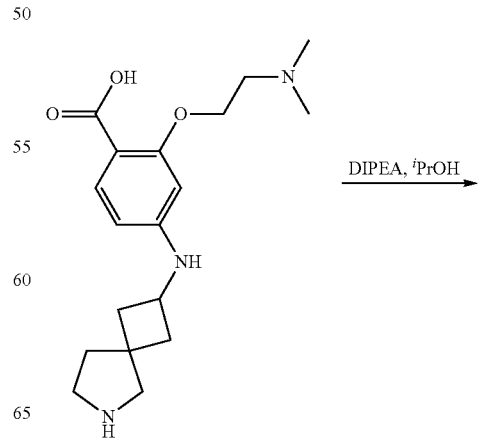

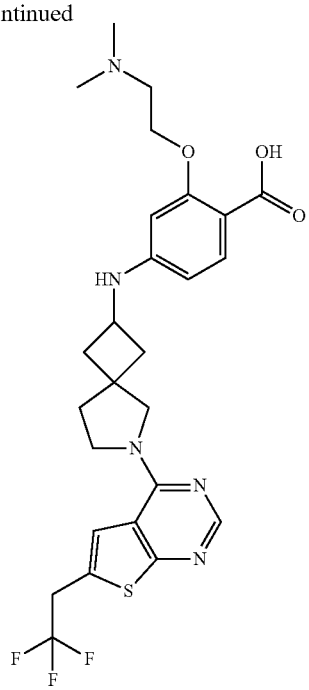

To a solution of intermediate 37 (4-(6-azaspiro[3.4]octan-2-ylamino)-2-(2-(dimethyl-amino)ethoxy)benzoic acid HCl salt) (700 mg, crude) in $^i$PrOH (10 ml) was added 4-chloro-6-(2,2,2-trifluoroethyl)thieno[2,3-d]pyrimidine (480 mg, 1.89 mmol) and DIEA (5 ml). After being stirred at room temperature for 3 hours, the resulting mixture was diluted with EA (30 mL), washed with brine (15 mL×2), dried over Na$_2$SO$_4$, filtered and concentrated. The residue was purified by prep-TLC (DCM:MeOH=10:1) to afford intermediate 38 (250 mg, 23% yield over 4 steps) as a white solid.

Example A13

Preparation of Intermediate 39

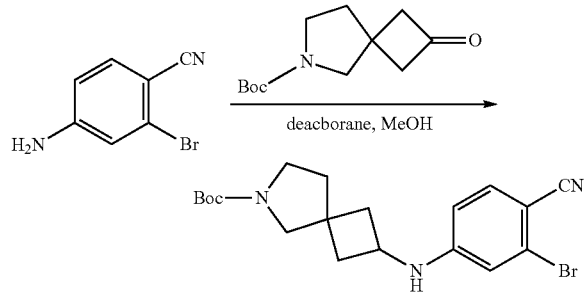

A mixture of 4-amino-2-bromobenzonitrile (440 mg, 2.2 mmol), tert-butyl 2-oxo-6-azaspiro[3.4]octane-6-carboxylate (495 mg, 2.2 mmol) and decaborane (43 mg, 0.35 mmol) in MeOH (20 mL) was stirred at 50° C. overnight under Ar. The reaction mixture was concentrated under reduced pressure. The residue was purified by silica gel column chromatography (Petroleum ether/EtOAc=3/1) to afford intermediate 39 (406 mg, 45% yield) as a white solid.

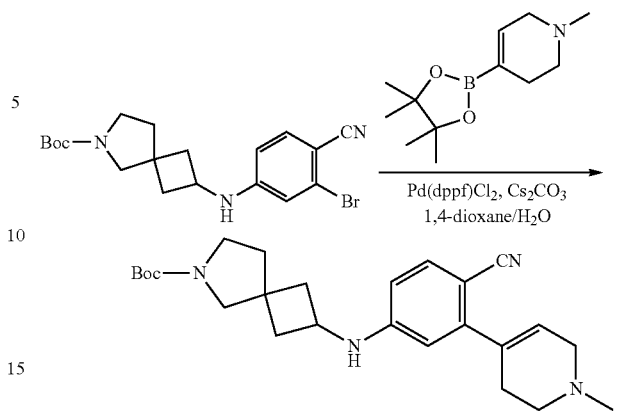

A mixture of intermediate 39 (tert-butyl 2-((3-bromo-4-cyanophenyl)amino)-6-aza-spiro[3.4]octane-6-carboxylate) (406 mg, 1.0 mmol), 1-methyl-4-(4,4,5,5-tetramethyl-1,3,2-dioxaborolan-2-yl)-1,2,3,6-tetrahydropyridine (335 mg, 1.5 mmol), Pd(dppf)Cl$_2$ (73 mg, 0.1 mmol) and Cs$_2$CO$_3$ (489 mg, 1.5 mmol) in 1,4-dioxane (20 mL) and H$_2$O (4 mL) was stirred at 110° C. overnight. The reaction mixture was filtered and the filtrate was concentrated under reduced pressure. The residue was purified by silica gel column chromatography (DCM/MeOH=20/1) to afford intermediate 40 (380 mg, 90% yield) as a brown solid.

Preparation of Intermediate 41

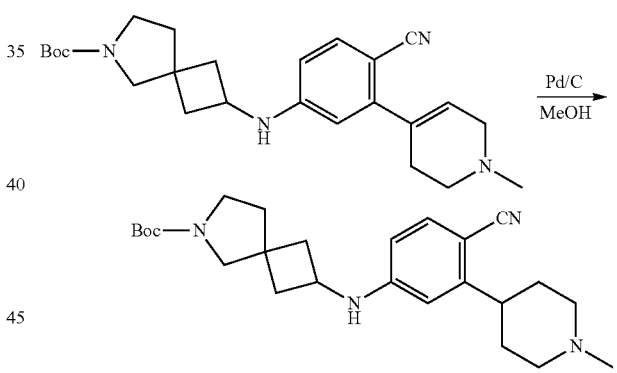

A mixture of intermediate 40 tert-butyl 2-((4-cyano-3-(1-methyl-1,2,3,6-tetrahydropyridin-4-yl)phenyl)amino)-6-azaspiro[3.4]octane-6-carboxylate (380 mg, 0.9 mmol) and Pd/C (380 mg) in MeOH (20 mL) was stirred at 50° C. for 4 h under H$_2$. The reaction mixture was filtered and the filtrate was concentrated to afford intermediate 41 (340 mg, crude) as orange oil.

Preparation of Intermediate 42

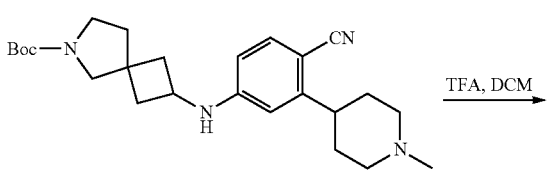

-continued

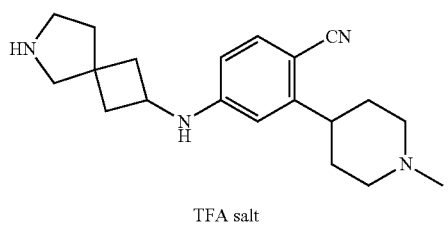

TFA salt

A mixture of intermediate 41 (tert-butyl 2-((4-cyano-3-(1-methylpiperidin-4-yl)phenyl)amino)-6-azaspiro[3.4]octane-6-carboxylate) (340 mg, crude) and TFA (2 mL) in DCM (2 mL) was stirred at room temperature for 2 h. The mixture was concentrated under pressure to afford intermediate 42 (280 mg, TFA salt) as orange oil, which was used in the next step without further purification.

Example A14

Preparation of Intermediate 43

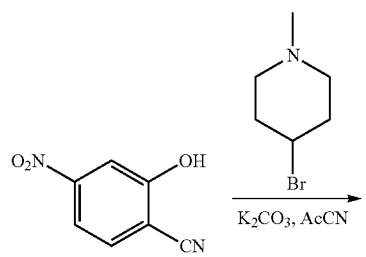

To a solution of 2-hydroxy-4-nitrobenzonitrile (500 mg, 3.05 mmol) in 50 ml of $CH_3CN$ was added $K_2CO_3$ (1.30 g, 9.15 mmol) and 4-bromo-1-methylpiperidine (2.20 g, 12.2 mmol). After being stirred at 80° C. overnight, the reaction mixture was concentrated and the residue was filtered through a silica gel pad (DCM/MeOH=15:1). The filtrate was concentrated under reduced pressure to yield intermediate 43 (400 mg; crude), which was used in the next step without further purification.

Preparation of Intermediate 44

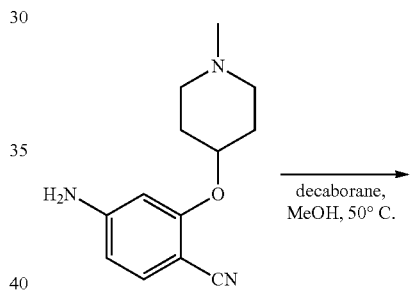

To a solution of intermediate 43 (2-((1-methylpiperidin-4-yl)oxy)-4-nitrobenzonitrile) (400 mg, crude) in MeOH (3 mL) was added Pd/C (40 mg). After being stirred at 50° C. for 2 h under $H_2$ atmosphere, the reaction mixture was filtered through a pad of celite and washed with MeOH. The filtrate was concentrated under reduced pressure to give intermediate 44 (500 mg, 70% yield over 2 steps), which was used in the next step without further purification.

Preparation of Intermediate 45

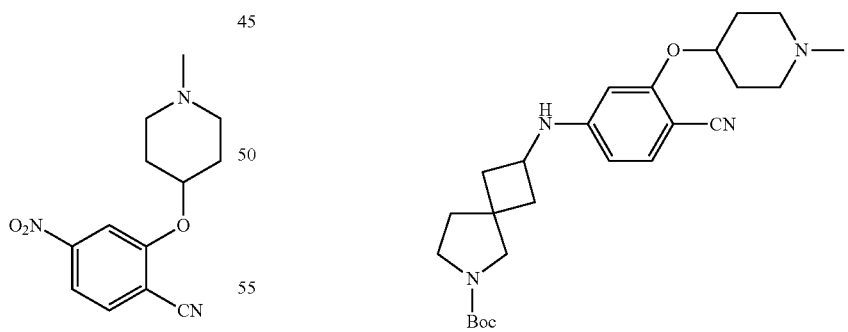

To a solution of intermediate 44 (4-amino-2-((1-methylpiperidin-4-yl)oxy)benzonitrile) (500 mg, crude, approximately 90% purity) in MeOH (10 mL) were added tert-butyl 2-oxo-6-azaspiro[3.4]octane-6-carboxylate (300 mg, 1.33 mmol) and decaborane (56 mg, 0.46 mmol). After being stirred at 50° C. overnight, the mixture was concentrated under reduced pressure. The residue was purified by silica gel chromatography (DCM/MeOH=10/1) to yield intermediate 45 (500 mg).

Preparation of Intermediate 46

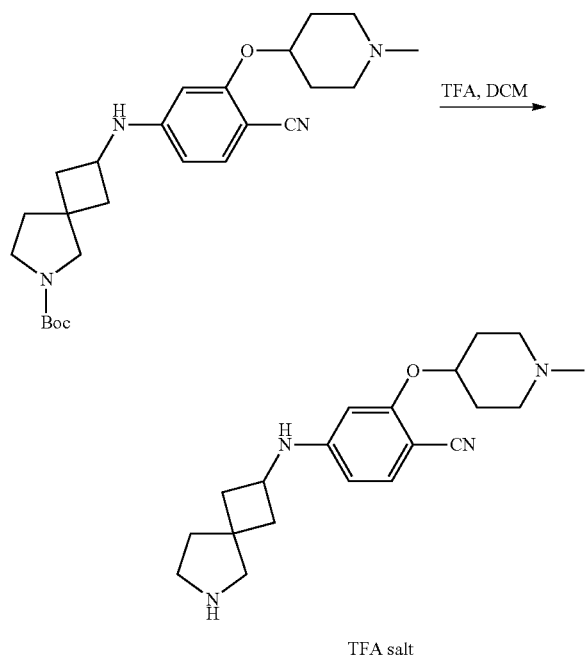

TFA salt

To a solution of intermediate 45 (tert-butyl 2-((4-cyano-3-((1-methylpiperidin-4-yl)-oxy)phenyl)amino)-6-azaspiro[3.4]octane-6-carboxylate) (500 mg, crude) in DCM (10 mL) was added TFA (2 mL). After being stirred at room temperature for 2 h, the mixture was concentrated under reduced pressure to yield intermediate 46 (500 mg, crude TFA salt) as oil.

Example A15

Preparation of Intermediate 47

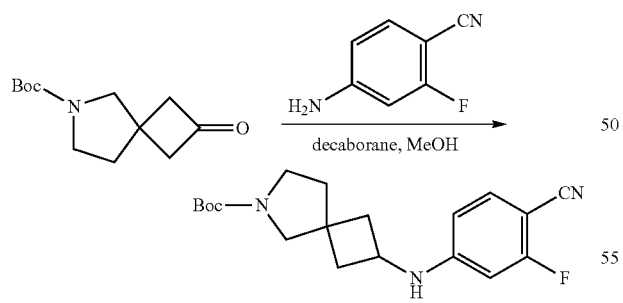

A mixture of tert-butyl 2-oxo-6-azaspiro[3.4]octane-6-carboxylate (CAS #: 203661-71-6) (675 mg, 3.0 mmol), 4-amino-2-fluorobenzonitrile (408 mg, 3.0 mmol) and decaborane (128 mg, 1.05 mmol) in MeOH (10 mL) was stirred at 50° C. overnight. After the reaction was completed, the reaction mixture was concentrated under reduced pressure. The residue was purified by silica gel column chromatography (Petroleum ether/EtOAc=3/1) to afford intermediate 47 (500 mg, 48% yield) as a white solid.

Preparation of Intermediate 48

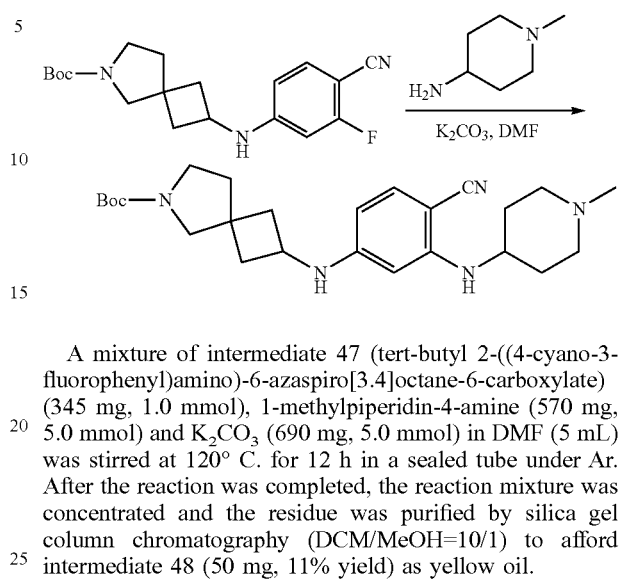

A mixture of intermediate 47 (tert-butyl 2-((4-cyano-3-fluorophenyl)amino)-6-azaspiro[3.4]octane-6-carboxylate) (345 mg, 1.0 mmol), 1-methylpiperidin-4-amine (570 mg, 5.0 mmol) and K$_2$CO$_3$ (690 mg, 5.0 mmol) in DMF (5 mL) was stirred at 120° C. for 12 h in a sealed tube under Ar. After the reaction was completed, the reaction mixture was concentrated and the residue was purified by silica gel column chromatography (DCM/MeOH=10/1) to afford intermediate 48 (50 mg, 11% yield) as yellow oil.

Preparation of Intermediate 49

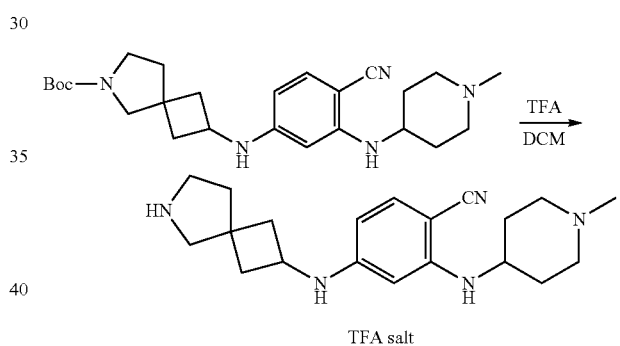

TFA salt

A mixture of intermediate 48 (tert-butyl 2-((4-cyano-3-((1-methylpiperidin-4-yl)amino)phenyl)amino)-6-azaspiro[3.4]octane-6-carboxylate) (50 mg, 0.11 mmol) and TFA (2 mL) in DCM (0.5 mL) was stirred at room temperature for 2 h. After the reaction was completed, the mixture was concentrated to afford intermediate 49 (60 mg, TFA salt) which was used in the next step without further purification.

Example A16

Preparation of Intermediate 50

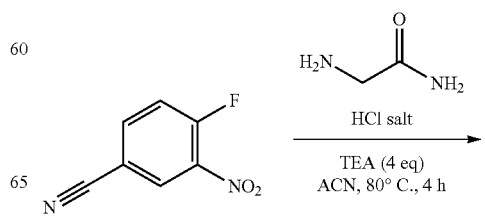

TEA (4 eq)
ACN, 80° C., 4 h

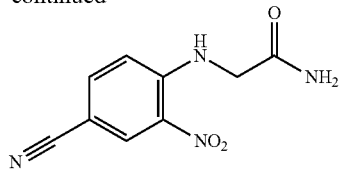

To a solution of 3-fluoro-4-nitrobenzonitrile (3.00 g, 18.1 mmol) and ACN (40 mL) was added TEA (10.0 mL, 72.2 mmol) and glycinamide hydrochloride (2.00 g, 18.1 mmol). After stirring at 80° C. for 4 h, the mixture was cooled to room temperature and the mixture was filtered to obtain yellow solid, which was washed with water (10 mL×3). The yellow solid was concentrated to dryness under reduced pressure to give crude intermediate 50 (4.30 g, 92% yield) as a yellow solid.

Preparation of Intermediate 51

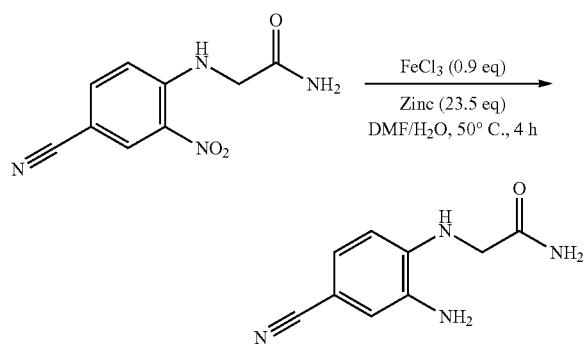

To a solution of intermediate 50 (2-((4-cyano-2-nitrophenyl)amino)acetamide) (3.00 g, 11.6 mmol), DMF (124 mL), and water (50 mL) was added FeCl₃ (1.77 g, 10.9 mmol) and zinc (17.8 g, 272 mmol). After stirring at 50° C. for 4 h, the reaction mixture was filtered and the filtrate was diluted with EtOAc (1000 mL). The organic layer was washed with water (400 mL), dried over Na₂SO₄, filtered and concentrated under reduced pressure to afford intermediate 51 (3.00 g, 82% yield) as a yellow solid.

Preparation of Intermediate 52

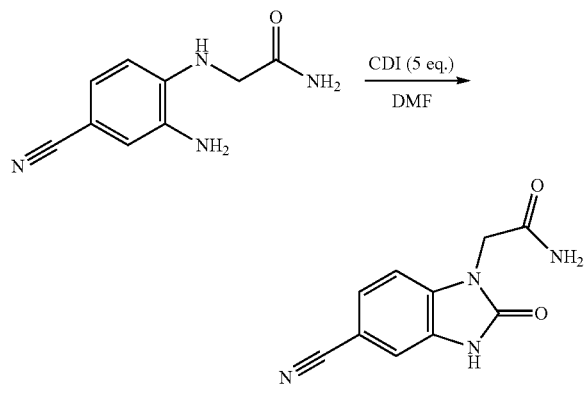

A solution of intermediate 51 (2-((2-amino-4-cyanophenyl)amino)acetamide) (1.50 g, 4.73 mmol), CDI (3.83 g, 23.6 mmol) and DMF (15 mL) was stirred at 20° C. for 2 h. The reaction mixture was then diluted with water (15 mL) and extracted with ethyl acetate (60 mL×3). The combined organic phases were concentrated to dryness under reduced pressure to afford the crude product, which was purified by prep-HPLC (Gilson 281, Xtimate C18 150×25 mm×5 m column (eluent: 8% to 38% (v/v) water (0.225% FA)-ACN)). The pure fractions were collected and evaporated under reduced pressure to obtain a residue, which was lyophilized to dryness to afford intermediate 52 (400 mg, 35% yield) as a white solid.

Preparation of Intermediate 53

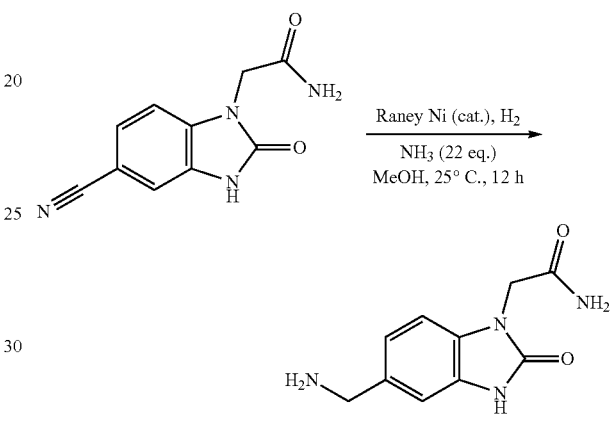

A mixture of intermediate 52 (2-(5-cyano-2-oxo-2,3-dihydro-1H-benzo[d]imidazol-1-yl)acetamide) (200 mg, 0.833 mmol), Raney Ni (100 mg), ammonia (2.6 mL, 7 M in MeOH), and MeOH (30 mL) was stirred at 25° C. for 12 h under H₂ (40-50 psi). The mixture was filtered through Celite® and the filtrate was concentrated under reduced pressure to give intermediate 53 (200 mg, 93% yield) as a brown solid.

Example A17

Preparation of Intermediate 54

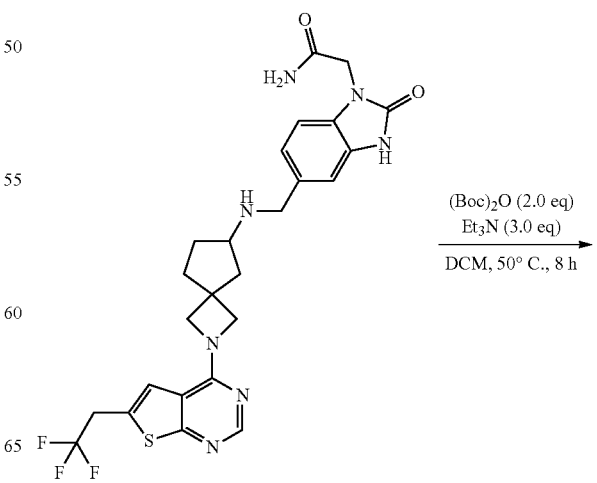

147

-continued

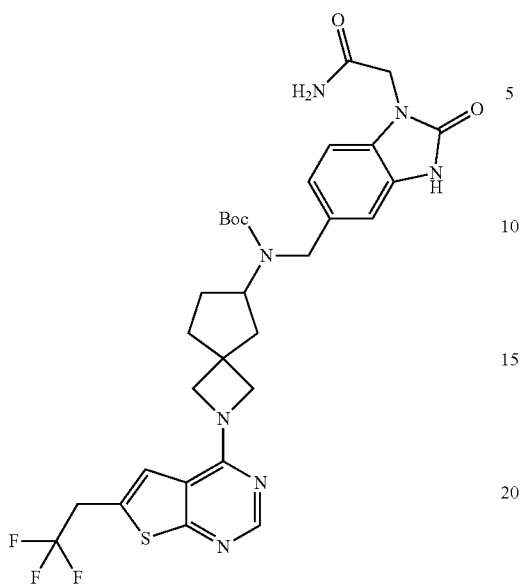

To a solution of Compound 53 (2-(2-oxo-5-(((2-(6-(2,2,2-trifluoroethyl)thieno[2,3-d]-pyrimidin-4-yl)-2-azaspiro[3.4]octan-6-yl)amino)methyl)-2,3-dihydro-1H-benzo[d]-imidazol-1-yl)acetamide) (70.0 mg, 0.128 mmol) in DCM (3 mL) was added Et₃N (39.0 mg, 0.385 mmol) and (Boc)₂O (56.0 mg, 0.257 mmol) at 0° C. The mixture was then heated and stirred at 50° C. for 8 h. The reaction mixture was concentrated under reduced pressure to obtain intermediate 54 (70 mg, crude), which was used in the next step without purification.

Preparation of Intermediate 55

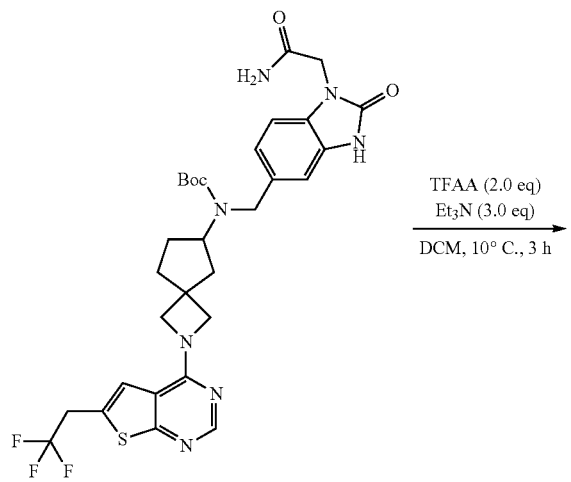

148

-continued

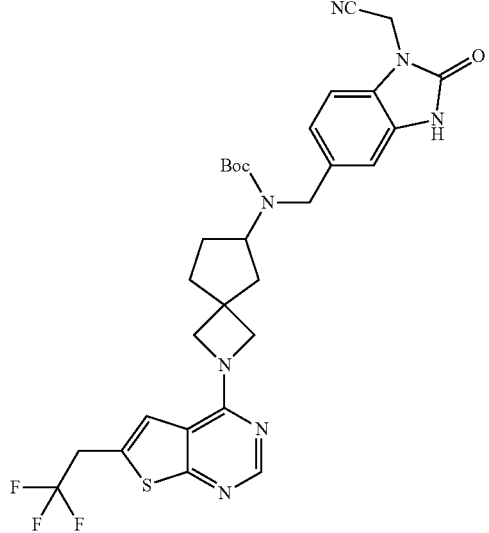

To a solution of intermediate 54 (tert-butyl ((1-(2-amino-2-oxoethyl)-2-oxo-2,3-dihydro-1H-benzo[d]imidazol-5-yl)methyl)(2-(6-(2,2,2-trifluoroethyl)thieno[2,3-d]-pyrimidin-4-yl)-2-azaspiro[3.4]octan-6-yl)carbamate) (70.0 mg, crude) in DCM (1.5 mL) was added Et₃N (33.0 mg, 0.325 mmol) at 0° C. Then a solution of TFAA (46.0 mg, 0.217 mmol) in DCM (0.5 mL) was added to the solution dropwise at 0° C. The reaction was stirred at 10° C. for 3 h and concentrated under reduced pressure to give intermediate 55 (60 mg, crude) as a white solid, which was used in the next step without further purification.

Example A19

Preparation of Intermediate 58

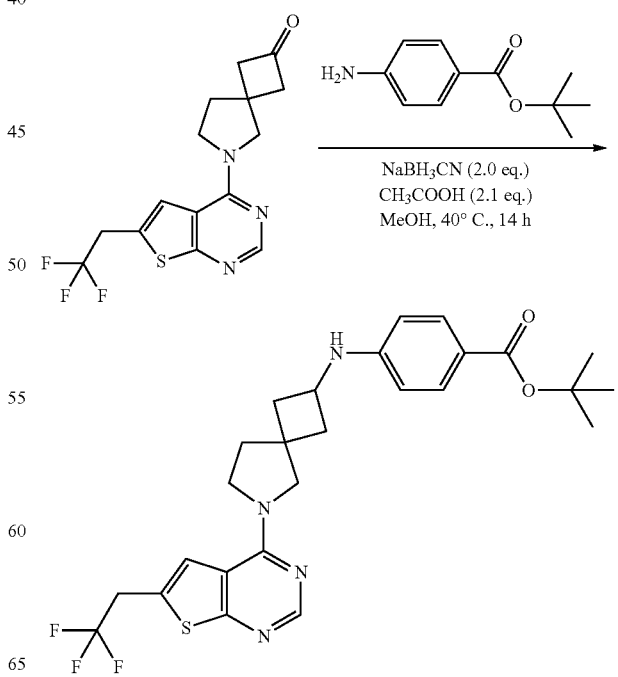

To a solution of intermediate 5 (6-(6-(2,2,2-trifluoroethyl)thieno[2,3-d]pyrimidin-4-yl)-6-azaspiro[3.4]octan-2-one) (1000 mg, 2.93 mmol), tert-butyl 4-aminobenzoate (750 mg, 3.88 mmol), sodium cyanoborohydride (365 mg, 5.81 mmol) and MeOH (28.0 mL) was added a solution of acetic acid (365 mg, 6.08 mmol) in MeOH (2.0 mL). After stirring at 40° C. for 14 h, the mixture was concentrated under reduced pressure, then diluted with water (30 mL) and extracted with EtOAc (20 mL×3). The combined organic layers were dried over anhydrous $Na_2SO_4$, filtered and concentrated in vacuo to obtain crude residue, which was purified by Flash Column Chromatography (PE:EA from 100:0 to 50:50) to give intermediate 58 (680 mg, 43% yield) as orange solid.

Preparation of Intermediate 59 (TFA Salt of intermediate 35)

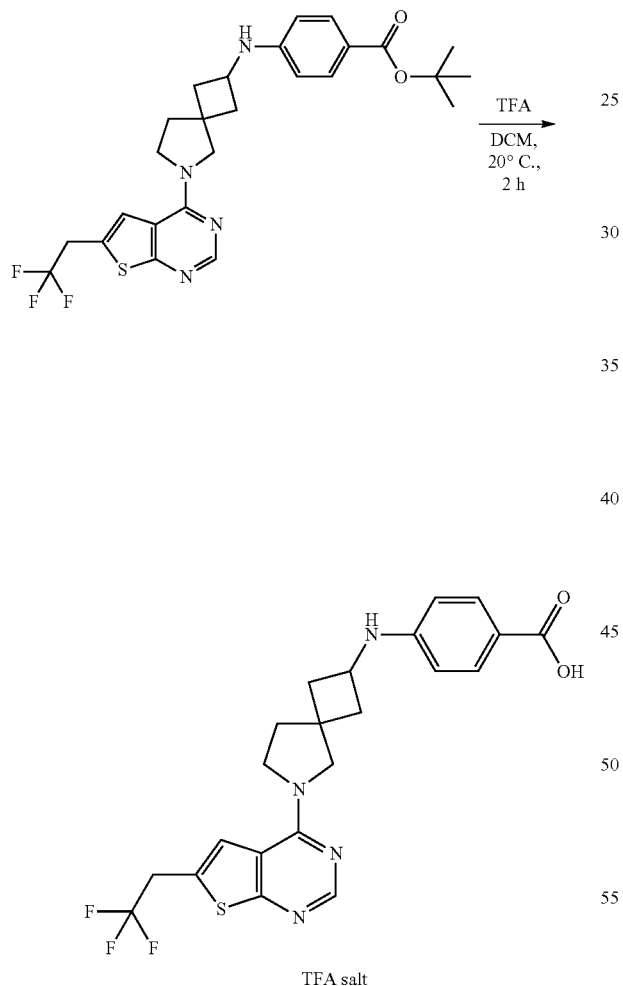

TFA salt

A solution of intermediate 58 (tert-butyl 4-((6-(6-(2,2,2-trifluoroethyl)thieno[2,3-d]-pyrimidin-4-yl)-6-azaspiro[3.4]octan-2-yl)amino)benzoate) (100 mg, 0.193 mmol), TFA (1 mL) and $CH_2Cl_2$ (1 mL) was stirred at 20° C. for 2 h. The reaction mixture was then concentrated to dryness under reduced pressure to afford the crude intermediate 59 (180 mg, 97% yield) as a yellow solid.

Example A20

Preparation of Intermediates 60, 61 and 62

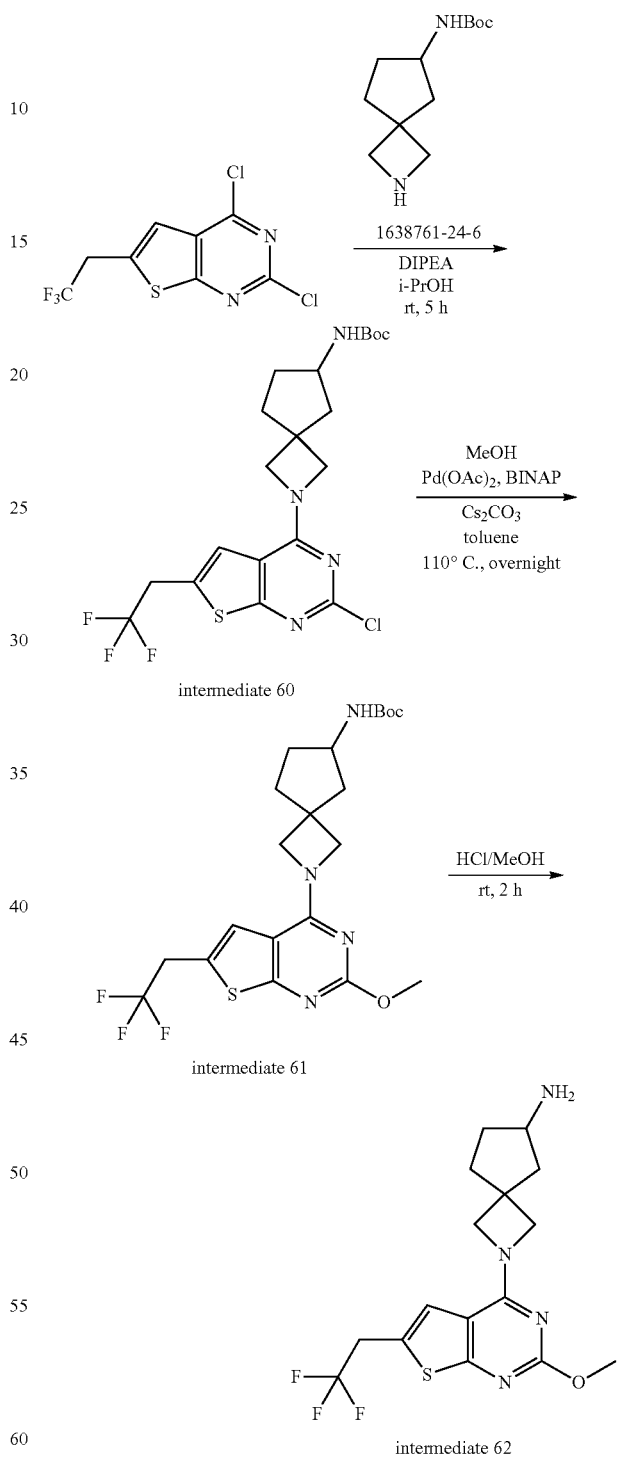

Intermediate 60, intermediate 61 and intermediate 62 were prepared respectively via an analogous reaction protocol as described for the preparation of intermediate 17, intermediate 18 and intermediate 20 respectively, starting from the respective starting materials.

Example A21

Preparation of Intermediates 63, 64 and 65

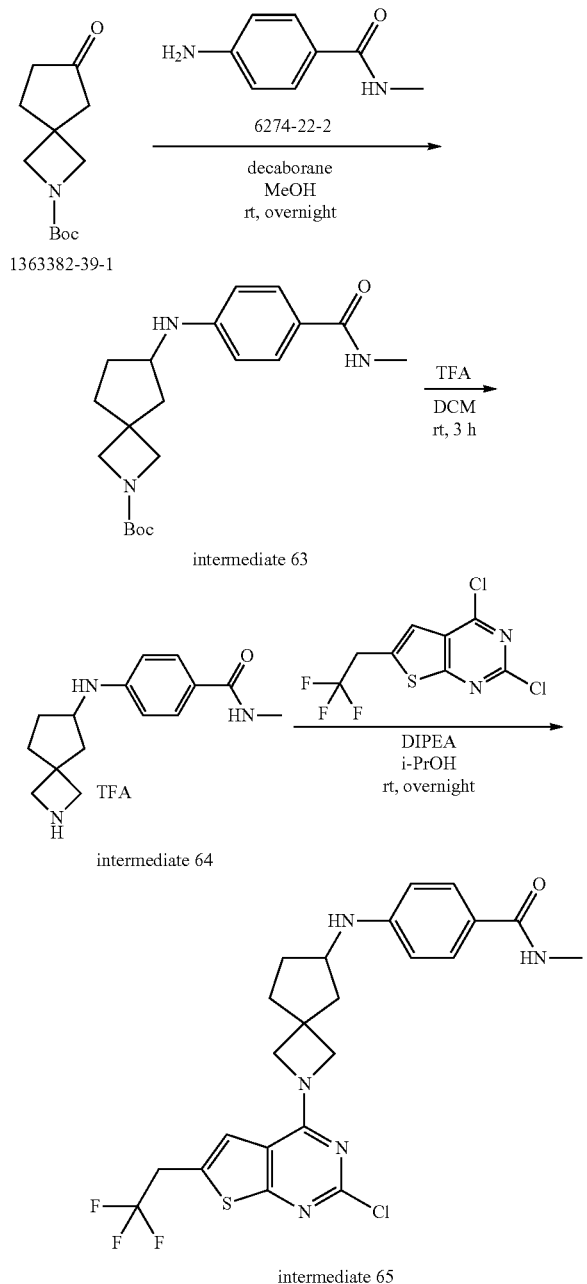

intermediate 63 intermediate 64 intermediate 65

Intermediate 63, intermediate 64 and intermediate 65 were prepared respectively via an analogous reaction protocol as described for the preparation of intermediate 79, intermediate 80 and intermediate 17 respectively, starting from the respective starting materials.

| Intermediate number (starting materials) | Method used |
| --- | --- |
| intermediate 63 (from tert-butyl 6-oxo-2-azaspiro[3.4]octane-2-carboxylate, CAS#: 1363382-39-1 and 4-amino-N-methylbenzamide, CAS#: 6274-22-2) | intermediate 79 |
| intermediate 64 (from intermediate 63) | intermediate 80 |
| intermediate 65 (from intermediate 64) | intermediate 17 |

Example A23

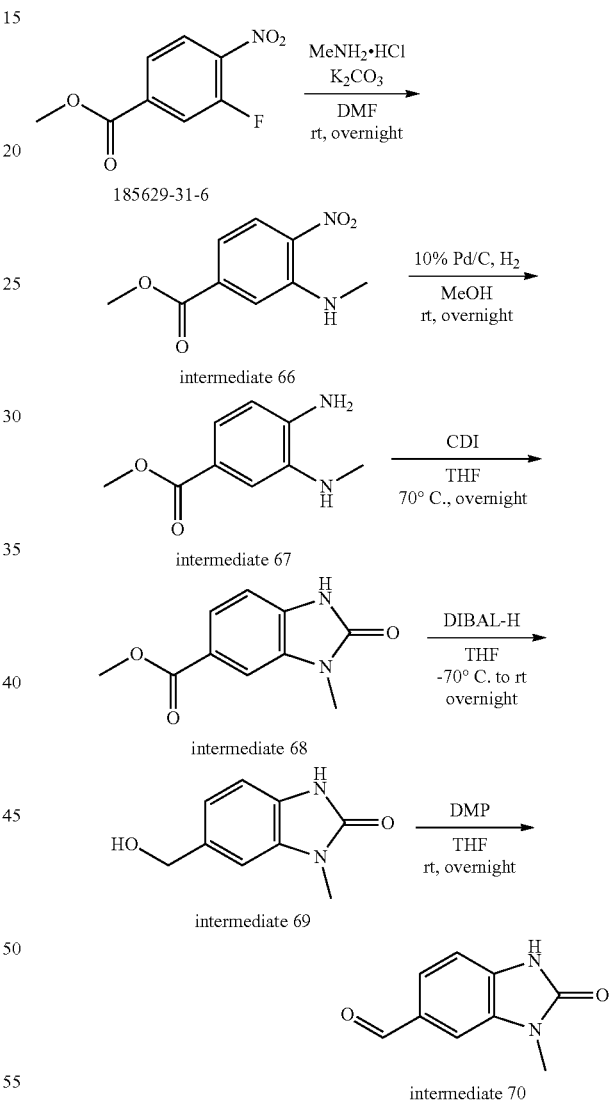

intermediate 66 intermediate 67 intermediate 68 intermediate 69 intermediate 70

Preparation of Intermediate 66

To a stirred solution of methyl 3-fluoro-4-nitrobenzoate (CAS #: 185629-31-6) (3.00 g, 15.1 mmol) in DMF (30 mL) at room temperature were added methylamine hydrochloride (1.20 g, 18.1 mmol) and $K_2CO_3$ (2.70 g, 19.6 mmol). The reaction was stirred at room temperature overnight. The reaction mixture was diluted with EtOAc (200 mL), washed with aq. HCl (1 M) (100 mL), brine, dried over anhydrous Na$_2$SO$_4$, filtered and concentrated to afford intermediate 66 (3.20 g, crude), which was used for the next step without further purification.

Preparation of Intermediate 67

To a solution of intermediate 66 (3.20 g, ca. 15.2 mmol) in MeOH (32 mL) was added 10% Pd/C (320 mg). After being stirred under H$_2$ atmosphere at room temperature overnight, the mixture was filtered through a pad of SiO$_2$ and the filter cake was washed with MeOH. The combined filtrate was concentrated under reduced pressure to afford intermediate 67 (2.70 g, crude), which was used for the next step without further purification.

Preparation of Intermediate 68

To a stirred solution of intermediate 67 (2.70 g, ca. 15.0 mmol) in THE (65 mL) at room temperature was added CDI (3.60 g, 22.5 mmol). After being stirred at 70° C. overnight, the cooled reaction mixture was filtered and the filter cake was washed with THE and petroleum ether. The filter cake was dried under vacuo to afford intermediate 68 (1.80 g, crude), which was used for the next step without further purification.

Preparation of Intermediate 69

To a stirred solution of intermediate 68 (1.80 g, ca. 8.74 mmol) in dry THF (180 mL) under Ar at −78° C. was added DIBAL-H (1.5 M in toluene) (35 mL, 52.5 mmol) dropwise. After addition, the reaction was allowed to warm to room temperature and stirred overnight. The reaction mixture was cooled to 0° C. and quenched with MeOH dropwise. After being stirred at room temperature for another 15 minutes, the mixture was filtered and the filter cake was washed with MeOH. The combined filtrate was extracted with EtOAc (100 mL×2), washed with brine, dried over anhydrous Na$_2$SO$_4$, filtered and concentrated under reduced pressure to afford intermediate 69(1.10 g, crude), which was used for the next step without further purification.

Preparation of Intermediate 70

To a stirred solution of intermediate 69 (1.10 g, ca. 6.18 mmol) in dry THF (110 mL) was added Dess-Martin periodinane (5.20 g, 12.4 mmol). After being stirred at room temperature overnight, the reaction mixture was diluted with water and extracted with EtOAc (50 mL×3). The combined organic extracts were washed with brine, dried over anhydrous Na$_2$SO$_4$ and concentrated under reduced pressure. The crude product was washed with EtOAc (50 mL×3), filtered and dried under reduced pressure to afford intermediate 70 (400 mg, ca. 37% yield) as a brown solid.

Example A24

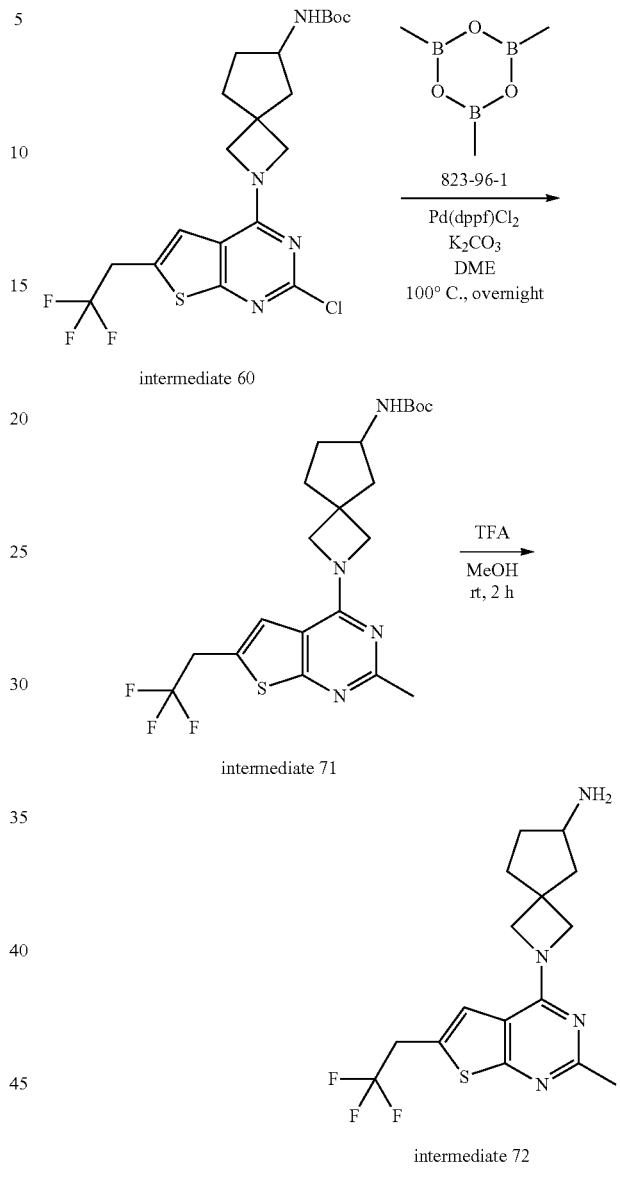

Preparation of Intermediate 71

To a solution of intermediate 60 (600 mg, 1.26 mmol) in DME (15 mL) under Ar at room temperature were added trimethylboroxine (CAS #: 823-96-1) (1.26 g, 5.03 mmol), K$_2$CO$_3$ (522 mg, 0.38 mmol) and Pd(dppf)Cl$_2$ (93 mg, 0.13 mmol). The reaction was stirred under Ar at 100° C. overnight. The cooled reaction mixture was diluted with water (60 mL) and extracted with EtOAc (60 mL×3). The combined organic extracts were washed with water (60 mL×3), dried over anhydrous Na$_2$SO$_4$, filtered and concentrated. The residue was purified by silica gel chromatography eluted with PE/EA (2/1, v/v) to give intermediate 71 (390 mg, 68% yield).

Preparation of Intermediate 72

To a stirred solution of intermediate 71 (390 mg, 0.86 mmol) in MeOH (4 mL) at room temperature was added TFA (4 mL). After stirring at room temperature for 2 h, the reaction mixture was concentrated under reduced pressure and the residue was treated with ion exchange resin to give the title compound intermediate 72 (304 mg, 100% yield), which was used directly for the next step without further purification.

Example A25

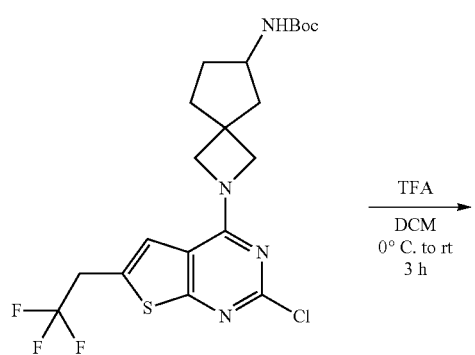

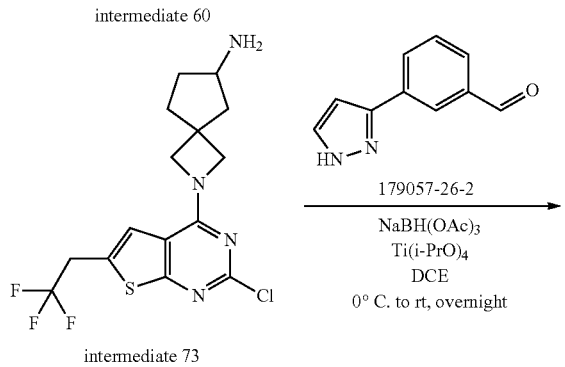

Preparation of Intermediate 73

To a stirred solution of intermediate 60 (500 mg, 1.05 mmol) in DCM (9 mL) at 0° C. was added TFA (3 mL) slowly. The reaction mixture was stirred at room temperature for 3 h. The reaction mixture was concentrated. The TFA salt of desired intermediate was treated with ion exchange resin to give intermediate 73 as a yellow solid (400 mg, crude), which was used for the next step directly without further purification.

Preparation of Intermediate 74

To a stirred mixture of intermediate 73 (400 mg, 1.05 mmol), 3-(1H-pyrazol-3-yl)-benzaldehyde (CAS #: 179057-26-2) (235 mg, 1.36 mmol) and Ti(i-PrO)$_4$ (300 mg, 1.05 mmol) in DCE (10 mL) at 0° C. was added NaBH(OAc)$_3$ (668 mg, 3.15 mmol) in portions. The reaction mixture was stirred at room temperature overnight. Subsequently, the reaction mixture was quenched with aq. NaHCO$_3$ and the resultant was extracted with DCM. The combined organic extracts were washed with brine, dried over anhydrous Na$_2$SO$_4$, filtered and concentrated. The residue was purified by column chromatography eluted with DCM/MeOH (from 50:1 to 30:1, v/v) to give the intermediate 74 (380 mg, yield: 68%) as a white solid.

Example A26

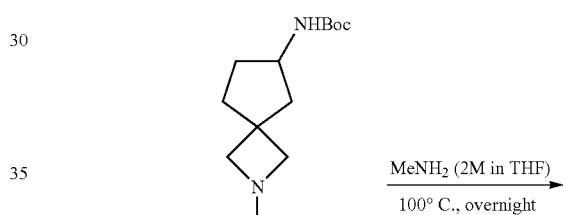

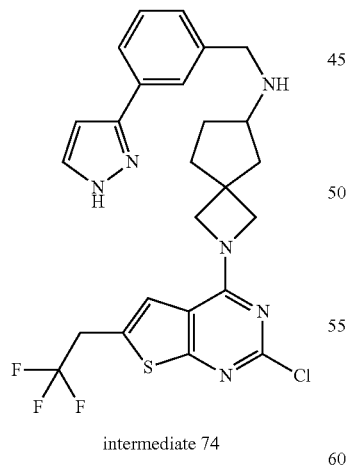

-continued

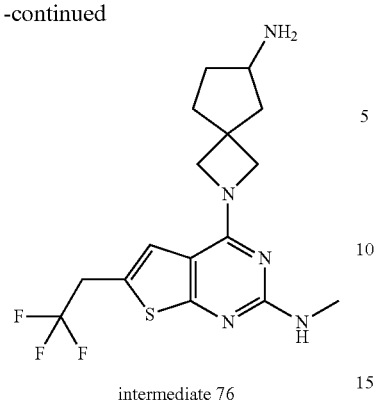

intermediate 76

Preparation of Intermediate 75

A solution of intermediate 60 (700 mg, 1.47 mmol) in methanamine (2 M in THF) (10 mL) in an autoclave was stirred at 100° C. overnight. The cooled reaction mixture was concentrated to give crude desired intermediate 75 (800 mg), which was used for the next step directly without further purification.

Preparation of Intermediate 76

A solution of intermediate 75 (800 mg, crude product, ca. 1.70 mmol) in HCl/MeOH (12 mL) was stirred at room temperature for 10 h. The reaction mixture was concentrated. The crude product was treated with ion exchange resin to give desired intermediate 76 as a yellow solid (700 mg, crude product), which was used for the next step directly without further purification.

Example A27

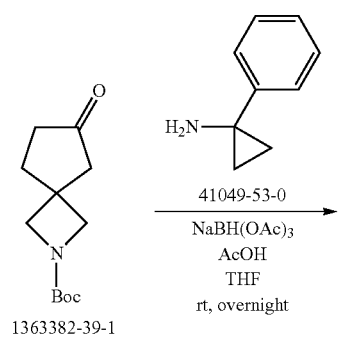

-continued

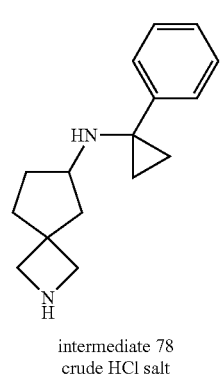

intermediate 78
crude HCl salt

Preparation of Intermediate 77

To a stirred mixture of 1-phenylcyclopropan-1-amine (CAS #: 41049-53-0) (400 mg, 3 mmol) and tert-butyl 6-oxo-2-azaspiro[3.4]octane-2-carboxylate (CAS #: 1363382-39-1) (1.0 g, 4.5 mmol) in THF (10 mL) at room temperature was added AcOH (180 mg, 3 mmol). After being stirred at room temperature for 4 h, NaBH(OAc)$_3$ (1.91 g, 9.01 mmol) was added in portions. The resulting mixture was stirred at room temperature overnight. The reaction mixture was diluted with H$_2$O (20 mL) and extracted with EtOAc (20 mL×3). The combined organic extracts were washed with brine (20 mL), dried over anhydrous Na$_2$SO$_4$, filtered and concentrated under reduced pressure. The residue was purified by silica gel chromatography (eluent: PE/EA=3/1, v/v) to give intermediate 77 (240 mg, 23% yield) as a yellow gum.

Preparation of Intermediate 78

To a stirred solution of intermediate 77 (240 mg, 0.7 mmol) in EtOAc (3 mL) at 0° C. was added HCl (4 M in 1,4-dioxane) (10 mL). After being stirred at room temperature for 2 h, the reaction mixture was concentrated under reduced pressure to give intermediate 78 (330 mg, crude HCl salt) as a yellow gum, which was used directly for the next step without further purification.

Example A28

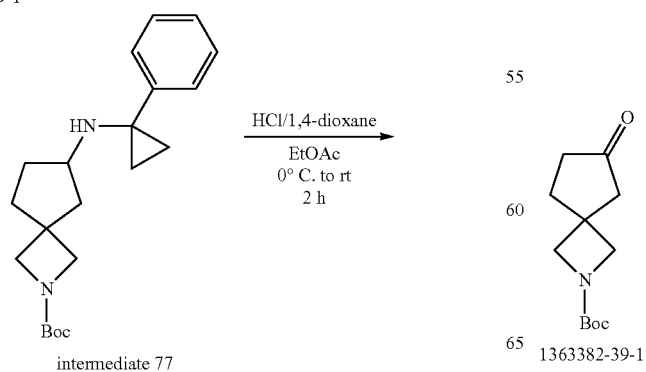

-continued

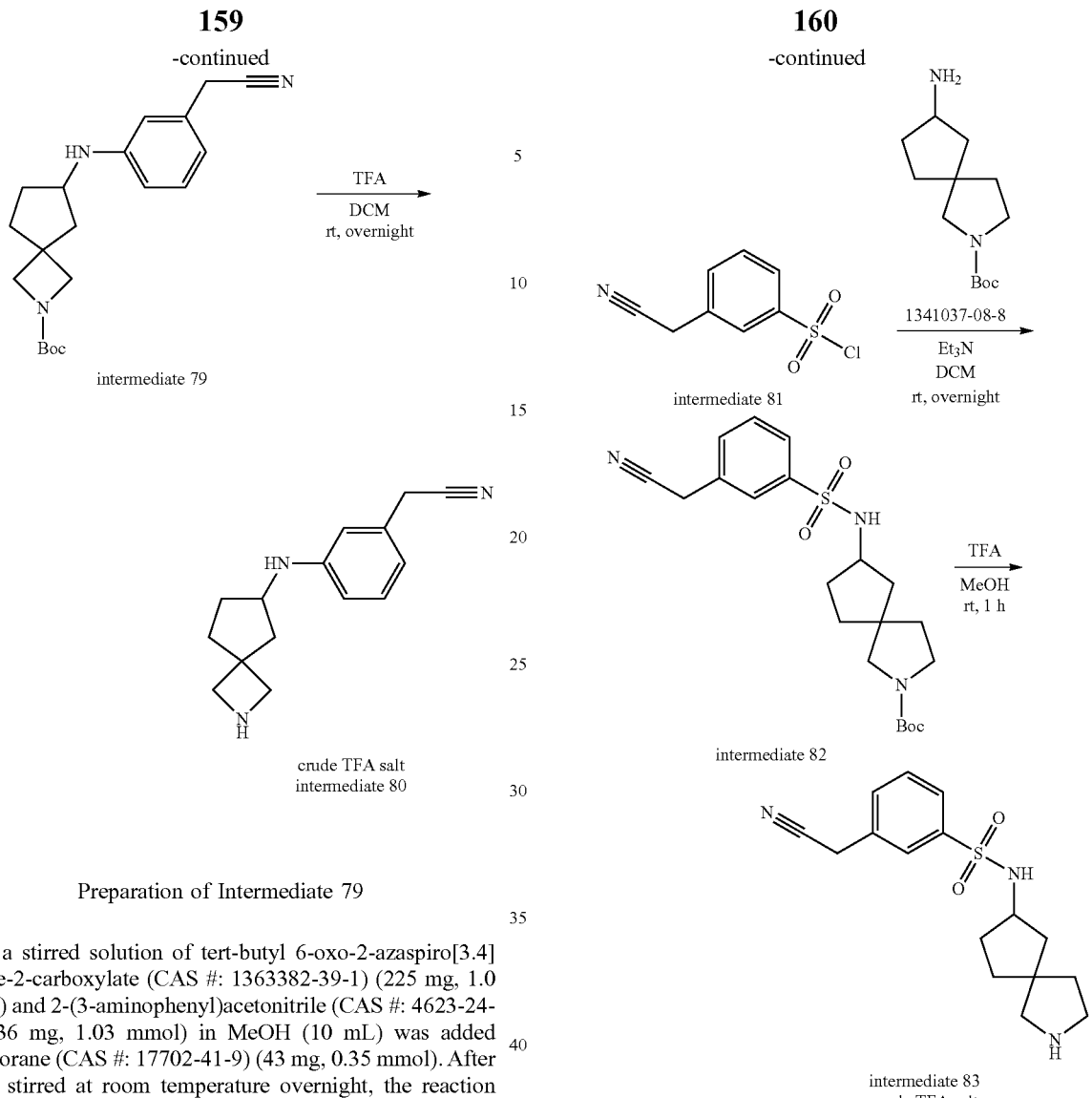

intermediate 79 crude TFA salt
intermediate 80 intermediate 82 intermediate 83
crude TFA salt

Preparation of Intermediate 79

To a stirred solution of tert-butyl 6-oxo-2-azaspiro[3.4]octane-2-carboxylate (CAS #: 1363382-39-1) (225 mg, 1.0 mmol) and 2-(3-aminophenyl)acetonitrile (CAS #: 4623-24-9) (136 mg, 1.03 mmol) in MeOH (10 mL) was added decaborane (CAS #: 17702-41-9) (43 mg, 0.35 mmol). After being stirred at room temperature overnight, the reaction mixture was concentrated under reduced pressure. The residue was purified by silica gel chromatography (eluent: PE/EtOAc=3/1, v/v) to afford intermediate 79 (340 mg, 99% yield) as a white solid.

Preparation of Intermediate 80

To a solution of intermediate 79 (340 mg, 1.0 mmol) in DCM (2 mL) was added TFA (2 mL). After being stirred at room temperature overnight, the mixture was concentrated to afford intermediate 80 (300 mg, crude TFA salt), which was used for the next step without further purification.

Example A30

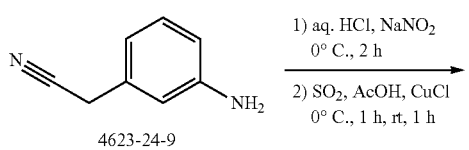

Preparation of Intermediate 81

To a stirred suspension of 2-(3-aminophenyl)acetonitrile (CAS #: 4623-24-9) (300 mg, 2.28 mmol) in 20 wt % aq. HCl (3 mL) cooled with an ice bath, was added a solution of NaNO$_2$ (156 mg, 2.28 mmol) in H$_2$O (3 mL) dropwise. The mixture was stirred while being cooled in an ice bath for 2 h to afford a diazonium salt solution.

To a stirred solution of AcOH (9 mL) and H$_2$O (2 mL) cooled with an ice bath, SO$_2$ (1.16 g, 18.2 mmol) was bubbled. To the resulting stirred solution CuCl (57 mg, 0.57 mmol) and the diazonium salt solution were added slowly. The reaction mixture was stirred and cooled with an ice bath for 1 h and at room temperature for another 1 h. The reaction mixture was poured into ice water and extracted with DCM (100 mL×3). The combined organic extracts were washed with saturated aq. NaHCO$_3$, dried over anhydrous Na$_2$SO$_4$, filtered and concentrated to afford intermediate 81 (70 mg, 14% yield), which was used directly for the next step without further purification.

Preparation of Intermediate 82

To a stirred solution of tert-butyl 7-amino-2-azaspiro[4.4]nonane-2-carboxylate (CAS #: 1341037-08-8) (75 mg, 0.32 mmol) in DCM (1 mL) were added intermediate 81 (70 mg, 0.32 mmol) and Et₃N (65 mg, 0.64 mmol). The reaction was stirred at room temperature overnight. The reaction mixture was concentrated to afford intermediate 82 (130 mg, crude), which was used directly for the next step without further purification.

Preparation of Intermediate 83

To a stirred solution of intermediate 82 (130 mg, crude product, ca. 0.31 mmol) in MeOH (2 mL) was added TFA (1 mL). After being stirred at room temperature for 1 h, the mixture was concentrated under reduced pressure to give intermediate 83 (150 mg, crude TFA salt) as a brown oil, which was used directly for the next step without further purification.

Example A31

Preparation of Intermediates 84 and 85

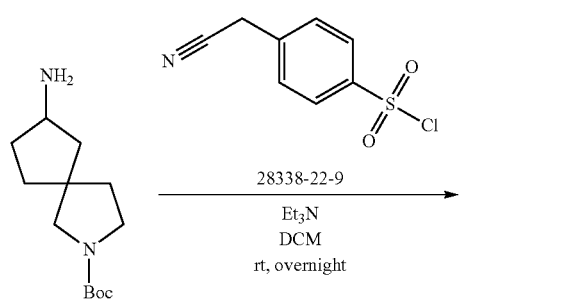

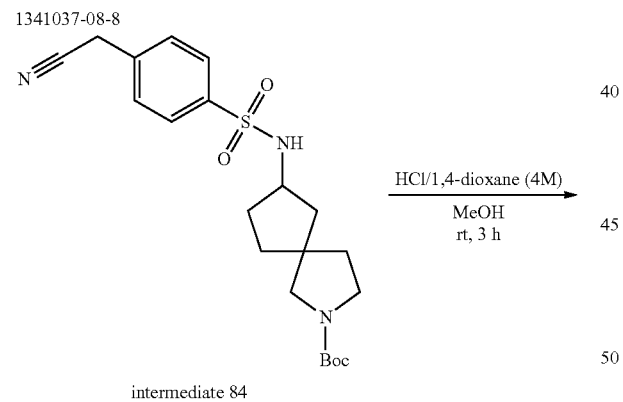

Intermediate 84 and intermediate 85 (HCl salt) were prepared respectively via an analogous reaction protocol as described for the preparation of intermediate 82 and intermediate 83 respectively, starting from the respective starting materials. For the preparation of intermediate 85 HCl was used as the acid instead of TFA.

Example A32

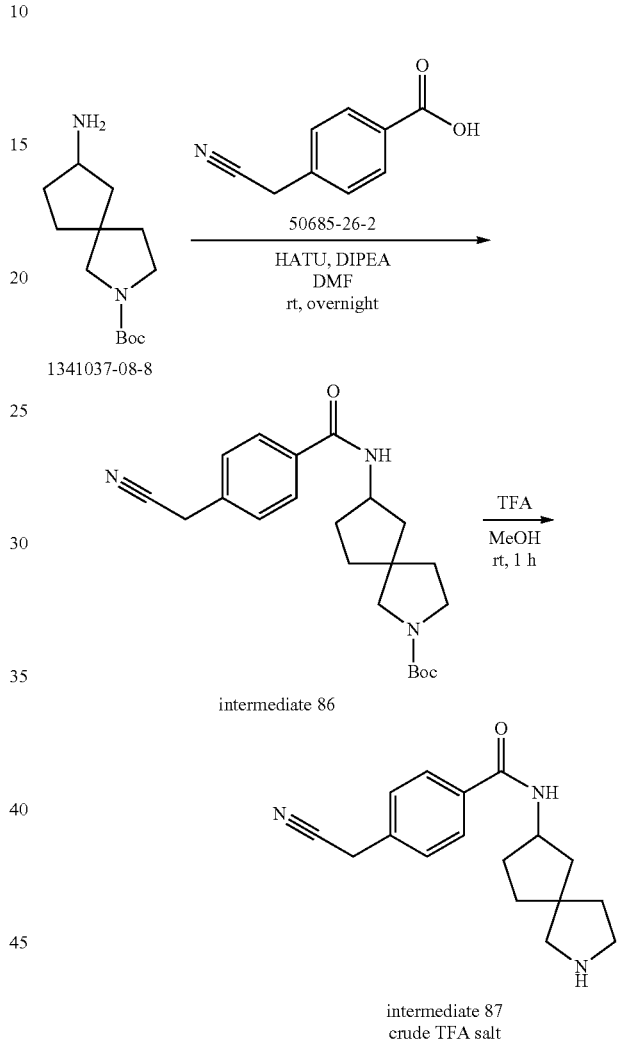

To a stirred solution of tert-butyl 7-amino-2-azaspiro[4.4]nonane-2-carboxylate (CAS #: 1341037-08-8) (50 mg, 0.21 mmol) in DMF (1 mL) were added 4-(cyano-methyl)benzoic acid (CAS #: 50685-26-2) (34 mg, 0.21 mmol), HATU (119 mg, 0.31 mmol) and DIPEA (54 mg, 0.42 mmol). The reaction was stirred at room temperature overnight. The reaction mixture was diluted with water (50 mL) and extracted with EtOAc (50 mL×3). The combined organic extracts were washed with water (50 mL×3), dried over anhydrous Na₂SO₄, filtered and concentrated to give intermediate 86 (70 mg, 86% yield), which was used directly for the next step without further purification.

Preparation of Intermediate 87

To a stirred solution of intermediate 86 (70 mg, 0.183 mmol) in MeOH (2 mL) was added TFA (1 mL). After being

Example A33

Preparation of Intermediates 88 and 89

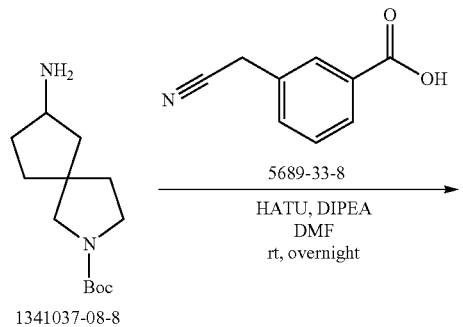

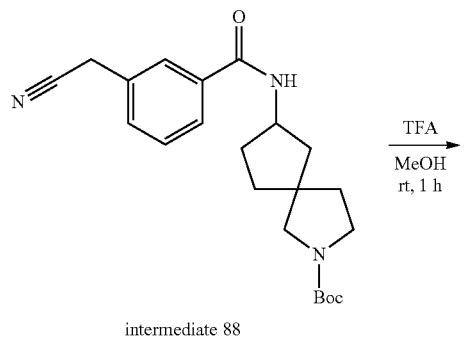

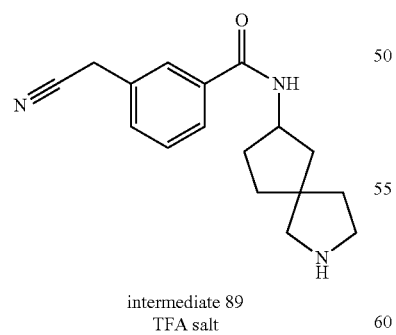

Intermediate 88 and intermediate 89 (TFA salt) were prepared respectively via an analogous reaction protocol as described for the preparation of intermediate 86 and intermediate 87 respectively, starting from the respective starting materials.

Example A34

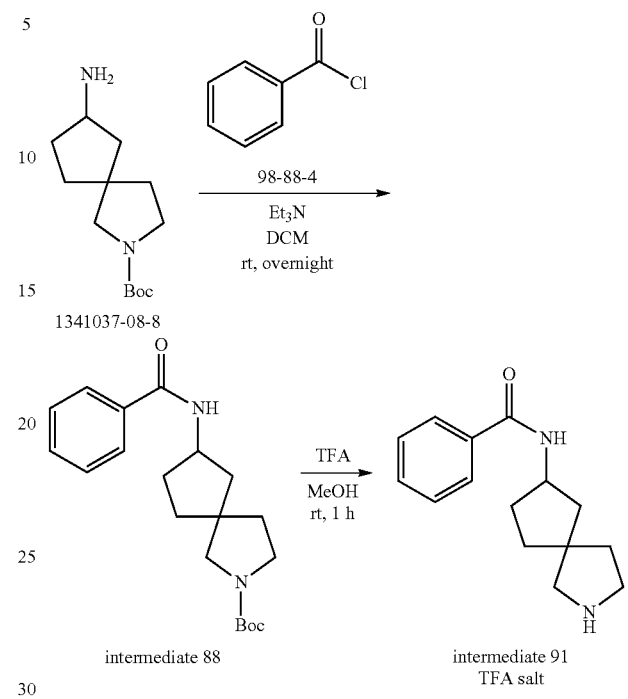

Preparation of Intermediate 90

To a stirred solution of tert-butyl 7-amino-2-azaspiro[4.4]nonane-2-carboxylate (CAS #: 1341037-08-8) (50 mg, 0.21 mmol) in DCM (1 mL) were added benzoyl chloride (44 mg, 0.31 mmol) and Et$_3$N (42 mg, 0.42 mmol). The reaction was stirred at room temperature overnight. The reaction mixture was concentrated to give intermediate 90 (70 mg, crude product, 100% yield) as a brown oil, which was used directly for the next step without further purification.

Preparation of Intermediate 91

The intermediate 91 (TFA salt) was prepared by an analogous reaction protocol as described for the preparation of intermediate 87, starting from the respective starting materials.

Example A35

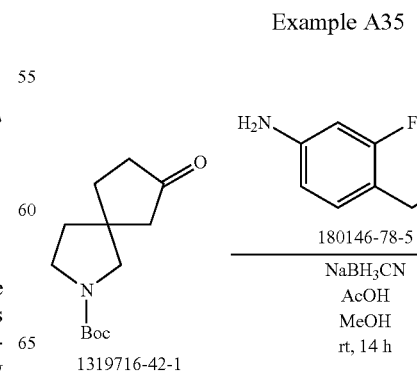

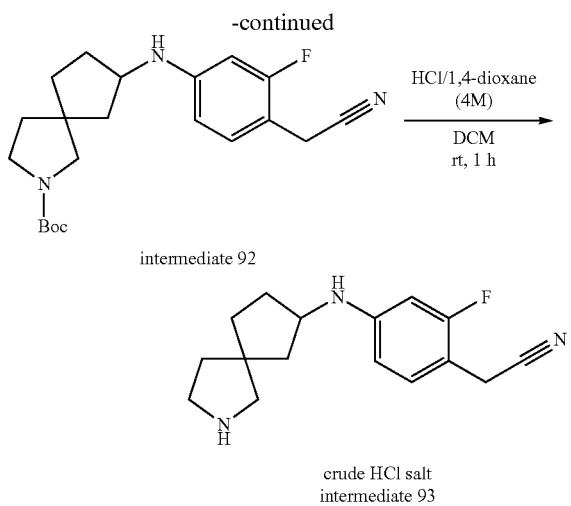

intermediate 92 crude HCl salt
intermediate 93

Preparation of Intermediate 92

To a stirred solution of tert-butyl 7-oxo-2-azaspiro[4.4]nonane-2-carboxylate (CAS #: 1319716-42-1) (60 mg, 0.251 mmol) and 2-(4-amino-2-fluorophenyl)acetonitrile (CAS #: 180146-78-5) (38 mg, 0.251 mmol) in MeOH (10 mL) was added AcOH (one drop). The reaction was stirred at room temperature for 12 h. NaBH₃CN (32 mg, 0.502 mmol) was added and the reaction was stirred at room temperature for another 2 h, The reaction mixture was diluted with water (20 mL) and extracted with EtOAc (50 mL×3). The combined organic extracts were washed with brine, dried over anhydrous Na₂SO₄, filtered and the filtrate was concentrated. The residue was purified by silica gel chromatography eluted with PE/EA (4/1, v/v) to give intermediate 92 (56 mg, 60%) as a yellow oil.

Preparation of Intermediate 93

To a stirred solution of intermediate 92 (56 mg, 0.150 mmol) in DCM (5 mL) was added HCl/1,4-dioxane (4 M) (5 mL). The reaction was stirred at room temperature for 1 h. The reaction mixture was concentrated to give intermediate 93 (40 mg, crude HCl salt), which was used for the next step without further purification.

Example A36

Preparation of Intermediates 94, 95, 96, 97, 98, and 99

Intermediates 94, 95, 96, 97, 98, and 99 were prepared from their respective starting materials in 2 steps by using analogous reaction protocols as described for the preparation of intermediate 93 (via intermediate 92), starting from tert-butyl 7-oxo-2-azaspiro[4.4]nonane-2-carboxylate (CAS #: 1319716-42-1) and the corresponding amines.

| Intermediate number (starting materials) | Method used | Intermediate structure |
|---|---|---|
| intermediate 94 (from 2-(4-aminophenyl)-2-methylpropanenitrile, CAS#: 115279-57-7) | Step 1: intermediate 92 Step 2: intermediate 93 | 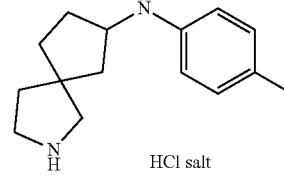 HCl salt |
| intermediate 95 (from 1-(4-aminophenyl)cyclopropane-1-carbonitrile, CAS#: 108858-86-2) | Step 1: intermediate 92 Step 2: intermediate 93 | 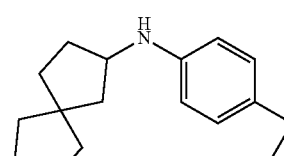 HCl salt |
| intermediate 96 (from 3-aminobenzonitrile, CAS#: 2237-30-1) | Step 1: intermediate 92 Step 2: intermediate 93 | 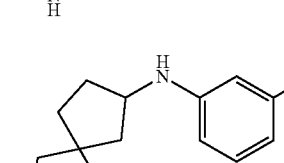 HCl salt |
| intermediate 97 (from 4-amino-N-methylbenzamide, CAS#: 6274-22-2) | Step 1: intermediate 92 Step 2: intermediate 93 | 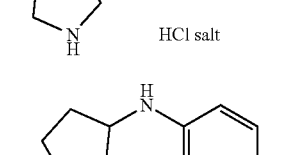 HCl salt |

-continued

| Intermediate number (starting materials) | Method used | Intermediate structure |
|---|---|---|
| Intermediate 97a | Step 1: intermediate 92 Step 2: intermediate 93 (TFA used as acid) | 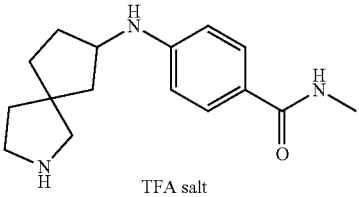 [SMILES: CNC(=O)c1ccc(NC2CCC3(CCNC3)C2)cc1] TFA salt |
| intermediate 98 (from 4-(1H-pyrazol-3-yl)aniline, CAS#: 89260-45-7) | Step 1: intermediate 92 Step 2: intermediate 93 | 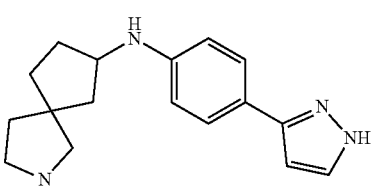 HCl salt |
| intermediate 98a | Step 1: intermediate 92 Step 2: intermediate 93 (TFA used as acid) | 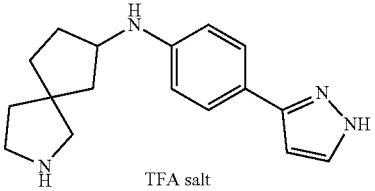 [SMILES: c1cc(-c2ccc(NC3CCC4(CCNC4)C3)cc2)n[nH]1] TFA salt |
| intermediate 99 (from 2-(4-aminophenyl)acetonitrile, CAS#: 3544-25-0) | Step 1: intermediate 92 Step 2: intermediate 93 with TFA for Boc deprotection | 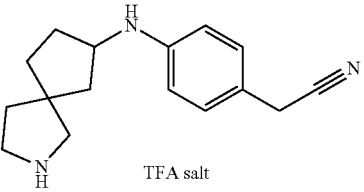 [SMILES: N#CCc1ccc(NC2CCC3(CCNC3)C2)cc1] TFA salt |

Example A37

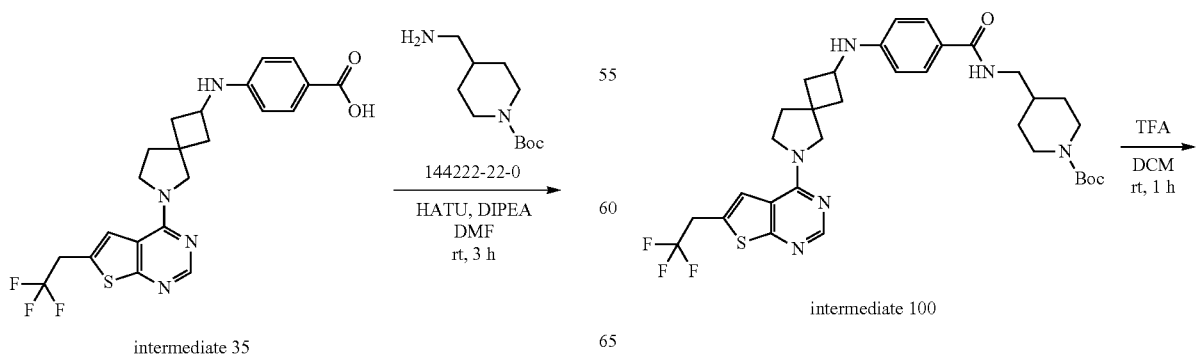

169
-continued

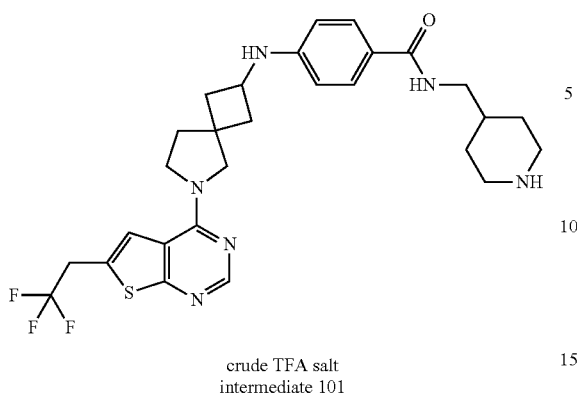

crude TFA salt
intermediate 101

Preparation of Intermediate 100

To a stirred solution of intermediate 35 (200 mg, 0.43 mmol) in DMF (2 mL) were added tert-butyl 4-(aminomethyl)piperidine-1-carboxylate (CAS #: 144222-22-0) (92 mg, 0.43 mmol), HATU (196 mg, 0.52 mmol) and DIPEA (168 mg, 1.29 mmol).

The reaction was stirred at room temperature for 3 h. The reaction mixture was diluted with water (20 mL) and extracted with EtOAc (20 mL×3). The combined organic extracts were washed with water (20 mL×3), dried over anhydrous Na$_2$SO$_4$, filtered and the filtrate was concentrated. The residue was purified by silica gel chromatography eluted with DCM/MeOH (20/1, v/v) to give intermediate 100 (238 mg, 84% yield).

Preparation of Intermediate 101

To a stirred solution of intermediate 100 (238 mg, 0.36 mmol) in DCM (2 mL) was added TFA (1 mL). The reaction was stirred at room temperature for 1 h. The reaction mixture was concentrated to give intermediate 101 (218 mg, crude TFA salt, 100% yield) as brown oil, which was used directly for the next step without further purification.

170
Example A38

Preparation of Intermediate 102

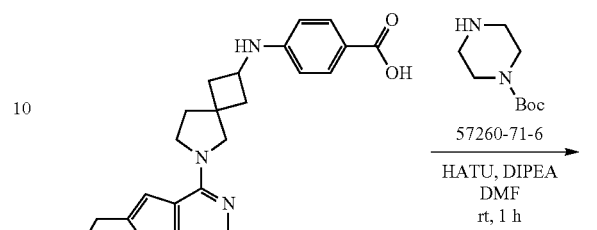

intermediate 35

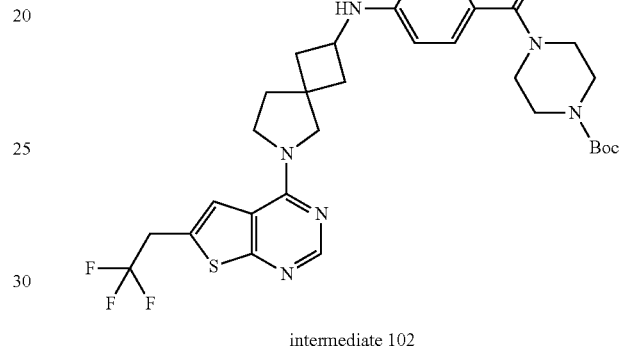

intermediate 102

To a stirred solution of intermediate 35 (300 mg, 0.65 mmol) in DMF (10 mL) at room temperature were added HATU (247 mg, 0.65 mmol) and DIPEA (251 mg, 1.95 mmol).

The reaction was stirred at room temperature for 5 minutes and tert-butyl piperazine-1-carboxylate (CAS #: 57260-71-6) (145 mg, 0.78 mmol) was added. The resulting mixture was stirred at room temperature for 1 h. The mixture was poured into H$_2$O (50 mL) and extracted with EtOAc (50 mL×3). The combined organic extracts were washed with H$_2$O, brine, dried over anhydrous Na$_2$SO$_4$, filtered and the filtrate was concentrated to give intermediate 102 (279 mg, 68% yield) as a yellow oil.

Example A39

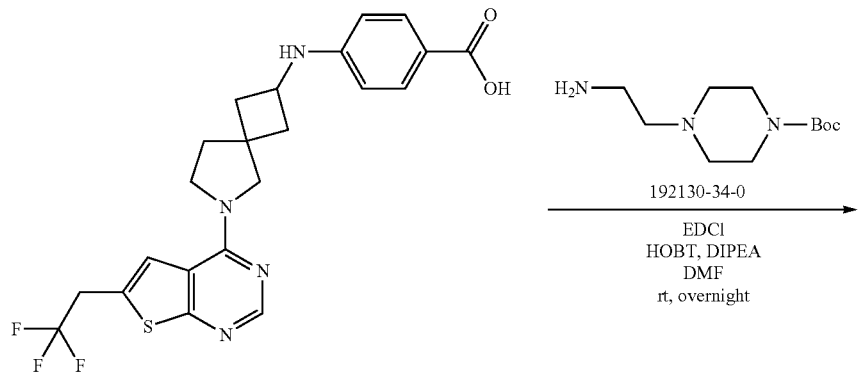

intermediate 35

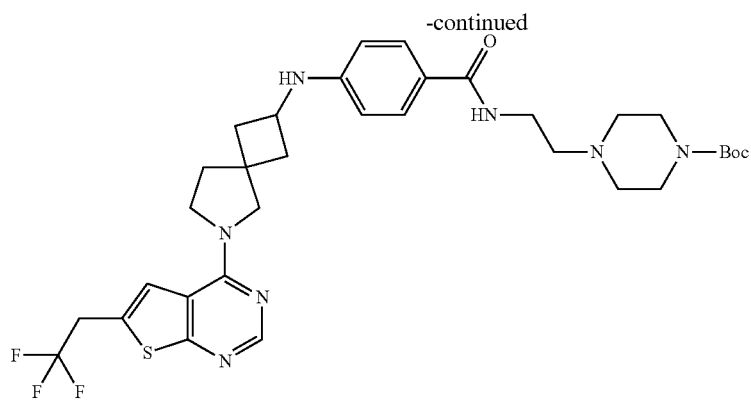

intermediate 103

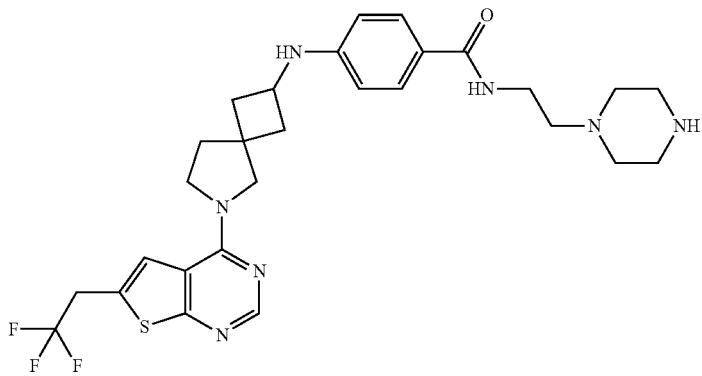

crude HCl salt
intermediate 104

Preparation of Intermediate 103

To a stirred suspension of tert-butyl 4-(2-aminoethyl)piperazine-1-carboxylate (CAS #: 192130-34-0) (297 mg, 1.68 mmol) and intermediate 35 (600 mg, 1.29 mmol) in DMF (4 mL) at room temperature were added HOBT (350 mg, 2.59 mmol), EDCI (498 mg, 2.59 mmol) and DIPEA (502 mg, 3.89 mmol). The reaction was stirred at room temperature overnight. The reaction mixture was diluted with saturated aqueous NH$_4$Cl (50 mL), solid precipitated. The resulting mixture was filtered. The filter cake was collected and dried to give intermediate 103 (600 mg, 68% yield).

Preparation of Intermediate 104

To a stirred solution of intermediate 103 (600 mg, 0.89 mmol) in MeOH (12 mL) was added HCl/1,4-dioxane (4 M) (4 mL). The reaction was stirred at room temperature for 5 h. The reaction mixture was concentrated to give intermediate 104 (600 mg, crude HCl salt), which was used for the next step without further purification.

Example A40

Preparation of Intermediates 105 and 106

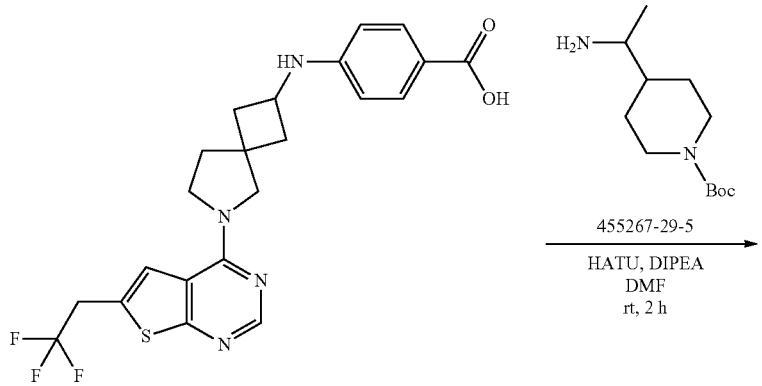

intermediate 35

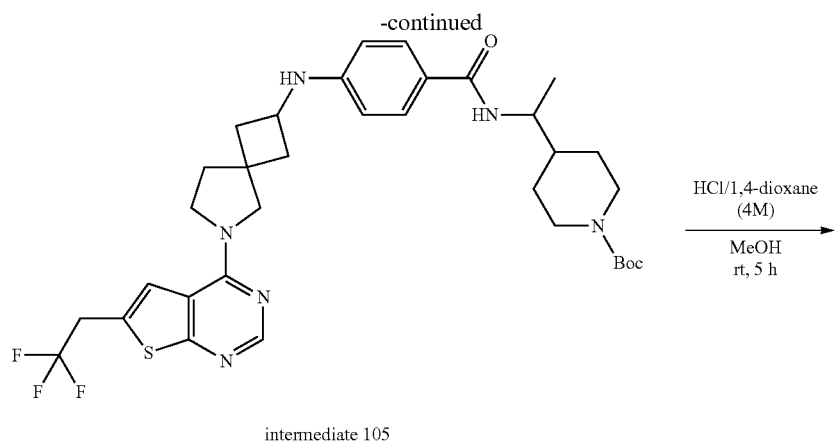
intermediate 105
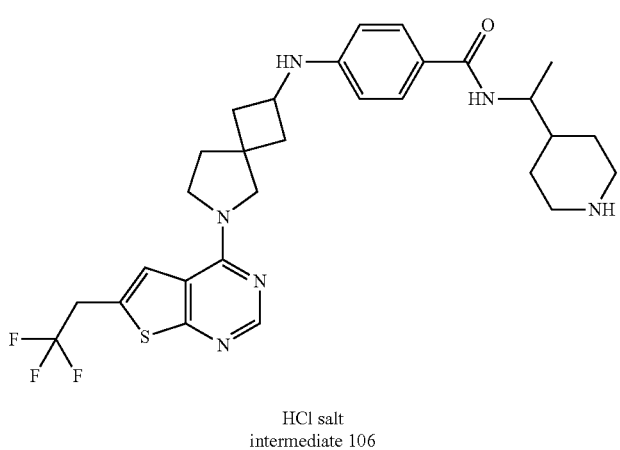
HCl salt
intermediate 106
Intermediate 105 and intermediate 106 (HCl salt) were prepared respectively via an analogous reaction protocol as described for the preparation of intermediate 100 and intermediate 104 respectively, starting from the respective starting materials.
Example A41
Preparation of Intermediates 107 and 108
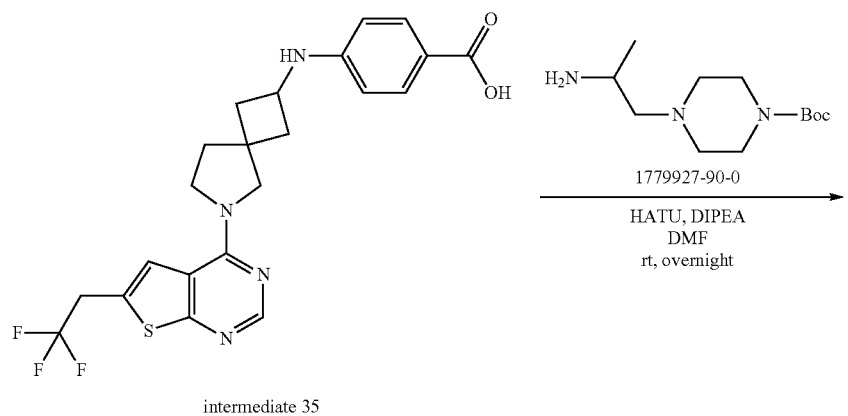
intermediate 35

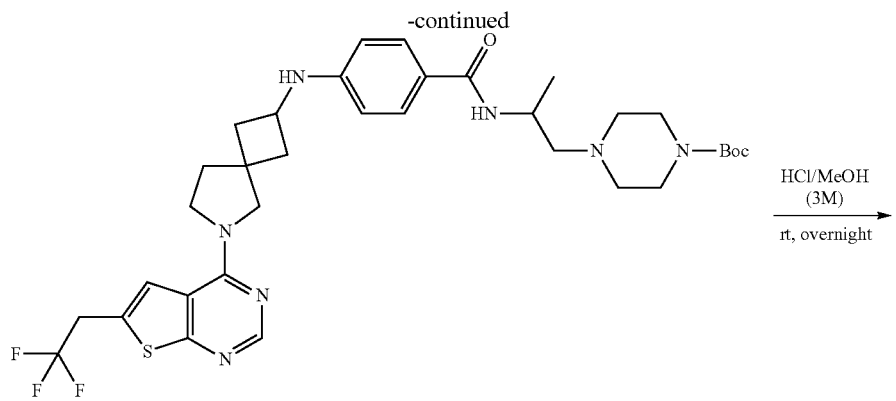

intermediate 107

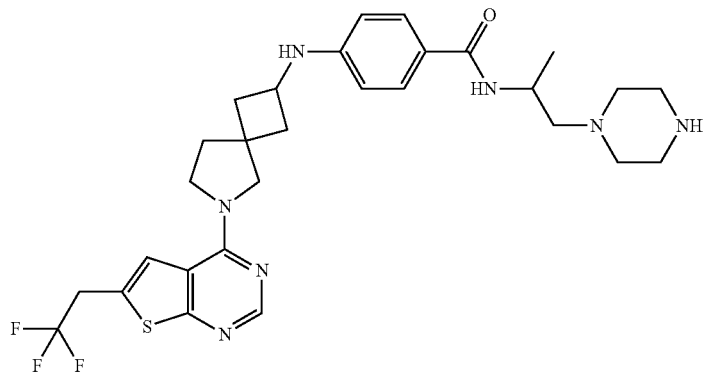

HCl salt
intermediate 108

Intermediate 107 and intermediate 108 (HCl salt) were prepared respectively via an analogous reaction protocol as described for the preparation of intermediate 100 and intermediate 104 respectively using HCl/MeOH (3M) instead of HCl/1,4-dioxane (4M) for Boc deprotection, starting from the respective starting materials.

Example A42

Preparation of Intermediates 109 and 110

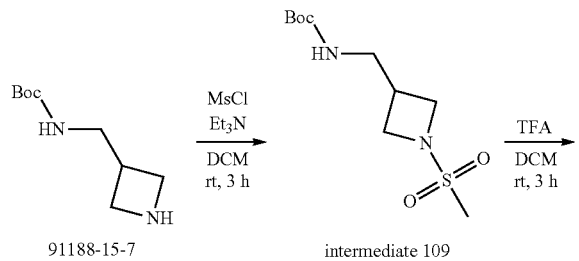

intermediate 110
crude TFA salt

Preparation of Intermediate 109

A solution of 3-(N-Boc-aminomethyl)azetidine (CAS #: 91188-15-7) (300 mg, 1.612 mmol), methanesulfonyl chloride (202 mg, 1.774 mmol) and Et$_3$N (488 mg, 4.836 mmol) in DCM (10 mL) was stirred at room temperature for 3 h. The reaction mixture was diluted with water (20 mL) and extracted with EtOAc (50 mL×3). The combined organic extracts were washed with brine, dried over anhydrous Na$_2$SO$_4$ and filtered. The filtrate was concentrated and the residue was purified by silica gel chromatography eluted with CH$_2$Cl$_2$/MeOH (20/1, v/v) to give intermediate 109 (357 mg, 84% yield) as a yellow solid.

Preparation of Intermediate 110

To a stirred solution of intermediate 109 (357 mg, 1.352 mmol) in DCM (10 mL) was added TFA (10 mL). The reaction mixture was stirred at room temperature for 3 h and then concentrated to give intermediate 110 (220 mg, crude TFA salt), which was used for the next step without further purification.

Example A43

Preparation of Intermediates 111 and 112

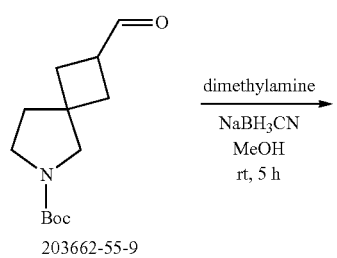

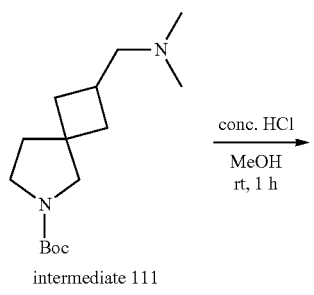

Preparation of Intermediate 111

To a stirred solution of tert-butyl 2-formyl-6-azaspiro[3.4]octane-6-carboxylate (CAS #: 203662-55-9) (150 mg, 0.627 mmol) and dimethylamine (2 M in MeOH) (0.63 mL, 1.26 mmol) in MeOH (4 mL) at room temperature was added NaBH$_3$CN (118 mg, 1.88 mmol). The reaction was stirred at room temperature for 5 h. The reaction mixture was diluted with water (20 mL) and extracted with EtOAc (50 mL×3). The combined organic extracts were washed with brine, dried over anhydrous Na$_2$SO$_4$, filtered and concentrated to give the crude intermediate 111 (120 mg), which was used for the next step without further purification.

Preparation of Intermediate 112

To a stirred solution of crude intermediate 111 (120 mg, ca. 0.627 mmol) in MeOH (5 mL) at room temperature was added conc. HCl (12 M, 3 mL). The reaction was stirred at room temperature for 1 h. The reaction mixture was concentrated to dryness afforded intermediate 112 (100 mg, crude HCl salt), which was used for the next step without further purification.

Example A44

Preparation of Intermediates 113 and 114

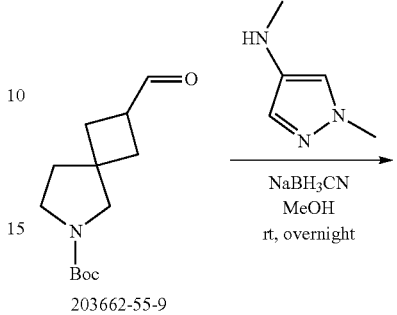

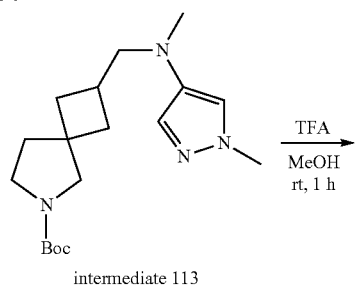

intermediate 113

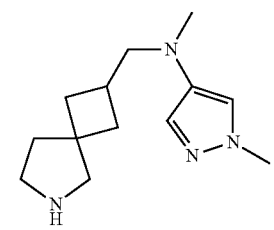

intermediate 114
crude TFA salt

Preparation of Intermediate 113

To a stirred solution of N,1-dimethyl-1H-pyrazol-4-amine (CAS #: 948572-94-9) (50 mg, 0.450 mmol) in MeOH (1 mL) at room temperature was added tert-butyl 2-formyl-6-azaspiro[3.4]octane-6-carboxylate (CAS #: 203662-55-9) (162 mg, 0.68 mmol). The reaction was stirred at room temperature for 30 minutes. NaBH$_3$CN (57 mg, 0.90 mmol) was added. The reaction was stirred at room temperature overnight. The reaction mixture was diluted with water (50 mL) and extracted with EtOAc (50 mL×3). The combined organic extracts were washed with water (50 ml×3), dried over anhydrous Na$_2$SO$_4$, filtered and the filtrate was concentrated to give crude intermediate 113 (150 mg), which was used directly for the next step without further purification.

Preparation of Intermediate 114

To a stirred solution of intermediate 113 (150 ng, crude product, ca. 0.450 mmol) in MeOH (2 mL) at room temperature was added TFA (1 mL). The reaction was stirred at room temperature for 1 h. The reaction mixture was concentrated to give intermediate 114 (160 mg, crude TFA salt) as a brown oil, which was used directly for the next step without further purification.

Example A45

Preparation of Intermediates 115 and 116

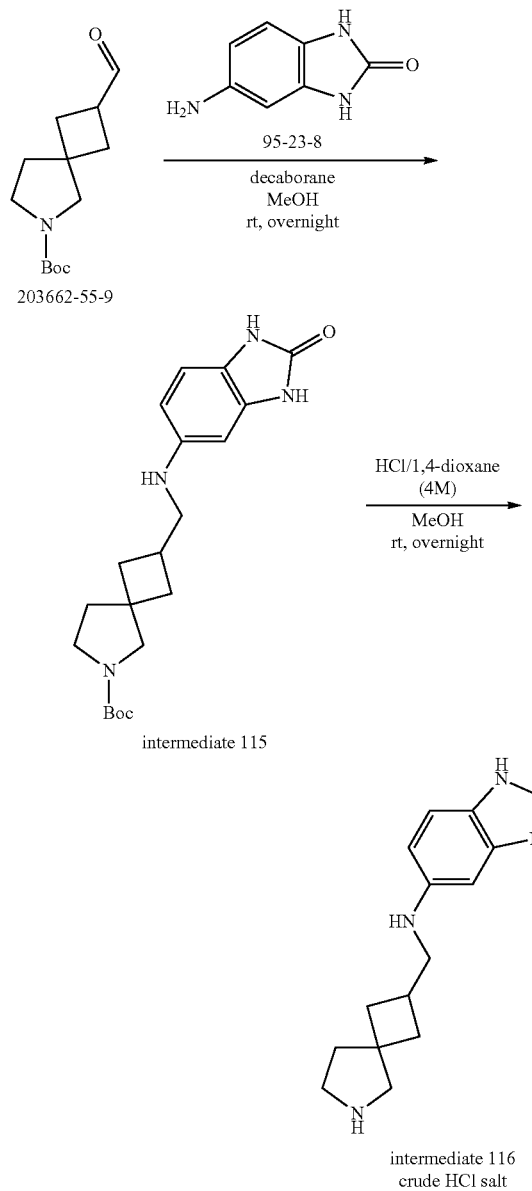

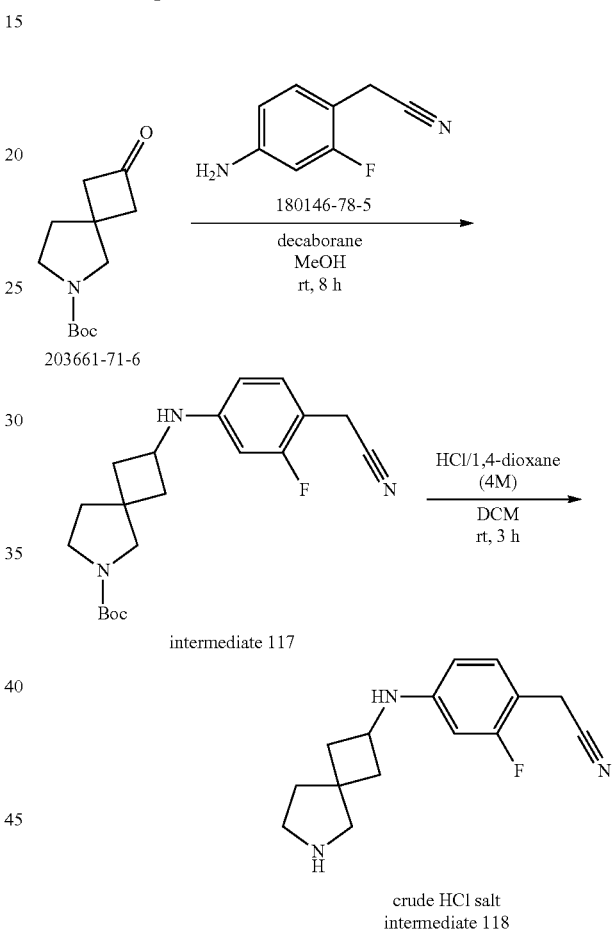

Preparation of Intermediate 115

To a stirred solution of tert-butyl 2-formyl-6-azaspiro[3.4]octane-6-carboxylate (CAS #: 203662-55-9) (120 mg, 0.501 mmol) in MeOH (3.0 mL) at room temperature were added 5-amino-1,3-dihydro-2H-benzo[d]imidazol-2-one (CAS #: 95-23-8) (85 mg, 1.0 mmol) and decaborane (11 mg, 0.1 mmol). The reaction was stirred at room temperature overnight. The reaction mixture was diluted with water (10 mL) and extracted with $CH_2Cl_2$ (20 mL×3). The combined organic extracts were washed with brine, dried over anhydrous $Na_2SO_4$ and filtered. The filtrate was concentrated in vacuo to give crude intermediate 115 (220 mg), which was used for the next step without further purification.

Preparation of Intermediate 116

To a stirred solution of intermediate 115 (220 mg, crude product, ca. 0.501 mmol) in MeOH (4.0 mL) was added HCl/1,4-dioxane (4 M) (4.0 mL). The reaction mixture was stirred at room temperature overnight. The reaction mixture was concentrated in vacuo to give desired intermediate 116 (250 mg, crude HCl salt), which was used for the next step without further purification.

Example A46

Preparation of Intermediates 117 and 118

Preparation of Intermediate 117

To a stirred solution of 2-(4-amino-2-fluorophenyl)acetonitrile (CAS #: 180146-78-5) (220 mg, 1.47 mmol) and tert-butyl 2-formyl-6-azaspiro[3.4]octane-6-carboxylate (CAS #: 203662-55-9) (330 mg, 1.46 mmol) in MeOH (4 mL) at room temperature was added decaborane (53 mg, 0.44 mmol). The reaction was stirred at room temperature for 8 h. The reaction mixture was diluted with water (20 mL) and extracted with EtOAc (50 mL×3). The combined organic extracts were washed with brine, dried over anhydrous $Na_2SO_4$ and filtered. The filtrate was concentrated and the residue was purified by silica gel chromatography eluted with PE/LA (10/1, v/v) to give intermediate 117 (380 mg, 72% yield) as a white solid.

181

Preparation of Intermediate 118

To a stirred solution of intermediate 117 (380 ng, 1.06 mmol) in DCM (2 mL) at room temperature was added HCl/1,4-dioxane (4 M) (2 mL). The reaction mixture was stirred at room temperature for 3 h. The reaction mixture was concentrated to afford intermediate 118 (250 mg, crude HCl salt, 91% yield) as a white solid.

Example A47

Preparation of Intermediates 119 and 120

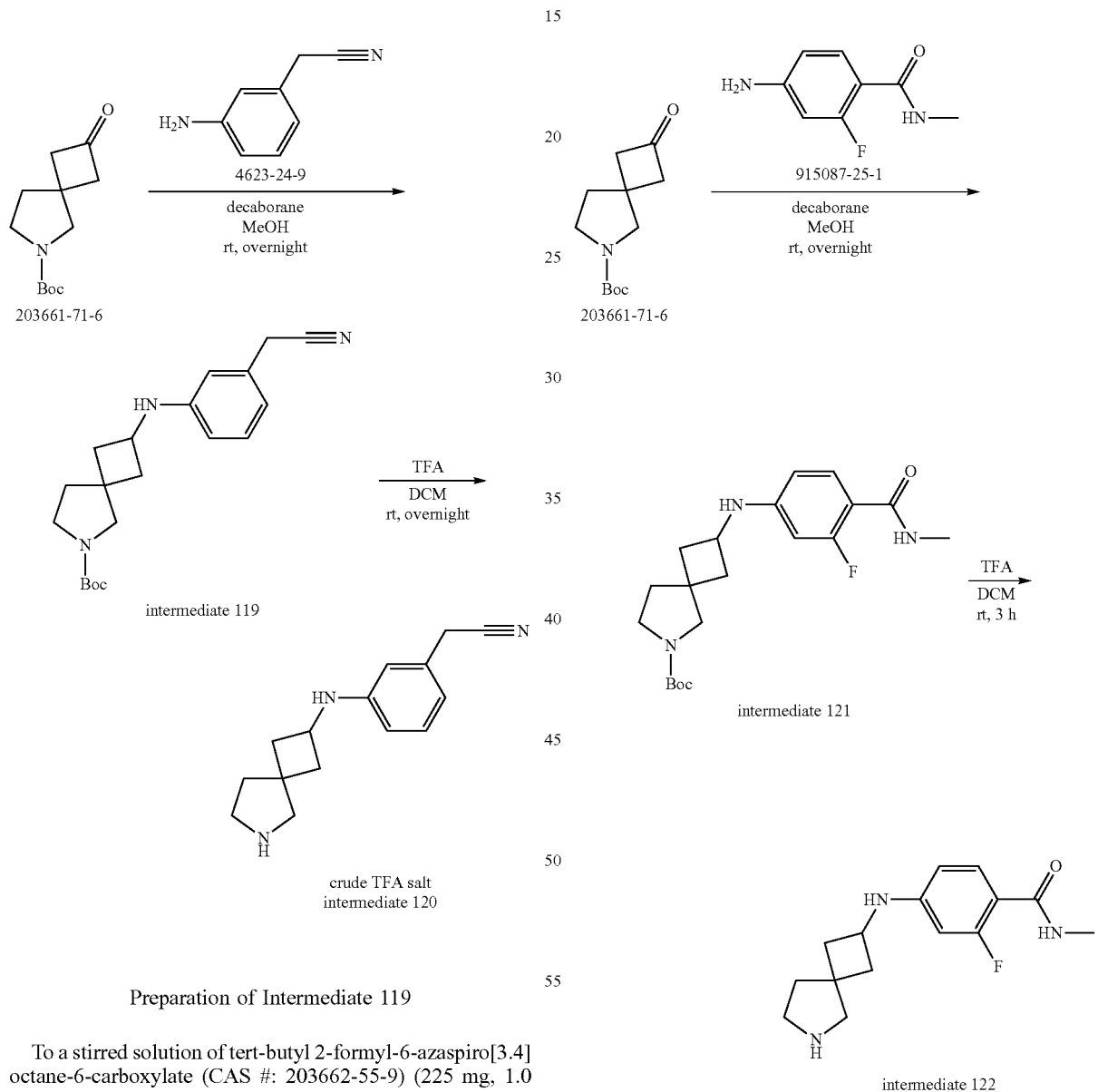

Preparation of Intermediate 119

To a stirred solution of tert-butyl 2-formyl-6-azaspiro[3.4]octane-6-carboxylate (CAS #: 203662-55-9) (225 mg, 1.0 mmol) and 2-(3-aminophenyl)acetonitrile (CAS #: 4623-24-9) (136 mg, 1.03 mmol) in MeOH (10 mL) at room temperature was added decaborane (43 mg, 0.35 mmol). The reaction mixture was stirred at room temperature overnight. The reaction mixture was concentrated. The residue was purified by silica gel chromatography eluted with PE/EtOAc (3/1, v/v) to afford intermediate 119 (340 mg, 99% yield) as a yellow solid.

182

Preparation of Intermediate 120

To a stirred solution of intermediate 119 (340 mg, 1.0 mmol) in DCM (2 mL) at room temperature was added TFA (2 mL). The reaction mixture was stirred at room temperature overnight. The reaction mixture was concentrated to afford intermediate 120 (400 mg, crude TFA salt), which was used for the next step without further purification.

Example A48

Preparation of Intermediates 121 and 122

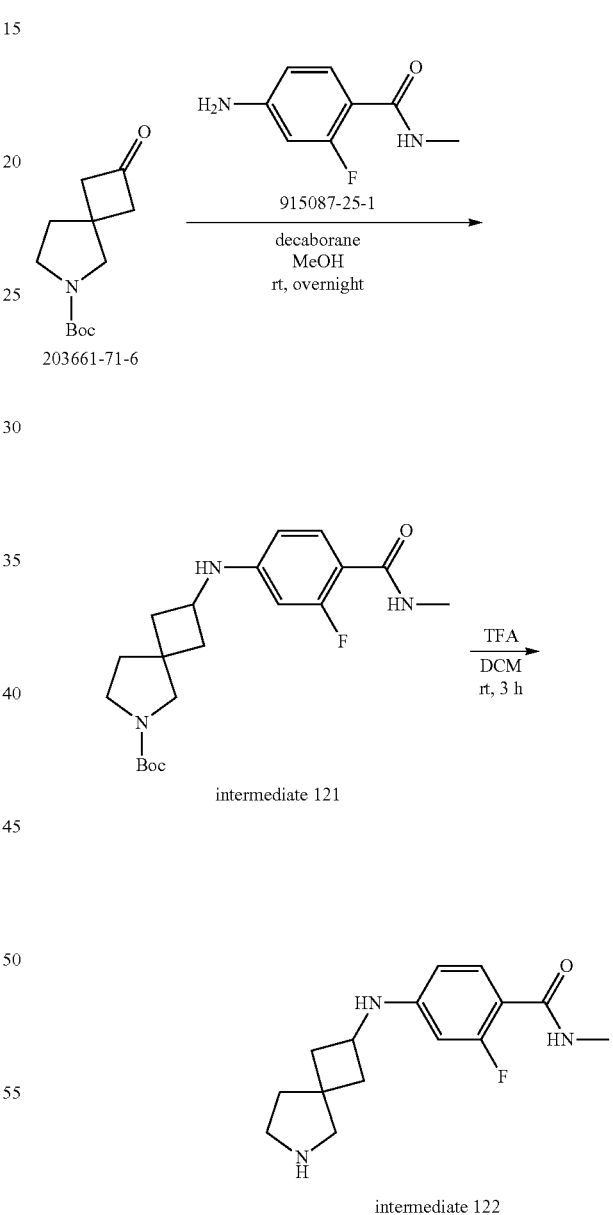

intermediate 122

Intermediate 121 and intermediate 122 were prepared respectively via an analogous reaction protocol as described for the preparation of intermediate 119 and intermediate 120 respectively, starting from the respective starting materials. Intermediate 122 was obtained as the free base (The reaction mixture was basified with aqueous $NaHCO_3$).

183

Example A49

Preparation of Intermediates 123 and 124

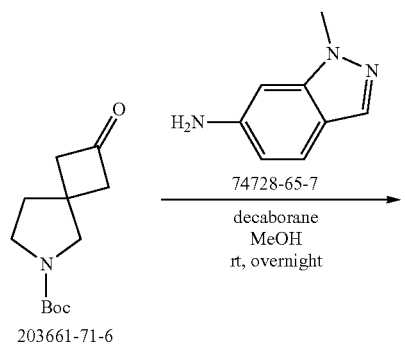

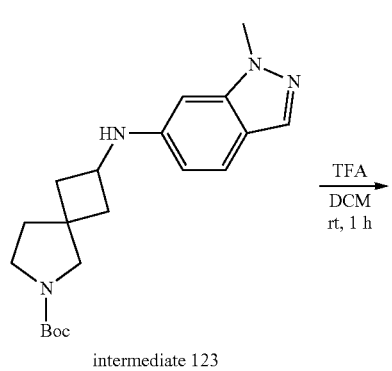

Intermediate 123 and intermediate 124 (TFA salt) were prepared respectively via an analogous reaction protocol as described for the preparation of intermediate 119 and intermediate 120 respectively, starting from the respective starting materials.

184

Example A50

Preparation of Intermediates 125 and 126

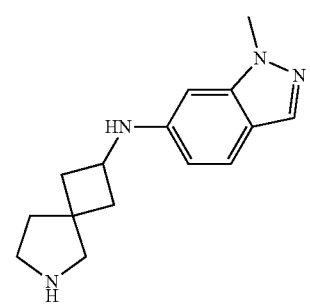

Intermediate 125 and intermediate 126 (HCl salt) were prepared respectively via an analogous reaction protocol as described for the preparation of intermediate 119 and intermediate 112 respectively, starting from the respective starting materials.

Example A51

Preparation of Intermediates 127, 128, 129, 130, 131, 132, 133 and 134

Intermediates 127, 128, 129, 130, 131, 132, 133 and 134 were prepared from their respective starting materials in 2 steps (reductive amination and then deprotection) by using analogous reaction protocols as described for the preparation of intermediate 120 or intermediate 116, starting from the respective starting materials.

| Intermediate number (starting materials) | Method used | Intermediate structure |
|---|---|---|
| intermediate 127 (from tert-butyl 2-oxo-6-azaspiro[3.4]octane-6-carboxylate, CAS#: 203661-71-6 and 2-(4-amino-3-chlorophenyl)acetonitrile, CAS#: 80199-02-6) | Step 1: intermediate 119 Step 2: intermediate 120 | 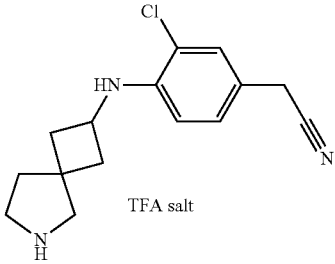 [SMILES: N#CCc1ccc(NC2CC3(CCNC3)C2)c(Cl)c1] TFA salt |
| intermediate 128 (from tert-butyl 2-oxo-6-azaspiro[3.4]octane-6-carboxylate, CAS#: 203661-71-6 and 2-(4-amino-2-chlorophenyl)acetonitrile, CAS#: 180150-18-9) | Step 1: intermediate 119 Step 2: intermediate 116 | 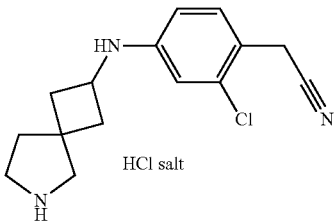 [SMILES: N#CCc1ccc(NC2CC3(CCNC3)C2)cc1Cl] HCl salt |
| intermediate 129 (from tert-butyl 2-oxo-6-azaspiro[3.4]octane-6-carboxylate, CAS#: 203661-71-6 and 4-amino-N,3-dimethylbenzamide, CAS#: 926263-13-0) | Step 1: intermediate 119 Step 2: intermediate 116 | 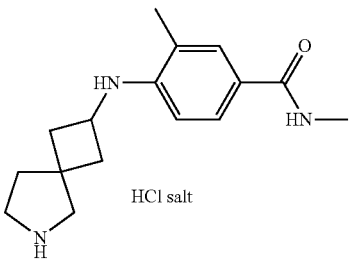 [SMILES: CNC(=O)c1ccc(NC2CC3(CCNC3)C2)c(C)c1] HCl salt |
| intermediate 130 (from tert-butyl 2-oxo-6-azaspiro[3.4]octane-6-carboxylate, CAS#: 203661-71-6 and 4-amino-2-chloro-N-methylbenzamide, CAS#: 926203-17-0) | Step 1: intermediate 119 Step 2: intermediate 116 | 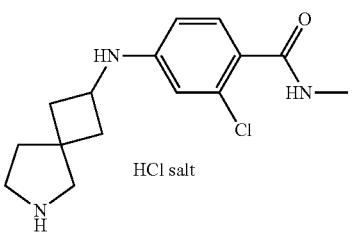 [SMILES: CNC(=O)c1ccc(NC2CC3(CCNC3)C2)cc1Cl] HCl salt |
| intermediate 131 (from tert-butyl 2-oxo-6-azaspiro[3.4]octane-6-carboxylate, CAS#: 203661-71-6 and 3-methylbenzo[d]isoxazol-6-amine, CAS#: 157640-14-7) | Step 1: intermediate 119 Step 2: intermediate 120 | 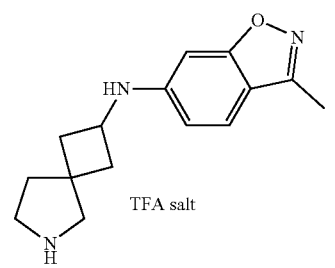 [SMILES: Cc1noc2cc(NC3CC4(CCNC4)C3)ccc12] TFA salt |
| intermediate 132 (from tert-butyl 2-oxo-6-azaspiro[3.4]octane-6-carboxylate, CAS#: 203661-71-6 and 1-methyl-1H-benzo[d][1,2,3]triazol-6-amine, CAS#: 26861-23-4) | Step 1: intermediate 119 Step 2: intermediate 120 | 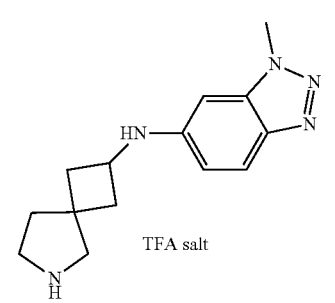 [SMILES: Cn1nnc2ccc(NC3CC4(CCNC4)C3)cc21] TFA salt |

-continued

| Intermediate number (starting materials) | Method used | Intermediate structure |
|---|---|---|
| intermediate 133 (from tert-butyl 2-oxo-6-azaspiro[3.4]octane-6-carboxylate, CAS#: 203661-71-6 and 5-amino-N-methylpicolinamide, CAS#: 941284-74-8) | Step 1: intermediate 119 Step 2: intermediate 116 | HCl salt |
| intermediate 134 (from tert-butyl 2-oxo-6-azaspiro[3.4]octane-6-carboxylate, CAS#: 203661-71-6 and 4-(morpholinosulfonyl)aniline, CAS#: 21626-70-0) | Step 1: intermediate 119 Step 2: intermediate 120 | TFA salt |

Example A52

Preparation of Intermediates 135, 136, 137 and 138

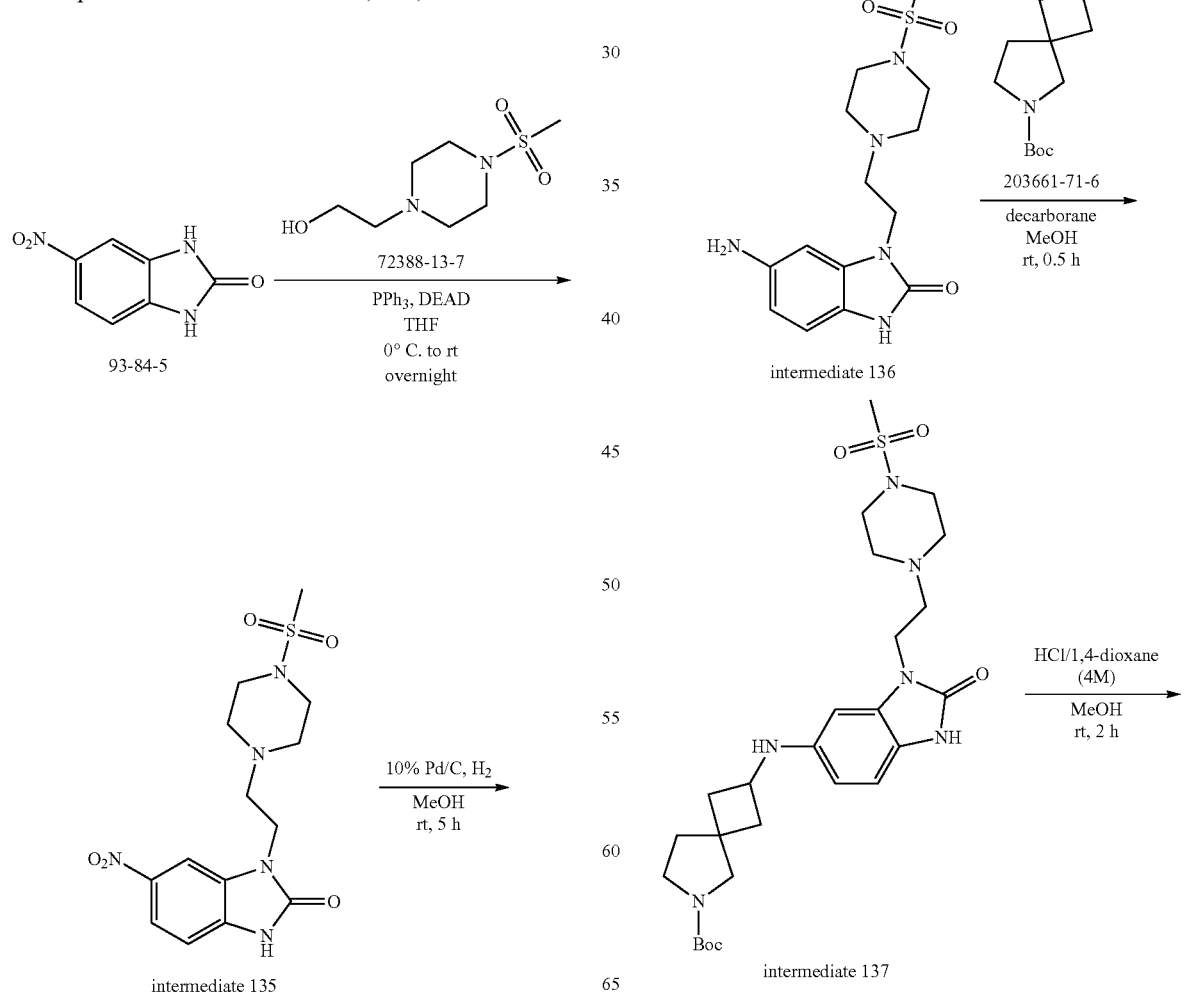

189
-continued

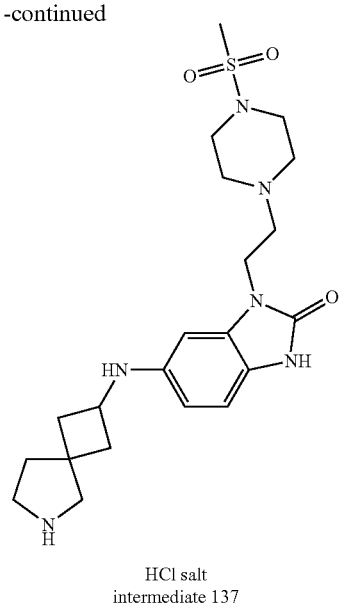

HCl salt
intermediate 137

Preparation of Intermediate 135

To a stirred solution of 5-nitro-1,3-dihydro-2H-benzo[d]imidazol-2-one (CAS #: 93-84-5) (1.00 g, 5.58 mmol), 2-(4-(methylsulfonyl)piperazin-1-yl)ethanol (CAS: 72388-13-7) (1.16 g, 5.58 mmol) and Ph$_3$P (2.93 g, 11.16 mmol) in THF (20 mL) under Ar atmosphere at 0° C. was added DEAD (1.94 g, 11.16 mmol). The reaction was stirred under Ar atmosphere at room temperature for 16 h. The resulting mixture was concentrated and the residue was purified by silica gel chromatography (PE/EA=5/1, v/v) to give impure desired product (500 mg), which was further purified by prep-HPLC (Waters 2767/Qda, Column: SunFire 19*250 mm 10 um, Mobile Phase A: 0.1% TFA/H$_2$O, B: ACN). The resulting fractions were basified by NaHCO$_3$ (solid), extracted with ErOAc (10 mL×3). The combined organic extracts were washed with brine (20 mL), dried over anhydrous Na$_2$SO$_4$, filtered and concentrated to give desired product (mixture of two isomers, ca. 180 mg) as a white solid. The product was then separated by SFC (SFC80, Waters; IA-H (2.5*25 cm, 2.5*25 cm, 10 um; A: Supercritical CO$_2$, Mobile phase B: MeOH/NH$_3$ (100/0.1); A:B=67/33; Flow rate: 60 mL/min; column temperature (T): 25° C.; Backpressure (BPR): 100 bar) to give intermediate 135 (86 mg, 4% yield, peak 2) as a white solid.

Preparation of Intermediate 136

To a solution of intermediate 135 (86 mg, 0.233 mmol) in MeOH (5 mL) at room temperature was added 10% Pd/C (10 mg). The reaction was stirred tinder H$_2$ atmosphere at room temperature for 5 h. The mixture was filtered and the filtrate was concentrated to get intermediate 136 (65 mg) as a pale yellow solid.

Intermediate 137 and intermediate 138 (HCl salt) were prepared respectively via an analogous reaction protocol as described for the preparation of intermediate 119 and intermediate 116 respectively, starting from the respective starting materials.

190

Example A53

Preparation of Intermediates 139, 140, 141 and 142

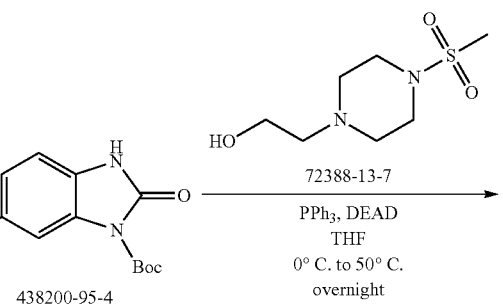

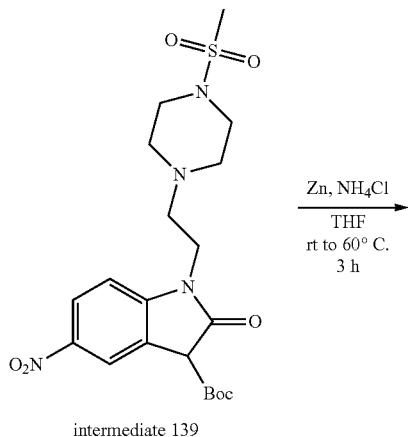

intermediate 139

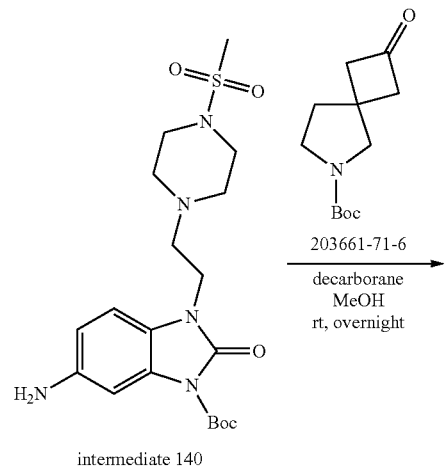

intermediate 140

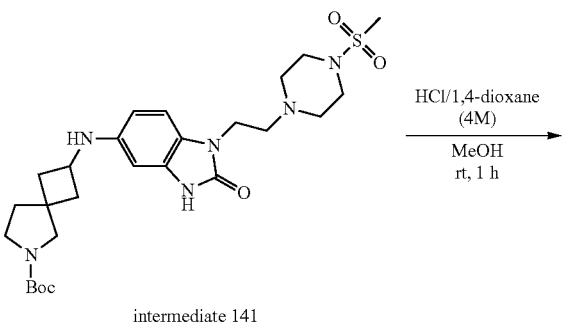

intermediate 141

191

-continued

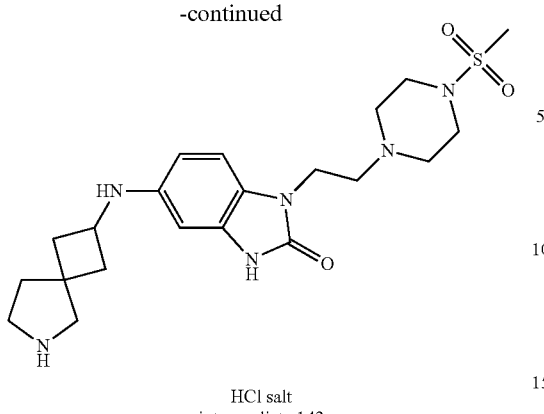

HCl salt
intermediate 142

Preparation of Intermediate 139

To a stirred solution of tert-butyl 6-nitro-2-oxo-2,3-dihydro-1H-benzo[d]imidazole-1-carboxylate (CAS #: 438200-95-4) (630 mg, 2.26 mmol), 2-(4-(methylsulfonyl)-piperazin-1-yl)ethanol (CAS #: 72388-13-7) (940 mg, 4.52 mmol) and PPh$_3$ (11186 mg, 4.52 mmol) in THF (30 mL) under Ar atmosphere at 0° C. was added DEAD (984 mg, 5.65 mmol). The reaction mixture was stirred under Ar atmosphere at 50° C. overnight.

The reaction mixture was diluted with H$_2$O (50 mL) and extracted with EtOAc (3×50 mL). The combined organic extracts were washed with brine (50 mL), dried over anhydrous Na$_2$SO$_4$, filtered and the filtrate was concentrated. The residue was purified by silica gel chromatography (PE: EA=1:1, v/v). The fractions were concentrated. The residue was dissolved in PE/EA (3/1, v/v, 20 mL), stirred at room temperature for 16 h, during which time white precipitate was formed. The mixture was filtered and the filter cake was collected to give intermediate 139 (1.36 g, 59% yield) as a white solid.

Preparation of Intermediate 140

To a stirred solution of intermediate 139 (600 mug, 1.28 mmol) in THF (10 mil) at room temperature were added NH$_4$Cl (410 mg, 7.68 mmol) and Zn (498 mg, 7.68 mmol). The reaction was stirred at 60° C. for 3 h. The reaction mixture was filtered and the filtrate was concentrated. The residue was purified by chromatography on silica gel (PE: EA=1:1) to afford intermediate 140 (230 mg, 40% yield) as a white solid.

Intermediate 141 and intermediate 142 (HCl salt) were prepared respectively via an analogous reaction protocol as described for the preparation of intermediate 119 and intermediate 116 respectively, starting from the respective starting materials.

192

Example A55

Preparation of Intermediates 146, 147, 148 and 149

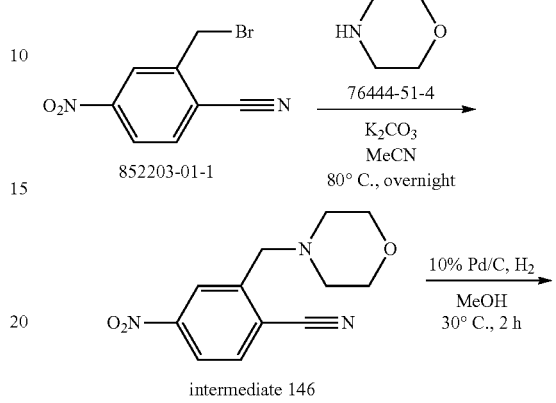

intermediate 146

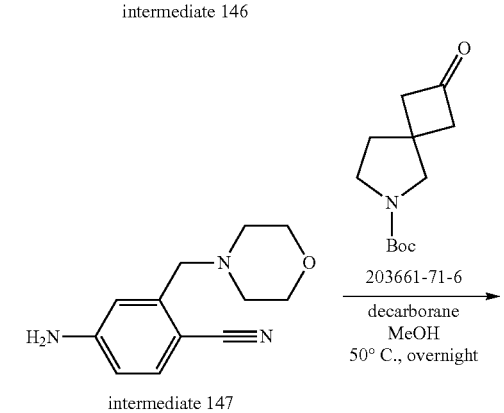

intermediate 147

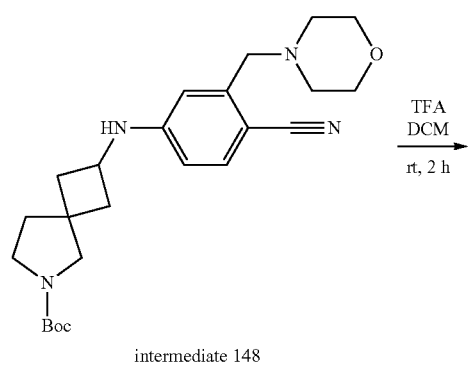

intermediate 148

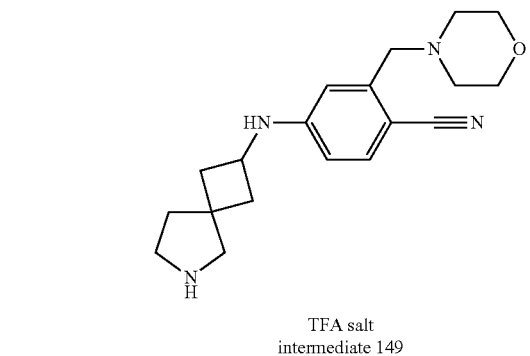

TFA salt
intermediate 149

Preparation of Intermediate 146

A mixture of 2-(bromomethyl)-4-nitrobenzonitrile (CAS #: 852203-01-1) (310 mg, 1.29 mmol), morpholine (336 mg, 3.86 mmol) and K$_2$CO$_3$ (532 mg, 3.86 mmol) in CH$_3$CN (6 mL) was stirred under Ar at 80° C. overnight. The cooled reaction mixture was filtered and the filtrate was concentrated. The residue was purified by silica gel chromatography eluted with PE/EtOAc (from 10:1 to 5:1, v/v) to give intermediate 146 (300 mg, 94% yield) as a yellow solid.

Preparation of Intermediate 147

A suspension of intermediate 146 (300 mg, 1.21 mmol) and 10% Pd/C (30 mg) in MeOH (10 mL) was stirred under H$_2$ at 30° C. for 2 h. The reaction mixture was filtered through Celite and the filtrate was concentrated to give crude intermediate 147 as a white solid (250 mg, yield: 95%), which was used for the next step directly.

Intermediate 148 and intermediate 149 (TFA salt) were prepared respectively via an analogous reaction protocol as described for the preparation of intermediate 119 and intermediate 120 respectively, starting from the respective starting materials.

Example A56

Preparation of Intermediates 150, 151, 152 and 153

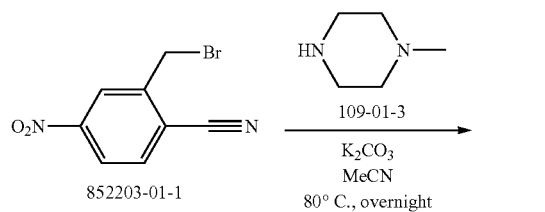

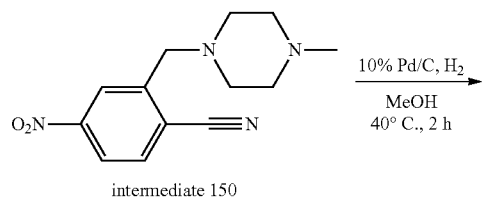

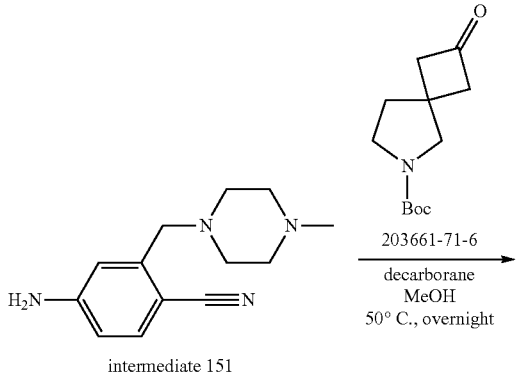

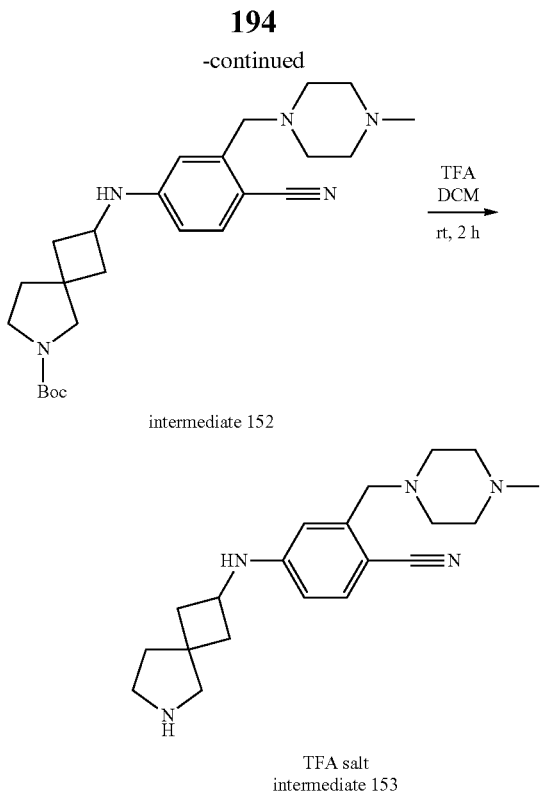

Intermediate 150, intermediate 151, intermediate 152 and intermediate 153 (TFA salt) were prepared respectively via an analogous reaction protocol as described for the preparation of intermediate 146, intermediate 147, intermediate 119, and intermediate 120 respectively, starting from the respective starting materials.

Example A57

Preparation of Intermediates 154, 155, and 156

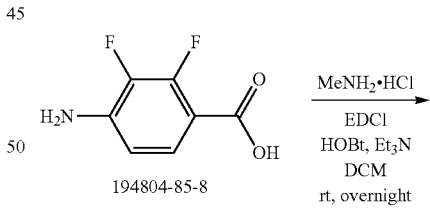

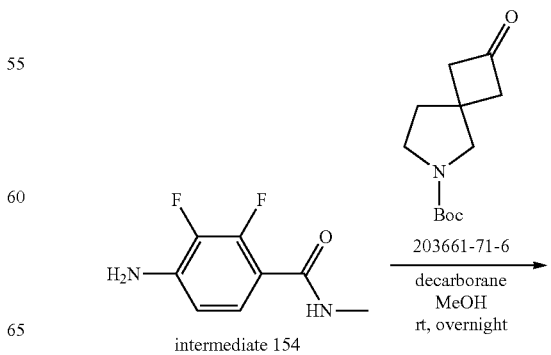

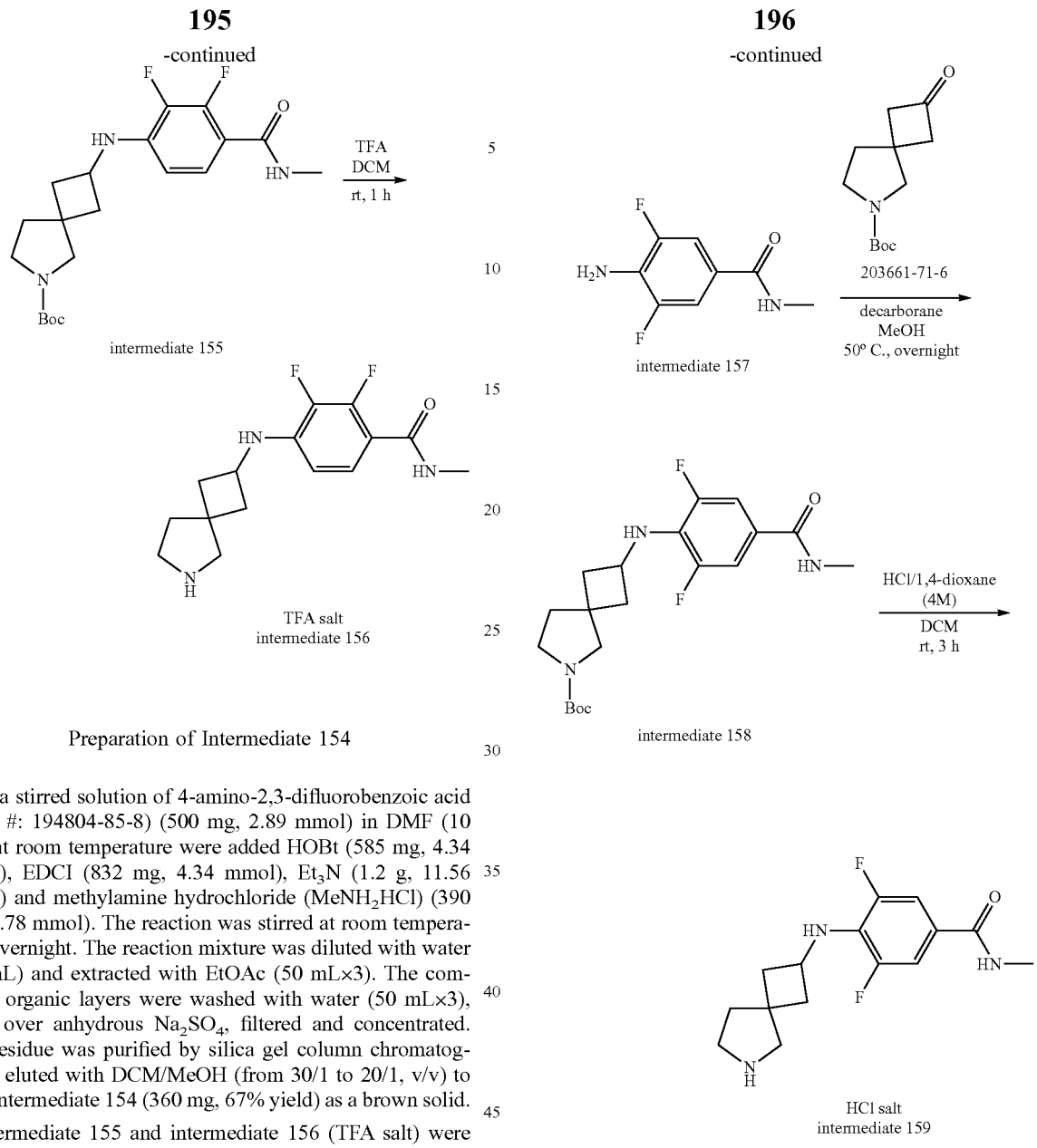

Preparation of Intermediate 154

To a stirred solution of 4-amino-2,3-difluorobenzoic acid (CAS #: 194804-85-8) (500 mg, 2.89 mmol) in DMF (10 mL) at room temperature were added HOBt (585 mg, 4.34 mmol), EDCI (832 mg, 4.34 mmol), Et$_3$N (1.2 g, 11.56 mmol) and methylamine hydrochloride (MeNH$_2$HCl) (390 mg, 5.78 mmol). The reaction was stirred at room temperature overnight. The reaction mixture was diluted with water (50 mL) and extracted with EtOAc (50 mL×3). The combined organic layers were washed with water (50 mL×3), dried over anhydrous Na$_2$SO$_4$, filtered and concentrated. The residue was purified by silica gel column chromatography eluted with DCM/MeOH (from 30/1 to 20/1, v/v) to give intermediate 154 (360 mg, 67% yield) as a brown solid.

Intermediate 155 and intermediate 156 (TFA salt) were prepared respectively via an analogous reaction protocol as described for the preparation of intermediate 119 and intermediate 120 respectively, starting from the respective starting materials.

Example A58

Preparation of Intermediates 157, 158, and 159

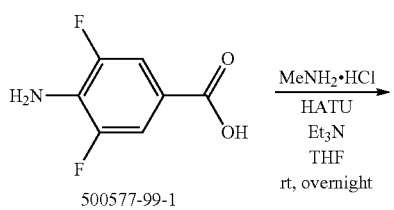

Preparation of Intermediate 157

A mixture of 4-amino-3,5-difluorobenzoic acid (CAS #: 500577-99-1) (500 mg, 2.89 mmol), methylamine hydrochloride (393 mg, 5.78 mmol), HATU (1098 mg, 2.89 mmol) and Et$_3$N (875 mg, 8.67 mmol) in THF (10 mL) was stirred at room temperature overnight. The reaction mixture was diluted with water (20 mL) and extracted with EtOAc (50 mL×3). The combined organic extracts were washed with brine, dried over anhydrous Na$_2$SO$_4$ and filtered. The filtrate was concentrated and the residue was purified by chromatography on silica gel eluted with PE/EtOAc (3/1, v/v) to give intermediate 157 (400 mg, 74%) as a white solid.

Intermediate 158 and intermediate 159 (HCl salt) were prepared respectively via an analogous reaction protocol as described for the preparation of intermediate 119 and intermediate 116 respectively, starting from the respective starting materials.

Example A59

Preparation of Intermediates 160, 161, 162, 163, 164, and 165

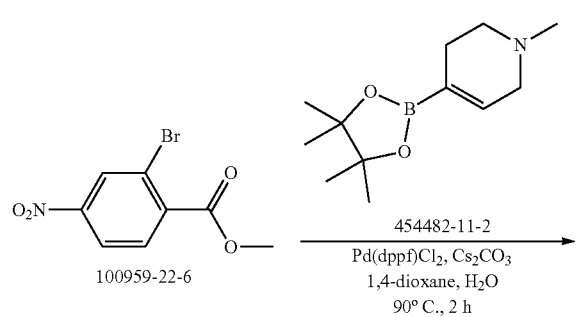

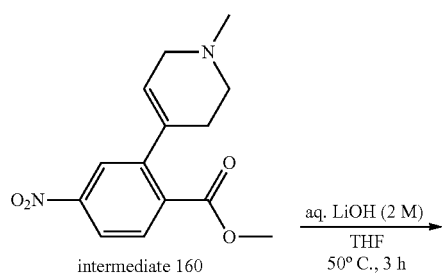

intermediate 160

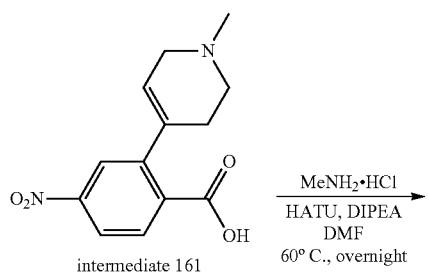

intermediate 161

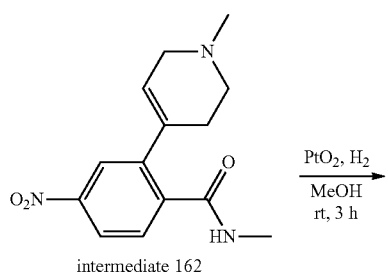

intermediate 162

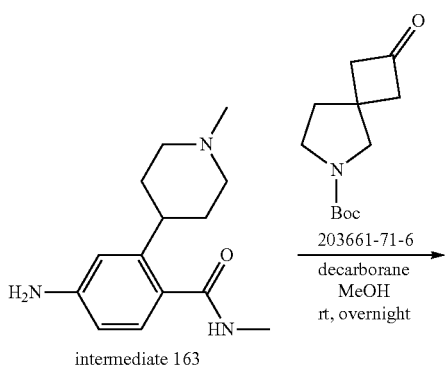

intermediate 163

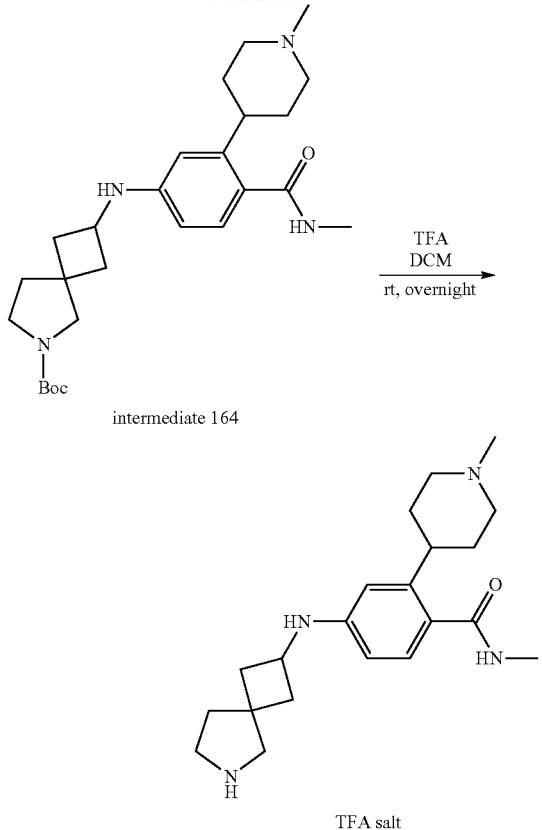

intermediate 164 intermediate 165
TFA salt

Preparation of Intermediate 160

To a solution of methyl 2-bromo-4-nitrobenzoate (CAS #: 100959-22-6) (200 g, 7.69 mmol) in 1,4-dioxane (20 mL) were added H$_2$O (10 mL), Cs$_2$CO$_3$ (5.00 g, 15.38 mmol), 1-methyl-4-(4,4,5,5-tetramethyl-1,3,2-dioxaborolan-2-yl)-1,2,3,6-tetrahydropyridine (CAS #: 454482-11-2) (2.60 g, 11.54 mmol) and Pd(dppf)Cl$_2$ (562 ng, 0.77 mmol). The reaction was stirred under Ar at 90° C. for 2 h. The cooled reaction mixture was diluted with water (200 mL) and extracted with EtOAc (200 mL×3). The combined organic extracts were washed with water (200 mL×3), dried over anhydrous Na$_2$SO$_4$, filtered and concentrated. The residue was purified by silica gel chromatography (eluent: DCM/MeOH from 40/1 to 30/1, v/v) to give intermediate 160 (2.1 g, 99% yield) as a brown oil.

Preparation of Intermediate 161

To a stirred solution of intermediate 160 (210 g, 7.61 mmol) in THF (14 mL) was added aqueous LiOH (2 M, 7 mL). The reaction was stirred at 50° C. for 3 h. The reaction mixture was concentrated. The residue was suspended in water (20 mL) and acidified with aqueous HCl (5 M) till pH equals 4. The resulting precipitate was collected by filtration and dried under reduced pressure to give intermediate 161 (1.10 g, 55% yield) as a brown solid.

Preparation of Intermediate 162

To a stirred solution of intermediate 161 (500 mg, 1.91 mmol) in DMF (20 mL) were added methylamine hydrochloride (644 mg, 9.54 mmol), HATU (1.50 g, 3.82 mmol) and DIPEA (4 mL). The reaction was stirred at 60° C. overnight. The cooled reaction mixture was diluted with water (50 mL) and extracted with EtOAc (50 mL×3). The combined organic layers were washed with water (50 mL×3), dried over anhydrous Na$_2$SO$_4$, filtered and concentrated to give intermediate 162 (524 mg, 100% yield) as a brown solid, which was used directly for the next step without further purification.

Preparation of Intermediate 163

To a solution of intermediate 162 (715 mg, 2.60 mmol) in MeOH (7 mL) was added PtO$_2$ (70 mg). The reaction was stirred under H$_2$ atmosphere at room temperature for 3 h. The reaction mixture was filtered and the filter cake was washed with MeOH. The combined filtrate was concentrated to give intermediate 163 (642 mg, 100% yield), which was used directly for the next step without further purification.

Intermediate 164 and intermediate 165 (TFA salt) were prepared respectively via an analogous reaction protocol as described for the preparation of intermediate 119 and intermediate 120 respectively, starting from the respective starting materials.

Example A60

Preparation of Intermediates 166, 167, 168, and 169

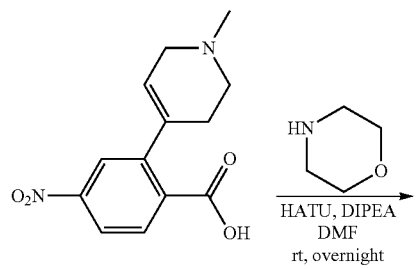

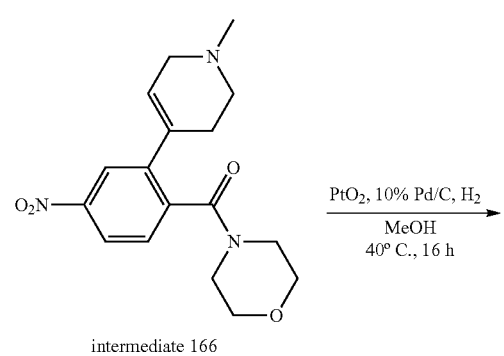

intermediate 166

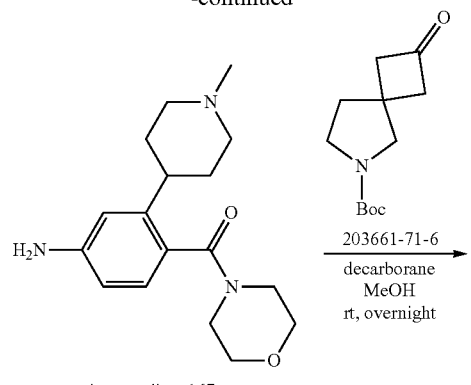

intermediate 167

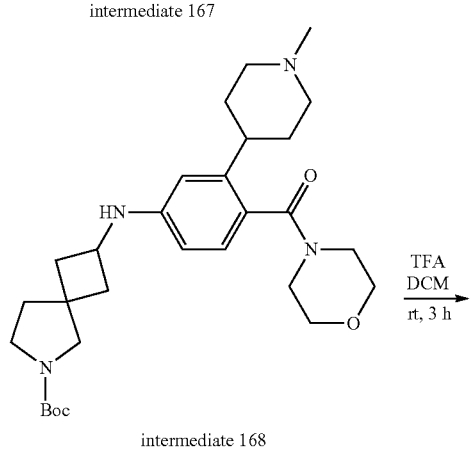

intermediate 168

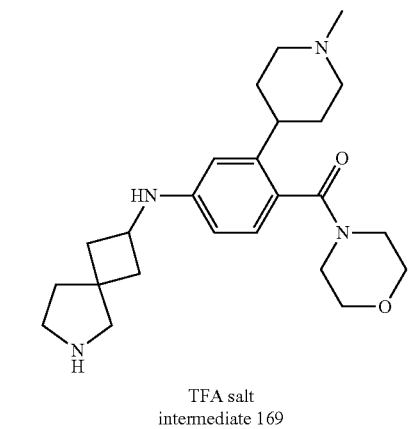 [SMILES: CN1CCC(c2cc(NC3CC4(CCNC4)C3)ccc2C(=O)N2CCOCC2)CC1]

TFA salt
intermediate 169

Preparation of Intermediate 166

To a suspension of intermediate 161 (310 mg, 1.34 mmol) and morpholine (349 mg, 4.00 mmol) in DMF (5 mL) at room temperature were added HATU (1.05 g, 2.67 mmol) and DIPEA (861 mg, 6.68 mmol). The reaction was stirred at room temperature overnight. The reaction mixture was diluted with saturated aqueous ammonium chloride (50 mL). The precipitated solid was collected by filtration and dried to give intermediate 166 (450 mg, 75% purity).

Preparation of Intermediate 167

To a solution of intermediate 166 (300 mg, crude product, ca. 0.89 mmol) in MeOH (50 mL) were added 10% Pd/C (30 mg) and PtO$_2$ (30 mg, 10%). The reaction was stirred under $H_2$ at 40° C. for 16 h. The reaction mixture was filtered and the filtrate was concentrated to give intermediate 167 (400 mg, impure), which was used for the next step without further purification.

Intermediate 168 and intermediate 169 (TFA salt) were prepared respectively via an analogous reaction protocol as described for the preparation of intermediate 119 and intermediate 120 respectively, starting from the respective starting materials.

Example A61

Preparation of Intermediates 170, 171, and 172

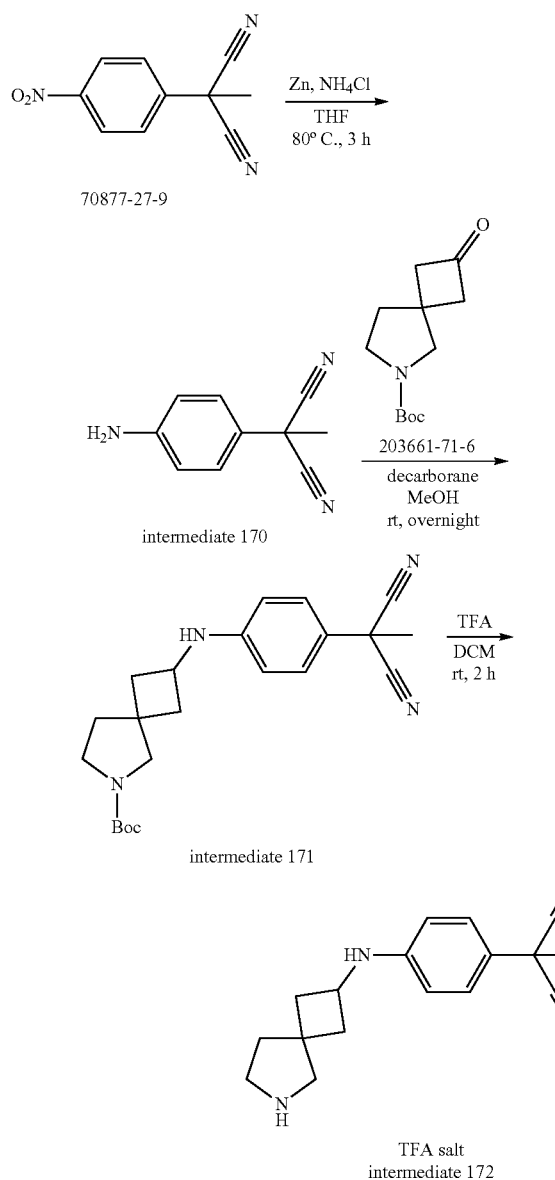

Preparation of Intermediate 170

To a solution of 2-methyl-2-(4-nitrophenyl)malononitrile (CAS #: 70877-27-9) (350 mg, crude product) in THF (5 mL) were added $NH_4Cl$ (932 mg, 17.41 mmol) and Zn (1.1 g, 17.41 mmol). The reaction was stirred at 80° C. for 3 h. The reaction mixture was filtered and the filtrate was concentrated. The residue dark oil was purified by prep-TLC (PE:EA=1:1, v/v) to get intermediate 170 (150 mg) as a white solid.

Intermediate 171 and intermediate 172 (TFA salt) were prepared respectively via an analogous reaction protocol as described for the preparation of intermediate 119 and intermediate 120 respectively, starting from the respective starting materials.

Example A62

Preparation of Intermediate 173, 174, 175, 176, and 177

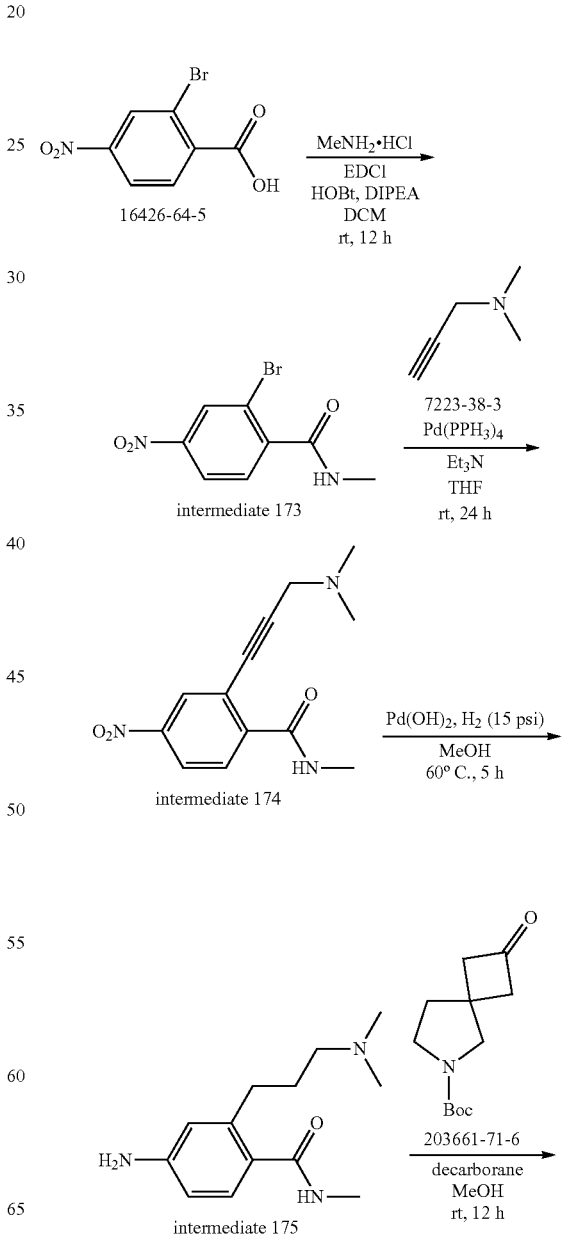

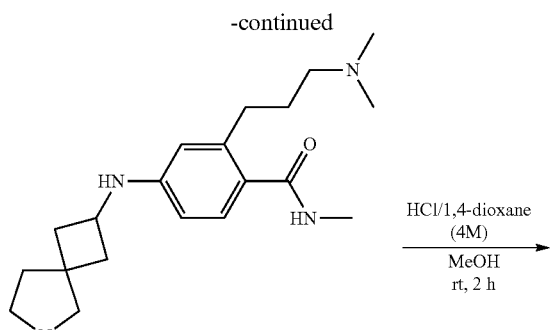

intermediate 176

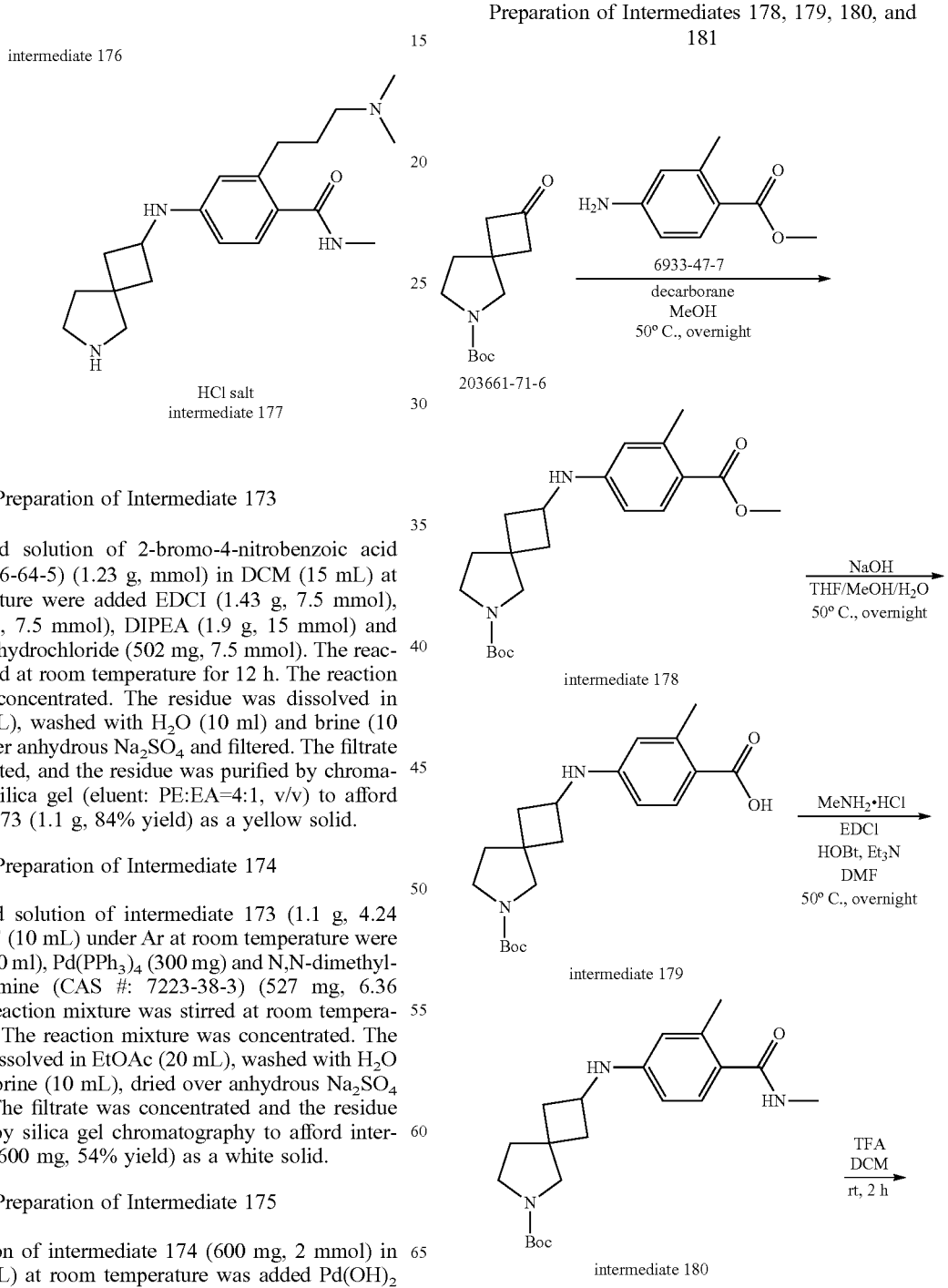

HCl salt
intermediate 177

Preparation of Intermediate 173

To a stirred solution of 2-bromo-4-nitrobenzoic acid (CAS #: 16426-64-5) (1.23 g, mmol) in DCM (15 mL) at room temperature were added EDCI (1.43 g, 7.5 mmol), HOBt (1.02 g, 7.5 mmol), DIPEA (1.9 g, 15 mmol) and methanamine hydrochloride (502 mg, 7.5 mmol). The reaction was stirred at room temperature for 12 h. The reaction mixture was concentrated. The residue was dissolved in EtOAc (20 mL), washed with $H_2O$ (10 ml) and brine (10 mL), dried over anhydrous $Na_2SO_4$ and filtered. The filtrate was concentrated, and the residue was purified by chromatography on silica gel (eluent: PE:EA=4:1, v/v) to afford intermediate 173 (1.1 g, 84% yield) as a yellow solid.

Preparation of Intermediate 174

To a stirred solution of intermediate 173 (1.1 g, 4.24 mmol) in THF (10 mL) under Ar at room temperature were added $Et_3N$ (10 ml), $Pd(PPh_3)_4$ (300 mg) and N,N-dimethyl-prop-2-yn-1-amine (CAS #: 7223-38-3) (527 mg, 6.36 mmol). The reaction mixture was stirred at room temperature for 24 h. The reaction mixture was concentrated. The residue was dissolved in EtOAc (20 mL), washed with $H_2O$ (10 mL) and brine (10 mL), dried over anhydrous $Na_2SO_4$ and filtered. The filtrate was concentrated and the residue was purified by silica gel chromatography to afford intermediate 174 (600 mg, 54% yield) as a white solid.

Preparation of Intermediate 175

To a solution of intermediate 174 (600 mg, 2 mmol) in MeOH (20 mL) at room temperature was added $Pd(OH)_2$ (100 mg). The reaction mixture was stirred under $H_2$ (15 psi) at 60° C. for 5 h. The cooled reaction mixture was filtered. The filtrate was concentrated to give intermediate 175 (400 mg, 85% yield).

Intermediate 176 and intermediate 177 (HCl salt) were prepared respectively via an analogous reaction protocol as described for the preparation of intermediate 119 and intermediate 116 respectively, starting from the respective starting materials.

Example A63

Preparation of Intermediates 178, 179, 180, and 181

-continued

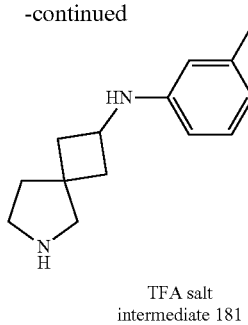

TFA salt
intermediate 181

Intermediate 178 was prepared via an analogous reaction protocol as described for the preparation of intermediate 119, starting from the respective starting materials.

Preparation of Intermediate 179

A mixture of intermediate 178 (561 mg, 1.5 mmol) and NaOH (1.20 g, 30 mmol) in THF (10 mL), H$_2$O (10 mL) and MeOH (10 mL) was stirred at 50° C. overnight. The reaction mixture was concentrated and acidified with conc. HCl till pH equals 2. The resulting mixture was extracted with EtOAc (30 mL×3). The combined organic extracts were washed with brine (50 mL), dried over anhydrous Na$_2$SO$_4$, filtered and concentrated to afford intermediate 179 (480 mg, 89% yield) as a yellow solid.

Preparation of Intermediate 180

A mixture of intermediate 179 (480 mg, 1.3 mmol), methanamine hydrochloride (174 mg, 2.6 mmol), HOBT (270 mg, 1.95 mmol), EDCI (384 mg. 1.95 mmol) and Et$_3$N (525 mg, 5.2 mmol) in DMF (20 mL) was stirred at 50° C. overnight. The cooled reaction mixture was diluted with H$_2$O (60 mL) and extracted with EtOAc (30 mL×3). The combined organic extracts were washed with brine (50 mL), dried over anhydrous Na$_2$SO$_4$, filtered and concentrated to afford intermediate 180 (410 mg, 84% yield) as colorless oil.

described for the preparation of intermediate 120, starting from the respective starting materials.

Example A64

Preparation of Intermediates 182, 183, and 184

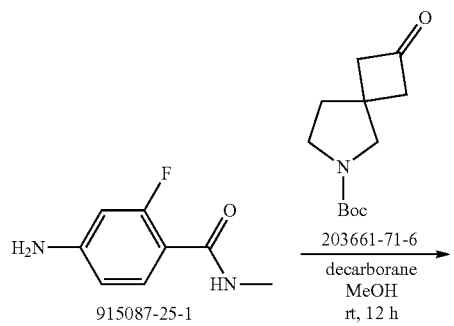

-continued

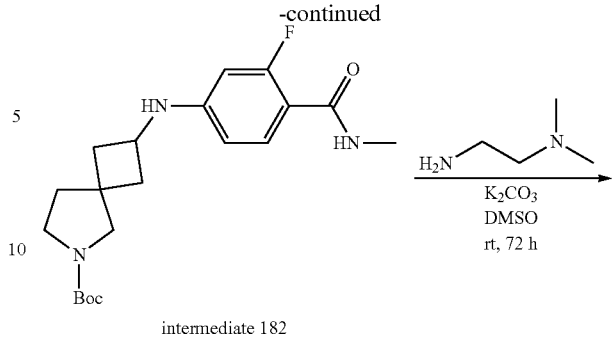

intermediate 182

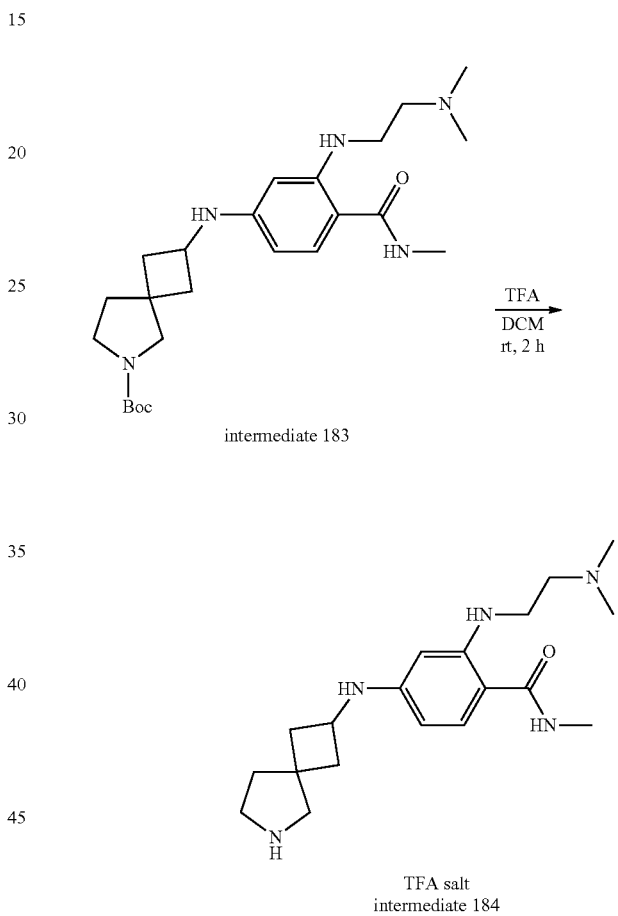

Intermediate 182 was prepared via an analogous reaction protocol as described for the preparation of intermediate 119, starting from the respective starting materials.

Preparation of Intermediate 183

A mixture of intermediate 182 (300 mg, 0.796 mmol), N$^1$,N$^1$-dimethylethane-1,2-diamine (700 mg, 7.96 mmol) and K$_2$CO$_3$ (329 mg, 2.387 mmol) in DMSO (10 mL) was stirred at room temperature for 72 h. The reaction mixture was concentrated. The residue was purified by chromatography on silica gel eluted with CH$_2$Cl$_2$/MeOH (3/1) to give intermediate 183 (328 mg, 92% yield) as a yellow oil.

Intermediate 184 (TFA salt) was prepared via an analogous reaction protocol as described for the preparation of intermediate 120, starting from the respective starting materials.

Example A65

Preparation of Intermediates 185, 186, and 187

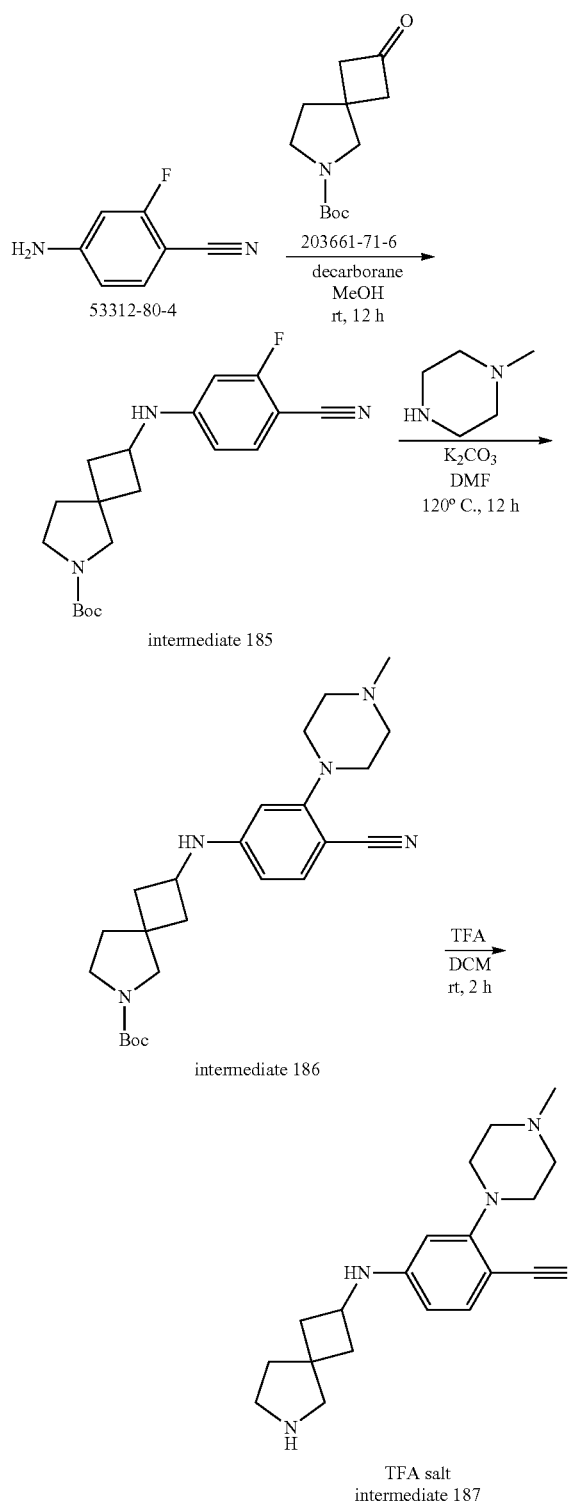

Intermediate 185 was prepared via an analogous reaction protocol as described for the preparation of intermediate 119, starting from the respective starting materials.

Preparation of Intermediate 186

A mixture of intermediate 185 (345 mg, 1.0 mmol), 1-methylpiperazine (500 mg, 5.0 mmol) and $K_2CO_3$ (690 mg, 5.0 mmol) in DMF (5 mL) was stirred at 120° C. for 12 h in a sealed tube under Ar. The reaction mixture was concentrated and the residue was purified by silica gel chromatography (DCM/MeOH=10/1, v/v) to afford intermediate 186 (60 mg, 14% yield) as a yellow oil.

Intermediate 187 (TFA salt) was prepared via an analogous reaction protocol as described for the preparation of intermediate 120, starting from the respective starting materials.

Example A66

Preparation of Intermediates 188, 189, 190, 191, 192, and 193

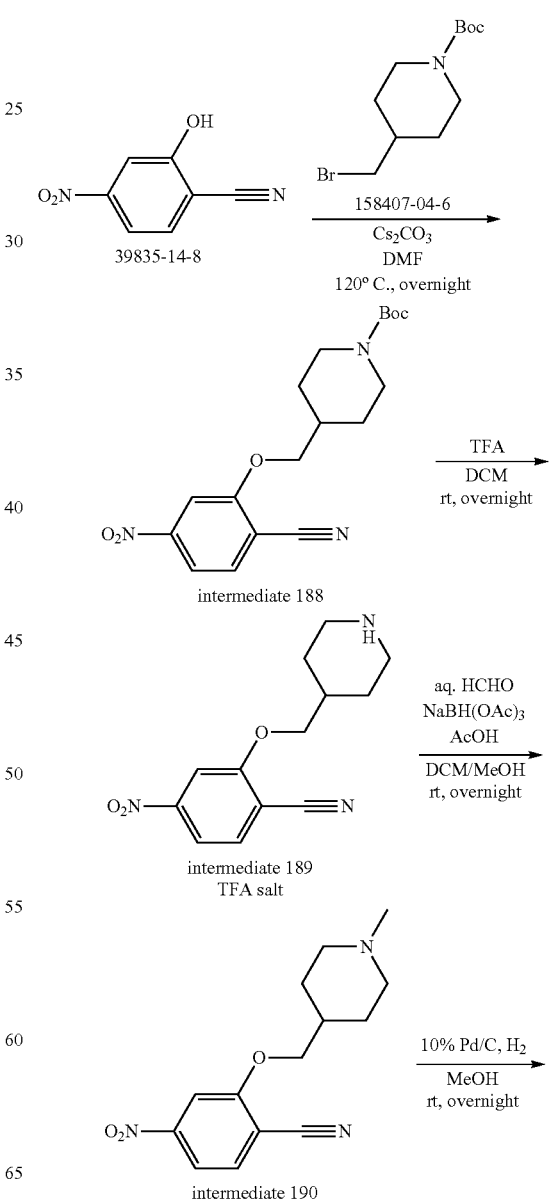

209
-continued

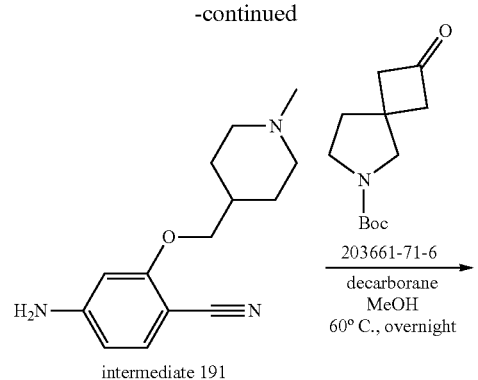

intermediate 191

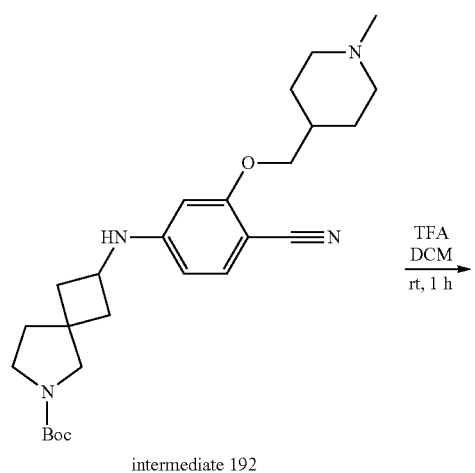

intermediate 192

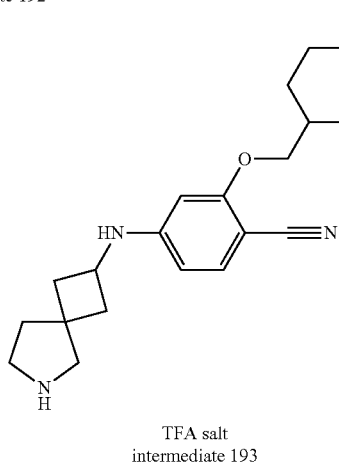

TFA salt
intermediate 193

Preparation of Intermediate 188

To a stirred solution of 2-hydroxy-4-nitrobenzonitrile (CAS #: 39835-14-8) (500 mg, 3.05 mmol) in DMF (50 mL) were added $Cs_2CO_3$ (1.5 g, 4.57 mmol) and tert-butyl 4-(bromomethyl)piperidine-1-carboxylate (CAS #: 158407-04-6) (1.0 g, 3.66 mmol). The reaction was stirred at 120° C. overnight. The cooled reaction mixture was diluted with water (50 mL) and extracted with EtOAc (50 ml×3). The combined organic extracts were washed with water (50 ml×3), dried over anhydrous $Na_2SO_4$, filtered and concentrated. The residue was purified by silica gel chromatography eluted with PE/EtOAc (from 5/1 to 3/1, v/v) to give intermediate 188 (364 mg, 33% yield) as a yellow solid.

210

Intermediate 189 (TFA salt) was prepared by an analogous reaction protocol as described for the preparation of intermediate 120, starting from the respective starting materials.

Preparation of Intermediate 190

To a stirred solution of intermediate 189 (312 mg, 1.20 mmol) in MeOH (5 mL) and DCM (5 mL) were added HCHO (37% in $H_2O$, 485 mg, 5.98 mmol) and AcOH (108 mg, 1.79 mmol). The resulting mixture was stirred at room temperature for 1 h, followed by the addition of $NaBH(OAc)_3$ (507 mg, 2.39 mmol). The reaction was stirred at room temperature overnight. The reaction mixture was diluted with water (50 mL) and extracted with DCM (50 ml×3). The combined organic extracts were dried over anhydrous $Na_2SO_4$, filtered and concentrated under reduced pressure to give intermediate 190 (329 mg, 100% yield).

Intermediate 191, intermediate 192 and intermediate 193 (TFA salt) were prepared respectively via an analogous reaction protocol as described for the preparation of intermediate 44, intermediate 119, and intermediate 120 respectively, starting from the respective starting materials.

Example A67

Preparation of Intermediates 194, 195, 196, and 197

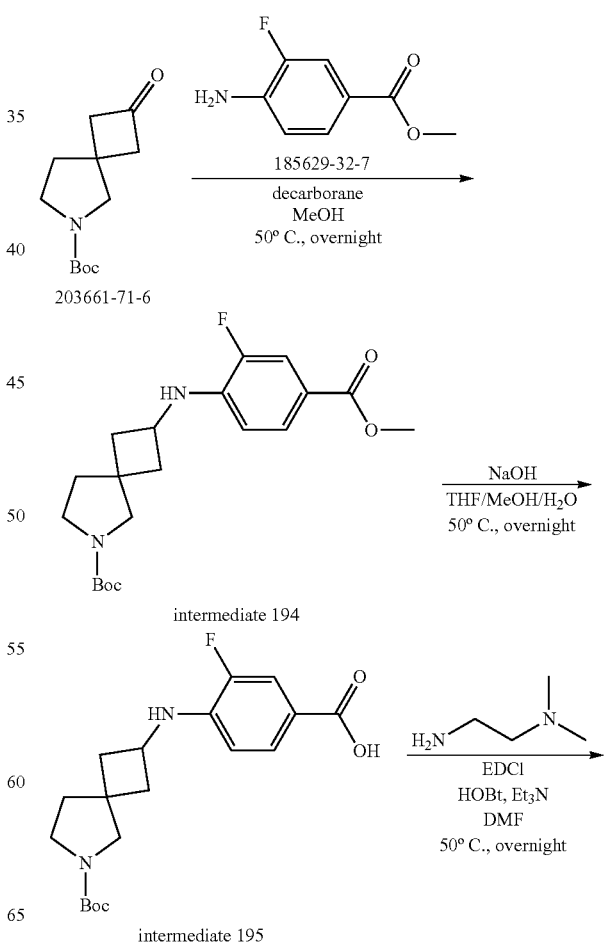

intermediate 195

211
-continued

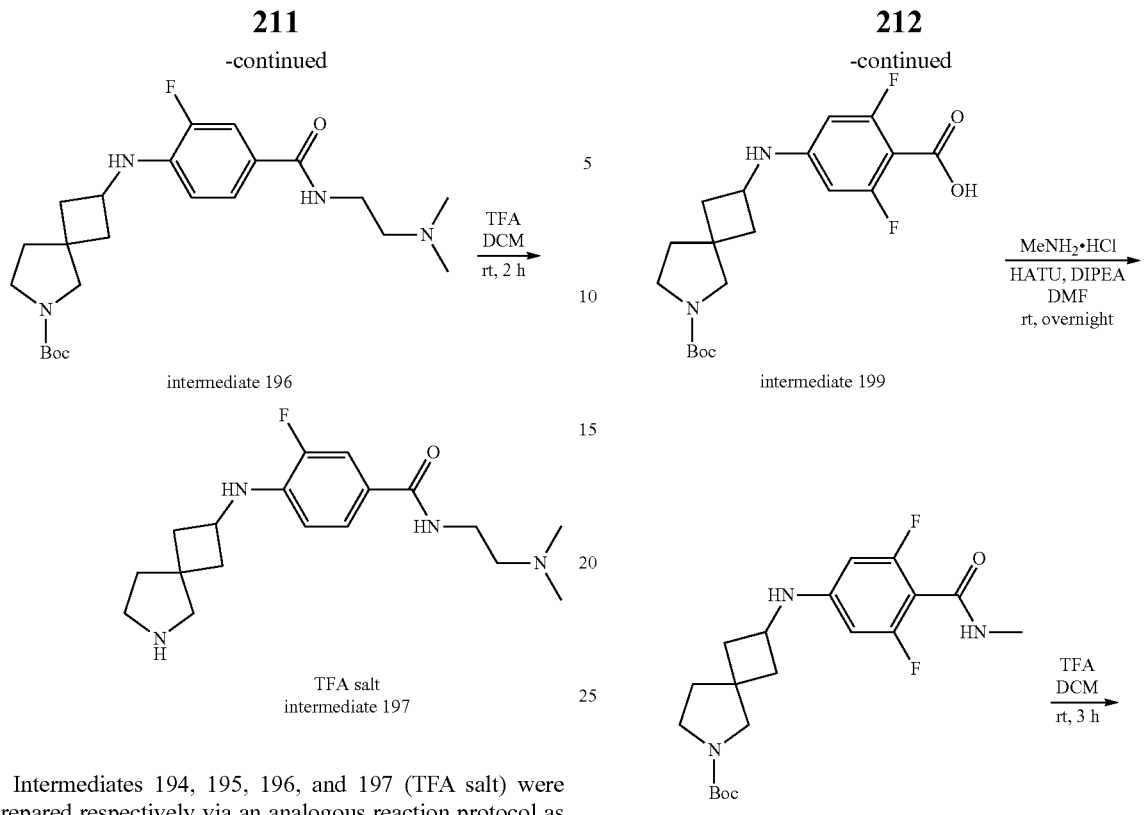

Intermediates 194, 195, 196, and 197 (TFA salt) were prepared respectively via an analogous reaction protocol as described for the preparation of intermediates 119, 179, 180 and intermediate 120 respectively, starting from the respective starting materials.

Example A68

Preparation of Intermediates 198, 199, 200 and 201

212
-continued

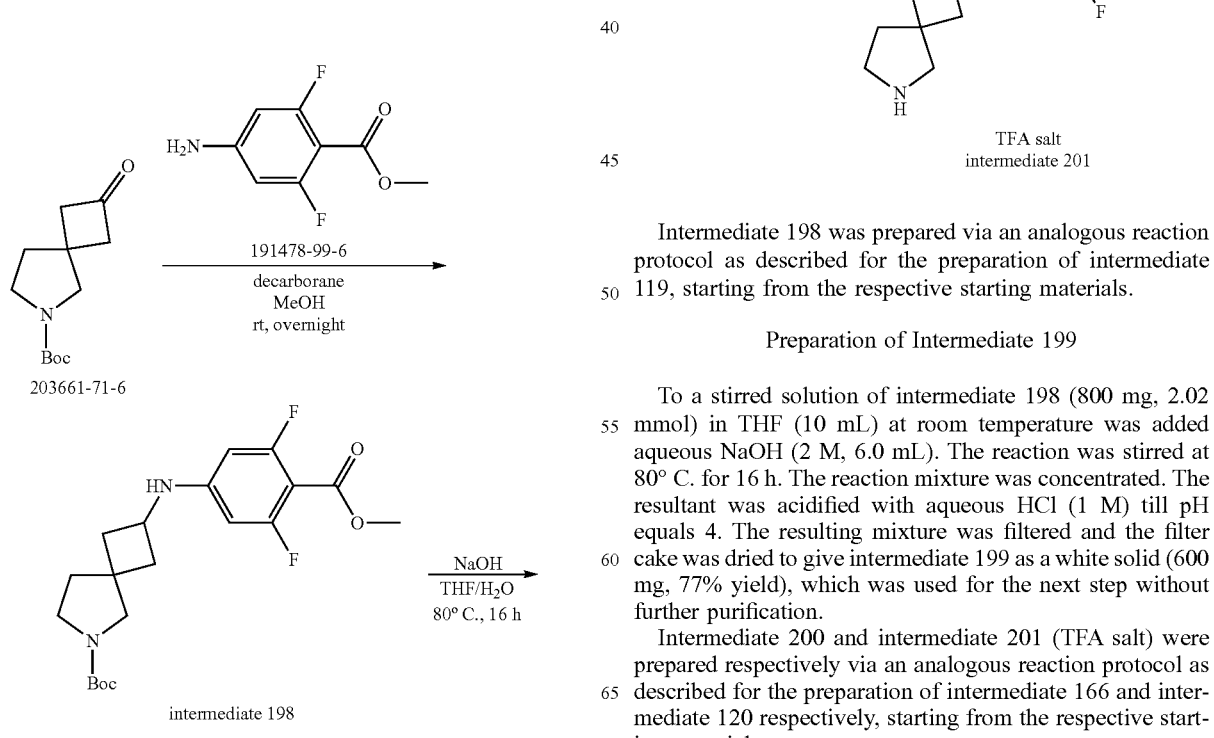

Intermediate 198 was prepared via an analogous reaction protocol as described for the preparation of intermediate 119, starting from the respective starting materials.

Preparation of Intermediate 199

To a stirred solution of intermediate 198 (800 mg, 2.02 mmol) in THF (10 mL) at room temperature was added aqueous NaOH (2 M, 6.0 mL). The reaction was stirred at 80° C. for 16 h. The reaction mixture was concentrated. The resultant was acidified with aqueous HCl (1 M) till pH equals 4. The resulting mixture was filtered and the filter cake was dried to give intermediate 199 as a white solid (600 mg, 77% yield), which was used for the next step without further purification.

Intermediate 200 and intermediate 201 (TFA salt) were prepared respectively via an analogous reaction protocol as described for the preparation of intermediate 166 and intermediate 120 respectively, starting from the respective starting materials.

Example A69

Preparation of Intermediates 202, 203, 204, 205, 206, and 207

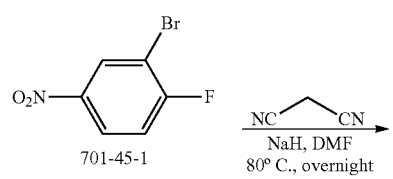

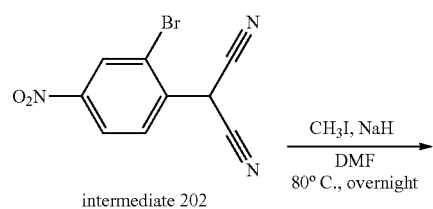

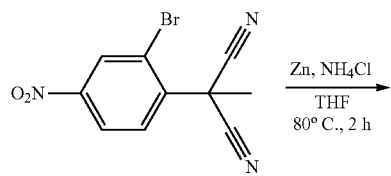

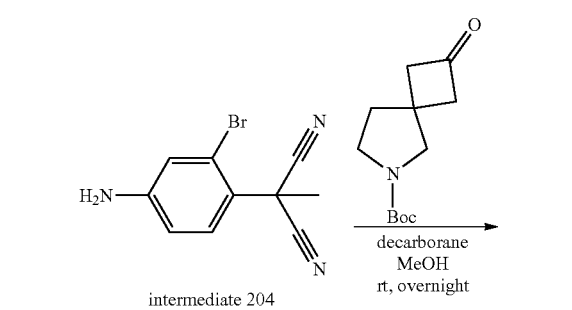

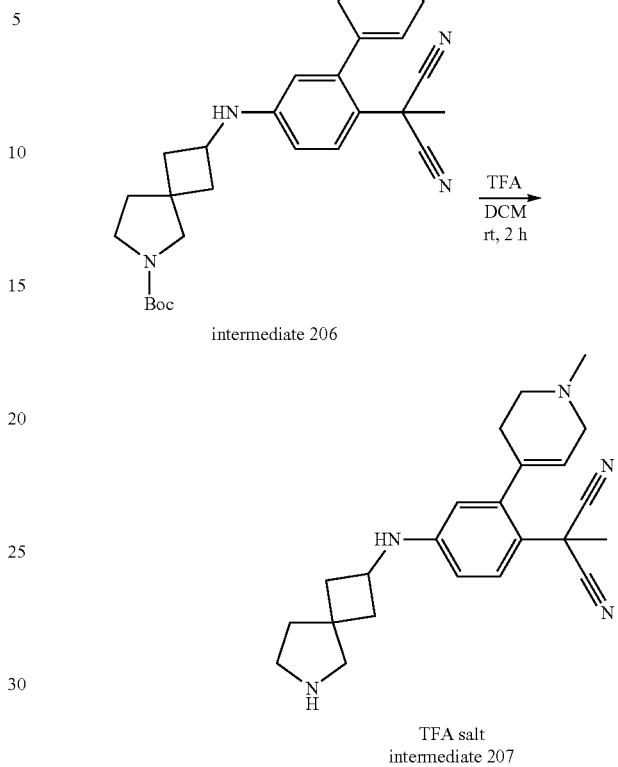

Preparation of Intermediate 202

To a stirred solution of malononitrile (3.0 g, 45.45 mmol) in DMF (40 mL) under Ar at 0° C. was added NaH (2.6 g, 68.18 mmol) portionwise. After no gas created and colour changed from pink to yellow, 2-bromo-1-fluoro-4-nitrobenzene (CAS #: 701-45-1) (5.0 g, 22.73 mmol) was added into the mixture and the mixture was stirred at 80° C. overnight. The reaction mixture was cooled down and aqueous HCl (5-6 M) was slowly added. The resulting mixture was extracted with EtOAc (500 mL×3). The combined organic extracts were washed with brine, dried over anhydrous Na$_2$SO$_4$, filtered and the filtrate was concentrated in vacuo to get crude intermediate 202 (6.2 g) as brown oil. The product was used for the next step without further purification.

Preparation of Intermediate 203

To a stirred solution of intermediate 202 (6.2 g, crude product) in DMF (4 mL) at 0° C. was added NaH (1.3 g, 34.05 mmol) potionwise. After stirring for 0.5 h, CH$_3$I (3.2 g, 22.70 mmol) was added into the mixture and the reaction was stirred at 80° C. overnight. The mixture was cooled and diluted with aq. HCl (6 M, 100 mL). The resultant was extracted with EtOAc (500 mL×3). The combined organic extracts were washed with brine, dried over anhydrous Na$_2$SO$_4$, filtered and concentrated in vacuo to get the desired product as a brown oil. The oil was purified by silica gel column chromatography (DCM:MeOH=10:1, v/v) to afford intermediate 203 (4.1 g, 64% yield over 2 steps) as yellow oil.

Intermediates 204, 205, 206, and 207 (TFA salt) were prepared respectively via an analogous reaction protocol as described for the preparation of intermediates 170, 119, 160, and 120 respectively, starting from the respective starting materials.

Example A70

Preparation of Intermediates 208, 209, 210, and 211

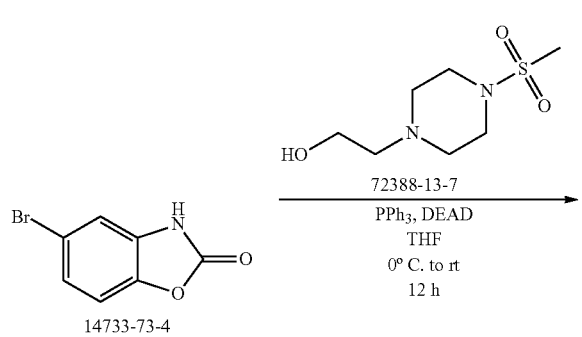

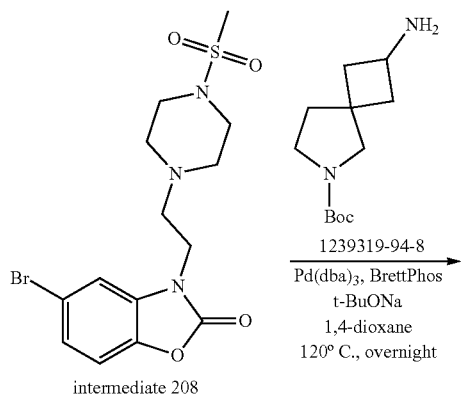

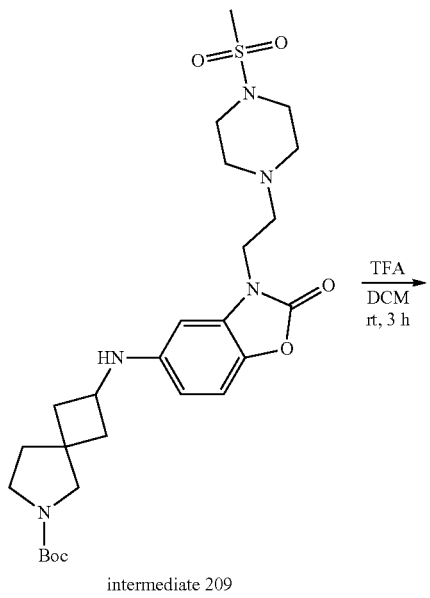

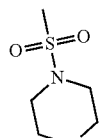

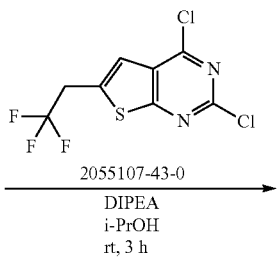

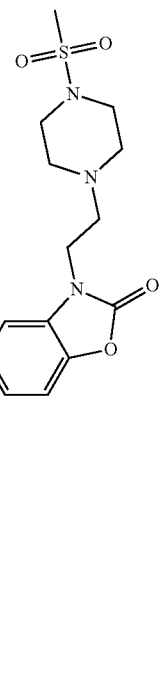

Intermediates 208, 209, 210 (TFA salt), and 211 were prepared respectively via an analogous reaction protocol as described for the preparation of following intermediates in the column 'Method used', starting from the respective starting materials.

| Intermediate number (starting materials) | Method used |
| --- | --- |
| intermediate 208 (from 5-bromobenzo[d]oxazol-2(3H)-one, CAS#: 14733-73-4 and 2-(4-(methylsulfonyl)-piperazin-1-yl)ethan-1-ol, CAS#: 72388-13-7) | intermediate 139 |
| intermediate 209 (from intermediate 208) | Compound 151 |
| intermediate 210 (from intermediate 209) | intermediate 120 |
| intermediate 211 (from intermediate 210) | intermediate 24 |

Example A71

Preparation of Intermediates 212, 213, and 214

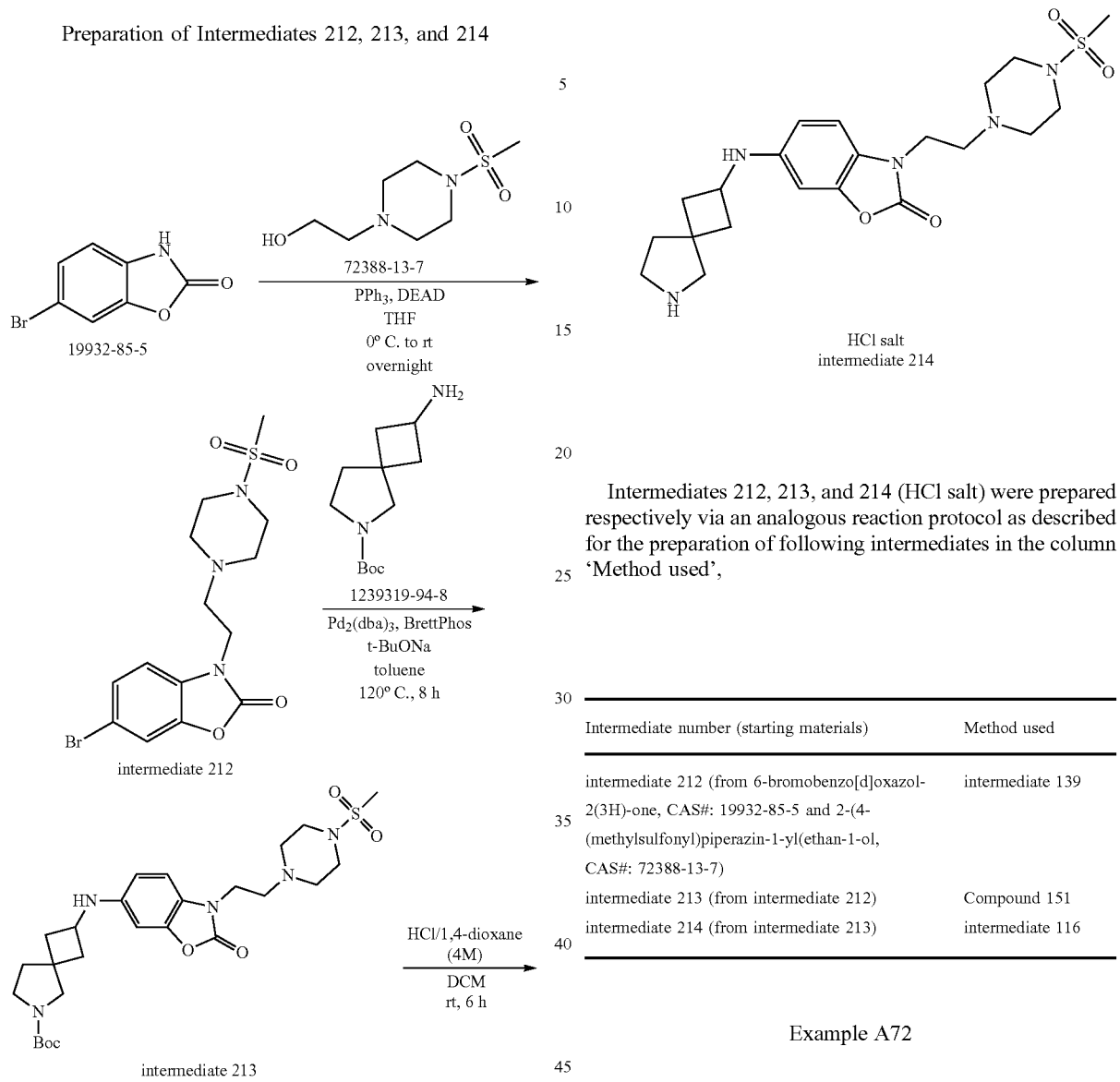

Intermediates 212, 213, and 214 (HCl salt) were prepared respectively via an analogous reaction protocol as described for the preparation of following intermediates in the column 'Method used',

| Intermediate number (starting materials) | Method used |
|---|---|
| intermediate 212 (from 6-bromobenzo[d]oxazol-2(3H)-one, CAS#: 19932-85-5 and 2-(4-(methylsulfonyl)piperazin-1-yl(ethan-1-ol, CAS#: 72388-13-7) | intermediate 139 |
| intermediate 213 (from intermediate 212) | Compound 151 |
| intermediate 214 (from intermediate 213) | intermediate 116 |

Example A72

Preparation of Intermediate 215

-continued
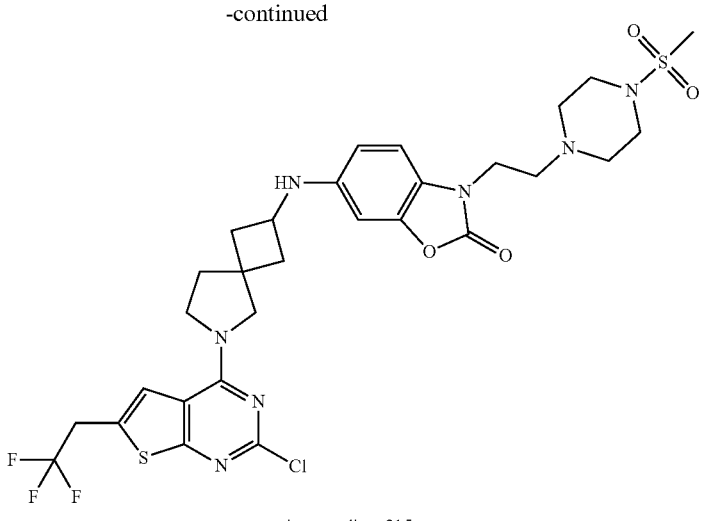
intermediate 215
Intermediate 215 was prepared via an analogous reaction protocol as described for the preparation of Compound 249, starting from the respective starting materials.
Example A73
Preparation of Intermediates 216, 217, 218, 219, and 220
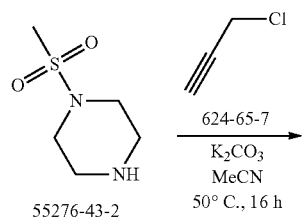
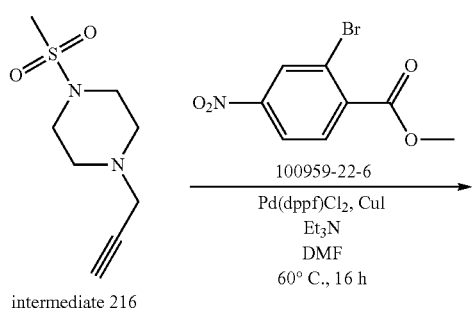
intermediate 216
-continued
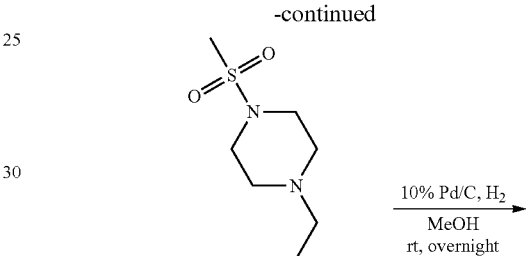
intermediate 217
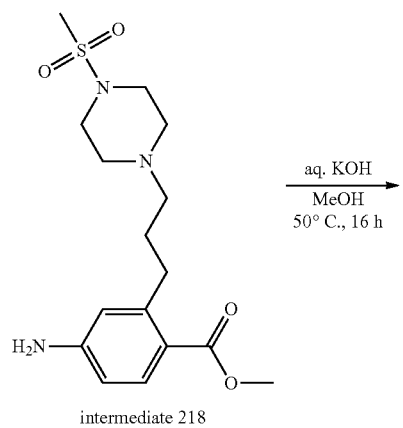
intermediate 218

221

-continued

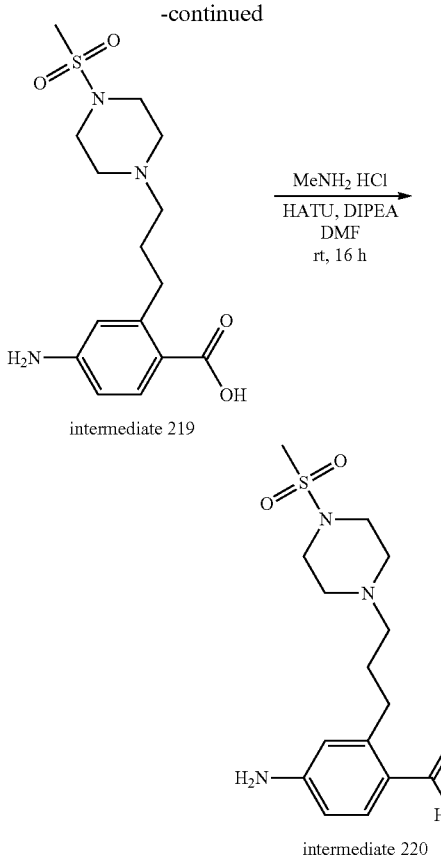

intermediate 219 intermediate 220

Preparation of Intermediate 216

To a stirred solution of 3-chloroprop-1-yne (CAS #: 624-65-7) (500 mg, 6.7 mmol) in MeCN (10 ml) at room temperature were added 1-(methylsulfonyl)piperazine (CAS #: 55276-43-2) (1.1 g, 6.7 mmol) and $K_2CO_3$ (2.8 g, 20.1 mmol). The reaction mixture was stirred at 50° C. for 16 h and cooled to room temperature. Then, the reaction mixture was diluted with water (100 mL) and extracted with EA (100 mL×3). The combined organic extracts were washed with brine (100 mL), dried over anhydrous $Na_2SO_4$, filtered and the filtrate was concentrated. The residue was purified by silica gel chromatography (DCM:MeOH=20:1 to 10:1, v/v) to give intermediate 216 (1.1 g, 81% yield) as a white solid.

Preparation of Intermediate 217

A mixture of intermediate 216 (1.6 g, 8.1 mmol), methyl 2-bromo-4-nitrobenzoate (CAS #: 100959-22-6) (2.1 g, 8.1 mmol), CuI (308 mg, 1.62 mmol), Pd(dppf)Cl$_2$ (592 mg, 0.81 mmol) and Et$_3$N (2.46 g, 24.3 mmol) in DMF (60 mL) was stirred at 60° C. for 16 h and cooled to room temperature. Then, the reaction mixture was filtered and the filtrate was concentrated. The residue was diluted with water (20 ml) and extracted with EA (50 mL×3). The combined organic extracts were washed with brine (50 mL), dried over anhydrous Na$_2$SO$_4$, filtered and the filtrate was concentrated. The residue was purified by silica gel chromatography (eluent: PE:EA from 5:1 to 1:1, v/v) to give intermediate 217 (2.6 g, 84% yield) as a white solid.

Preparation of Intermediate 218

To a solution of intermediate 217 (200 mg, 0.52 mmol) in MeOH (5 mL) at room temperature was added 10% Pd/C

222

(50 mg). The reaction mixture was stirred under H$_2$ atmosphere at room temperature overnight. The reaction mixture was filtered and the filtrate was concentrated to give crude intermediate 218 (200 mg) as a white solid, which was used directly for the next step without further purification.

Preparation of Intermediate 219

To a stirred solution of intermediate 218 (100 mg, 0.28 mmol) in MeOH (10 mL) at room temperature was added aq. KOH (5 M) (10 mL). The reaction mixture was stirred at 50° C. for 16 h. The cooled reaction mixture was directly purified by reversed phase chromatography (C18, 100% H$_2$O v/v) to give intermediate 219 (100 mg, impure) as a colorless oil

Preparation of Intermediate 220

A mixture of intermediate 219 (100 mg, ca. 0.3 mmol), methylamine hydrochloride (102 mg, 1.5 mmol), HATU (171 mg, 0.45 mmol) and DIPEA (232 mg, 1.8 mmol) in DMF (5 mL) was stirred at room temperature for 16 h. The reaction mixture was diluted with water (50 mL) and extracted with EA (10 mL×3). The combined organic extracts were washed with brine (50 mL), dried over anhydrous Na$_2$SO$_4$, filtered and concentrated. The residue was purified by prep-TLC (DCM:MeOH=10:1) to give intermediate 220 (30 mg) as a white solid.

Example A75

Preparation of Intermediates 226, 227, 228, and 229

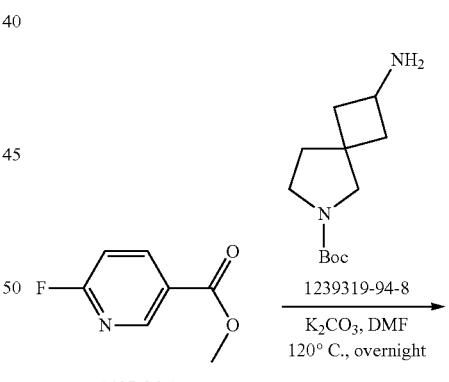

1427-06-1

1239319-94-8

K$_2$CO$_3$, DMF
120° C., overnight

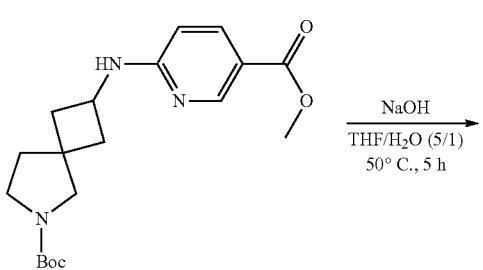

intermediate 226

NaOH
THF/H$_2$O (5/1)
50° C., 5 h

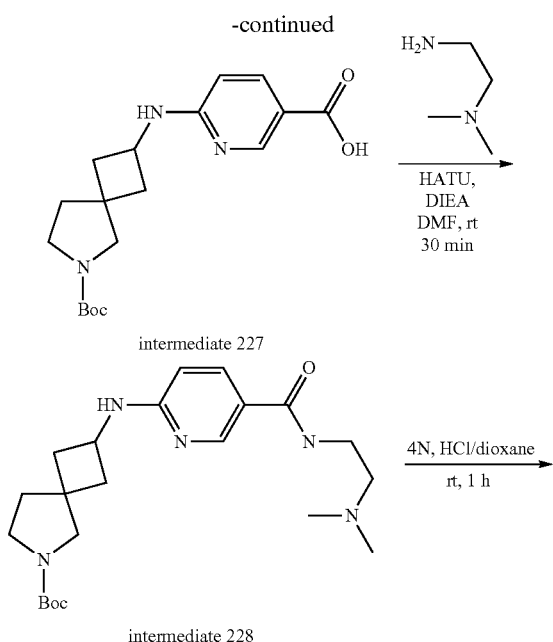

Preparation of Intermediate 226

A mixture of methyl 6-fluoronicotinate (CAS #: 1427-06-1) (106 mg, 0.69 mmol), tert-butyl 2-amino-6-azaspiro[3.4]octane-6-carboxylate (CAS #: 1239319-94-8) (155 mg, 0.69 mmol) and K$_2$CO$_3$ (283 mg, 2.06 mmol) in DMF (2 mL) was stirred at 120° C. overnight. The mixture was poured into water and extracted with EtOAc (15 mL×3). The combined organic layers were washed with brine, dried over Na$_2$SO$_4$, filtered and concentrated to give the intermediate 226 (453 mg, 84% yield) as a light-yellow solid.

Preparation of Intermediate 227

A mixture of intermediate 226 (200 mg, 0.55 mmol), NaOH (90 mg, 1.66 mmol) and THF/H$_2$O (5:1, 6 mL) was stirred at 50° C. for 5 hours. The mixture was diluted with water (5 mL) and adjusted to pH=4~5 with 1N HCl aqueous, extracted with EtOAc (15 mL×3). The combined organic layers were washed with brine, dried over Na$_2$SO$_4$, filtered and concentrated to give intermediate 227 (188 mg, 98% yield) as a white solid.

Preparation of Intermediate 228

To a solution of intermediate 227 (190 mg, 0.55 mmol) in DMF (2.5 mL) was added HATU (481 mg, 1.1 mmol) and DIPEA (245 mg, 1.64 mmol) under Ar. After being stirred at room temperature for 20 min, N$^1$,N$^1$-dimethylethane-1,2-diamine (56 mg, 0.55 mmol) was added. The resulting mixture was stirred at room temperature for another 30 min. The mixture was poured into water and extracted with EtOAc (15 mL×3). The combined organic layers were washed with brine, dried over Na$_2$SO$_4$, filtered and concentrated to give intermediate 228 (200 mg, 88% yield) as a brown solid.

Preparation of Intermediate 229

A mixture of intermediate 228 (200 mg, 0.48 mmol) in 4 M HCl/dioxane (2 mL) was stirred at room temperature for 1 hour. The solvent was removed via vacuum to give the title compound intermediate 229 as a HCl salt (160 mg, 95% yield), which was used to the next step without further purification.

Example A77

Preparation of Intermediates 236, 237, 238, and 239

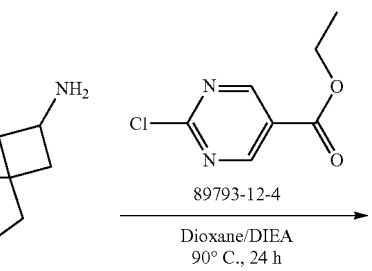

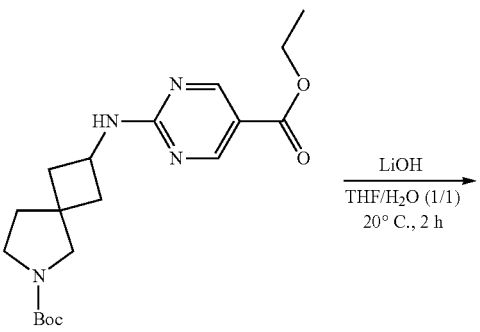

intermediate 236

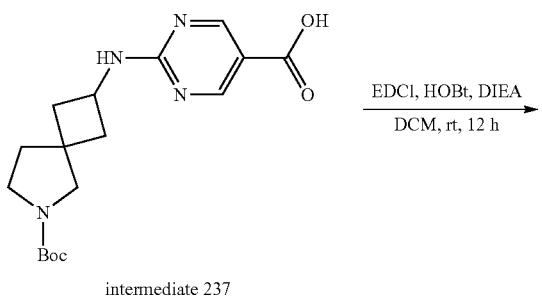

intermediate 237

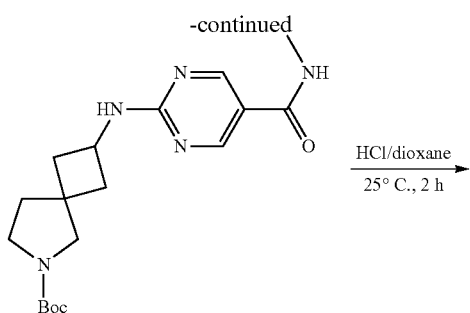

intermediate 238

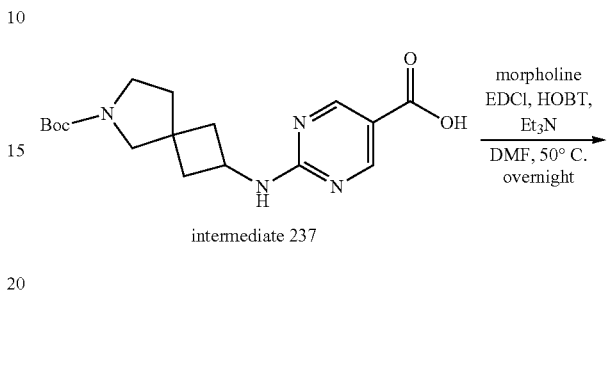

intermediate 237

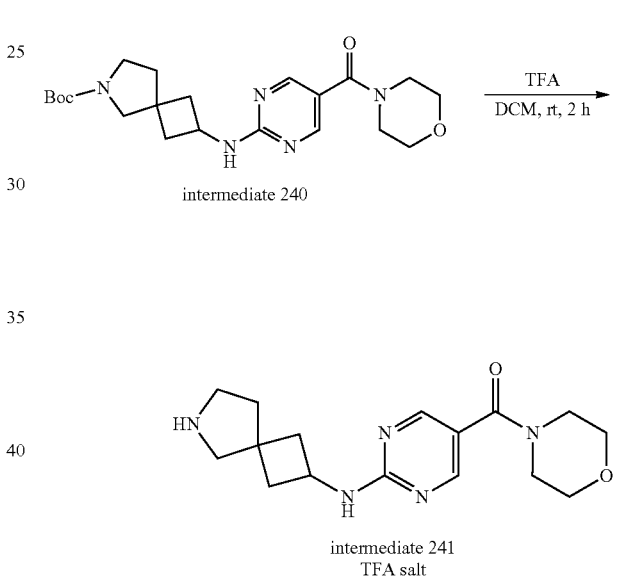

intermediate 239 (400 mg, crude HCl salt) as a yellow solid, which was used to the next step without further purification.

Example A78

Preparation of Intermediates 240 and 241

Preparation of Intermediate 236

To a solution of tert-butyl 2-amino-6-azaspiro[3.4]octane-6-carboxylate (CAS #: 1239319-94-8) (1.86 g, 10 mmol) in dioxane (15 mL) was added 2-chloropyrimidine-5-carboxylate (CAS #: 89793-12-4) (2.26 g, 10 mmol) and DIEA (2.52 g, 20 mmol) at room temperature. After stirring at 90° C. for 24 h, the reaction mixture was concentrated, washed $H_2O$ (30 mL), extracted with EA (3×10 mL). The combined organic layer was concentrated to give a residue which was purified by chromatograph on silica gel (PE:EA=4:1) to afford intermediate 236 (1.2 g, 46.10%) as a white solid.

Preparation of Intermediate 237

To a solution of intermediate 236, tert-butyl 2-((5-(ethoxycarbonyl)pyrimidin-2-yl)-amino)-6-azaspiro[3.4]octane-6-carboxylate (1.2 g, 3.19 mmol) in THF (10 mL) and $H_2O$ (10 mL) was added $LiOH \cdot 1H_2O$ (2.30 g, 9.57 mmol). After stirring at 20° C. for 2 h, the mixture was concentrated. The resultant was acidified by aq. HCl (1 M) till pH equals 4. The precipitate was collected and dried to afford intermediate 237 (1.0 g, 90% yield) as a white solid.

Preparation of Intermediate 238

To a solution of intermediate 237, 2-((6-(tert-butoxycarbonyl)-6-azaspiro[3.4]octan-2-yl)amino)pyrimidine-5-carboxylic acid (720 mg, 3 mmol) in DCM (3 mL) was added EDCI (859 mg, 4.5 mmol), HOBt (612 mg, 4.5 mmol) and DIEA (1.16 g, 9 mmol). After stirring at room temperature for 12 h, the mixture was concentrated, the residue was diluted with EA (20 mL), washed with $H_2O$ (10 ml) and brine (10 mL), dried over anhydrous $Na_2SO_4$, filtered and concentrated to give intermediate 238 (500 mg, 69% yield).

Preparation of Intermediate 239

To a solution of intermediate 238 (500 mg, 1.21 mmol) in HCl/1.4-dioxane (4 M, 10 mL) was stirred at 25° C. for 2 h.

Preparation of Intermediate 240

A mixture of intermediate 237 (348 mg, 1.0 mmol), morpholine (344 mg, 4.0 mmol), HOBT (203 mg, 1.5 mmol), EDCI (288 mg. 1.5 mmol) and $Et_3N$ (202 mg, 2.0 mmol) in DMF (20 mL) was stirred at 50° C. overnight. The cooled reaction mixture was diluted with $H_2O$ (60 mL) and extracted with EtOAc (30 mL×3). The combined organic extracts were washed with brine (50 mL), dried over anhydrous $Na_2SO_4$, filtered and concentrated to afford intermediate 240 (410 mg, 98% yield) as a yellow oil.

A mixture of intermediate 240, tert-butyl 2-((5-(morpholine-4-carbonyl)pyrimidin-2-yl)amino)-6-azaspiro[3.4]octane-6-carboxylate (410 mg, 0.98 mmol) and TFA (2 mL) in DCM (2 mL) was stirred at room temperature for 2 hours. After the reaction was completed, the mixture was concentrated to afford intermediate 241 (430 mg, TFA salt) as an orange oil, which was used to the next step without further purification.

Example A80

Preparation of Intermediates 243 and 244

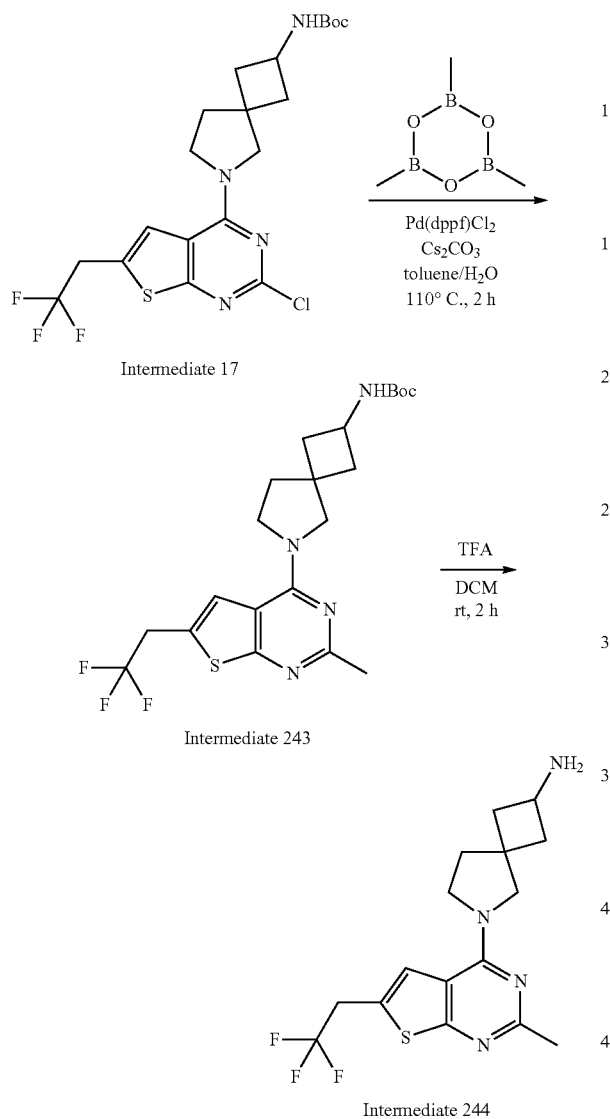

Preparation of Intermediate 243

A mixture of intermediate 17 (600 mg, 1.26 mmol), 2,4,6-trimethyl-1,3,5,2,4,6-trioxatriborinane (790 mg, 6.30 mmol), Pd(dppf)Cl$_2$ (88 mg, 0.12 mmol) and Cs$_2$CO$_3$ (822 mg, 2.52 mmol) in toluene (20 mL) and H$_2$O (4 mL) was stirred under Ar at 110° C. for 2 h. The cooled reaction mixture was diluted with H$_2$O (20 mL) and extracted with EtOAc (20 mL×3). The combined organic extracts were washed with brine (40 mL), dried over anhydrous Na$_2$SO$_4$, filtered and concentrated. The residue was purified by silica gel chromatography (Petroleum ether/EtOAc=3/1, v/v) to give intermediate 243 (400 mg, 70% yield) as a white solid.

Preparation of Intermediate 244

TFA (2 mL) was added to a mixture of intermediate 243 (400 mg, 0.88 mmol) in DCM (2 mL) was added. The reaction was stirred at room temperature for 2 h. The reaction mixture was concentrated. The residue was treated with amberlyst A-21 ion exchange resin in MeOH (5 mL) for 10 minutes, filtered and concentrated to give intermediate 244 (300 mg, 96% yield) as a white solid.

Example A81

Preparation of Intermediates 245, 246, 247, and 248

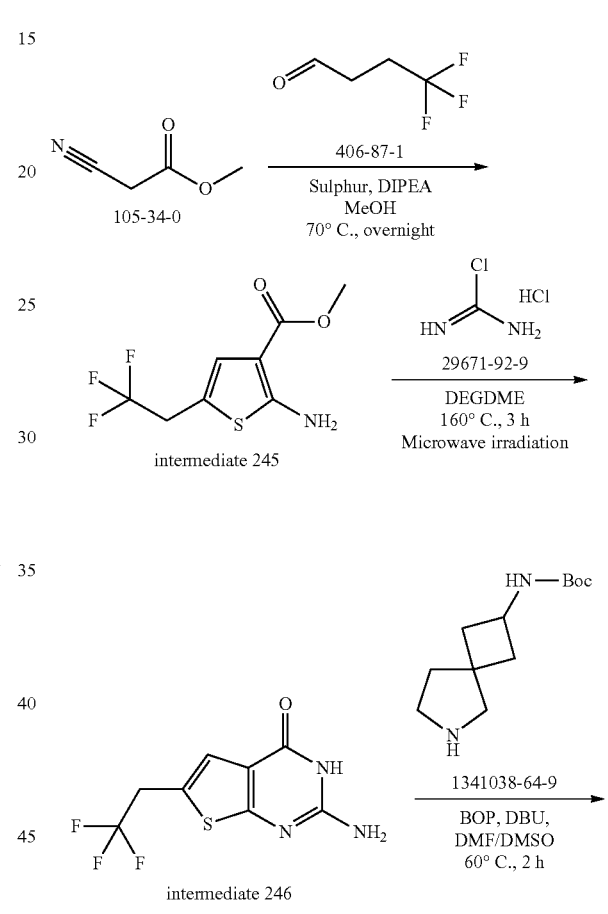

229
-continued

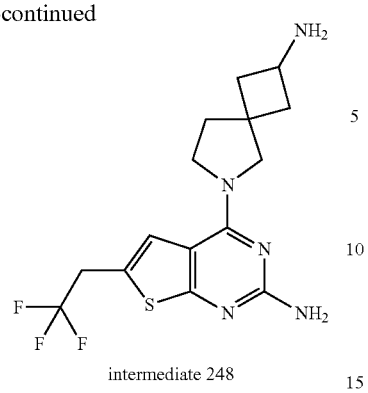

intermediate 248

Preparation of Intermediate 245

To a stirred solution of methyl 2-cyanoacetate (CAS #: 105-34-0) (22.0 g, 220 mmol) and 4,4,4-trifluorobutanal (CAS #: 406-87-1) (25.0 g, 200 mmol) in MeOH (16 mL) was added DIPEA (42.0 g, 340 mmol) and Sulphur (7.1 g, 220 mmol). The reaction was stirred at 70° C. overnight. The cooled reaction mixture was concentrated under reduced pressure. The residue was purified by silica gel chromatography (eluent: PE:EA=10:1, v/v) to afford intermediate 245 (31.0 g, 64% yield) as a light yellow solid.

Preparation of Intermediate 246

A suspension of intermediate 245 (200 mg, 0.84 mmol) and carbamimidic chloride (CAS #: 29671-92-9) (106 mg, 0.92 mmol) in di-ethylene Glycol Dimethyl Ether (DGEDME) (2 mL) was stirred at 160° C. for 3 h with microwave irradiation. Subsequently, the cooled reaction mixture was diluted with water and filtered to give intermediate 246 (110 mg) as a white solid.

Preparation of Intermediate 247

A solution of intermediate 246 (110 mg, 0.441 mmol), tert-butyl 6-azaspiro[3.4]octan-2-ylcarbamate (CAS #: 1341038-64-9) (200 mg, 0.882 mmol), BOP (293 mg, 0.661 mmol) and DBU (201 mg, 1.32 mmol) in DMF/DMSO (2 mL/2 mL) was stirred at 60° C. for 2 h. Subsequently, the cooled reaction mixture was diluted with water and extracted with EtOAc. The combined organic extracts were washed with brine, dried over anhydrous Na$_2$SO$_4$, filtered and the filtrate was concentrated. The residue was purified by silica gel chromatography eluted with DCM/MeOH (from 100:1 to 50:1) to give intermediate 247 (200 mg, 68% yield) as a yellow solid.

Preparation of Intermediate 248

A solution of intermediate 247 (200 mg, 0.437 mmol) in HCl/MeOH (3 M) (4 mL) was stirred at room temperature for 2 h. The reaction mixture was concentrated. The residue was treated with amberlyst A-21 ion exchange resin to give intermediate 248 as a yellow solid (160 mg), which was used for the next step without further purification.

230

Example A82

Preparation of Intermediates 249, 250, and 251

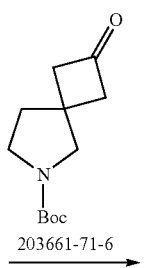

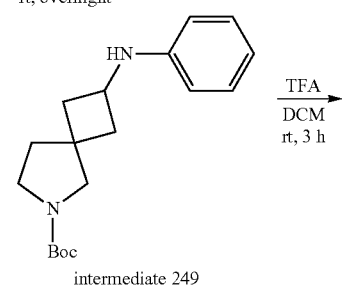

intermediate 249

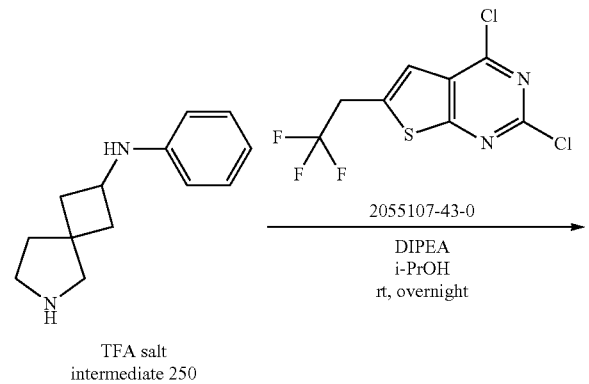

TFA salt
intermediate 250

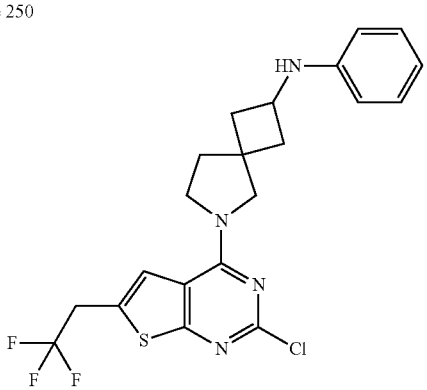

intermediate 251

Preparation of Intermediate 249

A mixture of aniline (100 mg, 1.07 mmol) and tert-butyl 2-oxo-6-azaspiro[3.4]octane-6-carboxylate (CAS #: 203661-71-6) (242 mg, 1.07 mmol) was dissolved in DCE (4 mL) and Ti(i-PrO)$_4$ (305 mg, 1.07 mmol) was added. The mixture was stirred at room temperature for 2 h. NaBH(OAc)₃ (684 mg, 3.21 mmol) was added. The resulting mixture was stirred at room temperature overnight. The mixture was diluted with water and extracted with EA (20 mL×3). The combined organic extracts were concentrated under reduced pressure to give crude intermediate 249, which was used for the next step without further purification.

Preparation of Intermediate 250

Intermediate 250 (TFA salt) and intermediate 251 were prepared respectively via an analogous reaction protocol as described for the preparation of intermediate 120 and intermediate 24 respectively, starting from the respective starting materials.

Example A83

Preparation of Intermediates 252, 253, and 254

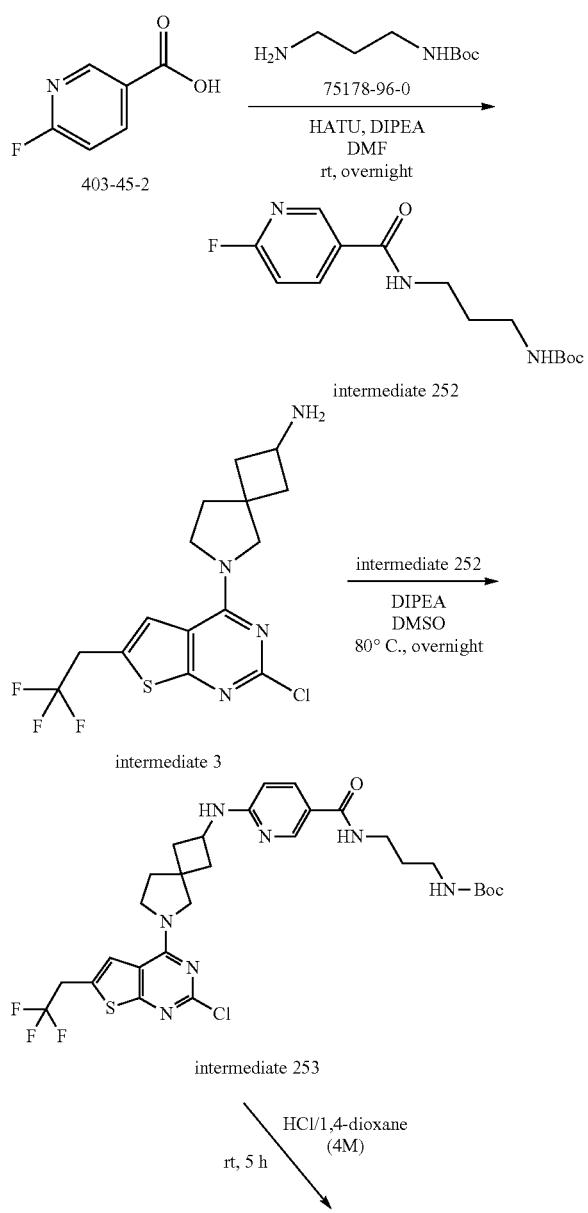

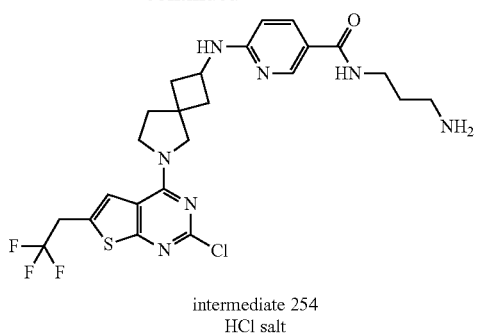

intermediate 254
HCl salt

Preparation of Intermediate 252

A mixture of 6-fluoronicotinic acid (CAS #: 403-45-2) (200 mg, 1.41 mmol), DIPEA (364 mg, 2.82 mmol), tert-butyl (3-aminopropyl)carbamate (CAS #: 75178-96-0) (246 mg, 1.41 mmol) and HATU (643 mg, 1.68 mmol) in DMF (2 mL) was stirred at room temperature overnight. The mixture was poured into water and extracted with ethyl acetate (5 mL×3). The combined organic extracts were washed with brine, dried over anhydrous Na₂SO₄, filtered and concentrated to give intermediate 252 (250 mg, 60% yield) as a white solid, which was used to the next step without further purification.

Preparation of Intermediate 253

A mixture of intermediate 3 (482 mg, 1.41 mmol; TFA salt), DIPEA (546 mg, 4.23 mmol) and intermediate 252 (419 mg, 1.41 mmol) in DMSO (10 mL) was stirred at 80° C. overnight. The cooled reaction mixture was poured into water and the suspension was filtered. The filter cake was washed with water, dried under vacuo to give intermediate 253 (448 mg, 51% yield) as a white solid.

Intermediate 254 (HCl salt) was prepared by an analogous reaction protocol as described for the preparation of intermediate 116, starting from the respective starting materials.

Example A84

Preparation of Intermediate 255

Intermediate 255 was prepared by the method indicated in the scheme below:

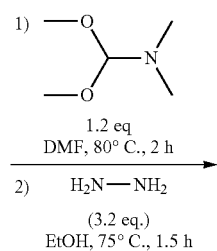

233
-continued

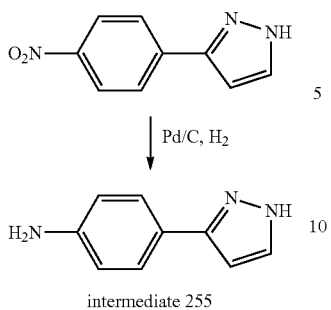

intermediate 255

Example A85

Intermediate 256 was prepared by the method indicated in the scheme below:

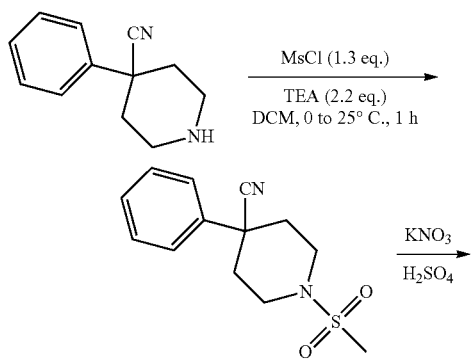

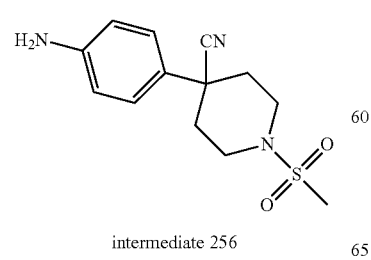

intermediate 256

234

Example A85

Preparation of Intermediate 258

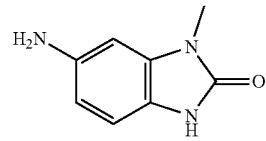

intermediate 258

Intermediate 258 corresponds with CAS #: 73778-92-4.

Example A86

Preparation of Intermediates 259 and 260

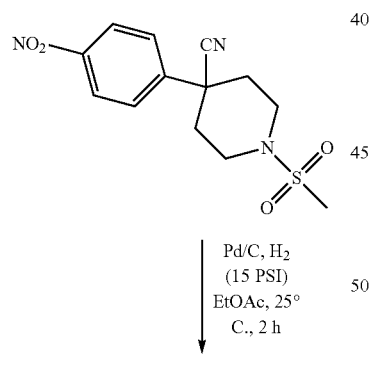

Intermediate 259 corresponds with CAS #: 114474-26-9. Hydrogenation of the nitro group according to well-known methods afforded intermediate 260.

Example A87

Preparation of Intermediate 261

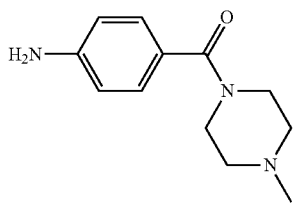

intermediate 261

Intermediate 261 was prepared by analogy to the procedure described in *European Journal of Medicinal Chemistry*, 2011, 46(7), 2917-2929.

Example A88

Preparation of Intermediate 262

Intermediate 262 was prepared by the method indicated in the scheme below:

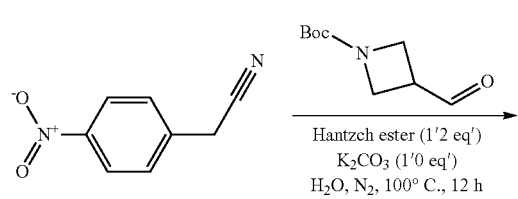

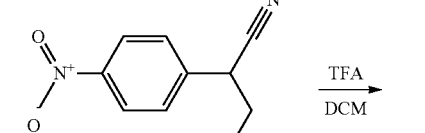

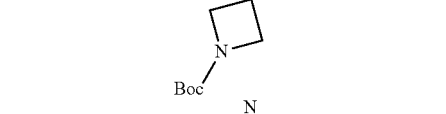

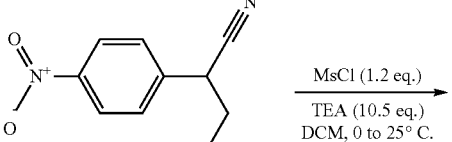

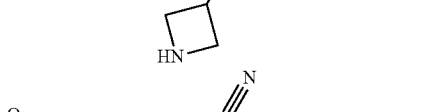

intermediate 262

Example A89

Preparation of Intermediate 263 intermediate 263

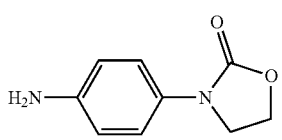

Intermediate 263 was prepared by analogy to the procedure described in *European Journal of Medicinal Chemistry,* 2016, 117, 197-211.

Example A90

Preparation of Intermediate 264 intermediate 264

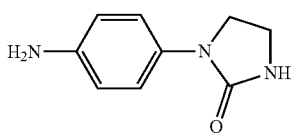

Intermediate 264 was prepared by analogy to the procedure described in *Tetrahedron Letters,* 2010, 51(24), 3232-3235.

Example A91

Preparation of Intermediate 265 intermediate 265

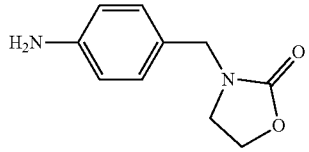

Intermediate 265 corresponds with CAS #: 99068-33-4

Example A92

Preparation of Intermediate 266

Intermediate 266 was prepared by the method indicated in the scheme below using well known synthetic procedures

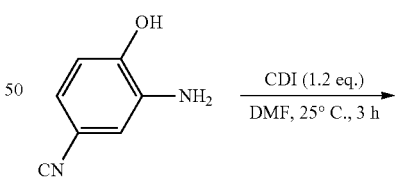

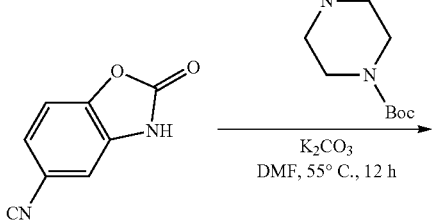

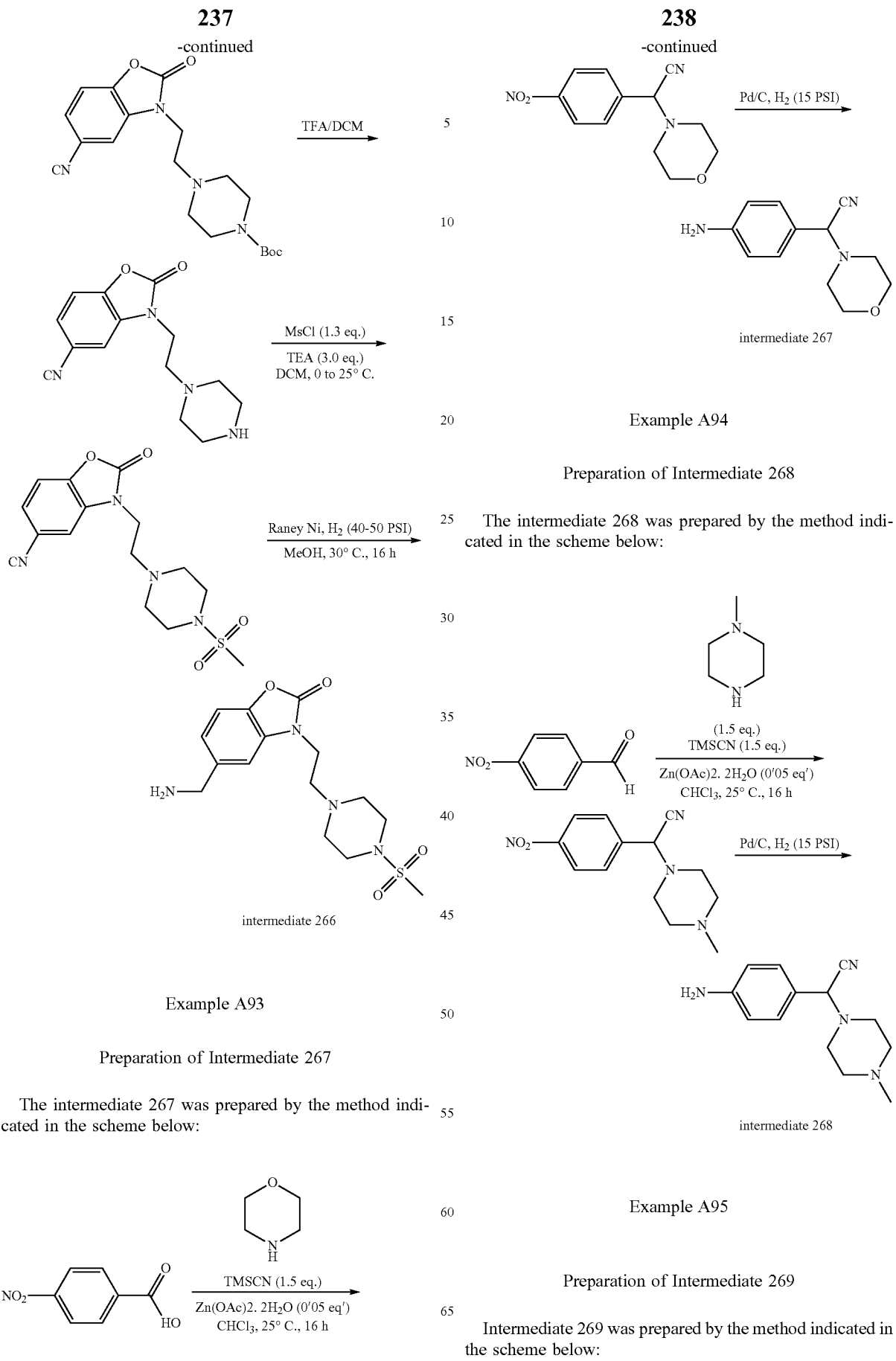
Example A93
Preparation of Intermediate 267
The intermediate 267 was prepared by the method indicated in the scheme below:
Example A94
Preparation of Intermediate 268
The intermediate 268 was prepared by the method indicated in the scheme below:
Example A95
Preparation of Intermediate 269
Intermediate 269 was prepared by the method indicated in the scheme below:

239

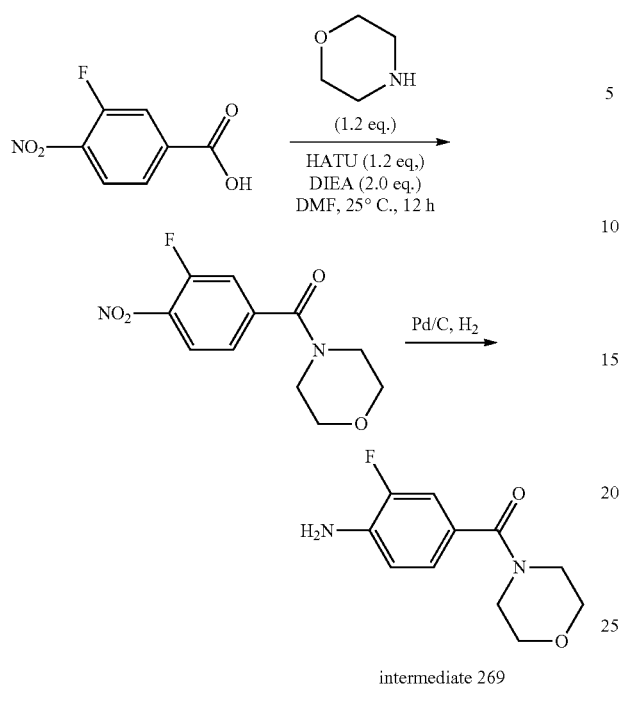

Example A96

Preparation of Intermediate 270

Intermediate 270 was prepared by the method indicated in the scheme below:

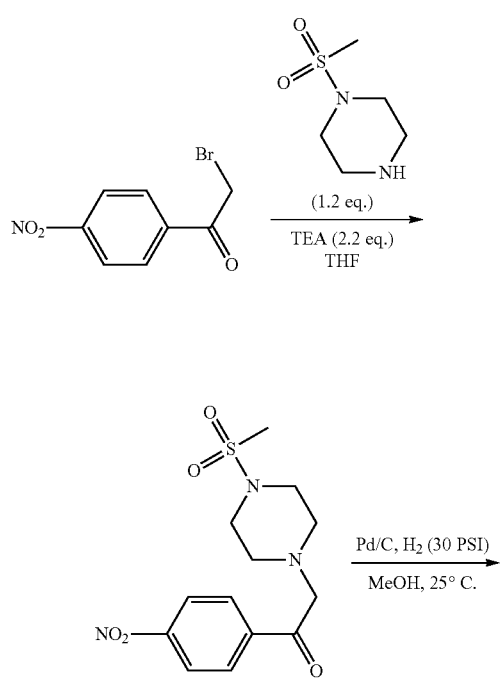

240

-continued

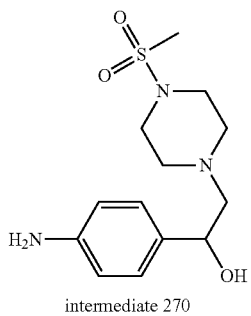

intermediate 270

Example A97

Preparation of Intermediate 271

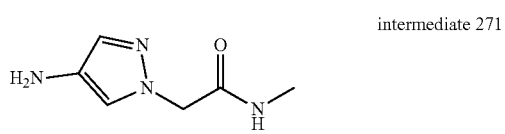

Intermediate 271 was prepared by analogy to the procedure described in WO201314162.

Example A98

Preparation of Intermediates 301, 302 and 272

Intermediate 301 was prepared from 5-nitro-1,3-dihydro-2H-benzo[d]imidazol-2-one (CAS #: 984-5) and bromoacetamide (CAS #: 683-57-8) by the method indicated in the scheme below:

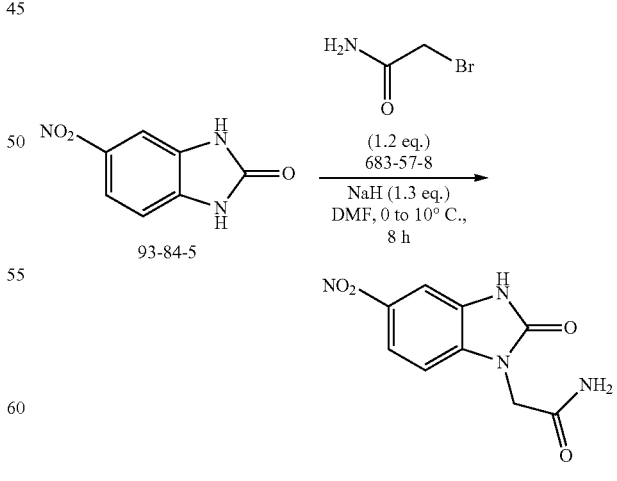

The intermediate 272 was prepared from intermediate 301 by the method indicated in the scheme below:

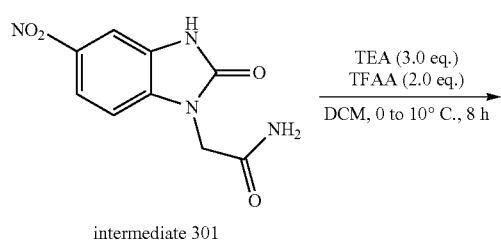

intermediate 301

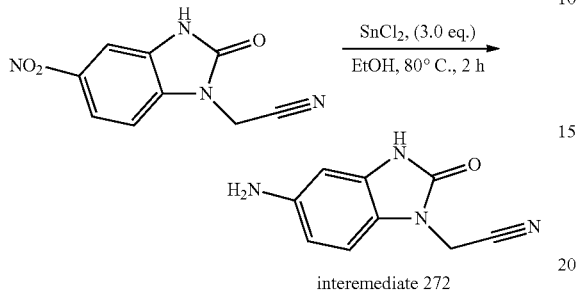

interemediate 272

The intermediate 302 was prepared from intermediate 301 by the method indicated in the scheme below:

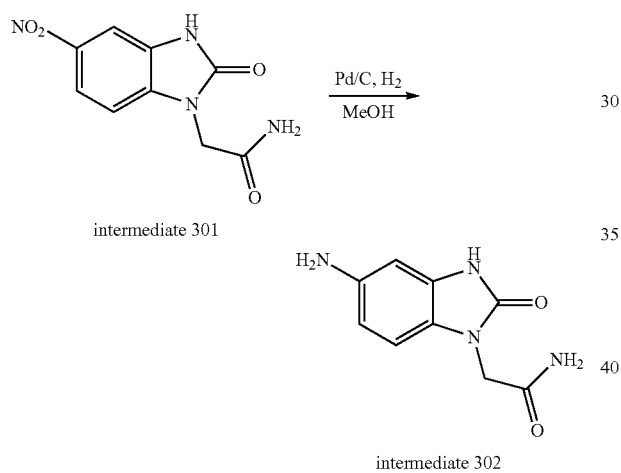

intermediate 302

Example A99

Preparation of Intermediate 273

Intermediate 273 was prepared by the method indicated in the scheme below:

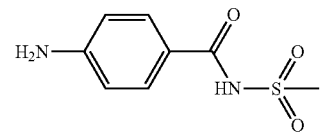

intermediate 273

Example A100

Preparation of Intermediate 274

Intermediate 274 was prepared by the method indicated in the scheme below:

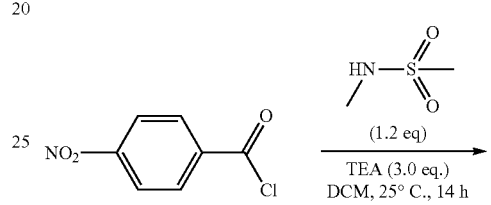

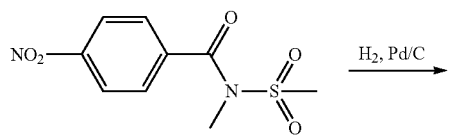

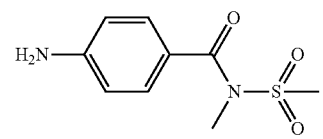

intermediate 274

Example A101

Preparation of Intermediate 275

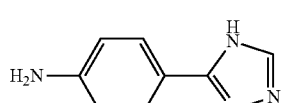

intermediate 275

Intermediate 275 was prepared by analogy to the procedure described in WO201657834.

243

Example A102

Preparation of Intermediates 276 and 277

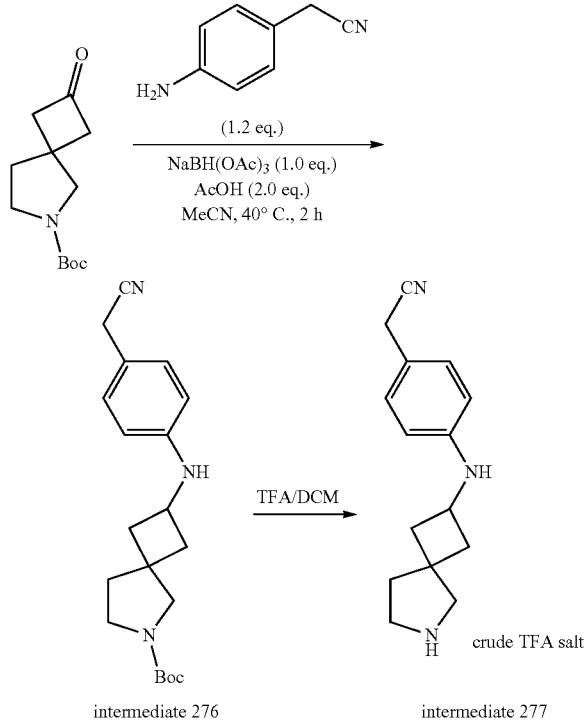

intermediate 276 intermediate 277

Preparation of Intermediate 276

Tert-butyl 2-oxo-6-azaspiro[3.4]octane-6-carboxylate (800 mg, 3.55 mmol), 2-(4-aminophenyl)acetonitrile (563 mg, 4.26 mmol), acetic acid (426 mg, 7.09 mmol) and acetonitrile (20 mL) were added to a 40 mL glass vial. The resulting mixture was stirred at 40° C. for 1 hour and then sodium triacetoxyborohydride (3.01 g, 14.2 mmol) was added. The resulting mixture was stirred at 40° C. for another 1 hour. The reaction mixture was poured into DCM (100 mL) before washed with water (50 mL×3). The organic extracts were dried over anhydrous Na₂SO₄, filtered and concentrated to dryness under reduced pressure to give a residue, which was purified by FCC (eluent: petroleum ether:ethyl acetate from 1:0 to 0:1) to give intermediate 276 (800 mg, 64.5% yield) as yellow oil.

Preparation of Intermediate 277

Tert-butyl 2-((4-(cyanomethyl)phenyl)amino)-6-azaspiro [3.4]octane-6-carboxylate intermediate 276 (400 mg, 1.17 mmol), trifluoroacetic acid (2 mL) and dry dichloromethane (5 mL) were added to a 100 mL round-bottomed flask. The resulting mixture was stirred at 25° C. for 2 hours. The mixture was concentrated under reduced pressure to give intermediate 277 (500 mg, crude TFA salt) as yellow oil.

244

Example A103-a

Preparation of Intermediate 279

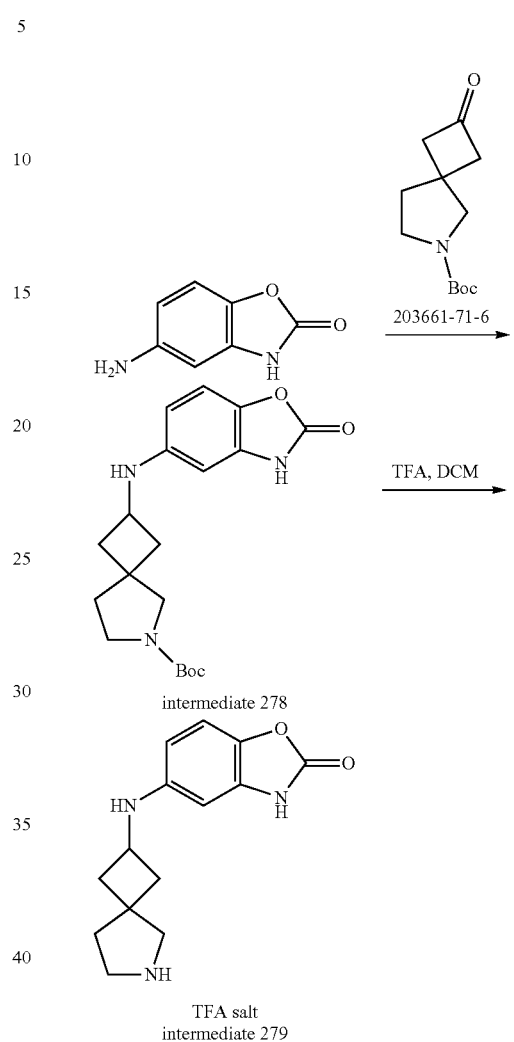

intermediate 278

TFA salt
intermediate 279

Intermediate 278 and intermediate 279 (TFA salt) were prepared respectively via an analogous reaction protocol as described for the preparation of Compound 277 and intermediate 120 respectively, starting from the respective starting materials.

Example A103-b

Preparation of Intermediates 280 and 281

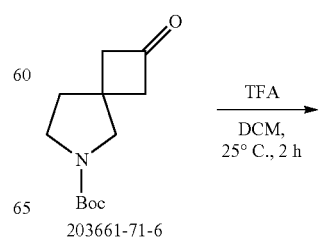

203661-71-6

245
-continued

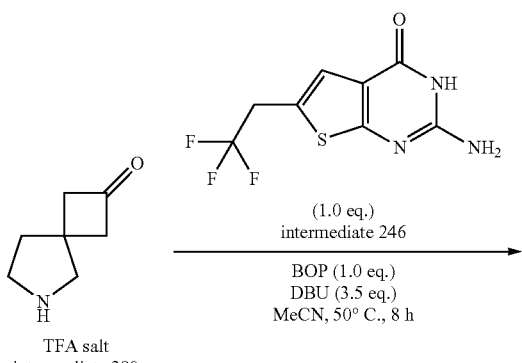

Intermediate 280 (TFA salt) and intermediate 281 were prepared respectively via an analogous reaction protocol as described for the preparation of intermediate 120 and Compound 377 respectively, starting from the respective starting materials.

Example A104-a

Preparation of Intermediates 282 and 283 ID-282

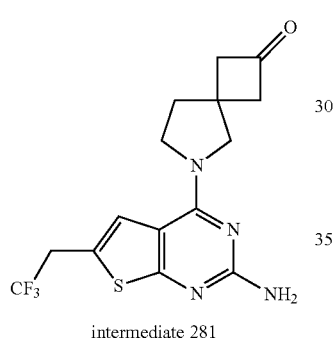

246
-continued

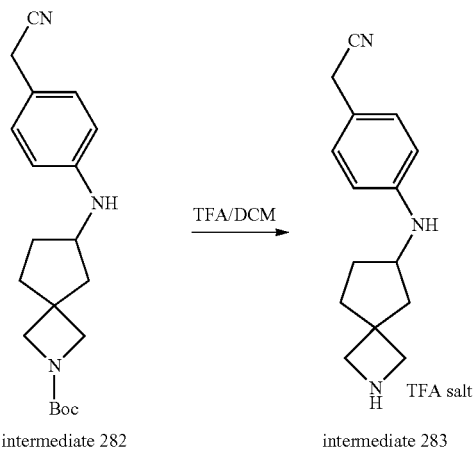

Intermediate 282 and intermediate 283 (TFA salt) were prepared respectively via an analogous reaction protocol as described for the preparation of intermediate 276 and intermediate 80 respectively, starting from the respective starting materials.

Example A104-b

Preparation of Intermediates 284 and 285

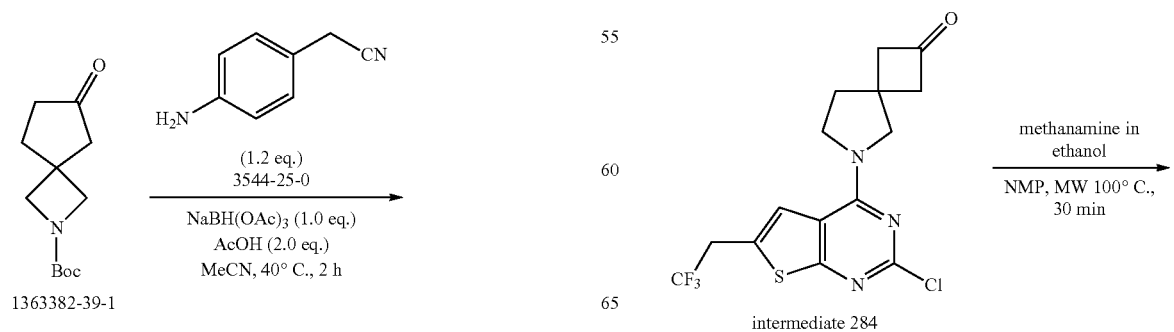

-continued

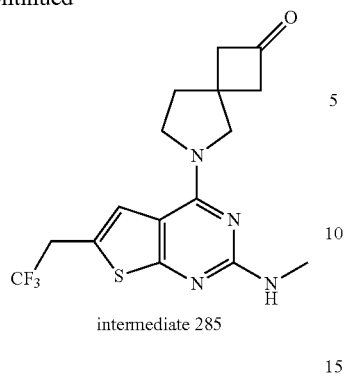

intermediate 285

Preparation of Intermediate 284

2,4-dichloro-6-(2,2,2-trifluoroethyl)thieno[2,3-d]pyrimidine (CAS #: 2055107-43-0) (850 mg, 2.96 mmol), 6-azaspiro[3.4]octan-2-one hydrochloride (479 mg, 2.96 mmol), N,N-diisopropylethylamine (1.92 g, 14.9 mmol) and dry THF (10 mL) were added to a 50 mL round-bottomed flask which was stirred at 75° C. for 5 h. The mixture was cooled to 25° C. and diluted into dichloromethane (50 mL), washed with water (20 mL×3), dried over anhydrous $Na_2SO_4$, filtered and concentrated under reduced pressure to give the crude product which was purified by FCC (ethyl acetate/petroleum ether=0% to 70%) give intermediate 284 (1.20 g, 90.0% purity by $^1H$ NMR, 97.0% yield) as a white powder.

Intermediate 284 (1.20 g, 3.19 mmol) and N-methyl 2-pyrrolidone (5 mL) were added to a microwave tube before methanamine (1.98 g, 63.8 mmol, 30-40% in ethanol) was added to the mixture. The sealed tube was heated at 100° C. for 30 min under microwave irradiation. The mixture was cooled to 25° C. and diluted into dichloromethane (40 mL), washed with water (20 mL×3), dried over anhydrous $Na_2SO_4$, filtered and concentrated under reduced pressure to give the crude which was purified by FCC (ethyl acetate/petroleum ether=0% to 70%) to give intermediate 285 (500 mg, 40.2% yield) as a light yellow powder.

Example A105

Preparation of Intermediates 286 and 287

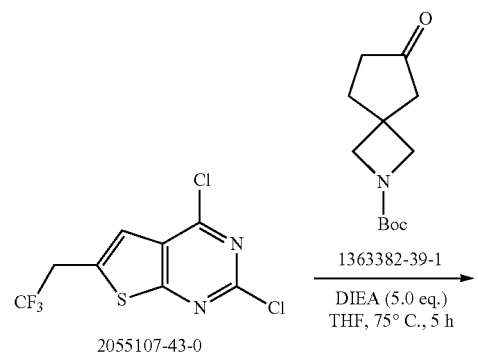

-continued

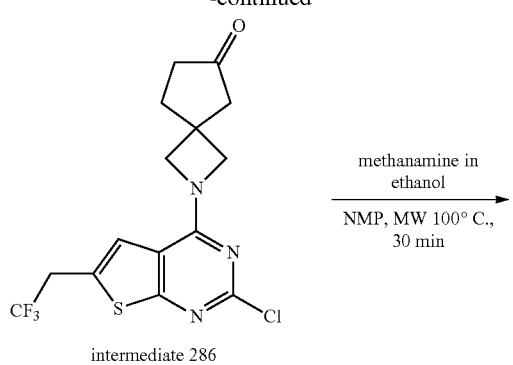

intermediate 286

Intermediate 286 and intermediate 287 were prepared respectively via an analogous reaction protocol as described for the preparation of intermediate 284 and intermediate 285 respectively, starting from the respective starting materials.

Example A106

Preparation of Intermediates 288 and 289

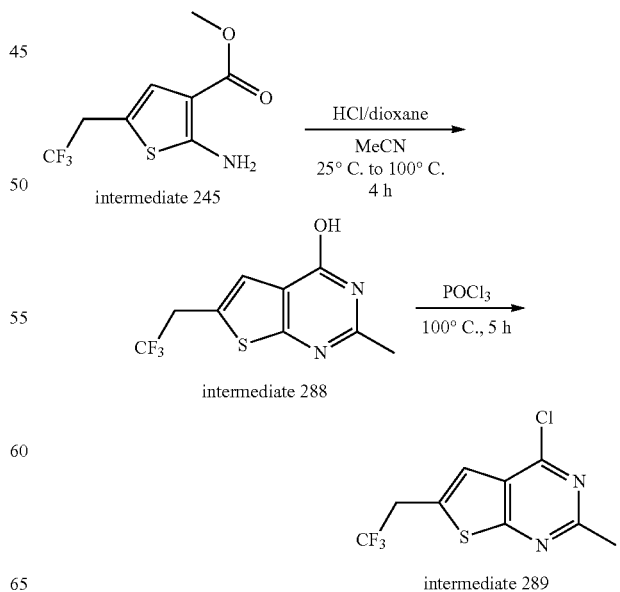

Preparation of Intermediate 288

Intermediate 245 (3 g, 12.54 mmol) was dissolved in MeCN (75 ml). HCl (1,4-dioxane) (75 mL, 300 mmol) was added at 25° C. and stirred at rt for 1.5 hours. The mixture then was stirred at 100° C. for 4 hours. The mixture was concentrated under reduced pressure to obtain the crude intermediate 288, which was used directly for the next step without further purification.

Preparation of Intermediate 289

Intermediate 288 (4.5 g, 18.129 mmol) was added to a 250 mL round-bottomed flask. Phosphoryl chloride (40 g, 260.872 mmol) was added to the flask in portions. The mixture was stirred at 100° C. for 5 h. The mixture was concentrated under reduced pressure to give a residue which was dissolved in EtOAc (200 mL). The EtOAc layer was poured into ice and the pH was adjusted to 10-11 with NaHCO$_3$ (sat. aq.). The organic layer was washed with water (100 mL×3), brine (100 mL), dried over Na$_2$SO$_4$, filtered and concentrated under reduced pressure to give a residue which was purified by FCC (EA:PE=0 to 5%) to give intermediate 289 as yellow solid.

Example A107

Preparation of Intermediates 290 and 291

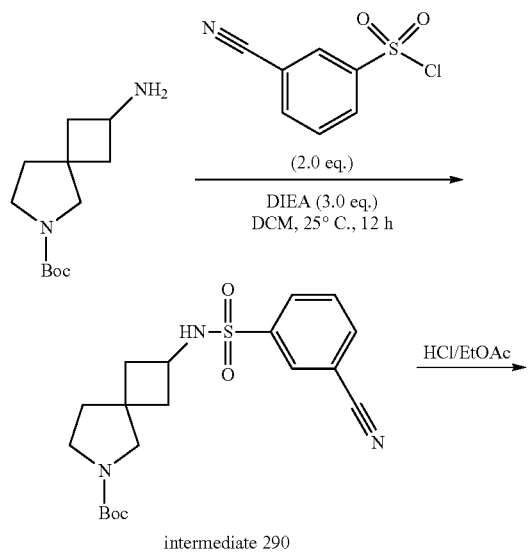

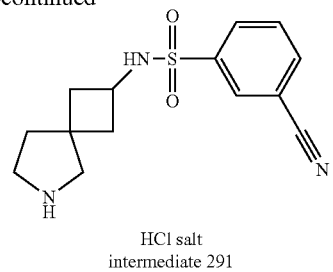

HCl salt
intermediate 291

Preparation of Intermediate 290

Tert-butyl 2-amino-6-azaspiro[3.4]octane-6-carboxylate (CAS #: 1239319-94-8) (100 mg, 0.442 mmol), 3-cyanobenzene-1-sulfonyl chloride (178 mg, 0.883 mmol), N,N-diisopropylethylamine (172 mg, 1.33 mmol) and dry dichloromethane (4 mL) were added to a 40 mL glass bottle, the resultant mixture was stirred at 25° C. for 12 h. The mixture was diluted into dichloromethane (50 mL). The organic was washed with water (20 mL×3), dried over anhydrous Na$_2$SO$_4$, filtered and concentrated under reduced pressure to give the crude which was purified by prep-TLC (petroleum ether/ethyl acetate=1/1, R$_f$=0.2) to give intermediate 290 (150 mg, 90.0% purity, 78.0% yield) as a light yellow powder.

Preparation of Intermediate 291

Intermediate 290 (150 mg, 0.383 mmol), acetonitrile (4 mL) and hydrochloric acid/ethyl acetate (10.0 mL, 40.0 mmol) were added to a 100 mL round-bottomed flask which was stirred at 25° C. for 1 h. The mixture was concentrated under reduced pressure to give intermediate 291 (120 mg, HCl salt, 90.0% purity, 86.0% yield) as a white powder.

Example A108

Preparation of Intermediate 292 and intermediate 293

Intermediates 292 (HCl salt) and 293 (HCl salt) were prepared from their respective starting materials in 2 steps by using analogous reaction protocols as described for the preparation of intermediate 291 (via intermediate 290), starting from tert-butyl 2-amino-6-azaspiro[3.4]octane-6-carboxylate (CAS #: 1239319-94-8) and the corresponding sulfonyl chlorides.

| Intermediate number (starting materials) | Method used | Intermediate structure |
|---|---|---|
| intermediate 292 (from 3-(trifluoromethyl)benzenesulfonyl chloride, CAS#: 777-44-6) | Step 1: intermediate 290 Step 2: intermediate 291 | HCl salt Intermediate 292 |

| Intermediate number (starting materials) | Method used | Intermediate structure |
|---|---|---|
| intermediate 293 (from 4-(trifluoromethyl)benzenesulfonyl chloride, CAS#: 2991-42-6) | Step 1: intermediate 290 Step 2: intermediate 291 | 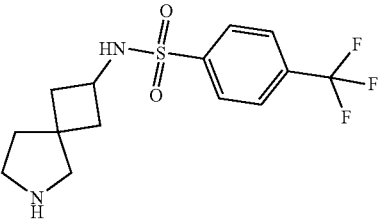 [SMILES: O=S(=O)(NC1CC2(CCNC2)C1)c1ccc(C(F)(F)F)cc1]<br>HCl salt<br>Intermediate 293 |

Example A109

Preparation of Intermediate 294

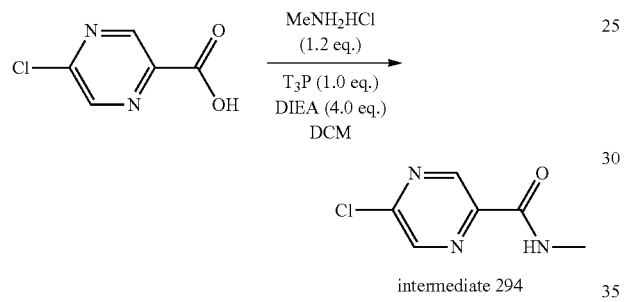

A stir bar, 5-chloropyrazine-2-carboxylic acid (800 mg, 5.05 mmol), methylamine hydrochloride (409 mg, 6.06 mmol), DIEA (2.61 g, 20.2 mmol), and $CH_2Cl_2$ (40 mL) was added to a 50 mL round-bottom flask. The mixture was cooled to 0° C. $T_3P$ (3.21 g, 5.05 mmol, 50% in EtOAc) was added to the mixture. The mixture was stirred at room temperature for 1 hour. The reaction mixture was concentrated to dryness under reduced pressure to afford the crude product, which was purified by flash column chromatography (eluent: petroleum ether:ethyl acetate=1:0 to 4:6) to give intermediate 294 as a yellow solid.

Example A110

Preparation of Intermediate 295

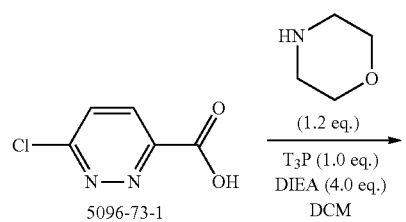

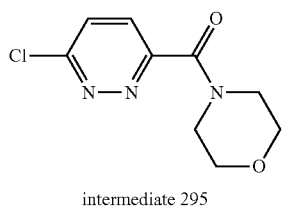

intermediate 295

Intermediate 295 was prepared via an analogous reaction protocol as described for the preparation of intermediate 294, starting from 6-chloropyridazine-3-carboxylic acid (CAS #: 5096-73-1) and morpholine.

Example A111

Preparation of Intermediate 296

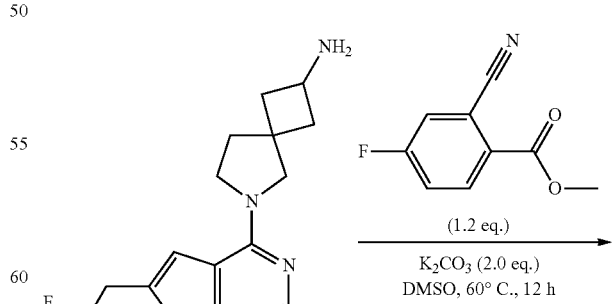

253
-continued

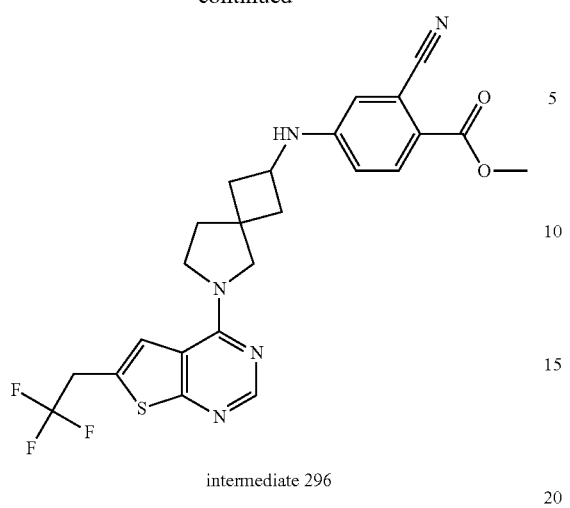

intermediate 296

A stir bar, 6-(6-(2,2,2-trifluoroethyl)thieno[2,3-d]pyrimidin-4-yl)-6-azaspiro[3.4]octan-2-amine hydrochloride (intermediate 3a) (500 mg, HCl salt, 1.32 mmol), methyl 2-cyano-4-fluorobenzoate (284 mg, 1.59 mmol), potassium carbonate (365 mg, 2.64 mmol) and dimethylsulfoxide (6 mL) were added to a 25 mL round-bottomed flask, the resultant mixture was heated and stirred at 60° C. for 12 h. The mixture was cooled to room temperature and suspended into dichloromethane (40 mL) and washed with water (20 mL×3). The combined organic layers were dried over anhydrous $Na_2SO_4$, filtered and concentrated under reduced pressure to give the crude which was purified by prep. HPLC (Column: Xtimate C18 150*25 mm*5 um, Mobile Phase A: water (0.04% $N1H_3H_2O$+10 mM $NH_4OHCO_3$), Mobile Phase B: acetonitrile, Flow rate: 30 mL/min, gradient condition from 40% B to 70%). The pure fractions were collected and the solvent was evaporated under vacuum to give a residue. The residue was partitioned between acetonitrile (2 mL) and water (10 mL). The solution was lyophilized to dryness to give intermediate 296 as a white powder.

Example A112

Preparation of Intermediates 297 and 298

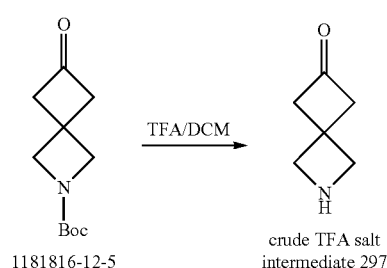

254
-continued

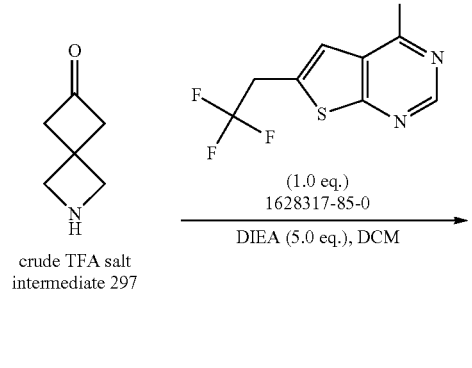

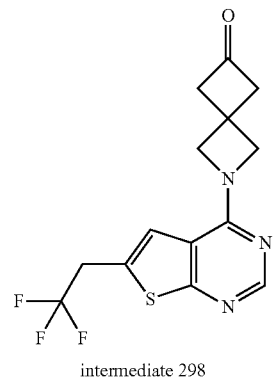

intermediate 298

Preparation of Intermediate 297

Tert-butyl 6-oxo-2-azaspiro[3.3]heptane-2-carboxylate (CAS #: 1181816-12-5) (250 mg, 1.18 mmol), trifluoroacetic acid (2 mL) and dry dichloromethane (2 mL) were added to a 100 mL round-bottomed flask. The reaction mixture was stirred at 25° C. for 1 hour. The mixture was concentrated under reduced pressure to give intermediate 297 (300 mg, crude TFA salt) as yellow oil.

Preparation of Intermediate 298

Intermediate 297 (200 mg, 0.89 mmol), 4-chloro-6-(2,2,2-trifluoroethyl)thieno[2,3-d]-pyrimidine (CAS #: 1628317-85-0) (224 mg, 0.89 mmol) and dry dichloromethane (8 mL) were added to a 40 mL glass bottle. N,N-diisopropylethylamine (574 mg, 4.44 mmol) was added to the reaction solution. The reaction mixture was stirred at 25° C. for 8 hours. The reaction mixture was poured into DCM (30 mL) before washed with water (20 mL×3). The organic extracts were dried over anhydrous $Na_2SO_4$, filtered, and concentrated to dryness under reduced pressure to give a residue, which was purified by preparative-TLC ($SiO_2$, PE:EtOAc=1:1, Rf=0.6) to give intermediate 298 (250 mg, 91.1% purity, 78.3% yield) as yellow solid.

Example A113

Preparation of Intermediates 299 and 300

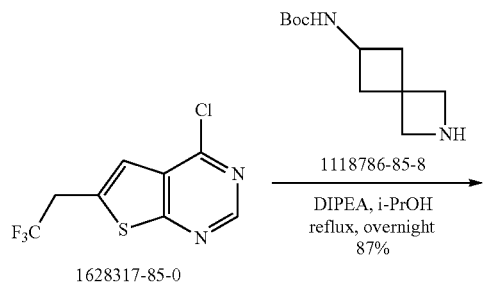

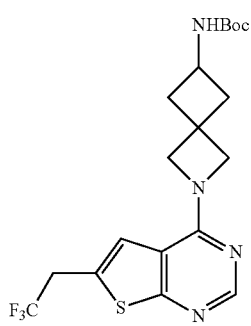

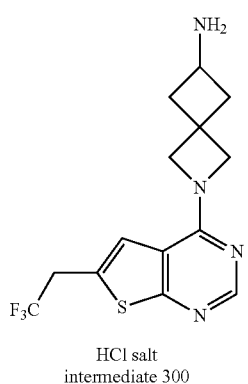

Intermediate 299 and intermediate 300 (HCl salt) were prepared respectively via an analogous reaction protocol as described for the preparation of intermediate 4 and intermediate 16 respectively, starting from the respective starting materials.

B. PREPARATION OF THE COMPOUNDS

Example B1

Preparation of Compounds 1 and 2

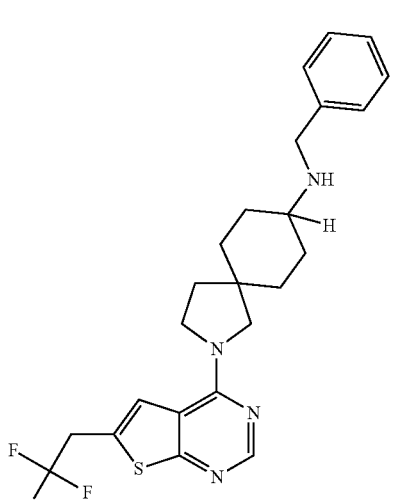

Compound 1: trans or cis
Compound 2: cis or trans

To a solution of Intermediate 7 (216 mg) in $^i$PrOH (10 mL) was added 4-chloro-6-(2,2,2-trifluoroethyl) thieno[2,3-d]pyrimidine (233 mg, 0.88 mmol) and DIPEA (457 mg, 3.54 mmol). After stirring at room temperature for 2 h, the mixture was concentrated, diluted with EtOAc and $H_2O$, the aqueous layer was extracted twice with EtOAc. The combined extracts ware concentrated in vacuo and purified by prep-HPLC (Waters 2767, Column: Xbridge C18 19*150 mm 10 um, Mobile Phase A: $H_2O$ (10 mmol $NH_4HCO_3$), B: ACN) to give the Compound 1 (61.9 mg) as a white solid and Compound 2 (99.0 mg) as a white solid.

Compound 1 $^1$H NMR MeOD-d4 (400 MHz): δ 8.25 (s, 1H), 7.61 (s, 1H), 7.36-7.30 (m, 4H), 7.26-7.23 (m, 1H), 3.90-3.80 (m, 6H), 3.58 (s, 2H), 2.62-2.60 (m, 1H), 2.10-2.00 (m, 21H), 1.95-1.92 (n, 2H), 1.75-1.72 (m, 2H), 1.53-1.35 (m, 41H).

Compound 2 $^1$H NMR MeOD-d4 (400 MHz): δ 8.27 (s, 1H), 7.64 (s, 1H), 7.36-7.26 (m, 4H), 7.26-7.25 (m, 1H), 3.92-3.83 (m, 4H), 3.83-3.78 (m, 2H), 3.74 (s, 2H), 2.60-2.56 (m, 1H), 1.98-1.95 (m, 2H), 1.95-1.88 (m, 2H), 1.77-1.74 (m, 2H), 1.50-1.43 (m, 2H), 1.37-1.28 (m, 2H).

Example B2

Preparation of Compounds 3, 4, 5 and 6

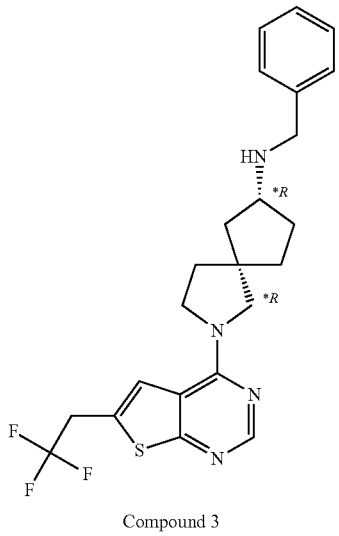 [SMILES: FC(F)(F)Cc1cc2c(N3CC[C@@]4(CC[C@H](NCc5ccccc5)C4)C3)ncnc2s1]

Compound 3

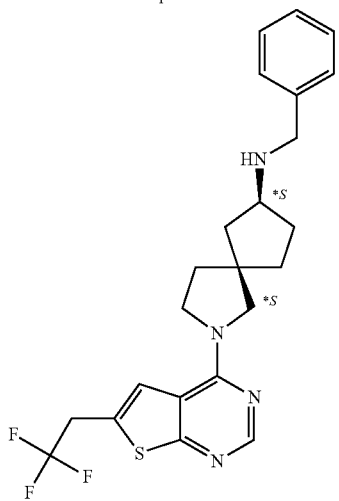

Compound 4

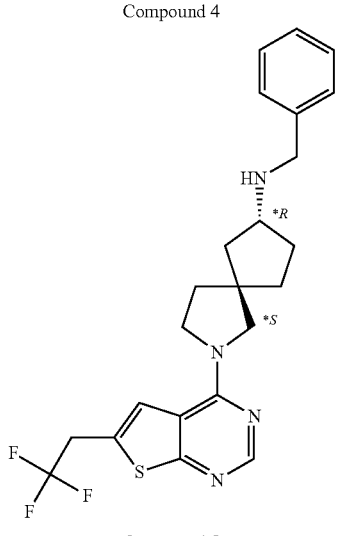

Compound 5

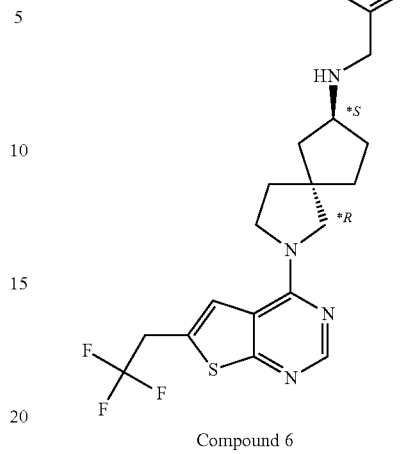

Compound 6

To a solution of crude Intermediate 8 (550 mg) in isopropanol (6 mL) was added DIPEA (806 mg, 6.25 mmol) and 4-chloro-6-(2,2,2-trifluoroethyl)thieno[2,3-d]pyrimidine (525 mg, 2.08 mmol). After stirring at room temperature for 5 h, the reaction mixture was added water (20 mL) and extracted with EtOAc (50 mL×3). The organic phase was washed with brine, dried over $Na_2SO_4$ and concentrated. The crude product was purified by prep-HPLC (Waters 2767/Qda, Column: Waters Xbridge19*150 mm 10 um, Mobile Phase A: $H_2O$ (0.1% $NH_4OH$), B: ACN) to give the two diastereoisomers. The two diastereoisomers were separated by SFC (condition: Waters, stationary phase: AD 2.5*25 cm, 10 um, mobile phase: $CO_2$/EtOH (40% ACN, 0.2% DEA)=60/40) condition 2: Waters, stationary phase: IA 2.5*25 cm, 10 um, mobile phase: $CO_2$/IPA (15% ACN, 0.2% DEA)=50/50) to give Compound 3 (59.8 mg), Compound 4 (54.9 mg), Compound 5 (105.9 mg), and Compound 6 (103.6 mg).

Compound 3 $^1$H NMR: MeOD-d4 (400 MHz): δ 8.30 (s, 1H), 7.69 (s, 1H), 7.33-7.27 (m, 4H), 7.22-7.20 (m, 1H), 4.05 (q, J=11.2 Hz, 2H), 3.83-3.67 (m, 2H), 3.66 (s, 2H), 3.64-3.58 (m, 2H), 3.16-3.13 (m, 1H), 2.02-1.98 (m, 1H), 1.95-1.86 (m, 2H), 1.75-1.70 (m, 1H), 1.60-1.44 (m, 4H).

Compound 4 $^1$HNMR MeOD-d4 (400 MHz): δ 8.28 (s, 1H), 7.63 (s, 1H), 7.37-7.30 (m, 4H), 7.27-7.25 (m, 1H), 3.92-3.84 (m, 4H), 3.76 (s, 2H), 3.76-3.66 (m, 2H), 3.29-3.25 (m, 1H), 2.11-2.06 (m, 4H), 1.86-1.83 (m, 1H), 1.74-1.72 (m, 1H), 1.66-1.62 (m, 1H), 1.57-1.51 (m, 2H).

Compound 5 $^1$H NMR MeOD-d4 (400 MHz): δ 8.26 (s, 1H), 7.62 (s, 1H), 7.35-7.29 (m, 4H), 7.26-7.24 (m, 1H), 3.89-3.84 (m, 4H), 3.81-3.77 (m, 2H), 3.74 (s, 2H), 3.28-3.26 (m, 1H), 2.09-2.03 (m, 2H), 1.93-1.88 (m, 2H), 1.86-1.83 (m, 1H), 1.67-1.55 (m, 3H).

Compound 6 $^1$H NMR MeOD-d4 (400 MHz): δ 8.26 (s, 1H), 7.62 (s, 1H), 7.35-7.29 (m, 4H), 7.25-7.22 (m, 1H), 3.89-3.84 (m, 4H), 3.81-3.78 (m, 2H) 3.74 (s, 2H), 3.28-3.26 (m, 1H), 2.11-2.03 (m, 2H), 1.94-1.89 (m, 2H), 1.86-1.83 (m, 1H), 1.67-1.55 (m, 3H).

Example B3

Preparation of Compound 7

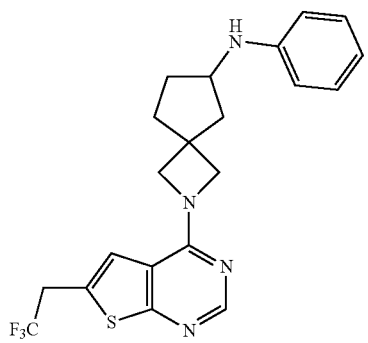

To a solution of Intermediate 2 (130 mg) in dioxane (3 mL) was added bromobenzene (50.0 mg, 0.32 mmol), $^t$BuONa (88.3 mg, 0.64 mmol), Brettphos (5 mg), Pd$_2$(dba)$_3$ (5 mg). The mixture was stirred at 130° C. under microwave for 2 h. The mixture was washed by H$_2$O, extracted with EtOAc twice, and combined the organic layers. The extracts ware concentrated in vacuo and purified by prep-HPLC (Waters 2767/Qda, Column: Waters Xbridge19*150 mm 10 um, Mobile Phase A: H$_2$O (0.1% NH$_4$OH), B: ACN) to afford Compound 7 (28.7 ng) as white solid.

Compound 7 $^1$H NMR MeOD-d4 (400 MHz):): δ (8.25 (s, 1H), 7.36 (s, 1H), 7.14-7.06 (m, 2H), 6.70-6.58 (m, 3H), 4.50-4.20 (m, 4H), 3.96-3.80 (m, 3H), 2.44-2.34 (m, 1H), 2.24-2.10 (m, 2-1), 2.08-1.88 (m, 2H), 1.72-1.58 (m, 1H)

Example B4

Preparation of Compound 8

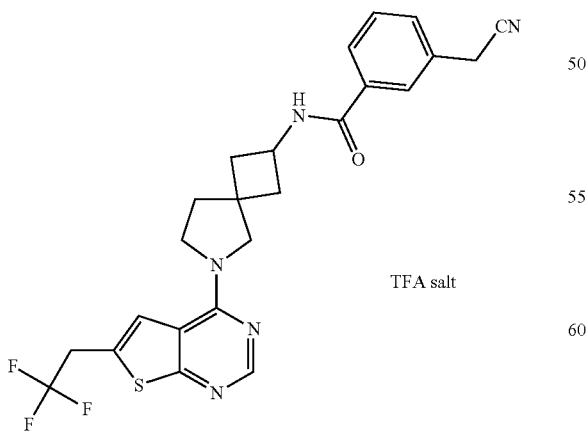

To a solution of intermediate 3 (200 mg) in DCM (10 mL) was added 3-(cyanomethyl)benzoic acid (47.0 mg, 0.292 mmol) and EDCI (84 mg, 0.438 mmol), HOBT (67.4 mg, 0.438 mmol), TEA (88.5 mg, 0.876 mmol) at room temperature. After stirring at room temperature for 16 h, the mixture was concentrated to give a residue which was purified by prep-HPLC (Waters 2767/Qda, Column: SunFire 19*250 mm 10 um, Mobile Phase A: 0.1% TFA/H$_2$O, B: ACN) to give Compound 8 (110 mg) as a light yellow solid (a TFA salt).

Compound 8 $^1$H NMR MeOD-d4 (400 MHz): δ 8.45 (d, 1H, J=8.8 Hz), 7.82 (s, 1H), 7.78-7.75 (m, 2H), 7.51-7.43 (m, 2H), 4.59-4.55 (m, 1H), 4.00-3.90 (m, 8H), 2.56-2.47 (m, 2H), 2.36-2.18 (m, 4H).

Example B5

Preparation of Compound 9

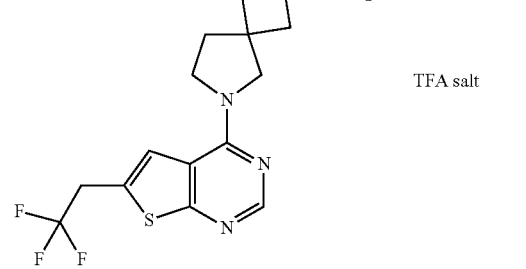

To a solution of intermediate 3 (200 mg) in DCM (10 mL) was added 3-(2-cyanopropan-2-yl)benzoic acid (55.2 mg, 0.292 mmol) and EDCI (84 mg, 0.438 mmol), HOBT (67.4 mg, 0.438 mmol), TEA (88.5 mg, 0.876 mmol) at room temperature. After stirring at room temperature 16 h, the mixture was concentrated to give a residue which was purified by prep-HPLC (Waters 2767/Qda, Column: SunFire 19*250 mm 10 um, Mobile Phase A: 0.1% TFA/H$_2$O, B: ACN) to give Compound 9 (105 mg) as a light yellow solid (a TFA salt).

Compound 9 $^1$H NMR MeOD-d4 (400 MHz): δ 8.43 (d, 1H, J=11.2 Hz), 7.99 (s, 1H), 7.81-7.70 (m, 3H), 7.54-7.50 (m, 1H), 4.62-4.58 (m, 1H), 4.04-3.90 (m, 6H), 2.60-2.50 (m, 2H), 2.36-2.18 (m, 4H), 1.76 (s, 6H).

261

Example B6

Preparation of Compounds 10, 11 and 12

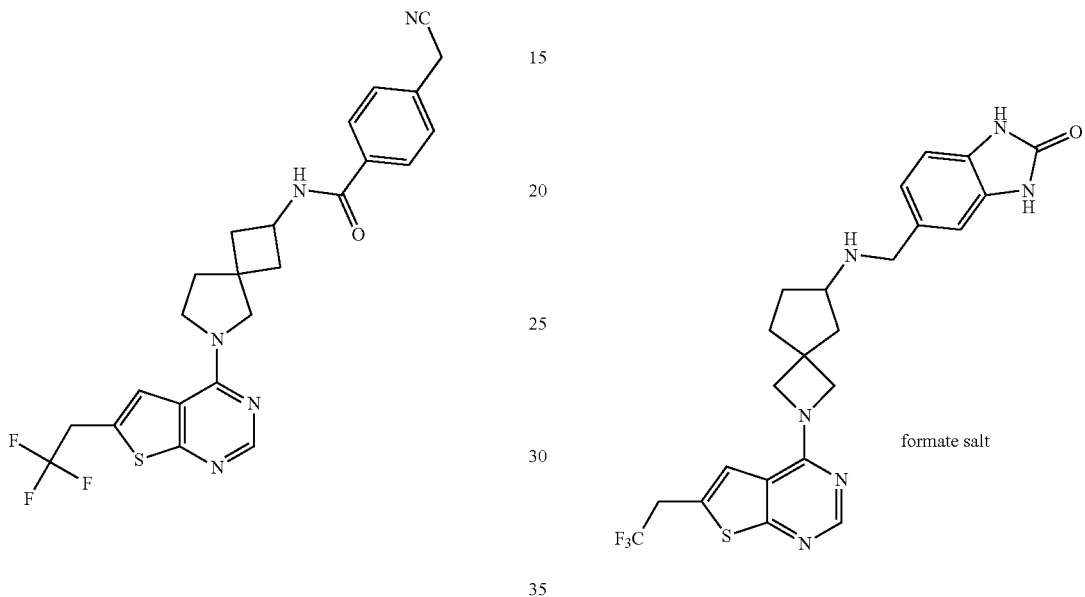

Compound 10: mixture of cis and trans—a TFA salt
Compound 11: trans or cis
Compound 12: cis or trans To a solution of intermediate 3 (200 mg) in DCM (10 mL) was added 4-(cyano-methyl)benzoic acid (47.0 mg, 0.292 mmol) and EDCI (84 mg, 0.438 mmol), HOBT (67.4 mg, 0.438 mmol), TEA (88.5 mg, 0.876 mmol) at room temperature. After stirring at room temperature for 16 h, the mixture was concentrated to give a residue which was purified by prep-HPLC (Waters® 2767/Qda, Column: SunFire 19*250 mm 10 um, Mobile Phase A: 0.1% TFA/$H_2O$, B: ACN) to give Compound 10 (65 mg) (as a TFA salt) as a light yellow solid (TFA salt), which was separated by SFC (condition: UPC²™ (Waters®), stationary phase: AS, 3 um, 3*100, mobile phase: $CO_2$/MeOH (0.3% DEA)=70/30) to afford Compound 11 (trans or cis) (10.7 mg) (free base) as pink solid and Compound 12 (cis or trans) (9.9 mg) as white solid (free base).

Compound 10 $^1$H NMR MeOD-d4 (400 MHz): δ 8.47 (d, J=9.6 Hz 1H,), 7.88-7.79 (m, 3H), 7.78 (d, J=7.6 Hz 2H,), 4.61-4.59 (m, 1H), 4.03-3.93 (m, 8H), 2.58-2.50 (m, 2H), 2.36-2.20 (m, 4H).

262

Example B8

Preparation of Compound 14 formate salt

To a solution of Intermediate 2 (100 mg) in MeOH (2 mL) was added 2-oxo-1,3-dihydrobenzimidazole-5-carbaldehyde (71 mg, 0.44 mmol). The mixture was stirred at room temperature for 2 h. $NaBH_3CN$ (37 mg, 0.58 mmol) was then added into the mixture and stirred overnight at room temperature. The mixture was concentrated, diluted with EtOAc and $H_2O$, separated and extracted twice with EtOAc. The combined extracts were concentrated in vacuo and purified by prep-HPLC (Waters® 2767/Qda, Column: SunFire 19*250 mm 10 um, Mobile Phase A: 0.1% Formate/$H_2O$, B: ACN) to afford Compound 14 (49.1 mg) (a formate salt).

Compound 14 $^1$H NMR MeOD-d4 (400 MHz): 8.50 (s, 1H, formate CHO), 8.29 (s, 1H), 7.35 (s, 1H), 7.20-7.16 (m, 2H), 7.12-7.10 (m, 1H), 4.39-4.30 (m, 4H), 4.19 (s, 2H), 3.87 (q, J=10.4 Hz, 2H), 3.71-3.61 (m, 1H), 2.62-2.57 (m, 1H), 2.30-2.15 (m, 2H), 2.12-2.01 (m, 2H), 1.86-1.80 (m, 1H).

Example B9

Preparation of Compounds 15, 55 and 56

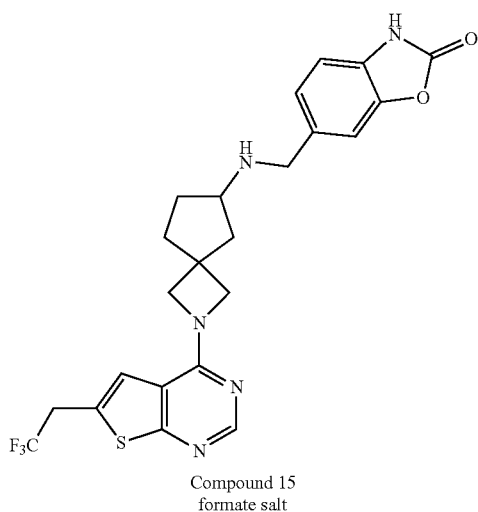

Compound 15
formate salt

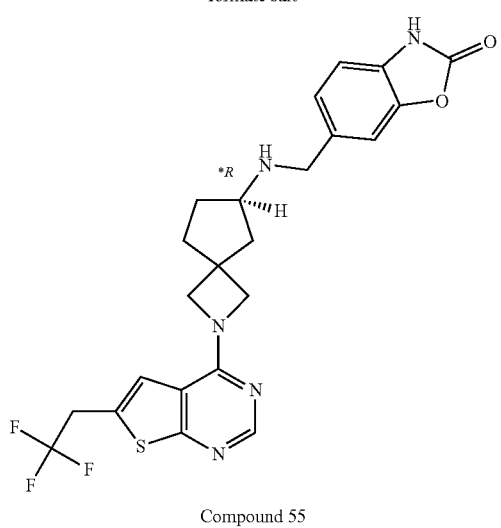

Compound 55

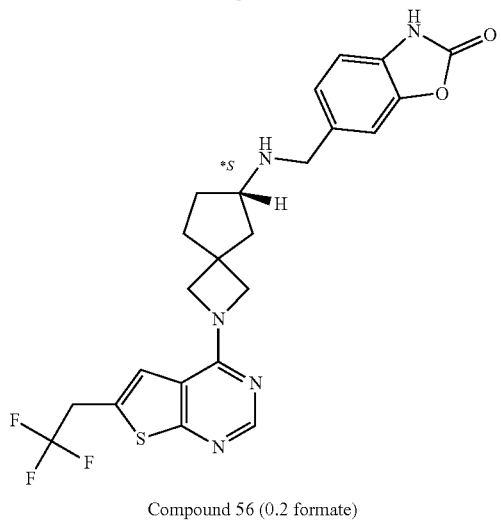

Compound 56 (0.2 formate)

To a solution of 2-oxo-3H-1,3-benzoxazole-6-carbaldehyde (300 mg, crude) in MeOH (4 mL) was added Intermediate 2 (200 mg), AcOH (3 drops). The solution was stirred at room temperature for 1 h, then NaBH$_3$CN (115.6 mg, 1.84 mmol) was allowed to added into the solution at 0° C. and the mixture was stirred at room temperature overnight. The mixture was washed with H$_2$O, extracted with EA twice, and combined. The organic layers ware concentrated in vacuo and purified by prep-HPLC (Waters® 2767/Qda, Column: SunFire 19*250 mm 10 um, Mobile Phase A: 0.1% Formate/H$_2$O, B: ACN) to afford Compound 15 (184.6 mg) (a formate salt) as a white solid. Compound 15 was separated by SFC (OJ, 2.5*25 cm, 10 um, mobile phase: CO$_2$/MeOH (0.03% DEA)=70/30, 70 ml/min) to afford Compound 55 (36.54 mg, R$_T$=1.836 min 13% yield) and Compound 56 (52.05 mg, 0.2 formate, R$_T$=2.175 min 18% yield).

Compound 15: $^1$H NMR MeOD-d4 (400 MHz): δ 8.50 (s, 1H, formate CHO), 8.28 (s, 1H), 7.40 (s, 1H), 7.35-7.31 (m, 2H), 7.17-7.15 (m, 1H), 4.44-4.31 (m, 4H), 4.22 (s, 2H), 3.87 (q, J=10.4 Hz, 2H), 3.73-3.69 (m, 1H), 2.63-2.57 (m, 1H), 2.30-2.17 (m, 2H), 2.16-2.03 (m, 2H), 1.87-1.82 (m, 1H).

Compound 55: $^1$H NMR MeOD-d$_4$ (400 MHz): δ 8.47 (brs, 1H), 8.28 (s, 1H), 7.40 (s, 1H), 7.35-7.31 (m, 2H), 7.16 (d, J=7.6 Hz, 1H), 4.40-4.31 (m, 4H), 4.22 (s, 2H), 3.87 (q, J=10.4 Hz, 2H), 3.73-3.69 (m, 1H), 2.63-2.57 (m, 1H), 2.30-2.17 (m, 2H), 2.12-2.03 (m, 2H), 1.87-1.82 (m, 1H).

Compound 56: $^1$H NMR DMSO-d$_6$ (400 MHz): δ 8.33 (s, 1H), 7.39-7.37 (m, 2H), 7.20 (d, J=8.0 Hz, 1H), 7.08 (d, J=7.6 Hz, 1H), 4.31-4.12 (m, 5H), 4.06 (q, J=11.2 Hz, 2H), 2.24-2.20 (m, 1H), 2.08-2.02 (m, 1H), 1.96-1.86 (m, 3H), 1.64-1.59 (m, 1H).

Example B10

Preparation of Compounds 16, 57 and 58

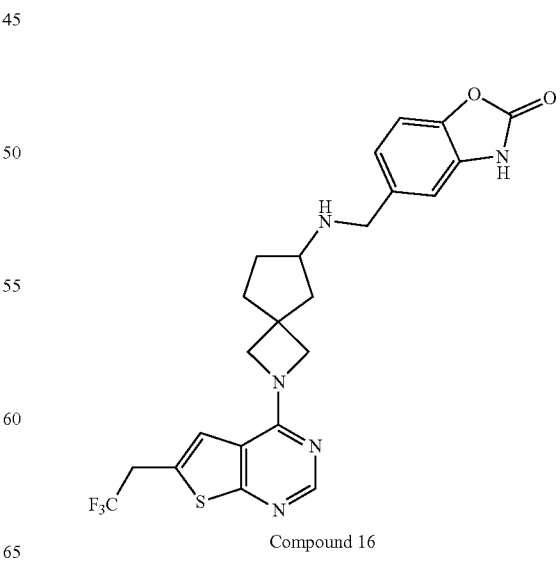

Compound 16

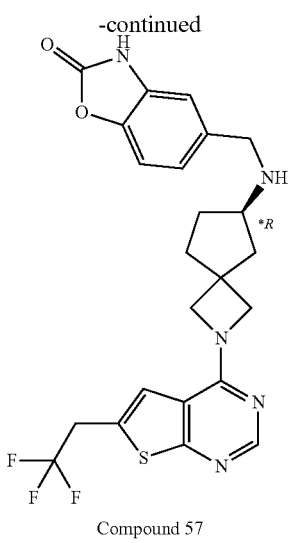

Compound 57

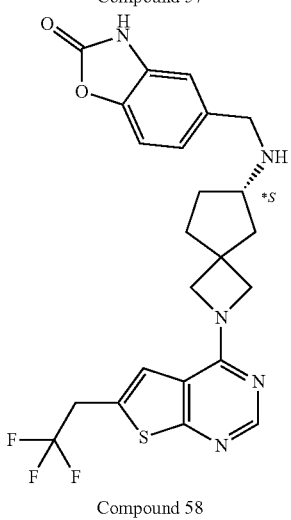

Compound 58

To a solution of 2-oxo-3H-1,3-benzoxazole-5-carbaldehyde (200.0 mg, 1.23 mmol) in MeOH (4 mL) was added Intermediate 2 (419 mg), AcOH (3 drops). The solution was stirred at room temperature for 1 h, then NaBH$_3$CN (115.60 mg, 1.84 mmol) was added to the solution at 0° C. and the mixture was stirred at room temperature overnight. The mixture was washed with H$_2$O, extracted with EtOAc twice, and the organic layers were combined. The extracts ware concentrated in vacuo and purified by prep-HPLC (Waters 2767/Qda, Column: Waters Xbridge19*150 mm 10 um, Mobile Phase A: H$_2$O (0.1% NH$_4$OH), B: ACN) to afford Compound 16 (55.9 mg) as a white solid.

Alternative Synthesis of Compound 16

To a solution of 2-oxo-2,3-dihydrobenzo[d]oxazole-5-carbaldehyde (200 mg, 1.23 mmol) in MeOH (5 mL) was added Intermediate 2 (503 mg, 1.47 mmol) and AcOH (2 drops) at room temperature. After being stirred for 2 hours, NaBH(OAc)$_3$ (522 mg, 2.46 mmol) was added into the solution and the obtained mixture was stirred at room temperature overnight. The mixture was concentrated under reduced pressure and purified by prep-HPLC (Waters® 2767/Qda, Column: SunFire 19*250 mm 10 um, Mobile Phase A: 0.1% NH$_4$OH/H$_2$O, B: ACN) to give Compound 16.

Compound 16 was separated by SFC (IE, 2.5*25 cm, 10 um, mobile phase: CO$_2$/MeOH=65/35, 60 ml/min) to afford Compound 57 (41.81 mg, 6.97%, R$_T$=6.248) as a white solid and Compound 58 (37.71 mg, 6.28%, R$_T$=6.683) as a white solid.

Compound 16: $^1$H NMR MeOD-d4 (400 MHz):): δ 8.26 (s, 1H), 7.35 (s, 1H), 7.19-7.08 (m, 3H), 4.50-4.10 (m, 3H), 3.86 (q, J=10.8 Hz, 2H), 3.79 (s, 2H), 3.28-3.20 (m, 2H), 2.38-2.28 (m, 1H), 2.16-1.90 (m, 3H), 1.85-1.77 (m, 1H), 1.64-1.52 (m, 1H)

Compound 57: $^1$H NMR MeOH-d$_4$ (400 MHz): δ 8.29 (s, 1H), 7.36 (s, 1H), 7.28-7.21 (m, 3H), 4.42-4.29 (m, 4H), 4.11 (s, 2H), 3.87 (q, J=10.4 Hz, 2H), 3.61-3.58 (m, 1H), 2.56-2.51 (m, 1H), 2.24-2.14 (m, 2H), 2.08-1.96 (m, 2H), 1.80-1.75 (m, 1H) Compound 58: $^1$H NMR MeOH-d$_4$ (400 MHz): δ 8.29 (s, 1H), 7.37 (s, 1H), 7.31-7.24 (m, 3H), 4.43-4.27 (m, 4H), 4.20 (s, 2H), 3.88 (q, J=10.4 Hz, 2H), 3.71-3.67 (m, 1H), 2.62-2.57 (m, 1H), 2.30-2.16 (m, 2H), 2.12-2.01 (m, 2H), 1.88-1.80 (m, 1H)

Example B11

Preparation of Compound 17

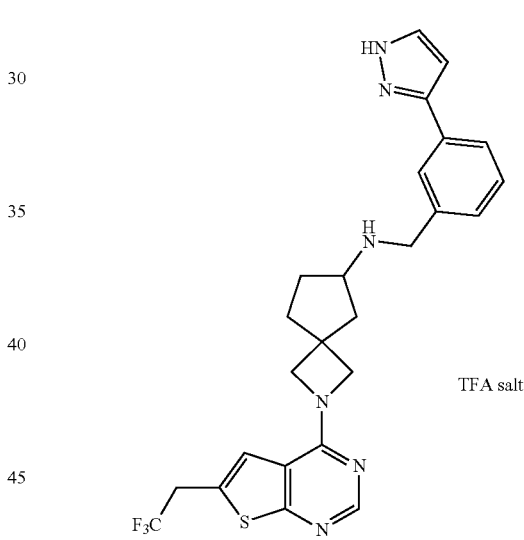

TFA salt

To a solution of 3-(1H-pyrazol-3-yl)benzaldehyde (200 mg, 1.16 mmol) in 1,2-Di-chloroethane (4 mL) was added Intermediate 2 (419 mg), AcOH (3 drops) and the solution was stirred at room temperature for 1 h, then NaBH(OAc)$_3$ (390 mg, 1.84 mmol) was added to the solution at 0° C. and the mixture was stirred at room temperature overnight. The mixture was washed with H$_2$O, extracted with EtOAc twice, and the organic layers were combined. The extracts ware concentrated in vacuo and purified by prep-HPLC (Waters 2767/Qda, Column: Waters Xbridge19*150 mm 10 um, Mobile Phase A: H$_2$O (0.1% TFA), B: ACN) to afford Compound 17 (84.0 mg, a TFA salt) as a white solid.

Compound 17 $^1$H NMR DMSO-d6 (400 MHz): δ 9.06 (brs, 2H), 8.36 (s, 1H), 8.00 (s, 1H), 7.86 (d, J=8.0 Hz, 1H), 7.79 (d, J=2.0 Hz, 1), 7.50 (t, J=3.2 Hz, 1H), 7.43 (d, J=7.6 Hz, 1H), 7.39 (s, 1H), 6.73 (d, J=2.54 Hz, 1H), 4.30-4.20 (m, 5H), 4.02-4.08 (m, 2H), 3.64-3.67 (m, 1H), 2.12 (m, 2H), 2.11-1.96 (m, 4H), 1.81-1.79 (m, 1H)

Example B12

Preparation of Compound 18

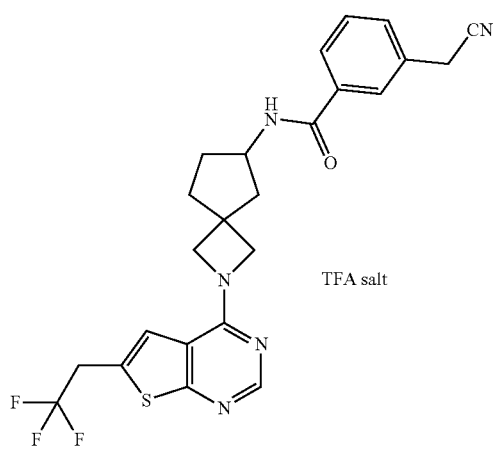

TFA salt

To a solution of intermediate 2 (200 mg) in DCM (10 mL) was added 3-(cyanomethyl)-benzoic acid (47.0 mg, 0.292 mmol) and EDCI (84 mg, 0.438 mmol), HOBT (67.4 mg, 0.438 mmol), TEA (88.5 mg, 0.876 mmol) at room temperature. After stirring at room temperature 16 h, the mixture was concentrated to give a residue which was purified by prep-HPLC (Waters 2767/Qda, Column: SunFire 19*250 mm 10 um, Mobile Phase A: 0.1% TFA/H$_2$O, B: ACN) to give Compound 18 (106 mg) (a TFA salt) as yellow oil.

Compound 18 $^1$H NMR MeOD-d4 (400 MHz): δ 8.41 (s, 1H), 7.82 (s, 1H), 7.79-7.77 (d, J=7.6 Hz, 1H), 7.56-7.47 (m, 3H), 4.73-4.40 (m, 5H), 3.98-3.91 (m, 4H), 2.56-2.49 (m, 1H), 2.24-2.03 (m, 4H), 1.83-1.80 (m, 1H).

Example B13

Preparation of Compound 19

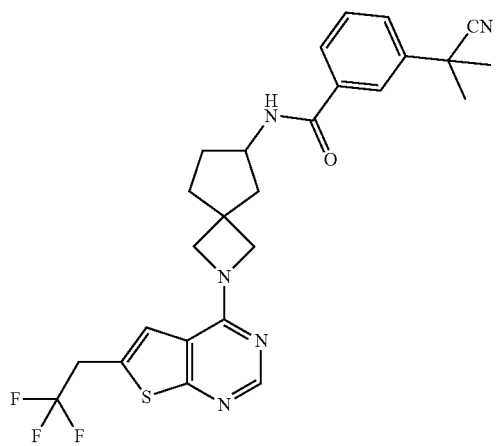

To a solution of intermediate 2 (200 mg) in DCM (10 mL) was added 4-(cyano-methyl)benzoic acid (55.2 mg, 0.292 mmol) and EDCI (84 mg, 0.438 mmol), HOBT (67.4 mg, 0.438 mmol), TEA (88.5 mg, 0.876 mmol) at room temperature. After stirring at room temperature 16 h, the mixture was concentrated to give a residue which was purified by prep-HPLC (Waters 2767/Qda, Column: Waters Xbridge19*150 mm um, Mobile Phase A: H$_2$O (0.1% NH$_4$OH), B: ACN) to give Compound 19 (50 mg) as a light yellow solid.

Compound 19 $^1$H NMR MeOH-d4 (400 MHz): δ 8.27 (s, 1H), 7.97 (s, 1H), 7.78 (d, J=7.6 Hz, 1H), 7.71 (d, J=8.0 Hz, 1H), 7.54-7.50 (m, 1H), 7.38 (s, 1H), 4.47-4.41 (m, 5H), 3.91-3.83 (m, 2H), 2.51-2.46 (m, 1H), 2.22-2.17 (m, 2H), 2.07-2.01 (m, 2H), 1.81-1.76 (m, 7H).

Example B14

Preparation of Compound 20

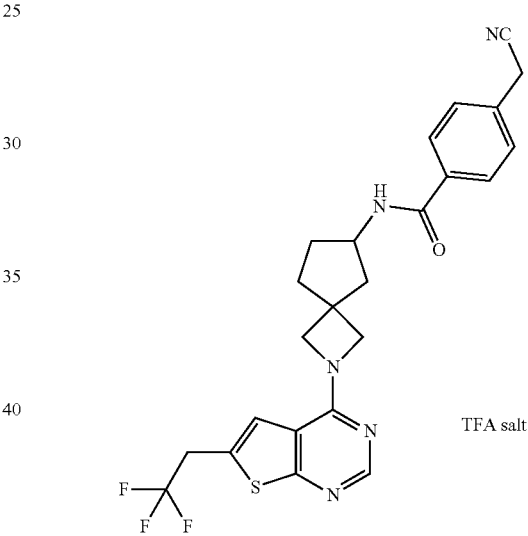

TFA salt

To a solution Intermediate 2 (200 mg) in DCM (10 mL) was added 4-(cyano-methyl)benzoic acid (47.0 mg, 0.292 mmol) and EDCI (84 mg, 0.438 mmol), HOBT (67.4 mg, 0.438 mmol), TEA (88.5 mg, 0.876 mmol) at room temperature. After stirring at room temperature 16 h, the mixture was concentrated to give a residue which was purified by prep-HPLC (Waters 2767/Qda, Column: SunFire 19*250 mm 10 um, Mobile Phase A: 0.1% TFA/H$_2$O, B: ACN) to give Compound 20 (65 mg) (a TFA salt) as yellow oil.

Compound 20 $^1$H NMR MeOH-d4 (400 MHz): δ 8.42 (s, 1H), 7.85 (d, J=8.0 Hz, 2H), 7.51 (s, 1H), 7.46 (d, J=8.4 Hz, 2H), 4.45-4.41 (m, 5H), 4.00-3.91 (m, 4H), 2.54-2.48 (m, 1H), 2.22-2.03 (m, 4H), 1.83-1.77 (m, 1H).

Example B16

Preparation of Compounds 22, 23 and 24

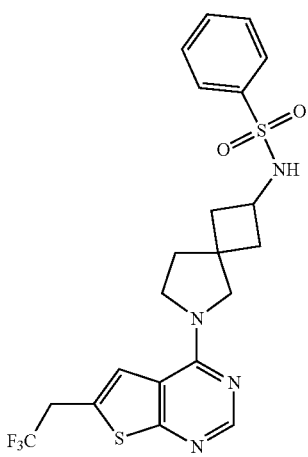

Compound 22: mixture of cis and trans - a TFA salt
Compound 23: trans or cis
Compound 24: cis or trans

Example B17

Alternative Preparation Compound 22, and Conversion to Compounds 25 and 26

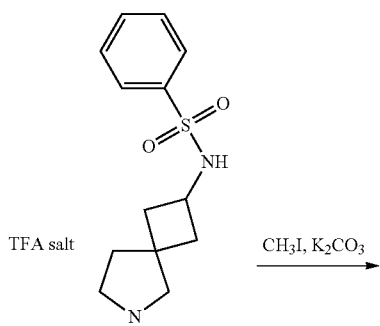

Compound 22

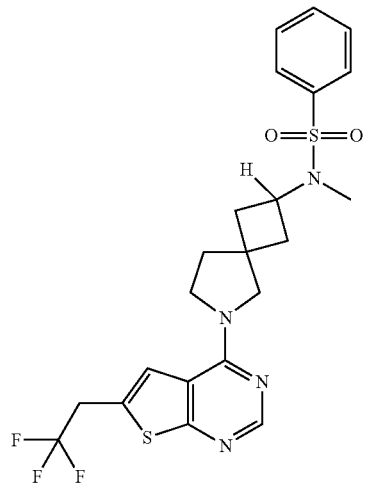

Compound 25: trans or cis
Compound 26: cis or trans

To a solution of intermediate 3 (200 mg) in DCM (8 mL) was added benzenesulfonyl chloride (52.0 mg, 0.292 mmol) and TEA (88.5 mg, 0.876 mmol) at room temperature. After stirring at room temperature for 16 h, the mixture was concentrated to give a residue which was purified by prep-HPLC (Waters 2767/Qda, Column: SunFire 19*250 mm 10 um, Mobile Phase A: 0.1% TFA/H$_2$O, B: ACN) to give Compound 22 (50 mg, 35.48% yield (a TFA salt) as a yellow solid. Compound 22 was separated by SFC (condition: SFC80(Waters), stationary phase: OJ 2.5*25 cm, 10 um, mobile phase: CO$_2$/MeOH (0.1% DEA)=75/25) to afford Compound 23 (trans or cis) (free base) (3.99 mg) as a pink solid and Compound 24 (cis or trans) (free base) (8.26 mg) as a white solid.

Compound 22 $^1$H NMR MeOH-d4 (400 MHz): δ 8.43 (d, J=6.0 Hz, 1H), 7.87-7.84 (m, 2H), 7.77-7.71 (m, 1H), 7.63-7.52 (m, 3H), 3.98-3.75 (m, 7H), 2.29-1.91 (m, 6H).

To a solution of intermediate 3 (400 mg) and TEA (177 mg, 1.75 mmol) in DCM (20 mL) was added benzenesulfonyl chloride (133 mg, 0.76 mmol) at 0° C. After stirring at 0° C. for 2 h, the reaction mixture was added water (20 mL) and extracted with DCM (50 mL×3). The organic phase was washed with brine, dried over Na$_2$SO$_4$ and concentrated. The crude product was purified by prep-TLC to give Compound 22 (280 mg).

To a solution of Compound 22 (280 mg) and K$_2$CO$_3$ (240 mg, 1.74 mmol) in DMF (20 mL) was added iodomethane (247 mg, 1.74 mmol) at 0° C. After stirring at 0° C. for 2 h, the reaction mixture was added water (20 mL) and extracted with EA (50 mL×3). The organic phase was washed with brine, dried over Na$_2$SO$_4$ and concentrated. The crude product was purified by prep-HPLC (Waters 2767/Qda, Column: SunFire 19*250 mm 10 um, Mobile Phase A: 0.1% TFA/H$_2$O, B: ACN) to give 100 mg racemic product. The racemic product was separated by SFC (condition: SFC80(Waters), stationary phase: AS 2.5*25 cm, 10 um, mobile phase: CO$_2$/MeOH (0.3% DEA)=60/40) to give Compound 25 (trans or cis) (45.50 mg, 97.5% purity) as a white solid, and Compound 26 (cis or trans) (48.52 mg, 99.3% purity) as a white solid.

Compound 25 $^1$H NMR MeOD-d4 (400 MHz): δ 8.27 (s, 1H), 7.81-7.79 (m, 2H), 7.65-7.63 (m, 2H), 7.60-7.57 (m, 2H), 4.12 (m, 1H), 3.91-3.86 (m, 3H), 3.83-3.79 (m, 3H), 2.71 (s, 3H), 2.24-2.19 (m, 4H), 2.03 (m, 2H).

Compound 26 $^1$H NMR MeOD-d4 (400 MHz): δ 8.25 (s, 1H), 7.82-7.79 (m, 2H), 7.65-7.64 (m, 1H), 7.62-7.58 (m, 3H), 4.10-4.08 (m, 1H), 3.89-3.81 (m, 4H), 3.73 (m, 2H), 2.72 (s, 3H), 2.31-2.26 (m, 2H), 2.15-2.10 (m, 4H).

Example B18

Preparation of Compounds 27, 28 and 29

DEA)=70/30) to afford Compound 28 (trans or cis) (6.88 mg) as a pink solid and Compound 29 (cis or trans) (9.91 mg) as a white solid.

Compound 27 $^1$H NMR meOH-d4 (400 MHz): δ 8.29 (d, J=6.4 Hz, 1H), 7.82 (d, J=6.4 Hz, 2H), 7.68-7.62 (m, 1H), 7.30 (d, J=8.4 Hz, 2H), 4.60-4.56 (m, 1H), 3.96-3.83 (m, 6H), 3.02 (s, 3H), 2.54-2.46 (m, 2H), 2.30-2.12 (m, 4H).

Example B19

Preparation of Compound 30

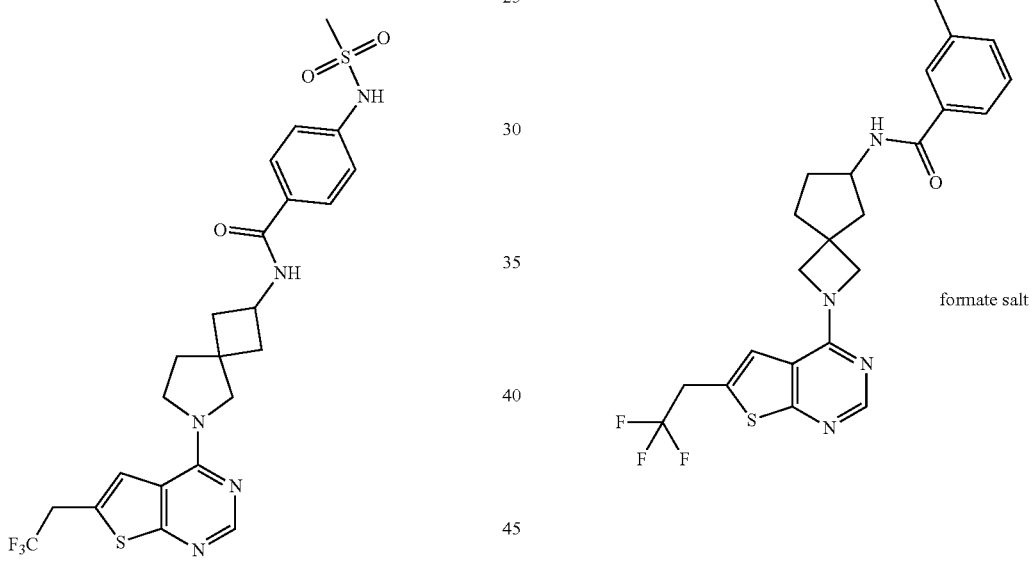

Compound 27: mixture of cis and trans
Compound 28: trans or cis
Compound 29: cis or trans To a solution of 4-(methanesulfonamido)benzoic acid (100 mg, 0.292 mmol) in DCM (10 mL) was added intermediate 3 (63 mg) and EDCI (84 mg, 0.438 mmol), HOBT (67.4 mg, 0.438 mmol), TEA (88.5 mg, 0.876 mmol) at room temperature. After stirring at room temperature 16 h, the mixture was concentrated to give a residue which was purified by prep-HPLC (Waters 2767/Qda, Column: Waters Xbridge19*150 mm um, Mobile Phase A: H$_2$O (0.1% NH$_4$OH), B: ACN) to give Compound 27 (55 mg) as a light yellow solid. A part of Compound 27 (26.4 mg) was separated by SFC (condition: SFC80(Waters), stationary phase: OJ 2.5*25 cm, 10 um, mobile phase: CO$_2$/MeOH (0.3%

To a solution of 3-(1H-pyrazol-3-yl)benzoic acid (130 mg, 0.69 mmol) in DCM (10 mL) was added Intermediate 2 (340 mg) and EDCI (197 mg, 1.0 mmol), HOBT (139 mg, 1.0 mmol), DIPEA (267 mg, 2.07 mmol), After stirring at room temperature for 12 h, The mixture was concentrated, diluted with EtOAc and H$_2$O, the aqueous layer was extracted twice with EA. The combined extracts ware concentrated and purified by prep-HPLC (Waters 2767/Qda, Column: Waters Xbridge19*150 mm 10 um, Mobile Phase A: H$_2$O (0.1% HCOOH), B: ACN) to give Compound 30 (50.1 mg) (a formate salt) as a white solid.

Compound 30 $^1$H NMR DMSO-d$_6$ (400 MHz): δ 13.0 (brs, 1H), 8.51-8.48 (m, 2H, formate CHO), 8.25 (s, 1H), 7.93-7.91 (m, 1H), 7.81-7.74 (m, 2H), 7.50-7.43 (m, 2H), 6.77 (s, 1H), 4.38-4.20 (m, 4H), 4.09-4.01 (m, 2H), 2.38-2.31 (m, 1H), 2.11-1.91 (m, 5H), 1.73-1.63 (m, 1H)

Example B20

Preparation of Compounds 31, 32, 33 and 34

Compound 31

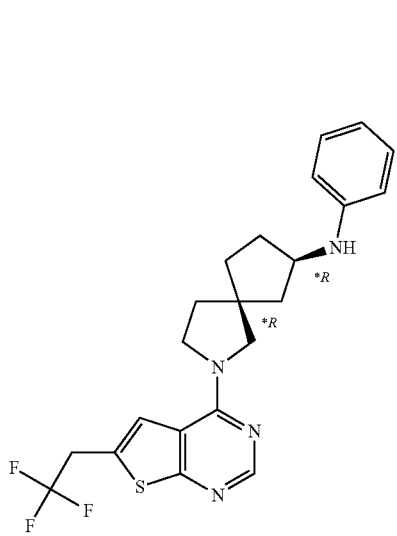

Compound 32

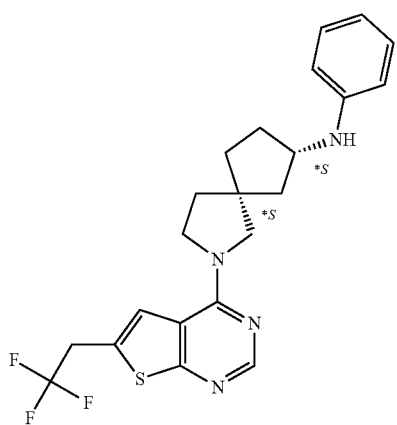

Compound 33

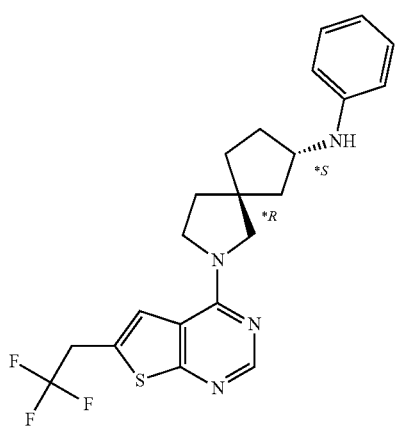

Compound 34

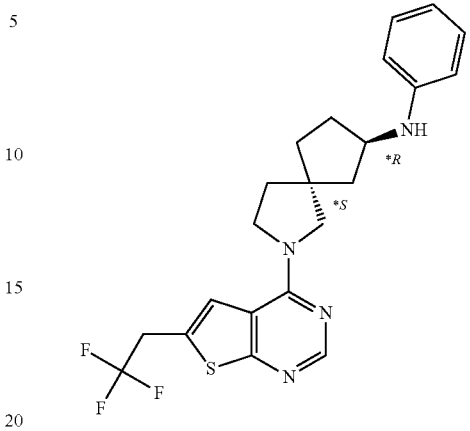

To a solution of Intermediate 11 (517 mg (crude)) in Isopropanol (15 mL) was added 4-chloro-6-(2,2,2-trifluoroethyl)thieno[2,3-d]pyrimidine (369 mg, 1.459 mmol) and DIPEA (753 mg, 5.836 mmol). After stirring at room temperature for 2 h, the mixture was concentrated, and the residue was purified by column chromatography (PE/EA=1/1) to afford non-racemic product (418 mg), which was separated by SFC (condition: SFC80 (Waters), stationary phase: IE 2.5*25 cm, 10 um, mobile phase: $CO_2$/EtOH (15% ACN)=65/35) to afford Compound 31 (81.7 mg), Compound 32 (52.8 mg), Compound 33 (60.8 mg) and Compound 34 (60.8 mg).

Compound 31 $^1$H NMR MeOD-d4 (400 MHz): δ 8.27 (s, 1H), 7.64 (s, 1H), 7.10-7.06 (m, 2H), 6.65-6.57 (m, 3H), 4.00-3.85 (m, 5H), 3.72-3.50 (m, 2H), 2.24-2.19 (m, 2H), 2.09-2.04 (m, 2H), 1.80-1.73 (m, 11-1), 1.70-1.59 (m, 31-).

Compound 32 $^1$H NMR MeOD-d4 (400 MHz): δ 8.27 (s, 1H), 7.64 (s, 1H), 7.10-7.06 (m, 2H), 6.65-6.57 (m, 3H), 4.00-3.85 (m, 5H), 3.72-3.50 (m, 2H), 2.24-2.19 (m, 2H), 2.09-2.04 (m, 2H), 1.80-1.73 (m, 1H), 1.70-1.59 (m, 3H).

Compound 33 $^1$H NMR MeOD-d4 (400 MHz): δ 8.26 (s, 1H), 7.61 (s, 1H), 7.11-7.07 (m, 2H), 6.66-6.58 (m, 3H), 3.96-3.82 (m, 7H), 2.24-2.19 (m, 2H), 2.09-2.04 (m, 2H), 1.80-1.73 (m, 1H), 1.70-1.59 (n, 31-).

Compound 34 $^1$H NMR MeOD-d4 (400 MHz): δ 8.26 (s, 1-), 7.61 (s, 1H), 7.10-7.06 (m, 2H), 6.66-6.58 (m, 3H), 3.98-3.82 (m, 7H), 2.24-2.19 (m, 2H), 2.09-2.04 (m, 2H), 1.80-1.73 (m, 1H), 1.70-1.59 (m, 3H).

Example B21

Preparation of Compound 35

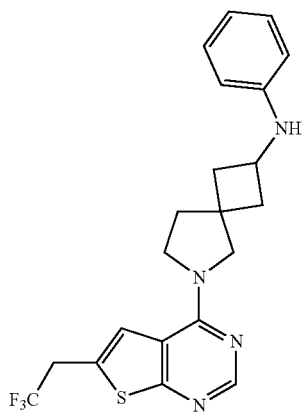 [SMILES: FC(F)(F)Cc1cc2c(N3CCC4(CC(Nc5ccccc5)C4)C3)ncnc2s1]

A mixture of Intermediate 3 (131 mg), bromobenzene (50 mg, 0.32 mmol), Pd$_2$(dba)$_3$ (5 mg, 10%), BrettPhos (5 mg, 10%) and $^t$BuONa (92 mg, 0.95 mmol) in dioxane (3 mL) was stirred under microwaved at 130° C. for 2 h. The reaction was diluted with water and extracted with EtOAc (50 mL×3). The organic phase was washed with brine, dried over Na$_2$SO$_4$ and concentrated. The crude product was purified by prep-HPLC (Waters 2767/Qda, Column: Waters Xbridge19*150 mm 10 um, Mobile Phase A: H$_2$O (0.10% NH$_4$OH), B: ACN) to give Compound 35 (42.26 mg) as a yellow solid.

Compound 35 $^1$H NMR DMSO-d6 (400 MHz): δ 8.32 (d, J=4.8 Hz, 1H), 7.72 (d, J=14.8 Hz, 1H), 7.08-7.03 (m, 2H), 6.52-6.50 (m, 3H), 5.89-5.85 (m, 1H), 4.05 (q, J=10.8 Hz, 2H), 3.92-3.87 (m, 2H), 3.80-3.75 (m, 2H), 3.25 (m, 1H), 2.46-2.41 (m, 2H), 211-2.09 (m, 1H), 2.07-2.02 (m, 1H), 1.96-1.87 (m, 2H).

Example B22

Preparation of Compounds 36 and 37

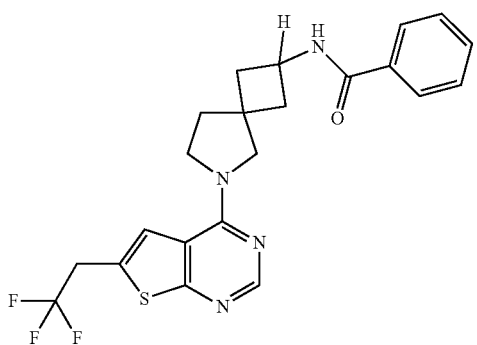

Compound 36: trans or cis
Compound 37: cis or trans

To a solution of intermediate 3 (400 mg) and TEA (354 mg, 3.50 mmol) in DCM (20 mL) was added benzoyl chloride (163 mg, 1.17 mmol) at 0° C. After stirring at 0° C. for 2 h, the reaction mixture was added water (20 mL) and extracted with DCM (50 mL×3). The organic phase was washed with brine, dried over Na$_2$SO$_4$ and concentrated. The crude product was purified by prep-HPLC (Waters 2767/Qda, Column: Waters Xbridge19*150 mm 10 um, Mobile Phase A: H$_2$O (0.1% NH$_4$OH), B: ACN) to give 120 mg of residue which was separated by SFC (condition: SFC80(Waters), stationary phase: OJ 2.5*25 cm, 10 um, mobile phase: CO$_2$/MeOH (0.3% DEA)=60/40) to give Compound 36 (30.92 mg, 98.8% purity) as a white solid, and Compound 37 (43.84 mg, 99.5% purity) as a white solid.

Compound 36 $^1$H NMR MeOD-d4 (400 MHz): δ 8.29 (s, 1H), 7.83-7.81 (m, 2H), 7.67 (s, 1H), 7.54-7.51 (m, 1H), 7.47-7.43 (m, 2H), 4.61-4.57 (m, 1H), 3.96-3.93 (m, 2H), 3.90-3.85 (m, 4H), 2.56-2.51 (m, 2H), 2.27-2.22 (m, 2H), 2.16-2.08 (m, 2H).

Compound 37 $^1$H NMR MeOD-d4 (400 MHz): δ 8.27 (s, 1H), 7.83-7.81 (m, 2H), 7.62 (s, 1H), 7.54-7.51 (m, 1H), 7.47-7.43 (m, 2H), 4.61-4.57 (m, 1H), 3.91-3.88 (m, 3H), 3.86-3.83 (m, 3H), 2.52-2.47 (m, 2H), 2.30-2.28 (m, 2H), 2.27-2.25 (m, 2H).

Example B23

Preparation of Compound 38

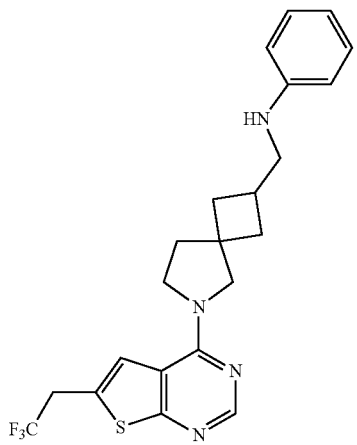 [SMILES: FC(F)(F)Cc1cc2c(N3CCC4(CC(CNc5ccccc5)C4)C3)ncnc2s1]

To a solution of Intermediate 10 (157 mg (crude)) in isopropanol (5 mL) was added 4-chloro-6-(2,2,2-trifluoroethyl)thieno[2,3-d]pyrimidine (184 mg, 0.727 mmol) and DIPEA (0.48 mL, 2.91 mmol). After stirring at room temperature for 2 h, the mixture was concentrated, the residue was purified by prep-HPLC (Waters 2767/Qda, Column: Waters Xbridge19*150 mm 10 um, Mobile Phase A: H$_2$O (0.1% NH$_4$OH), B: ACN). The desired fraction were collected and the solvent was evaporated to give Compound 38 (109.5 mg, 99.2% purity).

Compound 38 $^1$H NMR CDCl$_3$ (400 MHz): δ 8.42 (d, J=3.2 Hz, 1H), 7.34 (d, J=4.0 Hz, 1H), 7.19-7.16 (m, 2H), 6.72-6.69 (m, 1H), 6.62-6.59 (m, 2H), 3.84-3.80 (m, 3H), 3.72 (s, 1H), 3.62 (q, J=10.4 Hz, 2H), 3.21-3.18 (m, 2H), 2.66-2.60 (m, 1H), 2.27-2.01 (m, 4H), 1.91-1.83 (m, 2H)

Example B24

Preparation of Compound 39

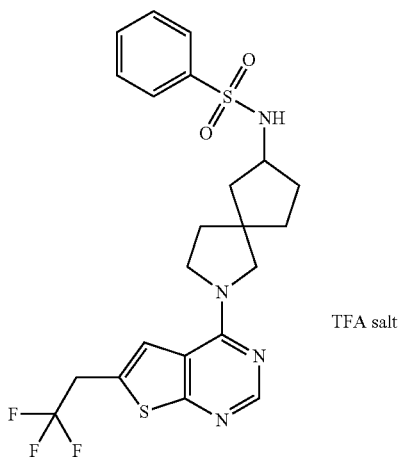 [SMILES: O=S(=O)(NC1CCC2(CCN(c3ncnc4sc(CC(F)(F)F)cc34)C2)C1)c1ccccc1]

TFA salt

To a solution of crude Intermediate 15 (35 mg, 0.125 mmol) in isopropanol (6 mL) was added DIPEA (48 mg, 0.375 mmol) and 4-chloro-6-(2,2,2-trifluoroethyl)thieno[2,3-d]-pyrimidine (32 mg, 0.125 mmol). After stirring at room temperature for 5 h, the reaction mixture was added water (20 mL) and extracted with EtOAc (50 mL×3). The organic phase was washed with brine, dried over $Na_2SO_4$ and concentrated. The crude product was purified by prep-HPLC (Waters 2767/Qda, Column: SunFire 19*250 mm 10 um, Mobile Phase A: 0.1% TFA/$H_2O$, B: ACN). The desired fraction were collected and the solvent was evaporated to give Compound 39 (35.1 mg, 98.70% purity).

Compound 39 $^1H$ NMR DMSO-$d_6$ (400 MHz): δ 8.36 (s, 1H), 7.82-7.80 (m, 3H), 7.70 (s, 1H), 7.62-7.56 (m, 3H), 4.07 (q, J=10.8 Hz, 2H), 3.63-3.60 (m, 3H), 3.58-3.55 (m, 2H), 2.37 (m, 1H), 1.84-1.72 (m, 3H), 1.68-1.64 (m, 1H), 1.54-1.44 (m, 3H).

Example B25

Preparation of Compound 40

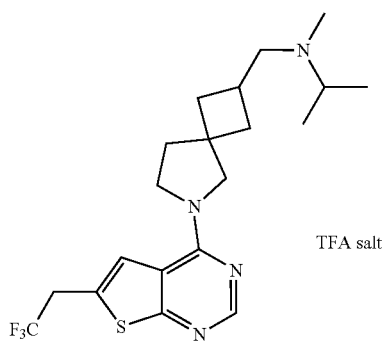 [SMILES: CC(C)N(C)CC1CC2(CCN(c3ncnc4sc(CC(F)(F)F)cc34)C2)C1]

TFA salt

To a solution of crude Intermediate 12 (120 mg) in isopropanol (6 mL) was added DIPEA (129 mg, 1.004 mmol) and 4-chloro-6-(2,2,2-trifluoroethyl)thieno[2,3-d]pyrimidine (84 mg, 0.334 mmol). After stirring at room temperature for 5 h, the reaction mixture was added water (20 mL) and extracted with EtOAc (50 mL×3). The organic phase was washed with brine, dried over $Na_2SO_4$ and concentrated. The crude product was purified by prep-HPLC (Waters 2767/Qda, Column: SunFire 19*250 mm 10 um, Mobile Phase A: 0.1% TFA/$H_2O$, B: ACN) to give Compound 40 (66.8 mg).

Compound 40 $^1H$ NMR DMSO-$d_6$ (400 MHz): δ 9.06 (brs, 1H), 8.34 (d, J=3.6 Hz, 1H), 7.69 (d, J=13.6 Hz, 1H), 4.06 (q, J=10.8 Hz, 2H), 3.87-3.67 (m, 4H), 3.52-3.44 (m, 1H), 3.26-3.19 (m, 1H), 3.13-3.03 (m, 1H), 2.76-2.66 (m, 1H), 2.63-2.61 (m, 3H), 2.26-2.05 (m, 3H), 2.00-1.81 (m, 3H), 1.23-1.1 (m, 6H).

Example B26

Preparation of Compound 41

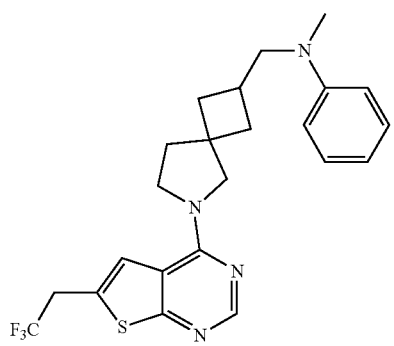

Compound 41

To a solution of crude Intermediate 13 (50 mg) in isopropanol (6 mL) was added DIPEA (84 mg, 0.652 mmol) and 4-chloro-6-(2,2,2-trifluoroethyl)thieno[2,3-d]pyrimidine (55 mg, 0.217 mmol). After stirring at room temperature for 5 h, the reaction mixture was added water (20 mL) and extracted with EtOAc (50 mL×3). The organic phase was washed with brine, dried over $Na_2SO_4$ and concentrated. The crude product was purified by prep-HPLC (Waters 2767/Qda, Column: Waters Xbridge19*150 mm 10 um, Mobile Phase A: $H_2O$ (0.1% $NH_4OH$), B: ACN) to give Compound 41 (50 mg, 98.71% purity).

Compound 41 $^1H$ NMR MeOD-$d_4$ (400 MHz): δ 8.25 (s, 1H), 7.61 (s, 1H), 7.17-7.13 (m, 2H), 6.75-6.72 (m, 2H), 6.65-6.61 (m, 1H), 3.90-3.78 (m, 5H), 3.78-3.73 (m, 1H), 3.42-3.39 (m, 2H), 2.92 (s, 3H), 2.80-2.72 (m, 1H), 2.16-2.08 (m, 3H), 2.07-1.98 (m, 1H), 1.97-1.90 (m, 2H).

Example B27

Preparation of Compound 42

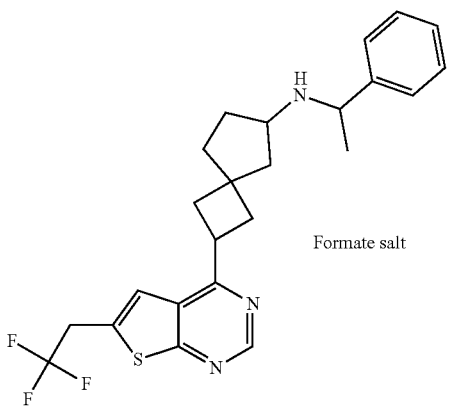

Formate salt

Intermediate 4 (70.0 mg, 0.205 mmol), DL-alpha-methylbenzylamine (62.1 mg, 0.512 mmol), $CH_3COOH$ (0.1 mL) and DCM (5 mL) were added to a 50 mL round-bottomed flask. The reaction mixture was treated with sodium triacetoxyborohydride (174 mg, 0.821 mmol) and stirred at 20° C. for 2 hours. The reaction mixture was diluted with water (20 mL), extracted with DCM (20 mL×2), washed with brine and dried over $Na_2SO_4$. The organic layer was filtered and concentrated under reduced pressure to give crude product which was purified by prep-HPLC condition: (Xtimate C18 150*25 mm*5 um, Flow rate: 22 ml/min, Mobile Phase A: water (0.225% FA)-ACN, Mobile Phase B: acetonitrile, Gradient: 23-53% (% B)). The desired fraction was collected and evaporated to remove off $CH_3CN$ in vacuum. The residue was lyophilized to yield Compound 42 (a formate salt) (34.1 mg, white solids).

Compound 41 $^1H$ NMR DMSO-$d_6$ (400 MHz): δ 8.32-8.29 (m, 1H), 7.40-7.30 (m, 5H), 7.26-7.20 (m, 1H), 4.40-3.90 (m, 6H), 3.84-3.75 (m, 1H), 2.94-2.87 (m, 1H), 2.06-1.94 (m, 2H), 1.84-1.65 (m, 3H), 1.54-1.35 (m, 1H), 1.30-1.25 (m, 3H)

Example B28

Preparation of Compound 43

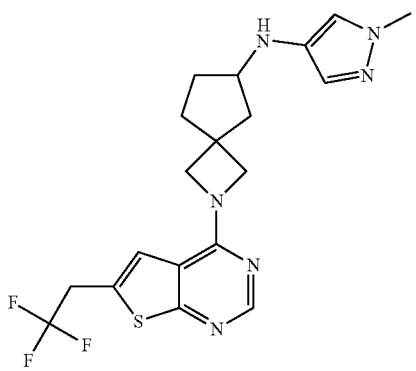

Intermediate 4 (70.0 mg, 0.205 mmol), 1-methyl-1H-pyrazol-4-amine (49.8 mg, 0.513 mmol), $CH_3COOH$ (0.1 mL) and DCM (5 mL) were added to a 50 mL round-bottomed flask. The reaction mixture was treated with sodium triacetoxyborohydride (174 mg, 0.821 mmol) and stirred at 20° C. for 2 hours. The reaction mixture was diluted with water (20 mL), extracted with DCM (20 mL×2), washed with brine and dried over $Na_2SO_4$. The organic layer was filtered and concentrated under reduced pressure to give crude product which was purified by prep-HPLC condition: (Xtimate C18 150*25 mm*5 um, Flow rate: 22 ml/min, Mobile Phase A: water (0.225% FA)-ACN, Mobile Phase B: acetonitrile, Gradient: 18-48% (% B)). The desired fraction was collected and evaporated to remove off $CH_3CN$ in vacuum. The residue was lyophilized to yield Compound 43 (28.6 mg, 31.5% yield, white solids).

Compound 43 $^1H$ NMR DMSO-$d_6$ (400 MHz): δ 8.32 (s, 1H), 7.41 (s, 1H), 7.06 (s, 1H), 6.93 (s, 1H), 4.41-3.96 (m, 6H), 3.69 (s, 3H), 3.47-3.46 (m, 1H), 2.28-2.17 (m, 1H), 2.09-1.85 (m, 3H), 1.83-1.74 (m, 1H), 1.56-1.46 (m, 1H).

Example B29

Preparation of Compound 44

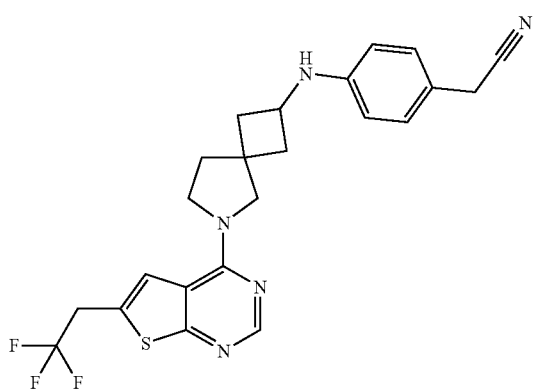

A stir bar, intermediate 5 (110 mg, 0.322 mmol), 2-(4-aminophenyl)acetonitrile (51.1 mg, 0.387 mmol), acetic acid (one drop), sodium triacetoxyborohydride (342 mg, 1.61 mmol) and dry dichloromethane (5 mL) were added to a 40 mL glass bottle which was stirred at 40° C. for 12 hours. The mixture was treated with water (50 mL) and the aqueous layer was extracted with dichloromethane (20 mL×3). The combined organic layers were dried over anhydrous $Na_2SO_4$, filtered and concentrated under reduced pressure to give the crude product which was purified by Prep-TLC (eluent: ethyl acetate) to give a residue. The residue was partitioned between acetonitrile (2 mL) and water (10 mL). The solution was lyophilized to dryness to give Compound 44 (54.2 mg, 35.7% yield) as a light yellow powder.

Compound 44 $^1H$ NMR DMSO-$d_6$ (400 MHz): δ 8.36-8.30 (m, 1H), 7.77-7.66 (m, 1H), 7.07-7.00 (m, 2H), 6.57-6.50 (m, 2H), 6.03 (t, J 7.2 Hz, 1H), 4.12-4.02 (m, 2H), 3.96-3.67 (m, 7H), 2.50-2.40 (m, 2H), 2.17-1.84 (m, 4H).

Example B30

Preparation of Compounds 45, 46 and 47

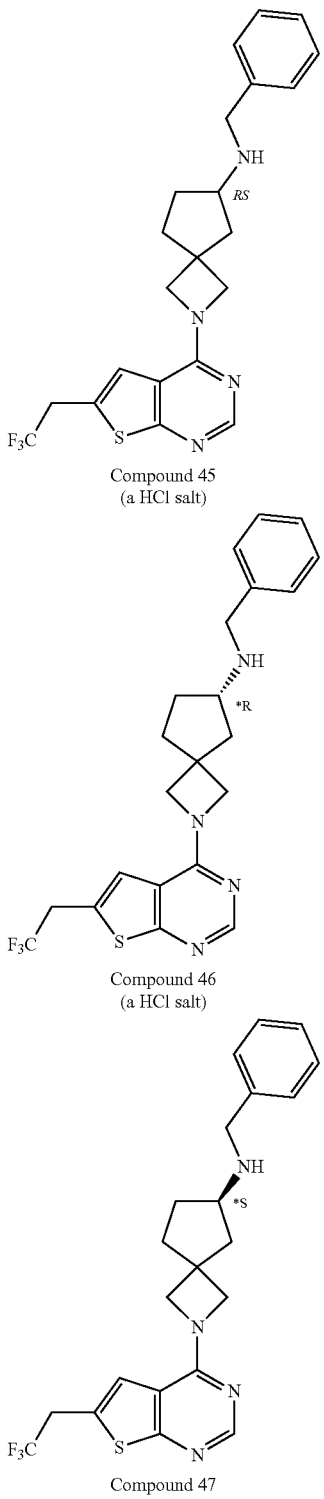

Compound 45 (a HCl salt)

Compound 46 (a HCl salt)

Compound 47

Intermediate 4 (200 mg, 0.575 mmol), benzylamine (62 mg, 0.575 mmol), DIPEA (175 mg, 1.73 mmol) and NaBH(OAc)$_3$ (609 mg, 2.48 mmol) were added to DCE (8 mL). The reaction was stirred at rt overnight. The solvent was removed to afford a clean oil. This oil was purified by preparative high-performance liquid chromatography (column: Xtimate C18 150*25 mm*5 um, condition: water (0.05% ammonia hydroxide v/v)/ACN 60/40 from to 30/70). The pure fractions were collected and the solvent was evaporated under vacuum to afford a clean oil. To this oil was added 15 mL of HCl 12N and 5 mL ACN. The solvent was freeze-dried yielding 75 mg of Compound 45 (a HCl salt). Compound 45 (60.5 mg) was separated by chromatography via chiral SFC (stationary phase: Chiralpak Ad-H 5 μm 250*30 mm, mobile phase: CO$_2$/MeOH (0.3% iPrNH$_2$): 60/40). The pure fractions were collected and the solvent was evaporated under vacuum to give 20 mg of enantiomer A and 24 mg of the enantiomer B (not pure enough). Enantiomer A was dissolved in 2 mL of ACN and 3 equivalents of HCl 4N (15 μL, 0.18 mmol) were added dropwise at 10° C. Then, Et$_2$O was added and, after 30 min, the solution was evaporated to dryness. Et$_2$O was added and the precipitate was filtered and dried giving 15 mg of Compound 46 (a HCl salt). Enantiomer B (24 mg) was purified by chromatography over silica gel via reverse phase (stationary phase: YMC-actus Triart C18 10 μm 30*150 mm, mobile phase: NH$_4$HCO$_3$ 0.2%/ACN: gradient from 60/40 to 0/100). The residue was taken up with Et$_2$O and evaporated till dryness yielding 12 mg of Compound 47 (free base).

Compound 47 $^1$H NMR (500 MHz, DMSO-d$_6$): δ ppm 8.31 (s, 1H) 7.41 (s, 1H) 7.28-7.37 (m, 4H) 7.18-7.25 (m, 1H) 4.05 (q, J=11.0 Hz, 2H) 3.68 (br s, 2H) 3.11 (br s, 1H) 2.43-2.48 (m, 4H) 1.98-2.13 (m, 3H) 1.75-1.89 (m, 3H) 1.44-1.54 (m, 1H)

Example B31

Preparation of Compound 48

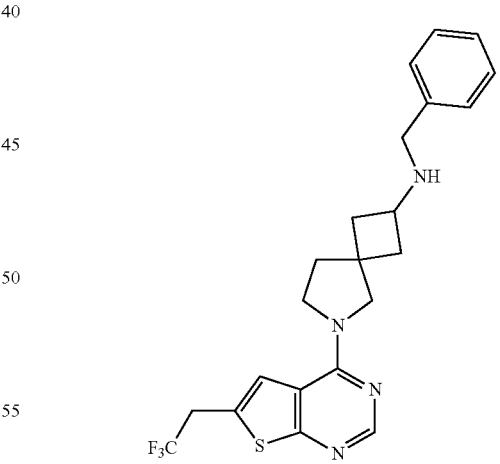

Intermediate 5 (400 mg, 0.791), benzylamine (85 mg, 0.791 mmol), DIPEA (240 mg, 2.37 mmol) and NaBH(OAc)$_3$ (838 mg, 3.96 mmol) were added to DCE (15 mL). The reaction was stirred at rt overnight. The solvent was removed to afford a clean oil. This oil was purified by preparative high-performance liquid chromatography (column Xtimate C18 150*25 mm*5 um, condition: water (0.05% ammonia hydroxide v/v)/ACN: gradient from 50/50 to 40/60). The pure fractions were collected and the solvent was evaporated under vacuum. The aqueous layer was freeze-dried with acetonitrile/water 20/80 yielding 75 mg of Compound 48 (28% yield).

Example B32

Preparation of Compounds 49 and 50

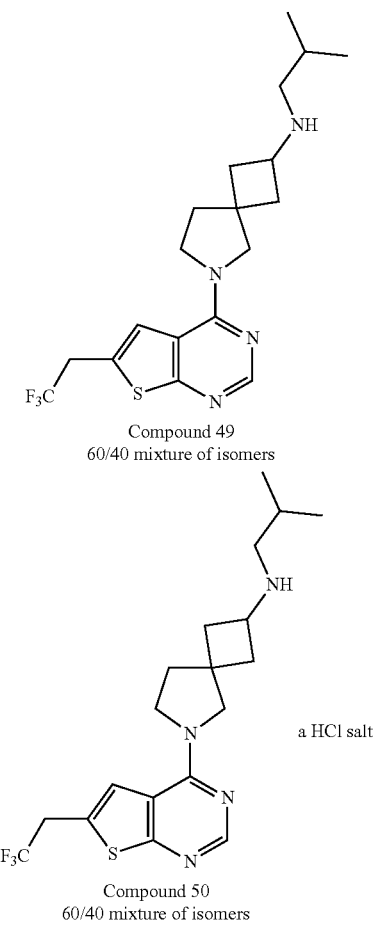

Compound 49
60/40 mixture of isomers a HCl salt

Compound 50
60/40 mixture of isomers

A mixture of intermediate 5 (558 mg; 1.63 mmol), isobutylamine (151 μL; 1.76 mmol) and AcOH (33.5 μL; 0.586 mmol) in DCE (5 mL) was stirred at 50° C. for 2 hours. The reaction mixture was cooled to room temperature and NaBH(OAc)₃ (372 mg; 1.76 mmol) was added. The reaction mixture was stirred at room temperature overnight, poured onto a 10% aqueous solution of K₂CO₃ and extracted with DCM. The organic layer was decanted, dried over MgSO₄, filtered and evaporated to dryness. The residue was purified by chromatography over silica gel (irregular SiOH, 24 g; mobile phase: gradient from 0% MeOH, 100% DCM to 10% MeOH, 90% DCM). The pure fractions were collected and evaporated to dryness yielding 550 mg (84%) of Compound 49 as a 60/40 mixture of isomers. The hydrochloride salt was prepared by dissolving 50 mg of Compound 49 in Et₂O and by adding HCl 4N in 1,4-dioxane. Filtration of the precipitate yielded 56 mg of Compound 50 (a HCl salt) as a 60/40 mixture of isomers.

Compound 51 was prepared by using an analogous method as described for the preparation of Compound 50, starting from the respective starting materials.

| Compound number | Structure | Quantity (mg) | Yield (%) |
|---|---|---|---|
| Compound 51 as a 60/40 mixture of isomers (from intermediate 5 and isopropylamine) | 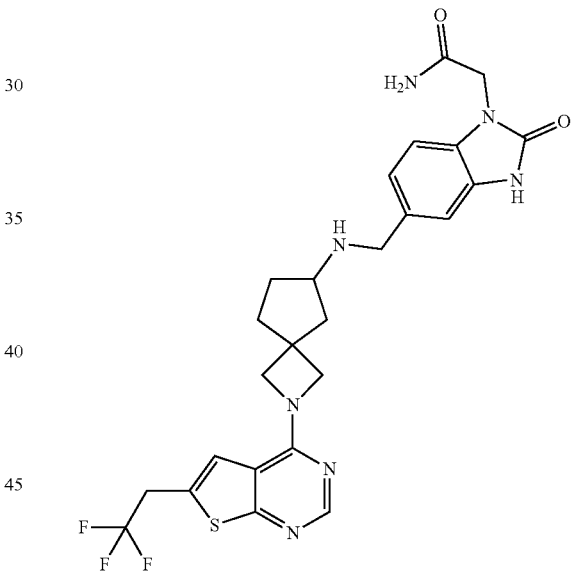<br>as a hydrochloride salt | 41 | 75 |

Example B33

Preparation of Compound 53

To a solution of intermediate 4 (2-(6-(2,2,2-trifluoroethyl)thieno[2,3-d]pyrimidin-4-yl)-2-azaspiro[3.4]octan-6-one) (165 mg, 0.435 mmol), intermediate 53 (2-(5-(aminomethyl)-2-oxo-2,3-dihydro-1H-benzo[d]imidazol-1-yl)acetamide) (170 mg, 0.656 mmol), sodium cyanoborohydride (60.6 mg, 0.964 mmol), and MeOH (12 mL) was added a solution of CH₃COOH (57.9 mg, 0.964 mmol) in MeOH (3 mL). After stirring at 45° C. for 12 hours, the reaction mixture was concentrated to dryness under reduced pressure to afford the crude product, which was purified by prep-HPLC (Gilson 281, Xtimate C18 150×25 mm×5 m column, Mobile phase A: water (0.225% FA), B: ACN). The pure fractions were collected and evaporated under reduced pressure to obtain a residue, which was lyophilized to dryness to give Compound 53 (200 mg, 84.3% yield) as white powder.

$^1$H NMR MeOD-d$_4$ (400 MHz): δ 8.40 (br s, 1H), 8.29 (s, 1H), 7.35 (s, 1H), 7.25 (s, 1H), 7.22 (d, J=8.4 Hz, 1H), 7.10

(d, J=8.0 Hz, 1H), 4.58 (s, 2H), 4.51-4.25 (m, 4H), 4.23 (s, 2H), 3.88 (q, J=11.6 Hz, 2H), 3.77-3.66 (m, 1H), 2.60 (dd, J=8.4, 13.6 Hz, 1H), 2.35-2.14 (m, 2H), 2.13-2.02 (m, 2H), 1.95-1.74 (m, 1H).

Example B34

Preparation of Compound 54

Example B35

Preparation of Compounds 59 and 60

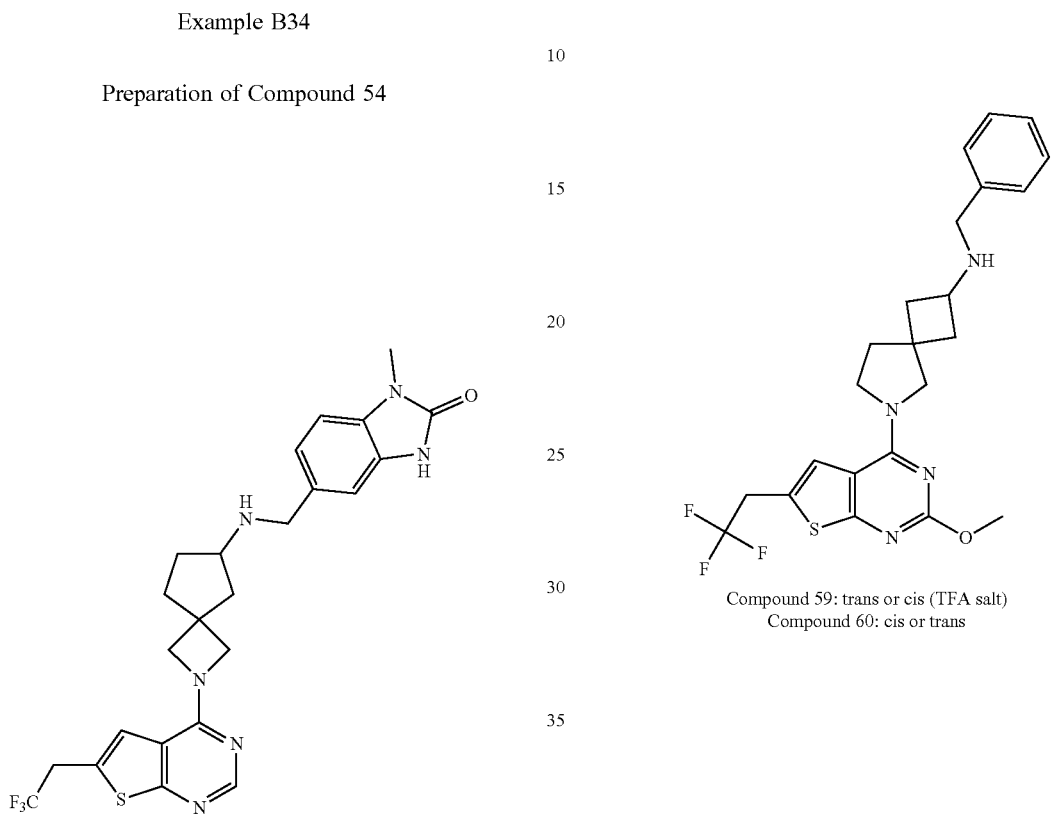

Compound 59: trans or cis (TFA salt)
Compound 60: cis or trans

To a solution of intermediate 2 (2-(6-(2,2,2-trifluoroethyl)thieno[2,3-d]pyrimidin-4-yl)-2-azaspiro[3.4]octan-6-amine HCl salt) (200 mg) in MeOH (6 mL) was added 1-methyl-2-oxo-2,3-dihydro-1H-benzo[d]imidazole-5-carbaldehyde (134 mg, 0.76 mmol) and AcOH (3 drops) at room temperature. The mixture was stirred at room temperature for 2 hours, then NaBH₃CN (73 mg, 1.16 mmol) was added and the mixture was stirred at room temperature overnight. The mixture was concentrated under residue and purified by prep-HPLC (Waters 2767/Qda, Column: Waters Xbridge 20*150 mm 10 um, Mobile Phase A: 0.1% NH₃.H₂O, B: ACN) to afford Compound 54 (78.71 mg) as a light yellow solid.

¹H NMR MeOD-d₄ (400 MHz): δ 8.29 (s, 1H), 7.36 (s, 1H), 7.27-7.25 (m, 2H), 7.19 (d, J=8.8 Hz, 1H), 4.40-4.31 (m, 4H), 4.22 (s, 2H), 3.88 (q, J=10.4 Hz, 2H), 3.73-3.69 (m, 1H), 3.40 (s, 3H), 2.63-2.58 (m, 1H), 2.29-2.16 (m, 2H), 2.12-2.02 (m, 2H), 1.87-1.83 (m, 1H)

To a solution of intermediate 19 (6-(2-methoxy-6-(2,2,2-trifluoroethyl)thieno[2,3-d]-pyrimidin-4-yl)-6-azaspiro[3.4]octan-2-amine) (150 mg, 0.42 mmol), benzaldehyde (58 mg, 1.3 mmol) and Titanium tetraisopropanolate (488 mg, 1.72 mmol) in MeOH (5 mL) was added NaBH(OAc)₃ (267 mg, 1.26 mmol). After being stirred at room temperature for 1 hour, the reaction mixture was quenched with H₂O (5 mL) and extracted with DCM (10 mL×2). The combined organic layers were washed with brine (20 mL), dried over Na₂SO₄, filtered and concentrated under reduced pressure. The residue was purified by prep-HPLC (Waters 2767/Qda, Column: SunFire 19*250 mm 10 um, Mobile Phase A: 0.1% TFA/H₂O, B: ACN) to afford the mixture of cis and trans (120 mg, 62% yield). The mixture was separated by SFC (OJ, 3*100 cm, 3 um, mobile phase: CO₂/MeOH (0.02% DEA)=80/20, 1.8 ml/min). The desired fractions were collected and the solvent evaporated to afford Compound 59 (35 mg, $R_T$=1.107 min, TFA salt, trans or cis) and Compound 60 (48 mg, $R_T$=1.377 min, cis or trans, 40.0% yield).

Compound 59: ¹H NMR MeOD-d₄ (400 MHz): δ 7.54 (s, 1H), 7.50-7.48 (m, 5H), 4.13 (s, 2H), 4.00 (s, 3H), 3.98-3.94 (m, 5H), 3.81 (q, J=10.4 Hz, 2H), 2.55-2.49 (m, 2H), 2.34-2.28 (m, 2H), 2.19-2.15 (m, 2H).

Compound 60: ¹H NMR MeOD-d₄ (400 MHz): δ 7.46 (s, 1H), 7.35-7.24 (m, 5H), 3.94 (s, 3H), 3.80-03.69 (m, 8H), 3.38-3.36 (m, 1H), 2.31-2.26 (m, 2H), 2.12-1.92 (m, 4H).

Example B36

Preparation of Compounds 61 and 62

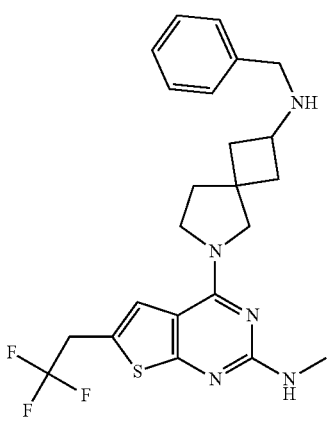

Compound 61: trans or cis
Compound 62: cis or trans

A solution of intermediate 21 (N-benzyl-6-(2-chloro-6-(2,2,2-trifluoroethyl)thieno-[2,3-d]pyrimidin-4-yl)-6-azaspiro[3.4]octan-2-amine) (250 mg, 0.535 mmol) in methanamine/THF (4 mL) in sealed tube was stirred at 100° C. for 16 hours. The reaction mixture was concentrated and purified by prep-HPLC (Waters 2767/Qda, Column: Waters Xbridge19*150 mm 10 um, Mobile Phase A: $H_2O$ (0.1% $NH_4OH$), B: ACN) to give the mixture of cis and trans (100 mg) as a white solid. The mixture was separated by SFC (OJ-H, 2.5*25 cm, 10 um, mobile phase: $CO_2$/MeOH ($NH_3$)=80/20, 70 ml/min). The desired fractions were collected and the solvent evaporated to afford Compound 61 (32.20 mg, $R_T$=1.083 min, 13% yield, trans or cis) and Compound 62 (37.8 mg, $R_T$=1.559 min, 15% yield, cis or trans).

Compound 61: $^1$H NMR MeOD-$d_4$ (400 MHz): δ 7.34-7.25 (m, 6H), 3.76-3.65 (m, 8H), 3.40-3.35 (m, 1H), 2.90 (s, 3H), 2.33-2.28 (m, 2H), 2.02-1.94 (m, 2H), 1.93-1.88 (m, 2H).

Compound 62: $^1$H NMR MeOD-$d_4$ (400 MHz): δ 7.35-7.24 (m, 6H), 3.78-3.72 (m, 2H), 3.69-3.64 (m, 6H), 3.38-3.34 (m, 1H), 2.90 (s, 3H), 2.30-2.25 (m, 2H), 2.04-2.02 (m, 2H), 1.96-1.91 (m, 2H).

Example B37

Preparation of Compound 63

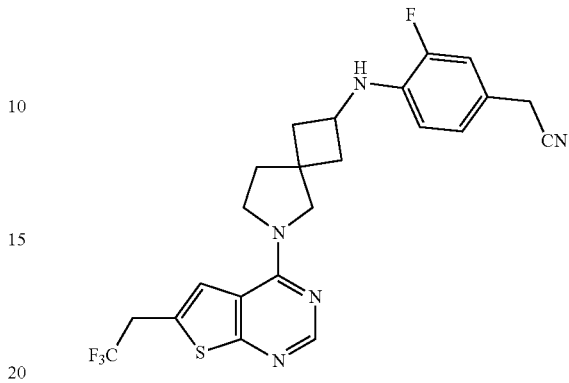

To a solution of intermediate 3 (6-(6-(2,2,2-trifluoroethyl)thieno[2,3-d]pyrimidin-4-yl)-6-azaspiro[3.4]octan-2-amine TFA salt) (200 mg) in 1,4-dioxane (2 mL) was added 2-(4-bromo-3-fluorophenyl)acetonitrile (250 mg, 1.170 mmol), t-sodium terbutylate (168 mg, 1.775 mmol), BrettPhos (30 mg, 0.056 mmol) and $Pd_2(dba)_3$ (53 mg, 0.056 mmol). The resulting mixture was bubbled with Ar and sealed in a microwave tube. After being heated at 140° C. for 2 hours under microwave. The mixture was cooled to room temperature, poured into water (100 mL) and extracted with ethyl acetate (100 mL×3). The combined organic layers were washed with brine (50 mL×2), dried over $Na_2SO_4$, filtered and concentrated under reduced pressure. The residue was purified by prep-HPLC (Waters 2767/Qda, Column: Waters Xbridge 20*150 mm um, Mobile Phase A: $H_2O$ (0.1% $NH_3.H_2O$), B: ACN). The desired fractions were collected and the solvent evaporated to afford Compound 63 (23.45 mg).

Compound 63: $^1$H NMR MeOD-$d_4$ (400 MHz): δ 8.29 (d, J=7.6 Hz, 1H), 7.67-7.63 (m, 1H), 6.98-6.96 (m, 2H), 6.70-6.64 (m, 1H), 4.07-3.99 (m, 1H), 3.94-3.83 (m, 6H), 3.74 (s, 2H), 2.61-2.53 (m, 2H), 2.20-2.03 (m, 4H).

Example B38

Preparation of Compounds 64 and 65

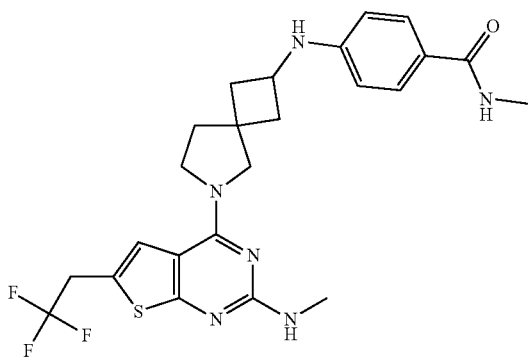

Compound 64: trans or cis
Compound 65: cis or trans

A solution of intermediate 24 ((6-(2-chloro-6-(2,2,2-trifluoroethyl)thieno[2,3-d]-pyrimidin-4-yl)-6-azaspiro[3.4]octan-2-yl)amino)-N-methylbenzamide) (200 mg, 0.393 mmol) in $CH_3NH_2$ (5 mL, 2N in THF) was stirred at 100° C. for 16 hours. After being concentrated under reduced pressure, the residue was purified by prep-TLC (DCM:MeOH=15:1) to give the mixture of trans and cis (150 mg). The mixture was separated by SFC (OJ-H, 2.5*25 cm, 10 um, mobile phase: $CO_2$/MeOH=65/35, 50 ml/min) to afford Compound 64 (52.16 mg, 26%, trans or cis) as a white solid and Compound 65 (45.70 mg, 23%, cis or trans) as a white solid.

Compound 64: $^1$H NMR MeOD-$d_4$ (400 MHz): δ 7.61 (d, J=8.4 Hz, 2H), 7.33 (s, 1H), 6.57 (d, J=8.4 Hz, 2H), 4.05-4.01 (m, 1H), 3.84-3.82 (m, 2H), 3.74-3.65 (m, 4H), 2.91 (s, 3H), 2.87 (s, 3H), 2.55-2.51 (m, 2H), 2.16-2.13 (m, 2H), 2.04-1.99 (m, 2H).

Compound 65: $^1$H NMR DMSO-$d_6$ (400 MHz): δ 7.96 (d, J=4.4 Hz, 1H), 7.59 (d, J=8.4 Hz 2H), 7.43 (s, 1H), 6.52-6.44 (m, 4H), 4.09-3.68 (s, 7H), 3.17 (d, J=5.2 Hz, 2H), 2.79-2.71 (m, 6H), 1.98-1.89 (m, 4H).

Example B39

Preparation of Compounds 66 and 67

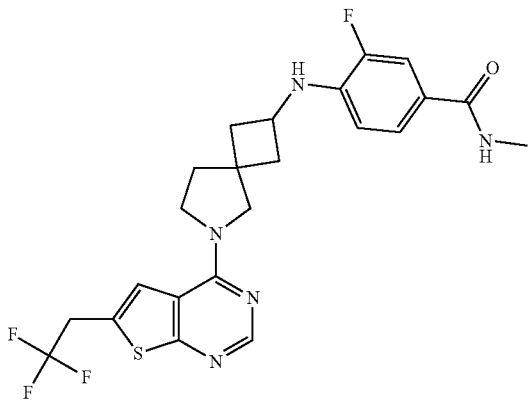

Compound 66: trans or cis
Compound 67: cis or trans

To a solution of intermediate 26 (4-((6-azaspiro[3.4]octan-2-yl)amino)-3-fluoro-N-methylbenzamide) (200 mg, 0.722 mmol) in iPrOH (4 mL) were added DIPEA (279 mg, 2.17 mmol) and 4-chloro-6-(2,2,2-trifluoroethyl)thieno[2,3-d]pyrimidine (182 mg, 0.722 mmol). After being stirred at room temperature for 12 hours, the mixture was concentrated. The residue was purified by prep-HPLC (Waters 2767/Qda, Column: Waters Xbridge19*150 mm 10 um, Mobile Phase A: $H_2O$ (0.1% $NH_4OH$), B: ACN) and treated with ion exchange resin to afford the mixture of cis and trans. The mixture was separated by SFC (AD-H, 3*25 cm, 5 um, mobile phase: $CO_2$/$^i$PrOH (0.1% DEA)=60/40, 50 ml/min) to afford Compound 66 (143 mg, 40% yield, trans or cis) as a white solid and Compound 67 (44 mg, 12% yield, cis or trans) as a white solid.

Compound 66: $^1$H NMR (400 MHz, MeOD-$d_4$): δ 8.30 (s, 1H), 7.68 (s, 1H), 7.52-7.45 (m, 2H), 6.68 (t, J=8.6 Hz, 1H), 4.16-4.08 (m, 1H), 3.96-3.80 (m, 6H), 2.88 (s, 3H), 2.65-2.60 (m, 2H), 2.14-2.09 (m, 4H).

Compound 67: $^1$H NMR (400 MHz, MeOD-$d_4$): δ 8.28 (s, 1H), 7.63 (s, 1H), 7.53-7.44 (m, 2H), 6.70 (t, J=8.4 Hz, 1H), 4.17-4.07 (m, 1H), 3.92-3.84 (m, 6H), 2.88 (s, 3H), 2.60-2.55 (m, 2H), 2.23-2.12 (m, 4H).

Example B40

Preparation of Compounds 68 and 69

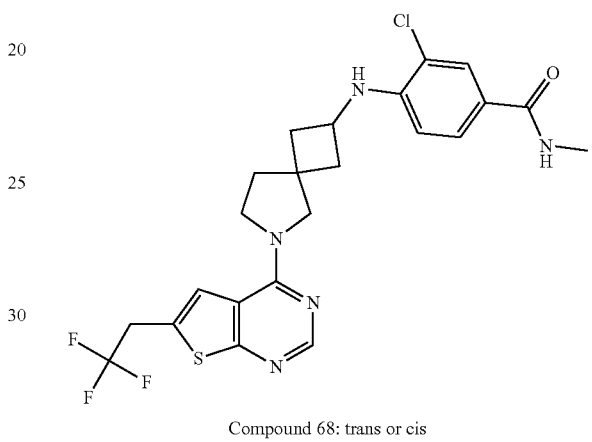

Compound 68: trans or cis
Compound 69: cis or trans

To a solution of intermediate 28 (260 mg, crude) in isopropanol (10 mL) was added 4-chloro-6-(2,2,2-trifluoroethyl)thieno[2,3-d]pyrimidine (224 mg, 0.887 mmol) and DIPEA (343 mg, 2.662 mmol). After being stirred at room temperature for 12 hours, the mixture was poured into water (30 mL) and extracted with EtOAc (30 mL×3).

The combined organic layers were dried over $Na_2SO_4$, filtered and concentrated under reduced pressure. The residue was purified by silica gel column chromatography (PE/EA=3/1). The desired fractions were collected and the solvent was evaporated to give the mixture of cis and trans isomers (260 mg). The mixture was separated by SFC (AD-H, 3*25 cm, 5um, mobile phase: $CO_2$/$^i$PrOH (0.1% DEA)=60/40, 50 ml/min) to afford Compound 68 (95.75 mg, trans or cis) and Compound 69 (40.27 mg, cis or trans).

Compound 68: $^1$H NMR DMSO-$d_6$ (400 MHz): δ 8.33 (s, 1H), 8.19-8.16 (m, 1H), 7.77-7.73 (m, 2H), 7.65-7.62 (m, 1H), 6.69 (d, J=8.8 Hz, 1H), 5.92 (d, J=6.4 Hz, 1H), 4.12-4.02 (m, 3H), 3.89-3.73 (m, 4H), 2.73 (d, J=4.4 Hz, 3H), 2.53-2.50 (m, 2H), 2.14-2.03 (m, 4H).

Compound 69: $^1$H NMR DMSO-$d_6$ (400 MHz): δ 8.32 (s, 1H), 8.19-8.16 (m, 1H), 7.77 (d, J=1.6 Hz, 1H), 7.69-7.65 (m, 2H), 6.70 (d, J=8.8 Hz, 1H), 5.90 (d, J=6.4 Hz, 1H), 4.09-4.02 (m, 3H), 3.77 (br s, 4H), 2.73 (d, J=4.4 Hz, 3H), 2.46-2.44 (m, 2H), 2.19-2.14 (m, 4H).

Example B41

Preparation of Compounds 70, 71 and 72

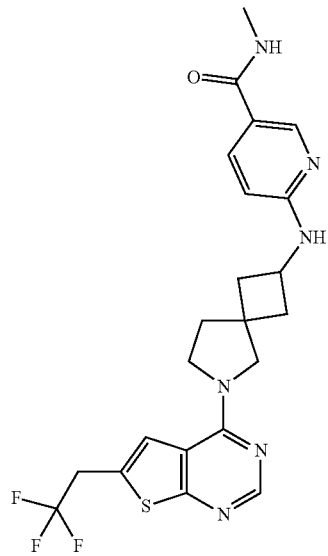

Compound 70: mixture of trans or cis (TFA salt)
Compound 71: trans or cis
Compound 72: cis or trans To a solution of intermediate 32 (6-(6-azaspiro[3.4]octan-2-ylamino)-N-methyl-nicotinamide TFA salt) (100 mg) in isopropanol (5 mL) were added DIPEA (230 mg, 1.78 mmol) and 4-chloro-6-(2,2,2-trifluoroethyl)thieno[2,3-d]pyrimidine (90 mg, 0.357 mmol). After being stirred at room temperature for 12 hours, the mixture was concentrated. The residue was purified by prep-HPLC (Waters 2767/Qda, Column: Waters Xbridge19*150 mm 10 um, Mobile Phase A: H$_2$O (0.1% TFA), B: ACN) and then treated with ion exchange resin. The desired fraction were collected and the solvent was evaporated to afford Compound 70 (123.82 mg, TFA salt; mixture of trans and cis) as a white solid. The mixture was separated by SFC (AD-H, 2.5*25 cm, 10 um, mobile phase: CO$_2$/MeOH=60/40, 60 ml/min). The desired fractions were collected and the solvent was evaporated to afford Compound 71 (16.02 mg, trans or cis) and Compound 72 (20.2 mg, cis or trans).

Compound 70: $^1$H NMR MeOD-d$_4$ (400 MHz): δ 8.47 (d, J=6.4 Hz, 1H), 8.38-8.36 (m, 1H), 8.25 (d, J=9.6 Hz, 1H), 7.80-7.78 (m, 1H), 7.08-7.05 (m, 1H), 4.43-4.39 (m, 1H), 4.07-3.93 (m, 6H), 2.93 (s, 3H), 2.75-2.67 (m, 2H), 2.35-2.25 (m, 4H).

Compound 71: $^1$H NMR MeOD-d$_4$ (400 MHz): δ 8.45 (d, J=2.0 Hz, 1H), 8.29 (s, 1H), 7.84-7.81 (m, 1H), 7.66 (s, 1H), 6.50 (d, J=8.4 Hz, 1H), 4.43-4.41 (m, 1H), 3.95-3.84 (m, 6H), 2.87 (s, 3H), 2.61-2.56 (m, 2H), 2.11-2.04 (m, 4H).

Compound 72: $^1$H NMR MeOD-d$_4$ (400 MHz): δ 8.46 (d, J=2.4 Hz, 1H), 8.27 (s, 1H), 7.84-7.81 (m, 1H), 7.62 (s, 1H), 6.50 (d, J=8.8 Hz, 1H), 4.47-4.39 (m, 1H), 3.91-3.81 (m, 6H), 2.87 (s, 3H), 2.57-2.52 (m, 2H), 2.22-2.20 (m, 2H), 2.12-2.07 (m, 2H).

Example B42

Preparation of Compounds 73, 74 and 75

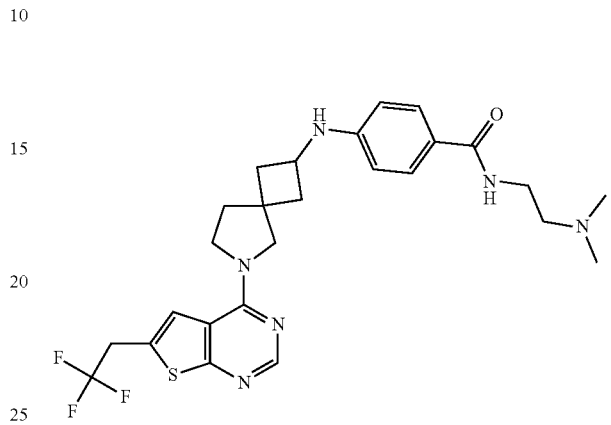

Compound 73: mixture of trans and cis
Compound 74: trans or cis
Compound 75: cis or trans To a solution of intermediate 35 (4-((6-(6-(2,2,2-trifluoroethyl)thieno[2,3-d]pyrimidin-4-yl)-6-azaspiro[3.4]octan-2-yl)amino)benzoic acid) (500 mg, 1.08 mmol) in THF (5 mL) were added N,N-dimethylethane-1,2-diamine (143 mg, 1.62 mmol), HOBT (219 mg, 1.62 mmol), EDCI (311 mg, 1.62 mmol) and Et$_3$N (163 mg, 1.62 mmol). The resulting mixture was stirred at room temperature overnight. After being concentrated under reduced pressure, the residue was purified by prep-HPLC (Waters 2767/Qda, Column: Waters Xbridge19*150 mm 10 um, Mobile Phase A: H$_2$O (0.1% NH$_4$OH), B: ACN). The desired fractions were collected and the solvent was evaporated to give Compound 73 as a mixture of cis and trans isomers (170 mg), which was separated by SFC (AD-H, 3*25 cm, 5um, mobile phase: CO$_2$/$^i$PrOH (0.1% DEA)=60/40, 50 ml/min) to afford Compound 74 (70 mg, 12% yield, trans or cis) and Compound 75 (38 mg, 7% yield, cis or trans).

Compound 74: $^1$H NMR MeOD-d$_4$ (400 MHz): δ 8.29 (s, 1H), 7.67-7.63 (m, 3H), 6.58 (d, J=8.4 Hz, 2H), 4.09-4.02 (m, 1H), 3.94-3.84 (m, 6H), 3.50 (t, J=6.4 Hz, 2H), 2.64-2.58 (m, 4H), 2.37 (s, 6H), 2.11 (br s, 2H), 2.04-1.99 (m, 2H).

Compound 75: $^1$H NMR MeOD-d$_4$ (400 MHz): δ 8.27 (s, 1H), 7.66-7.63 (m, 3H), 6.58 (d, J=8.4 Hz, 2H), 4.07-4.03 (m, 1H), 3.91-3.82 (m, 6H), 3.52 (t, J=6.4 Hz, 2H), 2.70 (t, J=6.4 Hz, 2H), 2.59-2.54 (m, 2H), 2.43 (s, 6H), 2.20 (br s, 2H), 2.08-2.03 (m, 2H).

Example B43

Preparation of Compounds 76 and 77

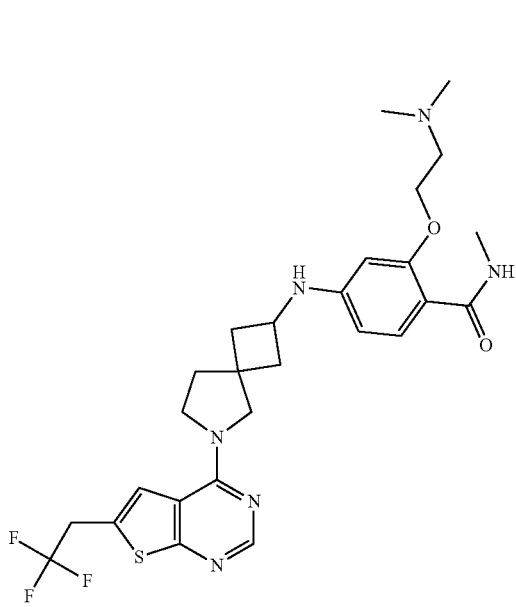

Compound 76 (trans or cis)
Compound 77 (cis or trans)

To a solution of intermediate 38 (250 mg, 0.45 mmol) in DMF (10 ml) was added methanamine (HCl salt, 30.4 mg), DIPEA (1 ml) and HATU (205 mg, 0.54 mmol). After being stirred at room temperature for 3 hours, the solution was concentrated and diluted with EA (15 mL). The organic layer was washed with brine (15 mL×2), dried over $Na_2SO_4$, filtered and concentrated under reduced pressure. The residue was purified by prep-HPLC (Waters 2767/Qda, Column: SunFire 19*250 mm 10 um, Mobile Phase A: 0.1% TFA/$H_2O$, B: ACN), then separated by SFC (OJ, 2.5*25 cm, 10 um, mobile phase: $CO_2$/MeOH (0.1% $NH_3$)=70/30, 50 ml/min) to afford Compound 76 (13.08 mg; trans or cis) as a white solid and Compound 77 (11.17 mg; cis or trans) as a white solid.

Compound 76: $^1$H NMR MeOD-$d_4$ (400 MHz): δ 8.29 (s, 1H), 7.72 (d, J=8.8 Hz, 1H), 7.67 (s, 1H), 6.27-6.24 (m, 1H), 6.19 (d, J=2.0 Hz, 1H), 4.19 (t, J=5.2 Hz, 2H), 4.07-4.06 (m, 1H), 3.95-3.85 (m, 6H), 2.88 (s, 3H), 2.79-2.77 (m, 2H), 2.64-2.59 (m, 2H), 2.35 (s, 6H), 2.12 (br s, 2H), 2.05-2.00 (m, 2H)

Compound 77: $^1$H NMR MeOD-$d_4$ (400 MHz): δ 8.27 (s, 1H), 7.71 (d, J=8.8 Hz, 1H), 7.63 (s, 1H), 6.27-6.25 (m, 1H), 6.20 (d, J=2.0 Hz, 1H), 4.22 (t, J=5.2 Hz, 2H), 4.08-4.04 (m, 1H), 3.91-3.82 (m, 6H), 2.88 (s, 3H), 2.81 (br s, 2H), 2.60-2.54 (m, 2H), 2.39 (s, 6H), 2.08 (br s, 2H), 2.06-2.02 (m, 2H)

Example B44

Preparation of Compounds 78, 79 and 80

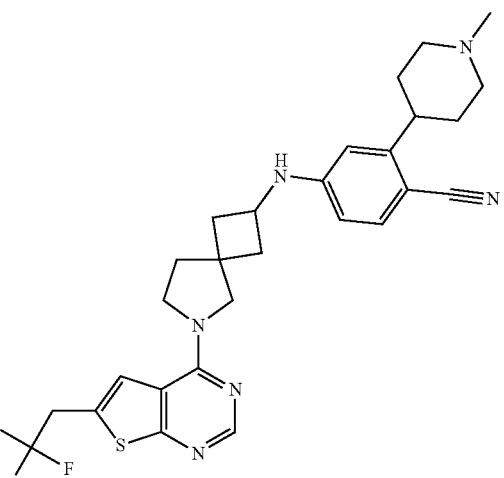

Compound 78: mixture of trans and cis
Compound 79: trans or cis
Compound 80: cis or trans A mixture of intermediate 42 (4-(6-azaspiro[3.4]octan-2-ylamino)-2-(1-methylpiperidin-4-yl)benzonitrile TFA salt) (280 mg), 4-chloro-6-(2,2,2-trifluoroethyl)thieno[2,3-d]pyrimidine (227 mg, 0.9 mmol) and DIPEA (387 mg, 3.0 mmol) in iPrOH (10 mL) was stirred at room temperature for 2 hours. The reaction mixture was concentrated and the residue was purified by prep-HPLC (Agilent G6120B G1315D DADVL Detector and G4260B ELSD, Xbridge C18 5 mm 150*4.6 mm, Mobile Phase A: $NH_4OH$ 0.1% in water, B: $NH_4OH$ 0.1% in $CH_3CN$). The desired fractions were collected and the solvent was evaporated to afford Compound 78 as a mixture of cis and trans isomers (87 mg) as a white solid. Compound 78 was separated by SFC (IA, 2.5*25 cm, 10 um, mobile phase: $CO_2$/EtOH (0.05% DEA) =75/25, 50 ml/min) to afford Compound 79 (16 mg; trans or cis) as a white solid and Compound 80 (20 mg; cis or trans) as a white solid.

Compound 79: $^1$H NMR MeOD-$d_4$ (400 MHz): δ 8.30 (s, 1H), 7.68 (s, 1H), 7.35 (d, J=8.8 Hz, 1H), 6.52-6.45 (m, 2H), 4.09-3.80 (m, 7H), 3.04-3.01 (m, 2H), 2.85-2.75 (m, 1H), 2.63-2.58 (m, 2H), 2.34 (s, 3H), 2.27-2.00 (m, 6H), 1.87-1.75 (m, 4H).

Compound 80: $^1$H NMR MeOD-$d_4$ (400 MHz): δ 8.27 (s, 1H), 7.63 (s, 1H), 7.36 (d, J=8.8 Hz, 1H), 6.53-6.46 (m, 2H), 4.07-3.79 (m, 7H), 3.05-3.02 (m, 2H), 2.84-2.76 (m, 1H), 2.59-2.54 (m, 2H), 2.36 (s, 3H), 2.24-2.18 (m, 4H), 2.08-2.03 (m, 2H), 1.85-1.78 (m, 4H).

Example B45

Preparation of Compound 81

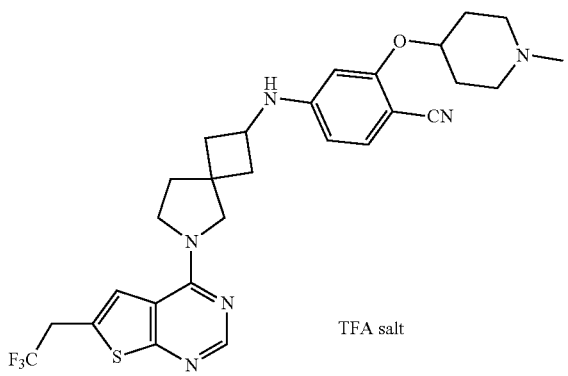

TFA salt

To a mixture of intermediate 46 (4-((6-azaspiro[3.4]octan-2-yl)amino)-2-((1-methyl-piperidin-4-yl)oxy)benzonitrile TFA salt) (500 mg) and 4-chloro-6-(2,2,2-trifluoroethyl)thieno[2,3-d]pyrimidine (300 mg, 1.19 mmol) in iPrOH (10 mL) was added DIPEA (767 mg, 5.95 mmol). After being stirred at room temperature overnight, the mixture was concentrated under reduced pressure. The residue was purified by prep-HPLC (Waters 2767/Qda, Column: Waters Xbridge19*150 mm 10 um, Mobile Phase A: $H_2O$ (0.1% TFA), B: ACN). The described fractions were collected and the solvent was evaporated to afford (142 mg) as a TFA salt.

Compound 81: $^1$H NMR MeOD-$d_4$ (400 MHz): δ 8.46-8.43 (m, 1H), 7.78-7.76 (m, 1H), 7.33-7.30 (m, 1H), 6.30-6.20 (m, 2H), 4.92-4.88 (m, 0.5H), 4.54-4.48 (m, 0.5H), 4.24-3.74 (m, 9H), 3.55-2.98 (m, 4H), 2.92-2.90 (m, 1H), 2.65-2.59 (m, 2H), 2.28-2.02 (m, 8H).

Example B46

Preparation of Compound 82

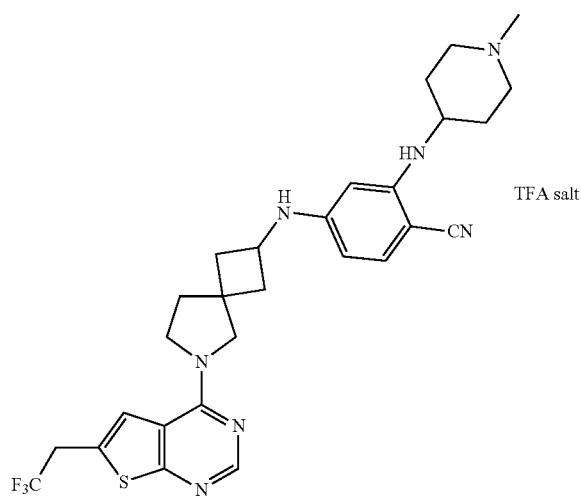

TFA salt

A mixture of intermediate 49 (4-(6-azaspiro[3.4]octan-2-ylamino)-2-((1-methyl-piperidin-4-yl)amino)benzonitrile TFA salt) (60 mg), 4-chloro-6-(2,2,2-trifluoroethyl)-thieno[2,3-d]pyrimidine (28 mg, 0.11 mmol) and DIPEA (43 mg, 0.33 mmol) in $^i$PrOH (5 mL) was stirred at room temperature for 2 hours. After the reaction was completed, the reaction mixture was concentrated and the residue was purified by prep-HPLC (Waters 2767/Qda, Column: SunFire 19*250 mm 10 um, Mobile Phase A: 0.1% TFA/$H_2O$, B: ACN). The desired fractions were collected and the solvent was evaporated to afford Compound 82 (34 mg; a TFA salt) as a yellow solid.

Compound 82: $^1$H NMR MeOD-$d_4$ (400 MHz): δ 8.29-8.27 (m, 1H), 7.67-7.63 (m, 1H), 7.15-7.12 (m, 1H), 6.03-6.00 (m, 1H), 5.88-5.86 (m, 1H), 3.93-3.70 (m, 8H), 3.50-3.38 (m, 2H), 3.16-3.04 (m, 2H), 2.84-2.82 (m, 3H), 2.63-2.51 (m, 2H), 2.27-2.03 (m, 6H), 1.86-1.72 (m, 2H).

Example B47

Preparation of Compounds 83 and 84

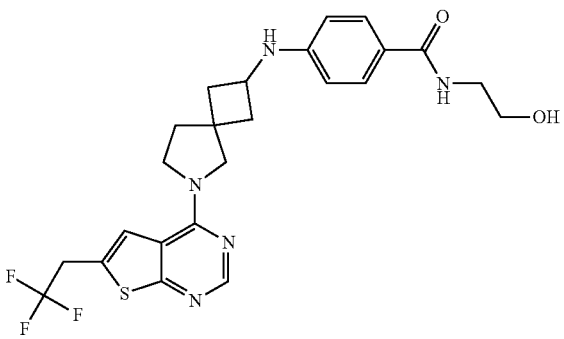

Compound 83: trans or cis
Compound 84: cis or trans

To a solution of intermediate 35 (4-((6-(6-(2,2,2-trifluoroethyl)thieno[2,3-d]pyrimidin-4-yl)-6-azaspiro[3.4]octan-2-yl)amino)benzoic acid) (300 mg, 0.65 mmol), 2-aminoethan-1-ol (74 mg, 1.3 mmol) in DMF (5 mL) was added HATU (246 mg, 0.65 mmol) and DIPEA (251 mg, 1.95 mmol). After being stirred at room temperature for 3 hours, the reaction mixture was purified by prep-HPLC (Waters 2767/Qda, Column: Waters Xbridge19*150 mm 10 um, Mobile Phase A: $H_2O$ (0.1% $NH_4OH$), B: ACN). The desired fractions were collected and the solvent was evaporated to give the mixture of cis and trans isomers (100 mg, 40% yield) as a white solid. This mixture of cis and trans isomers was separated by SFC (AD-H, 2.5*25 cm, 10 um, mobile phase: $CO_2$/EtOH (15% ACN)=60/40, 50 ml/min) to afford Compound 83 (40 mg, 80% yield; trans or cis) as a white solid and Compound 84 (37 mg, 74% yield; cis or trans) as a white solid.

Compound 83: $^1$H NMR MeOD-$d_4$ (400 MHz): δ 8.29 (s, 1H), 7.67-7.63 (m, 3H), 6.58 (d, J=8.8 Hz, 2H), 4.13-4.01 (m, 1H), 3.93-3.88 (m, 6H), 3.68 (t, J=5.9 Hz, 2H), 3.46 (t, J=5.9 Hz, 2H), 2.63-2.57 (m, 2H), 2.11 (br s, 2H), 2.04-1.99 (m, 2H).

Compound 84: $^1$H NMR MeOD-$d_4$ (400 MHz): δ 8.29 (s, 1H), 7.67-7.64 (m, 3H), 6.59 (d, J=8.8 Hz, 2H), 4.13-4.01 (m, 1H), 3.94-3.88 (m, 6H), 3.69 (t, J=6.0 Hz, 2H), 3.47 (t, J=6.0 Hz, 2H), 2.59-2.55 (m, 2H), 2.22 (br s, 2H), 2.08-2.03 (m, 2H).

Example B48

Preparation of Compounds 85 and 86

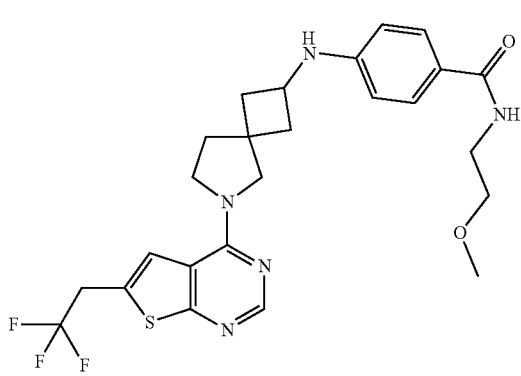

Compound 85: trans or cis
Compound 86: cis or trans

To a solution of intermediate 35 (4-(((6-(6-(2,2-trifluoroethyl)thieno[2,3-d]pyrimidin-4-yl)-6-azaspiro[3.4]octan-2-yl)amino)benzoic acid) (300 mg, 0.65 mmol), 2-methoxyethan-1-amine (197 mg, 1.3 mmol) in DMF (5 mL) was added HATU (246 mg, 0.65 mmol) and DIPEA (251 mg, 1.95 mmol). After being stirred at room temperature for 3 hours, the reaction mixture was purified by prep-HPLC (Waters 2767/Qda, Column: Waters Xbridge19*150 mm 10 um, Mobile Phase A: $H_2O$ (0.1% $NH_4OH$), B: ACN). The desired fractions were collected and the solvent was evaporated to give the mixture of cis and trans (100 mg, 30% yield) as a white solid. This mixture of cis and trans isomers was separated by SFC (AD-H, 3*25 cm, 5um, mobile phase: $CO_2$/$^i$PrOH (0.1% DEA)=60/40, 50 ml/min) to afford Compound 85 (35 mg, 70% yield; trans or cis) as a white solid and Compound 86 (33.67 mg, 67% yield; cis or trans) as a white solid.

Compound 85: $^1$H NMR MeOD-$d_4$ (400 MHz): δ 8.27 (s, 1H), 7.64-7.62 (m, 3H), 6.58 (d, J=8.4 Hz, 2H), 4.09-4.01 (m, 1H), 3.91-3.83 (m, 6H), 3.58-3.48 (m, 4H), 3.37 (s, 3H), 2.59-2.54 (m, 2H), 2.21 (br s, 2H), 2.102-2.03 (m, 2H).

Compound 86: $^1$H NMR MeOD-$d_4$ (400 MHz): δ 8.29 (s, 1H), 7.67-7.62 (m, 3H), 6.58 (d, J=8.4 Hz, 2H), 4.09-4.00 (m, 1H), 3.94-3.84 (m, 6H), 3.57-3.44 (m, 4H), 3.37 (s, 3H), 2.62-2.57 (m, 2H), 2.11 (br s, 2H), 2.04-1.99 (m, 2H).

Example B49

Preparation of Compounds 87 and 88

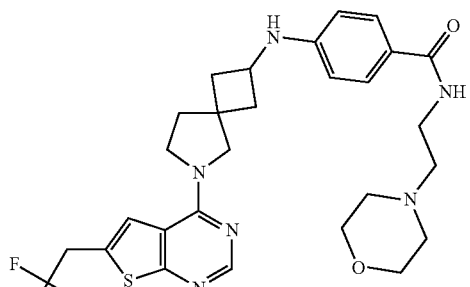

Compound 87: trans or cis
Compound 88: cis or trans

A solution of intermediate 35 (4-(((6-(6-(2,2-trifluoroethyl)thieno[2,3-d]pyrimidin-4-yl)-6-azaspiro[3.4]octan-2-yl)amino)benzoic acid) (300 mg, 0.649 mmol), 2-morpholinoethan-1-amine (85 mg, 0.649 mmol), EDCI (125 mg, 0.649 mmol), HOBT (88 mg, 0.649 mmol) and TEA (197 mg, 0.1.95 mmol) in DCM (5 mL) was stirred at room temperature for 8 hours. The solution was concentrated and diluted with EA (15 mL). The organic layer was washed with brine (15 mL×2), dried over $Na_2SO_4$, filtered and concentrated under reduced pressure. The residue was purified by prep-HPLC (Waters 2767/Qda, Column: Waters Xbridge19*150 mm 10 um, Mobile Phase A: $H_2O$ (0.1% $NH_4OH$), B: ACN) and treated with ion exchange resin to afford the mixture of cis and trans isomers (200 mg), which was separated by SFC (AD-H, 2.5*25 cm, um, mobile phase: $CO_2$/EtOH (0.1% DEA)=60/40, 50 ml/min) to afford Compound 87 (60 mg, 16% yield; trans or cis) as a white solid and Compound 88 (6 mg, 2% yield; cis or trans) as a white solid.

Compound 87: $^1$H NMR MeOD-$d_4$ (400 MHz): δ 8.29 (s, 1H), 7.67 (s, 1H), 7.62 (d, J=8.8 Hz, 2H), 6.58 (d, J=8.4 Hz, 2H), 4.08-4.04 (m, 1H), 3.94-3.84 (m, 6H), 3.71 (t, J=4.6 Hz, 4H), 3.51 (t, J=6.8 Hz, 2H), 2.62-2.57 (m, 8H), 2.12 (br s, 2H), 2.05-2.00 (m, 2H)

Compound 88: $^1$H NMR MeOD-$d_4$ (400 MHz): δ 8.27 (s, 1H), 7.64-7.62 (m, 3H), 6.59 (d, J=8.8 Hz, 2H), 4.07-4.03 (m, 1H), 3.91-3.83 (m, 6H), 3.70 (t, J=4.6 Hz, 4H), 3.50 (t, J=6.8 Hz, 2H), 2.60-2.54 (m, 8H), 2.21 (br s, 2H), 2.06-2.03 (m, 2H)

Example B50

Preparation of Compounds 89, 90 and 91

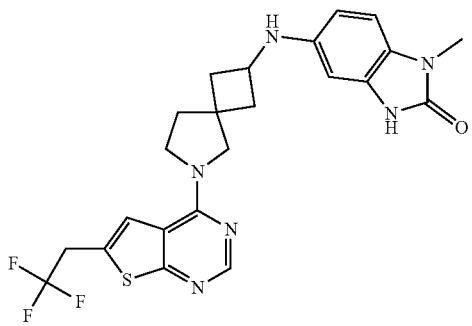

Compound 89: mixture of trans or cis
Compound 90: trans or cis
Compound 91: cis or trans To a solution of intermediate 5 (160 mg, 0.469 mmol), 5-amino-1-methyl-1H-benzo[d]-imidazol-2(3H)-one (122 mg, 0.750 mmol), sodium cyanoborohydride (58.9 mg, 0.937 mmol), and MeOH (12 mL) was added a solution of AcOH (56.3 mg, 0.937 mmol) in MeOH (4 mL). After stirring at 45° C. for 12 hours, the reaction mixture was concentrated to dryness under reduced pressure to afford the crude product, which was diluted with water (5 mL) and extracted with ethyl acetate (20 mL×3). The combined organic layers were concentrated to dryness under reduced pressure to afford the crude product, which was purified by prep-HPLC (Gilson 281, Xtimate C18 150×25 mm×m, Mobile Phase A: water (0.225% formic acid), B: ACN)). The pure fractions were collected and evaporated under vacuum to obtain a residue, which was lyophilized to dryness to afford Compound 89 as a white solid (73.2 mg, 30% yield). Compound 89 was further separated by SFC (Amylose-C, 3*25 cm, 10 um, mobile phase: $CO_2$/IPA (0.1% $NH_3.H_2O$)=45/55, 70 ml/min). The pure fractions were collected and evaporated under vacuum. The obtained residues were lyophilized to dryness to give Compound 90 (21.64 mg, 35% yield; trans or cis) as a white powder and Compound 91 (19.69 mg, 32% yield; cis or trans) as a white powder.

Compound 89: $^1$H NMR DMSO-$d_6$ (400 MHz): δ 10.45 (s, 1H), 8.38-8.31 (m, 1H), 7.75-7.70 (m, 1H), 6.80-6.77 (m, 1H), 6.24-6.22 (m, 2H), 5.59 (br s, 1H), 4.11-4.03 (m, 2H), 3.87-3.75 (m, 5H), 3.17 (s, 3H), 2.47-2.36 (m, 2H), 2.11-1.86 (m, 4H).

Compound 90:
$^1$H NMR DMSO-$d_6$ (400 MHz): δ 10.46 (s, 1H), 8.32 (s, 1H), 7.70 (s, 1H), 6.79 (d, J=8.8 Hz, 1H), 6.24-6.22 (m, 2H), 5.60-5.58 (m, 1H), 4.07 (q, J=11.2 Hz, 2H), 3.89-3.76 (m, 5H), 3.17 (s, 3H), 2.44-2.37 (m, 2H), 2.33 (br s, 2H), 1.94-1.89 (m, 2H)

Compound 91: $^1$H NMR DMSO-$d_6$ (400 MHz): δ 10.46 (s, 1H), 8.33 (s, 1H), 7.75 (br s., 1H), 6.78 (d, J=8.8 Hz, 1H), 6.24-6.22 (m, 2H), 5.61 (d, J=6.4 Hz1H), 4.07 (q, J=10.8 Hz, 2H), 3.91-3.78 (m, 5H), 3.17 (s, 3H), 2.47-2.40 (m, 2H), 2.01 (br s, 2H), 1.90-1.86 (m, 2H)

Example B51

Preparation of Compound 92

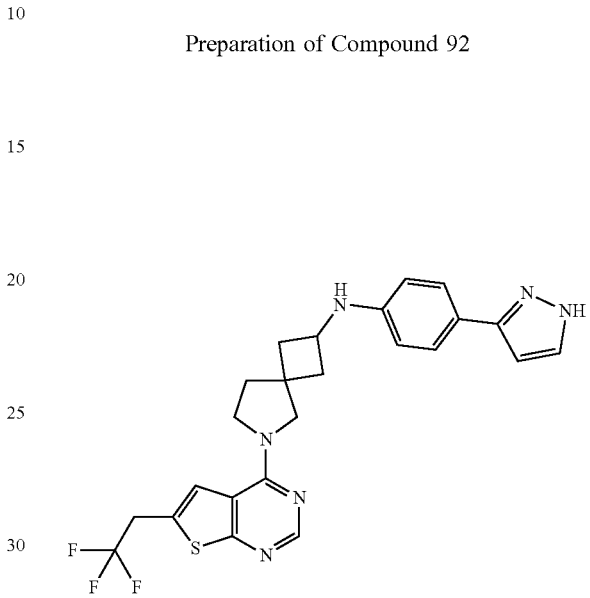

To a solution of Intermediate 5 (150 mg, 0.439 mmol), 4-(1H-pyrazol-3-yl)aniline (105 mg, 0.660 mmol), sodium cyanotrihydroborate (55.2 mg, 0.878 mmol) and dry methanol (10 mL) was added a solution of acetic acid (52.8 mg, 0.879 mmol) in methanol (2 mL). After stirring at 45° C. for 6 h, the mixture was cooled to room temperature and diluted with water (20 mL). The mixture was adjusted to obtain pH=8 by saturated sodium bicarbonate and extracted with DCM (20 mL×3). The combined organic layers were dried over anhydrous $Na_2SO_4$, filtered and concentrated under reduced pressure to give the crude product, which was purified by prep-HPLC (Gilson 281, Column: Phenomenex Gemini 150*25 mm*10 um, Mobile Phase A: water (0.05% ammonia hydroxide v/v), Mobile Phase B: ACN). The pure fractions were collected and evaporated under vacuum to give a residue, which was lyophilized to dryness to give the Compound 92 (99.0 mg, 46% yield) as a light yellow powder.

Compound 92: $^1$H NMR DMSO-$d_6$ (400 MHz): δ 12.93 (br s., 0.5H), 12.59 (br s., 0.5H), 8.34 (d, J=6.0 Hz, 1H), 7.75-7.51 (m, 4H), 6.57 (d, J=8.0 Hz, 2H), 6.46 (br s., 1H), 6.19-6.03 (m, 1H), 4.11-3.77 (m, 7H), 2.49-2.46 (m, 2H), 2.08-1.93 (m, 4H).

Example B52

Preparation of Compounds 93, 94 and 95

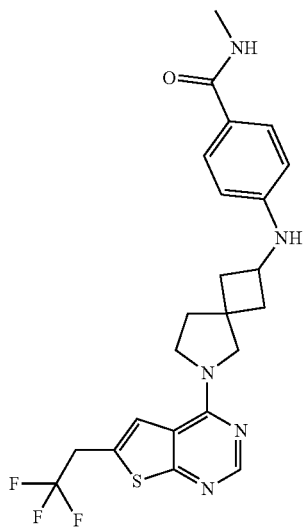

Compound 93: mixture of trans and cis
Compound 94: trans or cis
Compound 95: cis or trans To a solution of intermediate 5 (6-(6-(2,2,2-trifluoroethyl)thieno[2,3-d]pyrimidin-4-yl)-6-azaspiro[3.4]octan-2-one) (200 mg, 0.586 mmol), 4-amino-N-methylbenzamide (132 mg, 0.879 mmol), sodium cyanoborohydride (73.6 mg, 1.17 mmol), and MeOH (20 mL) was added a solution of AcOH (70.4 mg, 1.17 mmol) in MeOH (5 mL). After stirring at 45° C. for 12 h, the reaction mixture was concentrated to dryness under reduced pressure to afford the crude product, which was purified by prep-HPLC (Gilson 281, Column: Agela ASB 150×25 mm×5 m column, Mobile Phase A: water (0.05% HCl), B: ACN)). The pure fractions were collected and evaporated under vacuum to give a residue, which was lyophilized to dryness to give Compound 93 as a mixture of cis and trans isomers (173.9 mg, 61% yield). The mixture was separated by SFC (AS-H, 3*25 cm, Sum, mobile phase: CO$_2$/EtOH (0.1% NH$_3$.H$_2$O)=55/45, 40 ml/min). The pure fractions were collected and evaporated under vacuum to obtain residues, which were lyophilized to dryness to give the Compound 94 (36.83 mg, 23% yield; trans or cis) as a white solid and Compound 95 (48.21 mg, 30% yield; cis or trans) as a white solid.

Compound 93: $^1$H NMR (400 MHz, Methol-d4) δ 8.65-8.55 (m, 1H), 8.04-7.86 (m, 3H), 7.55-7.33 (m, 2H), 4.46-4.13 (m, 3H), 4.12-3.82 (m, 4H), 2.93 (s, 3H), 2.71-2.42 (m, 4H), 2.39-2.31 (m, 1H), 2.28-2.19 (m, 1H).

Compound 94: $^1$H NMR DMSO-d$_6$ (400 MHz): δ 8.32 (s, 1H), 7.99-7.96 (m, 1H), 7.70 (s, 1H), 7.60 (d, J=8.8 Hz, 2H), 6.51 (d, J=8.8 Hz, 2H), 6.45 (d, J=6.4 Hz, 1H), 4.36-3.75 (m, 7H), 2.72 (d, J=4.4 Hz, 3H), 2.47-2.44 (m, 2H), 2.12 (br s, 2H), 1.99-1.95 (m, 2H).

Compound 95: $^1$H NMR DMSO-d$_6$ (400 MHz): δ 8.33 (d, J=5.6 Hz, 1H), 7.99-7.97 (m, 1H), 7.74 (s, 1H), 7.60 (d, J=8.8 Hz, 2H), 6.53-6.47 (m, 2H), 4.11-3.76 (m, 7H), 2.72 (d, J=4.4 Hz, 3H), 2.58-2.51 (m, 2H), 2.02 (br s, 2H), 1.95-1.90 (m, 2H).

Example B53

Preparation of Compounds 96, 97 and 98

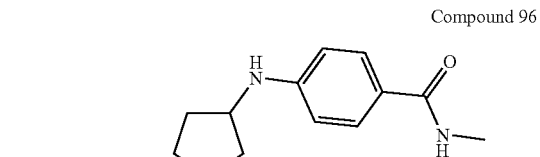

Compound 96

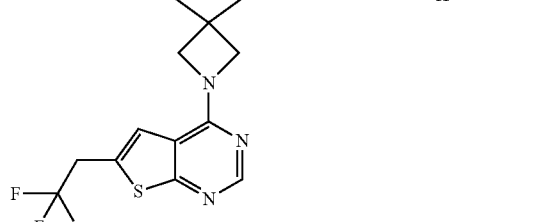

Compound 97

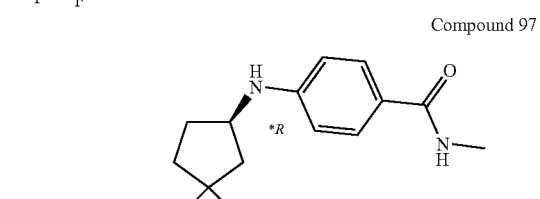

Compound 98

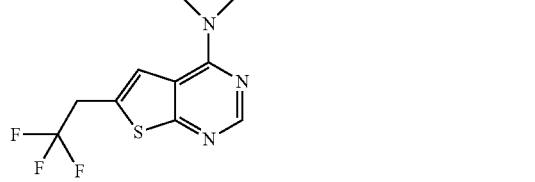

To a solution of intermediate 4 (200 mg, 0.586 mmol), 4-amino-N-methylbenzamide (132 mg, 0.879 mmol), sodium cyanoborohydride (73.6 mg, 1.17 mmol), and MeOH (20 mL) was added a solution of CH$_3$COOH (70.4 mg, 1.17 mmol) in MeOH (6 mL). After stirring at 45° C. for 12 hours, the reaction mixture was concentrated to dryness under reduced pressure to afford the crude product, which was purified by prep-HPLC (Gilson 281, Xtimate C18 150×25 mm×5 m column (eluent: 30% to 60% (v/v) water (0.225% FA)-ACN)). The pure fractions were collected and evaporated under reduced pressure to obtain a residue, which was lyophilized to dryness to give Compound 96 (150 mg) (white solid). Compound 96 was further separated by SFC (Amylose-C, 3*25 cm, 10 um, mobile phase: CO$_2$/EtOH (0.1% NH$_3$.H$_2$O)=45/55, 80 ml/min). The pure fractions were collected and the volatiles were removed under reduced pressure to obtain residues which were then lyophilized to dryness to give Compound 97 (38.8 mg, 14% yield) as a white solid and Compound 98 (41.2 mg, 15% yield) as a white solid.

Compound 96: $^1$H NMR (400 MHz, Methol-d4) δ 8.26 (s, 1H), 7.65-7.59 (m, 2H), 7.37 (s, 1H), 6.65-6.60 (m, 2H), 4.52-4.15 (m, 4H), 4.00-3.90 (m, 1H), 3.90-3.81 (m, 2H), 2.87 (s, 3H), 2.47-2.37 (m, 1H), 2.28-2.12 (m, 2H), 2.08-1.90 (m, 2H), 1.73-1.61 (m, 1H).

Compound 97: $^1$H NMR DMSO-$d_6$ (400 MHz): δ 8.26 (s, 1H), 7.65-7.58 (m, 2H), 7.37 (s, 1H), 6.68-6.55 (m, 2H), 4.53-4.06 (m, 4H), 4.01-3.90 (m, 1H), 3.90-3.78 (m, 2H), 2.87 (s, 3H), 2.48-2.36 (m, 1H), 2.28-2.10 (m, 2H), 2.08-1.90 (m, 2H), 1.73-1.59 (m, 1H).

Compound 98: $^1$H NMR DMSO-$d_6$ (400 MHz): δ 8.26 (s, 1H), 7.66-7.56 (m, 2H), 7.37 (s, 1H), 6.66-6.57 (m, 2H), 4.58-4.03 (m, 4H), 3.99-3.90 (m, 1H), 3.90-3.81 (m, 2H), 2.87 (s, 3H), 2.49-2.35 (m, 1H), 2.30-2.11 (m, 2H), 2.09-1.89 (m, 2H), 1.76-1.51 (m, 1H).

Example B54

Preparation of Compounds 99

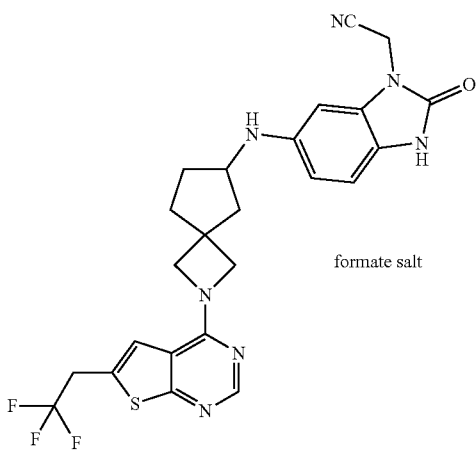

formate salt

To a solution of intermediate 55 (40.0 mg, crude) in DCM (0.5 mL) was added TFA (0.1 mL, 1.35 mmol). After stirring at 10° C. for 2 hours, the reaction mixture was adjusted to pH=6-7 with saturated NaHCO$_3$ (5 mL) before diluted with water (10 mL) and extracted with DCM (15 mL×3). The combined organic layers were dried over Na$_2$SO$_4$, filtered and concentrated under reduced pressure to obtain the crude product, which was purified by prep-HPLC (Gilson 281, Column: Xtimate C18 150*25 mm*5 um, Mobile phase A: water (0.225% formic acid), B: ACN). The desired fractions were collected and the solvent was evaporated to give the Compound 99 (8.35 mg; formate salt) as a white solid.

Compound 99: $^1$H NMR DMSO-$d_6$ (400 MHz): δ 11.18 (br s, 1H), 8.28 (s, 1H), 8.23 (s, 1H), 7.37 (s, 1H), 7.19 (d, J=8.4 Hz, 1H), 7.07-7.05 (m, 2H), 5.03 (s, 2H), 4.07-3.98 (m, 6H), 3.75 (s, 2H), 3.17-3.14 (m, 1H), 2.14-2.09 (m, 1H), 2.05-1.97 (m, 1H), 1.84-1.78 (m, 3H), 1.53-1.47 (m, 1H).

Example B56

Preparation of Compounds 102 and 103

Compound 102: trans or cis at spiro moiety
Compound 103: cis or trans at spiro moeity A solution of intermediate 5 (6-(6-(2,2,2-trifluoroethyl)thieno[2,3-d]pyrimidin-4-yl)-6-azaspiro[3.4]octan-2-one) (300 mg, 0.880 mmol), N-((1R,4R)-4-aminocyclohexyl)-methanesulfonamide (169 mg, 0.880 mmol) and titanium tetraisopropanolate (1.25 g, 4.40 mmol) in MeOH (5 mL) was stirred at 50° C. for 3 h. Subsequently the mixture was cooled to room temperature and NaBH$_3$CN (110 mg, 1.76 mmol) was added. The mixture was stirred at room temperature for another 3 h, and then poured into water (10 mL) and adjusted ph<7 with HCl (1M). The mixture was extracted with EtOAc (50 mL×3). The combined organic layers were washed with brine (50 mL×2), dried over Na$_2$SO$_4$, filtered and concentrated under reduced pressure. The residue was purified by flash (DCM:MeOH=10:1, v/v) to afford the mixture of cis and trans isomers (at the spiro moiety) (180 mg, free base). The mixture was separated by SFC (AD-H, 2.5*25 cm, 10 um, mobile phase: CO$_2$/MeOH (0.03% DEA)=80/20, 50 ml/min) to afford Compound 102 (50.0 mg) as a white solid and Compound 103 (16.8 mg) as a white solid.

Compound 102: $^1$H NMR MeOD-$d_4$ (400 MHz): δ 8.27 (s, 1H), 7.64 (s, 1H), 3.91-3.83 (m, 6H), 3.55-3.50 (m, 1H), 3.20-3.14 (m, 1H), 2.93 (s, 3H), 2.53-2.48 (m, 1H), 2.41-2.35 (m, 2H), 2.05-1.92 (m, 8H), 1.37-1.22 (m, 4H)

Compound 103: $^1$H NMR MeOD-$d_4$ (400 MHz): δ 8.27 (s, 1H), 7.61 (s, 1H), 3.86 (q, J=10.8 Hz, 4H), 3.75 (br s, 2H), 3.48-3.44 (m, 1H), 3.20-3.14 (m, 1H), 2.93 (s, 3H), 2.48-2.45 (m, 1H), 2.11 (br s, 2H), 2.04-2.01 (m, 2H), 1.97-1.92 (m, 4H), 1.37-1.16 (m, 4H)

Example B57

Preparation of Compounds 104 and 105

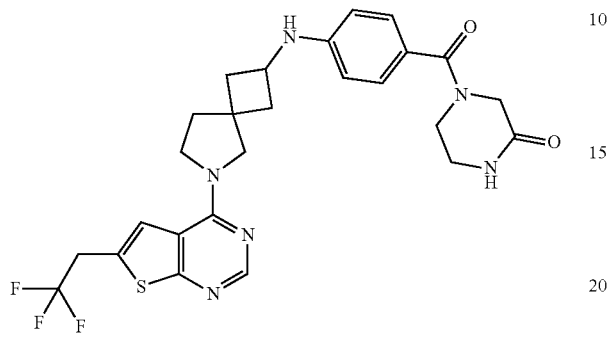

Compound 104: trans or cis
Compound 105: cis or trans

A solution of intermediate 59 (4-((6-(6-(2,2,2-trifluoroethyl)thieno[2,3-d]pyrimidin-4-yl)-6-azaspiro[3.4]octan-2-yl)amino)benzoic acid TFA salt) (160 mg) and DMF (8 mL) was added piperazin-2-one hydrochloride (56.7 mg, 0.415 mmol), DIEA (179 mg, 1.39 mmpl) and HATU (158 mg, 0.416 mmol) at 0° C. The reaction mixture was warmed to room temperature and stirred for 2 h. The reaction mixture was then concentrated to dryness under reduced pressure to afford the crude product, which was purified by prep-HPLC (Gilson 281, Column: Xtimate C18 150×25 mm×5 m column, Mobile Phase A: water (0.225% FA), B: ACN)). The pure fractions were lyophilized to dryness to give the mixture of cis and trans (70 mg, 77% yield) as a white solid, which was separated by SFC (AS, 3*25 cm, 10 um, mobile phase: $CO_2$/MeOH (0.1% $NH_3 \cdot H_2O$)=55/45, 70 ml/min). The pure fractions were collected and the volatiles were removed under reduced pressure to obtain two residues which were lyophilized to dryness to give the Compound 104 (4.76 mg, 6.77% yield) as a white solid and Compound 105 (4.36 mg) as a white solid.

Compound 104: $^1$H NMR DMSO-$d_6$ (400 MHz): δ 8.32 (s, 1H), 8.08 (s, 1H), 7.71 (s, 1H), 7.24 (d, J=8.4 Hz, 2H), 6.55 (d, J=8.4 Hz, 2H), 6.49 (d, J=6.0 Hz, 1H), 4.13-3.92 (m, 6H), 3.92-3.67 (m, 3H), 3.67-3.61 (m, 2H), 3.25-3.19 (m, 2H), 2.47-2.43 (m, 2H), 2.19-2.07 (m, 2H), 2.02-1.93 (m, 2H)

Compound 105: $^1$H NMR DMSO-$d_6$ (400 MHz): δ 8.33 (s, 1H), 8.08 (s, 1H), 7.74 (s, 1H), 7.23 (d, J=8.8 Hz, 2H), 6.54 (d, J=8.4 Hz, 2H), 6.51 (d, J=6.4 Hz, 1H), 4.13-3.93 (m, 6H), 3.93-3.67 (m, 3H), 3.67-3.58 (m, 2H), 3.25-3.18 (m, 2H), 2.56-2.52 (m, 2H), 2.06-1.99 (m, 2H), 1.96-1.88 (m, 2H)

Example B58

Preparation of Compound 106

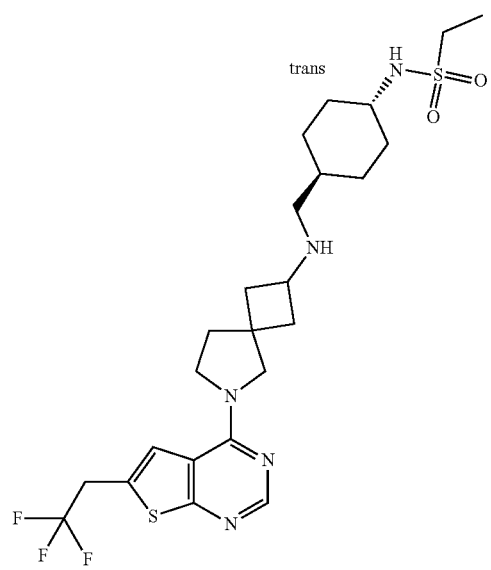

A solution of intermediate 5 (6-(6-(2,2,2-trifluoroethyl)thieno[2,3-d]pyrimidin-4-yl)-6-azaspiro[3.4]octan-2-one) (136 mg, 0.398 mmol), N-((1R,4R)-4-(aminomethyl)cyclohexyl)ethanesulfonamide trifluoroacetate (200 mg, 0.598 mmol), N,N-diisopropyl-ethylamine (155 mg, 1.20 mmol) and dry DCM (10 mL) was stirred at 25° C. for 2 h and then added sodium triacetoxyborohydride (338 mg, 1.60 mmol). After stirring at 25° C. for 8 h, the reaction mixture was diluted with DCM (30 mL) and washed with water (20 mL×3). The organic layer was dried over anhydrous $Na_2SO_4$, filtered, and concentrated under reduced pressure to give a residue, which was purified by prep-HPLC (Gilson 281, Column: Xtimate C18 150×25 mm×5 m column, Mobile Phase A: water (0.225% formic acid), B: ACN)). The pure fractions were collected and the solvent was evaporated under vacuum to give a residue, which was lyophilized to give the Compound 106 (163.08 mg, 73.8% yield) as a white powder.

Compound 106: $^1$H NMR DMSO-$d_6$ (400 MHz): δ 8.32 (s, 1H), 7.74-7.65 (m, 1H), 7.06-6.99 (m, 1H), 4.06 (q, J=10.8 Hz, 2H), 3.95-3.43 (m, 8H), 3.07-2.92 (m, 3H), 2.36-2.15 (m, 4H), 2.10-1.97 (m, 2H), 1.93-1.84 (m, 2H), 1.84-1.75 (m, 2H), 1.54-1.40 (m, 1H), 1.27-1.14 (m, 5H), 1.06-0.90 (m, 2H).

Example B59

Preparation of Compound 107

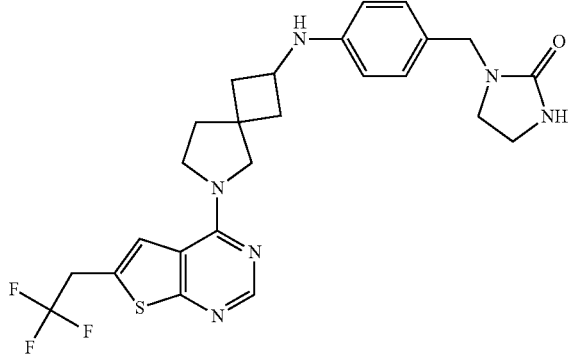

To a solution of intermediate 5 (6-(6-(2,2,2-trifluoroethyl)thieno[2,3-d]pyrimidin-4-yl)-6-azaspiro[3.4]octan-2-one) (250 mg, 0.549 mmol), 1-(4-aminobenzyl)imidazolidin-2-one (100 mg, 0.523 mmol), sodium cyanoborohydride (70.0 mg, 1.11 mmol) and MeOH (18.0 mL) was added a solution of acetic acid (70.0 mg, 1.17 mmol) in MeOH (2.0 mL). After stirring at 40° C. for 14 h, the mixture was poured into water (15 mL) and extracted by DCM (10 mL×3). The combined organic layer were dried over anhydrous $Na_2SO_4$, filtered and concentrated in vacuo to obtain the crude residue, which was purified by prep-HPLC (Gilson 281, Column: Xtimate C18 150×25 mm×m column, Mobile Phase A: water (0.225% FA), B: ACN)). The pure fractions were collected and lyophilized to dryness to give Compound 107 (46.2 mg, 16% yield) as a white powder.

Compound 107: $^1$H NMR DMSO-$d_6$ (400 MHz): δ 8.36-8.27 (m, 1H), 7.78-7.64 (m, 1H), 7.01-6.86 (m, 2H), 6.54-6.42 (m, 2H), 6.36-6.25 (m, 1H), 5.94-5.83 (m, 1H), 4.18-3.97 (m, 4H), 3.95-3.58 (m, 5H), 3.21-2.99 (m, 4H), 2.60-2.56 (m, 2H), 2.16-1.86 (m, 4H).

Example B60

Preparation of Compound 108 and Compound 109

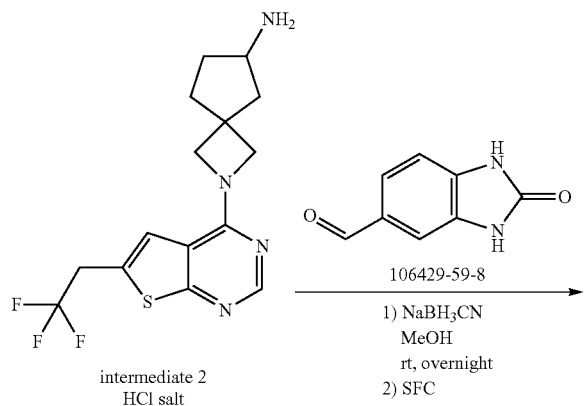

intermediate 2
HCl salt 106429-59-8

1) $NaBH_3CN$
MeOH
rt, overnight
2) SFC

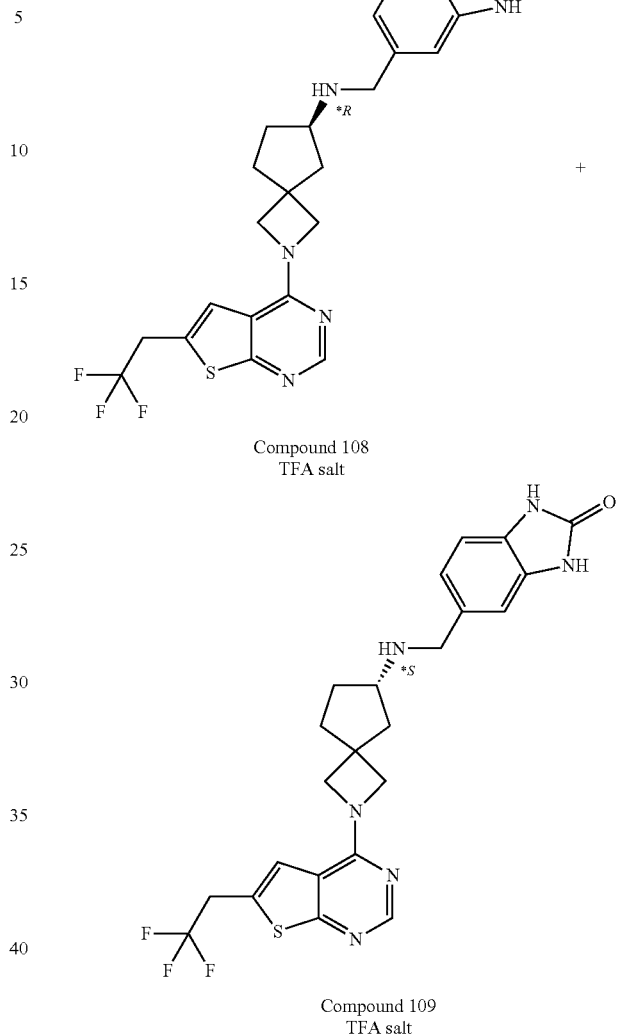

Compound 108
TFA salt

+

Compound 109
TFA salt

A solution of intermediate 2 (100 mg, crude HCl salt, 0.29 mmol) and 2-oxo-2,3-dihydro-1H-benzo[d]imidazole-5-carbaldehyde (CAS #: 106429-59-8) (71 mg, 0.44 mmol) in MeOH (2 mL) was stirred at room temperature for 2 h. $NaBH_3CN$ (37 mg, 0.58 mmol) was added and the reaction was stirred at room temperature overnight. The reaction mixture was diluted with $H_2O$ and extracted with EtOAc. The combined organic extracts were washed with brine, dried over anhydrous $Na_2SO_4$, filtered and concentrated. The residue was purified by prep-HPLC (Waters 2767/Qda, Column: Waters Xbridge 19*150 mm 10 um, Mobile Phase A: $H_2O$ (0.1% TFA), B: ACN) to give the racemic Compound 14 (49 mg, TFA salt). The obtained racemic Compound 14 was separated by SFC (SFC80, Waters, IC 2.5*25 cm, 10 um, A: Supercritical $CO_2$, B: MeOH/DEA=100/0.03; A:B=70/30; Flow rate: 70 mL/min; column temperature (T): 25° C.; Backpressure (BPR): 100 bar) to give Compound 108 (12 mg as TFA salt, 6.8% yield) as a white solid and Compound 109 (13 mg as TFA salt, 7.3% yield) as a white solid.

Example B61

Preparation of Compound 110 and Compound 111

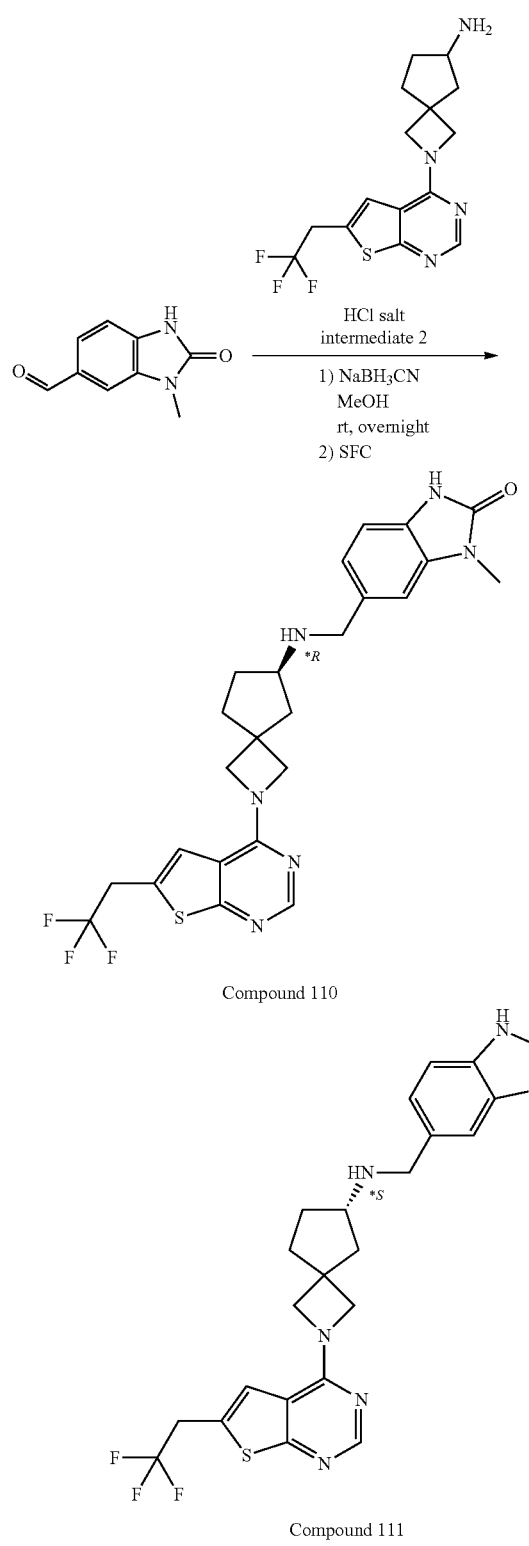

Compound 110

Compound 111

To a stirred solution of intermediate 2 (150 mg, crude HCl salt, ca. 0.44 mmol) in MeOH (3 mL) at room temperature were added intermediate 70 (185 mg, purity: ca. 50%, ca. 0.53 mmol) and AcOH (3 drops). After stirring for 2 h, NaBH$_3$CN (55.30 mg, 0.88 mmol) was added and the reaction was stirred at room temperature overnight. The reaction mixture was concentrated and the residue was purified by pre-HPLC (Waters 2767/Qda, Column: SunFire 19*250 mm 10 um, Mobile Phase A: 0.1% TFA/H$_2$O, B: ACN) and the obtained racemate was separated by SFC (SFC80, Waters; AD 25*25 cm, 10 um; A: Supercritical CO$_2$, Mobile phase B: MeOH; A:B=70/30; Flow rate: 60 mL/min; column temperature (T): 25° C.; Backpressure (BPR): 100 bar) to afford Compound 110 (38.78 ng, 17% yield) as a white solid and Compound 111 (24.88 ng, 11% yield) as a white solid.

Example B62

Preparation of Compound 112 and Compound 113

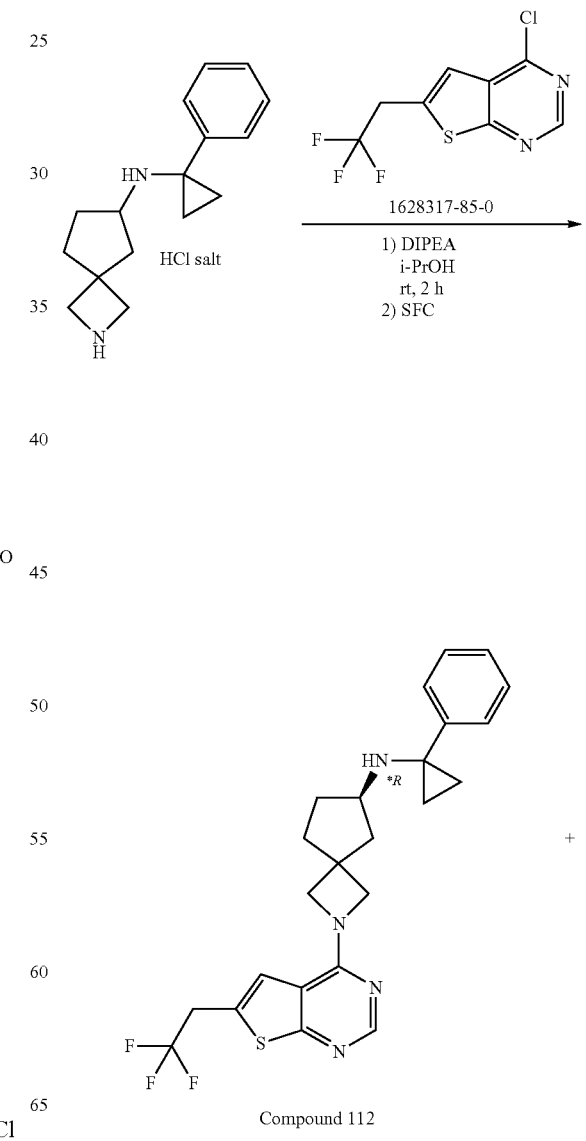

Compound 112

311

-continued

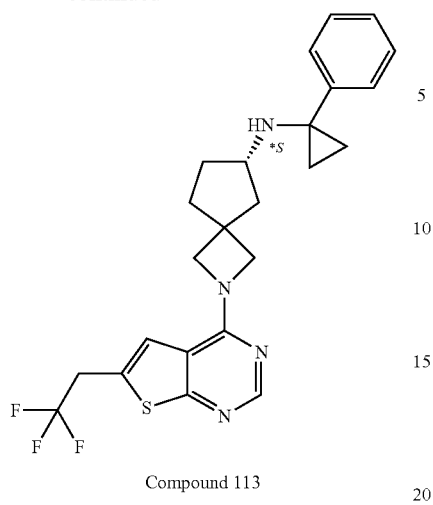

Compound 113

312

-continued

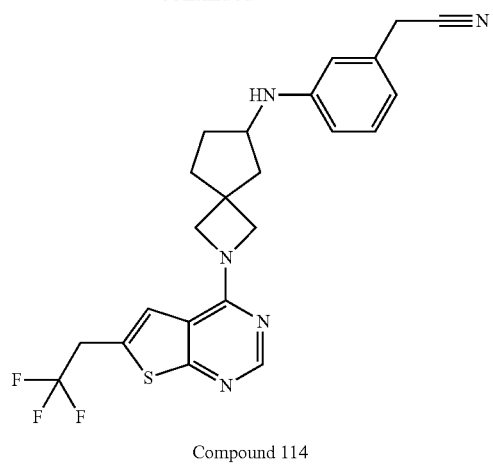

Compound 114

A mixture of intermediate 78 (330 mg, crude HCl salt), 4-chloro-6-(2,2,2-trifluoro-ethyl)thieno[2,3-d]pyrimidine (CAS #: 1628317-85-0) (212 mg, 0.84 mmol) and DIPEA (271 mg, 2.10 mmol) in i-PrOH (10 mL) was stirred at room temperature for 2 h. The reaction mixture was concentrated under reduced pressure. The residue was purified by prep-HPLC (Waters 2767/Qda, Column: SunFire 19*250 mm 10 um, Mobile Phase A: 0.1% TFA/H$_2$O, B: ACN) to give racemic desired product. The racemate was separated by SFC (SFC80, Waters; OJ-H 2.5*25 cm, 10 um; A: Supercritical CO$_2$, Mobile phase B: MeOH; A:B=70/30; Flow rate: 70 mL/min; column temperature (T): 25° C.; Backpressure (BPR): 100 bar) to give Compound 112 (63.38 mg, 19% yield) as a white solid and Compound 113 (46.77 mg, 14% yield) as a white solid.

Example B63

Preparation of Compound 114

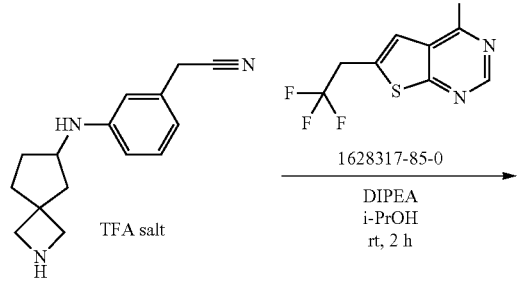

To a stirred solution of intermediate 80 (300 mg, crude TFA salt, ca. 0.84 mmol) and 4-chloro-6-(2,2,2-trifluoro-ethyl)thieno[2,3-d]pyrimidine (CAS #: 1628317-85-0) (252 mg, 1.0 mmol) in i-PrOH (10 mL) was added DIPEA (387 mg, 3.0 mmol). After being stirred at room temperature for 2 h, the reaction mixture was treated with H$_2$O (5 mL), filtered. The filter cake was purified by prep-HPLC (Agilent G6120B G1315D DADVL Detector and G4260B ELSD, Xbridge C18 5 mm 150*4.6 mm, Mobile Phase A: NH$_4$OH 0.1% in water, B: N—H$_4$OH 0.1% in CH$_3$CN) to afford Compound 114 (200 mg, 52% yield) as a white solid.

Example B64

Preparation of Compound 115 and Compound 116

Compound 115

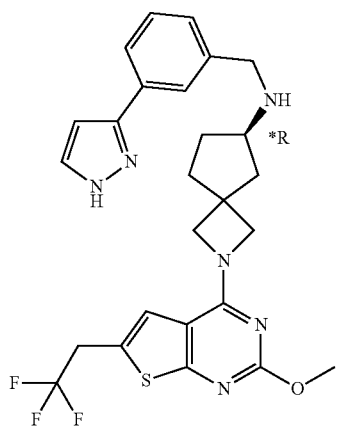

Compound 116

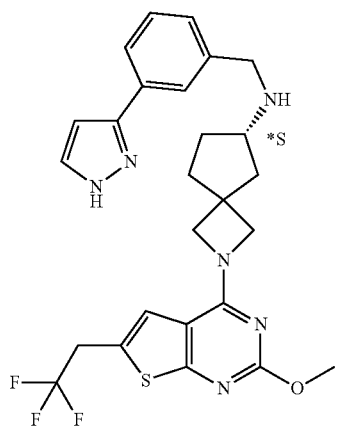

To a stirred mixture of intermediate 62 (100 mg, 0.268 mmol), 3-(1H-pyrazol-3-yl)-benzaldehyde (CAS #: 179057-26-2) (56 mg, 0.32 mmol) and Ti(i-PrO)$_4$ (76 mg, 0.27 mmol) in DCE (5 mL) at room temperature was added NaBH(OAc)$_3$ (171 mg, 0.81 mmol) in portions. The reaction mixture was stirred at room temperature overnight. The reaction was quenched with aq. NaHCO$_3$ and the resultant was extracted with DCM. The combined organic extracts were washed with brine, dried over anhydrous Na$_2$SO$_4$, filtered and concentrated. The crude product was purified by prep-HPLC (Waters 2767/Qda, Column: Waters Xbridge 19*150 mm 10 um, Mobile Phase A: H$_2$O (0.1% NH$_4$OH), B: ACN) to give the racemate (80 mg) as a white solid. The racemate was separated by SFC (Instrument: Waters-SFC80; Column: IA-H (2.5*25 cm, 10 um); Mobile phase A: Supercritical CO$_2$, Mobile phase B: MeOH; A:B=60/40 at 70 mL/min; Circle Time: 18 min; Injection Volume: 3.5 mL; Detector Wavelength: 214 nm; Column temperature (T): 25° C.; BPR: 100 bar) to afford Compound 115 (25.8 mg, 18% yield) and Compound 116 (27.90 mg, 19% yield).

Example B65

Preparation of Compound 117

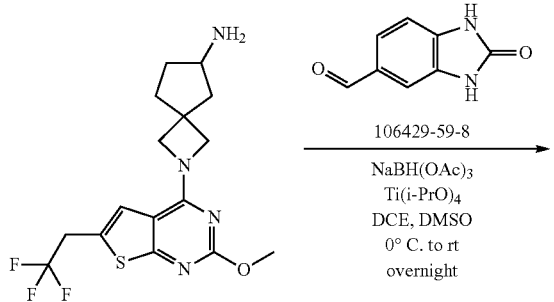

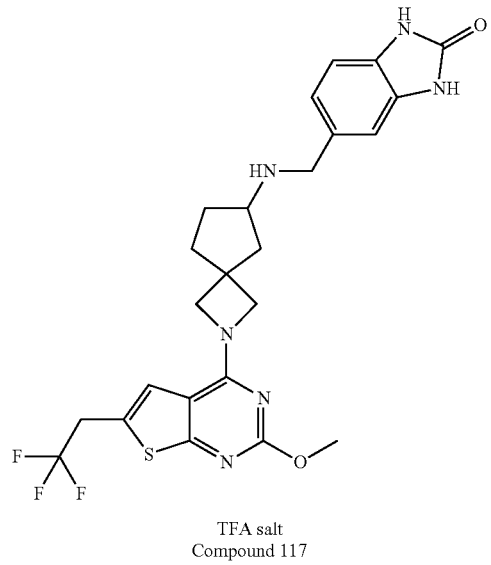

TFA salt
Compound 117

To a stirred mixture of intermediate 62 (120 mg, 0.32 mmol), 2-oxo-2,3-dihydro-1H-benzo[d]imidazole-5-carbaldehyde (CAS #: 106429-59-8) (104 mg, 0.64 mmol) and Ti(i-PrO)$_4$ (92 mg, 0.32 mmol) in DCE/DMSO (6 mL/2 mL) at 0° C. was added NaBH(OAc)$_3$ (205 mg, 0.97 mmol) in portions. The reaction mixture was stirred at room temperature overnight. The reaction was quenched with aq. NaHCO$_3$ and the resultant was extracted with DCM. The combined organic extracts were washed with brine, dried over anhydrous Na$_2$SO$_4$, filtered and concentrated. The residue was purified by prep-HPLC (Waters 2767/Qda, Column: Waters Xbridge 19*150 mm um, Mobile Phase A: H$_2$O (0.1% TFA), B: ACN) to give Compound 117 (22 mg TFA salt, yield: 13%) as a white solid.

Example B66

Preparation of Compound 118

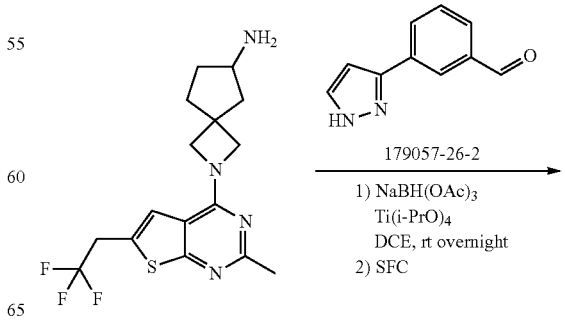

315
-continued

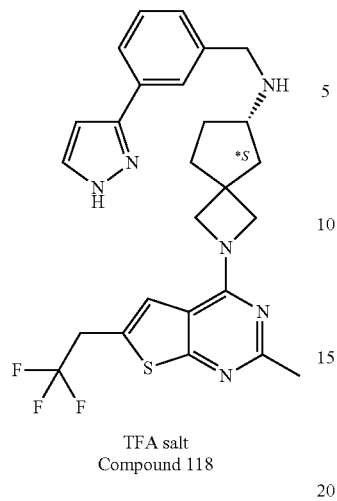

TFA salt
Compound 118

To a stirred solution of intermediate 72 (150 mg, 0.421 mmol) in DCE (2 mL) at room temperature were added 3-(1H-pyrazol-3-yl)benzaldehyde (CAS #: 179057-26-2) (108 mg, 0.63 mmol) and Ti(i-PrO)$_4$ (120 mg, 0.42 mmol). The reaction was stirred at room temperature for 30 minutes. NaBH$_3$CN (54 mg, 0.84 mmol) was added. The reaction was stirred at room temperature overnight. The reaction mixture was concentrated under reduced pressure. The residue was purified by prep-HPLC (Waters 2767/Qda, Column: Waters Xbridge 19*150 mm 10 um, Mobile Phase A: H$_2$O (0.1% TFA), B: ACN) to give the racemic desired product (120 mg, TFA salt). The racemate was separated by SFC (SFC80, Waters, AD-H 2.5*25 cm, 10 um, A: Supercritical CO$_2$, B: EtOH/ACN=85/15; A:B=55/45; Flow rate: 50 mL/min; column temperature (T): 25° C.; BPR: 100 bar) to afford Compound 118 (28 mg TFA salt, 10% yield).

Example B67

Preparation of Compound 119

316
-continued

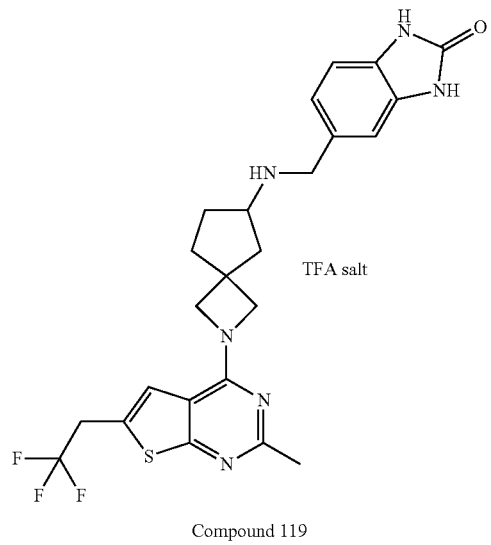

TFA salt

Compound 119

To a stirred solution of intermediate 72 (250 mg, 0.70 mmol) in DCE (2.5 mL) were added 2-oxo-2,3-dihydro-1H-benzo[d]imidazole-5-carbaldehyde (CAS #: 106429-59-8) (170 mg, 1.06 mmol), DMSO (0.5 mL) and Ti(i-PrO)$_4$ (200 mg, 0.70 mmol). The mixture was stirred for 30 minutes. NaBH(OAc)$_3$ (295 mg, 1.40 mmol) was added. The reaction was stirred at room temperature overnight. The reaction mixture was concentrated under reduced pressure and the residue was purified by prep-HPLC (Waters 2767/Qda, Column: Waters Xbridge 19*150 mm 10 um, Mobile Phase A: H$_2$O (0.1% TFA), B: ACN) to afford Compound 119 (156 mg TFA salt, 44% yield).

Example B68

Preparation of Compound 120

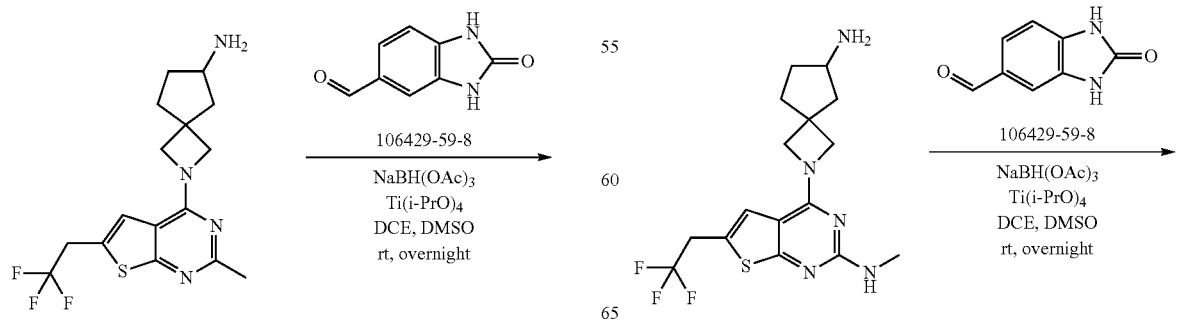

-continued

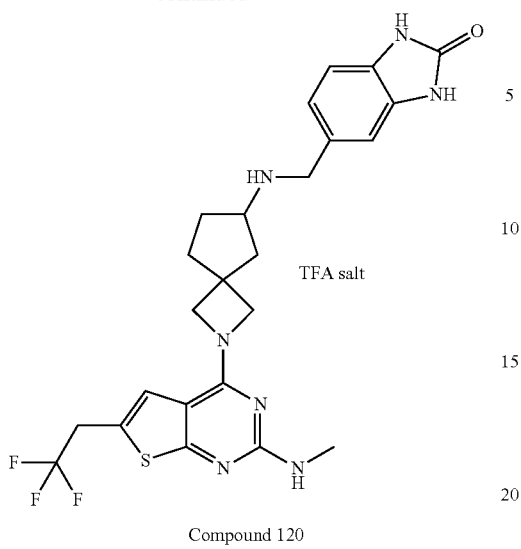

TFA salt

Compound 120

-continued

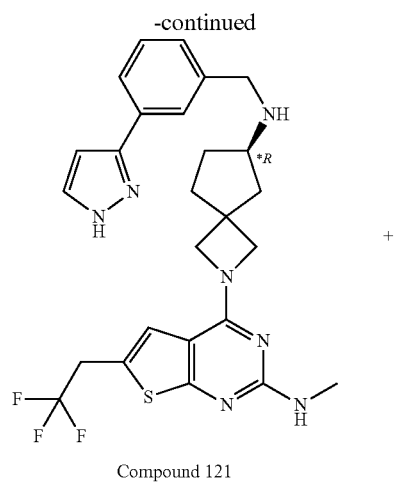

Compound 121

To a stirred mixture of intermediate 76 (250 mg, 0.67 mmol), 2-oxo-2,3-dihydro-1H-benzo[d]imidazole-5-carbaldehyde (CAS #: 106429-59-8) (218 mg, 1.35 mmol) and Ti(i-PrO)$_4$ (192 mg, 0.67 mmol) in DCE/DMSO (6 mL/2 mL) at 0° C. was added NaBH(OAc)$_3$ (428 mg, 2.02 mmol) in portions. The reaction mixture was stirred at room temperature overnight. The reaction was quenched with aq. NaHCO$_3$ and the resultant was extracted with DCM. The combined organic extracts were washed with brine, dried over anhydrous Na$_2$SO$_4$, filtered and concentrated. The residue was purified by prep-HPLC (Waters 2767/Qda, Column: Waters Xbridge 19*150 mm 10 um, Mobile Phase A: H$_2$O (0.1% TFA), B: ACN) to give Compound 120 (60 mg, TFA salt, yield: 17%) as a white solid.

Example B69

Preparation of Compound 121 and Compound 122

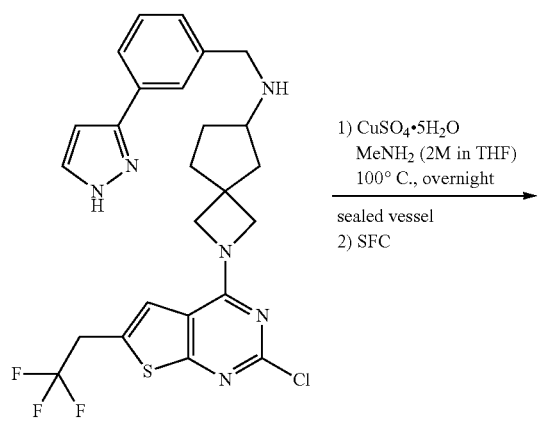

1) CuSO$_4$·5H$_2$O
MeNH$_2$ (2M in THF)
100° C., overnight
sealed vessel
2) SFC

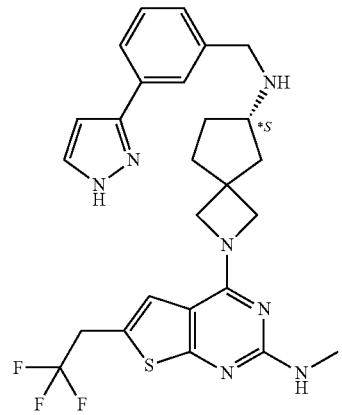

Compound 122

A suspension of intermediate 74 (160 mg, 0.300 mmol) and CuSO$_4$.5H$_2$O (8 mg, 0.030 mmol) in methanamine (2 M in THF) (2 mL) in a sealed vessel was stirred at 100° C. overnight. The reaction mixture was concentrated. The residue was purified by column chromatography eluted with DCM/MeOH (from 50:1 to 15:1, v/v) to give racemate of desired product as a yellow solid. The racemate was separated by SFC (Instrument: Waters-SFC80; Column: OJ-H (2.5*25 cm, 10 um); Mobile phase A: Supercritical CO$_2$, Mobile phase B: MeOH; A:B=80/20 at 80 mL/min; Circle Time: 8.5 min; Injection Volume: 1.3 mL; Detector Wavelength: 214 nm; Column temperature (T): 25° C.; BPR: 100 bar) to afford Compound 121 (32.9 mg, 20% yield) and Compound 122 (31.3 mg, 19% yield).

Example B70

Preparation of Compound 123

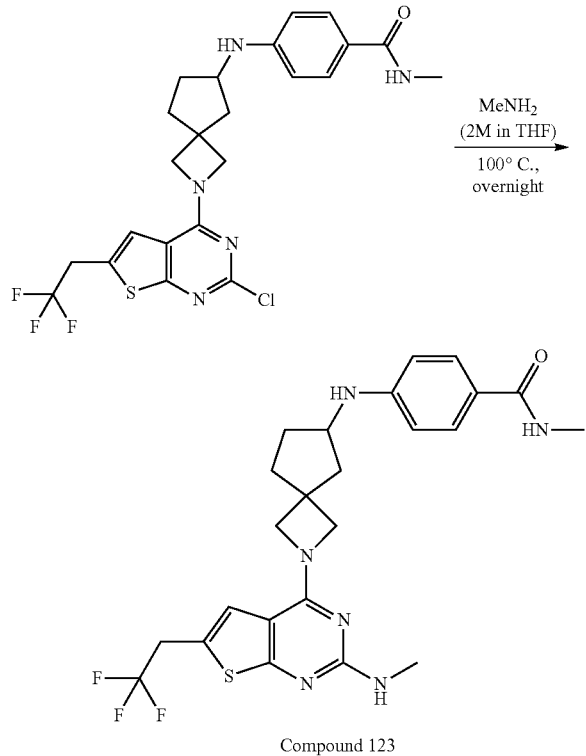

Compound 123

A solution of intermediate 65 (400 mg, 0.786 mmol) in MeNH₂ (2 M in THF) (10 mL) was stirred at 100° C. overnight. The cooled reaction mixture was concentrated. The residue was purified by prep-TLC (DCM:MeOH=15:1, v/v) to give Compound 123 (180 mg, 45% yield).

Example B71

Preparation of Compound 124

Compound 124

To a stirred solution of intermediate 83 (150 mg, crude TFA salt, ca. 0.31 mmol) in i-PrOH (1 mL) were added 4-chloro-6-(2,2,2-trifluoroethyl)thieno[2,3-d]pyrimidine (CAS #: 1628317-85-0) (79 mg, 0.31 mmol) and DIPEA (202 mg, 1.57 mmol). After being stirred at room temperature overnight, the reaction mixture was concentrated under reduced pressure. The residue was purified by prep-HPLC (Waters 2767/Qda, Column: Waters Xbridge 19*150 mm 10 um, Mobile Phase A: H₂O (0.1% TFA), B: ACN) to afford Compound 124 (85 mg, TFA salt., ca. 42% yield over 2 steps) as a white solid.

Example B72

Preparation of Compound 125

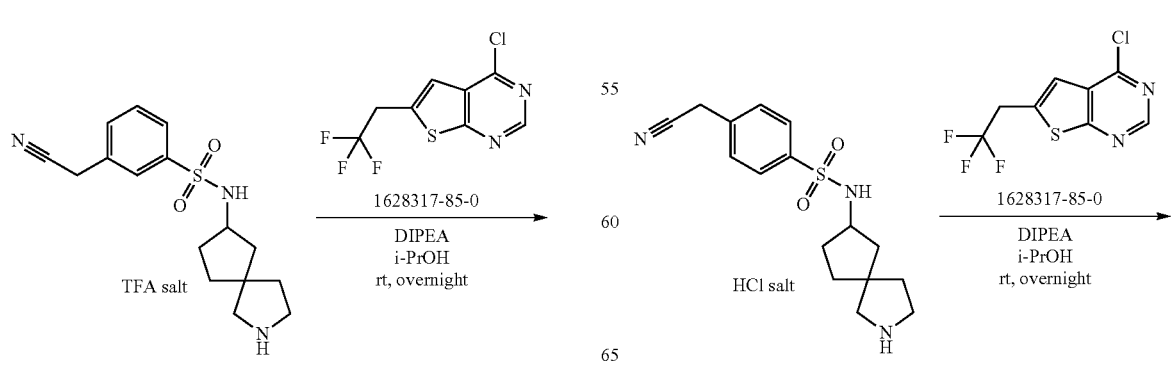

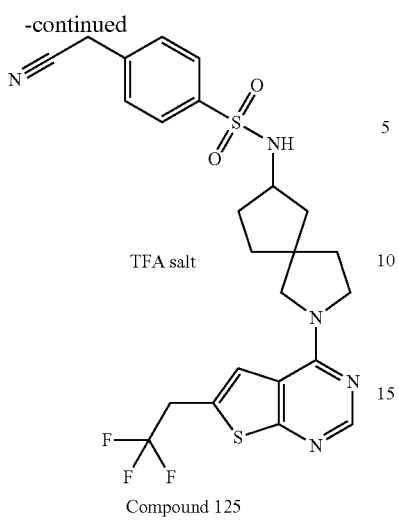

Compound 125

A solution of intermediate 85 (50 mg, crude HCl salt, ca. 0.107 mmol), DIPEA (70 mg, 0.55 mmol) and 4-chloro-6-(2,2,2-trifluoroethyl)thieno[2,3-d]pyrimidine (CAS #: 1628317-85-0) (27 mg, 0.11 mmol) in dry i-PrOH (1 mL) was stirred at room temperature overnight. The reaction mixture was concentrated and the residue was purified by prep-HPLC (Waters 2767/Qda, Column: Waters Xbridge 19*150 mm um, Mobile Phase A: H$_2$O (0.1% TFA), B: ACN) to give Compound 125 (28 mg as TFA salt, ca. 40% yield over 2 steps) as a white solid.

Example B73

Preparation of Compound 126

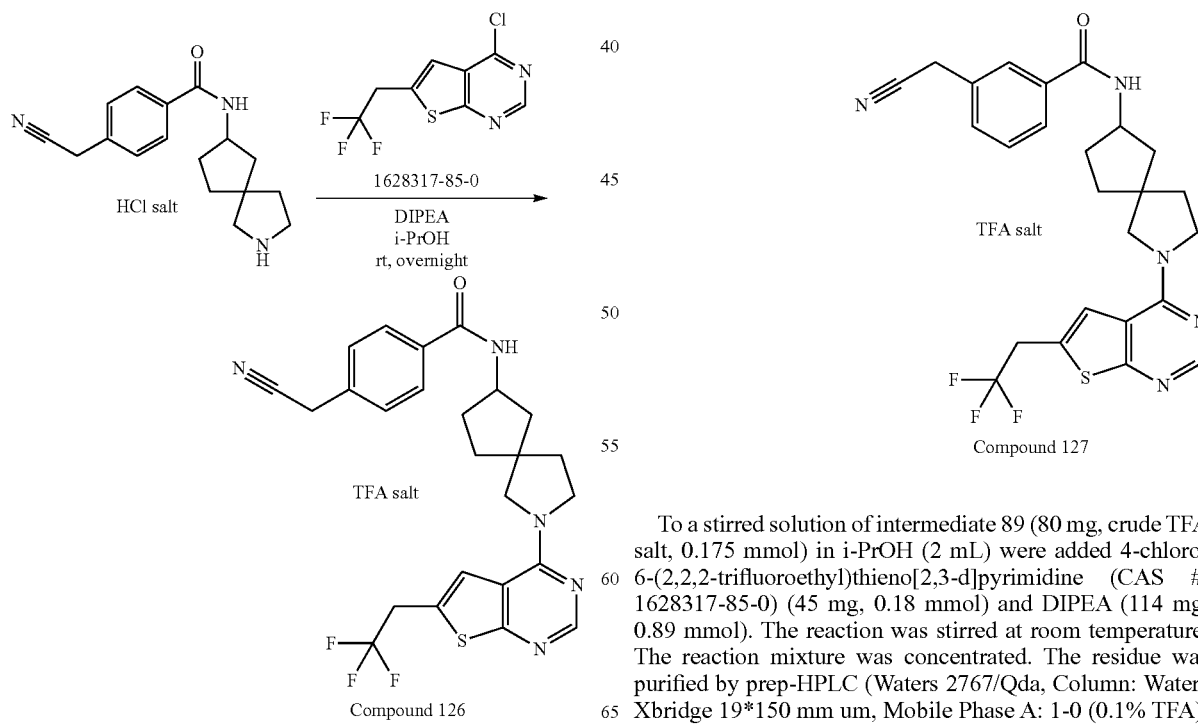

Compound 126

To a stirred solution of intermediate 87 (90 mg, crude TFA salt, ca. 0.183 mmol) in i-PrOH (1 mL) were added 4-chloro-6-(2,2,2-trifluoroethyl)thieno[2,3-d]pyrimidine (CAS #: 1628317-85-0) (46 mg, 0.18 mmol) and DIPEA (202 mg, 1.57 mmol). The reaction was stirred at room temperature overnight. The reaction mixture was concentrated. The residue was purified by prep-HPLC (Waters 2767/Qda, Column: Waters Xbridge 19*150 mm 10 urn, Mobile Phase A: H$_2$O (0.1% TFA), B: ACN) to afford Compound 126 (66 mg TEA salt, 58% yield over 2 steps) as a white solid.

Example B74

Preparation of Compound 127

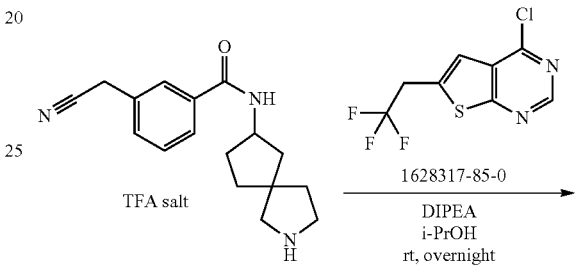

Compound 127

To a stirred solution of intermediate 89 (80 mg, crude TFA salt, 0.175 mmol) in i-PrOH (2 mL) were added 4-chloro-6-(2,2,2-trifluoroethyl)thieno[2,3-d]pyrimidine (CAS #: 1628317-85-0) (45 mg, 0.18 mmol) and DIPEA (114 mg, 0.89 mmol). The reaction was stirred at room temperature. The reaction mixture was concentrated. The residue was purified by prep-HPLC (Waters 2767/Qda, Column: Waters Xbridge 19*150 mm um, Mobile Phase A: 1-0 (0.1% TFA), B: ACN) to afford Compound 127 (61 mg TFA salt, 56% yield over 2 steps) as a white solid.

Example B75

Preparation of Compound 128

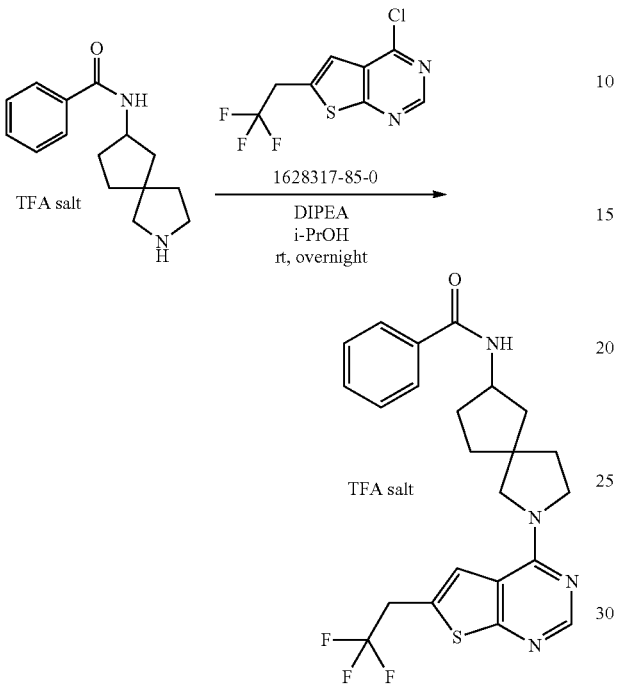

Compound 128

To a stirred solution of intermediate 91 (100 mg, crude TFA salt, ca. 0.203 mmol) in i-PrOH (1 mL) were added 4-chloro-6-(2,2,2-trifluoroethyl)thieno[2,3-d]pyrimidine (CAS #: 1628317-85-0) (53 mg, 0.21 mmol) and DIPEA (135 mg, 1.05 mmol). The reaction was stirred at room temperature overnight. The reaction mixture was concentrated. The residue was purified by prep-HPLC (Waters 2767/Qda, Column: Waters Xbridge 19*150 mm 10 um, Mobile Phase A: H$_2$O (0.1% TFA), B: ACN) to afford Compound 128 (69 mg TFA salt, 59% yield over 2 steps) as a white solid.

Example B76

Preparation of Compound 129

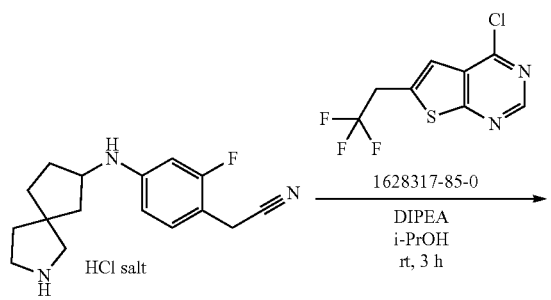

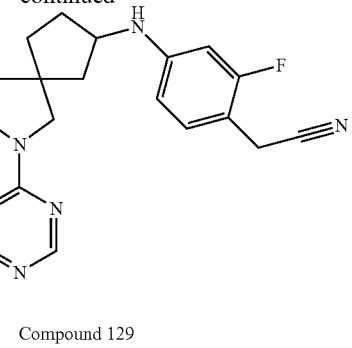

Compound 129

To a solution of intermediate 93 (40 mg, crude HCl salt, ca. 0.146 mmol) in i-PrOH (10 mL) were added DIPEA (56 mg, 0.438 mmol) and 4-chloro-6-(2,2,2-trifluoro-ethyl)thieno[2,3-d]pyrimidine (CAS #: 1628317-85-0) (36 mg, 0.146 mmol). The reaction was stirred at room temperature for 3 h. The reaction mixture was concentrated. The residue was purified by prep-HPLC (Waters 2767/Qda, Column: SunFire 19*250 mm 10 um, Mobile Phase A: 0.1% TFA/H$_2$O, B: ACN) to afford Compound 129 (18 mg, 25% yield).

Example B77

Preparation of Compound 130

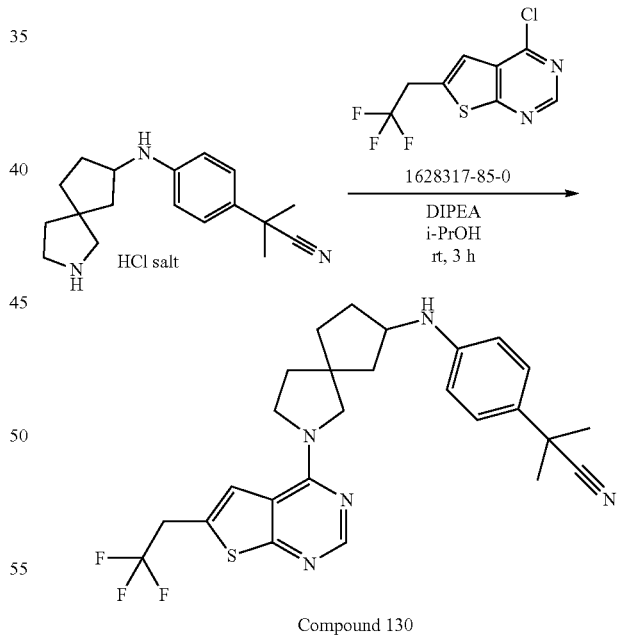

Compound 130

To a stirred solution of intermediate 94 (88 mg, crude HCl salt, ca. 0.310 mmol) in i-PrOH (5 mL) were added DIPEA (80 mg, 0.930 mmol) and 4-chloro-6-(2,2,2-tri-fluoroethyl)thieno[2,3-d]pyrimidine (CAS #: 1628317-85-0) (78 mg, 0.310 mmol). The reaction mixture was stirred at room temperature for 3 h. The reaction mixture was concentrated. The residue was purified by prep-HPLC (Waters 2767/Qda, Column: Waters Xbridge 19*150 mm 10 um, Mobile Phase A: 1-120

(0.1% NH₄OH), B: ACN) and the obtained product was further treated with ion exchange resin to afford Compound 130 (95.53 mg, 61% yield).

Example B78

Preparation of Compound 131

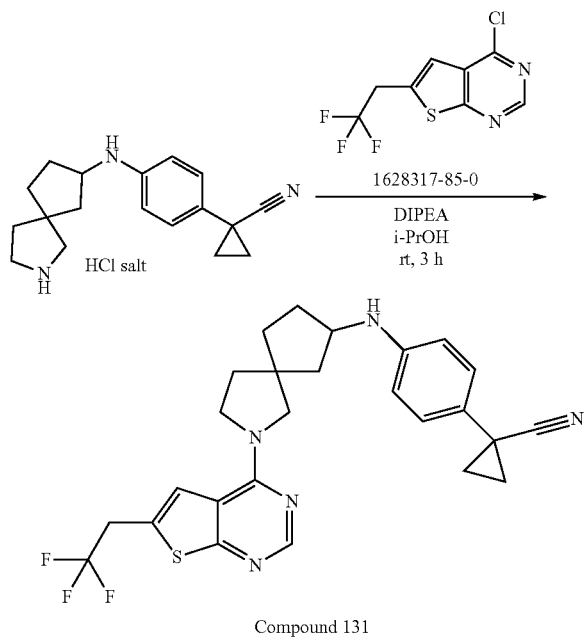

Compound 131

To a stirred solution of intermediate 95 (44 mg, crude HCl salt, ca. 0.156 mmol) in i-PrOH (10 mL) were added DIPEA (60 mg, 0.409 mmol) and 4-chloro-6-(2,2,2-tri-fluoroethyl) thieno[2,3-d]pyrimidine (CAS #: 1628317-85-0) (39 mg, 0.154 mmol). The reaction was stirred at room temperature for 3 h. The reaction mixture was concentrated. The residue was purified by prep-HPLC (Waters 2767/Qda, Column: Waters Xbridge 19*150 mm 10 um, Mobile Phase A: H₂O (0.1% NH₄OH), B: ACN) and the obtained product was treated with ion exchange resin to afford Compound 131 (43.22 mg, 75% yield).

Example B79

Preparation of Compound 132

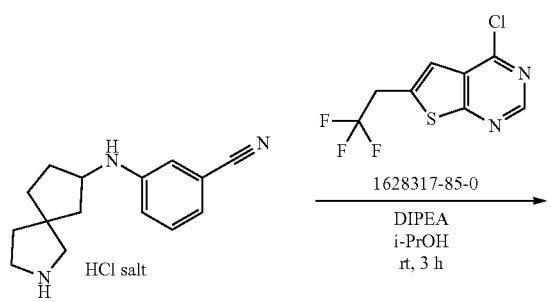

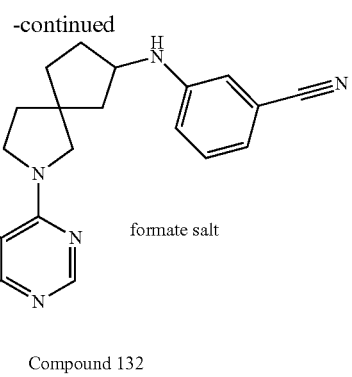

Compound 132

To a stirred solution of intermediate 96 (35 mg, crude HCl salt, ca. 0.145 mmol) in i-PrOH (5 mL) were added DIPEA (56 mg, 0.435 mmol) and 4-chloro-6-(2,2,2-tri-fluoroethyl) thieno[2,3-d]pyrimidine (CAS #: 1628317-85-0) (37 mg, 0.145 mmol). The reaction was stirred at room temperature for 3 h. The reaction mixture was concentrated. The residue was purified by prep-HPLC (Waters 2767/Qda, Column: Waters Xbridge 19*150 mm 10 um, Mobile Phase A: H₂O (0.1% NH₄OH), B: ACN) and the obtained product was treated with ion exchange resin to afford Compound 132 (27.8 mg, 40% yield, formate salt).

Example B80

Preparation of Compound 133

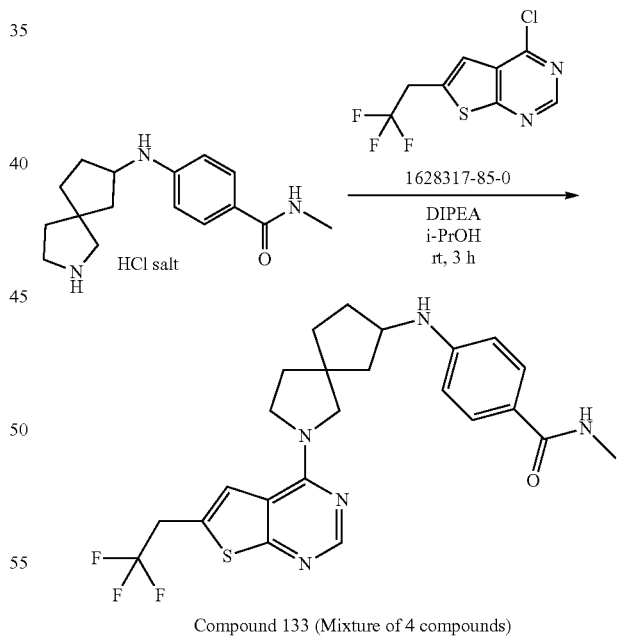

Compound 133 (Mixture of 4 compounds)

To a solution of intermediate 97 (58 mg, crude HCl salt, ca. 0.212 mmol) in i-PrOH (5 mL) were added DIPEA (82 mg, 0.634 mmol) and 4-chloro-6-(2,2,2-trifluoroethyl)-thieno[2,3-d]pyrimidine (53 mg, 0.212 mmol). The reaction was stirred at rt for 3 h. Subsequently, the reaction mixture was concentrated. The residue was purified by prep-HPLC (Waters 2767/Qda, Column: Waters Xbridge 19*150 mm 10 um, Mobile Phase A: H₂O (0.1% NH₄OH), B: ACN) and the obtained product was treated with ion exchange resin to afford Compound 133 (32.5 mg, 31% yield).

Example B81

Preparation of Compound 134, Compound 135, Compound 136 and Compound 137

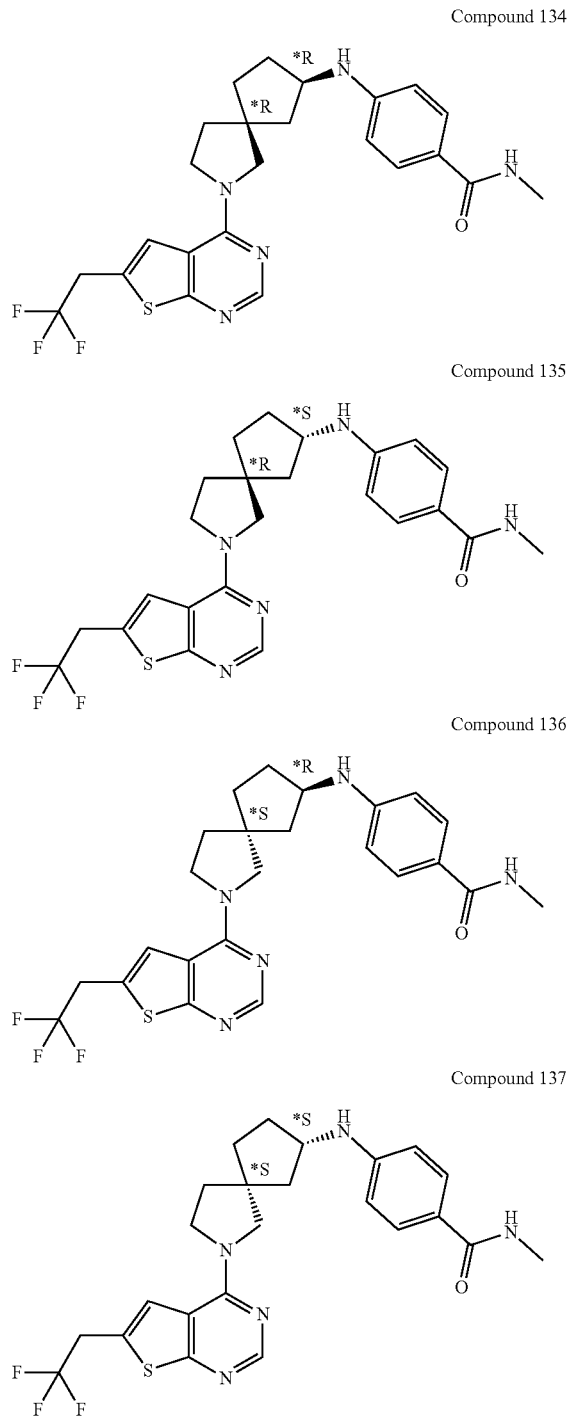

To a stirred solution of intermediate 97a (1.3 g, crude TFA salt, ca. 3.202 mmol) in i-PrOH (10 mL) were added DIPEA (1.24 g, 9.615 mmol) and 4-chloro-6-(2,2,2-tri-fluoroethyl)thieno[2,3-d]pyrimidine (CAS #: 1628317-85-0) (808 mg, 3.205 mmol). The reaction was stirred at room temperature for 3 h. The reaction mixture was concentrated. The residue was purified by silica gel chromatography eluted with PE/EA (5/1, v/v) to give Compound 133 (701 mg). The racemate was separated by SFC (SFC80, Waters; IA-H 2.5*25 cm, 10 um; A: Supercritical $CO_2$, Mobile phase B: EtOH/ACN=85/15; A:B=63/37; Flow rate: 50 mL/min; column temperature (T): 25° C.; BPR: 100 bar) to afford Compound 134 (105.15 mg, 6.7% yield), Compound 135 (76.2 mg, 4.8% yield), Compound 136 (79.30 mg, 5.0% yield) and Compound 137 (84.5 mg, 53% yield).

Example B82

Preparation of Compound 138

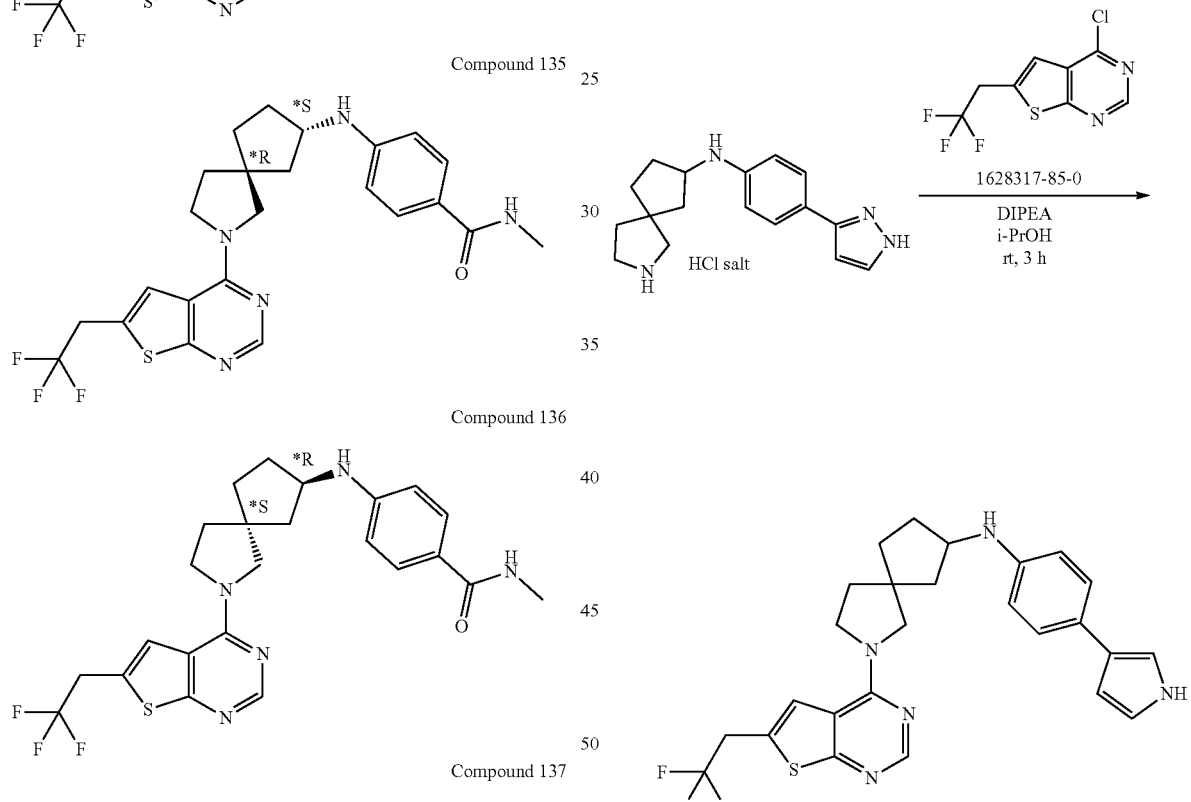

Compound 138 (Mixture of 4 compounds; formate salt)

To a stirred solution of intermediate 98 (88 mg, crude HCl salt, ca. 0.312 mmol) in i-PrOH (10 mL) were added DIPEA (120 mg, 0.936 mmol) and 4-chloro-6-(2,2,2-tri-fluoroethyl)thieno[2,3-d]pyrimidine (CAS #: 1628317-85-0) (78 mg, 0.312 mmol). The reaction was stirred at room temperature for 3 h. The reaction mixture was concentrated. The residue was purified by prep-HPLC (Waters 2767/Qda, Column: Waters Xbridge 19*150 mm 10 um, Mobile Phase A: $H_2O$ (0.1% $NH_4OH$), B: ACN) and the obtained product was treated with ion exchange resin to afford Compound 138 (70.1 mg, 45% yield, formate salt).

Example B83

Preparation of Compound 139, Compound 140, Compound 141 and Compound 142

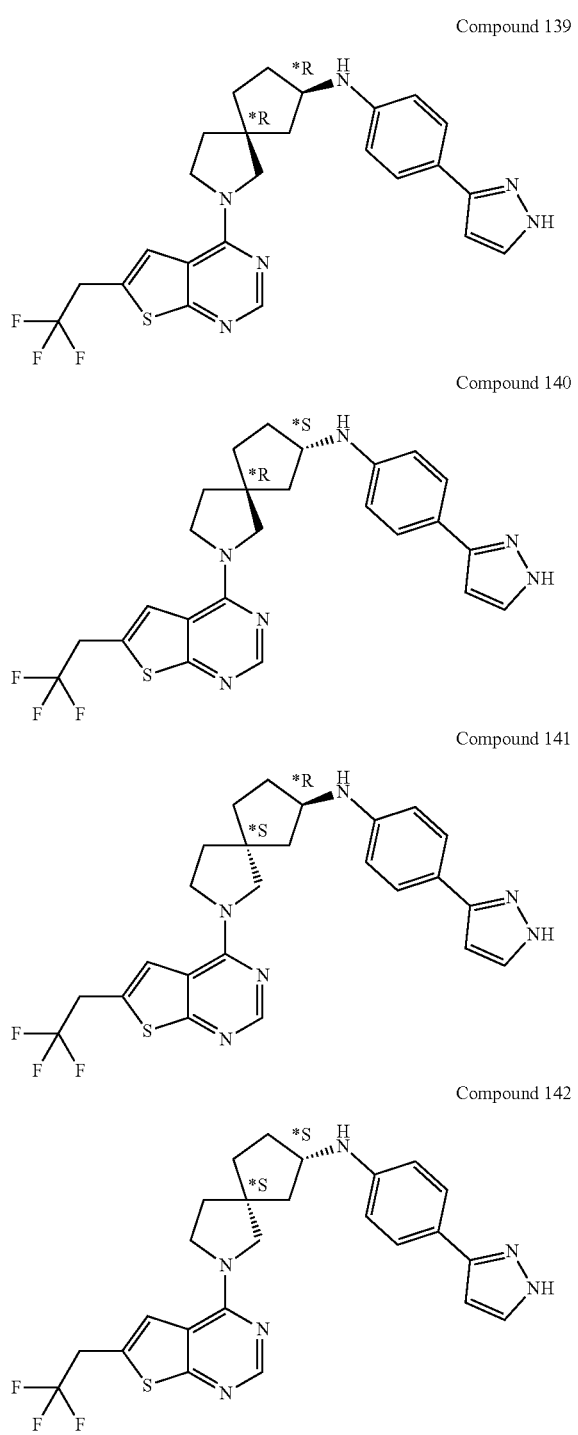

Compound 139

Compound 140

Compound 141

Compound 142

To a stirred solution of intermediate 98a (1.0 g, crude TFA salt, ca. 2.395 mmol) in i-PrOH (10 mL) were added DIPEA (928 mg, 7.191 mmol) and 4-chloro-6-(2,2,2-tri-fluoroethyl)thieno[2,3-d]pyrimidine (CAS #: 1628317-85-0) (604 mg, 2.397 mmol). The reaction was stirred at room temperature for 12 h. The reaction mixture was concentrated. The residue was purified by prep-HPLC (Waters 2767/Qda, Column: Waters Xbridge 19*150 mm 10 um, Mobile Phase A: H$_2$O (0.1% NH$_4$OH), B: ACN) afforded racemic Compound 138 (488 mg). The racemate was separated by SFC (SFC80, Waters; OJ-H 0.46*15 cm, 2 ul; HEP: EtOH (0.05% DEA) =60/40; Flow rate: 70 g/min; Column temperature (T): 25° C.; BPR: 100 bar) afforded Compound 139 (48.2 mg, 4.0% yield), Compound 140 (25.3 mg, 2.1% yield), Compound 141 (92.6 mg, 7.7% yield) and Compound 142 (126.2 mg, 10% yield).

Example B84

Preparation of Compound 143

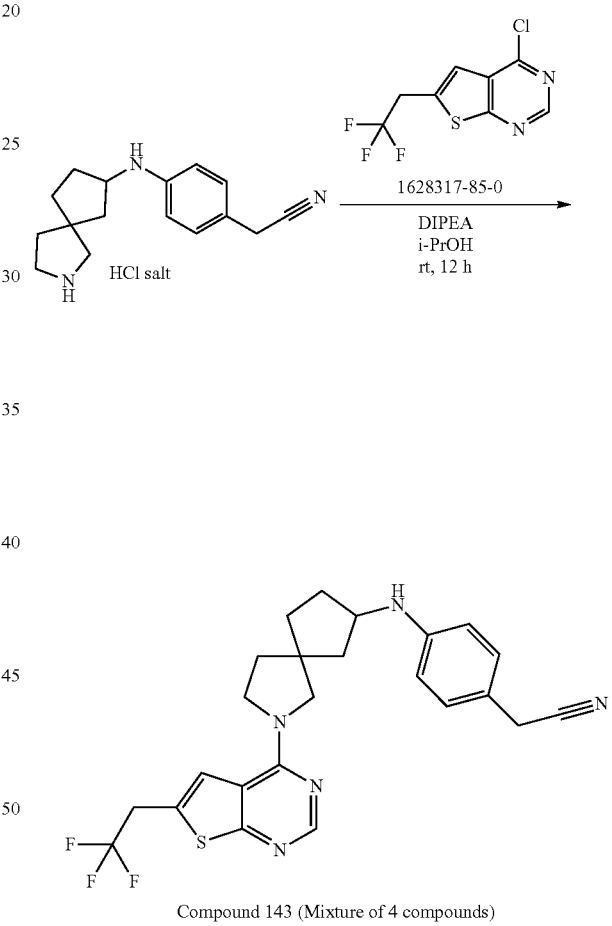

Compound 143 (Mixture of 4 compounds)

To a stirred solution of intermediate 99 (120 mg, crude TFA salt, ca. 0.338 mmol) in i-PrOH (10 mL) were added DIPEA (182 mg, 1.41 mmol) and 4-chloro-6-(2,2,2-tri-fluoroethyl)thieno[2,3-d]pyrimidine (CAS #: 1628317-85-0) (118 mg, 0.47 mmol). The reaction was stirred at room temperature for 12 h. The reaction mixture was concentrated. The residue was purified by prep-HPLC (Waters 2767/Qda, Column: Waters Xbridge 19*150 mm 10 um, Mobile Phase A: H$_2$O (0.1% NH$_4$OH), B: ACN) and the obtained product was further treated with ion exchange resin to afford Compound 143 (34.16 mg, 15% yield).

Example B85

Preparation of Compound 144, 145, 146 and 147

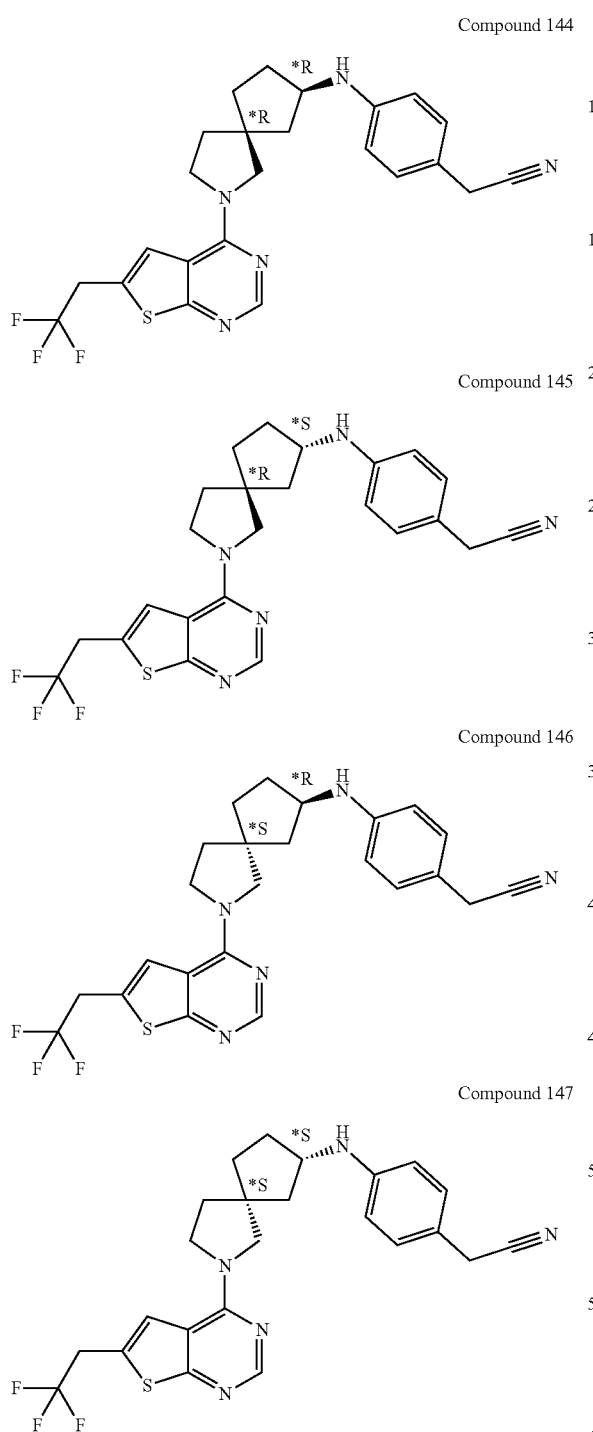

Compound 144

Compound 145

Compound 146

Compound 147

To a stirred solution of intermediate 99 (287 mg, crude TFA salt, 1.125 mmol) in i-PrOH (10 mL) were added DIPEA (435 mg, 3.376 mnol) and 4-chloro-6-(2,2,2-trifluoroethyl)thieno[2,3-d]pyrimidine (CAS #: 1628317-85-0) (283 mg, 1.125 mmol). The reaction was stirred at room temperature for 12 h. The reaction mixture was concentrated. The residue was purified by prep-HPLC (Waters 2767/Qda, Column: Waters Xbridge 19*150 mm 10 um, Mobile Phase A: $H_2O$ (0.1% $NH_4OH$), B: ACN) afforded racemic Compound 143 (280 mg). The racemate was separated by SFC (SFC80, Waters; IA-H 2.5*25 cm, 10 um; A: Supercritical $CO_2$, Mobile phase B: EtOH/IPA=38.3/61.7; A:B=60/40; Flow rate: 70 g/min; column temperature (T): 25° C.; BPR: 100 bar) to afford Compound 144 (18.9 mg, 14% yield), Compound 145 (16.2 mg, 11% yield), Compound 146 (21.7 mg, 16% yield), Compound 147 (17.0 mg, 12% yield).

Example B86

Preparation of Compound 35, 149 and 150

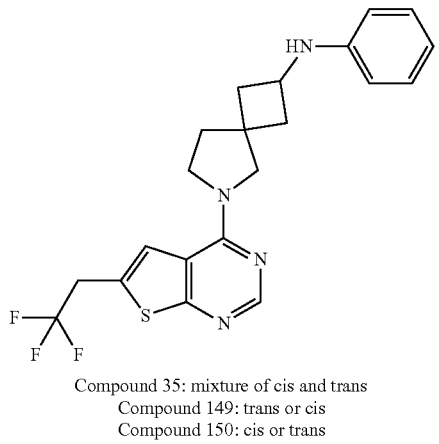 [SMILES: FC(F)(F)Cc1cc2c(N3CCC4(CC(Nc5ccccc5)C4)C3)ncnc2s1]

Compound 35: mixture of cis and trans
Compound 149: trans or cis
Compound 150: cis or trans A mixture of intermediate 3 (131 mg, 0.38 mmol), bromobenzene (CAS #: 108-86-1) (50 mg, 0.32 mmol), $Pd_2(dba)_3$ (5 mg), BrettPhos (5 mg) and t-BuONa (92 mg, 0.95 mmol) in 1,4-dioxane (3 mL) was stirred at 130° C. for 2 h with microwave irradiation. The cooled reaction mixture was diluted with water and extracted with EtOAc (50 mL×3). The combined organic extracts were washed with brine, dried over anhydrous $Na_2SO_4$, filtered and concentrated. The residue was purified by prep-HPLC (Waters 2767/Qda, Column: Waters Xbridge 19*150 mm 10 um, Mobile Phase A: $H_2O$ (0.1% $NH_4OH$), B: ACN) to give Compound 35 (mixture of cis and trans) (42.3 mg, 23% yield) as a yellow solid. Compound 35 (mixture of cis and trans) (18 mg) was separated by SFC (ChiralCel OJ-H Daicel chemical Industries, Ltd, I.D. 250*30 mm, 5 um, A: Supercritical $CO_2$, B: MeOH (0.1% DEA); A:B=60/40; Flow rate: 50 mL/min; Column temperature (T): 38° C.; Nozzle Pressure: 100 Bar; Nozzle Temp: 60° C.; Evaporator Temp: 20° C.; Trimmer Temp: 25° C.; Wavelength: 220 nm) to give Compound 149 (trans or cis) (5 mg, 27% yield) as a white solid and Compound 150 (cis or trans) (6 mg, 33% yield) as a white solid.

Example B87

Preparation of Compound 151

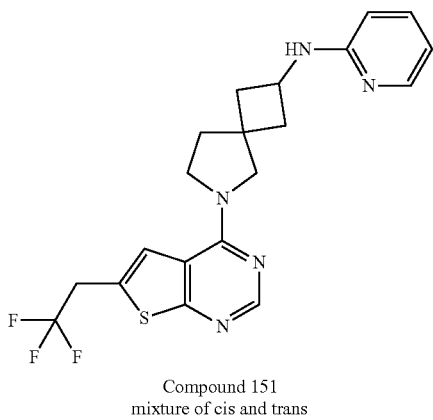 [SMILES: FC(F)(F)Cc1cc2c(N3CCC4(CC(Nc5ccccn5)C4)C3)ncnc2s1]

Compound 151
mixture of cis and trans

To a solution of intermediate 3 (300 mg, 0.88 mmol, TFA salt) in 1,4-dioxane (3 mL) under Ar at room temperature were added 2-bromopyridine (CAS #: 109-04-6) (157 mg 1.0 mmol), t-BuONa (192 mg, 2.00 mmol), BrettPhos (48 mg, 0.09 mmol) and $Pd_2(dba)_3$ (82 mg, 0.09 mmol). The reaction mixture was stirred under Ar atmosphere at 110° C. for 12 h. The reaction mixture was cooled to room temperature, diluted with water and extracted with EtOAc (100 mL×3). The combined organic extracts were washed with brine (50 mL×2), dried over anhydrous $Na_2SO_4$, filtered and the filtrate was concentrated. The residue was purified by prep-HPLC (Waters 2767/Qda, Column: SunFire 19*250 mm 10 um, Mobile Phase A: 0.1% $NH_3H_2O$ B: ACN) to afford Compound 151 (25.06 mg, 6.7% yield).

Example B88

Preparation of Compound 152 and Compound 153

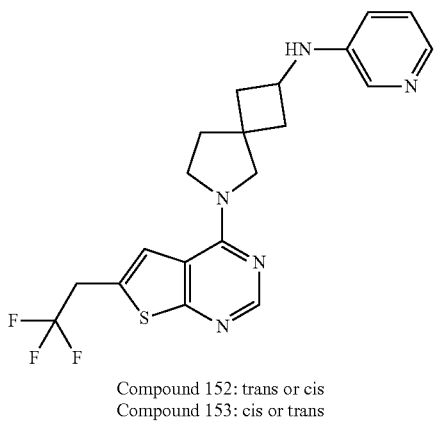 [SMILES: FC(F)(F)Cc1cc2c(N3CCC4(CC(Nc5cccnc5)C4)C3)ncnc2s1]

Compound 152: trans or cis
Compound 153: cis or trans

To a solution of intermediate 3 (300 mg, 0.88 mmol, TFA salt) in 1,4-dioxane (3 mL) under Ar at room temperature were added 3-bromopyridine (CAS #: 626-55-1) (158 mg, 1.0 mmol), t-BuONa (192 mg, 2.00 mmol), BrettPhos (48 mg, 0.09 mmol) and $Pd_2(dba)_3$ (82 mg, 0.09 mmol). The reaction mixture was stirred under Ar at 110° C. for 12 h. The reaction mixture was cooled to room temperature, diluted with water and extracted with EtOAc (10 mL×3). The combined organic extracts were washed with brine (25 mL×2), dried over anhydrous $Na_2SO_4$, filtered and concentrated. The residue was purified by prep-HPLC (Waters 2767/Qda, Column: SunFire 19*250 mm um, Mobile Phase A: 0.1% $TFA/H_2O$, B: ACN) to give desired product (mixture of cis and trans). The obtained product was separated by SFC (SFC80, Waters; OJ 2.5*25 cm, 10 um; A: Supercritical $CO_2$, Mobile phase B: EtOH/ACN=85/15; A:B=60/40; Flow rate: 70 mL/min; column temperature (T): 25° C.; BPR: 100 bar) to afford Compound 152 (trans or cis) (8.8 mg, 2.3% yield) and Compound 153 (cis or trans) (19.8 mg, 5.3% yield).

Example B89

Preparation of Compound 154 and Compound 155

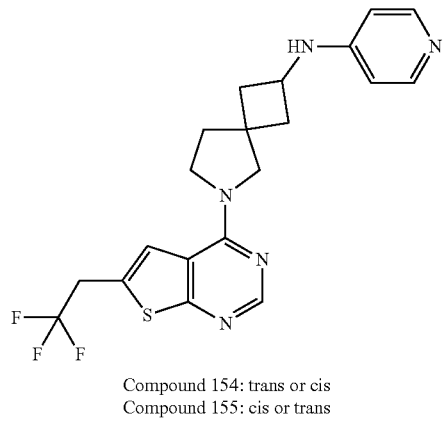 [SMILES: FC(F)(F)Cc1cc2c(N3CCC4(CC(Nc5ccncc5)C4)C3)ncnc2s1]

Compound 154: trans or cis
Compound 155: cis or trans

To a solution of intermediate 3 (300 mg, 0.88 mmol, TFA salt) in 1,4-dioxane (3 mL) under Ar at room temperature were added 4-bromopyridine (CAS #: 1120-87-2) (157 mg, 1.0 mmol), t-BuONa (192 mg, 2.00 mmol), BrettPhos (48 mg, 0.09 mmol) and $Pd_2(dba)_3$ (82 mg, 0.09 mmol). The reaction was stirred under Ar at 110° C. for 12 h. The reaction mixture was cooled to room temperature, poured into water (10 mL) and extracted with EtOAc (20 mL×3). The combined organic extracts were washed with brine (50 mL×2), dried over anhydrous $Na_2SO_4$, filtered and the filtrate was concentrated. The residue was purified by prep-HPLC (Waters 2767/Qda, Column: SunFire 19*250 mm 10 um, Mobile Phase A: 0.1% $TFA/H_2O$, B: ACN) to give desired product (mixture of cis and trans). The obtained product was separated by SFC (SFC80, Waters; OJ 2.5*25 cm, 10 um; A: Supercritical $CO_2$, Mobile phase B: EtOH/ACN=85/15; A:B=60/40; Flow rate: 80 mL/min; column temperature (T): 25° C.; BPR: 100 bar) to afford Compound 154 (trans or cis) (14.19 mg, 3.8% yield) and Compound 155 (cis or trans) (14.95 mg, 4.0% yield).

Example B90

Preparation of Compound 156

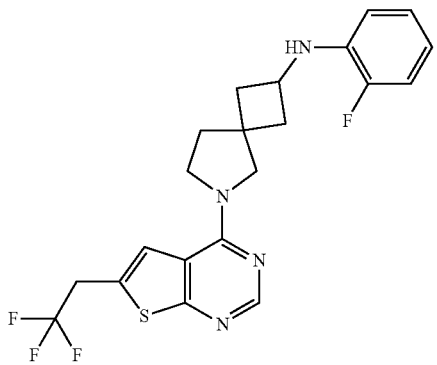

Compound 156: mixture of cis and trans

To a solution of intermediate 3 (300 mg, 0.88 mmol, TFA salt) in 1,4-dioxane (3 mL) under Ar at room temperature were added 1-bromo-2-fluorobenzene (CAS #: 1072-85-1) (175 mg, 1.0 mmol), t-BuONa (192 mg, 2.00 mmol), BrettPhos (48 mg, 0.09 mmol) and $Pd_2(dba)_3$ (82 mg, 0.09 mmol). The reaction was stirred under Ar atmosphere at 130° C. for 12 h. The reaction mixture was cooled to room temperature, diluted with water (20 mL) and extracted with EtOAc (20 mL×3). The combined organic extracts were washed with brine (10 mL×2), dried over anhydrous $Na_2SO_4$, filtered and the filtrate was concentrated. The residue was purified by prep-HPLC (Waters 2767/Qda, Column: SunFire 19*250 mm 10 um, Mobile Phase A: 0.1% $NH_3/H_2O$, B: ACN) to afford Compound 156 (mixture of cis and trans) (65.00 mg, 97% yield).

Example B91

Preparation of Compound 157

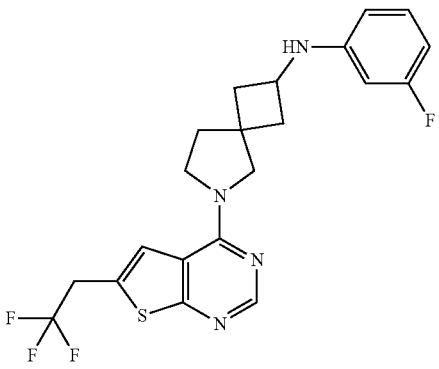

Compound 157: mixture of cis and trans

To a solution of intermediate 3 (300 mg, 0.88 mmol, TFA salt) in 1,4-dioxane (3 mL) under Ar at room temperature were added 1-bromo-3-fluorobenzene (CAS #: 1073-06-9) (175 mg, 1.0 mmol), t-BuONa (192 mg, 2.00 mmol), BrettPhos (48 mg, 0.09 mmol) and $Pd_2(dba)_3$ (82 mg, 0.09 mmol). The reaction was stirred under Ar atmosphere at 110° C. for 2 h. The reaction mixture was cooled to room temperature, poured into water (50 ml) and extracted with EtOAc (50 mL×3). The combined organic extracts were washed with brine (50 mL×2), dried over anhydrous $Na_2SO_4$, filtered and the filtrate was concentrated. The residue was purified by prep-HPLC (Waters 2767/Qda, Column: SunFire 19*250 mm 10 um, Mobile Phase A: 0.1% $NH_3H_2O$, B: ACN) to afford Compound 157 (mixture of cis and trans) (45.8 mg, 96%) as a white solid.

Example B92

Preparation of Compound 158

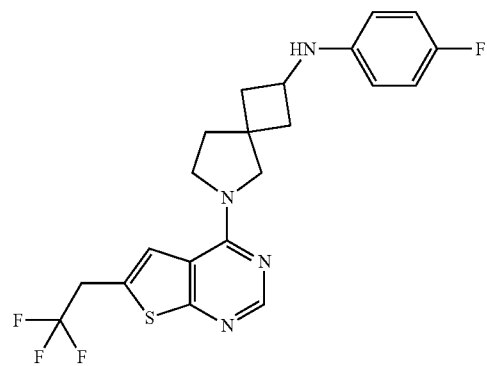

Compound 158: mixture of cis and trans

To a solution of intermediate 3 (300 mg, 0.88 mmol, TFA salt) in 1,4-dioxane (3 mL) under Ar at room temperature were added 1-bromo-4-fluorobenzene (CAS #: 460-00-4) (175 mg, 1.0 mmol), t-BuONa (192 mg, 2.00 mmol), BrettPhos (48 mg, 0.09 mmol) and $Pd_2(dba)_3$ (82 rug, 0.09 mmol). The reaction was stirred under Ar atmosphere at 110° C. for 12 h. The reaction mixture was cooled to room temperature, diluted with water (50 mL) and extracted with EtOAc (50 mL×3). The combined organic extracts were washed with brine (50 mL×2), dried over anhydrous $Na_2SO_4$, filtered and the filtrate was concentrated. The residue was purified by prep-HPLC (Waters 2767/Qda, Column: SunFire 19*250 mm 10 um, Mobile Phase A: 0.1% $NH_3.H_2O$, B: ACN) to afford Compound 158 (mixture of cis and trans) (58.7 mg, 15% yield).

Example B93

Preparation of Compound 159

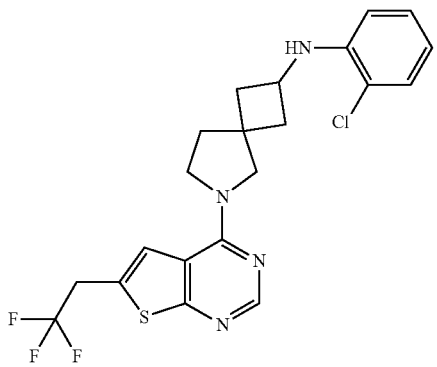

Compound 159: mixture of cis and trans

A mixture of intermediate 3 (200 mg, 0.584 mmol, TFA salt), 1-bromo-2-chloro-benzene (112 mg, 0.584 mmol), Pd$_2$(dba)$_3$ (53 mg, 0.058 mmol), BrettPhos (31 mg, 0.058 mmol) and t-BuONa (168 mg, 1.754 mmol) in 1,4-dioxane (10 mL) was stirred at 120° C. for 2 h under microwave irradiation. The cooled reaction mixture was concentrated. The residue was purified by prep-HPLC (Waters 2767/Qda, Column: Waters Xbridge 19*150 mm 10 um, Mobile Phase A: H$_2$O (0.1% NH$_4$OH), B: ACN) to afford Compound 159 (mixture of cis and trans) (46.9 mg, 17%).

Example B94

Preparation of Compound 160

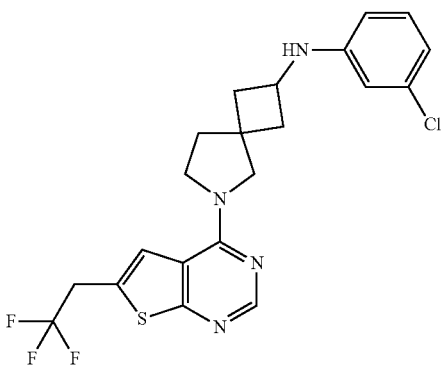

Compound 160: mixture of cis and trans

A mixture of intermediate 3 (200 mg, 0.584 mmol, TFA salt), 1-bromo-3-chloro-benzene (112 mg, 0.584 mmol), Pd$_2$(dba)$_3$ (53 mg, 0.058 mmol), BrettPhos (31 mg, 0.058 mmol) and t-BuONa (168 mg, 1.754 mmol) in 1,4-dioxane (10 mL) was stirred at 120° C. for 2 h under microwave irradiation. The cooled reaction mixture was concentrated. The residue was purified by prep-HPLC (Waters 2767/Qda, Column: Waters Xbridge 19*150 mm 10 um, Mobile Phase A: 120 (0.1% NH$_4$OH), B: ACN) to afford Compound 160 (mixture of cis and trans) (53.8 mg, 20% yield).

Example B95

Preparation of Compound 161

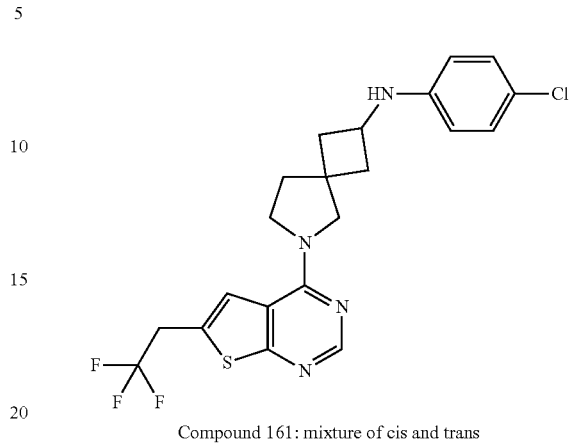

Compound 161: mixture of cis and trans

A mixture of intermediate 3 (300 mg, 0.877 mmol, TFA salt), 1-bromo-4-chlorobenzene (CAS #: 106-39-8) (168 mg, 0.877 mmol), Pd$_2$(dba)$_3$ (80 mg, 0.088 mmol), Brettphos (47 mg, 0.088 mmol) and K$_2$CO$_3$ (363 mg, 2.631 mmol) in 1,4-dioxane (10 mL) was stirred under Ar at 80° C. overnight. The cooled reaction mixture was concentrated. The residue was purified by prep-HPLC (Waters 2767/Qda, Column: Waters Xbridge 19*150 mm 10 um, Mobile Phase A: 1120 (0.1% NH$_1$40H), B: ACN) to afford Compound 161 (mixture of cis and trans) (39.7 mg, 10% yield).

Example B96

Preparation of Compound 162

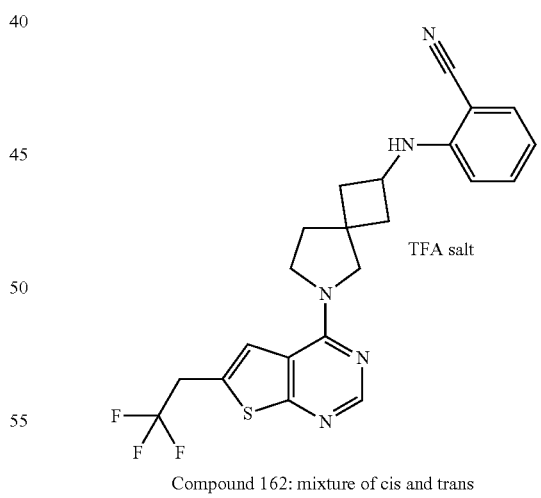

Compound 162: mixture of cis and trans

To a solution of intermediate 3 (220 mg, 0.64 mmol, TFA salt) in 1,4-dioxane (2 mL) in a microwave tube were added 2-bromobenzonitrile (CAS #: 2042-37-7) (351 mg, 1.93 mmol), Cs$_2$CO$_3$ (629 mg, 1.93 mmol), BrettPhos (34 mg, 0.06 mmol) and Pd$_2$(dba)$_3$ (59 mg, 0.06 mmol). The reaction mixture was bubbled with Ar and the reaction mixture was then stirred at 100° C. for 2 h with microwave irradiation. The cooled reaction mixture was diluted with water (20 mL)

339 and extracted with EtOAc (20 mL×3). The combined organic extracts were washed with water (20 mL×3), dried over anhydrous Na$_2$SO$_4$, filtered and the filtrate was concentrated. The residue was purified by prep-HPLC (Waters 2767/Qda, Column: Waters Xbridge 19*150 mm um, Mobile Phase A: H$_2$O (0.1% TFA), B: ACN) to afford Compound 162 (mixture of cis and trans) (72 mg, TFA salt, 25% yield).

Example B97

Preparation of Compound 163

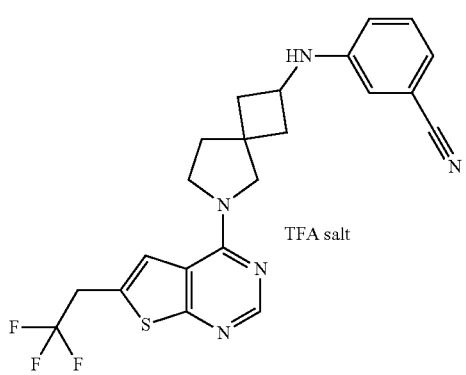

Compound 163: mixture of cis and trans

To a solution of intermediate 3 (200 mg, 0.584 mmol, TFA salt) in 1,4-dioxane (2 mL) in a microwave tube were added 3-bromobenzonitrile (CAS #: 6952-59-6) (319 mg, 1.75 mmol), Cs$_2$CO$_3$ (572 mg, 1.75 mmol), BrettPhos (50 mg, 0.06 mmol) and Pd$_2$(dba)$_3$ (50 mg, 0.09 mmol). The reaction mixture was bubbled with Ar and the reaction mixture was then stirred at 100° C. for 2 h with microwave irradiation. The cooled reaction mixture was diluted with water (20 mL) and extracted with EtOAc (20 mL×3). The combined organic extracts were washed with water (20 mL×3), dried over anhydrous Na$_2$SO$_4$, filtered and the filtrate was concentrated. The residue was purified by prep-HPLC (Waters 2767/Qda, Column: Waters Xbridge 19*150 mm um, Mobile Phase A: H$_2$O (0.1% TFA), B: ACN) to afford Compound 163 (mixture of cis and trans) (206 mg, TFA salt, 63% yield).

Example B98

Preparation of Compound 164

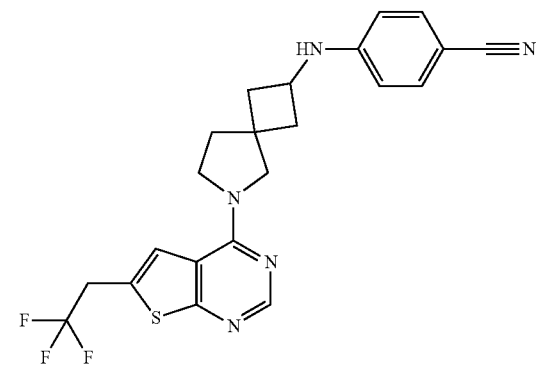

Compound 164: mixture of cis and trans

To a solution of intermediate 3 (300 mg, 0.88 mmol, TFA salt) in 1,4-dioxane (3 mL) under Ar at room temperature were added 4-bromobenzonitrile (CAS #: 623-00-7) (479 mg, 2.63 mmol), Cs$_2$CO$_3$ (858 mg, 2.63 mmol), BrettPhos (75 mg, 0.08 mmol) and Pd$_2$(dba)$_3$ (76 mg, 0.14 mmol). The reaction mixture was stirred under Ar at 80° C. for 2 h. The cooled reaction mixture was diluted with water (30 mL) and extracted with EtOAc (30 ml×3). The combined organic extracts were washed with water (30 mL×3), dried over anhydrous Na$_2$SO$_4$, filtered and the filtrate was concentrated.

The residue was purified by prep-HPLC (Waters 2767/Qda, Column: Waters Xbridge 19*150 mm 10 um, Mobile Phase A: H$_2$O (0.1% NH$_4$OH), B: ACN) to afford Compound 164 (mixture of cis and trans) (266 mg, 68% yield).

Example B99

Preparation of Compound 165

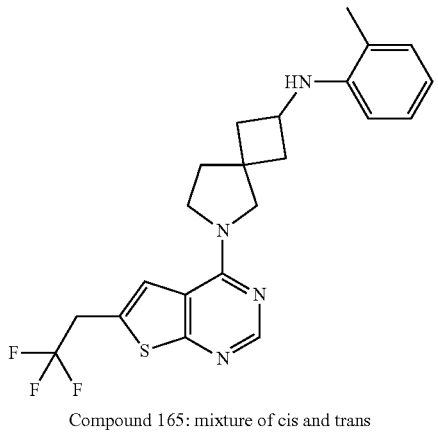 [SMILES: Cc1ccccc1NC1CC2(CCN(c3ncnc4sc(CC(F)(F)F)cc34)C2)C1]

Compound 165: mixture of cis and trans

A mixture of intermediate 3 (200 mg, 0.58 mmol, TFA salt), 1-bromo-2-methylbenzene (CAS #: 95-46-5) (300 mg, 1.75 mmol), Pd$_2$(dba)$_3$ (30 mg), BrettPhos (30 mg) and t-BuONa (168 mg, 1.75 mmol) in 1,4-dioxane (5 mL) was stirred at 110° C. for 2 h with microwave irradiation. The cooled reaction mixture was diluted with water and extracted with EtOAc (50 mL×3). The combined organic extracts were washed with brine, dried over anhydrous Na₂SO₄, filtered and the filtrate was concentrated. The residue was purified by prep-HPLC (Waters 2767/Qda, Column: Waters Xbridge 20*150 mm 10 um, Mobile Phase A: H₂O (0.1% NH₄OH), B: ACN) to give Compound 165 (mixture of cis and trans) (33.3 mg, 13% yield) as a white solid.

Example B100

Preparation of Compound 166

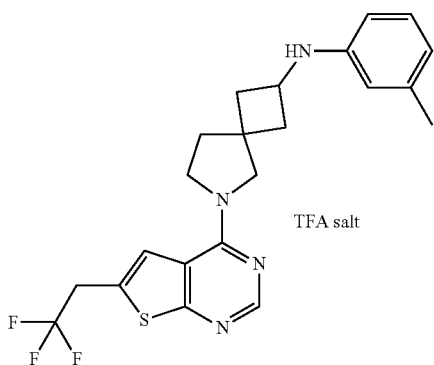

Compound 166: mixture of cis and trans

A mixture of intermediate 3 (200 mg, 0.584 mmol, TFA salt), 1-bromo-3-methyl-benzene (CAS #: 591-17-3) (300 mg, 1.75 mmol), Pd₂(dba)₃ (30 mg), BrettPhos (30 mg) and t-BuONa (168 mg, 1.75 mmol) in 1,4-dioxane (5 mL) was stirred at 110° C. for 2 h with microwave irradiation. The cooled reaction mixture was diluted with water and extracted with EtOAc (50 mL×3). The combined organic extracts were washed with brine, dried over anhydrous Na₂SO₄, filtered and the filtrate was concentrated. The residue was purified by prep-HPLC (Waters 2767/Qda, Column: Prep C18 OBD 19*250 mm 10 um, Mobile Phase A: H₂O (0.1% TFA), B: ACN) to give Compound 166 (mixture of cis and trans) (101.0 mg, TFA salt, 31% yield) as a colorless oil.

Example B101

Preparation of Compound 167

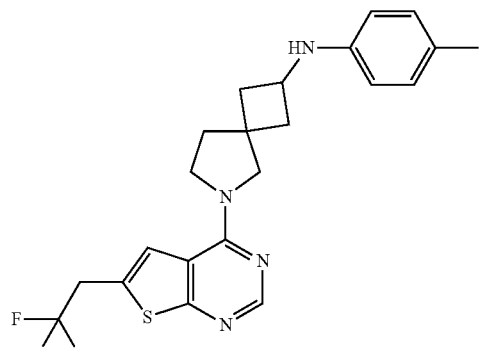

Compound 167: mixture of cis and trans

A mixture of intermediate 3 (200 mg, 0.58 mmol, TFA salt), 1-bromo-4-methylbenzene (CAS #: 106-38-7) (300 mg, 1.75 mmol), Pd₂(dba)₃ (30 mug), BrettPhos (30 mg) and t-BuONa (168 mg, 1.75 mmol) in 1,4-dioxane (5 mL) was stirred at 110° C. for 2 h with microwave irradiation. The reaction mixture was diluted with water and extracted with EA (50 mL×3). The cooled reaction mixture was diluted with water and extracted with EtOAc (50 mL×3). The combined organic extracts were washed with brine, dried over anhydrous Na₂SO₄, filtered and the filtrate was concentrated. The residue was purified by prep-HPLC (Waters 2767/Qda, Column: Waters Xbridge 20*150 mm um, Mobile Phase A: H₂O (0.1% NH₄OH), B: ACN) to give Compound 167 (mixture of cis and trans) (45.9 mg, 18% yield) as a white solid.

Example B102

Preparation of Compound 168

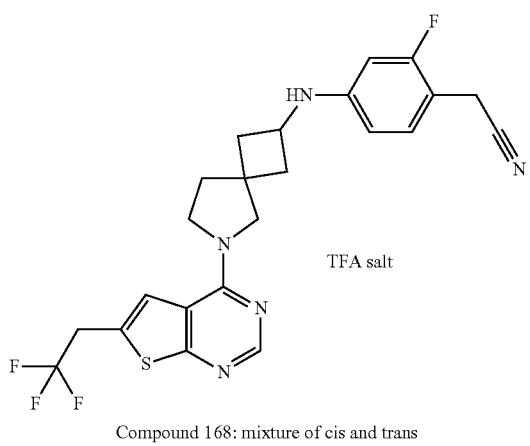 [SMILES: N#CCc1ccc(NC2CC3(CCN(c4ncnc5sc(CC(F)(F)F)cc45)C3)C2)cc1F]

Compound 168: mixture of cis and trans

To a solution of intermediate 3 (200 mg, 0.584 mmol, TFA salt) in 1,4-dioxane (2 mL) in a microwave tube were added 2-(4-bromo-2-fluorophenyl)acetonitrile (CAS #: 114897-91-5) (250 mg, 1.170 mmol), t-BuONa (168 mg, 1.775 mmol), BrettPhos (30 mg, 0.056 mmol) and Pd₂(dba)₃

(53 mg, 0.056 mmol). The resulting mixture was bubbled with Ar and the reaction was stirred at 140° C. for 2 h with microwave irradiation. The cooled reaction mixture was diluted with water and extracted with EtOAc (100 mL×3). The combined organic extracts were washed with brine (50 mL×2), dried over anhydrous Na₂SO₄, filtered and the filtrate was concentrated. The residue was purified by prep-HPLC (Waters 2767/Qda, Column: SunFire 19*250 mm um, Mobile Phase A: 0.1% TFA/H₂O, B: ACN) to afford Compound 168 (mixture of cis and trans) (9.5 mg, TFA salt, 2.7% yield).

Example B103

Preparation of Compound 169 and Compound 170

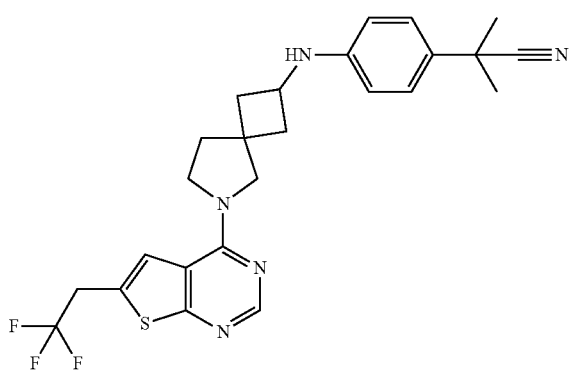

Compound 169: trans or cis
Compound 170: cis or trans

A mixture of intermediate 3 (300 mg, 0.877 mmol, TFA salt), 2-(4-bromophenyl)-2-methylpropanenitrile (CAS #: 101184-73-0) (196 mg, 0.877 mmol), Pd₂(dba)₃ (80 mg, 0.087 mmol), BrettPhos (47 mg, 0.087 mmol) and K₂CO₃ (363 mg, 2.632 mmol) in 1,4-dioxane (10 mL) was stirred at 100° C. for 2 h with microwave irradiation. The cooled reaction mixture was concentrated. The residue was purified by prep-HPLC (Waters 2767/Qda, Column: Waters Xbridge 19*150 mm 10 um, Mobile Phase A: H₂O (0.1% NH₄OH), B: ACN) to afford desired product (mixture of cis and trans) (90 mg). The obtained product was separated by SFC (SFC80, Waters; OD-H 2.5*25 cm, 10 um; A: Supercritical CO₂, Mobile phase B: MeOH=100; A:B=70/30; Flow rate: 60 mL/min; column temperature (T): 25° C.; Backpressure (BPR): 100 bar) to afford Compound 169 (23.6 mg, 11% yield) and Compound 170 (cis or trans) (39.1 mg, 18% yield).

Example B104

Preparation of Compound 171 and Compound 172

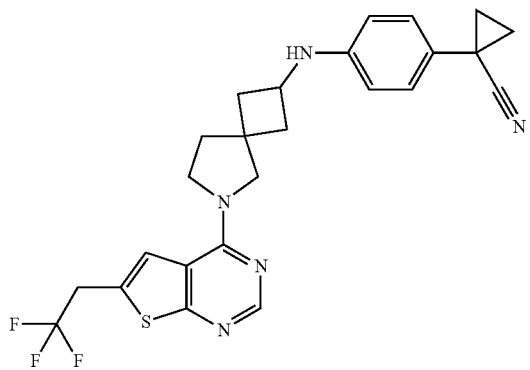

Compound 172: trans or cis
Compound 172: cis or trans

A mixture of intermediate 3 (300 mg, 0.877 mmol, TFA salt), 1-(4-bromophenyl)-cyclopropanecarbonitrile (CAS #: 124276-67-1) (195 mg, 0.877 mmol), Pd₂(dba)₃ (80 mg, 0.087 mmol), BrettPhos (47 mg, 0.087 mmol) and K₂CO₃ (363 mg, 2.631 mmol) in 1,4-dioxane (5 mL) was stirred under Ar at 70° C. for 12 h. The cooled reaction mixture was concentrated. The residue was purified by prep-HPLC (Waters 2767/Qda, Column: Waters Xbridge 19*150 mm 10 um, Mobile Phase A: H₂O (0.1NH₄OH), B: ACN) to afford desired product (mixture of cis and trans) (188 mg). The obtained product was separated by SFC (SFC80, Waters; OD-H 2.5*25 cm, 10 um; A: Supercritical CO₂, Mobile phase B: MeOH=100; A:B=67/33; Flow rate: 70 g/min; column temperature (T): 25° C.; Backpressure (BPR): 100 bar) to afford Compound 171 (trans or cis) (36.7 mg, 17% yield) and Compound 172 (cis or trans) (23.3 mg, 11% yield).

Example B105

Preparation of Compound 173

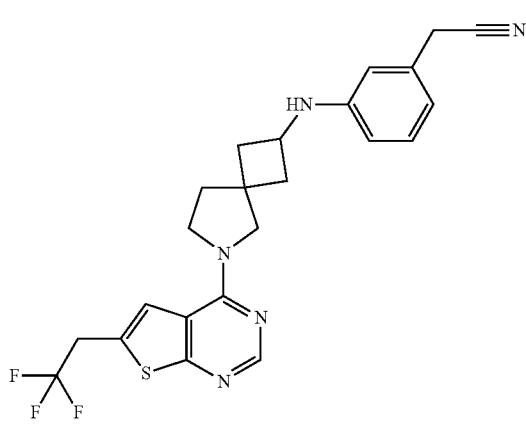

Compound 173: mixture of cis and trans

To a solution of intermediate 3 (200 mg, 0.584 mmol, TFA salt) in 1,4-dioxane (2 mL) in a sealable vessel at room temperature were added 2-(3-bromophenyl)acetonitrile (CAS #: 31938-07-5) (230 mg, 1.170 mmol), t-BuONa (168 mg, 1.775 mmol), BrettPhos (30 mg, 0.056 mmol) and Pd₂(dba)₃ (53 mg, 0.056 mmol). The vessel was bubbled with Ar, sealed and the reaction mixture was stirred at 130° C. overnight. The cooled reaction mixture was diluted with water and extracted with EtOAc (100 mL×3). The combined organic extracts were washed with brine (50 mL×2), dried over anhydrous Na₂SO₄, filtered and the filtrate was concentrated. The residue was purified by prep-HPLC (Waters 2767/Qda, Column: Waters Xbridge 20*150 mm 10 um, Mobile Phase A: 1120 (0.1% NH₃H₂O), B: ACN) to afford Compound 173 (mixture of cis and trans) (9.9 mg, 3.7% yield).

Example B106

Preparation of Compound 174 and Compound 175

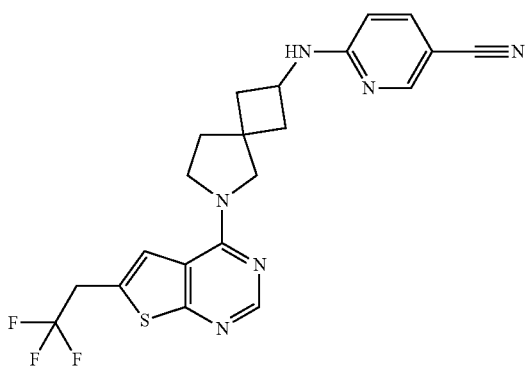

Compound 174: trans or cis
Compound 175: cis or trans

A mixture of intermediate 3 (300 mg, 0.876 mmol, TFA salt), 5-cyano-2-fluoropyridine (CAS #: 3939-12-6) (107 mg, 0.88 mmol) and DIPEA (341 mg, 2.64 mmol) in i-PrOH (10 mL) was stirred at 90° C. for 16 h. The cooled reaction mixture was concentrated. The residue was purified by prep-HPLC (Waters 2767/Qda, Column: SunFire 19*250 mm 10 urn, Mobile Phase A: 0.1% TFA/H₂O, B: ACN) afforded desired product (mixture of cis and trans). The obtained product was separated by SFC (SFC80, Waters; AD-H 2.5*25 cm, 10 um; A: Supercritical CO₂, Mobile phase B: MeOH; A:B=60/40; Flow rate: 60 mL/min; column temperature (T): 25° C.; Backpressure (BPR): 100 bar) to give Compound 174 (trans or cis) (58 mg, 14% yield) as a white solid and Compound 175 (cis or trans) (55 mg, 14% yield) as a white solid.

Example B107

Preparation of Compound 176

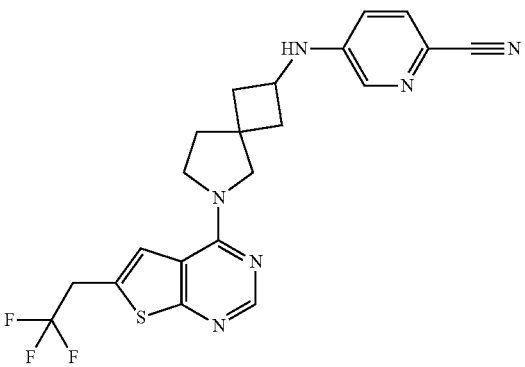

Compound 176: mixture of cis and trans

A mixture of intermediate 3 (300 mg, 0.88 mmol, TFA salt), 2-cyano-5-fluoropyridine (CAS #: 327056-62-2) (107 mg, 0.88 mmol) and DIPEA (341 mg, 2.64 mmol) in n-BuOH (10 mL) was stirred at 120° C. for 16 h. The cooled reaction mixture was concentrated. The residue was purified by prep-HPLC (Waters 2767/Qda, Column: SunFire 19*250 mm 10 um, Mobile Phase A: 0.1% TFA/H₂O, B: ACN). The fractions were basified by NaHCO₃ (solid), extracted with EtOAc (30 mL×3). The combined organic extracts were washed with brine (20 mL×2), dried over anhydrous Na₂SO₄, filtered and the filtrate was concentrated. The residue was lyophilized to give Compound 176 (mixture of cis and trans) (55 mg, 14% yield) as a white solid.

Example B108

Preparation of Compound 177

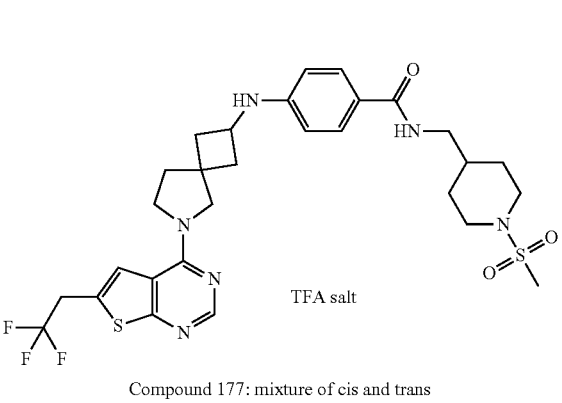 [SMILES: CS(=O)(=O)N1CCC(CNC(=O)c2ccc(NC3CC4(CCN(c5ncnc6sc(CC(F)(F)F)cc56)C4)C3)cc2)CC1]

Compound 177: mixture of cis and trans

To a stirred solution of intermediate 101 (152 mg, crude TFA salt, ca. 0.27 mmol) in DCM (2 mL) was added Et₃N (110 mg, 1.09 mmol). The resulting mixture was cooled with an ice bath and methanesulfonyl chloride (38 mg, 0.33 mmol) was added slowly. The reaction was stirred at room temperature for 2 h. The reaction mixture was concentrated. The residue was purified by prep-HPLC (Waters 2767/Qda, Column: Waters Xbridge 19*150 mm 10 um, Mobile Phase A: H₂O (0.1% TFA), B: ACN) to give Compound 177 (mixture of cis and trans) (23 mg, TFA salt, 13% yield) as a white solid.

Example B109

Preparation of Compound 178 and Compound 179

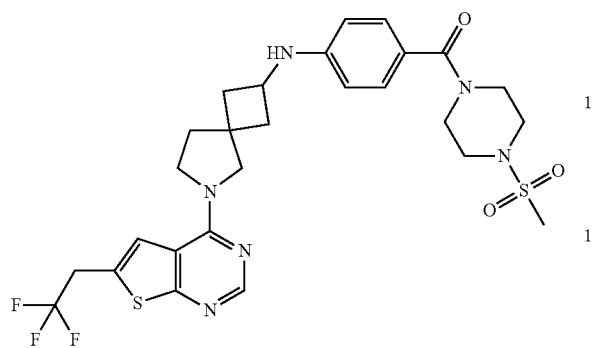

Compound 178: trans or cis
Compound 179: cis or trans

A solution of intermediate 35 (400 mg, 0.86 mmol), DIPEA (210 mg, 1.7 mmol), 1-(methylsulfonyl)piperazine (CAS #: 55276-43-2) (200 mg, 1.2 mmol) and HATU (460 mg, 1.2 mmol) in DMF (5 mL) was stirred at room temperature overnight. The crude product was directly purified by prep-HPLC (Waters 2767/Qda, Column: Waters Xbridge 19*150 mm 10 um, Mobile Phase A: $H_2O$ (0.1% $NH_4OH$), B: ACN) to give desired product (mixture of cis and trans) (90 mg). The obtained product was separated by SFC (SFC80, Waters, AS-H 2.5*25 cm, 10 um, A: Supercritical $CO_2$, B: MeOH/0.1% $NH_3$; A:B=65/35; Flow rate: 50 mL/min; column temperature (T): 25° C.; BPR: 100 bar) to give Compound 178 (trans or cis) (20 mug, 3.8% yield) as a white solid and Compound 179 (cis or trans) (70 mg, 13% yield) as a white solid.

Example B110

Preparation of Compound 180

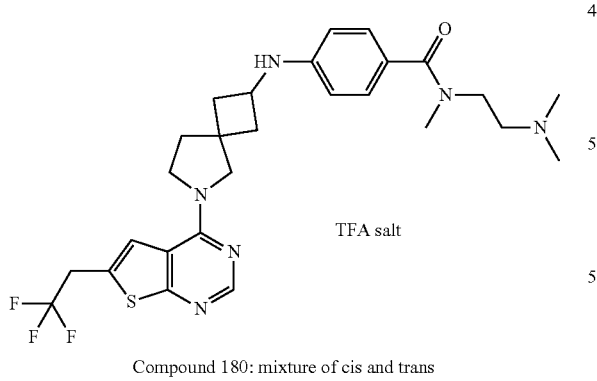

TFA salt

Compound 180: mixture of cis and trans

To a stirred solution of intermediate 35 (150 mg, 0.32 mmol) in THF (2 mL) were added N,N,N'-trimethylethylenediamine (CAS #: 142-25-6) (50 mg, 0.49 mmol), HOBt (66 mg, 0.49 mmol), EDCI (93 mg, 0.49 mmol) and $Et_3N$ (49 mg, 0.49 mmol). The resulting mixture was stirred at room temperature overnight. The reaction mixture was concentrated. The residue was purified by prep-HPLC (Waters 2767/Qda, Column: Waters Xbridge 19*150 mm 10 um, Mobile Phase A: $H_2O$ (0.1% TFA), B: ACN) to afford Compound 180 (mixture of cis and trans) (65 mg TFA salt, 36% yield) as a white solid.

Example B111

Preparation of Compound 181 and Compound 182

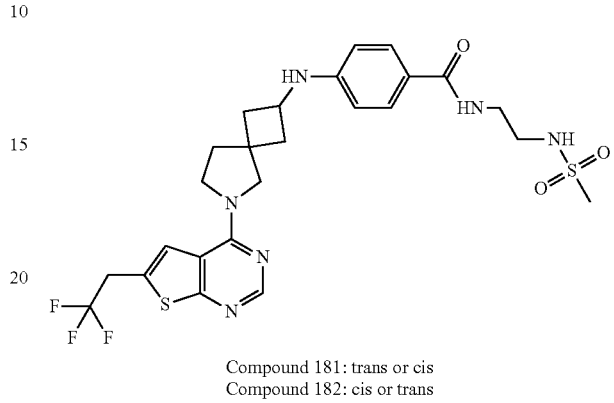

Compound 181: trans or cis
Compound 182: cis or trans

To a stirred solution of intermediate 35 (300 mg, 0.65 mmol) and N-(2-aminoethyl)-methanesulfonamide (CAS #: 83019-89-0) (180 mg, 1.3 mmol) in DMF (5 mL) were added HATU (246 mg, 0.65 mmol) and DIPEA (251 mg, 1.95 mmol). The reaction mixture was stirred at room temperature for 3 h. The resulting mixture was directly purified by prep-HPLC (Waters 2767/Qda, Column: Waters Xbridge 19*150 mm um, Mobile Phase A: $H_2O$ (0.1% $NH_4OH$), B: ACN) to give desired product (mixture of cis and trans) (60 mg, 13% yield) as a white solid. The obtained product was separated by SFC (Separation condition: Column: AD-H Daicel chemical Industries, Ltd, 250*30 mm I.D., 5 um; Mobile phase A: Supercritical $CO_2$, Mobile phase B: EtOH (0.1% DEA)=60/40, at 50 mL/min; Detector Wavelength: 254 nm; Column temperature: 25° C.) to give Compound 181 (trans or cis) (17.8 mg, 4.7% yield) as a white solid and Compound 182 (cis or trans) (13.5 mg, 3.6% yield) as a white solid.

Example B112

Preparation of Compound 183 and Compound 184

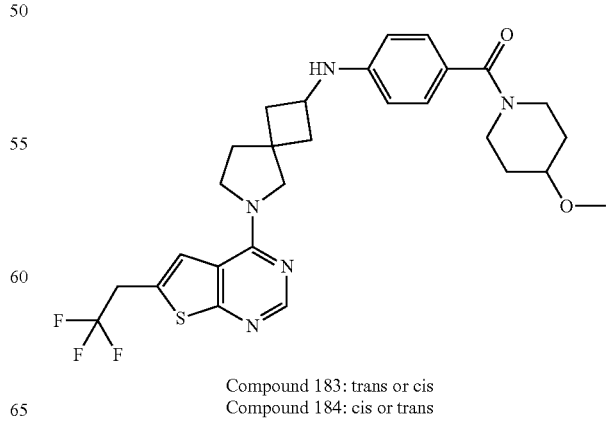

Compound 183: trans or cis
Compound 184: cis or trans

To a stirred solution of intermediate 35 (300 mg, 0.65 mmol) and 4-methoxypiperidine (CAS #: 4045-24-3) (150 mg, 1.3 mmol) in DMF (5 mL) were added HATU (246 mg, 0.65 mmol) and DIPEA (251 mg, 1.95 mmol). The reaction mixture was stirred at room temperature for 3 h. The resulting mixture was directly purified by prep-HPLC (Waters 2767/Qda, Column: Waters Xbridge 19*150 mm 10 um, Mobile Phase A: 1-0 (0.1% NH$_4$OH), B: ACN) to give desired product (mixture of cis and trans) (122 mg, 32% yield) as a yellow oil. The obtained product was separated by SFC (SFC80, Waters; OJ-H (2.5*25 cm, 10 um); A: Supercritical CO$_2$, Mobile phase B: MeOH; A:B=80/20; Flow rate: 60 mL/min; column temperature (T): 25° C.; Backpressure (BPR): 100 bar) to give Compound 183 (trans or cis) (63.7 mg, 17% yield) as a white solid and Compound 184 (cis or trans) (36.7 mg, 10% yield) as a white solid.

Example B113

Preparation of Compound 185 and Compound 186

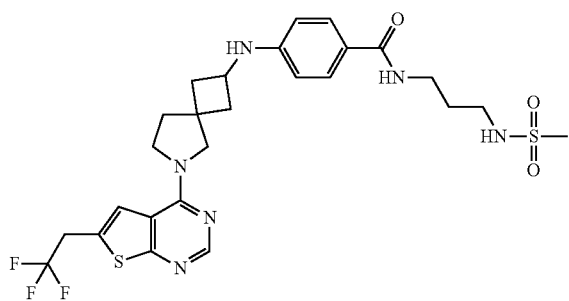

Compound 185: trans or cis
Compound 186: cis or trans

To a stirred solution of intermediate 35 (300 mg, 0.65 mmol) and N-(3-aminopropyl)-methanesulfonamide (CAS #: 88334-76-3) (197 mg, 1.3 mmol) in DMF (5 mL) were added HATU (246 mg, 0.65 mmol) and DIPEA (251 mg, 1.95 mmol). The reaction mixture was stirred at room temperature for 3 h. The resulting mixture was directly purified by prep-HPLC (Waters 2767/Qda, Column: Waters Xbridge 19*150 mm um, Mobile Phase A: H$_2$O (0.1% NH$_4$OH), B: ACN) to give desired product (mixture of cis and trans) (100 mg, 26% yield) as a yellow oil. The obtained product was separated by SFC (Separation condition: Column: AD-H Daicel chemical Industries, Ltd, 250*30 mm I.D., 5 um; Mobile phase A: Supercritical CO$_2$, Mobile phase B: EtOH (0.1% DEA)=60/40, at 50 mL/min; Detector Wavelength: 254 nm; Column temperature: 25° C.) to give Compound 185 (trans or cis) (40.6 mg, 11% yield) as a white solid and Compound 186 (cis or trans) (12.2 mg, 3.2% yield) as a white solid.

Example B114

Preparation of Compound 187 and Compound 188

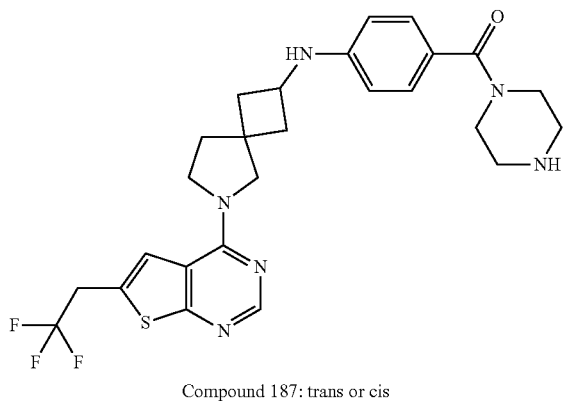

Compound 187: trans or cis
Compound 188: cis or trans

A solution of intermediate 102 (279 mg, 0.44 mmol) in HCl/MeOH (3 M) (3 mL) was stirred at room temperature for 16 h. The solvent was removed by concentration. The residue was suspended in H$_2$O (50 mL) and basified by saturated aqueous NaHCO$_3$ till pH equals 8. The resultant was extracted with EtOAc (50 mL×3). The combined organic extracts were dried over anhydrous Na$_2$SO$_4$, filtered and the filtrate was concentrated. The residue was purified by prep-HPLC (Waters 2767/Qda, Column: SunFire 19*250 mm 10 um, Mobile Phase A: 0.1% TFA/H$_2$O, B: ACN) to give desired product (mixture of cis and trans) as a yellow oil (61 mg). The obtained product was separated by SFC (SFC80, Waters; AD-H 2.5*25 cm, 10 um; A: Supercritical CO$_2$, Mobile phase B: EtOH/ACN=85/15; A:B=60/40; Flow rate: 50 mL/min; column temperature (T): 25° C.; Backpressure (BPR): 100 bar) to afford Compound 187 (trans or cis) (18.9 mg, 8.0% yield) as a light yellow solid and Compound 188 (cis or trans) (2.0 mg, 0.86% yield) as a yellow oil.

Example B115

Preparation of Compound 189 and Compound 190

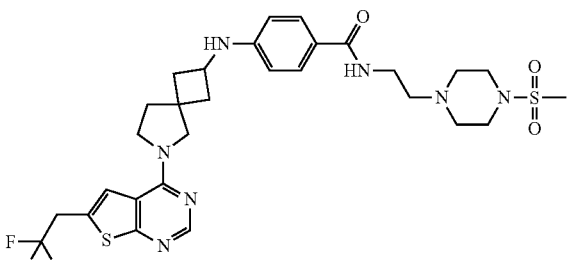

Compound 188: trans or cis
Compound 189: cis or trans

To a suspension of intermediate 104 (600 mg, crude HCl salt, ca. 0.89 mmol) and Et$_3$N (2 mL) in DCM (4 mL) at 0° C. was added methanesulfonyl chloride (2 mL) dropwise. The resulting mixture was stirred at room temperature for 2 h. The reaction mixture concentrated under reduced pressure. The residue was purified by prep-TLC (DCM/MeOH=15:1, v/v) to give desired product (mixture of cis and trans). The obtained product was separated by SFC (SFC80, Waters, OD-H (2.5*25 cm, 10 um) A: Supercritical $CO_2$, B: MeOH (0.1% $NH_3$); A:B=65/35; Flow rate: 50 mL/min; column temperature (T): 25° C.; BPR: 100 bar) to afford Compound 189 (trans or cis) (9.6 mg, 1.6% yield) and Compound 190 (cis or trans) (72.6 mg, 12% yield).

Example B116

Preparation of Compound 191

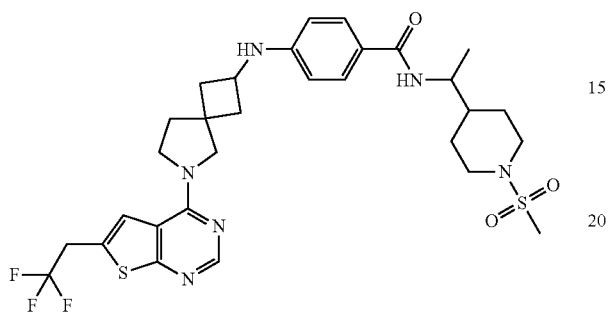

Compound 191
mixture of cis and trans at the spiro moiety

To a stirred solution of intermediate 106 (100 mg, crude HCl salt, ca. 0.174 mmol) in DCM (4 mL) at 0° C. were added methanesulfonyl chloride (20 mg, 0.174 mmol) and DIPEA (0.1 mL). The reaction was stirred at room temperature for 2 h. The resulting mixture was concentrated and the residue was purified by prep-HPLC (Waters 2767/Qda, Column: SunFire 19*250 mm 10 um, Mobile Phase A: 0.1% $NH_3H_2O/H_2O$, B: ACN) to get Compound 191 (mixture of cis and trans at the spiro moiety) (75 mg, yield: 66%) as a white solid.

Example B11

Preparation of Compound 192

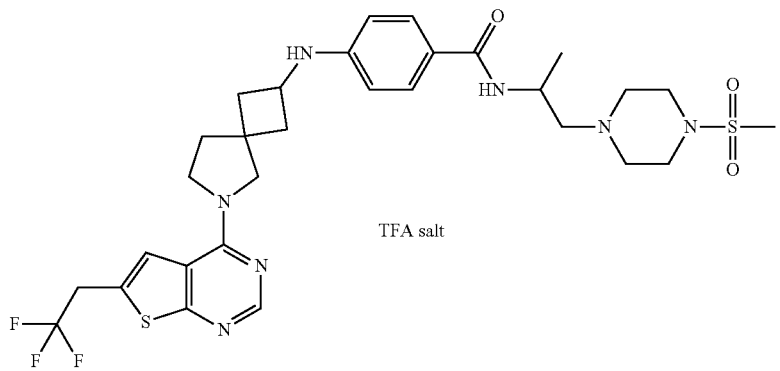

TFA salt

Compound 192: mixture of cis and trans at the spiro moiety

To a stirred mixture of intermediate 108 (190 mg, crude HCl salt, ca. 0.32 mmol) and $Et_3N$ (97 mg, 0.96 mmol) in DCM (5 mL) at 0° C. was added methanesulfonyl chloride (36 mg, 0.32 mmol). The reaction was stirred at room temperature for 2 h. The reaction mixture was quenched with water (20 mL) and extracted with DCM (20 mL×3). The combined organic extracts were washed with brine, dried over anhydrous $Na_2SO_4$, filtered and the filtrate was concentrated. The residue was purified by prep-HPLC (Waters 2767/Qda, Column: SunFire 19*250 mm 10 um, Mobile Phase A: 0.1% $TFA/H_2O$, B: ACN) to give Compound 192 (mixture of cis and trans at the spiro moiety) (43.1 mg, TFA salt, 12% yield) as a white solid.

Example B118

Preparation of Compound 193

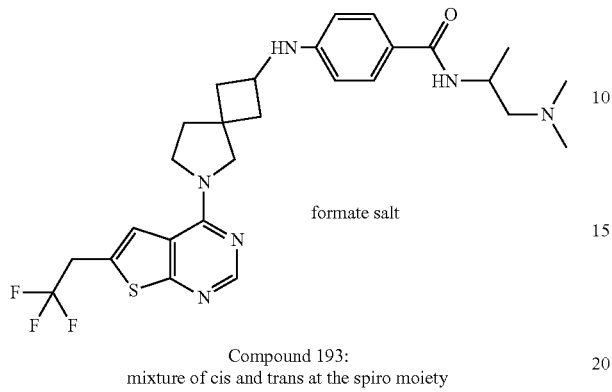

Compound 193:
mixture of cis and trans at the spiro moiety

A mixture of intermediate 35 (150 mg, 0.32 mmol), 1-dimethylamino-2-propylamine (CAS #: 108-15-6) (40 mg, 0.39 mmol), EDCI (92 mg, 0.48 mmol), HOBT (65 mg, 0.48 mmol) and DIPEA (124 mg, 0.0.96 mmol) in DMF (2 mL) was stirred at room temperature for 16 h. Subsequently, the reaction mixture was purified by prep-HPLC (Waters 2767/Qda, Column: SunFire 19*250 mm 10 um, Mobile Phase A: 0.1% FA/H$_2$O, B: ACN) to give Compound 193 (mixture of cis and trans at the spiro moiety) (43.59 mg, formate salt, 23% yield) as a white solid.

Example B119

Preparation of Compound 194 and Compound 195

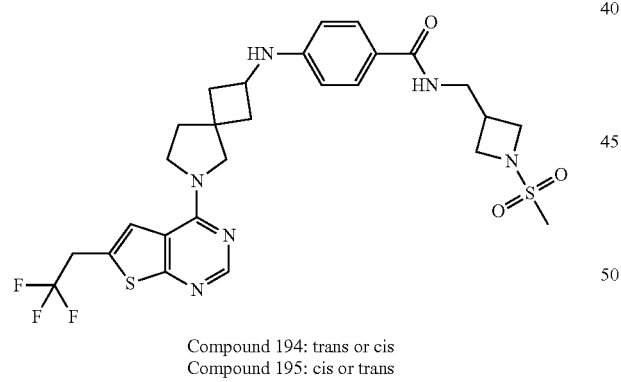

Compound 194: trans or cis
Compound 195: cis or trans

A mixture of intermediate 110 (220 mg, 1.341 mmol), intermediate 35 (619 mg, 1.341 mmol), HATU (509 mg, 1.341 mmol) and Et$_3$N (406 mg, 4.024 mmol) in THF (10 mL) was stirred at room temperature for 3 h and concentrated. The residue was purified by prep-HPLC (Waters 2767/Qda, Column: Waters Xbridge 19*150 mm um, Mobile Phase A: H$_2$O (0.1% NH$_4$OH), B: ACN) to afford desired product (mixture of cis and trans) (200 mg). The obtained product was separated by SFC (SFC80, Waters; AD-H (2.5*25 cm, 10 um); A: Supercritical CO$_2$, Mobile phase B: EtOH/ACN=85/15; A:B=60/40; Flow rate: 50 g/min; column temperature (T): 25° C.; Backpressure (BPR): 100 bar) to afford Compound 194 (trans or cis) (79.5 mg, 19% yield) and Compound 195 (cis or trans) (21.1 mg, 5.1% yield).

Example B120

Preparation of Compound 196

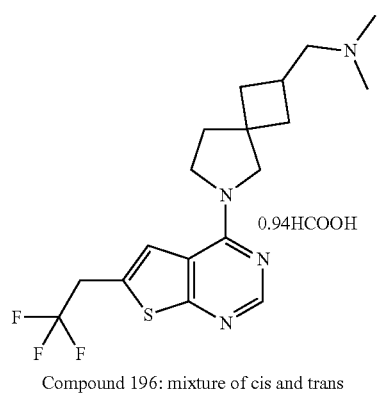 [SMILES: CN(C)CC1CC2(CCN(c3ncnc4sc(CC(F)(F)F)cc34)C2)C1]

Compound 196: mixture of cis and trans

To a stirred solution of crude intermediate 112 (100 mg, crude HCl salt, ca. 0.627 mmol) in i-PrOH (6 mL) at room temperature were added DIPEA (243 mg, 1.88 mmol) and 4-chloro-6-(2,2,2-trifluoroethyl)thieno[2,3-d]pyrimidine (CAS #: 1628317-85-0) (158 mg, 0.62 mmol). The reaction was stirred at room temperature for 5 h. The reaction mixture was poured into water (20 mL) and extracted with EtOAc (50 mL×3). The organic phase was washed with brine, dried over anhydrous Na$_2$SO$_4$, filtered and concentrated. The residue was purified by prep-HPLC (Waters 2767/Qda, Column: Waters Xbridge 20*150 mm 10 um, Mobile Phase A: 1-0 (0.1% FA), B: ACN) to give Compound 196 (mixture of cis and trans) (33.61 mg, 0.94 equivalent formate salt, 12% yield over 3 steps) (equivalents of formic acid was determined by $^1$H NMR).

Example B121

Preparation of Compound 197

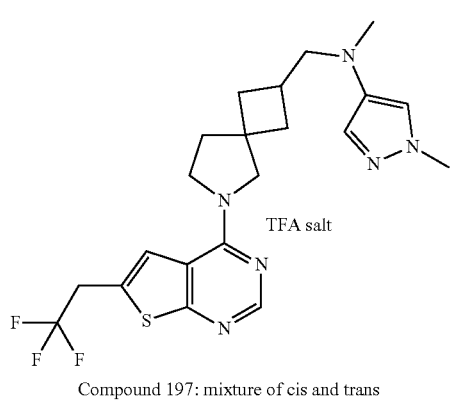 [SMILES: CN(CC1CC2(CCN(c3ncnc4sc(CC(F)(F)F)cc34)C2)C1)c1cnn(C)c1]

Compound 197: mixture of cis and trans

To a stirred solution of intermediate 114 (160 mg, crude TFA salt, ca. 0.450 mmol) in i-PrOH (2 mL) at room temperature were added 4-chloro-6-(2,2,2-trifluoroethyl)- thieno[2,3-d]pyrimidine (CAS #: 1628317-85-0) (113 mg, 0.45 mmol) and DIPEA (290 mg, 2.25 mmol). The reaction was stirred at room temperature overnight. The reaction mixture was concentrated. The residue was purified by prep-HPLC (Waters 2767/Qda, Column: Waters Xbridge 19*150 mm 10 um, Mobile Phase A: I₂O (0.1% TFA), B: ACN) to afford Compound 197 (mixture of cis and trans) (132 mg TFA salt, 51% yield over 3 steps) as a white solid.

Example B122

Preparation of Compound 198

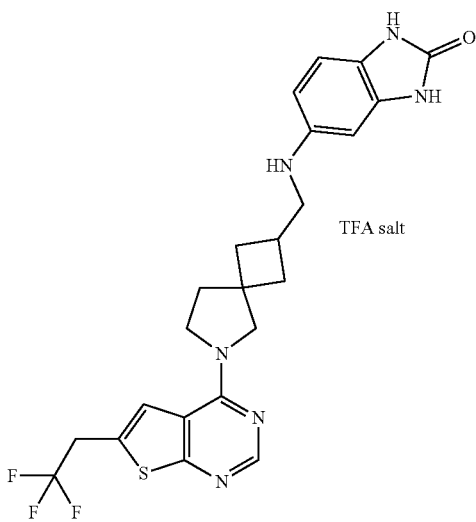

Compound 198: mixture of cis and trans

To a stirred solution of intermediate 116 (250 mg, crude HCl salt, ca. 0.501 mmol) in i-PrOH (5.0 mL) at room temperature were added DIPEA (260 mug, 2.0 mmol) and 4-chloro-6-(2,2,2-trifluoroethyl)thieno[2,3-d]pyrimidine (CAS #: 1628317-85-0) (100 mg, 0.4 mmol). The reaction mixture was stirred at room temperature overnight. The reaction mixture was concentrated and the residue was purified by prep-HPLC (Waters 2767/Qda, Column: Waters Xbridge 19*150 mm 10 um, Mobile Phase A: H₂O (0.1% TFA), B: ACN) to afford Compound 198 (mixture of cis and trans) (71 mg, TFA salt, 23% yield over 3 steps) as a white solid.

Example B123

Preparation of Compound 199 and Compound 200

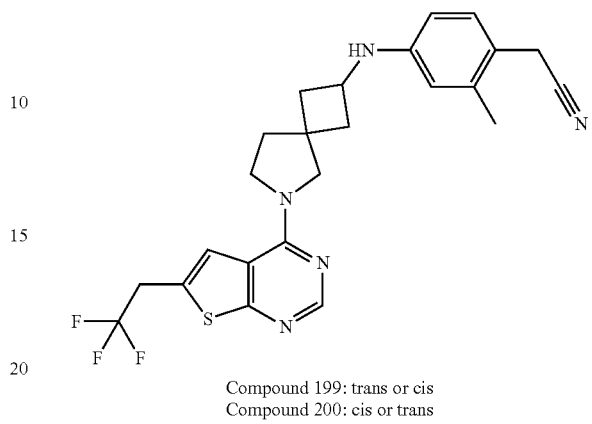

Compound 199: trans or cis
Compound 200: cis or trans

To a stirred solution of intermediate 118 (250 mg, crude ICl salt, ca. 0.965 mmol) in i-PrOH (5 mL) at room temperature were added DIPEA (373 mg, 2.896 mmol) and 4-chloro-6-(2,2,2-trifluoroethyl)thieno[2,3-d]pyrimidine (CAS #: 1628317-85-0) (243 mg, 0.965 mmol). The reaction was stirred at room temperature overnight. The reaction mixture was concentrated. The residue was purified by flash chromatography (eluent: PE/EA=3:1, v/v) to afford the free base form of Compound 168 (mixture of cis and trans) (220 mg). The obtained product was separated by SFC (SFC80, Waters; AD-H 2.5*25 cm, 10 ul; Supercritical CO₂: MeOH=60/40; Flow rate: 60 mL/min; column temperature (T): 35° C.; BPR: 100 bar) to afford Compound 199 (90 mg, 19% yield) and Compound 200 (67 mg, 14% yield) as a white solid.

Example B124

Preparation of Compound 201 and Compound 202

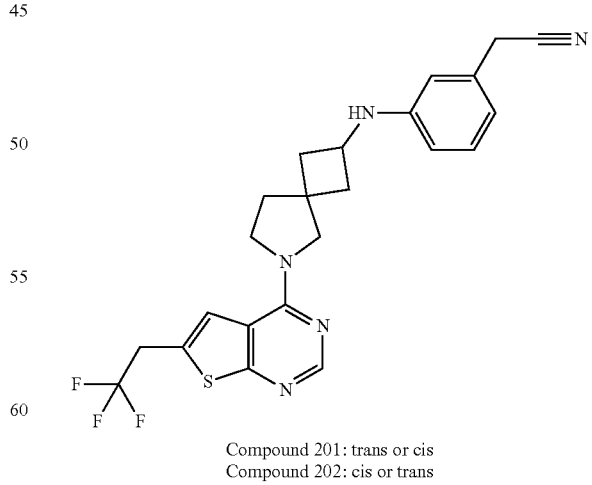

Compound 201: trans or cis
Compound 202: cis or trans

To a stirred solution of intermediate 120 (400 mg, crude TFA salt, ca. 1.0 mmol) and 4-chloro-6-(2,2,2-trifluoroethyl) thieno[2,3-d]pyrimidine (CAS #: 1628317-85-0) (252 mg, 1.0 mmol) in i-PrOH (5 mL) at room temperature was added DIPEA (387 mg, 3.0 mmol). The reaction mixture was stirred at room temperature for 2 h. The reaction mixture was diluted with H₂O (5 mL) and filtered. The filter cake was purified by prep-HPLC (Xbridge C18 5 mm 150*4.6 mm, Mobile Phase A: NH₄OH 0.1% in water, B: NH₄OH 0.1% in CH₃CN) to afford Compound 173 (mixture of cis and trans) (300 mg, 66% yield over 3 steps) as a white solid. The obtained product was separated by SFC (Waters-SFC80; AD-H, 10 um, 2.5*25 cm; Mobile phase A: Supercritical CO₂, Mobile phase B: MeOH/NH₃; A:B=60/40; Flow rate: 50 mL/min; column temperature (T): 25° C.; BPR: 100 bar) to afford Compound 201 (trans or cis) (92 mg, 30% yield) as a white solid and Compound 202 (cis or trans) (90 mg, 30% yield) as a white solid.

Example B125

Preparation of Compound 203, Compound 204 and Compound 205

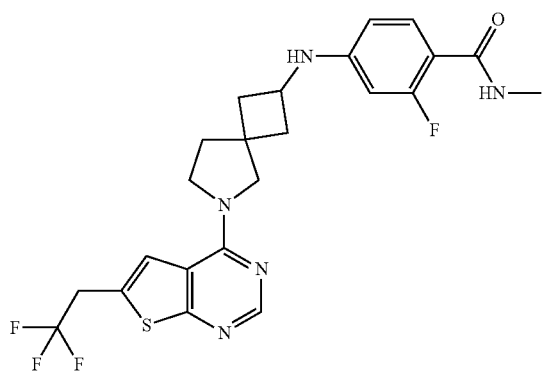

Compound 203: mixture of cis and trans
Compound 204: trans or cis
Compound 205: cis or trans To a stirred solution of intermediate 122 (140 mg, 0.505 mmol) in i-PrOH (5 mL) were added DIPEA (195 mg, 1.51 mmol) and 4-chloro-6-(2,2,2-trifluoroethyl)thieno[2,3-d]-pyrimidine (CAS #: 1628317-85-0) (127 mg, 0.505 mmol). The reaction was stirred at room temperature overnight. The reaction mixture was concentrated. The residue was purified by prep-HPLC (Waters 2767/Qda, Column: Waters Xbridge 19*150 mm 10 um, Mobile Phase A: H₂O (0.1% NH₄OH), B: ACN) to afford Compound 203 (mixture of cis and trans) (206 mg, 81% yield).

The obtained Compound 203 (mixture of cis and trans) (80 mg) was separated by SFC (SFC80, Waters; AD-H 2.5*25 cm, 10 ul; Supercritical CO₂: MeOH=60/40; Flow rate: 60 mL/min; column temperature (T): 25° C.; BPR: 100 bar) to afford Compound 204 (trans or cis) (19.2 mg, 24% yield) and Compound 205 (cis or trans) (15.3 mg, 19% yield) as a white solid.

Example B126

Preparation of Compound 206

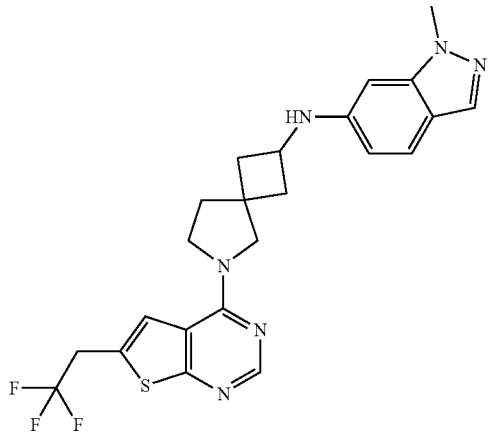

Compound 206: mixture of cis and trans

To a stirred solution of intermediate 124 (226 mg, 0.89 mmol) and 4-chloro-6-(2,2,2-trifluoroethyl)thieno[2,3-d]pyrimidine (CAS #: 1628317-85-0) (252 mg, 1.0 mmol) (224 mg, 0.89 mmol) in i-PrOH (4 mL) at room temperature was added DIPEA (574 mg, 4.45 mmol). The resulting mixture was stirred at room temperature overnight.

The reaction mixture was concentrated. The residue was purified by prep-HPLC (Waters 2767/Qda, Column: Waters Xbridge 19*150 mm 10 um, Mobile Phase A: H₂O (0.1% NH₄OH), B: ACN) to afford Compound 206 (mixture of cis and trans) (157 mg, 37% yield) as a white solid.

Example B127

Preparation of Compound 207

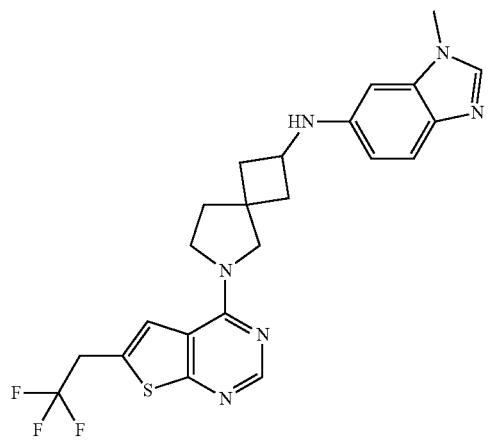

Compound 207: mixture of cis and trans

To a stirred solution of intermediate 126 (450 mg, crude) in i-PrOH (5 mL) at room temperature were added 4-chloro-6-(2,2,2-trifluoroethyl)thieno[2,3-d]pyrimidine (CAS #: 1628317-85-0) (252 mg, 1.0 mmol) (254 mg, 1.00 mmol) and DIPEA (217 mg, 1.68 mmol). The reaction was stirred at room temperature for 2 h. The reaction mixture was concentrated and the residue was purified by prep-HPLC (Waters 2767/Qda, Column: SunFire 19*250 mm 10 um, Mobile Phase A: 0.1% NH₄OH/H₂O, B: ACN) to afford Compound 207 (mixture of cis and trans) (52.8 mg, 11% yield over 3 steps) as a white solid.

Example B128

Preparation of Compound 208 and Compound 209

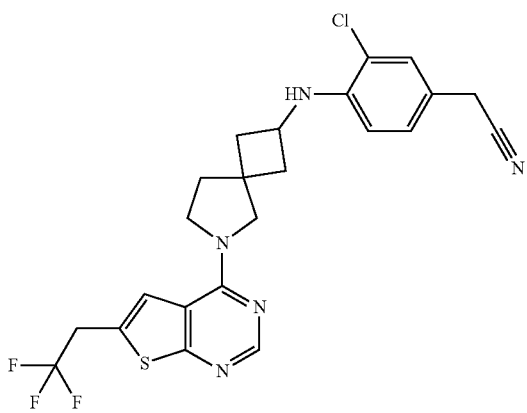

Compound 208: trans or cis
Compound 209: cis or trans

To a stirred solution of intermediate 127 (161 mg, crude TFA salt, ca. 0.59 mmol) in i-PrOH (2 mL) at room temperature were added 4-chloro-6-(2,2,2-trifluoroethyl)-thieno[2,3-d]pyrimidine (CAS #: 1628317-85-0) (148 mg, 0.59 mmol) and DIPEA (381 mg, 2.95 mmol) dropwise. The resulting mixture was stirred at room temperature overnight. The reaction mixture was concentrated. The residue was purified by prep-HPLC (Waters 2767/Qda, Column: Waters Xbridge 19*150 mm 10 um, Mobile Phase A: H₂O (0.1% NH₄OH), B: ACN) to give desired product (mixture of cis and trans) (160 mg). The obtained product was separated by SFC (SFC80, Waters, IE-H 2.5*25 cm, um, A: Supercritical CO₂, B: EtOH/ETOH/DEA=75/25/0.1; A:B=60/40; Flow rate: 70 mL/min; column temperature (T): 25° C.; Backpressure (BPR): 100 bar) to afford Compound 208 (trans or cis) (38 mg, 13% yield) and Compound 209 (cis or trans) (83 mg, 28% yield).

Example B129

Preparation of Compound 210 and Compound 211

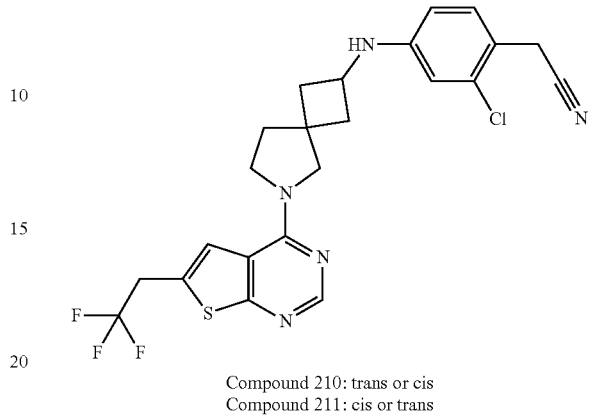

Compound 210: trans or cis
Compound 211: cis or trans

To a stirred solution of intermediate 128 (300 mg, crude HCl salt, ca. 2.25 mmol) in i-PrOH (5 mL) at room temperature were added 4-chloro-6-(2,2,2-trifluoroethyl)-thieno[2,3-d]pyrimidine (CAS #: 1628317-85-0) (274.9 mg, 1.09 mmol) and DIPEA (3 ml), The mixture was stirred at room temperature for 3 h and concentrated. The residue was purified by prep-HPLC (Waters 2767/Qda, Column: SunFire 19*250 mm um, Mobile Phase A: 0.1% TFA/H₂O, B: ACN) to give the mixture of cis and trans. The obtained product was separated by SFC (SFC80, Waters; OJ 2.5*25 cm, 10 um; A: Supercritical CO₂, Mobile phase B: MeOH; A:B=70/30; Flow rate: 70 mL/min; column temperature (T): 25° C.; BPR: 100 bars) to afford Compound 210 (trans or cis) (76.0 mg, 16% yield) and Compound 211 (cis or trans) (73.0 mg, 15% yield).

Example B130

Preparation of Compound 212 and Compound 213

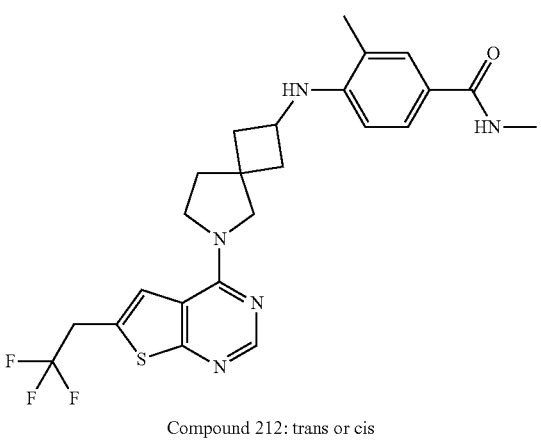

Compound 212: trans or cis
Compound 213: cis or trans

To a stirred solution of intermediate 129 (300 ng, crude HCl salt, ca. 1.09 mmol) in i-PrOH (15 mL) at room temperature were added DIPEA (1 mL) and 4-chloro-6-(2, 2,2-trifluoroethyl)thieno[2,3-d]pyrimidine (CAS #: 1628317-85-0) (274 mg, 1.09 mmol). The reaction was stirred at 50° C. for 1 h. The resulting mixture was concentrated and the residue was purified by prep-HPLC (Waters 2767/Qda, Column: SunFire 19*250 mm 10 um, Mobile Phase A: 0.1% $NH_3.H_2O/H_2O$, B: ACN) to give the mixture of cis and trans (50 mg, 9.3% yield) as a white solid. The obtained product was separated by SFC (SFC80, Waters; IA-H 2.5*25 cm, 10 um; A: Supercritical $CO_2$, Mobile phase B: MeOH; A:B=65/35; Flow rate: 50 mL/min; column temperature (T): 25° C.; BPR: 100 bar) to get Compound 212 (trans or cis) (24 mg, 48% yield) as a white solid and Compound 213 (cis or trans) (24 mg, 48% yield) as a white solid.

Example B131

Preparation of Compound 214

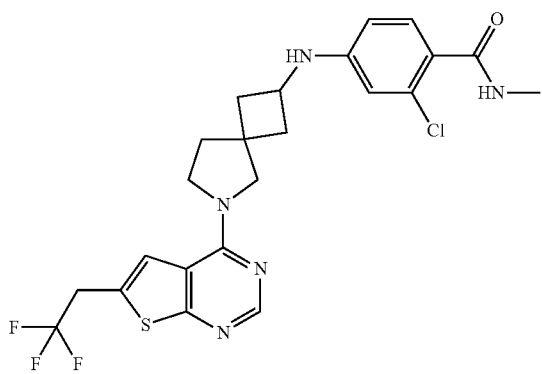

Compound 214: mixture of cis and trans

To a stirred solution of intermediate 130 (586 mg, crude HCl salt, ca. 2.0 mmol) in i-PrOH (5 mL) at room temperature were added 4-chloro-6-(2,2,2-trifluoroethyl)-thieno[2,3-d]pyrimidine (CAS #: 1628317-85-0) (310 mg, 2.0 mmol), DIPEA (1 mL). The reaction mixture was stirred at room temperature for 2 h and then concentrated and the residue was purified by prep-HPLC (Waters 2767/Qda, Column: SunFire 19*250 mm 10 um, Mobile Phase A: 0.1% $TFA/H_2O$, B: ACN) to afford Compound 214 (mixture of cis and trans) (297 mg, 29% yield).

Example B132

Preparation of Compound 215

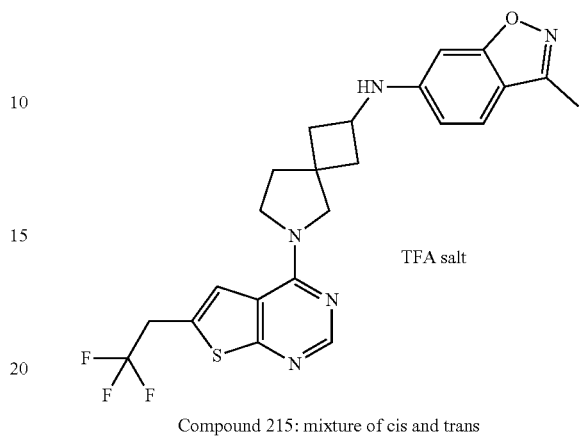

Compound 215: mixture of cis and trans

To a stirred solution of intermediate 131 (80 mg, crude TFA salt, ca. 0.42 mmol) in i-PrOH (3 mL) at room temperature were added 4-chloro-6-(2,2,2-trifluoroethyl)-thieno[2,3-d]pyrimidine (CAS #: 1628317-85-0) (86 mg, 0.34 mmol) and DIPEA (80 mg, 0.62 mmol). The reaction was stirred at room temperature for 1 h. The reaction mixture was concentrated and the residue was purified by prep-HPLC (Waters 2767/Qda, Column: SunFire 19*250 mm 10 um, Mobile Phase A: 0.1% $TFA/H_2O$, B: ACN) to afford Compound 215 (mixture of cis and trans) (33.84 mg, TFA salt, 17% yield) as a white solid.

Example B133

Preparation of Compound 216

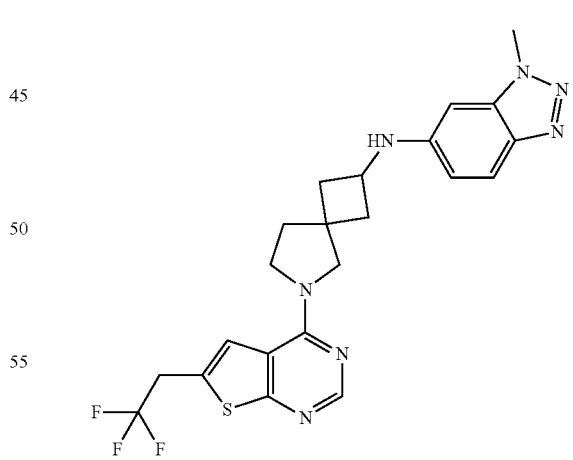

Compound 216: mixture of cis and trans

To a stirred solution of intermediate 132 (129 mg, crude TFA salt, ca. 0.501 mmol) in i-PrOH (10 mL) at room temperature were added DIPEA (194 mg, 1.505 mmol) and 4-chloro-6-(2,2,2-trifluoroethyl)thieno[2,3-d]pyrimidine (CAS #: 1628317-85-0) (126 mg, 0.501 mmol). The reaction mixture was stirred at room temperature for 12 h. The reaction mixture was concentrated. The residue was purified by prep-HPLC (Waters 2767/Qda, Column: Waters Xbridge 19*150 mm 10 um, Mobile Phase A: H₂O (0.1% NH₄OH), B: ACN) to give Compound 216 (mixture of cis and trans) (67.20 mg, 28% yield) as a yellow solid.

Example B134

Preparation of Compound 217 and Compound 218

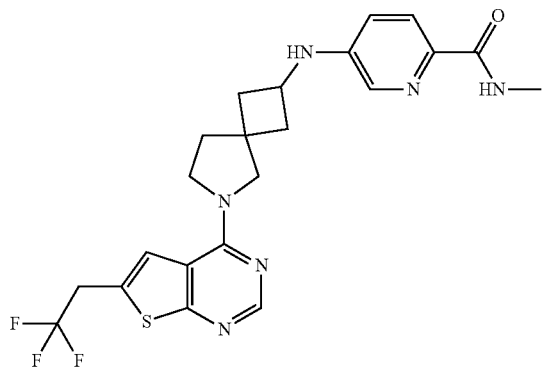

Compound 217: trans or cis (TFA salt)
Compound 218: cis or trans

A mixture of intermediate 133 (450 mg, crude HCl salt, ca. 1.65 mmol), 4-chloro-6-(2,2,2-trifluoroethyl)thieno[2,3-d]pyrimidine (CAS #: 1628317-85-0) (543 mg, 2.15 mmol) and DIPEA (925 mg, 7.16 mmol) in i-PrOH (5 mL) was stirred at room temperature for 16 h. The reaction mixture was concentrated and the residue was purified by prep-HPLC (Waters 2767/Qda, Column: SunFire 19*250 mm 10 um, Mobile Phase A: 0.1% TFA/H₂O, B: ACN) to give desired product (mixture of cis and trans). The obtained product was separated by SFC (SFC80, Waters; OJ-H 2.5*25 cm, 10 um; A: Supercritical CO₂, Mobile phase B: MeOH; A:B=70/30; Flow rate: 50 mL/min; column temperature (T): 25° C.; BPR: 100 bar) to afford Compound 217 (trans or cis) (11.95 mg, TFA salt, 1.3% yield over 3 steps) as a white solid and Compound 218 (cis or trans) (8.83 mg, 1.0% yield over 3 steps) as a white solid.

Example B135

Preparation of Compound 219 and Compound 220

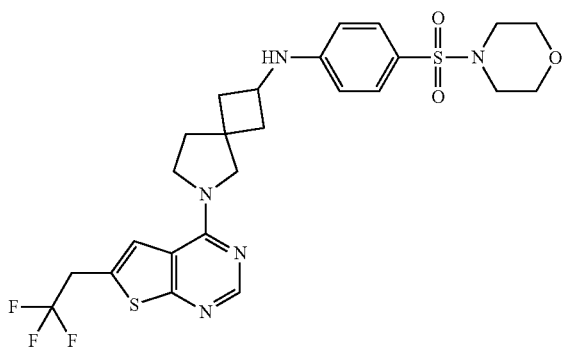

Compound 219: trans or cis
Compound 220: cis or trans (TFA salt)

To a stirred solution of intermediate 134 (380 ng, 1.08 mmol) and 4-chloro-6-(2,2,2-trifluoroethyl)thieno[2,3-d]pyrimidine (CAS #: 1628317-85-0) (273 mg, 1.08 mmol) in i-PrOH (5 mL) was added DIPEA (698 mg, 5.41 mmol). The resulting mixture was stirred at room temperature overnight. The reaction mixture was concentrated. The residue was purified by prep-HPLC (Waters 2767/Qda, Column: Waters Xbridge 19*150 mm 10 um, Mobile Phase A: H₂O (0.1% TFA), B: ACN) to give desired product (mixture of cis and trans) (247 mg, TFA salt). The obtained product was separated by SFC (SFC80, Waters, OJ-H 2.5*25 cm, 10 um, A: Supercritical CO₂, B: MeOH; A:B=75/25; Flow rate: 70 mL/min; column temperature (T): 25° C.; Backpressure (BPR): 100 bar) to afford Compound 219 (trans or cis) (79 mg, 12% yield) and Compound 220 (cis or trans) (97 mg, TFA salt., 15% yield).

Example B136

Preparation of Compound 221

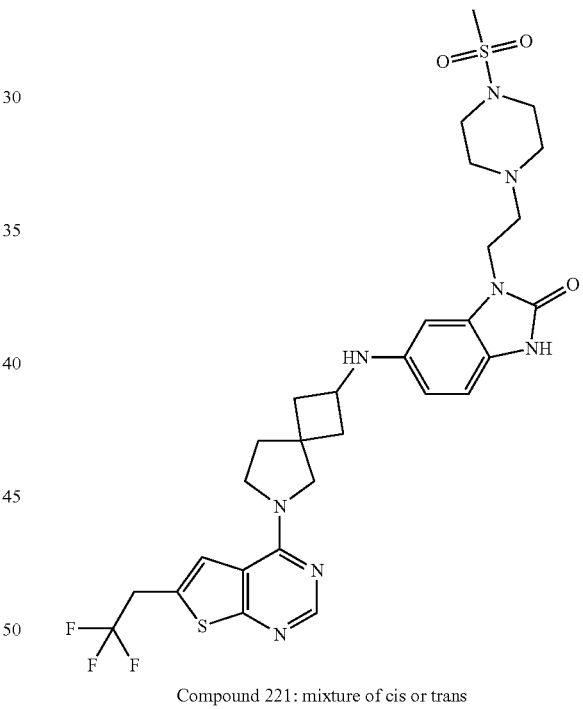

Compound 221: mixture of cis or trans

To a stirred solution of intermediate 138 (55 mg, crude HCl salt, ca. 0.12 mmol) in i-PrO-J (3 mL) were added 4-chloro-6-(2,2,2-trifluoroethyl)thieno[2,3-d]pyrimidine (CAS #: 1628317-85-0) (30.24 mg, 0.12 mmol) and DIPEA (0.05 mL). The reaction mixture was stirred at 50° C. for 5 h. The reaction mixture was concentrated and the residue was purified by prep-HPLC (Waters 2767/Qda, Column: SunFire 19*250 mm 10 um, Mobile Phase A: 0.1% NH₃.H₂O/H₂O, B: ACN) to get Compound 221 (mixture of cis and trans) (8 mg, 10% yield) as a white solid.

Example B137

Preparation of Compound 222

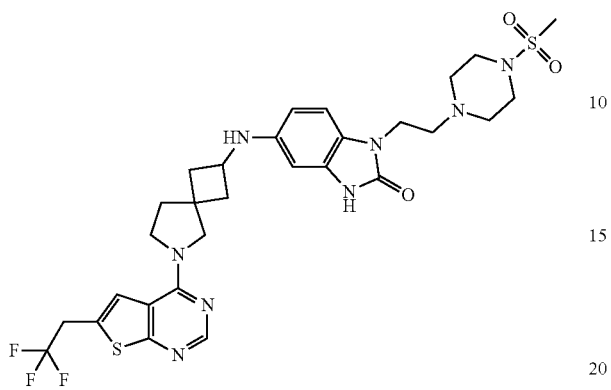

Compound 222: mixture of cis and trans

To a stirred solution of intermediate 142 (220 mg, crude HCl salt, ca. 0.28 mmol) in i-PrOH (3 mL) at room temperature were added 4-chloro-6-(2,2,2-trifluoroethyl)-thieno[2,3-d]pyrimidine (CAS #: 1628317-85-0) (135 mg, 0.54 mmol) and DIPEA (126 mg, 0.98 mmol). The reaction mixture was stirred at room temperature for 1 h.

The reaction mixture was concentrated and the residue was purified by prep-HPLC (Waters 2767/Qda, Column: SunFire 19*250 mm 10 um, Mobile Phase A: 0.1% NH$_4$OH/H$_2$O, B: ACN) to afford Compound 222 (mixture of cis and trans) (34.1 mg, 18% yield over 2 steps) as a white solid.

Example B138

Preparation of Compound 223

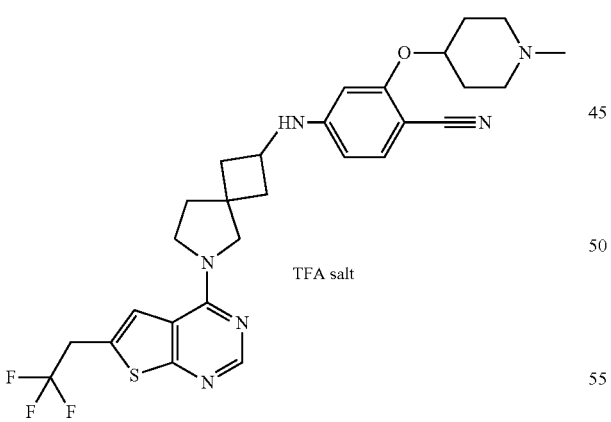

TFA salt

Compound 223: mixture of cis and trans

To a stirred mixture of intermediate 145 (500 mg, crude TFA salt, ca. 1.53 mmol) and 4-chloro-6-(2,2,2-trifluoroethyl)thieno[2,3-d]pyrimidine (CAS #: 1628317-85-0) (300 mg, 1.19 mmol) in i-PrOH (10 mL) was added DIPEA (767 mg, 5.95 mmol). The reaction was stirred at room temperature overnight. The reaction mixture was concentrated. The residue was purified by prep-HPLC (Waters 2767/Qda, Column: Waters Xbridge 19*150 mm 10 um, Mobile Phase A: H$_2$O (0.1% TFA), B: ACN) to afford Compound 223 (mixture of cis and trans) (142 mg, TFA salt, approximately 13% yield over 4 steps).

Example B139

Preparation of Compound 224

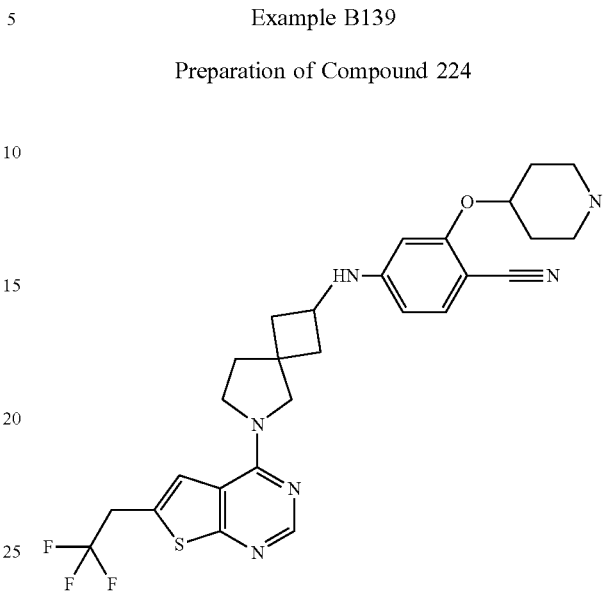

Compound 224: mixture of cis and trans

A mixture of intermediate 149 (380 mg, 1.17 mmol), 4-chloro-6-(2,2,2-trifluoro-ethyl)thieno[2,3-d]pyrimidine (CAS #: 1628317-85-0) (265 mg, 1.05 mmol) and DIPEA (604 mg, 4.68 mmol) in i-PrOH (6 mL) was stirred at 55° C. for 3 h. LC-MS indicated desired mass peak was formed. The reaction mixture was concentrated. The residue was purified by prep-HPLC (Waters 2767/Qda, Column: Waters Xbridge 19*150 mm um, Mobile Phase A: H$_2$O (0.1% NH$_4$OH), B: ACN) to give Compound 224 (mixture of cis and trans) (45 mg, 7.1% yield) as a white solid.

Example B140

Preparation of Compound 225

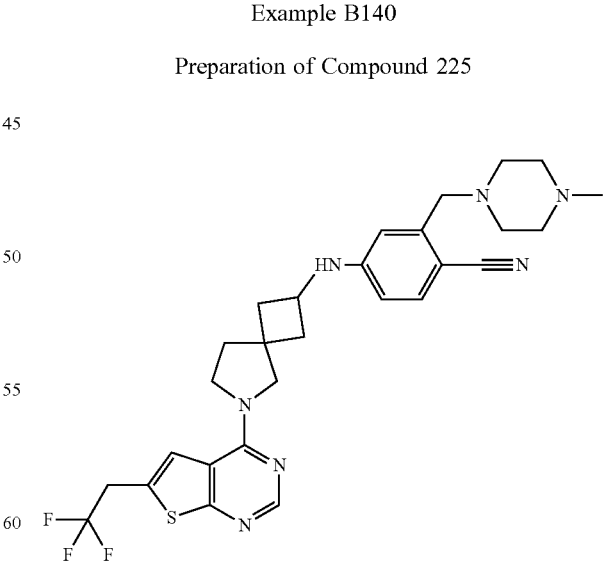

Compound 225: mixture of cis and trans

To a mixture of intermediate 153 (250 mg, crude TFA salt, ca. 0.341 mmol) and 4-chloro-6-(2,2,2-trifluoroethyl)thieno[2,3-d]pyrimidine (CAS #: 1628317-85-0) (150 mg, 0.595 mmol) in i-PrOH (10 mL) at room temperature was added DIPEA (230 mg, 1.78 mmol). The reaction was stirred at room temperature overnight. The reaction mixture was concentrated. The residue was purified by prep-HPLC (Waters 2767/Qda, Column: Waters Xbridge 19*150 mm 10 um, Mobile Phase A: H₂O (0.1% NH₄OH), B: ACN) to afford Compound 225 (mixture of cis and trans) (36 mg, 18% yield over 2 steps) as a white solid.

Example B141

Preparation of Compound 226 and Compound 227

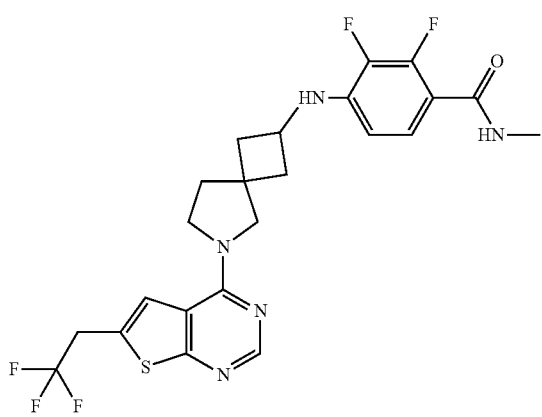

Compound 226: trans or cis
Compound 227: cis or trans

To a stirred solution of intermediate 156 (286 mg, crude TFA salt, ca. 0.97 mmol) and 4-chloro-6-(2,2,2-trifluoroethyl)thieno[2,3-d]pyrimidine (CAS #: 1628317-85-0) (244 mg, 0.97 mmol) in i-PrOH (5 mL) at room temperature was added DIPEA (624 mg, 4.84 mmol). The resulting mixture was stirred at room temperature overnight. The reaction mixture was concentrated. The residue was purified by prep-HPLC (Waters 2767/Qda, Column: Waters Xbridge 19*150 mm 10 um, Mobile Phase A: H₂O (0.1% NH₄OH), B: ACN) to give the desired product (mixture of cis and trans) (270 mg). The obtained product was separated by SFC (SFC80, Waters, IC 2.5*25 cm, 10 um, A: Supercritical CO₂, B: MeOH; A:B=75/25; Flow rate: 50 mL/min; column temperature (T): 25° C.; Backpressure (BPR): 100 bar) to afford Compound 226 (trans or cis) (86 mg, 17% yield) and Compound 227 (cis or trans) (114 mg, 23% yield).

Example B142

Preparation of Compound 228 and Compound 229

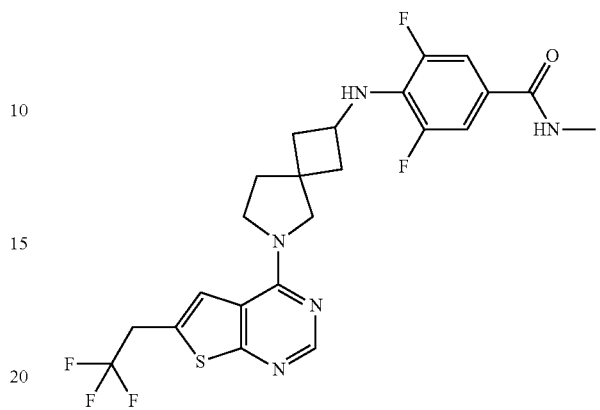

Compound 228: trans or cis
Compound 229: cis or trans

To a stirred solution of intermediate 159 (200 mg, crude HCl salt, 0.678 mmol) in i-PrOH (4 mL) were added DIPEA (262 mg, 2.03 mmol) and 4-chloro-6-(2,2,2-tri-fluoroethyl)thieno[2,3-d]pyrimidine (CAS #: 1628317-85-0) (171 mg, 0.678 mmol). The reaction was stirred at room temperature for 12 h. The reaction mixture was concentrated. The residue was purified by flash chromatography (PE/EtOAc=1:1, v/v) to obtain the mixture of cis and trans) (300 mg). The obtained product was separated by SFC (SFC80, Waters; OJ-H 2.5*25 cm, 10 ul; Supercritical CO2:MeOH=75/25; Flow rate: 65 mL/mm; column temperature (T): 25° C.; BPR: 100 bar) to afford Compound 228 (trans or cis) (110 mg, 31% yield) and Compound 229 (cis or trans) (82 mg, 23% yield) as a white solid.

Example B143

Preparation of Compound 230 and Compound 231

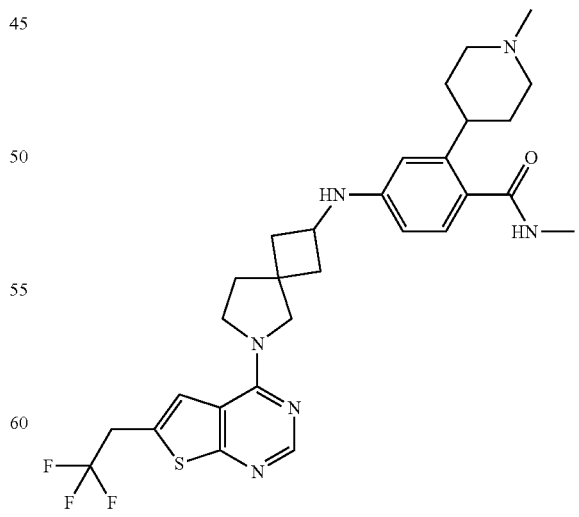

Compound 230: trans or cis
Compound 231: cis or trans

369

To a stirred solution of intermediate 165 (117 ng, 0.44 mmol) and 4-chloro-6-(2,2,2-trifluoroethyl)thieno[2,3-d]pyrimidine (CAS #: 1628317-85-0) (83 mg, 0.44 mmol) in i-PrOH (2 mL) was added DIPEA (212 mg, 2.20 mmol). The reaction was stirred at room temperature overnight. The reaction mixture was concentrated. The residue was purified by prep-HPLC (Waters 2767/Qda, Column: Waters Xbridge 19*150 mm 10 um, Mobile Phase A: $H_2O$ (0.1% $NH_4OH$), B: ACN) to give desired product (mixture of cis and trans) (70 mg). The obtained product was separated by SFC (SFC80, Waters, IC 2.5*25 cm, 10 um, A: Supercritical $CO_2$, B: EtOH/ACN=84:16 (0.1% $NH_3$); A:B 75/25; Flow rate: 70 mL/min; column temperature (T): 25° C.; Backpressure (BPR): 100 bar) to afford Compound 230 (trans or cis) (29 mg, 11% yield) and Compound 231 (cis or trans) (24 mg, 9.5% yield).

Example B144

Preparation of Compound 232 and Compound 233

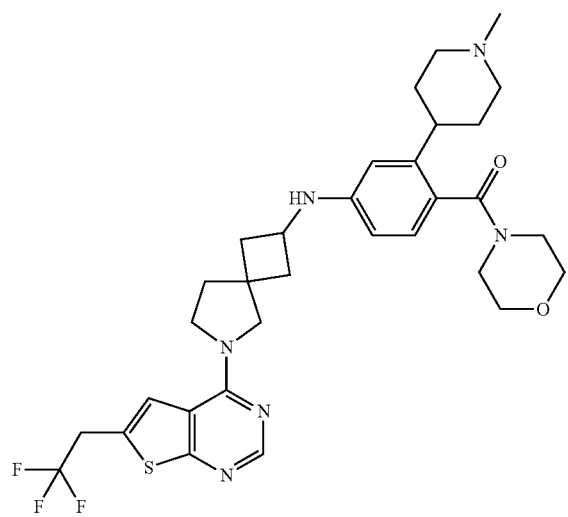

Compound 232: trans or cis
Compound 233: cis or trans

To a stirred mixture of intermediate 169 (130 mg, 0.317 mmol) and 4-chloro-6-(2,2,2-trifluoroethyl)thieno[2,3-d]pyrimidine (CAS #: 1628317-85-0) (80 mg, 0.317 mmol) in i-PrOH (5 mL) was added DIPEA (123 mg, 0.952 mmol). The reaction was stirred at room temperature overnight. The reaction mixture was concentrated. The residue was purified by prep-TLC (DCM/MeOH=15:1, v/v) to give desired product (mixture of cis and trans). The obtained product was separated by SFC (Instrument: Waters-SFC80; Column: AD-H (2.5*25 cm, 10 um); Mobile phase A: Supercritical $CO_2$, Mobile phase B: EtOH/ACN=85/15 (0.1% $NH_3$); A:B 70/30 at 60 mL/min; Detector Wavelength: 214 nm; Column temperature (T): 25° C.; Back pressure (BPR): 100 bar) to give Compound 232 (trans or cis) (13.6 mg,) and Compound 233 (cis or trans) (12.9 mg,).

370

Example B145

Preparation of Compound 234 and Compound 235

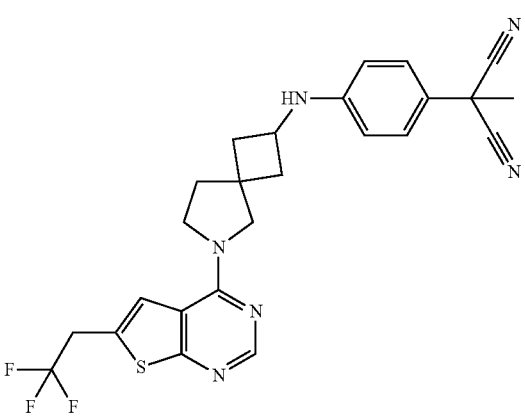

Compound 234: trans or cis
Compound 235: cis or trans

To a stirred solution of intermediate 172 (200 mg, crude TFA salt, ca. 0.736 mmol) in i-PrOH (3 mL) were added DIPEA (275 mg, 2.13 mmol) and 4-chloro-6-(2,2,2-trifluoroethyl)thieno[2,3-d]pyrimidine (CAS #: 1628317-85-0) (198 mg, 0.79 mmol). The reaction was stirred at room temperature for 2 h. The reaction mixture was concentrated. The residue was purified by prep-HPLC (Waters 2767/Qda, Column: Waters Xbridge 19*150 mm 10 um, Mobile Phase A: $H_2O$ (0.1% N401H), B: ACN) to get the desired product (mixture of cis and trans) (90 mg). The obtained product was separated by SFC (SFC80, Waters, AD-H 2.5*25 cm, 10 um, A: Supercritical $CO_2$, B: MeOH/$NH_3$; A:B=70/30; Flow rate: 55 mL/min; column temperature (T): 25° C.; BPR: 100 bar) to get Compound 234 (trans or cis) (42.9 mg, 11% yield over 2 steps) as a white solid and Compound 235 (cis or trans) (39.3 mg, 10% yield over 2 steps) as a white solid.

Example B146

Preparation of Compound 236

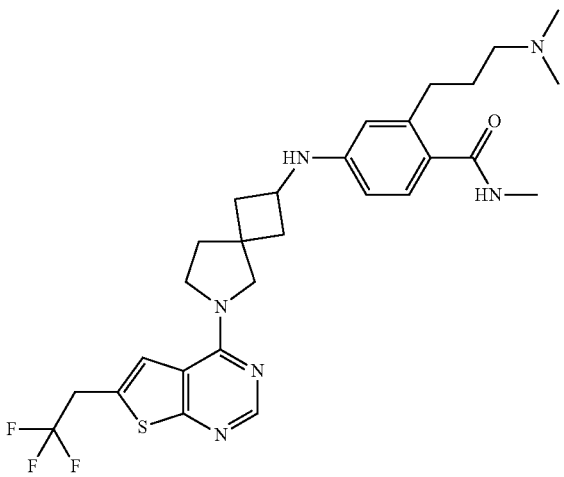

Compound 236: mixture of cis and trans

To a stirred solution of intermediate 177 (50 mg, crude HCl salt, ca. 0.67 mmol) in i-PrOH (5 mL) at room temperature were added 4-chloro-6-(2,2,2-trifluoroethyl)-thieno[2,3-d]pyrimidine (CAS #: 1628317-85-0) (37 mg, 0.15 mmol) and DIPEA (1 mL). The reaction mixture was stirred at room temperature for 2 h. The reaction mixture was concentrated, and the residue was purified by prep-HPLC (Waters 2767/Qda, Column: SunFire 19*250 mm 10 um, Mobile Phase A: 0.1% TFA/H$_2$O, B: ACN). The residue was basified to afford Compound 236 as the free base (mixture of cis and trans) (11.5 mg, 15% yield over 2 steps).

Example B147

Preparation of Compound 237 and Compound 238

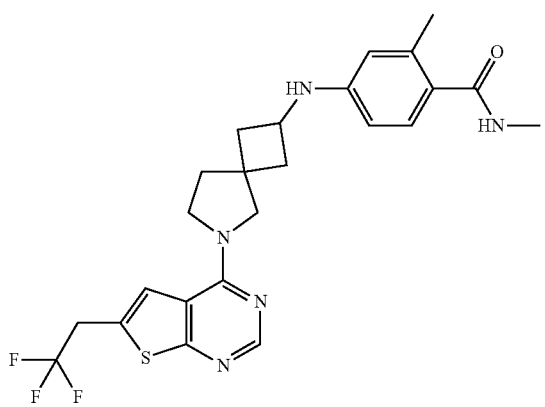

Compound 237: trans or cis
Compound 238: cis or trans

A mixture of intermediate 181 (200 mg, crude TFA salt, ca. 0.55 mmol), 4-chloro-6-(2,2,2-trifluoroethyl)thieno[2,3-d]pyrimidine (CAS #: 1628317-85-0) (139 mg, 0.55 mmol) and DIPEA (213 mg, 1.65 mmol) in i-PrOH (10 mL) was stirred at room temperature for 2 h. The reaction mixture was concentrated and the residue was purified by prep-HPLC (Xbridge C18 5 mm 150*4.6 mm, Mobile Phase A: NH$_4$OH 0.1% in water, B: NH$_4$OH 0.1% in CH$_3$CN) to afford desired product (mixture of cis and trans) (210 mg, 78% yield) as a white solid. The obtained product was separated by SFC (SFC80, Waters; OD-H (2.5*25 cm, 10 um); A: Supercritical CO$_2$, Mobile phase B: MeOH; A:B=75/25; Flow rate: 60 mL/min; column temperature (T): 25° C.; Backpressure (BPR): 100 bar) to afford Compound 237 (trans or cis) (94 mg) as a white solid and Compound 238 (cis or trans) (98 mg) as a white solid.

Example B148

Preparation of Compound 239

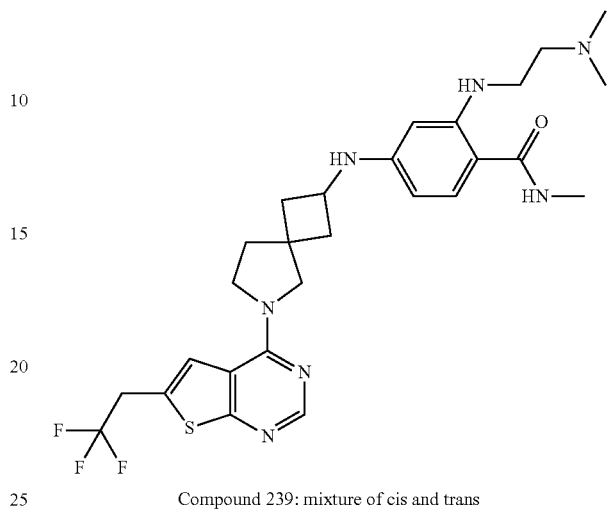

Compound 239: mixture of cis and trans

To a stirred solution of intermediate 184 (131 mg, crude TFA salt, ca. 0.379 mmol) in i-PrOH (10 mL) at room temperature were added DIPEA (147 mg, 1.139 mmol) and 4-chloro-6-(2,2,2-trifluoroethyl)thieno[2,3-d]pyrimidine (CAS #: 1628317-85-0) (95.5 mg, 0.379 mmol). The reaction was stirred at room temperature for 12 h. The reaction mixture was concentrated. The residue was purified by prep-HPLC (Waters 2767/Qda, Column: Waters Xbridge 19*150 mm 10 um, Mobile Phase A: H$_2$O (0.1% NH$_4$OH), B: ACN) to give Compound 239 (mixture of cis and trans) (14.3 mg, 6.7%) as a yellow solid.

Example B149

Preparation of Compound 240

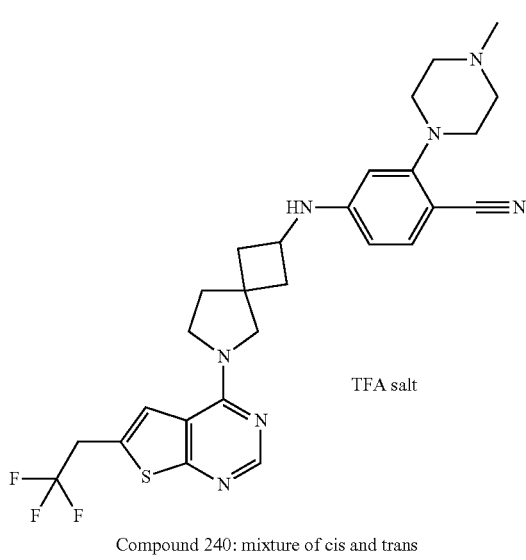 [SMILES: CN1CCN(c2cc(NC3CC4(CCN(c5ncnc6sc(CC(F)(F)F)cc56)C4)C3)ccc2C#N)CC1]

TFA salt

Compound 240: mixture of cis and trans

373

A mixture of intermediate 187 (80 mg, crude TFA salt, ca. 0.14 mmol), 4-chloro-6-(2,2,2-trifluoroethyl)thieno[2,3-d]pyrimidine (CAS #: 1628317-85-0) (35 mg, 0.14 mmol) and DIPEA (54 mg, 0.42 mmol) in i-PrOH (5 mL) was stirred at room temperature for 2 h. After the reaction was complete, the reaction mixture was concentrated and the residue was purified by prep-HPLC (Waters 2767/Qda, Column: SunFire 19*250 mm 10 um, Mobile Phase A: 0.1% TFA/H$_2$O, B: ACN) to afford Compound 240 (mixture of cis and trans) (41 mg, TFA salt, 54% yield) as an off-white solid.

Example B150

Preparation of Compound 241

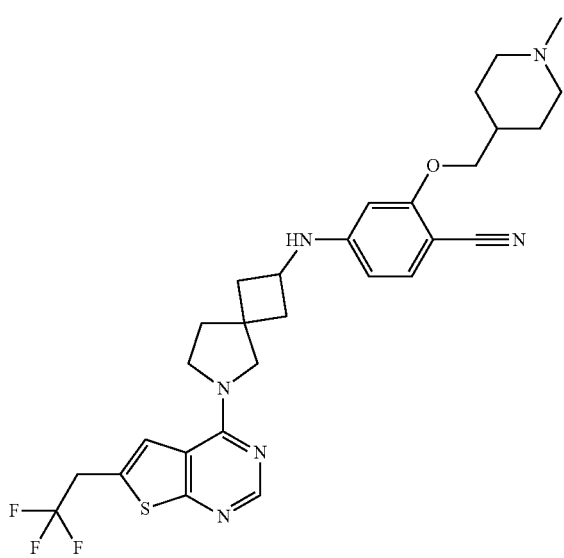

Compound 241: mixture of cis and trans

To a stirred solution of intermediate 193 (97 mg, crude TFA salt, ca. 0.28 mmol) and 4-chloro-6-(2,2,2-trifluoroethyl)thieno[2,3-d]pyrimidine (CAS #: 1628317-85-0) (69 mg, 0.28 mmol) in i-PrOH (3 mL) was added DIPEA (177 mg, 1.38 mmol). The resulting mixture was stirred at room temperature overnight. The mixture was concentrated under reduced pressure. The residue was purified by prep-HPLC (Waters 2767/Qda, Column: Waters Xbridge 19*150 mm 10 um, Mobile Phase A: H$_2$O (0.1% NH$_4$OH), B: ACN) to afford Compound 241 (mixture of cis and trans) (40 mg, 25% yield) as a white solid.

374

Example B151

Preparation of Compound 242 and Compound 243

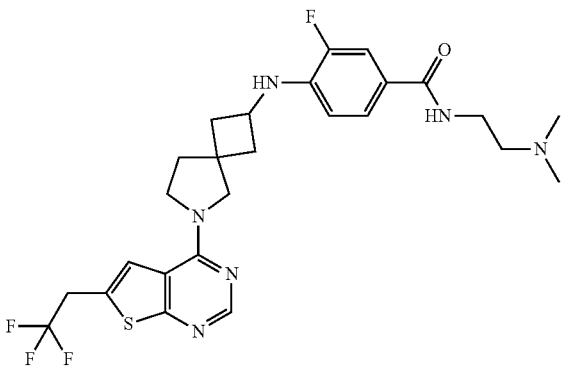

Compound 242: trans or cis
Compound 243: cis or trans

A mixture of intermediate 197 (200 mg, crude TFA salt, ca. 0.435 mmol), 4-chloro-6-(2,2,2-trifluoroethyl)thieno[2,3-d]pyrimidine (CAS #: 1628317-85-0) (124 mg, 0.49 mmol) and DIPEA (213 mg, 1.65 mmol) in i-PrOH (10 mL) was stirred at room temperature for 2 h. The reaction mixture was concentrated and the residue was purified by prep-HPLC (Agilent G6120B G1315D DADVL Detector and G4260B ELSD, Xbridge C18 5 mm 150*4.6 mm, Mobile Phase A: NH$_4$OH 0.1% in water, B: NH$_4$OH 0.1% in CH$_3$CN) to afford desired product (mixture of cis and trans) (200 mg, 74% yield) as a white solid. The obtained product was separated by SFC (SFC80, Waters; OJ-H (2.5*25 cm, 10 um); A: Supercritical CO$_2$, Mobile phase B: EtOH/ACN/NH$_3$=85/15/0.1; A:B=80/20; Flow rate: 50 mL/min; column temperature (T): 25° C.; Backpressure (BPR): 100 bar) to afford Compound 242 (trans or cis) (76 mg, 38.0% yield) as a white solid and Compound 243 (cis or trans) (68 mg, 34.0% yield) as a white solid.

Example B152

Preparation of Compound 244 and Compound 245

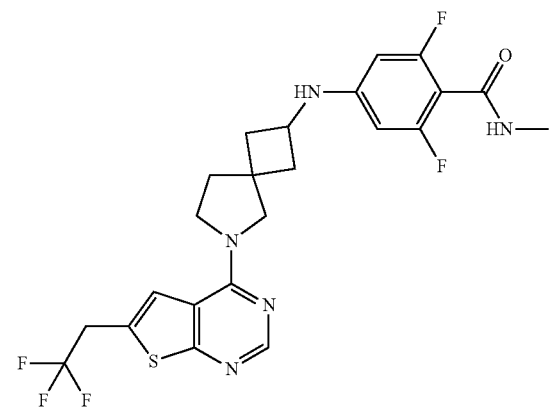

Compound 244: trans or cis (TFA salt)
Compound 245: cis or trans

375

To a stirred solution of intermediate 201 (500 mg, crude TFA salt, ca. 0.886 mmol) and 4-chloro-6-(2,2,2-trifluoroethyl)thieno[2,3-d]pyrimidine (CAS #: 1628317-85-0) (223 mg, 0.886 mmol) in i-PrOH (5 mL) at room temperature was added DIPEA (343 mg, 2.65 mmol). The reaction was stirred at room temperature overnight. The reaction mixture was concentrated. The residue was purified by prep-TLC (DCM/MeOH=20:1, v/v) to give the desired product (mixture of cis and trans). The obtained product was separated by SFC (SFC80, Waters, IA 2.5*25 cm, 10 um, A: Supercritical $CO_2$, B: MeOH; A:B=60/40; Flow rate: 40 mL/min; column temperature (T): 25° C.; Backpressure (BPR): 100 bar) to afford Compound 244 (trans or cis) (113 mg after prep-HPLC (Waters 2767/Qda, Column: SunFire 19*250 mm 10 um, Mobile Phase A: 0.1% TFA/$H_2O$, B: ACN), TFA salt) and Compound 245 (cis or trans) (115 mg).

Example B153

Preparation of Compound 246 and Compound 247

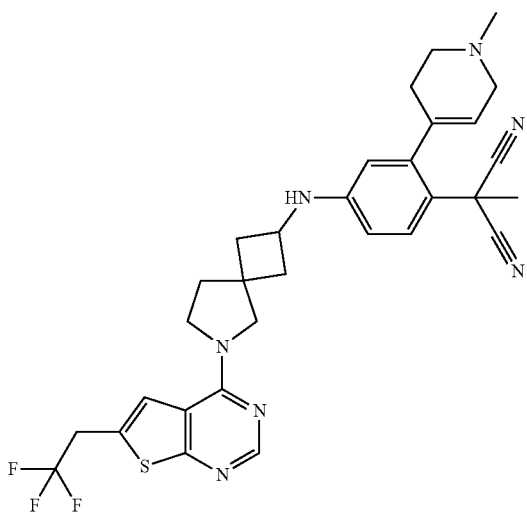

Compound 246: trans or cis
Compound 247: cis or trans

To a stirred solution of intermediate 207 (200 mg, crude TFA salt, ca. 0.409 mmol) in i-PrOH (3 mL) were added DIPEA (137 mg, 0.11 mmol) and 4-chloro-6-(2,2,2-trifluoroethyl)thieno[2,3-d]pyrimidine (CAS #: 1628317-85-0) (148 mg, 0.59 mmol). The reaction was stirred at room temperature for 2 h. The reaction mixture was concentrated and the residue was purified by prep-HPLC (Waters 2767/Qda, Column: Waters Xbridge 19*150 mm 10 um, Mobile Phase A: $H_2O$ (0.1% $NH_4OH$), B: ACN) to get the mixture of cis and trans (100 mg). The obtained product was separated by SFC (SFC80, Waters, IA-H 2.5*25 cm, 10 um, A: Supercritical $CO_2$, B: EtOH/$NH_3$; A:B=70/30; Flow rate: 50 mL/min; column temperature (T): 25° C.; Backpressure (BPR): 100 bar) to get Compound 246 (trans or cis) (43.8 mg, 8.5% yield over 3 steps) as a white solid and Compound 247 (cis or trans) (45.2 mg, 8.7% yield over 3 steps) as a white solid.

376

Example B154

Preparation of Compound 248

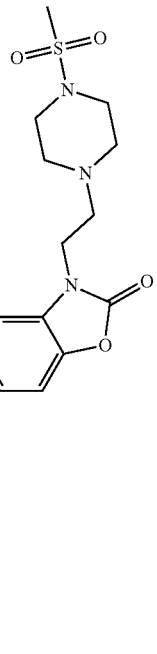

Compound 248: mixture of cis and trans

A solution of intermediate 211 (225 mg, 0.322 mmol) in $MeNH_2$ (2 M in THF) (5 mL) was stirred at 100° C. for 24 h under microwave irradiation. The cooled reaction mixture was concentrated. The residue was purified by prep-HPLC (Waters 2767/Qda, Column: Waters Xbridge 19*150 mm 10 um, Mobile Phase A: $H_2O$ (0.1% $NH_4OH$), B: ACN) to afford Compound 248 (mixture of cis and trans) (73.1 mg, 32% yield) as a pink solid.

Example B155

Preparation of Compound 249

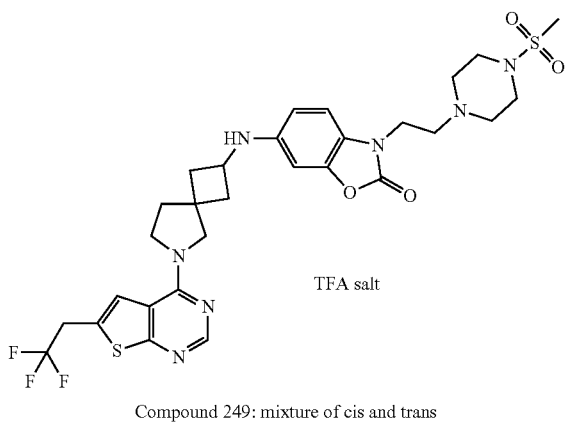 [SMILES: CS(=O)(=O)N1CCN(CCn2c(=O)oc3cc(NC4CC5(CCN(c6ncnc7sc(CC(F)(F)F)cc67)C5)C4)ccc32)CC1]

TFA salt

Compound 249: mixture of cis and trans

To a stirred solution of 4-chloro-6-(2,2,2-trifluoroethyl)thieno[2,3-d]pyrimidine (CAS #: 1628317-85-0) (300 mg, 1.82 mmol) and intermediate 214 (100 mg, crude HCl salt, ca. 0.182 mmol) in i-PrOH (3 mL) was added DIPEA (60 mg, 0.468 mmol). The reaction was stirred at rt for 12 h. The reaction mixture was concentrated and the residue was purified by prep-HPLC (Waters 2767/Qda, Column: Waters Xbridge 19*250 mm 10 um, Mobile Phase A: 1120 (0.1% NH₄OH), B: ACN) to give Compound 249 (mixture of cis and trans) (42.6 mg, 41% yield, TFA salt).

Example B156

Preparation of Compound 250

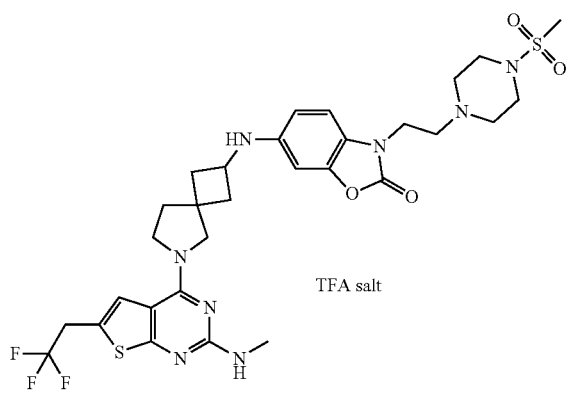

TFA salt

Compound 250: mixture of cis and trans

A solution of intermediate 215 (160 mg, 228 mmol) in methanamine (2.0 M in THF) (4 mL) was stirred at 100° C. in a sealed vessel overnight. The cooled reaction mixture was concentrated and the residue was purified by prep-HPLC (Waters 2767/Qda, Column: Waters Xbridge 19*250 mm 10 um, Mobile Phase A: H₂O (0.1% TFA), B: ACN) to give Compound 250 (mixture of cis and trans) (14 mg, 8.8% yield, TFA salt).

Example B157

Preparation of Compound 251

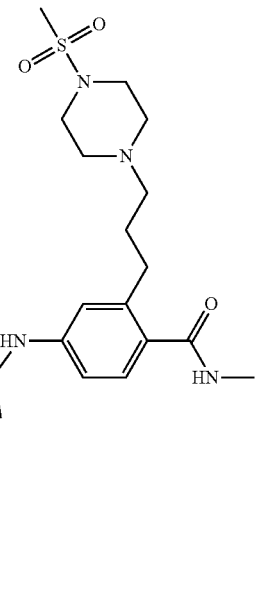

Compound 251: mixture of cis and trans

To a stirred solution of intermediate 220 (30 mg, 0.08 mmol) and intermediate 5 (27 mg, 0.08 mmol) in MeOH (5 ml) at room temperature was added decaborane (5 mg, 0.04 mmol). The reaction mixture was stirred at room temperature for 16 h. The reaction mixture was concentrated and the residue was purified by prep-HPLC to give Compound 251 (mixture of cis and trans) (9.2 mg, 16% yield) as a white solid.

Example B159

Preparation of Compound 253 and Compound 254

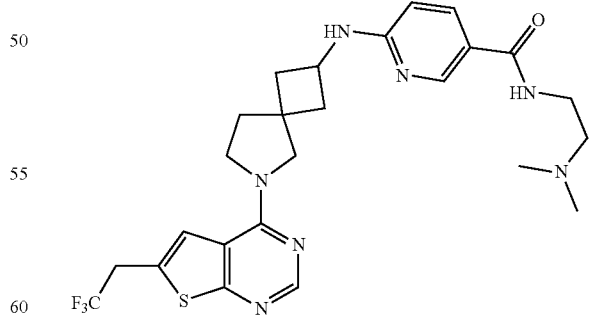

Compound 253: trans or cis
Compound 254: cis or trans

A mixture of 229 (150 mg, 0.47 mmol), 4-chloro-6-(2,2,2-Trifluoroethyl)thieno-[2,3-d]pyrimidine (119 mg, 0.47 mmol) and DIPEA (121 mg, 0.94 mmol) in ⁱ-PrOH (3 mL)

was stirred at room temperature for 40 min. The reaction mixture was concentrated under reduced pressure. The residue was purified by prep-HPLC (Waters 2767/Qda, Column: Waters Xbridge 20*150 mm 10 um, Mobile Phase A: 0.1% NH₃H₂O, B: ACN) to give the mixture of cis and trans (90 mg, 36% yield) as a white solid. The obtained product was separated by SFC (Separation condition: Instrument: Waters-SFC80, Column: AD-H (2.5*25 cm, 10 um), Mobile phase A: Supercritical CO₂, Mobile phase B: MeOH/0.1% NH₃, A:B=60/40 at 50 mL/min, Circle Time: 15 min, Injection Volume: 3 ml, Detector Wavelength: 254 nm, Column temperature: 25 centigrade, Back pressure: 100 bar) to give Compound 253 (35 mg, trans or cis) as a white solid and Compound 254 (53 mg, cis or trans) as a white solid.

Example B161

Preparation of Compound 257

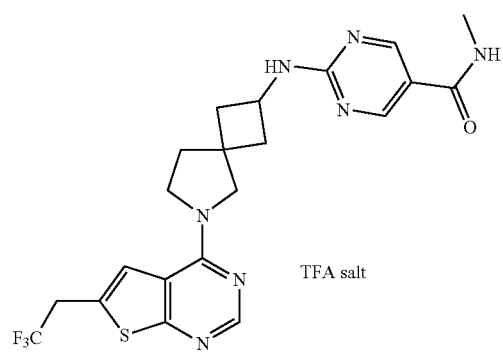

Compound 257: mixture of cis and trans

To a solution of intermediate 239, 2-(6-azaspiro[3.4]octan-2-ylamino)-N-methyl-pyrimidine-5-carboxamide (40 mg, crude) in IPA (10 mL) was added 4-chloro-6-(2,2,2-trifluoroethyl)-thieno[2,3-d]pyrimidine (38.6 mg, 0.15 mmol), Et₃N (30.9 mg, 0.30 mmol). After stirring at rt for 3 h. The mixture was concentrated, and the residue was purified by prep-HPLC (Waters 2767/Qda, Column: SunFire 19*250 mm 10 um, Mobile Phase A: 0.1% TFA/H₂O, B: ACN) to give Compound 257 (mixture of cis and trans) (15.72 mg, TFA salt, 22% yield over 2 steps).

Example B162

Preparation of Compound 258 and Compound 259

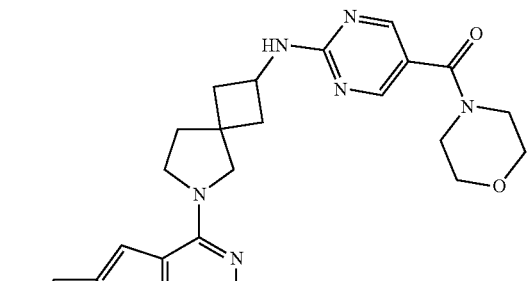

Compound 258: trans or cis
Compound 259: cis or trans

A mixture of intermediate 241 (430 mg, crude TFA salt), 4-chloro-6-(2,2,2-trifluoro-ethyl)-thieno[2,3-d]pyrimidine (247 mg, 0.98 mmol) and DIEA (379 mg, 2.94 mmol) in i-PrOH (10 mL) was stirred at rt for 2 h. After the reaction was completed, the reaction mixture was concentrated and the residue was purified by prep-HPLC (Agilent G6120B G1315D DADVL Detector and G4260B ELSD, Xbridge C18 5 mm 150*4.6 mm, Mobile Phase A: NH₄OH 0.1% in water, B: NH₄OH 0.1% in CH₃CN) to afford the mixture of cis and trans (350 mg, 67% yield) as a white solid. The mixture of cis and trans was separated by SFC (SFC80, Waters; AS-H (2.5*25 cm, 10 um); A: Supercritical CO₂, Mobile phase B: MeOH; A:B=80/20; Flow rate: 50 mL/min; column temperature (T): 25° C.; BPR: 100 bar) to afford Compound 258 (trans or cis) (120 mg, $R_t$=2.654 min) as a white solid and Compound 259 (cis or trans) (130 mg, $R_t$=3.371 min as a white solid.

Example B163

Preparation of Compound 260a

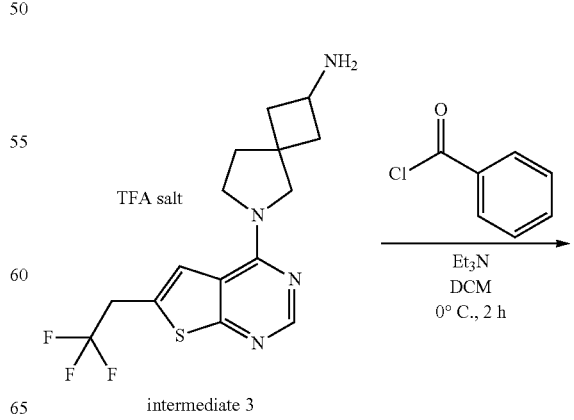

intermediate 3

-continued

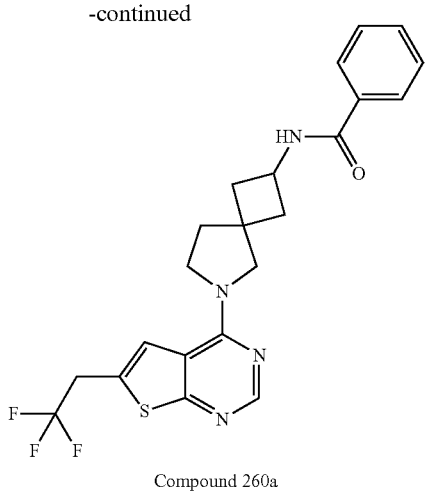

Compound 260a

To a stirred solution of intermediate 3 (400 mg, crude TFA salt, ca. 1.17 mmol) and Et₃N (354 mg, 3.50 mmol) in DCM (20 mL) at 0° C. was added benzoyl chloride (163 mg, 1.17 mmol). The reaction was stirred at 0° C. for 2 h. The reaction mixture was diluted with water (20 mL) and extracted with DCM (50 mL×3). The combined organic extracts were washed with brine, dried over anhydrous Na₂SO₄ and concentrated. The residue was purified by prep-HPLC (Waters 2767/Qda, Column: Waters Xbridge 19*150 mm 10 um, Mobile Phase A: H₂O (0.1% NH₄OH), B: ACN) to give desired Compound 260a (120 mg, 22% yield) as a white solid.

Example B164

Preparation of Compound 261 and Compound 262

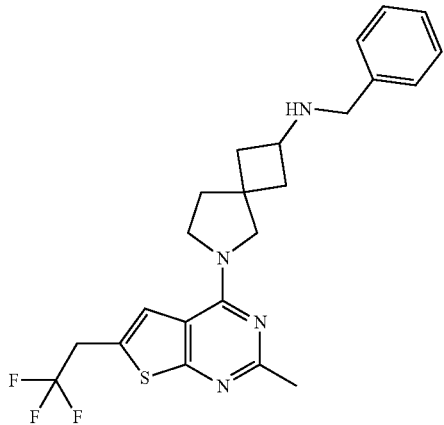

Compound 261: trans or cis
Compound 262: cis or trans

To a stirred solution of intermediate 244 (150 mg, 0.42 mmol), benzaldehyde (58 mg, 1.3 mmol) and Ti(i-PrO)₄ (488 mg, 1.72 mmol) in MeOH (5 mL) was added NaBH(OAc)₃ (267 mg, 1.26 mmol). The reaction was stirred at rt for 1 h. The reaction mixture was quenched with H₂O (5 mL) and extracted with DCM (10 mL×2). The combined organic layers were washed with brine (20 mL), dried (anhydrous Na₂SO₄), filtered and concentrated. The residue was purified by prep-HPLC (Waters 2767/Qda, Column: SunFire 19*250 mm 10 um, Mobile Phase A: 0.1% TFA/H₂O, B: ACN) and the obtained product was treated with amberlyst A-21 ion exchange resin in MeOH (5 mL) for 10 min and filtered. The filtrate was concentrated to afford desired product (mixture of cis and trans) (120 mg). The obtained product was separated by SFC (SFC80, Waters; AD (2.5*25 cm, 10 um); A: Supercritical CO₂, Mobile phase B: EtOH/ACN=85/15; A:B=60/40; Flow rate: 70 mL/min; Column temperature (T) in 25° C.; BPR: 100 bar) to afford Compound 261 (trans or cis) (46 mg, 38% yield) and Compound 262 (cis or trans) (32 mg, 26% yield).

Example B165

Preparation of Compound 263

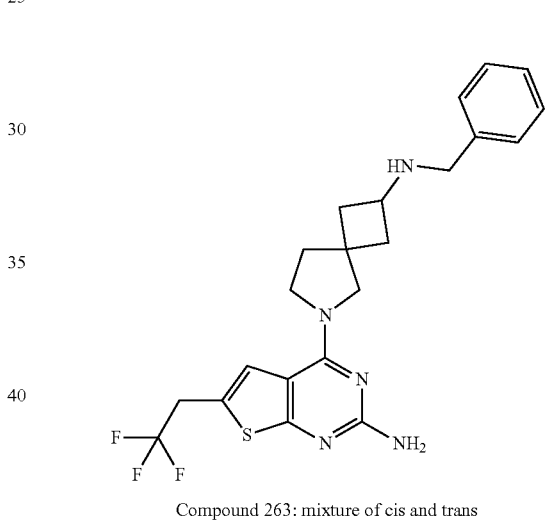

Compound 263: mixture of cis and trans

To a stirred mixture of intermediate 248 (160 mg, 0.448 mmol), benzaldehyde (95 mg, 0.895 mmol) and Ti(i-PrO)₄ (127 mg, 0.448 mmol) in DCE/DMSO (6 mL/1 mL) at room temperature was added NaBH(OAc)₃ (285 mg, 1.34 mmol) in portions. The reaction mixture was stirred at room temperature overnight. The reaction mixture was quenched with aq. NaHCO₃ and extracted with DCM. The combined organic extracts were washed with brine, dried over anhydrous Na₂SO₄, filtered and concentrated. The residue was purified by prep-HPLC (Waters 2767/Qda, Column: Waters Xbridge 19*150 mm 10 um, Mobile Phase A: H₂O (0.1% NH₄OH), B: ACN) to give Compound 263 (mixture of cis and trans) (20 mg) as a white solid.

Example B166

Preparation of Compound 264 and Compound 265

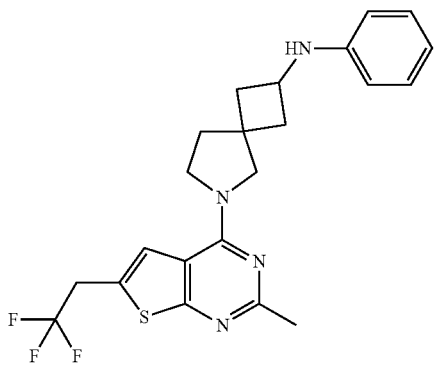

Compound 264: trans or cis
Compound 265: cis or trans

A mixture of intermediate 244 (150 mg, 0.42 mmol), bromobenzene (198 mg, 1.26 mmol), BrettPhos (30 mg, 0.06 mmol), Pd$_2$(dba)$_3$ (30 mg, 0.03 mmol) and t-BuONa (161 mg, 0.84 mmol) in 1,4-dioxane (4 mL) was stirred at 130° C. for 2 h with microwave irradiation. The cooled reaction mixture was diluted with H$_2$O (10 mL) and extracted with EtOAc (20 mL×3). The combined organic extracts were washed with brine (20 mL×2), dried over anhydrous Na$_2$SO$_4$, filtered and concentrated. The residue was purified by prep-HPLC (Xbridge C18 5 mm 150*4.6 mm, Mobile Phase A: NH$_4$OH 0.1% in water, B: NH$_4$OH 0,1% in CH$_3$CN) to afford desired product (mixture of cis and trans) (115 mg). The obtained product was separated by SFC (UPC$^2$, Waters; IE, 5um, 4.6*250 (Daicel); Mobile phase: CO$_2$/EtOH/ACN/DEA 60/34/6/0.08; Flow expressed in 2.8 mL/min; column T in 35° C.; BPR in 100 bars) to afford Compound 264 (trans or cis) (9 mg, 7.8% yield) and Compound 265 (cis or trans) (20 mg, 17% yield).

Example B167

Preparation of Compound 266 and Compound 267

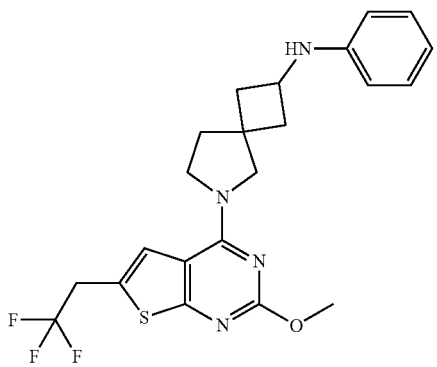

Compound 266: trans or cis
Compound 267: cis or trans

A mixture of intermediate 19 (150 mg, 0.40 mmol), bromobenzene (198 mg, 1.26 mmol), BrettPhos (30 mg, 0.06 mmol), Pd$_2$(dba)$_3$ (30 mg, 0.03 mmol) and t-BuONa (161 mg, 0.84 mmol) in 1,4-dioxane (4 mL) was stirred at 130° C. for 2 h with microwave irradiation. The cooled reaction mixture was diluted with water (10 mL) and extracted with EtOAc (20 mL×3). The combined organic extracts were washed with brine (20 mL×2), dried over anhydrous Na$_2$SO$_4$, filtered and concentrated. The residue was purified by prep-HPLC (Xbridge C18 5 mm 150*4.6 mm, Mobile Phase A: NH$_4$OH 0.1% in water, B: NH$_4$OH 0.1% in CH$_3$CN) to afford desired product (mixture of cis and trans) (150 mg). The obtained product was separated by SFC (SFC80, Waters, IE-H 2.5*25 cm, 10 um, A: Supercritical CO$_2$, B: MeOH; A:B=60/40; Flow rate: 80 mL/min; column temperature (T): 25° C.; BPR: 100 bar) to afford Compound 266 (trans or cis) (75 mg, 50% yield) and Compound 267 (cis or trans) (20 mg, 13% yield).

Example B168

Preparation of Compound 268 and Compound 269

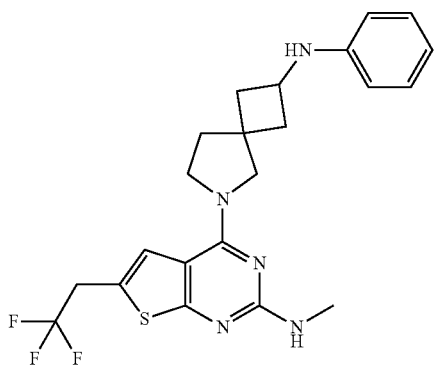

Compound 268: trans or cis
Compound 269: cis or trans

A mixture of intermediate 251 (400 mg, 0.883 mmol) in CH$_3$NH$_2$ (2 M in THF (10 mL) was sealed and stirred at 100° C. overnight. The mixture was concentrated. The residue was purified by prep-HPLC (Waters 2767/Qda, Column: Waters Xbridge 19*150 mm 10 um, Mobile Phase A: H$_2$O (0.1% TFA), B: ACN) to give the desired product (mixture of cis and trans). The obtained product was separated by SFC (SFC80, Waters; OD 2.5*25 cm, 10 um; A: Supercritical CO$_2$, Mobile phase B: EtOH/ACN=85/15; A:B=60/40; Flow rate: 50 g/min; column temperature (T): 35° C.; Backpressure (BPR): 100 bar) to afford Compound 268 (trans or cis) (61.1 mg, 15% yield) as a white solid and Compound 269 (cis or trans) (82.9 mg, 20% yield) as a white solid.

Example B169

Preparation of Compound 270

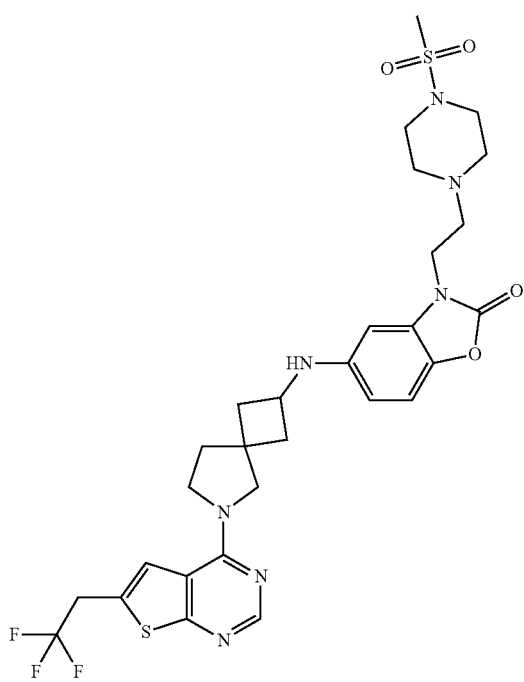

Compound 270: mixture of cis and trans

To a mixture of intermediate 208 (270 mg, 0.67 mmol), intermediate 3 (230 mg, 0.67 mmol, TFA salt), Cs₂CO₃ (655 mg, 2.0 mmol) and BrettPhos (72 mg, 0.13 mmol) in 1,4-dioxane (5 mL) under Ar at room temperature was added Pd(dba)₂ (61 mg, 0.06 mmol). The mixture was stirred under Ar at 90° C. for 16 h. The cooled reaction mixture was filtered and the filtrate was concentrated. The residue was purified by prep-HPLC (Waters 2767/Qda, Column: Waters Xbridge 19*150 mm 10 um, Mobile Phase A: H₂O (0.1% NH₄OH), B: ACN) to give Compound 270 (mixture of cis and trans) (60 mg, 13% yield) as a white solid.

Example B170

Preparation of Compound 271

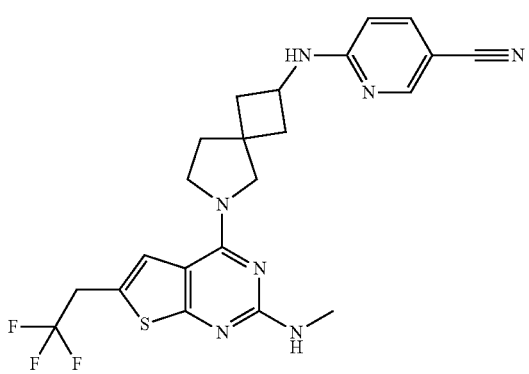

Compound 271: mixture of cis and trans

To a stirred solution of intermediate 20 (200 mg, 0.54 mmol) in i-PrOH (3 mL) at rt were added 6-fluoronicotinonitrile (CAS #: 3939-12-6) (65 mg, 0.54 mmol) and DIPEA (208 mg, 1.62 mmol). The reaction mixture was stirred at 80° C. overnight. The cooled reaction mixture was concentrated and the residue was purified by prep-HPLC (Waters 2767/Qda, Column: SunFire 19*250 mm 10 um, Mobile Phase A: 0.1% NH₄OH/H₂O, B: ACN) to afford Compound 271 (mixture of cis and trans) (36.5 mg, 21% yield over 4 steps) as a white solid.

Example B171

Preparation of Compound 272 and Compound 273

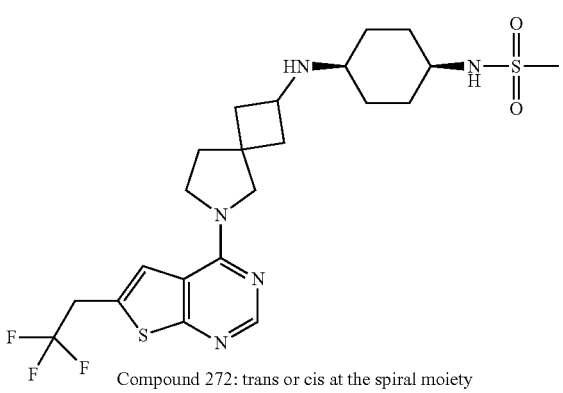

Compound 272: trans or cis at the spiral moiety
Compound 273: cis or trans at the spiral moiety A mixture of intermediate 5 (300 mg, 0.880 mmol), cis-N-4-aminocyclohexyl)-methane-sulfonamide (CAS #: 1259021-50-5) (169 mg, 0.880 mmol) and Ti(i-PrO)₄ (1250 mg, 4.40 mmol) in MeOH (5 mL) was stirred at 50° C. for 3 h. NaBH₃CN (110 mg, 1.76 mmol) was then added at rt. The reaction was stirred at rt for 3 h. Aq. HCl (1 M) was added till pH<7. The resultant was extracted with EtOAc (50 mL×3). The combined organic extracts were washed with brine (50 mL×2), dried over anhydrous Na₂SO₄, filtered and concentrated. The residue purified by flash chromatography on silica gel (eluent: DCM:MeOH=10:1, v/v) to afford desired product (mixture of cis and trans at the spiral moiety) (180 mg). The obtained product was separated by SFC (SFC80, Waters; AD-H 0.46*15 cm, 2 um; HEP:ETOH (0.1% DEA)=60:40; Flow rate: 50 mL/min; column temperature (T): 25° C.; BPR in 100 bar) to afford Compound 272 (trans or cis at the spiro moiety) (40 mg, 8.8% yield) and Compound 273 (cis or trans at the spiro moiety) (35 mg, 7.7% yield) as a white solid.

Example B172

Preparation of Compound 274 and Compound 275

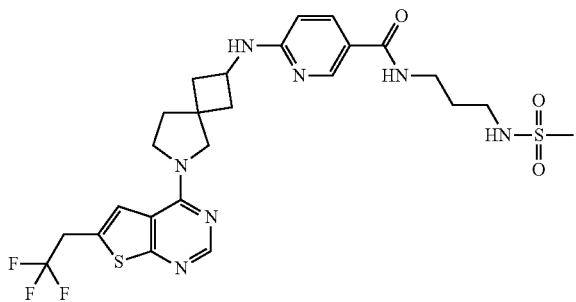

Compound 274: trans or cis
Compound 275: cis or trans

To a stirred mixture of intermediate 254 (414 mg, 0.80 mmol) in DCM (20 mL) at 0° C. were added Et₃N (1.5 ml) and MsCl (183 mg, 1.6 mmol) dropwise. The resulting mixture was stirred at rt for 4 h. The reaction mixture was diluted with water (40 mL) and extracted with EA (30 ml×2). The combined organic extracts were washed with brine twice, dried over anhydrous $Na_2SO_4$, filtered and concentrated. The residue was purified with prep-HPLC (Waters 2767/Qda, Column: Waters Xbridge 20*150 mm um, Mobile Phase A: 0.1% $NH_3H_2O$, B: ACN) to give desired product (mixture of cis and trans) (130 mg) as a white solid. The obtained product was separated by SFC (Waters-SFC80 Column: OJ (2.5*25 cm, 10 um) Mobile phase A: Supercritical $CO_2$ Mobile phase B: MeOH/0.01% $NH_3$ A:B=80/20 at 60 mL/min Detector Wavelength: 214 nm Column temperature (T): 25° C.; BPR: 100 bar) to give Compound 274 (trans or cis) (35 mg, 7% yield) as a white solid and Compound 275 (cis or trans) (60 mg, 12% yield) as a white solid.

Example B173

Preparation of Compound 276

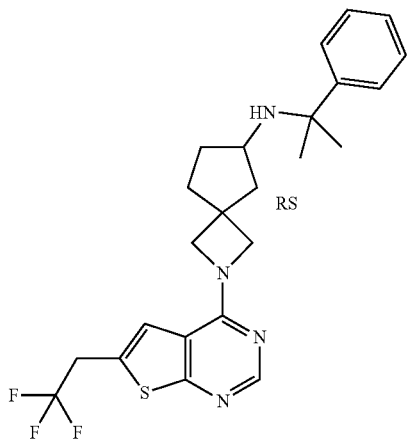

Compound 276
(racemate)

2-(6-(2,2,2-Trifluoroethyl)thieno[2,3-d]pyrimidin-4-yl)-2-azaspiro[3.4]octan-6-one intermediate 4 (180 mg, 0.53 mmol), 2-phenylpropan-2-amine (85.6 mg, 0.63 mmol), acetic acid (95.0 mg, 1.58 mmol) and 1,2-dichloroethane (10 mL) were added to a microwave tube. The resulting mixture was heated at 100° C. for 20 minutes via microwave irradiation and cooled to about 25° C. then sodium triacetoxyborohydride (335 mg, 1.58 mmol) was added. The resulting mixture was heated at 100° C. for another 20 minutes via microwave irradiation. The reaction mixture was cooled to 25° C. and poured into dichloromethane (30 mL) before washed with water (20 mL×3). The organic extracts were dried over anhydrous $Na_2SO_4$, filtered and concentrated to dryness under reduced pressure to give a residue, which was purified by reversed phase chromatography (Column: Phenomenex Gemini 150*25 mm*10 um, Mobile Phase A: water (0.05% ammonia hydroxide v/v)-ACN, Mobile Phase B: acetonitrile, Flow rate: 25 mL/min, gradient condition from 50% B to 80%). The pure fractions were collected and the solvent was evaporated under vacuum. The residue was partitioned between acetonitrile (2 mL) and water (10 mL). The mixture was lyophilized to dryness to give Compound 276 (racemate) (8.3 mg, 3.39% yield) as yellow sticky oil.

Example B174

Preparation of Compound 277

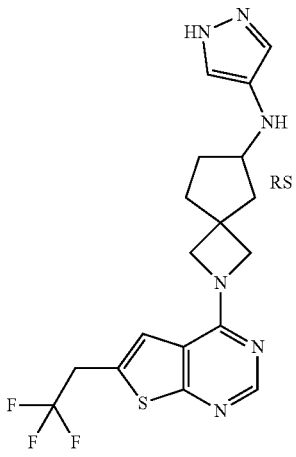

Compound 277
(racemate)

2-(6-(2,2,2-Trifluoroethyl)thieno[2,3-d]pyrimidin-4-yl)-2-azaspiro[3.4]octan-6-one intermediate 4 (110 mg, 0.32 mmol), 1H-pyrazol-4-amine (32.1 mg, 0.39 mmol), acetic acid (0.1 mL) and dry DCM (5 mL) were added to a 100 mL round-bottomed flask. The resulting mixture was stirred at 40° C. for 1 h. Then sodium triacetoxyborohydride (273 mg, 1.29 mmol) was added to the mixture. The resulting mixture was stirred at 40° C. for another 1 h. The reaction mixture was poured into DCM (30 mL) before washed with water (20 mL×3). The organic extracts were dried over anhydrous Na₂SO₄, filtered, and concentrated to dryness under reduced pressure to give a residue, which was purified by prep-TLC (SiO₂, dichloromethane:methanol=10:1, Rf=0.5) to give Compound 277 (racemate) (34.6 mg, 25.2% yield) as white solids.

Example B175

Preparation of Compound 278

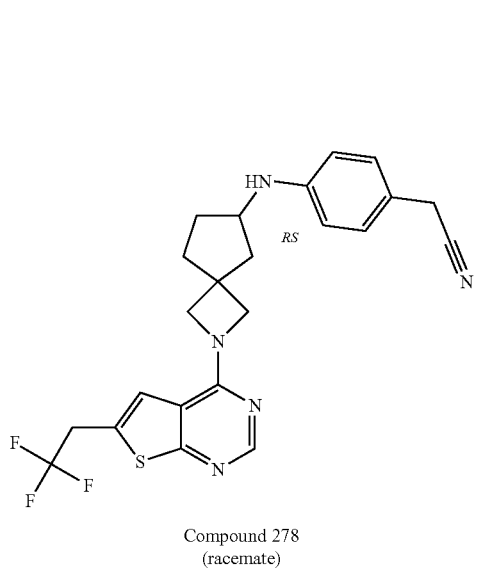 [SMILES: N#CCc1ccc(NC2CCC3(C2)CN(c2ncnc4sc(CC(F)(F)F)cc24)C3)cc1]

Compound 278
(racemate)

2-(6-(2,2,2-Trifluoroethyl)thieno[2,3-d]pyrimidin-4-yl)-2-azaspiro[3.4]octan-6-one Intermediate 4 (100 mg, 0.293 mmol), 2-(4-aminophenyl)acetonitrile (58.1 mg, 0.440 mmol), molecular sieve, acetic acid (0.1 mL) and acetonitrile (5 mL) were added to a 40 mL glass bottle, the resultant mixture was stirred at 40° C. for 2 h. Then sodium triacetoxyborohydride (248 mg, 1.17 mmol) was added to the mixture which was stirred at 40° C. for another 2 h. The mixture was suspended in water (50 mL) and the aqueous layer was extracted with DCM (20 mL×3). The combined organic layers were dried (anhydrous Na₂SO₄), filtered and concentrated under reduced pressure to give the crude product which was purified by prep.HPLC over (Column: DuraShell 150*25 mm*5 um, Mobile Phase A: water (10 mM NH₄HCO₃), Mobile Phase B: acetonitrile, Flow rate: 25 mL/min, gradient condition from 40% B to 70%). The pure fractions were collected and the solvent was evaporated under vacuum. The residue was partitioned between acetonitrile (2 mL) and water (10 mL). The solution was lyophilized to dryness to give Compound 278 (racemate) (36.8 mg, 26.6% yield) as a yellow powder.

Example B176

Preparation of Compound 279

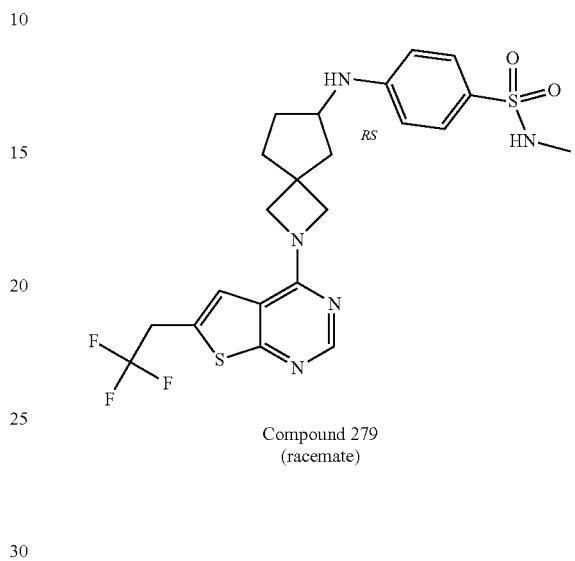

Compound 279
(racemate)

2-(6-(2,2,2-trifluoroethyl)thieno[2,3-d]pyrimidin-4-yl)-2-azaspiro[3.4]octan-6-one intermediate 4 (244 mg, 0.72 mmol), 4-amino-N-methylbenzenesulfonamide (200 mg, 1.07 mmol), sodium cyanoborohydride (90 mg, 1.43 mmol) and dry methanol (9.5 mL) were added to a 40 mL glass bottle, and then acetic acid (86.0 mg, 1.43 mmol) in dry methanol (0.5 mL) was added. The resulting mixture was stirred at 45° C. for 8 h. The mixture was concentrated under reduced pressure to give a residue, which was dissolved in DCM (30 mL) before washed with water (20 mL×3). The organic extracts were dried over anhydrous Na₂SO₄, filtered and concentrated to dryness under reduced pressure to give a residue, which was purified by prep-HPLC (Column: Xbridge 150*30 mm*10 um, Mobile Phase A: water (0.05% ammonia hydroxide v/v)-ACN, Mobile Phase B: acetonitrile, Flow rate: 25 mL/min, gradient condition from 35% B to 65%). The pure fractions were collected and the solvent was evaporated under vacuum. The residue was partitioned between CH₃CN (2 mL) and water (10 mL). The mixture was lyophilized to dryness to give Compound 279 (racemate) (115.0 mg, 29.9% yield) as a white powder.

The following Compounds were prepared starting from intermediate 4 and the corresponding amine, by using an analogous reductive amination method as was used for preparation of Compound 276, Compound 277 or Compound 279 as indicated in the table below; one of the following 4 solvents were used: DCM, DCE, MeOH, MeCN.

| Compound number | Method used | Compound structure |
|---|---|---|
| Compound 280 | Compound 276 | 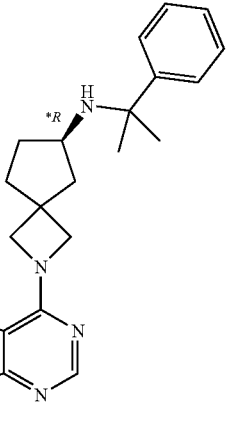 |
| Compound 281 | Compound 276 | 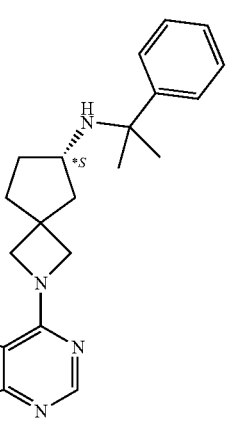 |
| Compound 277 | Compound 277 | 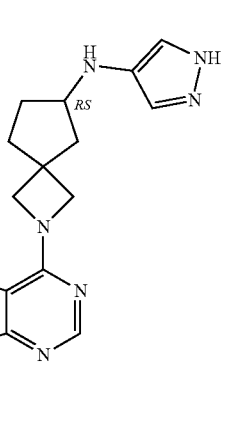 |
| Compound 279 | Compound 279 | 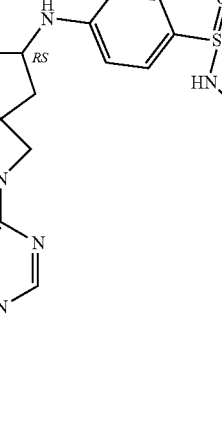 |

-continued
| Compound number | Method used | Compound structure |
|---|---|---|
| Compound 278 | Compound 278 | 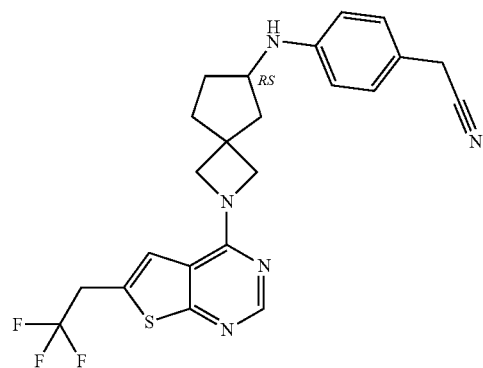 [SMILES: N#CCc1ccc(NC2CCC3(C2)CN(c2ncnc4sc(CC(F)(F)F)cc24)C3)cc1] |
| Compound 282 | Compound 276 | 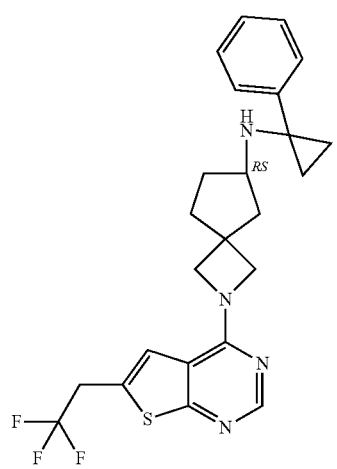 [SMILES: FC(F)(F)Cc1cc2c(N3CC4(CCC(NC5(c6ccccc6)CC5)C4)C3)ncnc2s1] |
| Compound 283 | Compound 279 | 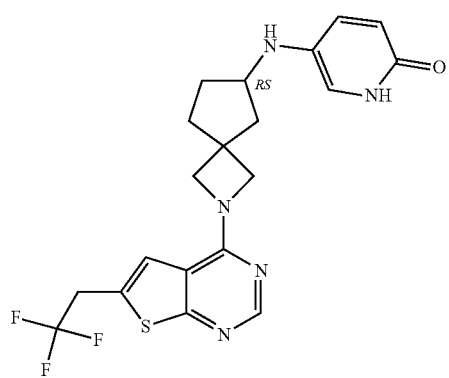 [SMILES: O=c1ccc(NC2CCC3(C2)CN(c2ncnc4sc(CC(F)(F)F)cc24)C3)c[nH]1] |

| Compound number | Method used | Compound structure |
|---|---|---|
| Compound 284 | Compound 277 | 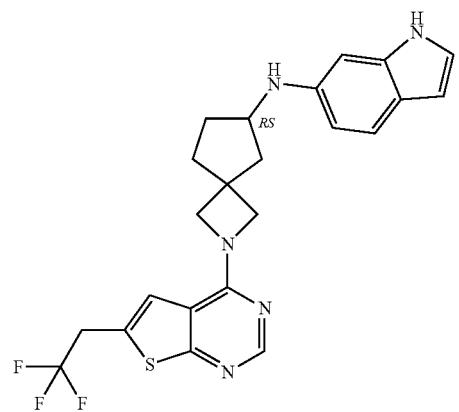 [SMILES: FC(F)(F)Cc1cc2c(N3CC4(CCC(Nc5ccc6cc[nH]c6c5)C4)C3)ncnc2s1] |
| Compound 285 | Compound 277 | 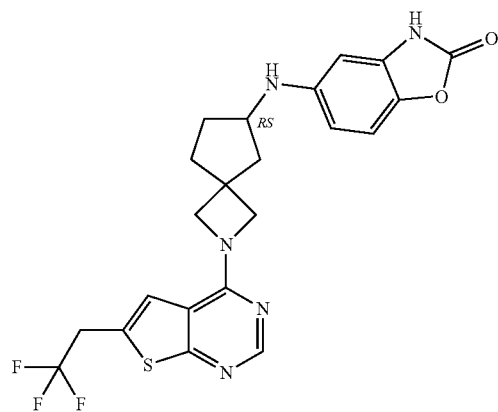 |
| Compound 286 | Compound 277 | 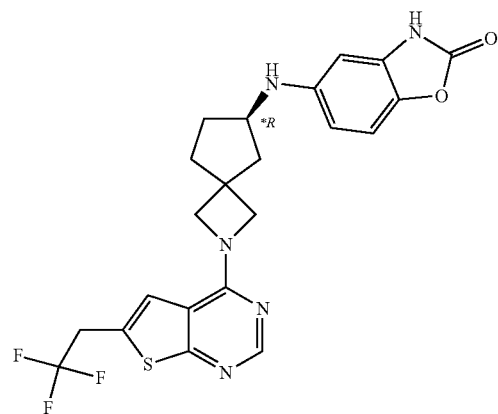 [SMILES: O=c1[nH]c2cc(N[C@@H]3CCC4(C3)CN(c3ncnc5sc(CC(F)(F)F)cc35)C4)ccc2o1] |

-continued
| Compound number | Method used | Compound structure |
|---|---|---|
| Compound 287 | Compound 277 | 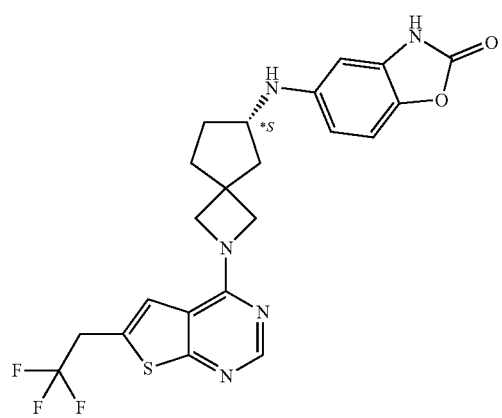 |
| Compound 288 | Compound 277 | 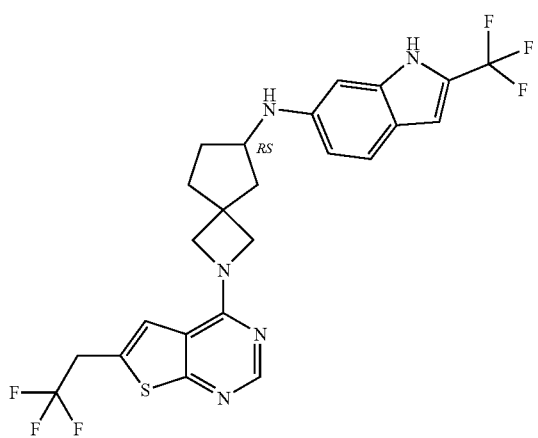 [SMILES: FC(F)(F)Cc1cc2c(N3CC4(CCC(Nc5ccc6cc(C(F)(F)F)[nH]c6c5)C4)C3)ncnc2s1] |
| Compound 289 | Compound 277 | 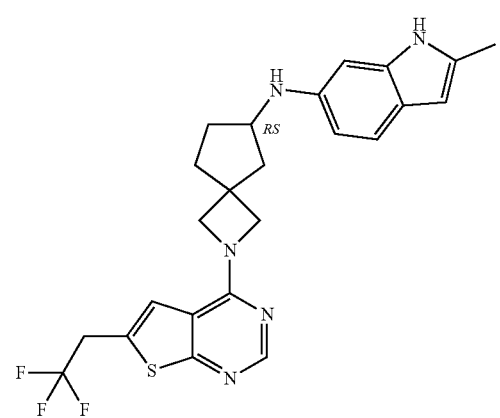 [SMILES: Cc1cc2ccc(NC3CCC4(C3)CN(c3ncnc5sc(CC(F)(F)F)cc35)C4)cc2[nH]1] |

-continued

| Compound number | Method used | Compound structure |
| --- | --- | --- |
| Compound 290 | Compound 279 | 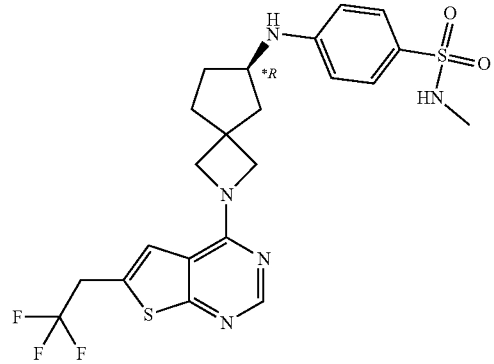 [SMILES: CNS(=O)(=O)c1ccc(N[C@@H]2CCC3(C2)CN(c2ncnc4sc(CC(F)(F)F)cc24)C3)cc1] |
| Compound 291 | Compound 279 | 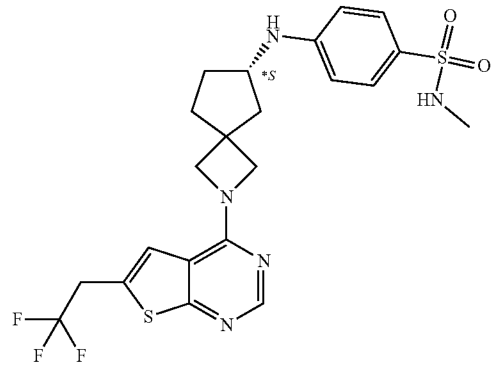 [SMILES: CNS(=O)(=O)c1ccc(N[C@H]2CCC3(C2)CN(c2ncnc4sc(CC(F)(F)F)cc24)C3)cc1] |
| Compound 292 | Compound 279 | 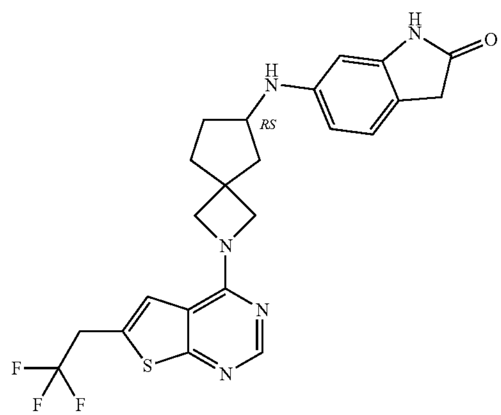 [SMILES: O=C1Cc2ccc(NC3CCC4(C3)CN(c3ncnc5sc(CC(F)(F)F)cc35)C4)cc2N1] |
| Compound 293 | Compound 279 | 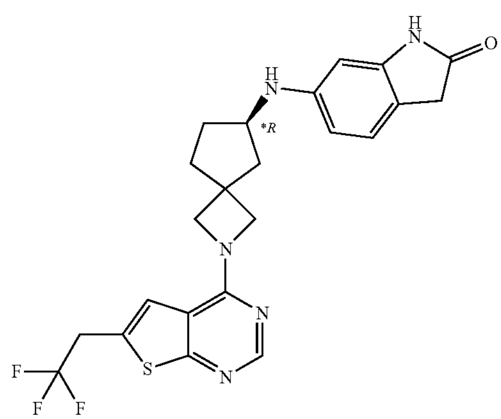 [SMILES: O=C1Cc2ccc(N[C@@H]3CCC4(C3)CN(c3ncnc5sc(CC(F)(F)F)cc35)C4)cc2N1] |

-continued
| Compound number | Method used | Compound structure |
|---|---|---|
| Compound 294 | Compound 279 | 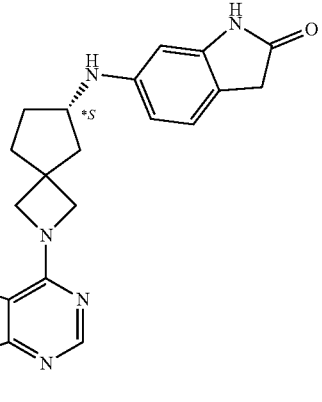 |
| Compound 295 | Compound 277 | 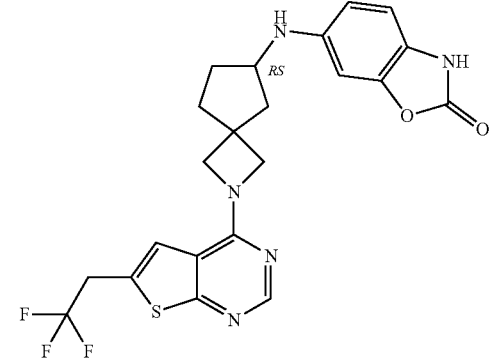 |
| Compound 296 | Compound 277 | 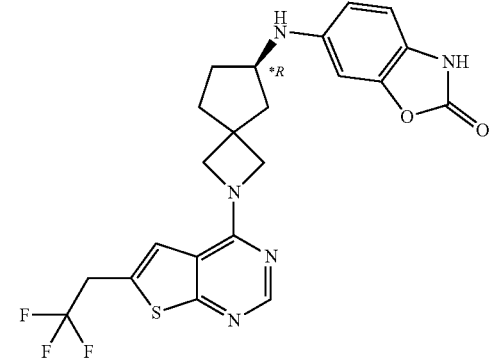 [SMILES: O=c1[nH]c2ccc(N[C@@H]3CCC4(C3)CN(c3ncnc5sc(CC(F)(F)F)cc35)C4)cc2o1] |
| Compound 297 | Compound 277 | 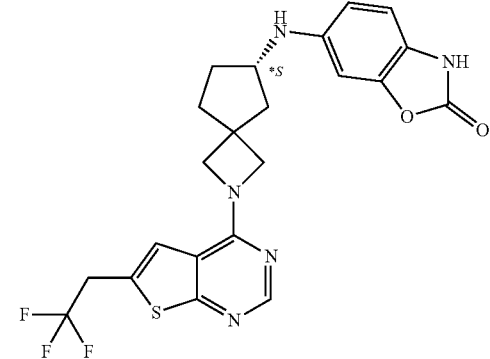 [SMILES: O=c1[nH]c2ccc(N[C@H]3CCC4(C3)CN(c3ncnc5sc(CC(F)(F)F)cc35)C4)cc2o1] |

-continued

| Compound number | Method used | Compound structure |
|---|---|---|
| Compound 298 | Compound 277 | 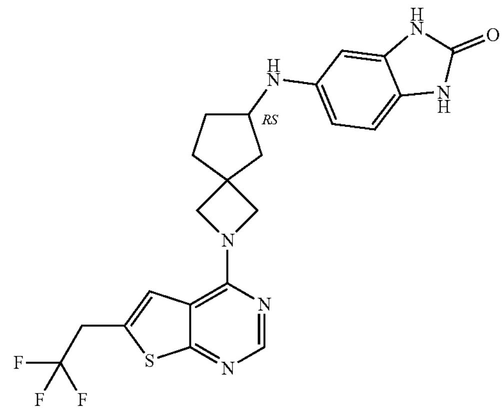 [SMILES: O=c1[nH]c2ccc(NC3CCC4(C3)CN(c3ncnc5sc(CC(F)(F)F)cc35)C4)cc2[nH]1] |
| Compound 299 | Compound 277 | 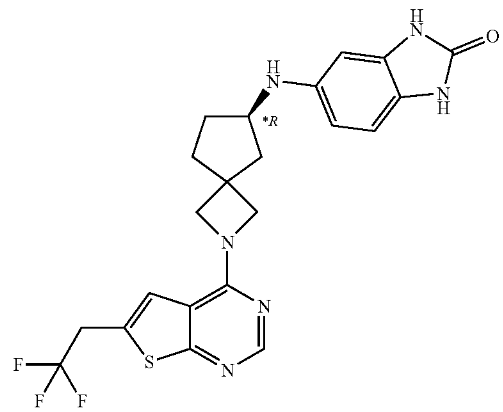 [SMILES: O=c1[nH]c2ccc(N[C@@H]3CCC4(C3)CN(c3ncnc5sc(CC(F)(F)F)cc35)C4)cc2[nH]1] |
| Compound 300 | Compound 277 | 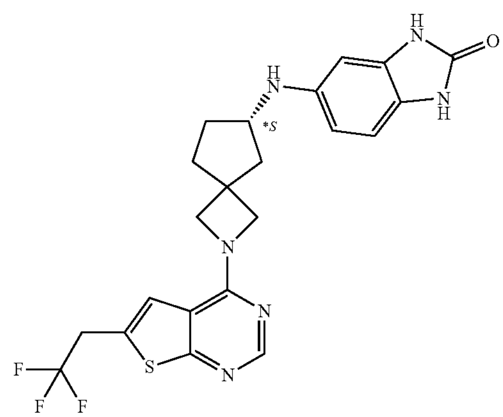 [SMILES: O=c1[nH]c2ccc(N[C@H]3CCC4(C3)CN(c3ncnc5sc(CC(F)(F)F)cc35)C4)cc2[nH]1] |
| Compound 301 (from intermediate 4 and intermediate 255) | Compound 279 | 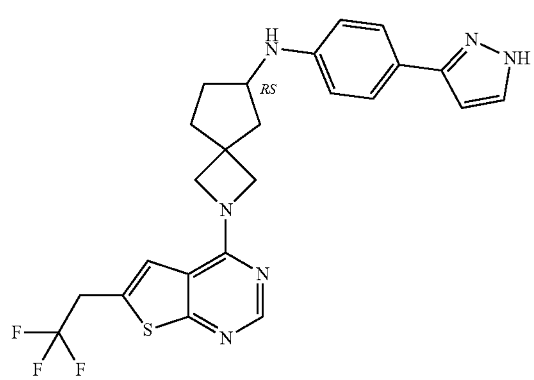 [SMILES: FC(F)(F)Cc1cc2c(N3CC4(CCC(Nc5ccc(-c6cc[nH]n6)cc5)C4)C3)ncnc2s1] |

-continued
| Compound number | Method used | Compound structure |
|---|---|---|
| Compound 302 (from intermediate 4 and intermediate 260) | Compound 279 | 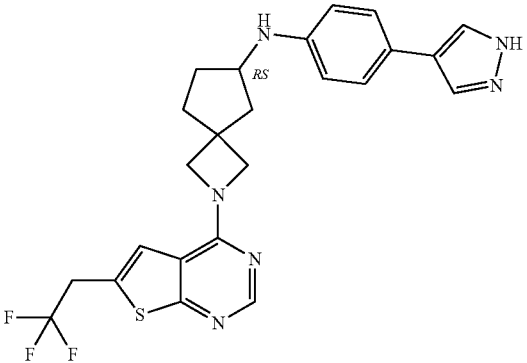 [SMILES: FC(F)(F)Cc1cc2c(N3CC4(CCC(Nc5ccc(-c6cn[nH]c6)cc5)C4)C3)ncnc2s1] |
| Compound 303 | Compound 279 | 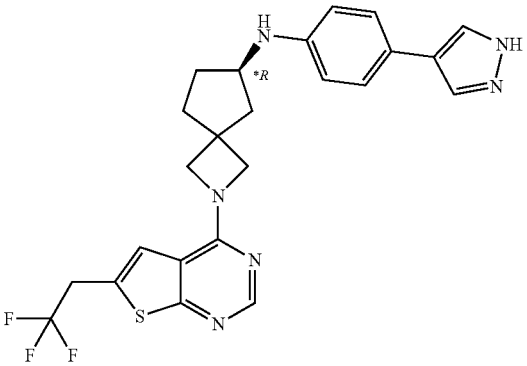 [SMILES: FC(F)(F)Cc1cc2c(N3CC4(CC[C@@H](Nc5ccc(-c6cn[nH]c6)cc5)C4)C3)ncnc2s1] |
| Compound 304 | Compound 279 | 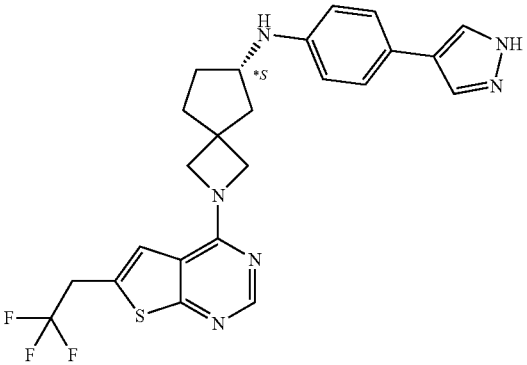 [SMILES: FC(F)(F)Cc1cc2c(N3CC4(CC[C@H](Nc5ccc(-c6cn[nH]c6)cc5)C4)C3)ncnc2s1] |

Example B177

Preparation of Compound 305

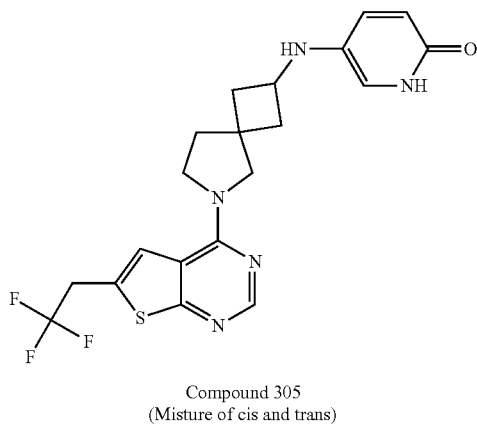 [SMILES: O=c1ccc(NC2CC3(CCN(c4ncnc5sc(CC(F)(F)F)cc45)C3)C2)c[nH]1]

Compound 305
(Mixture of cis and trans)

A solution mixture consisting of 6-(6-(2,2,2-trifluoroethyl)thieno[2,3-d]pyrimidin-4-yl)-6-azaspiro[3.4]octan-2-one intermediate 5 (160 mg, 0.469 mmol), 5-amino-pyridin-2(1H)-one (82.6 mg, 0.750 mmol), sodium cyanoborohydride (58.9 mg, 0.937 mmol) and MeOH (17 mL) was treated with a solution of AcOH (56.3 mg, 0.937 mmol) in MeOH (3 mL) and the solution was stirred for 12 h at 45° C. The reaction solution was cooled to rt and concentrated to dryness under reduced pressure to afford the crude product, which was purified by preparative HPLC (Xtimate C18 150×25 mm×5 pm column (eluent: 16% to 46% (v/v) water (0.225% FA)-ACN)). The pure fractions were concentrated under reduced pressure and then suspended in water (10 mL.). The mixture was lyophilized to dryness to afford the impure product. The impure product was then purified by preparative HPLC (Agela ASB 150×25 mm×5 μm column (eluent: 25% to 50% (v/v) water (0.05% HCl)-ACN)). The pure fractions was concentrated under reduced pressure and then suspended in water (10 mL). The mixture was lyophilized to dryness to afford Compound 305 (mixture of cis and trans) as a white solid (16.2 mg, 7.8% yield).

The following Compounds were prepared starting from intermediate 5 and the corresponding amine, by using an analogous reductive amination method as was used for preparation of Compound 276, Compound 277 or Compound 279 as indicated in the table below; one of the 4 following 4 solvents were used: DCM, DCE, MeOH, MeCN.

| Compound number | Method used | Compound structure |
| --- | --- | --- |
| Compound 305 | Compound 279 | 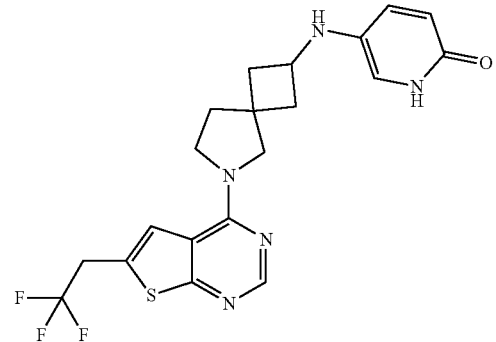 [SMILES: O=c1ccc(NC2CC3(CCN(c4ncnc5sc(CC(F)(F)F)cc45)C3)C2)c[nH]1]<br>Mixture of cis and trans |
| Compound 306 (trans or cis)<br>Compound 307 (cis or trans) | Compound 277 | 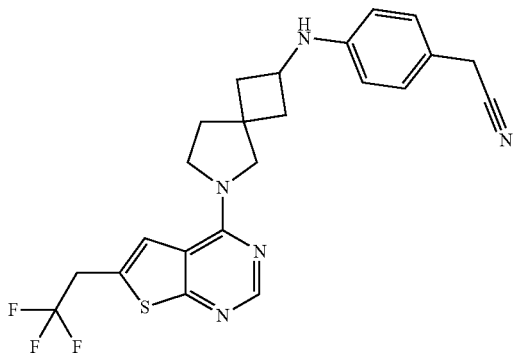 [SMILES: N#CCc1ccc(NC2CC3(CCN(c4ncnc5sc(CC(F)(F)F)cc45)C3)C2)cc1]<br>Compound 306: trans or cis<br>Compound 307: cis or trans |

| Compound number | Method used | Compound structure |
|---|---|---|
| Compound 308 | Compound 276 | 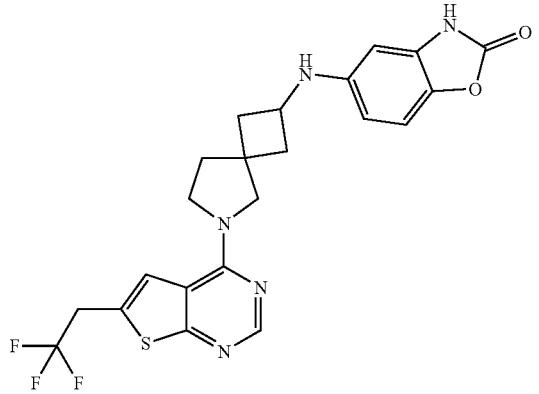 [SMILES: O=c1[nH]c2cc(NC3CC4(CCN(c5ncnc6sc(CC(F)(F)F)cc56)C4)C3)ccc2o1]<br>Mixture of cis and trans |
| Compound 309<br>(0.3 HCOOH; determined by residual signal of CHO group of HCOOH in HNMR) | Compound 277 | 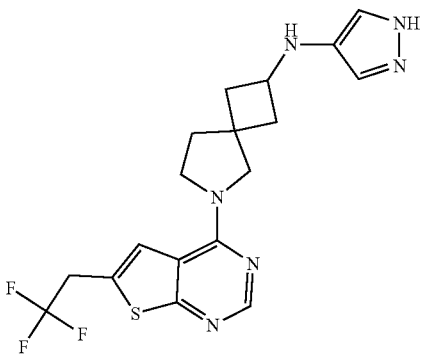 [SMILES: FC(F)(F)Cc1cc2c(N3CCC4(CC(Nc5cn[nH]c5)C4)C3)ncnc2s1]<br>0.3 HCOOH<br>Mixture of cis and trans |
| Compound 310 | Compound 277 | 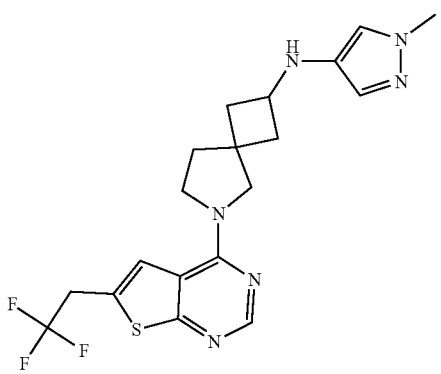 [SMILES: Cn1cc(NC2CC3(CCN(c4ncnc5sc(CC(F)(F)F)cc45)C3)C2)cn1]<br>Mixture of cis and trans |

| Compound number | Method used | Compound structure |
|---|---|---|
| Compound 311 | Compound 277 | 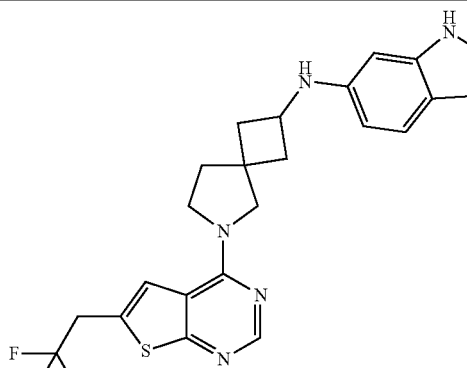<br>Mixture of cis and trans |
| Compound 312 (trans or cis)<br>Compound 313 (cis or trans) | Compound 277 | 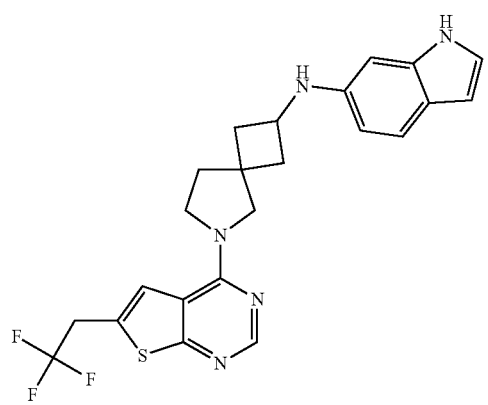 [SMILES: FC(F)(F)Cc1cc2c(N3CCC4(CC(Nc5ccc6cc[nH]c6c5)C4)C3)ncnc2s1]<br>Compound 312: trans or cis<br>Compound 313: cis or trans |
| Compound 314 | Compound 276 | 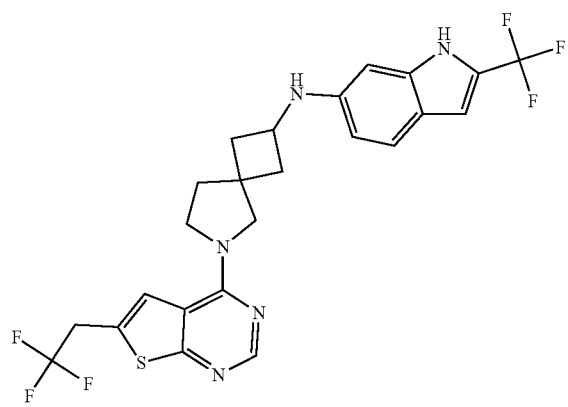 [SMILES: FC(F)(F)Cc1cc2c(N3CCC4(CC(Nc5ccc6cc(C(F)(F)F)[nH]c6c5)C4)C3)ncnc2s1]<br>Mixture of cis and trans |

-continued
| Compound number | Method used | Compound structure |
|---|---|---|
| Compound 315 | Compound 276 | 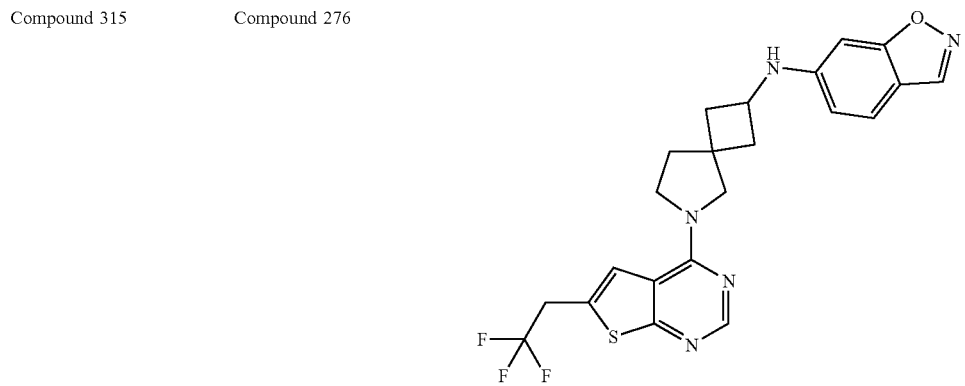<br>Mixture of cis and trans |
| Compound 316 | Compound 279 | 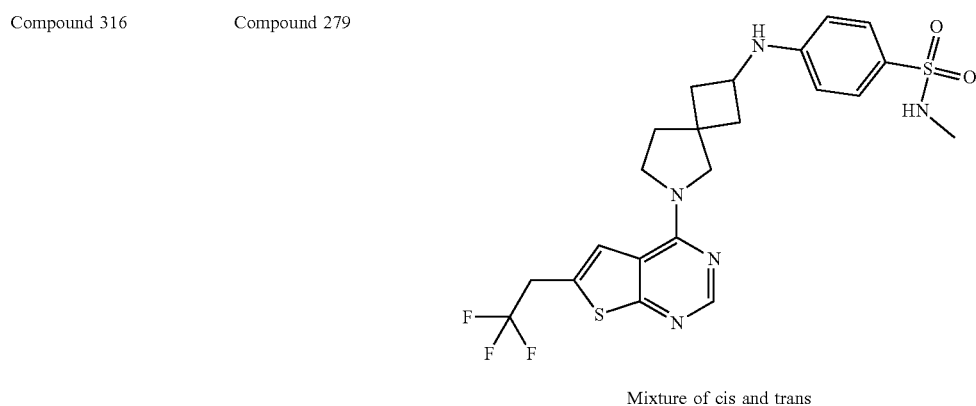<br>Mixture of cis and trans |
| Compound 317 (trans or cis)<br>Compound 318 (cis or trans) | Compound 279 | 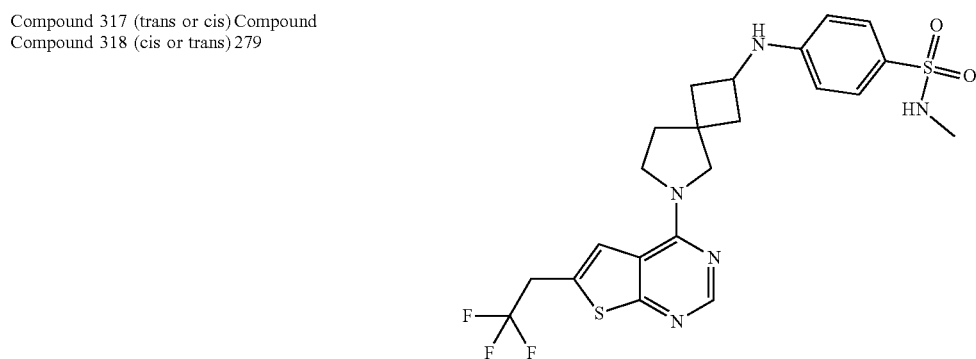<br>Compound 317: trans or cis<br>Compound 318: cis or trans |

-continued
| Compound number | Method used | Compound structure |
|---|---|---|
| Compound 319 | Compound 276 | 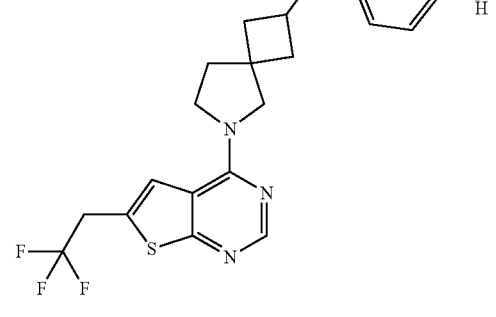<br>Mixture of cis and trans |
| Compound 320 (trans or cis)<br>Compound 321 (cis or trans) | Compound 276 | 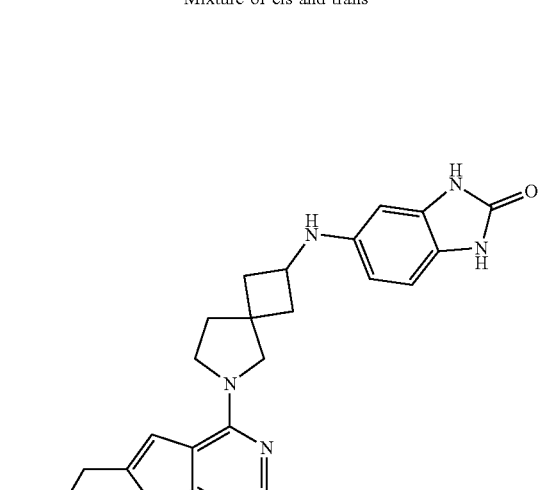<br>Compound 320: tans or cis<br>Compound 321: cis or trans |
| Compound 322 | Compound 276 | 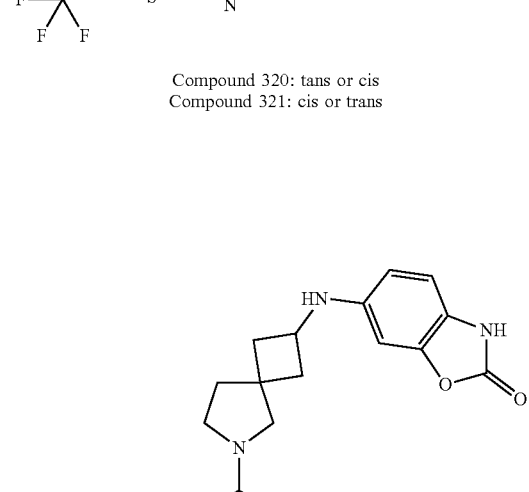<br>Mixture of cis and trans |

-continued

| Compound number | Method used | Compound structure |
|---|---|---|
| Compound 323 (trans or cis) Compound 324 (cis or trans) | Compound 276 | Compound 323: trans or cis<br>Compound 324: cis or trans |
| Compound 325 (from intermediate 5 and intermediate 258) | Compound 279 | Mixture of cis and trans |
| Compound 326 (from intermediate 5 and intermediate 260) | Compound 279 | Mixture of cis and trans |

-continued
| Compound number | Method used | Compound structure |
|---|---|---|
| Compound 327 (trans or cis) Compound 328 (cis or trans) | Compound 279 | 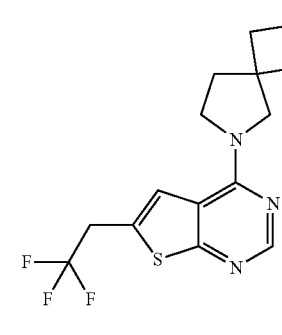<br>Compound 327: trans or cis<br>Compound 328: cis or trans |
| Compound 329 (formate salt) | Compound 279 | 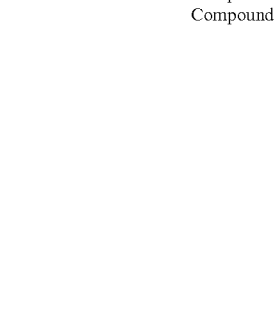<br>formate salt<br>Mixture of cis and trans |
| Compound 330 | Compound 279 | 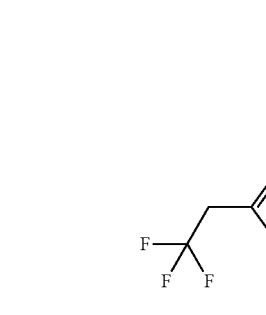<br>Mixture of cis and trans |

-continued
| Compound number | Method used | Compound structure |
|---|---|---|
| Compound 331 (trans or cis) Compound 332 (cis or trans) | Compound 279 | 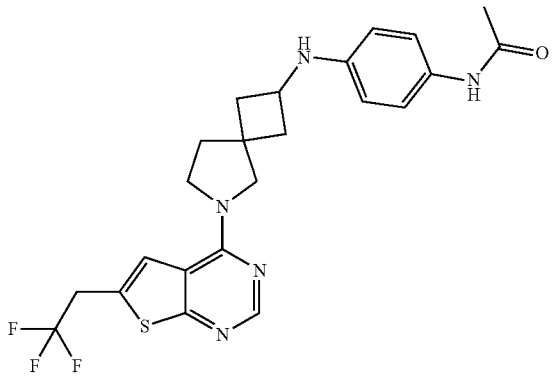 [SMILES: CC(=O)Nc1ccc(NC2CC3(CCN(c4ncnc5sc(CC(F)(F)F)cc45)C3)C2)cc1]<br>Compound 331: trans or cis<br>Compound 332: cis or trans |
| Compound 333 | Compound 279 | 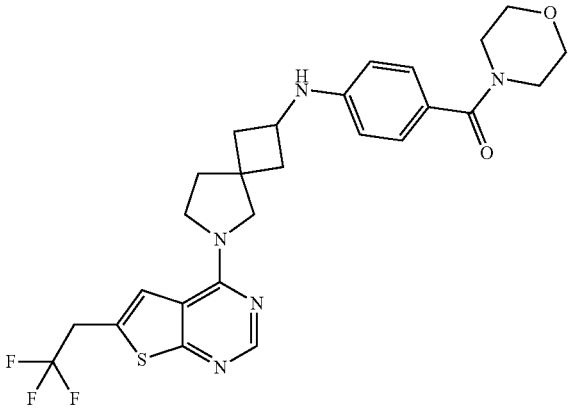 [SMILES: O=C(c1ccc(NC2CC3(CCN(c4ncnc5sc(CC(F)(F)F)cc45)C3)C2)cc1)N1CCOCC1]<br>Mixture of cis and trans |
| Compound 334 (trans or cis) Compound 335 (cis or trans) | Compound 279 | 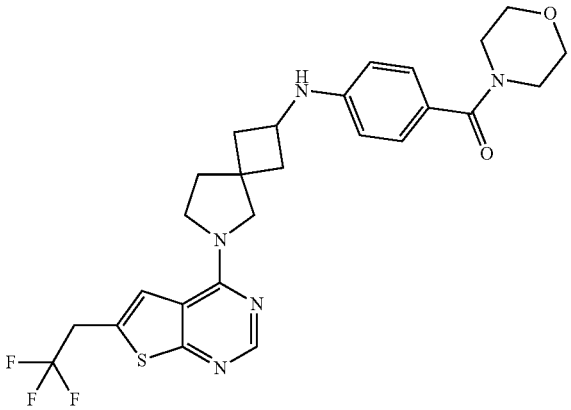 [SMILES: O=C(c1ccc(NC2CC3(CCN(c4ncnc5sc(CC(F)(F)F)cc45)C3)C2)cc1)N1CCOCC1]<br>Compound 334: trans or cis)<br>Compound 335: cis or trans) |

-continued

| Compound number | Method used | Compound structure |
|---|---|---|
| Compound 336 (formate salt) (from intermediate 5 and intermediate 261) | Compound 279 | 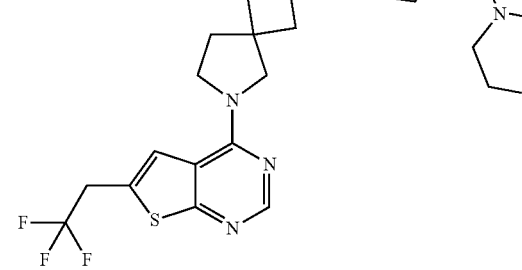<br>formate salt<br>Mixture of cis and trans |
| Compound 337 (trans or cis) Compound 338 (cis or trans; formate salt) | Compound 279 | 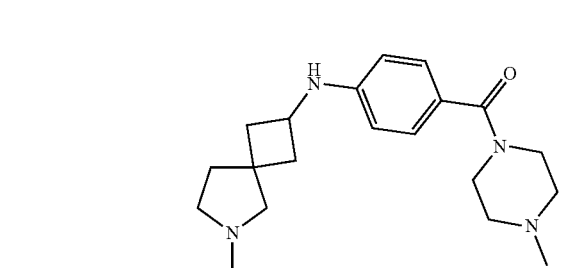<br>Compound 337 (trans or cis)<br>Compound 338 (cis or trans; formate salt) |
| Compound 339 (from intermediate 5 and intermediate 262) | Compound 279 | 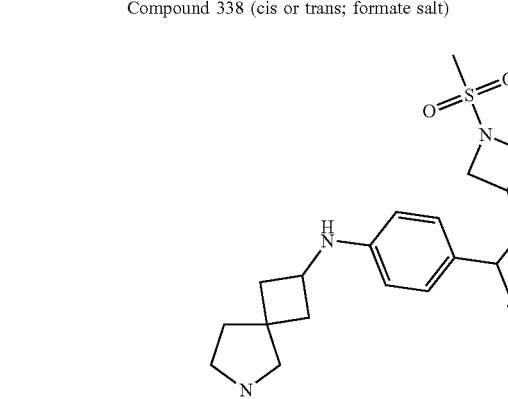<br>Mixture of 4 compounds |

| Compound number | Method used | Compound structure |
|---|---|---|
| Compound 340 (from intermediate 5 and intermediate 256) | Compound 279 | 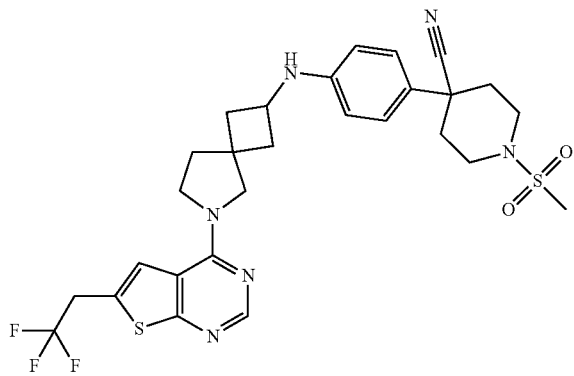 [SMILES: CS(=O)(=O)N1CCC(C#N)(c2ccc(NC3CC4(CCN(c5ncnc6sc(CC(F)(F)F)cc56)C4)C3)cc2)CC1]<br>Mixture of cis and trans |
| Compound 341 | Compound 279 | 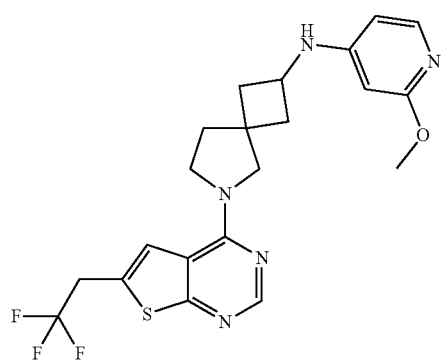 [SMILES: COc1cc(NC2CC3(CCN(c4ncnc5sc(CC(F)(F)F)cc45)C3)C2)ccn1]<br>Mixture of cis and trans |
| Compound 342 | Compound 279 | 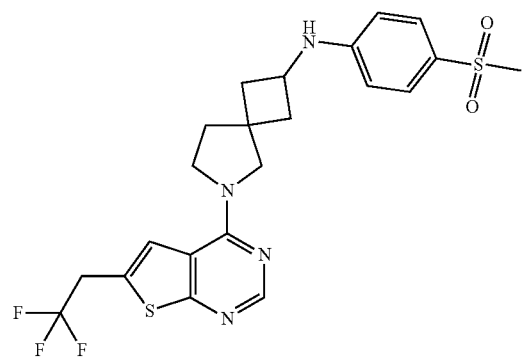 [SMILES: CS(=O)(=O)c1ccc(NC2CC3(CCN(c4ncnc5sc(CC(F)(F)F)cc45)C3)C2)cc1]<br>Mixture of cis and trans |

-continued
| Compound number | Method used | Compound structure |
|---|---|---|
| Compound 343 | Compound 279 | 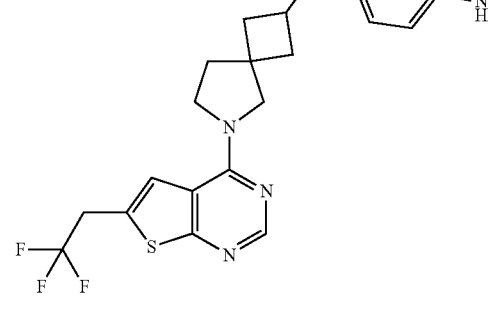<br>Mixture of cis and trans |
| Compound 344 | Compound 279 | 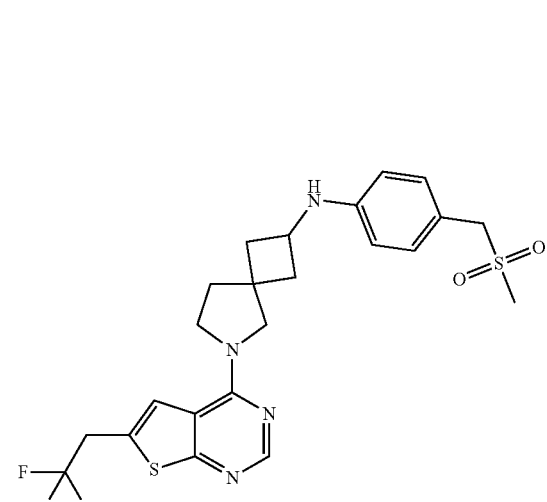<br>Mixture of cis and trans |
| Compound 345 (from intermediate 5 and intermediate 263) | Compound 279 | 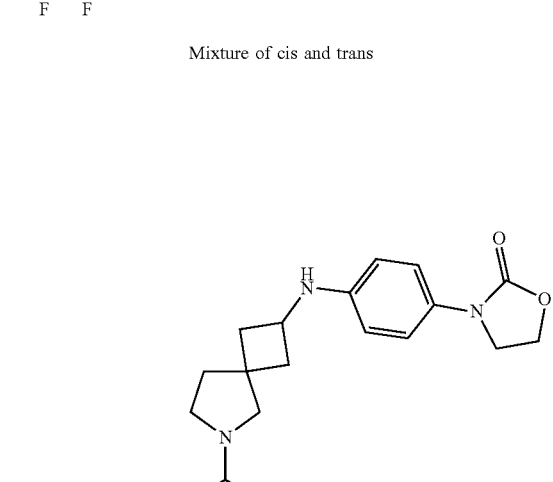<br>Mixture of cis and trans |

-continued
| Compound number | Method used | Compound structure |
|---|---|---|
| Compound 346 (from intermediate 5 and intermediate 264) | Compound 279 | 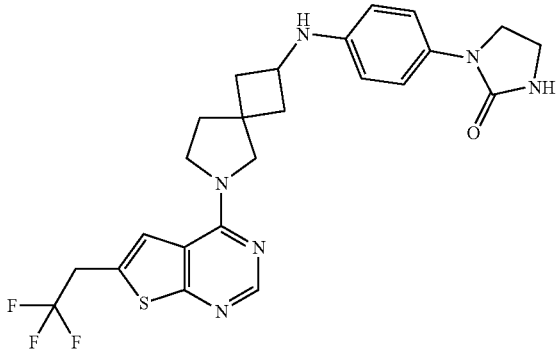 [SMILES: O=C1NCCN1c1ccc(NC2CC3(CCN(c4ncnc5sc(CC(F)(F)F)cc45)C3)C2)cc1]<br>Mixture of cis and trans |
| Compound 347 (from intermediate 5 and intermediate 265) | Compound 279 | 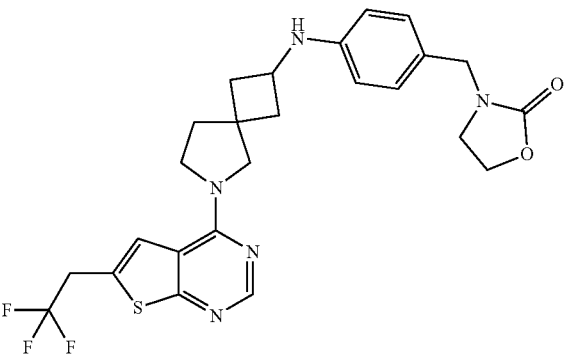 [SMILES: O=C1OCCN1Cc1ccc(NC2CC3(CCN(c4ncnc5sc(CC(F)(F)F)cc45)C3)C2)cc1]<br>Mixture of cis and trans |
| Compound 348 (formate salt) | Compound 279 | 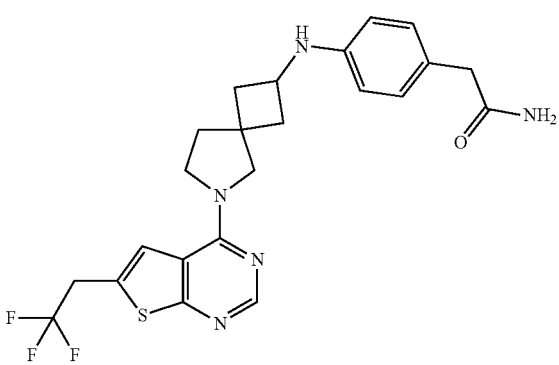 [SMILES: NC(=O)Cc1ccc(NC2CC3(CCN(c4ncnc5sc(CC(F)(F)F)cc45)C3)C2)cc1]<br>formate salt<br>Mixture of cis and trans |

-continued

| Compound number | Method used | Compound structure |
|---|---|---|
| Compound 349 (from intermediate 5 and intermediate 266) | Compound 279 | Mixture of cis and trans |
| Compound 350 (formate salt) (from intermediate 5 and intermediate 267) | Compound 279 | formate salt<br>Mixture of cis and trans |
| Compound 351 (formate salt) (from intermediate 5 and intermediate 268) | Compound 279 | formate salt<br>Mixture of cis and trans |

-continued

| Compound number | Method used | Compound structure |
|---|---|---|
| Compound 352 (trans or cis) Compound 353 (cis or trans) (from intermediate 5 and intermediate 269) | Compound 279 | 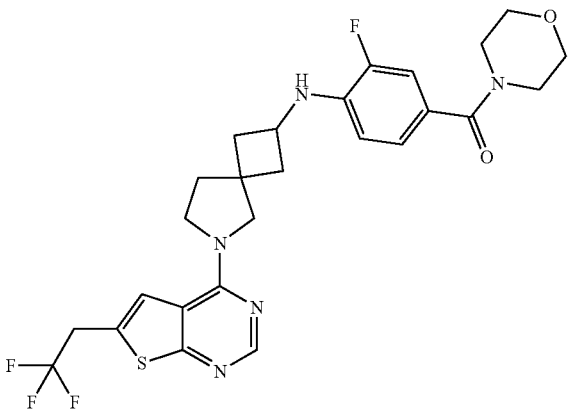 [SMILES: O=C(c1ccc(NC2CC3(CCN(c4ncnc5sc(CC(F)(F)F)cc45)C3)C2)c(F)c1)N1CCOCC1]<br>Compound 352: trans or cis<br>Compound 353: cis or trans |
| Compound 354 (from intermediate 5 and intermediate 270) | Compound 279 | 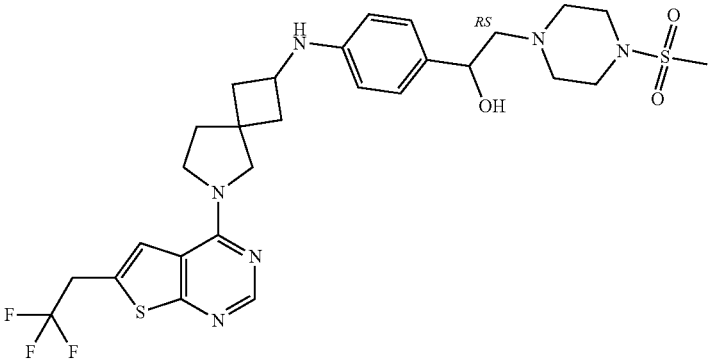 [SMILES: CS(=O)(=O)N1CCN(CC(O)c2ccc(NC3CC4(CCN(c5ncnc6sc(CC(F)(F)F)cc56)C4)C3)cc2)CC1]<br>Mixture of 4 compounds |
| Compound 355 (trans or cis) Compound 356 (cis or trans) (from intermediate 5 and intermediate 271) | Compound 279 | 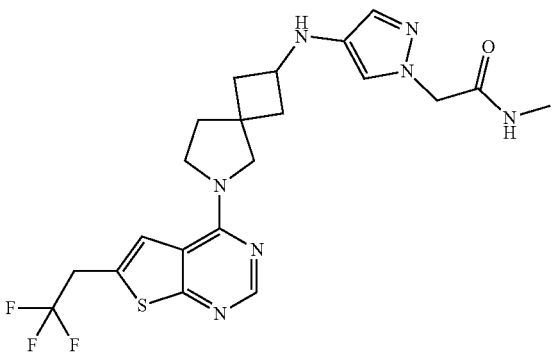 [SMILES: CNC(=O)Cn1cc(NC2CC3(CCN(c4ncnc5sc(CC(F)(F)F)cc45)C3)C2)cn1]<br>Compound 355: trans or cis<br>Compound 356: cis or trans |

| Compound number | Method used | Compound structure |
|---|---|---|
| Compound 357 (trans or cis) Compound 358 (cis or trans) (from intermediate 5 and intermediate 272) | Compound 279 | 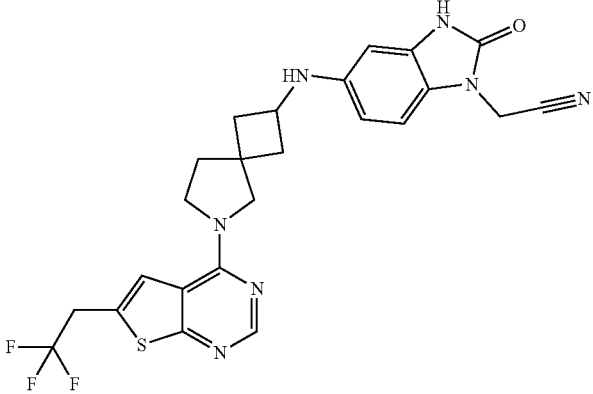 [SMILES: N#CCn1c(=O)[nH]c2cc(NC3CC4(CCN(c5ncnc6sc(CC(F)(F)F)cc56)C4)C3)ccc21]<br>Compound 357: trans or cis<br>Compound 358: cis or trans |
| Compound 359 (trans or cis) Compound 360 (cis or trans) (from intermediate 5 and intermediate 302) | Compound 279 | 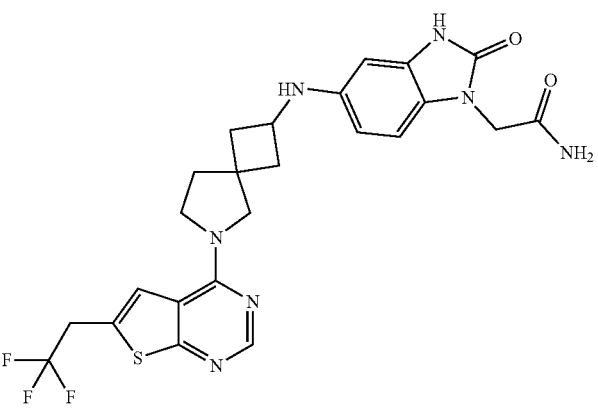 [SMILES: NC(=O)Cn1c(=O)[nH]c2cc(NC3CC4(CCN(c5ncnc6sc(CC(F)(F)F)cc56)C4)C3)ccc21]<br>Compound 359: trans or cis<br>Compound 360: cis or trans |
| Compound 361 (formate salt; trans or cis) Compound 362 (cis or trans) (from intermediate 5 and intermediate 273) | Compound 279 | 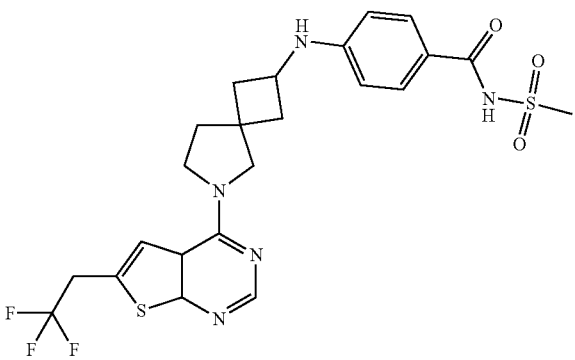<br>Compound 361: formate salt; trans or cis<br>Compound 362: cis or trans |

-continued

| Compound number | Method used | Compound structure |
|---|---|---|
| Compound 363 (trans or cis) Compound 364 (cis or trans) (from intermediate 5 and intermediate 274) | Compound 279 | 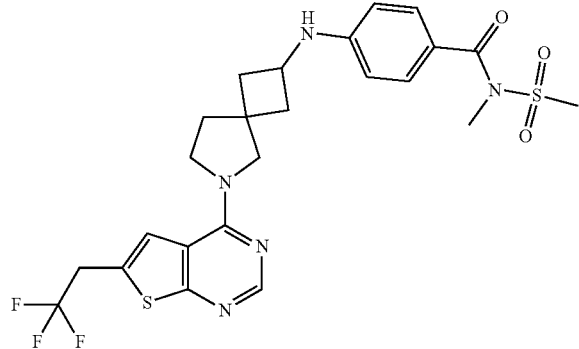<br>Compound 363: trans or cis<br>Compound 364: cis or trans |
| Compound 367 (trans or cis) Compound 368 (cis or trans) (from intermediate 5 and N-(4-aminobenzyl)-methanesulfonamide, CAS#: 81880-95-7) | Compound 279 | 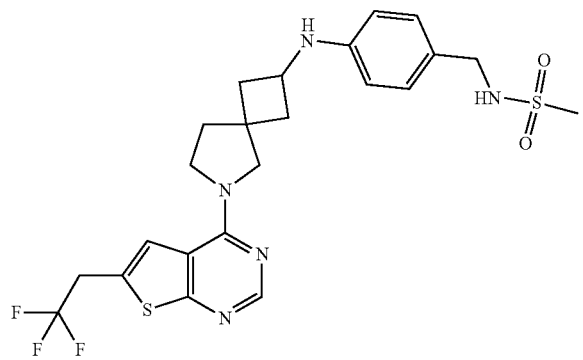<br>Compound 367: trans or cis<br>Compound 368: cis or trans |
| Compound 369 (trans or cis) Compound 370 (cis or trans) (from intermediate 5 and intermediate 275) | Compound 279 | 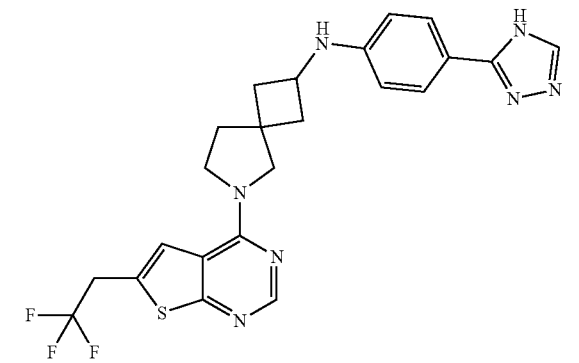<br>Compound 369: trans or cis<br>Compound 370: cis or trans |

| Compound number | Method used | Compound structure |
|---|---|---|
| Compound 371 (trans or cis) Compound 372 (cis or trans) (from intermediate 5 and 4-amino-N-(2,2,2-tri-fluoroethyl)benzamide, CAS#: 934524-28-4) | Compound 279 | Compound 371: trans or cis<br>Compound 372: cis or trans |
| Compound 373 (formate salt) (from intermediate 5 and 4-amino-N-(cyanomethyl)-benzamide, CAS-#: 20855-56-5) | Compound 279 | formate sale<br>Mixture of cis and trans |
| Compound 374 (trans or cis) Compound 375 (cis or trans) | Compound 279 | Compound 374: trans or cis<br>Compound 375: cis or trans |

Example B179

Preparation of Compound 377, Compound 378 and Compound 379

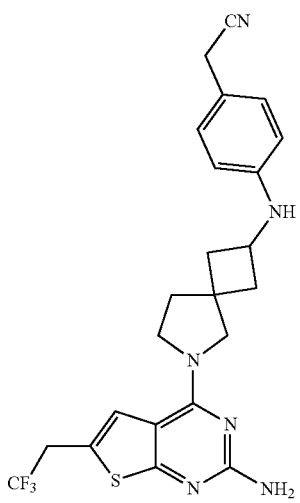

Compound 377: mixture of cis and trans; 0.5 HCOOH
Compound 378: trans or cis
Compound 379: cis or trans; formate salt Intermediate 246 (100 mg, 0.40 mmol) and 1,8-diazabicyclo[5.4.0]undec-7-ene (214 ng, 1.41 mmol) were dissolved in acetonitrile (8 mL) in a 40 mL glass vial. After 5 minutes BOP (177 mg, 0.40 mmol) was added. The resulting mixture was stirred for 5 minutes and then intermediate 277 (297 mg, crude TFA salt, 0.63 mmol) was added. The resulting mixture was stirred at 50° C. for 8 hours. The reaction mixture was poured into DCM (30 mL) before washed with water (20 mL×3). The organic extracts were dried over anhydrous $Na_2SO_4$, filtered, and concentrated to dryness under reduced pressure to give a residue, which was purified by prep-HPLC (Column: Xtimate C18 150*25 mm*5 um, Mobile Phase A: water (0.225% FA)-ACN, Mobile Phase B: acetonitrile, Flow rate: 22 mL/min, gradient condition from 32% B to 62%). The pure fractions were collected and the solvent was evaporated under vacuum. The residue was partitioned between acetonitrile (2 mL) and water (10 mL). The mixture was lyophilized to dryness to give Compound 377 (mixture of cis and trans; 0.5 HCOOH determined by residual signal of CHO group of HCOOH in HNMR) (13.4 mg, 6.79% yield) as yellow solids.

Compound 377 (100 mg, 0.19 mmol) was separated by supercritical fluid chromatography (separation condition: YMC CHIRAL Amylose-C (250 mm*30 mm, 10 um); Mobile phase: A: Supercritical CO2, B: 0.1% $NH_3H_2O$ EtOH, A:B=50:50 at 70 mL/min; Column Temp: 38° C.; Nozzle Pressure: 100 Bar; Nozzle Temp: 60° C.; Evaporator Temp: 20° C.; Trimmer Temp: 25° C.; Wavelength: 220 nm). The pure fraction was collected and the solvent was evaporated under vacuum. The residue was partitioned between $CH_3CN$ (2 mL) and water (10 mL). The solution was lyophilized to dryness to give Compound 378 (trans or cis) (35.8 mg, 38.0% yield) as a white powder and crude Compound 379.

Crude compound 379 was purified by prep-HPLC over (Column: Xtimate C18 150*25 mm*5 um, Mobile Phase A: water (0.225% formic acid)-ACN, Mobile Phase B: acetonitrile, Flow rate: 25 m/min, gradient condition from 28% B to 58%). The pure fractions were collected and the solvent was evaporated under vacuum. The residue was partitioned between $CH_3CN$ (2 mL) and water (10 mL). The mixture was lyophilized to dryness to give Compound 379 (cis or trans; formate salt) (17.12 mg, 17.0% yield) as a white powder.

Example B180

Preparation of Compound 380

Compound 380 was prepared via an analogous reaction protocol as described above for the preparation of Compound 377 starting from the respective starting materials.

| Compound number (starting materials) | Method used | Compound structure |
|---|---|---|
| Compound 380 (from intermediate 279 and intermediate 246) | Compound 377 | Compound 380<br>Mixture of cis and trans |

Example B181

Preparation of Compound 381, Compound 382 and Compound 383

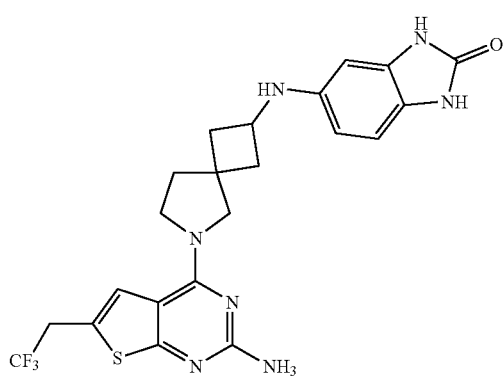

Compound 381: mixture of cis and trans; formate salt
Compound 382: trans or cis
Compound 383: cis or trans Intermediate 281 (250 mg, 0.700 mmol), 5-amino-1H-benzo[d]imidazol-2(3H)-one (CAS #: 95-23-8) (157 mg, 1.05 mmol), sodium cyanoborohydride (88.2 mg, 1.40 mmol) and dry methyl alcohol (9.5 mL) were added to a 40 mL glass bottle, and then acetic acid (84.3 mg, 1.40 mmol) in dry methyl alcohol (0.5 mL) was added. The resulting mixture was heated and stirred at 45° C. for 8 hours. The mixture was cooled to room temperature and concentrated under reduced pressure to give a residue, which was dissolved in dichloromethane (30 mL) before washed with water (20 mL×3). The organic extracts were dried over anhydrous $Na_2SO_4$, filtered and concentrated to dryness under reduced pressure to give a residue, which was purified by prep-HPLC (Column: Xtimate C18 150*25 mm*5 um, Mobile Phase A: water (0.225% FA)-ACN, Mobile Phase B: acetonitrile, Flow rate: 25 mL/min, gradient condition from 15% B to 45%). The pure fractions were collected and the solvent was evaporated under vacuum. The residue was partitioned between $CH_3CN$ (2 mL) and water (10 mL). The mixture was lyophilized to dryness to give the desired Compound 381 (mixture of cis and trans; formate salt) (62.4 mg, 16.1% yield) as a white powder. Further separation of the obtained Compound 381 by SFC afforded Compound 382 (trans or cis) and Compound 383 (cis or trans).

Example B182

Preparation of Compound 384, Compound 385 and Compound 386

Compound 384 (formate salt) was prepared via an analogous reaction protocol as described above for the preparation of Compound 381 starting from the respective starting materials.

| Compound number (starting materials) | Method used | Compound structure |
|---|---|---|
| Compound 384 (from intermediate 281 and 6-aminobenzo[d]-oxazol-2(3H)-one, CAS#: 22876-17-1) | Compound 381 | ![structure] formate salt  Mixture of cis and trans |

445

Further separation of the obtained Compound 384 (mixture of cis and trans) by SFC afforded Compound 385 (trans or cis) and Compound 386 (cis or trans).

Example B 183

Preparation of Compound 387, Compound 388 and Compound 389

Compound 387 was prepared via an analogous reaction protocol as described above for the preparation of Compound 377 starting from the respective starting materials.

| Compound number (starting materials) | Method used | Compound structure |
|---|---|---|
| Compound 387 (from intermediate 283 and 246) | Compound 377 | 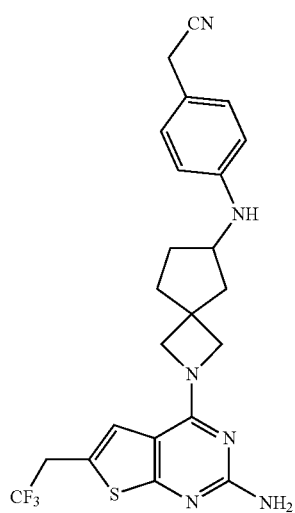 [SMILES: N#CCc1ccc(NC2CCC3(C2)CN(c2nc(N)nc4sc(CC(F)(F)F)cc24)C3)cc1] |

Further separation of the obtained Compound 387 (mixture of cis and trans) by SFC afforded Compound 388 (trans or cis) and Compound 389 (cis or trans).

446

Example B184

Preparation of Compound 390, Compound 391 and Compound 392

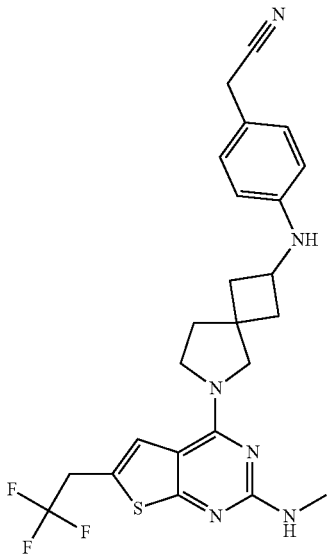

Compound 390: mixture of trans and cis
Compound 391: trans or cis
Compound 392: cis or trans Intermediate 285 (150 mg, 0.405 mmol), 2-(4-aminophenyl)acetonitrile (CAS #: 3544-25-0) (80.8 mg, 0.611 mmol), sodium cyanoborohydride (51.0 mg, 0.812 mmol) and dry methanol (12 mL) were added to a 40 mL glass bottle before acetic acid (50.0 mg, 0.833 mmol) in methanol (1 mL) was added to the mixture. The resultant mixture was stirred at 45° C. for 36 h. The mixture was suspended into water (20 mL), the aqueous layer was adjusted to pH=8 by adding the saturated solution of sodium bicarbonate, extracted with dichloromethane (20 mL×3). The combined organic layers were dried over anhydrous $Na_2SO_4$, filtered and concentrated under reduced pressure to give the crude which was purified by prep-HPLC (Column: Phenomenex Gemini 150*25 mm*10 um, Mobile Phase A: water (0.05% ammonia hydroxide v/v), Mobile Phase B: acetonitrile, Flow rate: 25 mL/min, gradient condition from 50% B to 80%). The pure fractions were collected and the solvent was evaporated under vacuum to give a residue. The residue was partitioned between acetonitrile (2 mL) and water (10 mL). The solution was lyophilized to dryness to give Compound 390 (mixture of cis and trans) (123.7 mg, 62.5% yield) as a light powder.

Further separation of the obtained Compound 390 by SFC afforded Compound 391 (trans or cis) and Compound 392 (cis or trans).

The following Compounds were prepared starting from intermediate 285, intermediate 287, and the corresponding amine, by using an analogous reductive amination method as was used for preparation of Compound 279; one of the 4 following solvents were used: DCM, DCE, MeOH, MeCN.

| Compound number (starting materials) | Compound structure |
|---|---|
| Compound 393 (formate salt)<br>(from intermediate 285 and 5-amino-1,3-dihydro-2H-benzo[d]imidazol-2-one, | 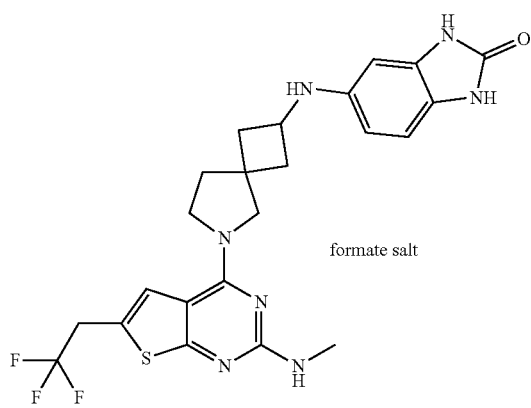 [SMILES: CNc1nc(N2CCC3(CC(Nc4ccc5[nH]c(=O)[nH]c5c4)C3)C2)c2cc(CC(F)(F)F)sc2n1]<br>formate salt<br>Mixture of cis and trans |
| Compound 394 (trans or cis)<br>Compound 395 (cis or trans)<br>(from intermediate 285 and 5-amino-1,3-dihydro-2H-benzo[d]imidazol-2-one, CAS#: 95-23-8) | 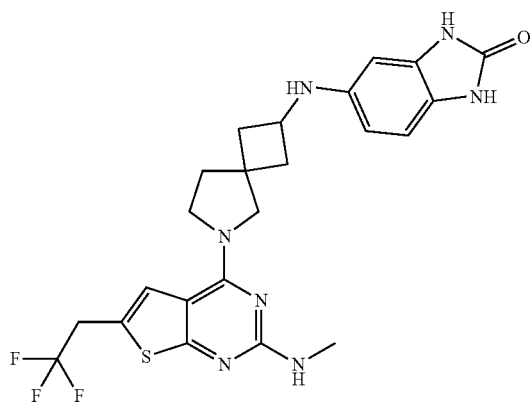<br>Compound 394: trans or cis<br>Compound 395: cis or trans |
| Compound 396 (formate salt)<br>(from intermediate 285 and 5-aminobenzo[d]oxazol-2(3H)-one, CAS#: 14733-77-8) | 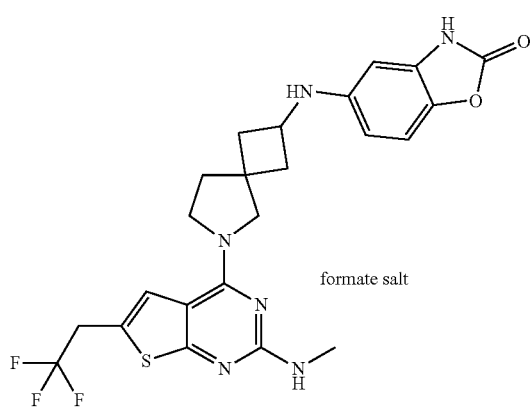 [SMILES: CNc1nc(N2CCC3(CC(Nc4ccc5oc(=O)[nH]c5c4)C3)C2)c2cc(CC(F)(F)F)sc2n1]<br>formate salt<br>Mixture of cis and trans |

| Compound number (starting materials) | Compound structure |
|---|---|
| Compound 397 (trans or cis)<br>Compound 398 (cis or trans)<br>(from intermediate 285 and<br>5-aminobenzo[d]oxazol-2(3H)-one, CAS#:<br>14733-77-8) | 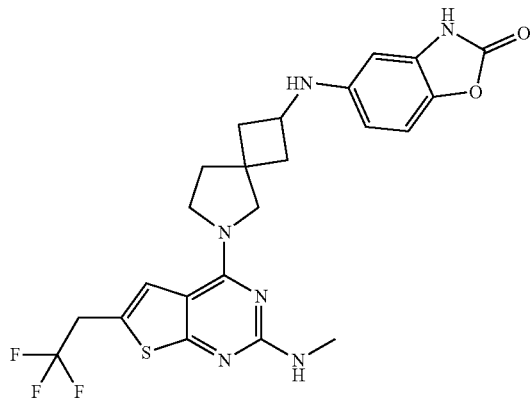 [SMILES: CNc1nc(N2CCC3(CC(Nc4ccc5oc(=O)[nH]c5c4)C3)C2)c2cc(CC(F)(F)F)sc2n1]<br>Compound 397: trans or cis<br>Compound 398: cis or trans |
| Compound 399<br>(from intermediate 285 and<br>6-aminobenzo[d]oxazol-2(3H)-one, CAS#:<br>22876-17-1) | 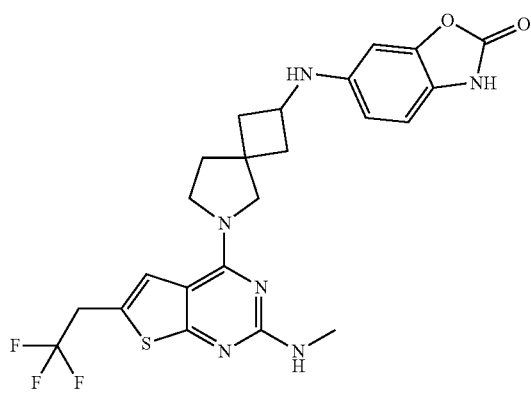 [SMILES: CNc1nc(N2CCC3(CC(Nc4ccc5[nH]c(=O)oc5c4)C3)C2)c2cc(CC(F)(F)F)sc2n1]<br>Mixture of cis and trans |
| Compound 400 (0.3 HCOOH; determined by residual signal of CHO group of HCOOH in HNMR)<br>(from intermediate 287 and 2-(4-amino-phenyl)acetonitrile, CAS#: 3544-25-0) | 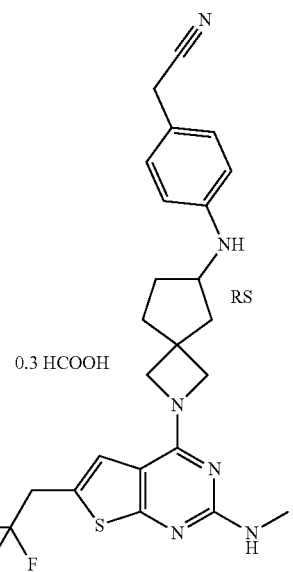 |

| Compound number (starting materials) | Compound structure |
|---|---|
| Compound 401 (from intermediate 287 and 5-aminobenzo[d]oxazol-2(3H)-one, CAS#: 14733-77-8) | 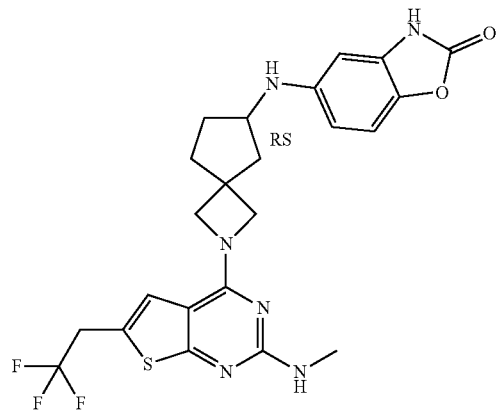 |
| Compound 402 (from intermediate 287 and 5-amino-1,3-dihydro-2H-benzo[d]imidazol-2-one, CAS#: 95-23-8) | 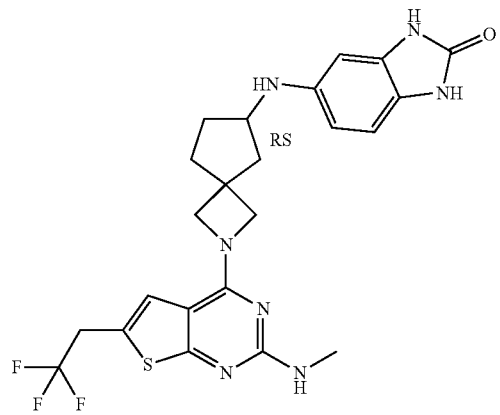 [SMILES: CNc1nc(N2CC3(CCC(Nc4ccc5[nH]c(=O)[nH]c5c4)C3)C2)c2cc(CC(F)(F)F)sc2n1] |

Example B185

Preparation of Compound 403

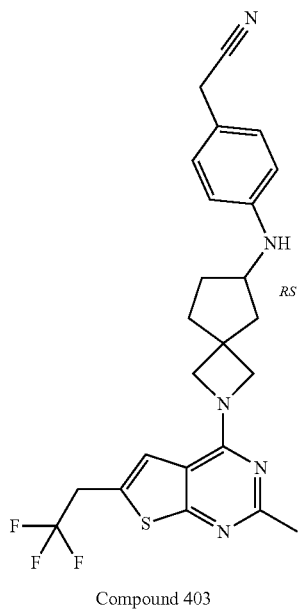 [SMILES: Cc1nc(N2CC3(CCC(Nc4ccc(CC#N)cc4)C3)C2)c2cc(CC(F)(F)F)sc2n1]

Compound 403

A stir bar, intermediate 289 (67.2 mg, 0.252 mmol), intermediate 283 (100 mg, 0.360 mmol), N,N-diisopropylethylamine (233 mg, 1.80 mmol) and acetonitrile (5 mL) were added to a 40 mL glass bottle which was stirred at 25° C. for 2 h. The mixture was diluted into DCM (50 mL) and extracted with water (20 mL×3), dried over anhydrous Na$_2$SO$_4$, filtered and concentrated under reduced pressure to give the crude product which was purified by prep-TLC (ethyl acetate/methanol=25/1, Rf=0.3) to give Compound 403 (racemate) (25.1 mg, 95.1% purity, 14.1% yield) as a white powder.

Example B186

Preparation of Compound 404

Compound 404 (mixture of cis and trans) was prepared via an analogous reaction protocol as described above for the preparation of Compound 403 starting from the respective starting materials.

| Compound number (starting materials) | Compound structure |
|---|---|
| Compound 404 (from intermediate 289 and intermediate 277) | 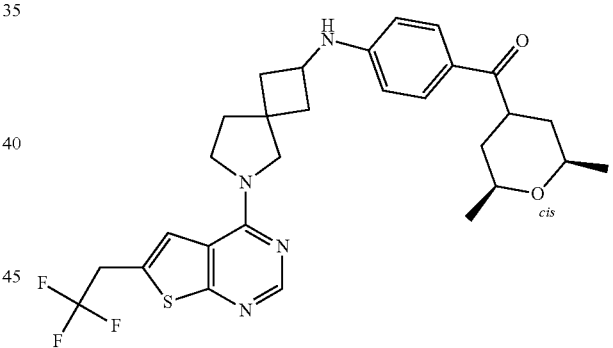<br>Mixture of cis and trans |

Example B187

Preparation of Compound 405 and Compound 406

![Compound 405/406 structure]

Compound 405: trans or cis at the spiro moiety
Compound 406: cis or trans at the spiro moiety cis-2,6-dimethylmorpholine (25.0 mg, 0.217 mmol) was added to a mixture consisting of intermediate 59 (50.0 mg, 0.087 mmol), HATU (60.0 mg, 0.158 mmol), DIEA (45.0 mg, 0.348 mmol) and DCM (4.0 mL). The resulting mixture was stirred at 25° C. for 16 hours. The mixture was poured into water (15 mL) and extracted by DCM (10 mL×3). The combined organic layers were dried over anhydrous Na$_2$SO$_4$, filtered and concentrated in vacuo. The crude residue was purified by pre-HPLC with a Phenomenex Gemini 150*25 mm*10 um (eluent: water (0.05% ammonia hydroxide v/v)-ACN from 45% to 75%). The product was suspended in water (50 mL) and then lyophilized to dryness to afford the product as a mixture of cis and trans at the spiro moiety as a white powder (18.0 mg, 37% yield).

Two batches of the product as a mixture of cis and trans at the spiro moiety were combined and further separated by SFC (separation condition: YMC CHIRAL Amylose-C (250 mm*30 mm, 10 um Mobile phase: A: Supercritical $CO_2$, B: 0.1% $NH_3H_2O$ IPA, A:B=60:40 at 50 mL/min; Column Temp: 38° C.; Nozzle Pressure: 100 Bar; Nozzle Temp: 60° C.; Evaporator Temp: 20° C.; Trimmer Temp: 25° C.; Wavelength: 220 nm). The two pure fractions were collected and the solvent was evaporated under vacuum. The two residues were respectively re-suspended in water (10 mL) and the resulting mixtures were lyophilized to dryness to give Compound 405 (trans or cis at the spiro moiety) as a white solid (9.2 mg 23% yield) and Compound 406 (cis or trans at the spiro moiety) as a white solid (17.5 mg, 44% yield).

The following Compounds were prepared starting from intermediate 59 and the corresponding amine by using an analogous method as was used for preparation of Compound 405.

| Compound number | Compound structure |
| --- | --- |
| Compound 407 (trans or cis at the spiro moiety)<br>Compound 408 (cis or trans at the spiro moiety) | 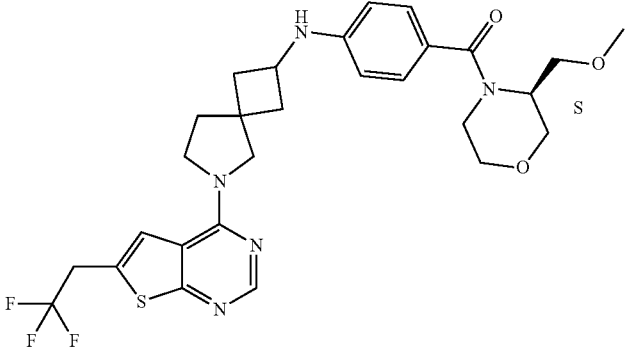<br>Compound 407 (trans or cis at the spiro moiety)<br>Compound 408 (cis or trans at the spiro moiety) |
| Compound 409 (trans or cis at the Spiro moiety)<br>Compound 410 (cis or trans at the spiro moiety) | 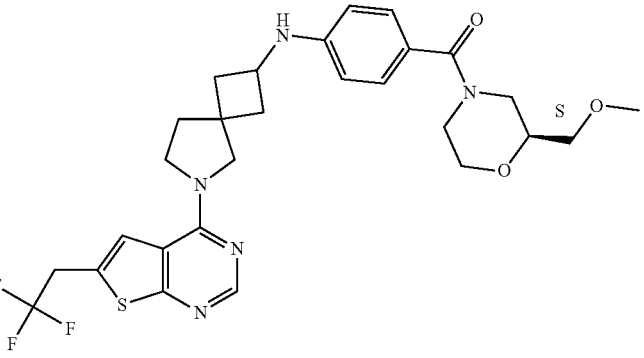<br>Compound 409 (trans or cis at the spiro moiety)<br>Compound 410 (cis or trans at the spiro moiety) |
| Compound 411 (trans or cis at the Spiro moiety)<br>Compound 412 (cis or trans at the Spiro moiety) | 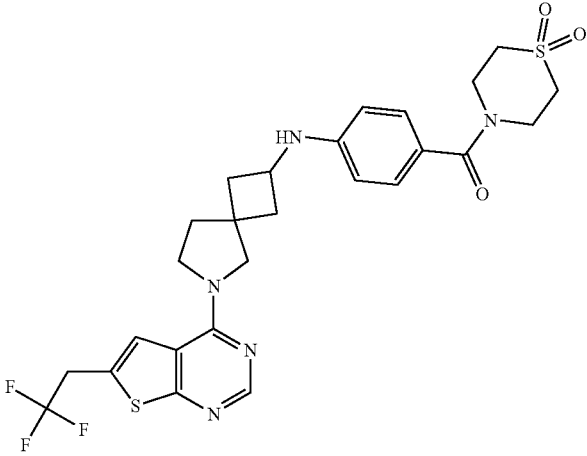 [SMILES: O=C(c1ccc(NC2CC3(CCN(c4ncnc5sc(CC(F)(F)F)cc45)C3)C2)cc1)N1CCS(=O)(=O)CC1]<br>Compound 411 (trans or cis at the spiro moiety)<br>Compound 412 (cis or trans at the spiro moiety) |

| Compound number | Compound structure |
|---|---|
| Compound 413 (trans or cis at the spiro moiety) Compound 414 (cis or trans at the spiro moiety) | 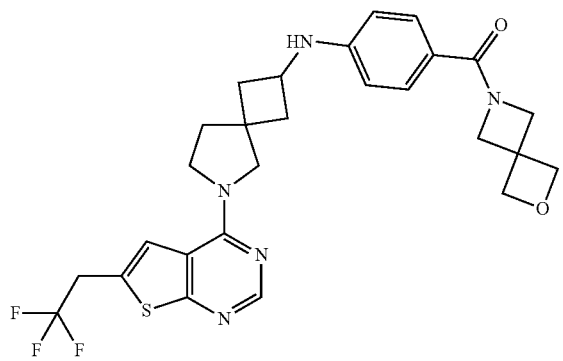 [SMILES: O=C(c1ccc(NC2CC3(CCN(c4ncnc5sc(CC(F)(F)F)cc45)C3)C2)cc1)N1CC2(COC2)C1] |

Compound 413 (trans or cis at the spiro moiety)
Compound 414 (cis or trans at the spiro moiety)

Example B 188

Preparation of Compound 415

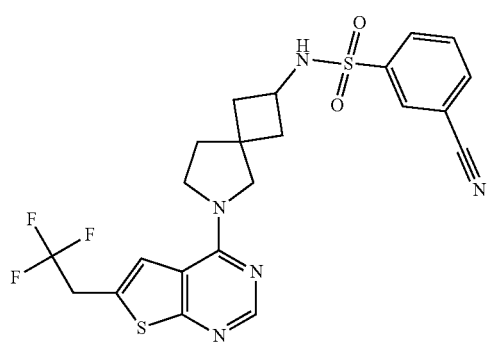

Compound 415
Mixture of cis and trans 4-chloro-6-(2,2,2-trifluoroethyl)thieno[2,3-d]pyrimidine (CAS #: 1628317-85-0) (92.5 mg, 0.366 mmol), intermediate 291 (120 mg, crude HCl salt, 0.366 mmol), N,N-diisopropylethylamine (238 mg, 1.84 mmol) and acetonitrile (5 mL) were added to a 40 mL glass bottle which was stirred at 25° C. for 2 h. The mixture was diluted into DCM (50 mL) and extracted with water (20 mL×3), the organic layer was dried over anhydrous $Na_2SO_4$, filtered and concentrated under reduced pressure to give the crude product which was purified by prep-TLC (ethyl acetate/methanol=25/1, $R_f$=0.3) to give a residue. The residue was partitioned between acetonitrile (2 mL) and water (10 mL). The solution was lyophilized to dryness to give Compound 415 (mixture of cis and trans) (145.6 mg, 77.3% yield) as a white powder.

Compound 416 and Compound 417 were prepared starting from 4-chloro-6-(2,2,2-trifluoroethyl)thieno[2,3-d]pyrimidine (CAS #: 1628317-85-0) and the corresponding amine via an analogous method as was used for the preparation of Compound 415.

| Compound number (starting material) | Compound structure |
|---|---|
| Compound 416 (from intermediate 292) | 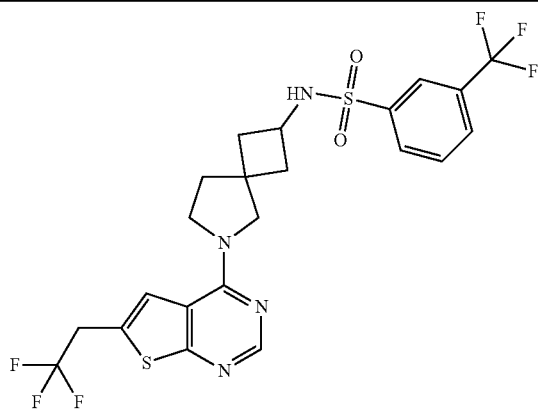 |

Compound 416
Mixture of cis and trans

| Compound number (starting material) | Compound structure |
|---|---|
| Compound 417 (from intermediate 293) | Compound 417<br>Mixture of cis and trans |

Example B189

Preparation of Compound 418 and Compound 419

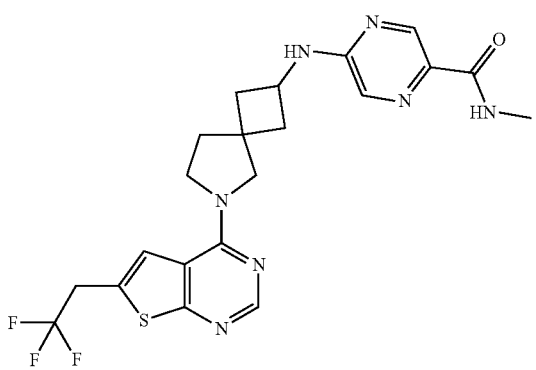

Compound 418: trans or cis
Compound 419: cis or trans

Intermediate 294 (200 mg, 1.16 mmol), 6-(6-(2,2,2-trifluoroethyl)thieno[2,3-d]-pyrimidin-4-yl)-6-azaspiro[3.4]octan-2-amine intermediate 3a (395 mg, HCl salt, 0.730 mmol), N,N-diisopropylethylamine (746 mg, 5.77 mmol), and n-BuOH (2 mL) were added to a 10 mL vial. The mixture was irradiated under microwave for 5 h at 140° C. The mixture was cool to room temperature, which was purified by preparative HPLC using a Boston Prime C18 150×30 mm×5 pm column (eluent: 32% to 62% (v/v) water (0.05% ammonia hydroxide v/v)-ACN) to afford pure product. The product was suspended in water (10 mL) and ACN (5 mL), the mixture frozen using dry ice/ethanol, and then lyophilized to dryness to afford the mixture of cis and trans) as a white solid.

The obtained mixture of cis and trans (200 mg, 0.419 mmol) was separated by SFC (separation condition: Column: DAICEL CHIRALPAK AD 250×30 mm, 10 un; Mobile phase: A: Supercritical $CO_2$, B: EtOH (0.1% $NH_3.H_2O$), A:B=60:40 at 70 mL/min;). The pure fractions were collected and the volatiles were removed under reduced pressure. The residue were partitioned between $CH_3CN$ (2 mL) and water (8 mL). The mixture was frozen using dry ice/ethanol, and then lyophilized to dryness to afford Compound 418 and Compound 419 as two white solids.

Compound 420 and Compound 421 were prepared starting from intermediate 3 and intermediate 295 by an analogous method as was used for the preparation of Compounds 418 and 419.

| Compound number | Compound structure |
|---|---|
| Compound 420 (trans or cis)<br>Compound 421 (cis or trans)<br>(from intermediate 3a and intermediate 295) | Compound 420: trans or cis<br>Compound 421: cis or trans |

Example B190

Preparation of Compound 422

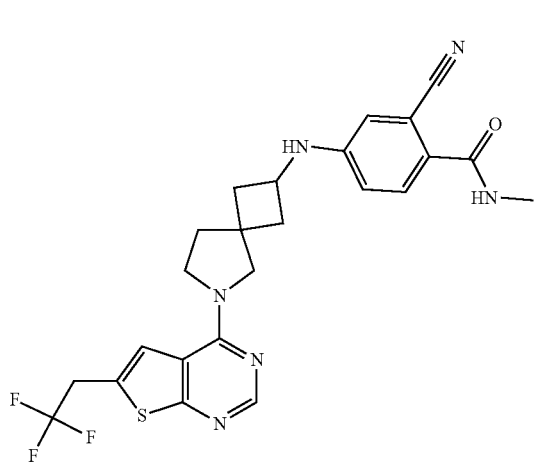

Compound 422
Mixture of cis and trans

A stir bar, methyl 2-cyano-4-((6-(6-(2,2,2-trifluoroethyl)thieno[2,3-d]pyrimidin-4-yl)-6-azaspiro[3.4]octan-2-yl)amino)benzoate intermediate 296 (60.0 mg, 0.120 mmol) and methanamine in ethanol (4.0 mL, 30% in ethanol) were added to a 8 mL glass bottle, the resultant mixture was heated and stirred at 45° C. for 8 h. The mixture was cooled to room temperature and concentrated under reduced pressure to give the crude which was purified by prep HPLC (Column: Boston Prime C18 150*30 mm 5 um, Mobile Phase A: water (0.04% $NH_3H_2O$+10 mM $NH_4HCO_3$), Mobile Phase B: acetonitrile, Flow rate: 25 mL/min, gradient condition from 43% B to 73%). The pure fractions were collected and the solvent was evaporated under vacuum to give a residue. The residue was partitioned between acetonitrile (2 mL) and water (10 mL). The solution was lyophilized to dryness to give Compound 422 (RS mixture of cis and trans) (5.43 mg, 93.68% purity by LCMS, 8.50% yield) as a yellow powder.

Example B191

Preparation of Compound 423

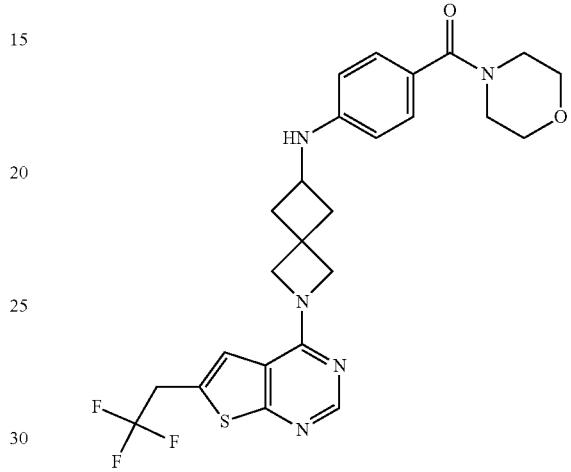

Compound 423

A stir bar, 2-(6-(2,2,2-trifluoroethyl)thieno[2,3-d]pyrimidin-4-yl)-2-azaspiro[3.3]-heptan-6-one intermediate 298 (150 mg, 0.46 mmol), (4-aminophenyl)(morpholino)-methanone (CAS #: 51207-86-4) (142 mg, 0.69 mmol), sodium cyanoborohydride (57.6 mg, 0.92 mmol) and dry methanol (9.5 mL) were added to a 40 mL glass bottle, and then acetic acid (55.0 mg, 0.92 mmol) in dry methanol (0.5 mL) was added. The reaction mixture was heated to 45° C. and stirred for 8 hours. The reaction mixture was diluted with DCM (50 mL) and washed with water (20 mL×3). The organic layer was dried over anhydrous $Na_2SO_4$, filtered, and concentrated under reduced pressure to give a residue, which was purified by preparative-HPLC (Column: Xtimate C18 150*25 mm*5 um, Mobile Phase A: water (0.225% FA), Mobile Phase B: acetonitrile, Flow rate: 25 mL/min, gradient condition from 28% B to 58%). The pure fractions were collected and the solvent was evaporated under vacuum. The residue was partitioned between $CH_3CN$ (2 mL) and water (10 mL). The mixture was lyophilized to dryness to give Compound 423 ((94.35 mg, 98.7% purity, 39.3% yield) as a white powder.

Example B192

Preparation of Compound 428

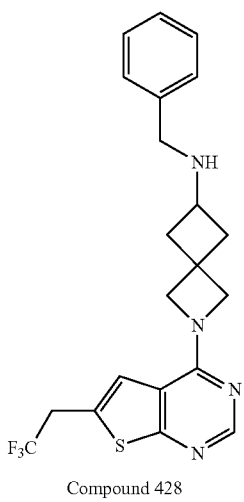 [SMILES: FC(F)(F)Cc1cc2c(N3CC4(CC(NCc5ccccc5)C4)C3)ncnc2s1]

Compound 428

Compound 428 was prepared starting from intermediate 300 and benzaldehyde via an analogous method as was used for preparation of Compound 48, indicated in the table below.

C. CONVERSION OF THE COMPOUNDS

Example C1

Preparation of Compound 52

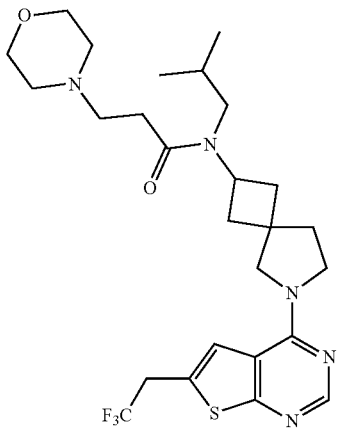 [SMILES: CC(C)CN(C(=O)CCN1CCOCC1)C1CC2(CCN(c3ncnc4sc(CC(F)(F)F)cc34)C2)C1]

A mixture of Compound 50 (100 mg; 0.251 mmol), 3-morpholinopropanoic acid cydrobromic acid (72 mg; 0.3 mmol), HBTU (95 mg; 0.251 mmol) and DIPEA (216 μL; 1.255 mmol) in DMF (4 mL) was stirred at room temperature overnight. The reaction mixture was poured onto a 10% aqueous solution of K$_2$CO$_3$ and extracted with EtOAc. The organic layer was decanted, washed with water then brine, dried over MgSO$_4$, filtered and evaporated to dryness. The residue was purified by chromatography over silica gel (irregular SiOH, 10 g; mobile phase: gradient from 0% NH$_4$OH, 0% MeOH, 100% DCM to 1% NH$_4$OH, 10% MeOH, 90% DCM). The fractions containing the product were collected and evaporated to dryness yielding 110 mg of an impure residue. A second purification was performed by chromatography over silica gel (irregular SiOH, 10 g; mobile phase: gradient from 0% NH$_4$OH, 0% MeOH, 100% DCM to 0.7% NH$_4$OH, 7% MeOH, 93% DCM). The pure fractions were collected and evaporated to dryness. The residue was freeze dried from water/ACN (80/20; 10 mL) yielding 82 mg (60%) of Compound 52 as a 70/30 mixture of isomers.

Example C2

Preparation of Compounds 25 and 26

See conversion of Compound 22 to Compounds 25 and 26 in Example B17.

Example C3

Preparation of Compound 424

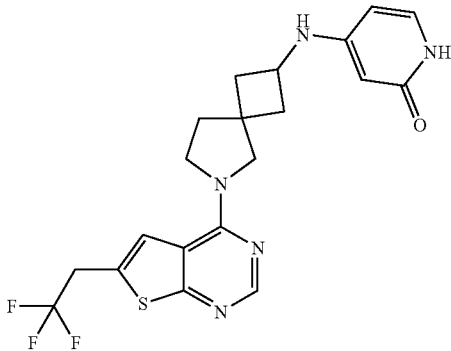

Mixture of cis and trans

The mixture of Compound 341 (80 mg, 0.178 mmol) and pyridine hydrochloride (800 mg, 6.923 mmol) in an Eggplant-shaped flask was heated at 200° C. for 1 h. The mixture cooled to 25° C. and added DCM (50 mL). The organic layer was washed with water (30 mL×3), brine (30 mL), dried over Na$_2$SO$_4$, filtered and concentrated under reduced pressure to give a residue which was purified by prep-HPLC (Column: Phenomenex Gemini 150*25 mm*10 um, Mobile Phase A: water (0.05% ammonia hydroxide v/v), Mobile Phase B: acetonitrile, Flow rate: 22 mL/min, gradient condition from 25% B to 55%). The pure fractions were collected and the solvent was evaporated under vacuum to give Compound 424 (mixture of cis and trans) as white solids.

Example C4

Preparation of Compound 425

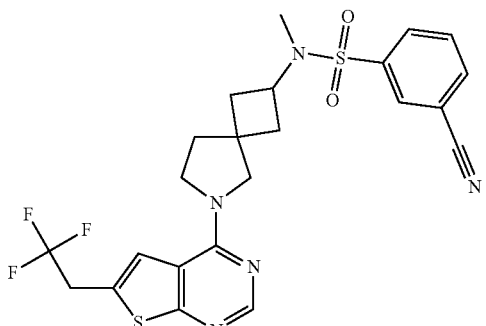

Mixture of cis and trans

A stir bar, Compound 415 (mixture of cis and trans) (100 mg, 0.197 mmol), potassium carbonate (273 mg, 1.98 mmol) and dry dimethyl formamide (4 mL) were added to a 10 mL round-bottomed flask before iodomethane (20.0 g, 141 mmol) was added to the mixture dropwise, the resultant mixture was stirred at 25° C. for 18 h. The mixture was suspended into water (50 mL), the aqueous layer was extracted with DCM (20 mL×3). The combined organic layers were dried over anhydrous $Na_2SO_4$, filtered and concentrated under reduced pressure to give the crude which was purified by prep-TLC (petroleum ether/ethyl acetate=1/1, $R_f$=0.4) to give a residue. The residue was partitioned between acetonitrile (2 mL) and water (10 mL). The solution was lyophilized to dryness to give Compound 425 (mixture of cis and trans) (33.2 mg, 98.7% purity, 31.9% yield) as a white powder.

Example C5

Preparation of Compound 426 and Compound 427

Compounds 426 and 427 respectively were prepared starting from Compounds 416 and 417 respectively via an analogous method as was used for preparation of Compound 425.

| Compound number | Compound structure |
|---|---|
| Compound 426 (from Compound 416) | Mixture of cis and trans |
| Compound 427 (from Compound 417) | Mixture of cis and trans |

Example C6

Preparation of Compound 376

Compound 376 was prepared from compound 340 by the method indicated in the scheme below:

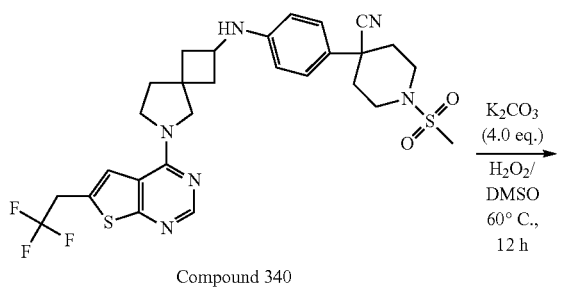

Compound 340

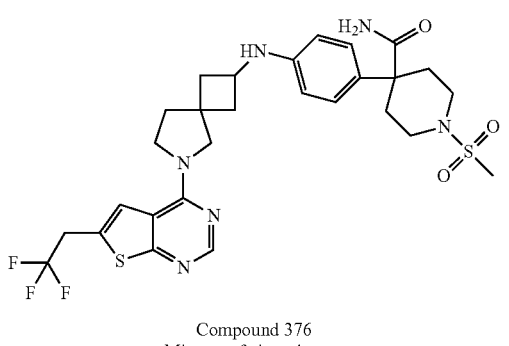

Compound 376
Mixture of cis and trans

Example C7

Preparation of Compound 260

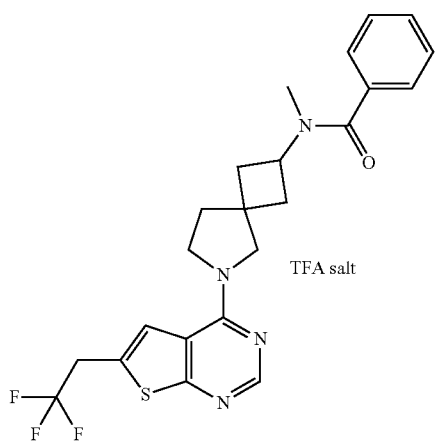

Compound 260: misture of cis and trans

To a stirred solution of compound 260a (350 mg, 0.78 mmol) and $K_2CO_3$ (269 mg, 1.95 mmol) in DMF (4 mL) at 0° C. was added dropwise $CH_3I$ (167 mg, 1.18 mmol). The reaction was stirred at room temperature overnight. The reaction mixture was filtered and concentrated. The residue was purified by prep-HPLC (Waters 2767/Qda, Column: SunFire 19*250 mm 10 um, Mobile Phase A: 0.1% TFA/ $H_2O$, B: ACN) to get desired Compound 260 (mixture of cis and trans) (63.9 mg, TFA salt, 17% yield) as a yellow solid.

Analytical Part

LCMS (Liquid Chromatography/Mass Spectrometry)

General Procedure

The High Performance Liquid Chromatography (HPLC) measurement was performed using a LC pump, a diode-array (DAD) or a UV detector and a column as specified in the respective methods. If necessary, additional detectors were included (see table of methods below).

Flow from the column was brought to the Mass Spectrometer (MS) which was configured with an atmospheric pressure ion source. It is within the knowledge of the skilled person to set the tune parameters (e.g. scanning range, dwell time . . . ) in order to obtain ions allowing the identification of the compound's nominal monoisotopic molecular weight (MW). Data acquisition was performed with appropriate software.

Compounds are described by their experimental retention times ($R_t$) and ions. If not specified differently in the table of data, the reported molecular ion corresponds to the $[M+H]^+$ (protonated molecule) and/or $[M-H]^-$ (deprotonated molecule). In case the compound was not directly ionizable the type of adduct is specified (i.e. $[M+NH_4]+$, $[M+HCOO]^-$, etc. . . . ). For molecules with multiple isotopic patterns (Br, Cl . . . ), the reported value is the one obtained for the lowest isotope mass. All results were obtained with experimental uncertainties that are commonly associated with the method used.

Hereinafter, "SQD" means Single Quadrupole Detector, "RT" room temperature, "BEH" bridged ethylsiloxane/silica hybrid, "HSS" High Strength Silica, "DAD" Diode Array Detector.

TABLE 1a

LCMS Method codes (Flow expressed in mL/min; column temperature (T) in °C.; Run time in minutes). "TFA" means trifluoroacetic acid

| Method code | Instrument | Column | Mobile phase | Gradient | Flow Column T | Run time |
|---|---|---|---|---|---|---|
| 1 | Waters | Xbridge-C18 | A: water with 0.04% TFA; mobile phase, B: acetonitrile with 0.02% TFA | 100% A was hold for 1 minute, A gradient from 100% A to 40% A is applied in 4 minutes, and 40% A down to 15% A in 2.5 minutes. And then return to 100% A in 2 minutes and hold for 0.5 minutes. The post time is 0.5 min | 0.8 — 50 | 10 |
| 2 | Waters | Xbridge-C18 | mobile phase A: water with 0.04% TFA; mobile phase B: acetonitrile with 0.02% TFA | First, 90% A was hold for 0.8 minute. Then a gradient was applied to 20% A and 80% B in 3.7 minutes and hold for 3 minutes. And then return to 90% A in 2 minutes and hold for 0.5 minutes. The post time is 0.5 min. | 0.8 50 | 10 |
| 3 | Agilent: 1200 - DAD and MSD6110 | Phenomenex: Luna-C18 (5 μm, 2 × 50 mm) | A $CF_3COOH$ 0.1% in water. B: $CF_3COOH$ 0.05% in $CH_3CN$ | 90% A for 0.8 min, to 20% A in 3.7 min, held for 3 min, back to 90% A in 2 min. | 0.8 50 | |
| 4 | Waters: Acquity UPLC® - DAD and Quattro Micro™ | Waters: BEH C18 (1.7 μm, 2.1 × 100 mm) | A: 95% $CH_3COONH_4$ 7 mM/5% $CH_3CN$, B: $CH_3CN$ | 84.2% A for 0.49 min, to 10.5% A in 2.18 min, held for 1.94 min, back to 84.2% A in 0.73 min, held for 0.73 mm. | 0.343 40 | 6.2 |
| 5 | Waters: Acquity® H-Class - DAD and SQD2 ™ | Waters: BEH C18 (1.7 μm, 2.1 × 100 mm) | A: 95% $CH_3COONH_4$ 7 mM/5% CH3CN, B: $CH_3CN$ | 84.2% A to 10.5% A in 2.18 min, held for 1.96 min, back to 84.2% A in 0.73 min, held for 0.73 min. | 0.343 40 | 6.1 |
| 6 | Agilent G6120B G1315D DADVL Detector and G4260B ELSD | Xbridge C18 5 mm 150 * 4.6mm | A $NH_4OH$ 0.1% in water. B: $NH_4OH$ 0.1% in $CH_3CN$ | 70% A for 1.0 min, to 5% A in 10.0 min, hold 5% A in 2.0 min. | 1.0 40 | 12.0 |
| 7 | Shimadzu: LC-MS2020 - SPD-M20A | SunFire C18 3.5 μm 50 * 4.6 mm | A: HCOOH 0.1% in water, B: HCOOH 0.1% in $CH_3CN$ | 30% A for 0.4 min, to 5% A in 1.2 min, to 1% A in 1.0 min. | 2.0 40 | 2.6 |
| 8 | Shimadzu: LC-MS2020 - SPD-M20A and ELSD-LTII | SunFire C18 5 μm 50 * 4.6 mm | A: HCOOH 0.1% in water, B: HCOOH 0.1% in $CH_3CN$ | 90% A for 0.4 min, to 5% A in 1.2 min, to 1% A in 1.0 min. | 2.0 40 | 2.6 |
| 9 | Shimadzu: LC-MS2020 - | SunFire | A HCOOH | 80% A for | 2.0 | |

TABLE 1a-continued

LCMS Method codes (Flow expressed in mL/min; column temperature (T) in ° C.; Run time in minutes). "TFA" means trifluoroacetic acid

| Method code | Instrument | Column | Mobile phase | Gradient | Flow Column T | Run time |
|---|---|---|---|---|---|---|
|  | SPD-M20A and ELSD-LTII | C18 5 μm 50 * 4.6 mm | 0.1% in water, B: HCOOH 0.1% in CH$_3$CN | 0.4 min, to 5% A in 1.2 min, to 1% A in 1.0 min. | 40 | 2.6 |
| 10 | Shimadzu: LC-MS2020 - SPD-M20A and ELSD-LTII | SunFire C18 5 μm 50 * 4.6 mm | A: HCOOH 0.1% in water, B: HCOOH 0.1% in CH$_3$CN | 70% A for 0.4 min, to 5% A in 1.2 min, to 1% A in 1.0 min. | 2.0 40 | 2.6 |
| 11 | Shimadzu: LC-MS2020-SPD-M20A | SunFire C18 3.5 μm 50 * 4.6 mm | A: HCOOH 0.1% in water, B: HCOOH 0.1% in CH$_3$CN | 80% A for 0.4 min, to 5% A in 1.2 min, to 1% A in 1.0 min. | 2.0 40 | 2.6 |
| 12 | Shimadzu: LC-MS2020-SPD-M20A | SunFire C18 3.5 μm 50 * 4.6 mm | A HCOOH 0.1% in water. B: HCOOH 0.1% in CH$_3$CN | 70% A for 0.4min, to 5% A in 1.2 min, to 1% A in 1.0 min. | 2.0 40 | 2.6 |
| 13 | Waters UPLC-QDa-PDA Detector | ACQUITY UPLC BEH C18 1.7 μm 2.1 * 50 mm | A: HCOOH 0.1% in water. B: HCOOH 0.1% in CH$_3$CN | 90% A for 0.1 min, to 5% A in 1.1 min, hold 5% A in 0.8 min. | 0.6 50 | 2.0 |
| 14 | Shimadzu: LC-MS2020-SPD-M20A | SunFire C18 3.5 μm 50 * 4.6 mm | A HCOOH 0.1% in water, B: HCOOH 0.1% in CH$_3$CN | 90% A for 0.4 min, to 5% A in 1.2 min, to 1% A in 1.0 min. | 2.0 40 | 2.6 |
| 15 | Agilent | X-bridge C18 | A: Water with 0.04% TFA, B: Acetonitrile with 0.02% TFA | 99% A for 0.4 min, to 10% A in 3 min, then to 0% A in 0.6 min, back to 99% A in 0.01 min and keep 99% A for 0.49 min. | 0.8 50 | 5 |
| 16 | Waters | XBridge Shield RP18 | A: water with 0.05% NH$_3$ · H$_2$O; B: acetonitrile | First, 100% A was hold for 1 minute. Then a gradient was applied to 40% A and 60% B in 4 minutes and then to 5% A and 95% B in 2.5 minutes. Finally return to 100% A in 2 minutes and hold for 0.5 minute. Post Time is 0.5 minute. | 0.8 40 | 10 |
| 17 | Agilent | MERCK C18 | A:water(4L) + TFA(1.5 mL); B: acetonitrile (4L) + TFA (0.75 mL) | from 95% A to 5% A, 95% B in 0.7 minutes, and hold at these conditions for 0.4 minutes, to 95% A and 5% B in 0.01 minutes and reequilibrate with 95% A for 0.49 minutes. | 1.2 50 | 1.5 |
| 18 | Shimadzu: LC-MS2020-SPD-M20A and Alltech 3300ELSD | SunFire C18 5 μm 50 * 4.6 mm | A: HCOOH 0.1% in water, B: HCOOH 0.1% in CH$_3$CN | 70% A for 0.4 min, to 5% A in 1.2 min, to 1% A in 1.0 min | 2.0 40 | 2.6 |
| 19 | Shimadzu: LC-MS2020- | SunFire C18 5 μm | A: HCOOH 0.1% in water, | 80% A for 0.4 min, to 5% A | 2.0 | 2.6 |

TABLE 1a-continued

LCMS Method codes (Flow expressed in mL/min; column temperature (T) in °C.; Run time in minutes). "TFA" means trifluoroacetic acid

| Method code | Instrument | Column | Mobile phase | Gradient | Flow Column T | Run time |
|---|---|---|---|---|---|---|
|  | SPD-M20A and Alltech 3300ELSD | 50 * 4.6 mm | B: HCOOH 0.1% in CH$_3$CN | in 1.2 min, to 1% A in 1.0 min | 40 |  |
| 20 | Shimadzu: LC-MS2020-SPD-M20A and Alltech 3300ELSD | SunFire C18 5 μm 50 * 4.6 mm | A: HCOOH 0.1% in water, B: HCOOH 0.1% in CH$_3$CN | 90% A for 0.4 min, to 5% A in 1.2 min, to 1% A in 1.0 min | 2.0 40 | 2.6 |
| 21 | Shimadzu: LC-MS2020-SPD-M20A and ELSD-LTII | SunFire C18 5 μm 150 * 4.6 mm | A: HCOOH 0.1% in water, B: HCOOH 0.1% in CH$_3$CN | 80% A for 0.4 min, to 5% A in 9.0 min, hold 5% A for 2.0 min | 1.0 40 | 12.0 |
| 22 | Shimadzu: LC-MS2020-SPD-M20A | SunFire C18 3.5 μm 50 * 4.6 mm | A: HCOOH 0.1% in water, B: HCOOH 0.1% in CH$_3$CN | 60% A for 0.4 min, to 5% A in 1.2 min, to 1% A in 1.0 min | 2.0 40 | 2.6 |
| 23 | Shimadzu: LC-MS2020-SPD-M20A | SunFire C18 3.5 μm 50 * 4.6 mm | A: HCOOH 0.1% in water, B: HCOOH 0.1% in CH$_3$CN | 95% A for 0.4 min, to 5% A in 1.2 min, to 1% A in 1.0 min | 2.0 40 | 2.6 |
| 24 | Agilent G612B G1315D DADVL Detector and G4260B ELSD | Xbridge C18 5 μm 50 * 4.6 mm | A: NH$_4$OH 0.1% in water; B: NH$_4$OH 0.1% in CH$_3$CN | 70% A for 0.4 min, to 5% A in 1.2 min, to 1% A in 1.0 min | 2.0 40 | 2.6 |
| 25 | Shimadzu: LC-MS2020-SPD-M20A and ELSD-LTII | SunFire C18 5 μm 50 * 4.6 mm | A: HCOOH 0.1% in water, B: HCOOH 0.1% in CH$_3$CN | 30% A for 0.4 min, to 5% A in 1.2 min, to 1% A for 1.0 min | 2.0 40 | 2.6 |
| 26 | Shimadzu: LC-MS2020-SPD-M20A and ELSD-LTII | SunFire C18 5 μm 50 * 4.6 mm | A: HCOOH 0.1% in water, B: HCOOH 0.1% in CH$_3$CN | 50% A for 0.4 min, to 5% A in 1.2 min, to 1% A for 1.0 min | 2.0 40 | 2.6 |
| 27 | Agilent: 1200-DAD and MSD6110 | Phenomenex: Luna-C18 (5 μm, 2 × 50 mm) | A: CF$_3$COOH 0.1% in water, B: CF$_3$COOH 0.05% in CH$_3$CN | 100% A for 1 min, to 40% A in 4 min, to 15% A in 2.5 min, back to 100% A in 2 min. | 0.8 50 | 10 |

TABLE 1b

LCMS and melting point data. Co. No. means compound number; R$_t$ means retention time in min.

| Co. No. | Rt (min) | [M + H]$^+$ | Adduct or [M − H]$^-$ | LCMS Method |
|---|---|---|---|---|
| 1 | 9.34 | 461.2 |  | 6 |
| 2 | 9.67 | 461.2 |  | 6 |
| 3 | 9.07 | 447.2 |  | 6 |
| 4 | 9.07 | 447.2 |  | 6 |
| 5 | 9.41 | 447.2 |  | 6 |
| 6 | 9.41 | 447.2 |  | 6 |
| 7 | 1.09 | 419.3 |  | 10 |
| 8 | 1.66 | 486.2 |  | 14 |
| 9 | 1.78 | 514.3 |  | 14 |
| 10 | 1.65 | 486.2 |  | 14 |
| 14 | 1.24 | 489.3 |  | 8 |
| 15 | 1.24 | 490.3 |  | 8 |
| 16 | 1.33 | 490.3 |  | 9 |
| 17 | 0.72 | 499.2 |  | 7 |
| 18 | 1.66 | 486.2 |  | 14 |
| 19 | 1.77 | 514.3 |  | 14 |

TABLE 1b-continued

LCMS and melting point data. Co. No. means compound number; Rt means retention time in min.

| Co. No. | Rt (min) | [M + H]+ | Adduct or [M − H]− | LCMS Method |
|---|---|---|---|---|
| 20 | 1.64 | 486.2 | | 14 |
| 22 | 1.50 | 483.4 | | 13 |
| 27 | 1.57 | 540.2 | | 14 |
| 30 | 0.89 | 513.3 | | 7 |
| 31 | 1.77 | 433.2 | | 11 |
| 32 | 1.77 | 433.2 | | 11 |
| 33 | 1.77 | 433.2 | | 11 |
| 34 | 1.77 | 433.2 | | 11 |
| 35 | 1.26 | 419.3 | | 7 |
| 36 | 1.52 | 447.3 | | 10 |
| 37 | 1.52 | 447.3 | | 10 |
| 38 | 1.81 | 433.2 | | 11 |
| 25 | 1.73 | 497.2 | | 17 |
| 26 | 1.73 | 497.2 | | 12 |
| 39 | 1.62 | 497.3 | | 10 |
| 40 | 0.92 | 413.4 | | 12 |
| 41 | 1.70 | 447.2 | | 12 |
| 42 | 2.651 | 447.0 | | 2 |
| 43 | 3.294 | 423.0 | | 1 |
| 44 | 4.366 | 458.0 | | 1 |
| 45 | 2.69 | 433 | | 3 |
| 46 | 2.62 | 433 | 491 | 4 |
| 47 | 2.65 | 433 | 491 | 4 |
| 48 | 2.68 | 433 | | 3 |
| 50 | 2.24 | 399 | 457 | 5 |
| 51 | 2.06 | 385 | 443 | 5 |
| 52 | 2.80; 2.84 | 540 | 598 | 4 |
| 53 | 3.23 | 546.2 | | 1 |
| 54 | 1.082 | 503.3 | | 11 |
| 55 | 1.139 | 490.3 | | 8 |
| 56 | 1.126 | 490.3 | | 8 |
| 57 | 1.093 | 490.3 | | 9 |
| 58 | 1.183 | 490.3 | | 9 |
| 59 | 1.363 | 463.4 | | 8 |
| 60 | 1.363 | 463.4 | | 8 |
| 61 | 1.253 | 462.4 | | 8 |
| 62 | 1.243 | 462.4 | | 8 |
| 63 | 1.722 | 476.2 | | 10 |
| 64 | 1.123 | 505.4 | | 10 |
| 65 | 1.123 | 505.4 | | 10 |
| 66 | 1.492 | 494.2 | | 10 |
| 67 | 1.492 | 494.2 | | 10 |
| 68 | 1.583 | 510.2 | 508.2 | 10 |
| 69 | 1.563 | 510.2 | 508.2 | 10 |
| 70 | 1.00 | 477.3 | | 10 |
| 71 | 1.002 | 477.3 | | 10 |
| 72 | 1.002 | 477.3 | | 10 |
| 73 | 1.140 | 533.3 | | 9 |
| 74 | 1.023 | 533.3 | | 10 |
| 75 | 1.023 | 533.3 | | 10 |
| 76 | 1.023 | 563.4 | | 10 |
| 77 | 1.023 | 563.4 | | 10 |
| 78 | 1.332 | 541.3 | | 8 |
| 79 | 1.332 | 541.3 | | 14 |
| 80 | 1.332 | 541.3 | | 14 |
| 81 | 1.032 | 557.2 | | 10 |
| 82 | 1.343 | 556.3 | | 8 |
| 83 | 1.280 | 506.3 | | 10 |
| 84 | 1.300 | 506.3 | | 10 |
| 85 | 1.463 | 520.3 | | 10 |
| 86 | 1.463 | 520.3 | | 10 |
| 87 | 1.002 | 575.3 | | 10 |
| 88 | 1.002 | 575.3 | | 10 |
| 89 | 3.28 | 489.2 | | 1 |
| 90 | 3.49 | 489.2 | | 1 |
| 91 | 3.48 | 489.2 | | 1 |
| 92 | 2.96 | 485.2 | | 2 |
| 93 | 4.00 | 476.2 | | 1 |
| 94 | 4.01 | 476.2 | | 1 |
| 95 | 4.01 | 476.2 | | 1 |
| 96 | 2.41 | 476.0 | | 15 |
| 97 | 4.01 | 476.0 | | 1 |
| 98 | 4.01 | 476.0 | | 1 |
| 99 | 4.56 | 528.2 | | 16 |
| 102 | 0.912 | 518.2 | | 10 |
| 103 | 0.912 | 518.2 | | 10 |
| 104 | 3.612 | 545.0 | | 1 |
| 105 | 3.611 | 545.0 | | 1 |
| 106 | 3.487 | 546.2 | | 1 |
| 107 | 3.773 | 517.3 | | 1 |
| 108 | 1.233 | 489.3 | | 8 |
| 109 | 1.233 | 489.3 | | 8 |
| 110 | 1.089 | 503.3 | | 11 |
| 111 | 1.089 | 503.3 | | 11 |
| 196 | 1.213 | 385.3 | | 8 |
| 148 | 1.263 | 419.3 | | 25 |
| 149 | 1.913 | 419.3 | | 8 |
| 150 | 1.903 | 419.3 | | 8 |
| 260 | 0.963 | 461.6 | | 19 |
| 125 | 1.733 | 536.3 | | 8 |
| 126 | 1.683 | 500.4 | | 8 |
| 128 | 1.563 | 461.3 | | 10 |
| 124 | 1.563 | 536.3 | | 10 |
| 127 | 1.803 | 500.3 | | 10 |
| 197 | 1.103 | 451.4 | | 10 |
| 143 | 1.683 | 472.3 | | 10 |
| 144 | 1.677 | 472.2 | | 12 |
| 145 | 1.673 | 472.2 | | 12 |
| 146 | 1.663 | 472.3 | | 10 |
| 147 | 1.676 | 472.3 | | 12 |
| 129 | 1.763 | 490.3 | | 10 |
| 130 | 1.843 | 500.4 | | 10 |
| 131 | 1.792 | 498.3 | | 12 |
| 132 | 1.803 | 458.3 | | 10 |
| 133 | 1.443 | 490.3 | | 10 |
| 134 | 1.432 | 490.3 | | 12 |
| 135 | 1.432 | 490.3 | | 12 |
| 136 | 1.432 | 490.3 | | 12 |
| 137 | 1.432 | 490.3 | | 12 |
| 138 | 1.503 | 499.4 | | 10 |
| 139 | 1.492 | 499.2 | | 12 |
| 140 | 1.482 | 499.2 | | 12 |
| 141 | 1.472 | 499.3 | | 12 |
| 142 | 1.482 | 499.3 | | 12 |
| 261 | 1.242 | 447.3 | | 14 |
| 262 | 1.242 | 447.3 | | 14 |
| 263 | 1.223 | 448.3 | | 8 |
| 264 | 1.772 | 433.2 | | 14 |
| 265 | 1.782 | 433.2 | | 14 |
| 266 | 2.012 | 449.2 | | 14 |
| 267 | 2.022 | 449.2 | | 14 |
| 268 | 1.303 | 448.4 | | 10 |
| 269 | 1.303 | 448.4 | | 10 |
| 118 | 0.943 | 513.3 | | 10 |
| 115 | 1.353 | 529.4 | | 8 |
| 116 | 1.333 | 529.4 | | 8 |
| 121 | 1.243 | 528.4 | | 8 |
| 122 | 1.223 | 528.4 | | 8 |
| 119 | 0.863 | 503.4 | | 10 |
| 117 | 1.293 | 519.3 | | 8 |
| 120 | 1.233 | 518.4 | | 8 |
| 112 | 1.233 | 459.3 | | 9 |
| 113 | 1.223 | 459.4 | | 9 |
| 151 | 0.962 | 420.2 | | 12 |
| 152 | 0.952 | 420.2 | | 12 |
| 153 | 0.952 | 420.2 | | 12 |
| 154 | 0.942 | 420.2 | | 12 |
| 155 | 0.942 | 420.2 | | 12 |
| 156 | 1.862 | 437.2 | | 12 |
| 157 | 1.802 | 437.2 | | 12 |
| 158 | 1.762 | 437.2 | | 12 |
| 159 | 1.992 | 453.2 | | 12 |
| 160 | 1.922 | 453.2 | | 12 |
| 161 | 1.882 | 453.2 | | 12 |
| 162 | 1.823 | 444.3 | | 10 |

TABLE 1b-continued

LCMS and melting point data. Co. No. means compound number; Rt means retention time in min.

| Co. No. | Rt (min) | [M + H]+ | Adduct or [M − H]− | LCMS Method |
|---|---|---|---|---|
| 163 | 1.513 | 444.3 | | 26 |
| 164 | 1.703 | 444.3 | | 10 |
| 165 | 1.903 | 433.4 | | 10 |
| 166 | 1.823 | 433.3 | | 10 |
| 167 | 1.803 | 433.3 | | 10 |
| 168 | 1.572 | 476.2 | | 22 |
| 199 | 1.683 | 476.3 | | 10 |
| 200 | 1.683 | 476.3 | | 10 |
| 169 | 1.803 | 486.3 | | 10 |
| 170 | 1.803 | 486.3 | | 10 |
| 171 | 1.722 | 484.2 | | 12 |
| 172 | 1.732 | 484.3 | | 12 |
| 208 | 1.822 | 492.2 | | 12 |
| 209 | 1.822 | 492.2 | | 12 |
| 210 | 1.752 | 492.2 | | 12 |
| 211 | 1.752 | 492.2 | | 12 |
| 114 | 1.872 | 458.2 | | 14 |
| 173 | 1.672 | 458.2 | | 12 |
| 201 | 1.832 | 458.2 | | 14 |
| 202 | 1.852 | 458.2 | | 14 |
| 270 | 1.230 | 666.3 | | 10 |
| 221 | 1.010 | 665.3 | | 10 |
| 237 | 1.632 | 490.2 | | 14 |
| 238 | 1.632 | 490.2 | | 14 |
| 212 | 1.480 | 490.3 | | 10 |
| 213 | 1.470 | 490.3 | | 10 |
| 123 | 1.143 | 505.3 | | 10 |
| 203 | 1.523 | 494.3 | | 10 |
| 204 | 1.523 | 494.3 | | 10 |
| 205 | 1.523 | 494.3 | | 10 |
| 214 | 1.512 | 510.2 | | 12 |
| 177 | 1.463 | 637.3 | | 10 |
| 178 | 1.430 | 609.2 | | 13 |
| 179 | 1.430 | 609.2 | | 13 |
| 248 | 1.103 | 695.3 | | 10 |
| 250 | 1.022 | 695.3 | | 12 |
| 249 | 1.282 | 666.3 | | 12 |
| 222 | 5.250 | 665.3 | | 21 |
| 180 | 1.142 | 547.3 | | 11 |
| 174 | 1.663 | 445.3 | | 9 |
| 175 | 1.693 | 445.2 | | 9 |
| 176 | 1.663 | 445.2 | | 9 |
| 271 | 1.984 | 474.2 | | 24 |
| 215 | 1.613 | 474.4 | | 18 |
| 206 | 1.583 | 473.3 | | 10 |
| 207 | 1.788 | 473.2 | | 24 |
| 216 | 1.472 | 474.3 | | 12 |
| 217 | 1.523 | 477.3 | | 9 |
| 218 | 1.523 | 477.3 | | 9 |
| 239 | 0.992 | 562.3 | | 12 |
| 240 | 1.313 | 542.3 | | 8 |
| 223 | 1.032 | 557.2 | | 12 |
| 241 | 1.123 | 571.3 | | 10 |
| 224 | 1.352 | 543.3 | | 14 |
| 225 | 1.342 | 556.3 | | 23 |
| 181 | 1.383 | 583.3 | | 10 |
| 182 | 1.383 | 583.3 | | 10 |
| 183 | 1.522 | 560.4 | | 10 |
| 184 | 1.523 | 560.4 | | 10 |
| 185 | 1.383 | 597.4 | | 10 |
| 186 | 1.383 | 597.4 | | 10 |
| 198 | 1.293 | 489.2 | | 20 |
| 187 | 1.010 | 531.3 | | 10 |
| 188 | 1.003 | 531.3 | | 10 |
| 242 | 1.272 | 551.2 | | 14 |
| 243 | 1.282 | 551.2 | | 14 |
| 253 | 0.880 | 534.3 | | 10 |
| 254 | 0.870 | 534.3 | | 10 |
| 244 | 1.472 | 512.2 | | 12 |
| 245 | 1.472 | 512.2 | | 12 |
| 226 | 1.563 | 512.3 | | 10 |
| 227 | 1.563 | 512.3 | | 10 |
| 228 | 1.542 | 512.2 | | 12 |
| 229 | 1.542 | 512.2 | | 12 |
| 257 | 1.242 | 478.2 | | 12 |
| 258 | 1.482 | 534.2 | | 14 |
| 259 | 1.482 | 534.2 | | 14 |
| 219 | 1.592 | 568.2 | | 12 |
| 220 | 1.592 | 568.2 | | 12 |
| 230 | 1.043 | 573.4 | | 10 |
| 231 | 1.043 | 573.4 | | 10 |
| 232 | 1.032 | 629.3 | | 12 |
| 233 | 1.032 | 629.3 | | 12 |
| 234 | 1.783 | 497.3 | | 10 |
| 235 | 1.723 | 497.3 | | 19 |
| 189 | 1.042 | 652.3 | | 12 |
| 190 | 1.042 | 652.3 | | 12 |
| 236 | 1.010 | 561.4 | | 12 |
| 251 | 1.233 | 680.5 | | 20 |
| 272 | 0.902 | 518.2 | | 12 |
| 273 | 0.912 | 518.2 | | 12 |
| 191 | 1.503 | 651.3 | | 10 |
| 192 | 1.330 | 666.4 | | 8 |
| 193 | 1.205 | 547.4 | | 20 |
| 274 | 1.297 | 598.2 | | 8 |
| 275 | 1.072 | 598.1 | | 10 |
| 246 | 1.113 | 592.4 | | 19 |
| 247 | 1.273 | 592.4 | | 19 |
| 194 | 1.382 | 609.4 | | 12 |
| 195 | 1.382 | 609.4 | | 12 |
| 276 | 2.747 | 461.0 | | 2 |
| 280 | 2.741 | 461.1 | | 2 |
| 281 | 2.763 | 461.0 | | 2 |
| 282 | 2.784 | 459.0 | | 2 |
| 277 | 3.174 | 409.0 | | 1 |
| 283 | 3.340 | 436.2 | | 1 |
| 278 | 4.229 | 458.0 | | 1 |
| 284 | 2.758 | 458.0 | | 2 |
| 285 | 3.746 | 476.0 | | 1 |
| 286 | 3.739 | 476.0 | | 1 |
| 287 | 3.737 | 476.0 | | 1 |
| 288 | 3.230 | 525.9 | | 2 |
| 289 | 2.879 | 472.0 | | 2 |
| 279 | 4.290 | 511.9 | | 1 |
| 290 | 4.133 | 512.1 | | 1 |
| 291 | 4.132 | 512.1 | | 1 |
| 292 | 3.619 | 474.0 | | 1 |
| 293 | 3.778 | 474.0 | | 1 |
| 294 | 3.775 | 474.0 | | 1 |
| 295 | 3.640 | 476.0 | | 1 |
| 296 | 3.613 | 476.2 | | 1 |
| 297 | 3.767 | 476.0 | | 1 |
| 298 | 3.277 | 475.0 | | 1 |
| 300 | 3.272 | 475.2 | | 1 |
| 299 | 3.100 | 475.1 | | 1 |
| 301 | 2.694 | 4851 | | 2 |
| 302 | 2.790 | 485.0 | | 2 |
| 303 | 2.453 | 485.1 | | 2 |
| 304 | 2.449 | 485.1 | | 2 |
| 424 | 4.086 | 436.1 | | 16 |
| 305 | 3.187 | 436.1 | | 1 |
| 306 | 4.357 | 458.0 | | 1 |
| 307 | 4.372 | 458.0 | | 1 |
| 308 | 3.632 | 476.1 | | 1 |
| 309 | 3.130 | 409.0 | | 1 |
| 310 | 3.265 | 423.0 | | 1 |
| 311 | 2.726 | 458.0 | | 2 |
| 312 | 2.700 | 458.0 | | 2 |
| 313 | 2.737 | 458.0 | | 2 |
| 314 | 3.390 | 525.9 | | 2 |
| 315 | 3.360 | 460.0 | | 2 |
| 316 | 4.288 | 511.9 | | 1 |
| 317 | 4.483 | 517.0 | | 1 |
| 318 | 4.484 | 512.0 | | 1 |
| 415 | 4.397 | 507.9 | | 1 |
| 425 | 4.707 | 521.9 | | 1 |

TABLE 1b-continued

LCMS and melting point data. Co. No. means compound number; $R_t$ means retention time in min.

| Co. No. | Rt (min) | [M + H]⁺ | Adduct or [M − H]⁻ | LCMS Method |
|---|---|---|---|---|
| 416 | 5.475 | 550.9 | | 16 |
| 426 | 3.850 | 564.9 | | 2 |
| 417 | 3.634 | 550.9 | | 2 |
| 427 | 3.879 | 564.9 | | 2 |
| 319 | 3.281 | 475.0 | | 1 |
| 320 | 3.137 | 475.1 | | 1 |
| 321 | 3.463 | 475.0 | | 1 |
| 322 | 3.772 | 475.9 | | 1 |
| 323 | 3.757 | 476.2 | | 1 |
| 324 | 3.679 | 476.1 | | 1 |
| 325 | 3.255 | 489.2 | | 1 |
| 326 | 2.899 | 485.0 | | 2 |
| 327 | 2.944 | 485.0 | | 2 |
| 328 | 2.933 | 485.0 | | 2 |
| 329 | 4.000 | 476.2 | | 1 |
| 330 | 3.773 | 476.0 | | 1 |
| 331 | 3.597 | 476.2 | | 1 |
| 332 | 3.585 | 476.7 | | 1 |
| 333 | 3.958 | 532.2 | | 1 |
| 334 | 4.162 | 532.2 | | 1 |
| 335 | 4.173 | 532.2 | | 1 |
| 336 | 2.706 | 545.1 | | 2 |
| 337 | 2.518 | 545.3 | | 2 |
| 338 | 2.547 | 545.3 | | 2 |
| 339 | 4.493 | 605.2 | | 1 |
| 340 | 4.604 | 605.3 | | 1 |
| 341 | 2.483 | 450.2 | | 2 |
| 342 | 4.282 | 497.1 | | 1 |
| 343 | 3.901 | 512.2 | | 1 |
| 344 | 4.109 | 511.2 | | 1 |
| 345 | 3.874 | 504.2 | | 1 |
| 346 | 3.586 | 503.2 | | 1 |
| 347 | 3.974 | 518.2 | | 1 |
| 348 | 3.531 | 476.2 | | 1 |
| 376 | 3.922 | 623.3 | | 1 |
| 349 | 3.388 | 680.3 | | 1 |
| 350 | 2.471 | 518.2 | | 2 |
| 351 | 2.702 | 595.2 | | 2 |
| 352 | 4.321 | 550.2 | | 1 |
| 353 | 4.932 | 550.2 | | 16 |
| 405 | 3.286 | 560.2 | | 2 |
| 406 | 3.292 | 560.2 | | 2 |
| 407 | 4.264 | 576.2 | | 1 |
| 408 | 4.269 | 576.3 | | 1 |
| 409 | 4.233 | 576.3 | | 1 |
| 410 | 4.238 | 576.3 | | 1 |
| 354 | 3.381 | 625.0 | | 1 |
| 418 | 3.839 | 478.2 | | 1 |
| 419 | 3.830 | 478.2 | | 1 |
| 411 | 4.943 | 580.0 | | 16 |
| 412 | 4.120 | 580.1 | | 1 |
| 355 | 3.184 | 480.2 | | 1 |
| 356 | 2.966 | 480.2 | | 1 |
| 357 | 3.607 | 514.2 | | 1 |
| 358 | 3.600 | 514.2 | | 1 |
| 359 | 3.247 | 532.2 | | 1 |
| 360 | 3.236 | 532.2 | | 1 |
| 413 | 4.071 | 544.2 | | 1 |
| 414 | 4.070 | 544.2 | | 1 |
| 420 | 3.476 | 534.2 | | 1 |
| 421 | 3.457 | 534.2 | | 1 |
| 361 | 4.203 | 540.1 | | 1 |
| 362 | 4.217 | 540.1 | | 1 |
| 363 | 4.454 | 554.2 | | 1 |
| 364 | 4.464 | 554.2 | | 1 |
| 422 | 3.753 | 501.1 | | 1 |
| 367 | 3.856 | 526.2 | | 1 |
| 368 | 3.867 | 526.2 | | 1 |
| 369 | 3.864 | 486.2 | | 1 |
| 370 | 3.850 | 486.2 | | 1 |
| 371 | 3.333 | 544.2 | | 2 |
| 372 | 3.336 | 544.2 | | 2 |
| 373 | 4.154 | 501.2 | | 1 |
| 374 | 2.696 | 485.2 | | 2 |
| 375 | 2.688 | 485.2 | | 2 |
| 403 | 2.908 | 472.0 | | 2 |
| 404 | 3.075 | 472.0 | | 2 |
| 400 | 2.993 | 487.0 | | 2 |
| 401 | 2.573 | 505.2 | | 2 |
| 402 | 2.156 | 504.2 | | 2 |
| 387 | 3.933 | 473.0 | | 1 |
| 388 | 3.959 | 473.2 | | 1 |
| 389 | 3.963 | 473.2 | | 1 |
| 423 | 4.050 | 518.2 | | 1 |
| 390 | 3.064/3.117 | 487.0 | | 2 |
| 391 | 3.086 | 487.2 | | 2 |
| 392 | 3.167 | 487.2 | | 2 |
| 393 | 2.070 | 504.1 | | 2 |
| 394 | 2.069 | 504.1 | | 2 |
| 395 | 3.259 | 504.2 | | 1 |
| 399 | 3.746 | 505.2 | | 1 |
| 396 | 2.721/2.751 | 505.3 | | 2 |
| 397 | 2.753 | 505.2 | | 2 |
| 398 | 2.724 | 505.2 | | 2 |
| 377 | 4.875 | 473.1 | | 16 |
| 378 | 4.070 | 473.2 | | 1 |
| 379 | 4.146 | 473.2 | | 1 |
| 381 | 3.104/3.132 | 490.2 | | 1 |
| 382 | 3.105 | 490.2 | | 1 |
| 383 | 3.090 | 490.2 | | 1 |
| 380 | 3.669/3.701 | 491.0 | | 1 |
| 384 | 2.146 | 491.0 | | 15 |
| 385 | 3.56 | 491.0 | | 1 |
| 386 | 3.56 | 491.0 | | 1 |
| 428 | 3.67 | 419.0 | | 27 |

Analytical Chiral-HPLC

General Procedure for SFC Methods

The SFC measurement was performed using an Analytical Supercritical fluid chromatography (SFC) system composed by a binary pump for delivering carbon dioxide ($CO_2$) and modifier, an autosampler, a column oven, a diode array detector equipped with a high-pressure flow cell standing up to 400 bars. If configured with a Mass Spectrometer (MS) the flow from the column was brought to the (MS). It is within the knowledge of the skilled person to set the tune parameters (e.g. scanning range, dwell time . . . ) in order to obtain ions allowing the identification of the compound's nominal monoisotopic molecular weight (MW). Data acquisition was performed with appropriate software.

Chiral HPLC-Methods

General Procedure for Chiral HPLC Methods

The Chiral HPLC measurement was performed using a Chiral High Performance Liquid Chromatography (Chiral HPLC) system composed by a LC pump, a diode-array (DAD) or a UV detector and a chiral column as specified in the respective methods. Data acquisition was performed with appropriate software.

Method Codes 15, 18, 39 and 57 in the Table below refer to Chiral-HPLC methods.

TABLE 2a

Analytical SFC Methods and Chiral-HPLC (method codes 15 and 18) (Flow expressed in mL/min; column temperature (T) in ° C; Run time in minutes, Backpressure (BPR) in bars (unless otherwise indicated). "ACN" means acetonitrile; "MeOH" means methanol; "EtOH" means ethanol; "DEA" means diethylamine. All other abbreviations used in the table below are as defined before)

| Method code | column | mobile phase | gradient | Flow Col T | Run time BPR |
|---|---|---|---|---|---|
| 1 | Agilent 1260 (OJ-3 100 × 4.6 mm) | A: SupercriticalCO$_2$ Mobile phase B: ethanol (0.05% DEA) | from 5% to 40% of B in 4.5 min and hold 40% for 2.5 min, then 5% of B for 1 min | 2.8 40 | 8 100 |
| 2 | Daicel Chiralpak ® AD-3 (3 μm, 100 × 4.6 mm) | A: CO$_2$ B: MeOH (+0.3% iPrNH$_2$) | 30% B hold 3 min, | 3.5 — 3.5 | 3 — 103 |
| 3 | UPC$^2$ ™ (Waters) AS, 3 um, 3 * 100 (Daicel) | CO$_2$/MeOH/DEA 75/25/0.025 | Hold 2 min | 1.8 35 | 2 100 |
| 4 | UPC$^2$ ™ (Waters) OJ, 3 um, 3 * 100 (Daicel) | CO$_2$/MeOH/DEA 70/30/0.03 | Hold 2.5 min | 1.8 35 | 2.5 100 |
| 5 | UPC$^2$ ™ (Waters) OJ, 3 um, 3 * 100 (Daicel) | CO$_2$/MeOH/DEA 75/25/0.025 | Hold 4.0 min | 1.8 35 | 4.0 100 |
| 6 | UPC$^2$ ™ (Waters) OJ, 3 um, 3 * 100 (Daicel) | CO$_2$/MeOH/DEA 70/30/0.03 | Hold 1.5 min | 1.8 35 | 1.5 100 |
| 7 | UPC$^2$ ™ (Waters) IE, 5 um, 4.6 * 250 (Daicel) | CO$_2$/EtOH/ACN/DEA 65/29.75/5.25/0.07 | Hold 15 min | 2.8 35 | 15 100 |
| 8 | UPC$^2$ ™ (Waters) IE, 5 um, 4.6 * 250 (Daicel) | CO$_2$/EtOH/ACN/DEA 60/34/6/0.8 | Hold 20 min | 2.8 35 | 20 100 |
| 9 | UPC$^2$ ™ (Waters) AD, 5 um, 4.6 * 250 (Daicel) | CO$_2$/EtOH/ACN/DEA 60/24/16/0.04 | Hold 5 min | 2.8 35 | 5 100 |
| 10 | UPC$^2$ ™ (Waters) AS, 3 um, 3 * 100 (Daicel) | CO$_2$/MeOH/DEA 70/30/0.03 | Hold 3 min | 1.8 35 | 3 100 |
| 11 | UPC$^2$ (Waters) OJ, 3 um, 3 * 100 | CO$_2$/MeOH/DEA 85/15/0.075 | Hold 4 min | 1.8 35 | 4 100 |
| 12 | UPC$^2$ (Waters) IE, 5 um, 4.6 * 250 | CO$_2$/MeOH/TFA 65/35/0.07 | Hold 15 min | 2.8 35 | 15 100 |
| 13 | UPC$^2$ (Waters) OJ, 3 um, 3 * 100 | CO$_2$/MeOH/DEA 80/20/0.02 | Hold 3 min | 1.8 35 | 3 100 |
| 14 | UPC$^2$ (Waters) OJ, 3 um, 3 * 100 | CO$_2$/MeOH/DEA 70/30/0.03 | Hold 3 min | 1.8 35 | 3 100 |
| 15 | Waters-80 AD-H, 0.46 cm I.D. × 15 cm L (Chiral-HPLC) | n-heptane:EtOH (0.1% DEA) = 60:40 | Hold 6-10 min | 0.5 25 | 6-10 100 |
| 16 | UPC$^2$ (Waters) IE, 5 um, 4.6 * 250) | CO$_2$/MeOH/DEA 60/40/0.04 | Hold 8-10 min | 2.8 35 | 8-10 100 |
| 17 | UPC$^2$ (Waters) AD, 5 um, 4.6 * 250 | CO$_2$/MeOH/DEA 60/40/0.04 | Hold 10-25 min | 3.0 35 | 10-25 100 |
| 18 | AD-H, 0.46 cm I.D. × 15 cm L (Chiral-HPLC) | n-heptane:EtOH (0.1% DEA) = 60:40 | Hold 10 min | 0.5 25 | 10 100 |
| 19 | UPC$^2$ (Waters) IA, 3 um, 3 * 100 | CO$_2$/MeOH/DEA 70/30/0.03 | Hold 10-15 min | 1.8 35 | 10-15 100 |
| 20 | UPC$^2$ (Waters) IA, 3 um, 3 * 100 | CO$_2$/EtOH/DEA 75/25/0.05 | Hold 11 min | 1.0 35 | 11 100 |
| 21 | UPC$^2$ (Waters) AD, 5 um, 4.6 * 250 | CO$_2$/MeOH 60/40 | Hold 11-15 min | 2.8 35 | 11-15 100 |
| 22 | UPC$^2$ (Waters) IA, 3 um, 3 * 100 | CO$_2$/MeOH/DEA 70/30/0.06 | Hold 15 min | 1.8 35 | 15 100 |
| 23 | Agilent 6110 (AD-3 | A: Supercritical CO$_2$, Mobile phase B: ethanol | A: CO$_2$ B: EtOH (0.05% | 4 40 | 8 100 |

TABLE 2a-continued

Analytical SFC Methods and Chiral-HPLC (method codes 15 and 18) (Flow expressed in mL/min; column temperature (T) in ° C; Run time in minutes, Backpressure (BPR) in bars (unless otherwise indicated). "ACN" means acetonitrile; "MeOH" means methanol; "EtOH" means ethanol; "DEA" means diethylamine. All other abbreviations used in the table below are as defined before)

| Method code | column | mobile phase | gradient | Flow Col T | Run time BPR |
|---|---|---|---|---|---|
|  | 50 × 4.6 mm) | (0.05% DEA) | DEA)) were hold 40% |  |  |
| 24 | Agilent 6110 (AS-H 150 * 4.6 mm) | A: Supercritical $CO_2$ Mobile phase B: ethanol (0.05% DEA) | hold 5% for 0.5 min, then from 5% to 40% of B in 3.5 min and hold 40% for 2.5 min, then 5% of B for 1.5 min | 3 40 | 8 100 |
| 25 | Agilent 6110 (AD-3 50 × 4.6 mm) | A: Supercritical $CO_2$, Mobile phase B: ethanol (0.05% DEA) | A: $CO_2$ B: EtOH (0.05% DEA)) were hold 40% | 4 40 | 3 100 |
| 26 | Agilent 6110 (AS-H 150 * 4.6 mm) | A: Supercritical $CO_2$, B: MeOH (0.05% DEA) | 40% of methanol (0.05% DEA) in $CO_2$ | 3 40 | 8 100 |
| 27 | Agilent 1260 (Lux Cellulose-2 150 × 4.6 mm) | A: Supercritical $CO_2$, B: ethanol (0.1% Ethanolamine) | 40% of Ethanol (0.1% Ethanolamine) in $CO_2$ | 2.5 40 | 15 100 |
| 28 | Agilent 6110 (OJ-H 150 * 4.6 mm) | A: Supercritical $CO_2$, B: ethanol (0.05% DEA) | hold 5% for 0.5 min, then from 5% to 40% of B in 3.5 min and hold 40% for 2.5 min, then 5% of B for 1.5 min | 3 40 | 8 100 |
| 29 | $UPC^2$ (Waters) AD, 5 um, 4.6 * 250 | $CO_2$/MeOH/DEA 70/30/0.03 | Hold 8 min | 2.8 35 | 8 100 |
| 30 | $UPC^2$ (Waters) AD, 5 um, 4.6 * 250 | $CO_2$/EtOH/ACN/DEA 60/34/6/0.08 | Hold 5-20 min | 2.8 35 | 5-20 100 |
| 31 | $UPC^2$ (Waters) AD, 5 um, 4.6 * 250 | $CO_2$/IPA/ACN/DEA 60/32/8/0.08 | Hold 20 min | 2.8 35 | 20 100 |
| 32 | $UPC^2$ (Waters) OJ, 3 um, 3 * 100 | $CO_2$/MeOH/DEA 80/20/0.02 | Hold 5-10 min | 1.0 35 | 5-10 100 |
| 33 | $UPC^2$ (Waters) OJ, 3 um, 3 * 100 | $CO_2$/MeOH/DEA 70/30/0.03 | Hold 2-12 min | 1.8 35 | 2-12 100 |
| 34 | $UPC^2$ (Waters) IA, 3 um, 3 * 100 | $CO_2$/EtOH/IPA 70/11.5/18.5 | Hold 15 min | 1.8 35 | 15 100 |
| 35 | $UPC^2$ (Waters) IC, 3 um, 3 * 100 | $CO_2$/EtOH/CAN/DEA 60/34/6/0.08 | Hold 10 min | 1.8 35 | 10 100 |
| 36 | $UPC^2$ (Waters) IC, 3 um, 3 * 100 | $CO_2$/MeOH/DEA 70/30/0.03 | Hold 5.5-7 min | 1.8 35 | 5.5-7 100 |
| 37 | $UPC^2$ (Waters) OD, 5 um, 4.6 * 250 | $CO_2$/MeOH/DEA 60/40/0.04 | Hold 8 min | 2.8 35 | 8 100 |
| 38 | $UPC^2$ (Waters) AS, 3 um, 3 * 100 | $CO_2$/MeOH/DEA 80/20/0.02 | Hold 15 min | 1.8 35 | 15 100 |
| 39 | Waters-80 AD-H, 0.46 cm I.D. × 15 cm L (Chiral-HPLC) | n-heptane:IPA (0.1% DEA) = 60:40 | Hold 10-15 min | 0.5 25 | 10-15 100 |
| 40 | $UPC^2$ (Waters) OJ, 3 um, 3 * 100 | $CO_2$/MeOH 80/20 | Hold 4.0 min | 1.8 35 | 4.0 100 |
| 41 | $UPC^2$ (Waters) OD, 5 um, 4.6 * 250 | $CO_2$/MeOH/DEA 60/40/0.04 | Hold 20 min | 2.0 35 | 20 100 |
| 42 | $UPC^2$ (Waters) AD, 5 um, 4.6 * 250 | $CO_2$/EtOH/ACN/DEA 60/34/6/0.08 | Hold 25 min | 2.0 35 | 25 100 |
| 43 | $UPC^2$ (Waters) AD, 5 um, 4 6 * 250 | $CO_2$/MeOH/DEA 60/40/0.04 | Hold 8-10 min | 2.8 35 | 8-10 100 |
| 44 | $UPC^2$ (Waters) OD, 5 um, 4.6 * 250 | $CO_2$/MeOH 60/40 | Hold 8 min | 2.8 35 | 8 100 |
| 45 | $UPC^2$ (Waters) OJ, 3 um, 3 * 100 | $CO_2$/MeOH/DEA 75/25/0.025 | Hold 5 min | 1.8 35 | 5 100 |
| 46 | $UPC^2$ (Waters) OJ, 3 um, 3 * 100 | $CO_2$/MeOH 70/30 | Hold 1.5-8 min | 1.8 35 | 1.5-8 100 |
| 47 | $UPC^2$ (Waters) IA, 3 um, 3 * 100 | $CO_2$/EtOH/ACN/DEA 75/21/4/0.05 | Hold 11 min. | 1.8 35 | 11 100 |
| 48 | $UPC^2$ (Waters) AD, 5 um, 4.6 * 250 | $CO_2$/EtOH/ACN/DEA 70/25.5/4.5/0.06 | Hold 15 min | 2.8 35 | 15 100 |
| 49 | $UPC^2$ (Waters) OD, 5 um, 4.6 * 250 | $CO_2$/MeOH 70/30 | Hold 11 min. | 2.8 35 | 11 100 |
| 50 | $UPC^2$ (Waters) OJ, 3 um, 3 * 100 | $CO_2$/EtOH/ACN/DEA 85/12.75/2.25/0.03 | Hold 8 min. | 1.8 35 | 8 100 |

TABLE 2a-continued

Analytical SFC Methods and Chiral-HPLC (method codes 15 and 18) (Flow expressed in mL/min; column temperature (T) in ° C; Run time in minutes, Backpressure (BPR) in bars (unless otherwise indicated). "ACN" means acetonitrile; "MeOH" means methanol; "EtOH" means ethanol; "DEA" means diethylamine. All other abbreviations used in the table below are as defined before)

| Method code | column | mobile phase | gradient | Flow Col T | Run time BPR |
|---|---|---|---|---|---|
| 51 | UPC² (Waters) IA, 3 um, 3 * 100 | CO₂/MeOH/DEA 70/30/0.03 | Hold 10 min. | 1.0 35 | 10 100 |
| 52 | UPC² (Waters) IA, 3 um, 3 * 100 | CO₂/EtOH/DEA 75/25/0.025 | Hold 8 min. | 1.8 35 | 8 100 |
| 53 | UPC² (Waters) AD, 5 um, 4.6 * 250 | CO₂/MeOH/CAN/DEA 60/24/16/0.04 | Hold 12 min. | 2.8 35 | 12 100 |
| 54 | UPC² (Waters) AS, 5 um, 3 * 100 | CO₂/MeOH 80/20 | Hold 6 min. | 1.8 35 | 6 100 |
| 55 | UPC² (Waters) OD, 5 um, 4.6 * 250 | CO₂/EtOH/CAN/DEA 60/34/6/0.08 | Hold 7 min. | 2.8 35 | 7 100 |
| 56 | UPC² (Waters) OJ, 3 um, 3 * 100 | CO₂/MeOH/DEA 85/15/0.015 | Hold 15 min | 1.8 35 | 1.5 100 |
| 57 | Waters-80 OJ-H, 0 46 cm I.D × 15 cm L (Chiral-HPLC) | n-heptane:EtOH (01.% DEA) = 60:40 | Hold 10 min | 0.5 25 | 10 100 |
| 58 | Agilent 1260 (Chiralpak AS-3 100 × 4.6 mm I.D., 3 um) | A: Supercritical CO₂, Mobile phase B: iso-propanol (0.05% DEA) | from 5% to 40% of B in 4.5 min and hold 40% for 2.5 min, then 5% of B for 1 min | 2.8 40 | 8 100 |
| 59 | Agilent 1260 (Chiralcel OD-3 100 × 4.6 mm I.D., 3 um) | A: Supercritical CO₂, Mobile phase B: ethanol (0.05% DEA) | from 5% to 40% of B in 4.5 min and hold 40% for 2.5 min, then 5% of B for 1 min | 2.8 40 | 8 100 |
| 60 | Agilent 1260 (Chiralcel OD-3 100 × 4.6 mm I.D., 3 um) | A: Supercritical CO₂, Mobile phase B: ethanol (0.05% DEA) | 40% of Ethanol (0.05% DEA) in CO₂ | 2.8 35 | 8 100 |
| 61 | Chiralcel OD-3 100 × 4.6 mm I.D., 3 um (Waters) | A: Supercritical CO₂, Mobile phase B: methanol (0.05% DEA) | from 5% to 40% of B in 5 min and hold 40% for 2.5 min, then 5% of B for 2.5 min | 2.5 35 | 10 1500 (PSI) |
| 62 | Chiralpak AD-3 50 * 4.6 mm I.D., 3 um (Berger) | A: Supercritical CO₂, Mobile phase B: iso-propanol (0.05% DEA) | 40% of isopropanol (0.05% DEA) in CO₂ | 2.8 35 | 8 100 |
| 63 | Agilent 1260 (Chiralcel OJ-3 100 × 4.6 mm I.D., 3 um) | A: Supercritical CO₂, B: ethanol (0.05% DEA) | 40% of ethanol (0.05% DEA) in CO₂ | 2.8 40 | 8 100 |
| 64 | Chiralcel OJ-3 150 × 4.6 mm I.D., 3 um (Waters) | A: Supercritical CO₂, B: ethanol (0.05% DEA) | 40% of ethanol (0.05% DEA) in CO₂ | 2.5 35 | 10 1500 (PSI) |
| 65 | Agilent 1260 (Chiralcel AD-3 50 * 3 mm I.D., 3 um) | A: Supercritical CO₂, B: ethanol (0.05% DEA) | 40% of ethanol (0.05% DEA) in CO₂ | 2 40 | 3 100 |
| 66 | Chiralpak AS-H 150 * 4.6 mm I.D., 5 um (Berger) | A: Supercritical CO₂, B: methanol (0.05% DEA) | hold 5% for 0.5 min, then from 5% to 40% of B in 3.5 min and hold 40% for 2.55 min, then 5% of B for 1.5 min | 3.0 40 | 8 100 |
| 67 | Chiralcel OJ-H 150 * 4.6 mm I.D., 5 um (Berger) | A: Supercritical CO₂, B: methanol (0.05% DEA) | 40% of methanol (0.05% DEA) in CO2 | 3.0 40 | 8 100 |
| 68 | Agilent 1260 (Chiralcel OJ-H 150 * 4.6 mm I.D., 5 um) | A: Supercritical CO₂, B: methanol (0.05% DEA) | from 5% to 40% of B in 5.5 min and hold 40% for 3 min, then 5% of B for 1.5 min | 2.5 40 | 10 100 |

TABLE 2a-continued

Analytical SFC Methods and Chiral-HPLC (method codes 15 and 18) (Flow expressed in mL/min; column temperature (T) in ° C; Run time in minutes, Backpressure (BPR) in bars (unless otherwise indicated). "ACN" means acetonitrile; "MeOH" means methanol; "EtOH" means ethanol; "DEA" means diethylamine. All other abbreviations used in the table below are as defined before)

| Method code | column | mobile phase | gradient | Flow Col T | Run time BPR |
|---|---|---|---|---|---|
| 69 | Chiralcel AD-3 150 * 4.6 mm I.D., 3 um (Waters) | A: Supercritical CO$_2$, B: iso-propanol (0.05% DEA) | 40% fo iso-propanol (0.05% DEA) in CO$_2$ | 2.5 35 | 10 1500 (PSI) |
| 70 | Chiralcel AD-3 50 * 4.6 mm I.D., 3 um (Berger) | A: Supercritical CO$_2$, B: ethanol (0.05% DEA) | hold 5% for 0.2 min, then from 5% to 40% of B in 1.4 min and hold 40% for 1.05 min, then 5% of B for 0.35 min | 4 40 | 3 100 |
| 72 | Agilent 1260 (Chiralcel AD-3 50 * 3 mm I.D., 3 um) | A: Supercritical CO$_2$, B: ethanol (0.05% DEA) | from 5% to 40% of B in 2.5 min and hold 40% for 0.35 min, then from 40% to 5% of B for 0.15 min | 2.5 40 | 3 100 |
| 73 | Chiralcel OD-3 50 * 4.6 mm I.D., 3 um (Berger) | A: Supercritical CO$_2$, B: ethanol (0.05% DEA) | hold 5% for 0.2 min, then from 5% to 40% of B in 1.4 min and hold 40% for 1.05 min, then 5% of B for 0.35 min | 4.0 40 | 4 100 |
| 74 | Chiralpak AD-3 50 * 3 mm I.D., 3 um (Berger) | A: Supercritical CO$_2$, B: methanol (0.05% DEA) | 40% of methanol (0.05% DEA) in CO2 | 2.2 40 | 5 100 |
| 75 | Chiralpak AD-3 50 * 4.6 mm I.D., 3 um (Berger) | A: Supercritical CO$_2$, B: methanol (0.05% DEA) | 40% of methanol (0.05% DEA) in CO2 | 4.0 40 | 5 100 |
| 76 | Chiralpak AS-H 150 * 4.6 mm I.D., 5 um (Berger) | A: Supercritical CO2 Mobile phase B: methanol (0.05% DEA) | 40% of ethanol (0.05% DEA) in CO$_2$ | 3 40 | 8 100 |
| 77 | Agilent 1260 (Chiralcel AD-3 100 × 4.6 mm I.D., 3 um) | A: Supercritical CO$_2$, B: ethanol (0.05% DEA) | 40% of ethanol (0.05% DEA) in CO$_2$ | 2.8 40 2.8 | 8 100 10 |
| 78 | Agilent 1260 (Chiralpak AD-3 100 × 4.6 mm I.D., 3 um) | A: Supercritical CO$_2$, B: iso-propanol (0.05% DEA) | 40% of iso-propanol (0.05% DEA) in CO$_2$ | 40 | 100 |
| 79 | Chiralcel AD-3 50 × 4.6 mm I.D., 3 um (Berger) | A: Supercritical CO$_2$, B: iso-propanol (0.05% DEA) | 40% of iso-propanol (0.05% DEA) in CO$_2$ | 4 40 | 8 100 |
| 80 | Chiralcel OD-3 150 × 4.6 mm I.D., 3 um (Waters) | A: Supercritical CO$_2$, B: ethanol (0.05% DEA) | 40% of ethanol (0.05% DEA) in CO$_2$ | 2.5 35 | 13 150 (PSI) |
| 81 | Agilent 1260 (Chiralcel OD-3 150 × 4.6 mm I.D., 5 um) | A: Supercritical CO$_2$, B: Methanol (0.05% DEA) | 40% of Methanol (0.05% DEA) in CO$_2$ | 2.5 40 | 10 100 |
| 82 | Chiralcel OJ-H 150 * 4.6 mm I.D., 5 um (Berger) | A: Supercritical CO$_2$, B: methanol (0.05% DEA) | hold 5% for 0.5 min, then from from 5% to 40% of B in 3.5 min and hold for 40% for 2.5 min, then 5% of B for 1.5 min | 3 40 | 8 100 |
| 83 | Chiralcel AD-3 50 * 3 mm I.D., 3 um (Berger) | A: Supercritical CO$_2$, B: iso-propanol (0.05% DEA) | hold 5% for 0.2 min, then from 5% to 40% of B in 5 min and hold for 40% for 2.5 min, then 5% of B for 2.5 min | 2.2 40 | 5 100 |
| 84 | Chiralcel AS-3 150 × 4.6 mm I.D., | A: Supercritical CO$_2$, B: ethanol (0.05% | from 5% to 40% of B in 5 min and | 2.5 35 | 10 1500 |

TABLE 2a-continued

Analytical SFC Methods and Chiral-HPLC (method codes 15 and 18) (Flow expressed in mL/min; column temperature (T) in ° C; Run time in minutes, Backpressure (BPR) in bars (unless otherwise indicated). "ACN" means acetonitrile; "MeOH" means methanol; "EtOH" means ethanol; "DEA" means diethylamine. All other abbreviations used in the table below are as defined before)

| Method code | column | mobile phase | gradient | Flow Col T | Run time BPR (PSI) |
|---|---|---|---|---|---|
| | 3 um (Waters) | DEA) | hold for 40% for 2.5 min, then 5% of B for 2.5 min | | |

TABLE 2b

SFC data (Isomer elution order 'A' elutes before 'B', 'B', 'C' elutes before 'D', elutes before 'C' under the described conditions)

| Co. No. | $R_t$ (min) | UV % Area | Isomer elution order | SFC Method |
|---|---|---|---|---|
| 3 | 9.33 | 100 | A | 8 |
| 4 | 11.63 | 99.12 | B | 8 |
| 5 | 1.98 | 99.32 | A | 9 |
| 6 | 2.76 | 99.82 | B | 9 |
| 11 | 0.80 | 100 | A | 10 |
| 12 | 1.53 | 100 | B | 10 |
| 31 | 5.63 | 100 | A | 7 |
| 32 | 6.28 | 98.66 | B | 7 |
| 33 | 6.66 | 98.84 | C | 7 |
| 34 | 8.17 | 100 | D | 7 |
| 36 | 0.55 | 100 | A | 6 |
| 37 | 0.77 | 100 | B | 6 |
| 23 | 0.77 | 100 | A | 5 |
| 24 | 2.17 | 99.85 | B | 5 |
| 28 | 0.72 | 100 | A | 4 |
| 29 | 1.15 | 99.65 | B | 4 |
| 25 | 0.88 | 99.04 | A | 3 |
| 26 | 1.04 | 99.34 | B | 3 |
| 42 | 2.822, | 25.552, | A | |
| | 2.919, | 24.332, | B | |
| | 3.094, | 26.343, | C | |
| | 3.242 | 23.773 | D | |
| 43 | 3.162, | 50.743, | A | 1 |
| | 3.415 | 49.257 | B | |
| 44 | 5.390, | 41.299, | A | 1 |
| | 5.727 | 58.701 | B | |
| 46 | 1.02 | 100 | A | 2 |
| 47 | 1.47 | 99.5 | B | 2 |
| 57 | 6.248 | 100 | A | 12 |
| 58 | 6.683 | 98.67 | B | 12 |
| 55 | 1.836 | 100 | A | 11 |
| 93 | 3.99, | 27.8, | A | 24 |
| | 4.15 | 72.2 | B | |
| 98 | 1.35 | 99.72 | B | 25 |
| 59 | 1.107 | 98.39 | A | 13 |
| 61 | 1.083 | 100 | A | 13 |
| 92 | 2.94, | 53.5, | A | 23 |
| | 3.56 | 46.5 | B | |
| 94 | 3.94 | 98.36 | A | 24 |
| 95 | 4.17 | 97.98 | B | 24 |
| 64 | 1.674 | 99.86 | A | 14 |
| 67 | 3.663 | 99.12 | B | 15 |
| 69 | 4.575 | 99.64 | B | 18 |
| 90 | 3.46 | 100 | A | 23 |
| 72 | 11.114 | 100 | B | 17 |
| 75 | 7.810 | 98.33 | B | 18 |
| 84 | 8.615 | 96.67 | B | 71 |
| 85 | 6.595 | 99.68 | A | 18 |
| 88 | 8.075 | 99.65 | B | 22 |
| 77 | 4.291 | 98.59 | B | 19 |
| 102 | 3.471 | 99.49 | A | 29 |
| 103 | 4.682 | 97.03 | B | 29 |
| 56 | 2.175 | 98.48 | B | 11 |
| 60 | 1.377 | 99.72 | B | 13 |
| 62 | 1.559 | 99.80 | B | 13 |
| 65 | 2.400 | 99.07 | B | 14 |
| 66 | 3.314 | 100 | A | 15 |
| 68 | 3.478 | 99.29 | A | 18 |
| 71 | 5.693 | 100 | A | 17 |
| 74 | 7.556 | 98.53 | A | 18 |
| 76 | 3.173 | 100 | A | 19 |
| 79 | 4.203 | 100 | A | 20 |
| 80 | 5.104 | 97.26 | B | 20 |
| 83 | 7.005 | 100 | A | 21 |
| 86 | 7.455 | 99.79 | B | 18 |
| 87 | 6.794 | 100 | A | 22 |
| 89 | 3.14, | 40.92 | A | 23 |
| | 5.70 | 59.08 | B | |
| 91 | 5.23 | 100 | B | 23 |
| 96 | 0.84, | 50.85, | A | 25 |
| | 1.34 | 49.15 | B | |
| 97 | 0.82 | 99.83 | A | 25 |
| 107 | 4.798, | 46, | A | 28 |
| | 4.896 | 54 | B | |
| 53 | 1.11, | 46.6, | A | 25 |
| | 1.42 | 52.1 | B | |
| 106 | 7.721, | 66.6, | A | 27 |
| | 10.212 | 33.4 | B | |
| 104 | 1.853 | 100 | A | 26 |
| 105 | 2.359 | 100 | B | 26 |
| 108 | 6.469 | 99.89 | A | 30 |
| 109 | 7.859 | 96.44 | B | 30 |
| 110 | 5.264 | 98.26 | A | 31 |
| 111 | 6.240 | 95.64 | B | 31 |
| 149 | 6.921 | 100 | A | 57 |
| 150 | 7.655 | 99.30 | B | 57 |
| 144 | 3.542 | 100 | A | 34 |
| 145 | 3.977 | 96.10 | B | 34 |
| 146 | 5.179 | 100 | C | 34 |
| 147 | 5.690 | 98.79 | D | 34 |
| 134 | 4.760 | 100 | A | 30 |
| 135 | 5.623 | 98.61 | B | 30 |
| 136 | 7.065 | 98.84 | C | 30 |
| 137 | 8.348 | 98.45 | D | 30 |
| 139 | 3.765 | 99.70 | A | 33 |
| 140 | 4.825 | 98.19 | B | 33 |
| 141 | 5.625 | 99.40 | C | 33 |
| 142 | 7.385 | 99.73 | D | 33 |
| 261 | 1.733 | 97.89 | A | 30 |
| 262 | 2.617 | 99.36 | B | 30 |
| 264 | 4.191 | 100 | A | 16 |
| 265 | 5.244 | 99.86 | B | 16 |
| 266 | 2.571 | 99.95 | A | 36 |
| 267 | 2.952 | 99.73 | B | 36 |
| 268 | 2.757 | 99.73 | A | 55 |
| 269 | 3.648 | 96.96 | B | 55 |
| 118 | 7.379 | 98.51 | B | 30 |
| 115 | 1.419 | 99.70 | A | 32 |
| 116 | 2.384 | 99.94 | B | 32 |
| 121 | 2.867 | 99.08 | A | 32 |

TABLE 2b-continued

SFC data (Isomer elution order 'A' elutes before 'B', 'B', 'C' elutes before 'D', elutes before 'C' under the described conditions)

| Co. No. | $R_t$ (min) | UV % Area | Isomer elution order | SFC Method |
|---|---|---|---|---|
| 122 | 3.415 | 96.47 | B | 32 |
| 112 | 0.601 | 99.71 | A | 33 |
| 113 | 0.787 | 99.29 | B | 33 |
| 152 | 3.387 | 100 | A | 17 |
| 153 | 4.842 | 98.33 | B | 17 |
| 154 | 2.815 | 100 | A | 35 |
| 155 | 3.293 | 98.96 | B | 35 |
| 199 | 2.79 | 100 | A | 19 |
| 200 | 4.98 | 99.76 | B | 19 |
| 169 | 3.003 | 100 | A | 36 |
| 170 | 3.474 | 99.69 | B | 36 |
| 171 | 3.261 | 99.84 | A | 37 |
| 172 | 3.732 | 99.23 | B | 37 |
| 208 | 3.513 | 98.97 | A | 37 |
| 209 | 4.275 | 99.83 | B | 37 |
| 210 | 2.944 | 99.80 | A | 19 |
| 211 | 4.658 | 99.44 | B | 19 |
| 201 | 3.417 | 99.87 | A | 43 |
| 202 | 4.214 | 99.40 | B | 43 |
| 237 | 4.892 | 100 | A | 49 |
| 238 | 5.899 | 99.01 | B | 49 |
| 212 | 3.501 | 100 | A | 44 |
| 213 | 4.773 | 100 | B | 44 |
| 204 | 4.597 | 100 | A | 43 |
| 205 | 5.811 | 99.07 | B | 43 |
| 178 | 6.607 | 99.46 | A | 38 |
| 179 | 8.395 | 100 | B | 38 |
| 174 | 3.537 | 99.97 | A | 17 |
| 175 | 5.199 | 99.60 | B | 17 |
| 217 | 1.727 | 99.36 | A | 45 |
| 218 | 2.498 | 99.10 | B | 45 |
| 181 | 7.081 | 100 | A | 39 |
| 182 | 7.760 | 98.07 | B | 39 |
| 183 | 1.924 | 100 | A | 40 |
| 184 | 2.295 | 99.16 | B | 40 |
| 185 | 10.839 | 100 | A | 39 |
| 186 | 11.959 | 94.320 | B | 39 |
| 187 | 6.012 | 99.76 | A | 30 |
| 188 | 8.103 | 95.63 | B | 30 |
| 242 | 3.130 | 99.88 | A | 50 |
| 243 | 4.024 | 99.28 | B | 50 |
| 253 | 4.641 | 99.91 | A | 53 |
| 254 | 6.242 | 99.86 | B | 53 |
| 244 | 3.429 | 100 | A | 51 |
| 245 | 5.255 | 99.67 | B | 51 |
| 226 | 4.362 | 100 | A | 32 |
| 227 | 5.019 | 97.65 | B | 32 |
| 228 | 0.598 | 100 | A | 46 |
| 229 | 0.766 | 99.81 | B | 46 |
| 258 | 2.654 | 100 | A | 54 |
| 259 | 3.371 | 99.88 | B | 54 |
| 219 | 3.036 | 100 | A | 46 |
| 220 | 4.224 | 99.67 | B | 46 |
| 230 | 4.434 | 100 | A | 47 |
| 231 | 6.177 | 97.36 | B | 47 |
| 232 | 3.837 | 100 | A | 48 |
| 233 | 5.249 | 99.20 | B | 48 |
| 234 | 5.509 | 99.58 | A | 21 |
| 235 | 7.371 | 97.81 | B | 21 |
| 189 | 8.953 | 99.61 | A | 41 |
| 190 | 11.113 | 99.95 | B | 41 |
| 272 | 5.547 | 100 | A | 15 |
| 273 | 5.793 | 99.76 | B | 15 |
| 274 | 6.637 | 100 | A | 56 |
| 275 | 8.484 | 99.37 | B | 56 |
| 246 | 3.422 | 100 | A | 52 |
| 247 | 4.787 | 98.9 | B | 52 |
| 194 | 12.274 | 100 | A | 42 |
| 195 | 14.956 | 100 | B | 42 |
| 276 | 3.221/3.754 | 48.970/51.030 | | 28 |
| 280 | 3.252 | 100 | A | 28 |
| 318 | 6.664 | 97.78 | B | 61 |
| 319 | 2.277/4649 | 56.013/43.987 | | 62 |
| 320 | 1.128 | 100 | A | 62 |
| 321 | 1.367 | 100 | B | 62 |
| 377 | 0.895/1.285 | 44.210/55.790 | | 62 |
| 323 | 0.790 | 99.852 | A | 62 |
| 324 | 1.173 | 99.784 | B | 62 |
| 326 | 3.381/5.607 | 41.275/58.725 | | 63 |
| 327 | 3.337 | 99.212 | A | 63 |
| 328 | 5.491 | 99.394 | B | 63 |
| 330 | 5.380/6.004 | 48.27/51.73 | | 84 |
| 331 | 5.372 | 100 | A | 84 |
| 332 | 5.993 | 99.69 | B | 84 |
| 333 | 1.015/1.160 | 50.438/49.562 | | 78 |
| 334 | 3.485 | 99.878 | A | 78 |
| 335 | 4.035 | 99.229 | B | 78 |
| 336 | 0.960/1.221 | 51.715/48.285 | | 74 |
| 337 | 1.229 | 99.590 | A | 75 |
| 338 | 1.638 | 99.344 | B | 75 |
| 346 | 4.890/5.900 | 46.865/53.135 | | 66 |
| 348 | 1.113/1.411 | 46.324/53.676 | | 23 |
| 376 | 2.554/3.151 | 51.092/48.908 | | 67 |
| 352 | 4.594 | 99.76 | A | 69 |
| 353 | 5.763 | 98.70 | B | 69 |
| 405 | 3.892 | 100 | A | 78 |
| 406 | 5.376 | 100 | B | 78 |
| 407 | 6.550 | 99.96 | A | 69 |
| 408 | 7.309 | 99.56 | B | 69 |
| 409 | 3.650 | 99.606 | A | 68 |
| 410 | 4.258 | 98.304 | B | 68 |
| 354 | 2.831/3.331/ 4.336/4.753 | 26.914/27.394/ 22.512/23.180 | | 23 |
| 418 | 3.907 | 99.785 | A | 28 |
| 419 | 4.080 | 99.961 | B | 28 |
| 411 | 1.368 | 98.482 | A | 79 |
| 412 | 1.826 | 100.000 | B | 79 |
| 355 | 4.166 | 99.803 | A | 68 |
| 356 | 4.496 | 98.409 | B | 68 |
| 357 | 2.142 | 99.050 | A | 65 |
| 358 | 3.466 | 95.550 | B | 65 |
| 359 | 8.043 | 100.000 | A | 69 (T:40) |
| 360 | 10.023 | 100.000 | B | 69 (T:40) |
| 413 | 5.531 | 99.672 | A | 79 |
| 414 | 6.605 | 99.188 | B | 79 |
| 420 | 0.627 | 100.000 | A | 25 |
| 421 | 1.677 | 100.000 | B | 25 |
| 361 | 1.510 | 97.130 | A | 23 |
| 362 | 2.389 | 100.000 | B | 23 |
| 363 | 6.045 | 99.210 | A | 82 |
| 364 | 5.486 | 99.686 | A | 82 |
| 422 | 4.868/5.181 | 46.895/53.105 | 59 | |
| 367 | 2.762 | 99.462 | A | 81 |
| 368 | 3.428 | 99.559 | B | 81 |
| 369 | 3.420 | 100 | A | 64 |
| 370 | 4.913 | 99.86 | B | 64 |
| 371 | 5.477 | 99.748 | A | 27(Run Time = 10 min) |
| 372 | 7.378 | 99.439 | B | 27(Run Time = 10 min) |
| 374 | 5.022 | 100.00 | A | 80 |
| 375 | 11.103 | 99.44 | B | 80 |
| 403 | 1.729/1.863 | 49.731/50.269 | | 70 |
| 404 | 2.206/2.328 | 50.272/49.728 | | 72 |
| 400 | 0.855/1.316 | 50.160/49.840 | | 65 |
| 401 | 1.085/2.094 | 49.775/47.918 | | 23 |
| 402 | 3.773/7.262 | 49.978/50.022 | | 76 |
| 387 | 0.873/1.177 | 49.647/50.353 | | 23 |
| 388 | 0.905 | 99.701 | A | 23 |
| 389 | 1.224 | 99.758 | B | 23 |
| 390 | 2.763/3.664 | 53.250/46.750 | | 77 |
| 391 | 2.918 | 100.000 | A | 77 |
| 392 | 3.888 | 99.413 | B | 77 |
| 393 | 4.241/5.918 | 39.155/60.845 | | 76 |

TABLE 2b-continued

SFC data (Isomer elution order 'A' elutes before 'B', 'B', 'C' elutes before 'D', elutes before 'C' under the described conditions)

| Co. No. | $R_t$ (min) | UV % Area | Isomer elution order | SFC Method |
|---|---|---|---|---|
| 394 | 3.658 | 100.000 | A | 76 |
| 395 | 4.916 | 99.790 | B | 76 |
| 399 | 1.199/1.428 | 71.421/28.579 | | 79 |
| 396 | 1.193/1.615 | 45.457/54.543 | | 25 |
| 397 | 1.084 | 100.000 | A | 25 |
| 398 | 1.446 | 99.588 | B | 25 |
| 377 | 2.054/2.462 | 50.454/49.546 | | 73 |
| 378 | 2.050 | 100.000 | A | 73 |
| 379 | 2.358 | 99.916 | B | 73 |
| 381 | 2.790/3.929 | 46.658/53.342 | | 23 |
| 382 | 3.339 | 100.000 | A | 23 |
| 383 | 4.800 | 100.000 | B | 23 |
| 384 | 1.636/3.040 | 42.075/57.925 | | 79 (Run Time = 5 min) |
| 385 | 2.35 | 100 | A | 83 |
| 386 | 2.92 | 100 | B | 83 |

Optical Rotation (OR)

Optical Rotation is measured with a polarimeter 341 Perkin Elmer. The polarized light is passed through a sample with a path length of 1 decimeter and a sample concentration of 0.2 to 0.4 gram per 100 milliliters. 2 to 4 mg of the product in vial are weight, then dissolved with 1 to 1.2 ml of spectroscopy solvent (DMF for example). The cell is filled with the solution and put into the polarimeter at a temperature of 20° C. The OR is read with 0.004° of precision.

Calculation of the concentration: weight in gram×100/volume in ml $[\alpha]_d^{20}$: (read rotation×100)/(1.000 dm×concentration).

$^d$ is sodium D line (589 nanometer).

TABLE

OR data: temperature: 20° C.; 'cone' means concentration (g/100 mL); 'OR' means optical rotation; "DMF" means N,N-dimethylformamide

| Co. No. | OR (°) | Conc. | Wavelength (nm) | Solvent |
|---|---|---|---|---|
| 46 | −7.64 | 0.275 | 589 | DMF |

NMR-Methods

For some compounds, NMR experiments were carried out using a Bruker Avance 500 spectrometer equipped with a Bruker 5 mm BBFO probe head with z gradients and operating at 500 MHz for the proton and 125 MHz for carbon, or using a Bruker Avance DRX 400 spectrometer using internal deuterium lock and equipped with reverse double-resonance ($^1$H, $^{13}$C, SEI) probe head with z gradients and operating at 400 MHz for the proton and 100 MHz for carbon. Chemical shifts (δ) are reported in parts per million (ppm). J values are expressed in Hz.

Alternatively, some NMR experiments were carried out using a Bruker Avance III 400 spectrometer at ambient temperature (298.6 K), using internal deuterium lock and equipped with 5 mm PABBO BB-probe head with z gradients and operating at 400 MHz for the proton and 100 MHz for carbon. Chemical shifts (δ) are reported in parts per million (ppm). J values are expressed in Hz.

Pharmacological Part

1) Menin/MLL Fluorescence Polarization Assay

To a non-surface binding, black 384-well microtiter plate was added 50 nL 160× test compound in DMSO and 4 µL 2× menin in assay buffer (40 mM Tris HCl, pH 7.5, 50 mM NaCl, 1 mM DTT (dithiothreitol) and 0.001% Tween 20). After incubation of test compound and menin for 10 min at ambient temperature, 4 µL 2× FITC-MBM1 peptide (FITC-β alanine-SARWRFPARPGT-NH$_2$ (SEQ ID NO: 2)) in assay buffer was added, the microtiter plate centrifuged at 1000 rpm for 1 min and the assay mixtures incubated for 15 min at ambient temperature. The relative amount of menin-.FITC-MBM1 complex present in an assay mixture is determined by measuring the fluorescence polarization (FP) of the FITC label with a BMG Pherastar plate reader (ex. 485 nm/em. 520 nm) at ambient temperature. The final concentrations of reagents in the binding assay are 100 nM menin, 5 nM FITC-MBM1 peptide and 0.625% DMSO in assay buffer. Dose-response titrations of test compounds are conducted using an 11 point, three-fold serial dilution scheme, starting at 31 µM.

Compound potencies were determined by first calculating % inhibition at each compound concentration according to equation 1:

% inhibition=((HC−LC)−(FP$^{compound}$−LC))/(HC−LC))*100     (Eqn 1)

Where LC and HC are the FP values of the assay in the presence or absence of a saturating concentration of a compound that competes with FITC-MBM1 for binding to menin, and FP$^{compound}$ is the measured FP value in the presence of the test compound. HC and LC FP values represent an average of at least 16 replicates per plate. For each test compound, % inhibition values were plotted vs. the logarithm of the test compound concentration, and the IC$_{50}$ value derived from fitting these data to equation 2:

% inhibition=Bottom+(Top−Bottom)/(1+10^((log IC$_{50}$−log[cmpd])*h))     (Eqn 2)

Where Bottom and Top are the lower and upper asymptotes of the dose-response curve, respectively, IC$_{50}$ is the concentration of compound that yields 50% inhibition of signal and h is the Hill coefficient.

2) Menin/MLL Homogenous Time-Resolved Fluorescence (HTRF) Assay

To an untreated, white 384-well microtiter plate was added 40 nL 200× test compound in DMSO and 4 µL 2× terbium chelate-labeled menin (vide infra for preparation) in assay buffer (40 mM Tris HCl, pH 7.5, 50 mM NaCl, 1 mM DTT and 0.05% Pluronic F-127). After incubation of test compound and terbium chelate-labeled menin for 5 min at ambient temperature, 4 µL 2× FITC-MBM1 peptide (FITC-β-alanine-SARWRFPARPGT-NH$_2$ (SEQ ID NO: 23)) in assay buffer was added, the microtiter plate centrifuged at 1000 rpm for 1 min and the assay mixtures incubated for 15 min at ambient temperature. The relative amount of menin-.FITC-MBM1 complex present in an assay mixture is determined by measuring the homogenous time-resolved fluorescence (HTRF) of the terbium/FITC donor/acceptor fluorphore pair using a BMG Pherastar plate reader (ex. 337 nm/terbium em. 490 nm/FITC em. 520 nm) at ambient temperature. The degree of fluorescence resonance energy transfer (the HTRF value) is expressed as the ratio of the fluorescence emission intensities of the FITC and terbium fluorophores (Fem 520 nm/Fem 490 nm). The final concentrations of reagents in the binding assay are 100 µM terbium chelate-labeled menin (location 1) or 600 µM terbium chelate-labeled menin (location 2), 75 nM FITC-MBM1 peptide and 0.5% DMSO in assay buffer. Dose-response titrations of test compounds are conducted using an 11 point, three-fold serial dilution scheme, starting typically at 25 µM (location 1) or starting typically at 10 µM (location 2).

Compound potencies were determined by first calculating % inhibition at each compound concentration according to equation 1:

$$\% \text{ inhibition} = ((HC-LC)-(HTRF^{compound}-LC))/(HC-LC))*100 \quad \text{(Eqn 1)}$$

Where LC and HC are the HTRF values of the assay in the presence or absence of a saturating concentration of a compound that competes with FITC-MBM1 for binding to menin, and $HTRF^{compound}$ is the measured HTRF value in the presence of the test compound. FTC and LC HTRF values represent an average of at least 16 replicates per plate. For each test compound, % inhibition values were plotted vs. the logarithm of the test compound concentration, and the $IC_{50}$ value derived from fitting these data to equation 2:

$$\% \text{ inhibition} = \text{Bottom} + (\text{Top}-\text{Bottom})/(1+10^{((\log IC_{50}-\log[cmpd])*h)}) \quad \text{(Eqn 2)}$$

Where Bottom and Top are the lower and upper asymptotes of the dose-response curve, respectively, $IC_{50}$ is the concentration of compound that yields 50% inhibition of signal and h is the Hill coefficient.

Preparation of Terbium cryptate labeling of Menin: Menin (a.a. 1-610-6×his tag ("6×his" disclosed as SEQ ID NO: 3)) was labeled with terbium cryptate as follows. 2 mg of Menin was buffer exchanged into 1× phosphate buffered saline. 16 uM Menin was incubated with 4-fold molar excess NHS-terbium cryptate (Cisbio Bioassays, Bedford, Mass.) for 2 hours at room temperature. The labeled protein was purified away from free label by running the reaction over a Superdex 200 Increase 10/300 GL column at 0.75 ml/min. Peak fractions were collected, aliquoted and frozen at −80° C.

```
MENIN Protein Sequence:              (SEQ ID NO: 1)
MGLKAAQKTLFPLRSIDDWRLFAAELGREEPDLVLLSLVLGFVEHFLAV

NRVIPTNVPELTFQPSPAPDPPGGLTYFPVADLSIIAALYARFTAQIRG

AVDLSLYPREGGVSSRELVKKVSDVIWNSLSRSYFKDRAHIQSLFSFIT

GTKLDSSGVAFAWGACQALGLRDVHLALSEDHAWWFGPNGEQTAEVTWH

GKGNEDRRGQTVNAGVAERSWLYLKGSYMRCDRKMEVAFMVCAINPSID

LHTDSLELLQLQQKLLWLLYDLGHLERYPMALGNLADLEELEPTPGRPD

PLTLYHKGIASAKTYYRDEHIYPYMYLAGYHCRNRNVREALQAWADTAT

VIQDYNYCREDEEIYKEFFEVANDVIPNLLKEAASLLEAGEERPGEQSQ

GTQSQGSALQDPECFAHLLRFYDGICKWEEGSPTPVLHVGWATFLVQSL

GRFEGQVRQKVRIVSREAEAAEAEEPWGEEAREGRRRGPRRESKPEEPP

PPKKPALDKGLGTGQGAVSGPPRKPPGTVAGTARGPEGGSTAQVPAPAA

SPPPEGPVLTFQSEKMKGMKELLVATKINSSAIKLQLTAQSQVQMKKQK

VSTPSDYTLSFLKRQRKGLHHHHHH
```

3a) Proliferation Assay A

The anti-proliferative effect of menin/MLL protein/protein interaction inhibitor test compounds was assessed in human leukemia cell lines. The cell lines MV-4-11 and MOLM14 harbor MlLL translocations and express the MlLL fusion proteins MLL-AF4 and MLL-AF9, respectively, as well as the wildtype protein from the second allele. Therefore, the MLL rearranged cell lines MV-4-11 and MOLM14 exhibit stem cell-like HOX4/MEIS1 gene expression signatures. K562 was used as a control cell line containing two MLL wildtype alleles in order to exclude compounds that display general cytotoxic effects.

MV-4-11 and MOLM14 were cultured in RPMI-1640 (Sigma Aldrich) supplemented with 10% fetal bovine serum (HyClone), 2 mM L-glutamine (Sigma Aldrich) and 50 µg/ml gentamycin (Gibco). K562 were propagated in RPMI-1640 (Sigma Aldrich) supplemented with 20% fetal bovine serum (HyClone), 2 mM L-glutamine (Sigma Aldrich) and 50 µg/ml gentamycin (Gibco). Cells were kept at 0.3-2.5 million cells per ml during culturing and passage numbers did not exceed 25.

In order to assess the anti-proliferative effects, 1,500 MV-4-11, 300 MOLM14 or 750 K562 cells were seeded in 200 µl media per well in 96-well round bottom, ultra-low attachment plates (Costar, catalogue number 7007). Cell seeding numbers were chosen based on growth curves to ensure linear growth throughout the experiment. Test compounds were added at different concentrations and the DMSO content was normalized to 0.3%. Cells were incubated for 8 d at 37° C. and 5% $CO_2$. Spheroid like growth was monitored in real-time by live-cell imaging (IncuCyt-eZOOM, Essenbio, 4× objective) acquiring one image every four hours for 8 d. Confluence (%) as a measure of spheroid size was determined using an integrated analysis tool.

In order to determine the cumulative effect of the test compounds over time, the area under the curve (AUC) in a plot of confluence against time was calculated. Confluence at the beginning of the experiment (t=0) was used as baseline for the AUC calculation.

Absolute $IC_{50}$ values were calculated according to the following procedure:

% Control=(AUC sample/AUC control)*100

AUC control mean AUC of control values (cells without compound/DMSO as vehicle control)

A non-linear curve fit was applied using the least squares (ordinary) fit method to the plot of % control versus compound concentration. Based on this, the absolute $IC_{50}$ value (half maximal inhibitory concentration of the test compound causing an anti-proliferative effect of 50% relative to the vehicle control) was calculated.

3b) Proliferation Assay B

The anti-proliferative effect of menin/MLL protein/protein interaction inhibitor test compounds was assessed in human leukemia cell lines. The cell lines MV-4-11 and MOLM14 harbor MILL translocations and express the MILL fusion proteins MLL-AF4 and MLL-AF9, respectively, as well as the wildtype protein from the second allele. Therefore, the MLL rearranged cell lines MV-4-11 and MOLM14 exhibit stem cell-like HOXA/MEIS1 gene expression signatures. K562 was used as a control cell line containing two MLL wildtype alleles in order to exclude compounds that display general cytotoxic effects.

MV-4-11 and MOLM14 were cultured in RPMI-1640 (Sigma Aldrich) supplemented with 10% fetal bovine serum (HyClone), 2 mM L-glutamine (Sigma Aldrich) and 50 µg/ml gentamycin (Gibco). K562 were propagated in RPMI-1640 (Sigma Aldrich) supplemented with 20% fetal bovine serum (HyClone), 2 mM L-glutamine (Sigma Aldrich) and 50 µg/ml gentamycin (Gibco). Cells were kept at 0.3-2.5 million cells per ml during culturing and passage numbers did not exceed 25.

In order to assess the anti-proliferative effects, 1,500 MV-4-11, 300 MOLM14 cells or 750 K562 cells were seeded in 200 μl media per well in 96-well round bottom, ultra-low attachment plates (Costar, catalogue number 7007). Cell seeding numbers were chosen based on growth curves to ensure linear growth throughout the experiment. Test compounds were added at different concentrations and the DMSO content was normalized to 0.3%. Cells were incubated for 8 d at 37° C. and 5% $CO_2$. Spheroid like growth was measured in real-time by live-cell imaging (IncuCyteZOOM, Essenbio, 4× objective) acquiring images at day 8. Confluence (%) as a measure of spheroid size was determined using an integrated analysis tool.

In order to determine the effect of the test compounds over time, the confluence in each well as a measure of spheroid size, was calculated. Confluence of the highest dose of reference compound was used as baseline for the at the beginning of the experiment (t=0) was used as baseline for the calculation.

Absolute $IC_{50}$ values were calculated as percent change in confluence as follows:

LC=Low Control: cells treated with 1 μM of the cytotoxic agent staurosporin

HC=High Control: Mean confluence (%) (DMSO treated cells)

% Effect=100−(100*(Sample−LC)/(HC−LC))

To determine the IC50 a curve is fitted to the plot of % Effect vs Log 10 compound concentration using a sigmoidal fit with a variable slope and fixing the maximum to 100% and the minimum to 0%.

TABLE 4a

Biological data in the Menin/MLL homogenous time-resolved fluorescence (HTRF) assay (2).

| Co. No. | (2) location 1 Menin HTRF assay ($IC_{50}$ (nM)) | (2) location 2 Menin HTRF assay ($IC_{50}$ (nM)) | Co. No. | (2) location 1 Menin HTRF assay ($IC_{50}$ (nM)) | (2) location 2 Menin HTRF assay ($IC_{50}$ (nM)) |
|---|---|---|---|---|---|
| 48 | 12.0 | | 32 | | 122.9 |
| 45 | 20.4 | | 33 | | 2049.8 |
| 428 | 23.8 | | 34 | | 338.5 |
| 51 | 61.3 | | 11 | | 3758.9 |
| 50 | 95.8 | | 12 | | 730.0 |
| 46 | 22.0 | | 36 | | 7520.2 |
| 47 | 15.5 | | 37 | | 8335.7 |
| 52 | 555.3 | | 42 | | 43.8 |
| 1 | 3.7 | 5.0 | 43 | | 1754.9 |
| 2 | 91.2 | 84.5 | 44 | | 11.3 |
| 8 | 1251.1 | 1014.6 | 23 | | 1312.6 |
| 10 | 843.3 | 948.0 | 24 | | 419.0 |
| 3 | 75.7 | 10.0 | 25 | | 509.9 |
| 4 | 188.2 | 39.9 | 26 | | 311.1 |
| 5 | 304.2 | 63.8 | 39 | | 1436.8 |
| 6 | 472.3 | 143.3 | 40 | | 90.9 |
| 9 | 3814.2 | 1221.5 | 41 | | 338.8 |
| 14 | 5.9 | 0.8 | 284 | | 422.7 |
| 18 | 3841.5 | 1617.5 | 310 | | >10000 |
| 19 | 3630.8 | 3556.8 | 126 | | >10000 |
| 20 | 2020.2 | 2793.8 | 128 | | >10000 |
| 15 | | 2.2 | 127 | | >10000 |
| 22 | | 450.3 | 197 | | 2351.1 |
| 27 | | 584.9 | 143 | | 32.2 |
| 7 | | 657.5 | 57 | | 3.6 |
| 16 | | 2.0 | 58 | | 2.9 |
| 196 | | 133.4 | 277 | | 949.3 |
| 30 | | 3886.2 | 278 | | 22.8 |
| 17 | | 7.2 | 285 | | 16.2 |
| 35 | | 48.6 | 309 | | 339.0 |
| 38 | | 446.6 | 55 | | 7.0 |
| 31 | | 240.6 | 56 | | 5.1 |
| 149 | | 37.5 | 426 | | 535.9 |
| 150 | | 369.5 | 427 | | >10000 |
| 260 | | >10000 | 319 | | 17.4 |
| 311 | | 70.5 | 380 | | 8.7 |
| 288 | | 135.2 | 146 | | 23.7 |
| 314 | | 27.1 | 147 | | 45.3 |
| 306 | | 78.2 | 113 | | 163.7 |
| 307 | | 3.1 | 387 | | 94.2 |
| 125 | | 5942.2 | 377 | | 7.5 |
| 132 | | 180.3 | 322 | | 51.4 |
| 138 | | 8.8 | 295 | | 97.7 |
| 29 | | 315.9 | 110 | | 5.5 |
| 28 | | >10000 | 111 | | 65 |
| 276 | | 97.3 | 144 | | 9.3 |
| 415 | | 473.0 | 145 | | 22.6 |
| 425 | | 234.2 | 131 | | 49.1 |
| 417 | | 221.2 | 115 | | 160.1 |
| 108 | | 5.2 | 116 | | 30.6 |
| 109 | | 1.6 | 121 | | 32.7 |
| 124 | | 2534.3 | 122 | | 49.3 |
| 130 | | 67.1 | 154 | | 13.0 |
| 282 | | 92.8 | 155 | | 97.0 |
| 289 | | 42.7 | 162 | | 90.0 |
| 308 | | 5.6 | 163 | | 77.6 |
| 403 | | 553.4 | 167 | | 98.1 |
| 404 | | 16.4 | 286 | | 23.7 |
| 54 | | 1.8 | 287 | | 22.8 |
| 129 | | 34.3 | 384 | | 32.6 |
| 133 | | 4.1 | 96 | | 43.4 |
| 112 | | 313.5 | 261 | | 529.4 |
| 298 | | 54.3 | 262 | | 15.1 |
| 315 | | 4.2 | 266 | | 1022.1 |
| 416 | | 433.1 | 267 | | 98.2 |
| 118 | | 255.5 | 172 | | 8.4 |
| 151 | | 31.0 | 302 | | 509 |
| 152 | | 288.1 | 326 | | 20.1 |
| 153 | | 34.7 | 336 | | 297.1 |
| 156 | | 155.3 | 279 | | 82.9 |
| 158 | | 72.2 | 292 | | 81.3 |
| 159 | | 199.2 | 316 | | 8.8 |
| 160 | | 150.4 | 400 | | 373.2 |
| 164 | | 12.2 | 385 | | 27.2 |
| 165 | | 655.5 | 297 | | 131.2 |
| 166 | | 399.6 | 263 | | 47.3 |
| 93 | | 5.8 | 171 | | 264.9 |
| 329 | | 2.0 | 173 | | 127.1 |
| 97 | | 213.3 | 299 | | 94.8 |
| 98 | | 2.6 | 300 | | 128.5 |
| 280 | | 157.9 | 402 | | 905.9 |
| 281 | | 62.7 | 301 | | 32.3 |
| 312 | | 136.4 | 92 | | 5.3 |
| 313 | | 55.2 | 303 | | 520.6 |
| 390 | | 14.6 | 327 | | 8.4 |
| 386 | | 86.8 | 328 | | 206.0 |
| 59 | | 4.5 | 94 | | 3.6 |
| 60 | | 23.2 | 330 | | 19.6 |
| 61 | | 2.4 | 290 | | 231.2 |
| 62 | | 115.4 | 305 | | 148.1 |
| 264 | | 912.9 | 317 | | 142.9 |
| 265 | | 246.2 | 318 | | 8.1 |
| 119 | | 47.9 | 320 | | 41.6 |
| 117 | | 111.0 | 321 | | 915 |
| 120 | | 52.4 | 393 | | 68.3 |
| 157 | | 117.9 | 396 | | 17.8 |
| 63 | | 44.3 | 401 | | 330.8 |
| 168 | | 20.8 | 268 | | 943.3 |
| 269 | | 78.6 | 135 | | 23.9 |
| 161 | | 101.1 | 136 | | 409 |
| 169 | | 424.9 | 137 | | 5.7 |
| 170 | | 12.4 | 139 | | 3.5 |
| 123 | | 137.4 | 140 | | 30.9 |
| 89 | | 27.8 | 141 | | 3.9 |
| 95 | | 34.6 | 142 | | 45.7 |
| 337 | | 2296.5 | 270 | | 518.1 |
| 341 | | 50.3 | 180 | | 43.4 |

TABLE 4a-continued

Biological data in the Menin/MLL homogenous time-resolved fluorescence (HTRF) assay (2).

| Co. No. | (2) location 1 Menin HTRF assay (IC$_{50}$ (nM)) | (2) location 2 Menin HTRF assay (IC$_{50}$ (nM)) | Co. No. | (2) location 1 Menin HTRF assay (IC$_{50}$ (nM)) | (2) location 2 Menin HTRF assay (IC$_{50}$ (nM)) | Co. No. | (2) location 1 Menin HTRF assay (IC$_{50}$ (nM)) | (2) location 2 Menin HTRF assay (IC$_{50}$ (nM)) |
|---|---|---|---|---|---|---|---|---|
| 291 |  | 51.9 | 174 |  | 11.4J0 | 410 |  | 68.7 |
| 293 |  | 11.0 | 175 |  | 33.4 | 414 |  | 100.0 |
| 294 |  | 58.4 | 176 |  | 18.7 | 104 |  | 16.6 |
| 378 |  | 42.9 | 206 |  | 223.9 | 105 |  | 3037.1 |
| 323 |  | 26.4 | 325 |  | 1685.3 | 100 |  | 14.2 |
| 296 |  | 146.3 | 304 |  | 17.3 | 220 |  | 118.4 |
| 199 |  | 58.3 | 331 |  | 3.4 | 359 |  | 16.2 |
| 200 |  | 3.6 | 332 |  | 329.9 | 360 |  | 448.1 |
| 208 |  | 37.7 | 339 |  | 5.1 | 101 |  | 471.2 |
| 210 |  | 70.4 | 342 |  | 4.8 | 228 |  | 84.2 |
| 211 |  | 18.2 | 343 |  | 4.9 | 229 |  | 0.9 |
| 114 |  | 156.9 | 424 |  | 576.3 | 219 |  | 2.6 |
| 201 |  | 174.9 | 388 |  | 216.5 | 230 |  | 488.9 |
| 202 |  | 58.3 | 389 |  | 96.0 | 231 |  | 207.7 |
| 64 |  | 2.4 | 391 |  | 162.7 | 232 |  | 667.2 |
| 65 |  | 133.1 | 392 |  | 16.8 | 233 |  | 108.5 |
| 333 |  | 10.3 | 395 |  | 113.3 | 85 |  | 0.7 |
| 338 |  | 89.5 | 382 |  | 27.9 | 86 |  | 91.8 |
| 379 |  | 1.4 | 383 |  | 70.8 | 273 |  | 168.3 |
| 394 |  | 13.8 | 324 |  | 85.9 | 367 |  | 63.6 |
| 381 |  | 9.4 | 209 |  | 65.3 | 368 |  | 2.9 |
| 397 |  | 4.4 | 203 |  | 2.8 | 236 |  | 80.0 |
| 398 |  | 16.2 | 66 |  | 26.8 | 362 |  | 836.0 |
| 134 |  | 1.6 | 67 |  | 1.0 | 361 |  | 61.7 |
| 68 |  | 39.6 | 82 |  | 73.6 | 251 |  | 171.0 |
| 69 |  | 1.7 | 198 |  | 140.6 | 275 |  | 2.4 |
| 214 |  | 9.4 | 204 |  | 84.6 | 422 |  | 34.1 |
| 70 |  | 2.7 | 205 |  | 2.2 | 246 |  | 205.8 |
| 73 |  | 2.5 | 71 |  | 433.2 | 247 |  | 30.2 |
| 207 |  | 209.6 | 72 |  | 2.8 | | | |
| 334 |  | 256.2 | 107 |  | 22.1 | | | |
| 335 |  | 5.2 | 250 |  | 146.0 | | | |
| 283 |  | 2160.7 | 217 |  | 3.7 | | | |
| 399 |  | 26.4 | 218 |  | 64.9 | | | |
| 271 |  | 22.5 | 349 |  | 19.3 | | | |
| 216 |  | 38.0 | 221 |  | 3997.6 | | | |
| 90 |  | 20.2 | 257 |  | 10.6 | | | |
| 91 |  | 166.0 | 53 |  | 8.7 | | | |
| 348 |  | 14.5 | 353 |  | 17.3 | | | |
| 346 |  | 7.3 | 354 |  | 43.7 | | | |
| 350 |  | 21.1 | 423 |  | 134.7 | | | |
| 351 |  | 15.5 | 241 |  | 113.8 | | | |
| 340 |  | 7.1 | 74 |  | 60.4 | | | |
| 345 |  | 6.8 | 75 |  | 1.3 | | | |
| 347 |  | 9.1 | 253 |  | 234.9 | | | |
| 344 |  | 13.4 | 254 |  | 2.8 | | | |
| 177 |  | 16.2 | 245 |  | 7.7 | | | |
| 215 |  | 62.0 | 226 |  | 7.8 | | | |
| 239 |  | 33.6 | 227 |  | 80.2 | | | |
| 224 |  | 54.1 | 405 |  | 1101.1 | | | |
| 225 |  | 22.7 | 406 |  | 36.0 | | | |
| 248 |  | 347.9 | 99 |  | 1.1 | | | |
| 249 |  | 271.5 | 355 |  | 1459.2 | | | |
| 240 |  | 8.6 | 356 |  | 2683.4 | | | |
| 78 |  | 2.9 | 352 |  | 139.4 | | | |
| 223 |  |  | 237 |  | 488.9 | | | |
| 81 |  | 6.8 | 238 |  | 11.8 | | | |
| 242 |  | 74.6 | 184 |  | 3427.1 | | | |
| 243 |  | 2.9 | 187 |  | 1575.4 | | | |
| 244 |  | 516.3 | 188 |  | 199.5 | | | |
| 258 |  | 107.7 | 106 |  | 17.8 | | | |
| 259 |  | >10000 | 407 |  | 1019.7 | | | |
| 222 |  | 418.4 | 408 |  | 16.4 | | | |
| 79 |  | 14.2 | 420 |  | 3384.6 | | | |
| 80 |  | 8.7 | 421 |  | 207.6 | | | |
| 83 |  | 58.7 | 178 |  | 127.0 | | | |
| 84 |  | 2.3 | 179 |  | 2901.5 | | | |
| 183 |  | 82.0 | 189 |  | 142.8 | | | |
| 212 |  | 58.1 | 190 |  | 9.2 | | | |
| 213 |  | 4.7 | 87 |  | 190.6 | | | |
| 413 |  | 2292.9 | 88 |  | 3.8 | | | |
| 409 |  | 1104.6 | 376 |  | 30.6 | | | |
| 418 |  | 749.3 | | | | | | |
| 419 |  | 10.8 | | | | | | |
| 76 |  | 354.3 | | | | | | |
| 77 |  | 1.8 | | | | | | |
| 102 | 341.9 | 362.4 | | | | | | |
| 103 | 1157.4 | 1195.1 | | | | | | |
| 363 | 44.1 | 46.0 | | | | | | |
| 364 | 0.8 | 1.3 | | | | | | |
| 357 |  | 3.1 | | | | | | |
| 411 |  | 101.4 | | | | | | |
| 412 |  | 7509.5 | | | | | | |
| 358 |  | 5.3 | | | | | | |
| 191 |  | 7.9 | | | | | | |
| 193 |  | 4.2 | | | | | | |
| 234 |  | 115.9 | | | | | | |
| 235 |  | 4.1 | | | | | | |
| 192 |  | 13.1 | | | | | | |
| 272 |  | 18.0 | | | | | | |
| 274 |  |  | | | | | | |
| 370 |  |  | | | | | | |
| 371 |  |  | | | | | | |
| 372 |  |  | | | | | | |
| 369 |  |  | | | | | | |
| 374 |  |  | | | | | | |
| 375 |  |  | | | | | | |
| 194 |  |  | | | | | | |
| 195 |  |  | | | | | | |
| 373 |  |  | | | | | | |

NT: not tested

TABLE 4b

Biological data in the proliferation assay (3).

| Co. No. | (3a) Spheroid assay MV-4-11 (IC$_{50}$(μM)) Assay A | (3a) Spheroid assay MOLM14 (IC$_{50}$(μM)) Assay A | (3a) Spheroid assay K562 Assay A | (3b) Spheroid assay MV-4-11 (IC$_{50}$(μM)) Assay B | (3b) Spheroid assay MOLM14 (IC$_{50}$(μM)) Assay B | (3b) Spheroid assay K562 Assay B |
|---|---|---|---|---|---|---|
| 48 | 0.35 | 1.58 | >15 | | | |
| 45 | 0.41 | 2.36 | | | | |
| 428 | 0.55 | 1.84 | | | | |
| 51 | 0.81 | 2.46 | | | | |
| 50 | 0.91 | | | | | |
| 46 | 0.31 | 1.87 | | | | |
| 47 | 0.14 | 1.02 | >15 | | | |
| 52 | | | | | | |
| 1 | 0.17 | 0.79 | | | | |
| 2 | 1.64 | | | | | |
| 8 | | | | | | |
| 10 | | | | | | |
| 3 | 0.75 | 2.39 | | | | |
| 4 | 0.50 | | | | | |
| 5 | 1.69 | | | | | |
| 6 | 1.12 | | | | | |
| 9 | | | | | | |
| 14 | 0.39 | 2.30 | | | | |
| 18 | | | | | | |
| 19 | | | | | | |
| 20 | | | | | | |
| 15 | 0.25 | 1.29 | | | | |
| 22 | 3.55 | | | | | |
| 27 | 11.89 | | | | | |
| 7 | 13.50 | | | | | |
| 16 | 0.03 | 0.19 | | | | |
| 196 | 3.91 | | | | | |

TABLE 4b-continued

Biological data in the proliferation assay (3).

| Co. No. | (3a) Spheroid assay MV-4-11 (IC$_{50}$(μM)) Assay A | (3a) Spheroid assay MOLM14 (IC$_{50}$(μM)) Assay A | (3a) Spheroid assay K562 Assay A | (3b) Spheroid assay MV-4-11 (IC$_{50}$(μM)) Assay B | (3b) Spheroid assay MOLM14 (IC$_{50}$(μM)) Assay B | (3b) Spheroid assay K562 Assay B |
|---|---|---|---|---|---|---|
| 30 | | | | | | |
| 17 | 1.36 | 3.51 | | | | |
| 35 | 4.90 | | | | | |
| 38 | 5.21 | | | | | |
| 31 | | | | | | |
| 32 | | | | | | |
| 33 | 5.11 | 4.45 | | | | |
| 34 | | | | | | |
| 11 | | | | | | |
| 12 | | | | | | |
| 36 | | | | | | |
| 37 | | | | | | |
| 42 | 1.24 | 0.69 | | | | |
| 43 | | | | | | |
| 44 | 2.08 | 2.61 | | | | |
| 23 | | | | | | |
| 24 | | | | | | |
| 25 | | | | | | |
| 26 | | | | | | |
| 39 | | | | | | |
| 40 | 3.13 | 2.64 | | | | |
| 41 | 10.00 | | | | | |
| 284 | | | | | | |
| 310 | | | | | | |
| 126 | | | | | | |
| 128 | | | | | | |
| 127 | | | | | | |
| 197 | | | | | | |
| 143 | 1.94 | 1.68 | | | | |
| 57 | 0.09 | 0.44 | | | | |
| 58 | 0.03 | 0.14 | | 0.11 | 0.20 | 14.06 |
| 277 | | | | | | |
| 278 | >3.75 | >3.75 | | | | |
| 285 | 2.65 | >3.75 | | | | |
| 309 | | | | | | |
| 55 | 0.28 | 1.27 | | | | |
| 56 | 0.45 | 2.00 | | | | |
| 149 | 3.67 | >3.75 | | | | |
| 150 | | | | | | |
| 260 | | | | | | |
| 311 | 2.13 | 3.98 | | 2.62 | >3.75 | |
| 288 | >3.75 | >3.75 | | | | |
| 314 | 3.83 | >3.75 | | | | |
| 306 | 2.25 | 3.82 | | | | |
| 307 | 1.05 | 3.38 | | | 2.44 | |
| 125 | | | | | | |
| 132 | | | | | | |
| 138 | 3.92 | >3.75 | | | | |
| 29 | | | | | | |
| 28 | | | | | | |
| 276 | | | | 2.43 | >3.75 | |
| 415 | | | | | | |
| 425 | | | | | | |
| 417 | | | | | | |
| 108 | 0.53 | >3.75 | | | | |
| 109 | 0.24 | 3.24 | | | 2.26 | |
| 124 | | | | | | |
| 130 | | | | >3.75 | >3.75 | |
| 282 | | | | >3.75 | >3.75 | |
| 289 | | | | >3.75 | >3.75 | |
| 308 | | | | 2.64 | >3.75 | |
| 403 | | | | | | |
| 404 | | | | >3.75 | >3.75 | |
| 54 | 0.16 | 0.82 | | 0.26 | 1.05 | |
| 129 | | | | 3.81 | >3.75 | |
| 133 | | | | 1.41 | >3.75 | |
| 112 | | | | | | |
| 298 | | | | >3.75 | >3.75 | |
| 315 | | | | 1.22 | 3.41 | |
| 416 | | | | | | |
| 426 | | | | | | |
| 427 | | | | | | |
| 319 | | | | >3.75 | >3.75 | |
| 380 | | | | | >3.75 | |
| 146 | | | | | | |
| 147 | | | | 2.07 | 2.90 | |
| 113 | | | | | | |
| 387 | >3.75 | | | >3.75 | >3.75 | |
| 377 | 1.12 | | | | | |
| 322 | >3.75 | | | >3.75 | >3.75 | |
| 295 | | | | >3.75 | >3.75 | |
| 110 | | | | 0.62 | 1.91 | |
| 111 | | | | 0.62 | 3.06 | |
| 144 | | | | 1.40 | 2.77 | |
| 145 | | | | 3.55 | >3.75 | |
| 131 | | | | 3.30 | >3.75 | |
| 115 | | | | | | |
| 116 | | | | 2.06 | 2.32 | |
| 121 | | | | 0.98 | 1.60 | |
| 122 | | | | 0.44 | 1.21 | |
| 154 | | | | 0.67 | 2.35 | |
| 155 | | | | 2.60 | >3.75 | |
| 162 | | | | 2.84 | >3.75 | |
| 163 | | | | >3.75 | >3.75 | |
| 167 | | | | | | |
| 286 | | | | 2.48 | >3.75 | |
| 287 | | | | 3.37 | >3.75 | |
| 384 | | | | >3.75 | 1.49 | |
| 96 | | | | 1.02 | 1.09 | |
| 261 | | | | | | |
| 262 | | | | 0.69 | 0.81 | |
| 266 | | | | | | |
| 267 | | | | >3.75 | >3.75 | |
| 118 | | | | | | |
| 151 | | | | 2.03 | 2.48 | |
| 152 | | | | | | |
| 153 | | | | 2.47 | >3.75 | |
| 156 | | | | | | |
| 158 | | | | 2.41 | 1.98 | |
| 159 | | | | | | |
| 160 | | | | | | |
| 164 | | | | 1.09 | 1.97 | |
| 165 | | | | | | |
| 166 | | | | | | |
| 93 | 0.09 | 0.70 | | 0.16 | 0.62 | |
| 329 | | | | | 2.54 | |
| 97 | | | | | | |
| 98 | 0.25 | 1.30 | | | 1.36 | |
| 280 | | | | | | |
| 281 | 1.11 | 1.78 | | | | |
| 312 | | | | | | |
| 313 | | | | | | |
| 390 | 2.84 | >3.75 | | | | |
| 386 | >3.75 | 1.99 | | | | |
| 59 | 0.28 | 0.85 | | | | |
| 60 | 3.20 | 3.46 | | | | |
| 61 | 0.10 | 0.29 | | | | |
| 62 | | | | | | |
| 264 | | | | | | |
| 265 | | | | | | |
| 119 | 2.15 | 2.28 | | | | |
| 117 | | | | | | |
| 120 | 2.13 | 2.90 | | | | |
| 157 | | | | | | |
| 63 | 1.01 | 1.13 | | | | |
| 168 | 1.65 | 2.52 | | | | |
| 172 | 0.90 | 3.05 | | | | |
| 302 | 2.56 | | | | | |
| 326 | 0.91 | | | | | |
| 336 | | | | | | |
| 279 | >3.75 | | | | | |
| 292 | >3.75 | | | | | |

TABLE 4b-continued

Biological data in the proliferation assay (3).

| Co. No. | (3a) Spheroid assay MV-4-11 (IC$_{50}$(μM)) Assay A | (3a) Spheroid assay MOLM14 (IC$_{50}$(μM)) Assay A | (3a) Spheroid assay K562 Assay A | (3b) Spheroid assay MV-4-11 (IC$_{50}$(μM)) Assay B | (3b) Spheroid assay MOLM14 (IC$_{50}$(μM)) Assay B | (3b) Spheroid assay K562 Assay B |
|---|---|---|---|---|---|---|
| 316 | 1.26 | | | | | |
| 400 | | | | | | |
| 385 | >3.75 | | | | | |
| 297 | | | | | | |
| 263 | 1.23 | | | | | |
| 171 | | | | | | |
| 173 | | | | | | |
| 299 | >3.75 | | | | | |
| 300 | | | | | | |
| 402 | | | | | | |
| 301 | 1.76 | | | | | |
| 92 | 0.48 | | | | | |
| 303 | | | | | | |
| 327 | 0.56 | | | | >3.75 | |
| 328 | | | | | | |
| 94 | 0.04 | | | 0.06 | 0.44 | |
| 330 | 1.26 | | | | | |
| 290 | | | | | | |
| 305 | | | | | | |
| 317 | | | | | | |
| 318 | 0.60 | | | | 3.07 | |
| 320 | 3.71 | | | | | |
| 321 | >3.75 | | | | | |
| 393 | 2.60 | | | | | |
| 396 | 1.80 | | | | | |
| 401 | | | | | | |
| 268 | | | | | | |
| 269 | >3.75 | | | | | |
| 161 | | | | | | |
| 169 | | | | | | |
| 170 | 0.95 | | | | | |
| 123 | | | | | | |
| 89 | 2.73 | | | | | |
| 95 | 1.27 | | | | 0.82 | |
| 337 | | | | | | |
| 341 | 0.84 | | | | 3.03 | |
| 291 | >3.75 | | | | | |
| 293 | 2.77 | | | | | |
| 294 | | | | | | |
| 378 | >3.75 | | | | | |
| 323 | 3.66 | | | | | |
| 296 | | | | | | |
| 199 | 3.16 | | | | | |
| 200 | 0.92 | | | | | |
| 208 | 3.16 | | | | | |
| 210 | | | | | | |
| 211 | 2.13 | | | | | |
| 114 | | | | | | |
| 201 | | | | | | |
| 202 | 2.30 | | | | | |
| 64 | 0.14 | | | | 0.92 | |
| 65 | | | | | | |
| 333 | | | | 0.12 | 0.14 | |
| 338 | | | | | | |
| 379 | | | | | >3.75 | |
| 394 | | | | | >3.75 | |
| 381 | | | | | >3.75 | |
| 397 | | | | | >3.75 | |
| 398 | | | | | >3.75 | |
| 134 | | | | | 1.29 | |
| 135 | | | | | >3.75 | |
| 136 | | | | | >3.75 | |
| 137 | | | | | >3.75 | |
| 139 | | | | | 0.56 | |
| 140 | | | | | 1.82 | |
| 141 | | | | | 2.30 | |
| 142 | | | | | 0.60 | |
| 270 | | | | | | |
| 180 | | | | | >3.75 | |
| 174 | | | | | 2.94 | |
| 175 | | | | | 1.09 | |
| 176 | | | | | 1.55 | |
| 206 | | | | | | |
| 325 | | | | | | |
| 304 | | | | | >3.75 | |
| 331 | | | | | 3.38 | |
| 332 | | | | | | |
| 339 | | | | | 2.41 | |
| 342 | | | | | >3.75 | |
| 343 | | | | | >3.75 | |
| 424 | | | | | | |
| 388 | | | | | | |
| 389 | | | | | | |
| 391 | | | | | | |
| 392 | | | | | | |
| 395 | | | | | | |
| 382 | | | | | >3.75 | |
| 383 | | | | | | |
| 324 | | | | | | |
| 209 | | | | | | |
| 203 | | | | | 2.39 | |
| 66 | | | | | >3.75 | |
| 67 | | | | 0.14 | 0.62 | |
| 68 | | | | | 2.24 | |
| 69 | | | | | 0.69 | |
| 214 | | | | | >3.75 | |
| 70 | | | | 0.30 | 1.08 | |
| 73 | | | | 0.30 | 1.21 | |
| 207 | | | | | | |
| 334 | | | | >3.75 | >3.75 | |
| 335 | | | | 0.46 | 1.55 | |
| 283 | | | | | | |
| 399 | | | | >3.75 | >3.75 | |
| 271 | | | | >3.75 | >3.75 | |
| 216 | | | | >3.75 | >3.75 | |
| 90 | | | | | 0.85 | |
| 91 | | | | | | |
| 348 | | | | | >3.75 | |
| 346 | | | | | 2.11 | |
| 350 | | | | | 3.55 | |
| 351 | | | | | 3.51 | |
| 340 | | | | | 2.47 | |
| 345 | | | | | 2.33 | |
| 347 | | | | | 3.18 | |
| 344 | | | | | >3.75 | |
| 177 | | | | 1.02 | 1.22 | |
| 215 | | | | | | |
| 239 | | | | >3.75 | | |
| 224 | | | | 3.03 | | |
| 225 | | | | 1.95 | | |
| 248 | | | | | | |
| 249 | | | | | | |
| 240 | | | | 1.14 | | |
| 78 | | | | 0.33 | 0.48 | |
| 223 | | | | | | |
| 81 | | | | 0.43 | 0.65 | |
| 82 | | | | 1.14 | 0.93 | |
| 198 | | | | | >3.75 | |
| 204 | | | | | | |
| 205 | | | | | 1.02 | |
| 71 | | | | | | |
| 72 | | | | 0.23 | 0.50 | |
| 107 | | | | | >3.75 | |
| 250 | | | | | >3.75 | |
| 217 | | | | | 1.69 | |
| 218 | | | | | >3.75 | |
| 349 | | | | | >3.75 | |
| 221 | | | | | >3.75 | |
| 257 | | | | | >3.75 | |
| 53 | | | | >3.75 | >3.75 | |
| 353 | | | | | >3.75 | |
| 354 | | | | | >3.75 | |

TABLE 4b-continued

Biological data in the proliferation assay (3).

| Co. No. | (3a) Spheroid assay MV-4-11 (IC$_{50}$(μM)) Assay A | (3a) Spheroid assay MOLM14 (IC$_{50}$(μM)) Assay A | (3a) Spheroid assay K562 Assay A | (3b) Spheroid assay MV-4-11 (IC$_{50}$(μM)) Assay B | (3b) Spheroid assay MOLM14 (IC$_{50}$(μM)) Assay B | (3b) Spheroid assay K562 Assay B |
|---|---|---|---|---|---|---|
| 423 | | | | | >3.75 | |
| 241 | | | | | 2.64 | |
| 74 | | | | | >3.75 | |
| 75 | | | | 0.05 | 0.46 | |
| 253 | | | | | >3.75 | |
| 254 | | | | 0.17 | 1.50 | |
| 245 | | | | | >3.75 | |
| 226 | | | | 0.43 | 2.83 | |
| 227 | | | | | >3.75 | |
| 405 | | | | | >3.75 | |
| 406 | | | | | >3.75 | |
| 99 | | | | 0.03 | 0.19 | |
| 355 | | | | | >3.75 | |
| 356 | | | | | >3.75 | |
| 352 | | | | | >3.75 | |
| 237 | | | | | >3.75 | |
| 238 | | | | | 2.90 | |
| 242 | | | | | >3.75 | |
| 243 | | | | | 1.11 | |
| 244 | | | | | >3.75 | |
| 258 | | | | | >3.75 | |
| 259 | | | | | >3.75 | |
| 222 | | | | | >3.75 | |
| 79 | | | | 0.17 | 0.59 | |
| 80 | | | | | 0.95 | |
| 83 | | | | | >3.75 | |
| 84 | | | | 0.06 | 0.56 | |
| 183 | | | | | >3.75 | |
| 212 | | | | | >3.75 | |
| 213 | | | | | 1.04 | |
| 413 | | | | >3.75 | >3.75 | |
| 409 | | | | | | |
| 410 | | | | >3.75 | >3.75 | |
| 414 | | | | | | |
| 104 | | | | | | |
| 105 | | | | | | |
| 100 | | | | 1.15 | 1.69 | |
| 220 | | | | | | |
| 359 | | | | | >3.75 | |
| 360 | | | | | >3.75 | |
| 101 | | | | | >3.75 | |
| 228 | | | | | >3.75 | |
| 229 | | | | | 1.00 | |
| 219 | | | | | 2.40 | |
| 230 | | | | | >3.75 | |
| 231 | | | | | >3.75 | |
| 232 | | | | | >3.75 | |
| 233 | | | | | >3.75 | |
| 85 | | | | | 1.13 | |
| 86 | | | | | >3.75 | |
| 184 | | | | | >3.75 | |
| 187 | | | | | >3.75 | |
| 188 | | | | | | |
| 106 | | | | | 3.39 | |
| 407 | | | | | >3.75 | |
| 408 | | | | | >3.75 | |
| 420 | | | | | >3.75 | |
| 421 | | | | | >3.75 | |
| 178 | | | | | >3.75 | |
| 179 | | | | | >3.75 | |
| 189 | | | | | >3.75 | |
| 190 | | | | | 2.10 | |
| 87 | | | | | >3.75 | |
| 88 | | | | | 0.99 | |
| 376 | | | | | >3.75 | |
| 418 | | | | | >3.75 | |
| 419 | | | | | 3.04 | |
| 76 | | | | | >3.75 | |
| 77 | | | | 0.19 | 0.63 | −7.85 |
| 102 | | | | | >3.75 | |
| 103 | | | | | >3.75 | |
| 363 | | | | | 2.10 | |
| 364 | | | | | 1.10 | |
| 357 | | | | | >3.75 | |
| 411 | | | | | >3.75 | |
| 412 | | | | | >3.75 | |
| 358 | | | | | 3.50 | |
| 191 | | | | | 1.22 | |
| 193 | | | | | 0.46 | |
| 234 | | | | | >3.75 | |
| 235 | | | | | 1.53 | |
| 192 | | | | | 1.00 | |
| 272 | | | | | 2.56 | |
| 273 | | | | | 2.94 | |
| 367 | | | | | >3.75 | |
| 368 | | | | | 2.61 | |
| 236 | | | | | >3.75 | |
| 362 | | | | >3.75 | >3.75 | |
| 361 | | | | >3.75 | >3.75 | |
| 251 | | | | >3.75 | >3.75 | |
| 275 | | | | | 1.09 | |
| 422 | | | | >3.75 | >3.75 | |
| 246 | | | | 0.26 | 0.13 | 3.97 |
| 247 | | | | 0.97 | 0.71 | |
| 274 | | | | | | |
| 370 | | | | 0.35 | 1.57 | 7.30 |
| 371 | | | | 0.08 | 0.30 | 6.48 |
| 372 | | | | | | |
| 369 | | | | | | |
| 374 | | | | | | |
| 375 | | | | | | |
| 194 | | | | | | |
| 195 | | | | | | |
| 373 | | | | | | |

The invention claimed is:
1. A compound of Formula (I)

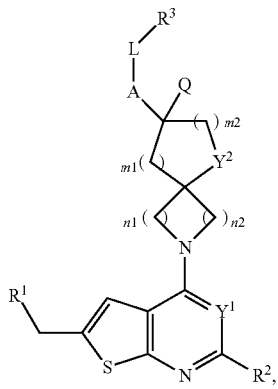

or a tautomer or a stereoisomeric form thereof, wherein
R$^1$ is selected from the group consisting of CH$_3$, CH$_2$F, CHF$_2$ and CF$_3$;
Y$^1$ is N or CR$^y$;
when Y$^1$ represents N, R$^2$ is selected from the group consisting of hydrogen, CH$_3$, —OCH$_3$, —NH$_2$, and —NH—CH$_3$;
when Y$^1$ represents CR$^y$, R$^2$ is hydrogen;
R$^y$ is selected from the group consisting of hydrogen, cyano, and C$_{1-4}$alkyl optionally substituted with hydroxy, —O—C$_{1-4}$alkyl, or —O—C$_{3-6}$cycloalkyl;
Y$^2$ is CH$_2$ or O;
A is a covalent bond or —CR$^{15a}$R$^{15b}$—;
R$^{15a}$ and R$^{15b}$ are each independently selected from the group consisting of hydrogen or C$_{1-4}$alkyl;
Q is hydrogen or C$_{1-4}$alkyl optionally substituted with phenyl;
L-R$^3$ is selected from (a), (b), (c), (d), (e), or (f):
(a) -L-R$^3$ is —NR$^A$R$^{14}$, wherein
R$^A$ is selected from the group consisting of hydrogen; cyclopropyl; C$_{1-4}$alkyl optionally substituted with a substituent selected from the group consisting of fluoro and —CN; and C$_{2-4}$alkyl substituted with a substituent selected from the group consisting of —OR$^{3a}$ and —NR$^{4a}$R$^{4aa}$,
R$^{14}$ is selected from the group consisting of C$_{1-6}$alkyl optionally substituted with one, two or three fluoro substituents; and C$_{2-6}$alkyl substituted with a substituent selected from the group consisting of —OR$^{1a}$ and —NR$^{2a}$R$^{2aa}$,
wherein R$^{1a}$, R$^{2a}$, R$^{2aa}$, R$^{3a}$, R$^{4a}$, and R$^{4aa}$ are each independently selected from the group consisting of hydrogen, C$_{1-4}$alkyl and cyclopropyl;
or
(b) L is selected from the group consisting of —N(R$^B$)—, —N(R$^B$)—CR$^{1B}$R$^{1BB}$—, and —(NR$^B$)—CHR$^{1B}$—CHR$^{2B}$—; and R$^3$ is selected from the group consisting of Ar; Het$^1$; Het$^2$; Het$^3$; R$^{17}$; and a 7- to 10-membered saturated spirocarbobicyclic system; wherein
R$^B$ is selected from the group consisting of hydrogen; cyclopropyl; C$_{1-4}$alkyl optionally substituted with a substituent selected from the group consisting of fluoro and —CN; and C$_{2-4}$alkyl substituted with a substituent selected from the group consisting of —OR$^{1b}$ and —NR$^{2b}$R$^{2bb}$; provided that when R$^3$ is R$^{17}$, R$^B$ is hydrogen; wherein R$^{1b}$, R$^{2b}$, and R$^{2bb}$ are each independently selected from the group consisting of hydrogen, C$_{1-4}$alkyl and cyclopropyl;
R$^{1B}$ is selected from the group consisting of hydrogen; halo; C$_{3-6}$cycloalkyl; C$_{1-4}$alkyl optionally substituted with a substituent selected from the group consisting of fluoro, hydroxy, and —CN; C$_{2-4}$alkyl substituted with a substituent selected from the group consisting of —OR$^{4B}$ and —NR$^{5B}$R$^{5BB}$; and C-linked 4- to 7-membered non-aromatic heterocyclyl containing at least one nitrogen, oxygen or sulfur atom; and R$^{1BB}$ is selected from the group consisting of hydrogen and methyl; or R$^{1B}$ and R$^{1BB}$ together with the carbon to which they are attached form a C$_{3-6}$cycloalkyl or a C-linked 4- to 7-membered non-aromatic heterocyclyl containing at least one nitrogen, oxygen or sulfur atom;
R$^{2B}$ is selected from the group consisting of hydrogen; —OR$^{6B}$; —NR$^{7B}$R$^{7BB}$; CF$_3$, C$_{1-4}$alkyl optionally substituted with a substituent selected from the group consisting of fluoro, —CN, —OR$^{4B}$, and —NR$^{5B}$R$^{5BB}$; and C-linked 4- to 7-membered non-aromatic heterocyclyl containing at least one nitrogen, oxygen or sulfur atom; wherein
R$^{4B}$, R$^{5B}$, R$^{5BB}$, R$^{6B}$, R$^{7B}$, and R$^{7BB}$ are each independently selected from the group consisting of hydrogen; C$_{1-4}$alkyl optionally substituted with a substituent selected from the group consisting of fluoro, —CN and
—C(=O)NR$^{9B}$R$^{9BB}$; and C$_{2-4}$alkyl substituted with a substituent selected from the group consisting of —OR$^{10B}$ and —NR$^{11B}$R$^{11BB}$; wherein
R$^{9B}$, R$^{9BB}$, R$^{10B}$, R$^{11B}$ and R$^{11BB}$ are each independently selected from the group consisting of hydrogen; C$_{1-4}$alkyl; and C-linked 4- to 7-membered non-aromatic heterocyclyl containing at least one nitrogen, oxygen or sulfur atom;
or
(c) -L-R$^3$ is selected from the group consisting of —N(R$^C$)—COR$^{5C}$; and
—N(R$^C$)—SO$_2$—R$^{13C}$ wherein
R$^C$ is selected from the group consisting of hydrogen; cyclopropyl; C$_{1-4}$alkyl optionally substituted with a substituent selected from the group consisting of fluoro and —CN; and C$_{2-4}$alkyl substituted with a substituent selected from the group consisting of —OR$^{1c}$ and —NR$^{2c}$R$^{2cc}$;
R$^{5C}$ and R$^{13C}$ are each independently selected from the group consisting of hydrogen; Ar; Het$^1$; Het$^2$; Het$^3$; R$^{17}$; a 7- to 10-membered saturated spirocarbobicyclic system; and C$_{1-4}$alkyl optionally substituted with —NR$^{2c}$R$^{2cc}$, Ar, Het$^1$ or Het$^2$; wherein
R$^{1c}$, R$^{2c}$, and R$^{2cc}$ are each independently selected from the group consisting of hydrogen and C$_{1-4}$alkyl;
or
(d) L is selected from —N(R$^D$)—CR$^{1D}$R$^{1DD}$— and —N(R$^D$)—CR$^{1D}$R$^{1DD}$—CR$^{2D}$R$^{2DD}$—; wherein
R$^D$ is selected from the group consisting of hydrogen; C$_{1-4}$alkyl optionally substituted with a substituent selected from the group consisting of fluoro and —CN; and C$_{2-4}$alkyl substituted with a substituent selected from —OR$^{1d}$ and —NR$^{2d}$R$^{2dd}$; wherein
R$^{1d}$, R$^{2d}$ and R$^{2dd}$ are each independently selected from the group consisting of hydrogen and C$_{1-4}$alkyl;

$R^{1D}$, $R^{1DD}$, $R^{2D}$ and $R^{2DD}$ are each independently selected from the group consisting of hydrogen and $C_{1-4}$alkyl; and $R^3$ is selected from the group consisting of

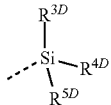

and

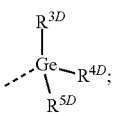

wherein
$R^{3D}$, $R^{4D}$, and $R^{5D}$ are each independently selected from the group consisting of $C_{1-6}$alkyl optionally substituted with OH, —$OC_{1-6}$alkyl, or $NH_2$ substituent;

or
(e) -L-$R^3$ is

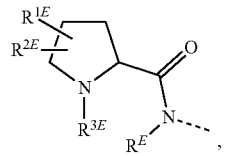

wherein
$R^E$ is selected from the group consisting of hydrogen and $C_{1-4}$alkyl;
$R^{1E}$ is selected from the group consisting of hydrogen, fluoro and $C_{1-4}$alkyl; and
$R^{2E}$ is selected from the group consisting of fluoro, —$OC_{1-4}$alkyl, and $C_{1-4}$alkyl optionally substituted with 1, 2 or 3 fluoro substituents; or $R^{1E}$ and $R^{2E}$ are bound to the same carbon atom and together form a $C_{3-5}$cycloalkyl or a C-linked 4- to 6-membered heterocyclyl containing an oxygen atom; and
$R^{3E}$ is selected from the group consisting of hydrogen; $C_{1-4}$alkyl optionally substituted with a fluoro or a —CN substituent; and $C_{2-4}$alkyl substituted with a substituent selected from the group consisting of —$OR^{4E}$ and —$NR^{5E}R^{5EE}$; wherein
$R^{4E}$, $R^{5E}$ and $R^{5EE}$ are each independently selected from the group consisting of hydrogen; $C_{1-4}$alkyl optionally substituted with a substituent selected from the group consisting of fluoro, —CN, and —C(=O)$NR^{6E}R^{6EE}$; $C_{2-4}$alkyl substituted with a substituent selected from the group consisting of —$OR^{7E}$ and —$NR^{8E}R^{8EE}$; and C-linked 4- to 7-membered non-aromatic heterocyclyl containing at least one nitrogen, oxygen or sulfur atom; wherein
$R^{6E}$, $R^{6EE}$, $R^{7E}$, $R^{8E}$ and $R^{8EE}$ are each independently selected from the group consisting of hydrogen and $C_{1-4}$alkyl;

or
(f) -L-$R^3$ is a radical

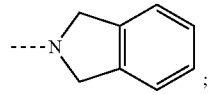

Ar is phenyl optionally substituted with one, two, or three substituents each independently selected from the group consisting of halo, —CN, —$OR^4$, —$NR^5R^{5'}$, —C(=O)$NR^5R^{5'}$, $Het^4$, —O-$Het^4$, —$NR^5$—$Het^4$, —C(=O)—$Het^4$, —S(=O)$_2$—$Het^4$, —S(=O)$_2$—$NR^5R^{5'}$, —S(=O)$_2$—$C_{1-4}$alkyl, $R^{14}$, $CF_3$, $C_{3-5}$cycloalkyl optionally substituted with —CN, and $C_{1-4}$alkyl optionally substituted with one or two substituents each independently selected from the group consisting of fluoro, $Het^4$, —CN, —$OR^6$, —$NR^7R^{7'}$, —S(=O)$_2$—$C_{1-4}$alkyl and —C(=O)$NR^8R^{8'}$;

$Het^1$ is a monocyclic heteroaryl selected from the group consisting of pyridyl, 2-, 4-, 5- or 6-pyrimidinyl, pyrazinyl, pyridazinyl, furanyl, thienyl, pyrrolyl, pyrazolyl, imidazolyl, 4- or 5-thiazolyl, isothiazolyl, and isoxazolyl; each of which may be optionally substituted with one, two, or three substituents each independently selected from the group consisting of halo, —CN, —$OR^4$, —$NR^5R^{5'}$, —C(=O)$NR^5R^{5'}$, —C(=O)—$Het^4$, and $C_{1-4}$alkyl optionally substituted with a substituent selected from the group consisting of fluoro, —CN, —$OR^6$, $Het^2$, —$NR^7R^{7'}$, and —C(=O)$NR^8R^{8'}$; and $Het^2$ is a non-aromatic heterocyclyl optionally substituted with one, two, or three substituents each independently selected from the group consisting of halo, —CN, —C(=O)—$C_{1-6}$alkyl, —C(=O)Ar, —C(=O)$Het^1$, —C(=O)$Het^2$, —$OR^4$, —$NR^5R^{5'}$, and $C_{1-4}$alkyl optionally substituted with a substituent selected from the group consisting of fluoro, —CN, —$OR^6$, —$NR^7R^{7'}$, $R^{12}$ and —C(=O)$NR^8R^{8'}$;

wherein
$R^{12}$ is C-linked 4- to 7-membered non-aromatic heterocyclyl containing at least one nitrogen, oxygen or sulfur atom;
$R^4$, $R^5$, $R^{5'}$, $R^6$, $R^7$, $R^{7'}$, $R^8$ and $R^{8'}$ are each independently selected from the group consisting of hydrogen; —C(=O)—$C_{1-4}$alkyl; —S(=O)$_2$—$C_{1-4}$alkyl; $C_{1-4}$alkyl optionally substituted with a substituent selected from the group consisting of fluoro, —CN, —C(=O)—$C_{1-4}$alkyl, —S(=O)$_2$—$C_{1-4}$alkyl, $R^{11'''}$, $R^{16}$ and —C(=O)$NR^9R^{9'}$;
$C_{1-4}$alkyl substituted with three fluoro atoms; and
$C_{2-4}$alkyl substituted with a substituent selected from the group consisting of —$OR^{10}$ and —$NR^{11}R^{11'}$;
wherein
$R^9$, $R^{9'}$, $R^{10}$, $R^{11}$, $R^{11'}$ and $R^{11''}$ are each independently selected from the group consisting of hydrogen; $C_{1-4}$alkyl; —S(=O)$_2$—$C_{1-4}$alkyl; and C-linked 4- to 7-membered non-aromatic heterocyclyl containing at least one nitrogen, oxygen or sulfur atom, wherein said heterocyclyl is optionally substituted with one, two, or three substituents each independently selected from the group consisting of —S(=O)$_2$—$C_{1-4}$alkyl, halo, cyano, and $C_{1-4}$alkyl optionally substituted with —O—$C_{1-4}$alkyl;

R$^{16}$ is N-linked 4- to 7-membered non-aromatic heterocyclyl containing at least one N-atom and optionally one additional heteroatom selected from nitrogen, oxygen and sulfur, wherein said heterocyclyl is optionally substituted with one, two, or three substituents each independently selected from the group consisting of —S(=O)$_2$—C$_{1-4}$alkyl, halo, cyano, and C$_{1-4}$alkyl optionally substituted with —O—C$_{1-4}$alkyl;

R$^{14}$ is a 5-membered monocyclic heteroaryl containing at least one nitrogen atom, and optionally 1, 2 or 3 additional heteroatoms each independently selected from nitrogen, oxygen and sulfur;

Het$^3$ is selected from the group consisting of formula (b-1) and (b-2):

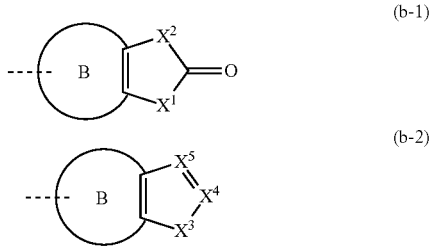

Ring B is phenyl;
X$^1$ represents CH$_2$, O or NH;
X$^2$ represents NH or O;
X$^3$ represents NH or O;
X$^4$ represents CH or N;
X$^5$ represents CH or N;
wherein one C-atom or one N-atom in the 5-membered ring of (b-1) or (b-2), including suitable C-atoms and N-atoms in the definition of X$^1$, X$^2$, X$^3$, X$^4$ and X$^5$, might be substituted with one or where possible two C$_{1-4}$alkyl groups optionally substituted with one, two or three substituents each independently selected from the group consisting of halo, cyano, —C(=O)NR$^5$R$^{5'}$, and Het$^4$;

Het$^4$ is a 4- to 7-membered non-aromatic heterocyclyl containing at least one nitrogen, oxygen or sulfur atom, wherein said heterocyclyl is optionally substituted with one, two, or three substituents each independently selected from the group consisting of halo, —CN, oxo, —C(=O)NR$^5$R$^{5'}$, —O—C$_{1-4}$alkyl, —S(=O)$_2$—C$_{1-4}$alkyl, and C$_{1-4}$alkyl optionally substituted with —O—C$_{1-4}$alkyl;

R$^{17}$ is C$_{3-6}$cycloalkyl optionally substituted with one or more substituents selected from the group consisting of halo, —CN, —OR$^4$, —NR$^5$R$^{5'}$, —C(=O)NR$^5$R$^{5'}$, and C$_{1-4}$alkyl optionally substituted with a substituent selected from the group consisting of fluoro, —CN, —OR$^6$, —NR$^7$R$^{7'}$, and —C(=O)NR$^8$R$^{8'}$;

n1, n2, and m1 are each independently selected from 1 and 2;
m2 is 0 or 1;
or a pharmaceutically acceptable salt or a solvate thereof.

2. The compound according to claim 1, wherein
R$^1$ is selected from the group consisting of CH$_3$, CH$_2$F, CHF$_2$ and CF$_3$;
Y$^1$ is N or CR$^y$;
when Y$^1$ represents N, R$^2$ is selected from the group consisting of hydrogen, CH$_3$, —OCH$_3$, —NH$_2$, and —NH—CH$_3$;

when Y$^1$ represents CR$^y$, R$^2$ is hydrogen;
R$^y$ is selected from the group consisting of hydrogen, cyano, and C$_{1-4}$alkyl optionally substituted with hydroxy, —O—C$_{1-4}$alkyl, or —O—C$_{3-6}$cycloalkyl;
Y$^2$ is CH$_2$ or O;
A is a covalent bond or —CR$^{15a}$R$^{15b}$—;
R$^{15a}$ and R$^{15b}$ are each independently selected from the group consisting of hydrogen or C$_{1-4}$alkyl;
Q is hydrogen or C$_{1-4}$alkyl optionally substituted with phenyl;
-L-R$^3$ is selected from (a), (b), (c), (d), (e), or (f):
(a) -L-R$^3$ is —NR$^A$R$^{1A}$, wherein
R$^A$ is selected from the group consisting of hydrogen; cyclopropyl; C$_{1-4}$alkyl optionally substituted with a substituent selected from the group consisting of fluoro and —CN; and C$_{2-4}$alkyl substituted with a substituent selected from the group consisting of —OR$^{3a}$ and —NR$^{4a}$R$^{4aa}$;
R$^{1A}$ is selected from the group consisting of C$_{1-6}$alkyl optionally substituted with one, two or three fluoro substituents; and C$_{2-6}$alkyl substituted with a substituent selected from the group consisting of —OR$^{1a}$ and —NR$^{2a}$R$^{2aa}$,
wherein R$^{1a}$, R$^{2a}$, R$^{2aa}$, R$^{3a}$, R$^{4a}$, and R$^{4aa}$ are each independently selected from the group consisting of hydrogen, C$_{1-4}$alkyl and cyclopropyl;
or
(b) L is selected from the group consisting of —N(R$^B$)—, —N(R$^B$)—CR$^{1B}$R$^{1BB}$—, and —(NR$^B$)—CHR$^{1B}$—CHR$^{2B}$—; and R$^3$ is selected from the group consisting of Ar; Het$^1$; Het$^2$; Het$^3$; and a 7- to 10-membered saturated spirocarbobicyclic system; wherein
R$^B$ is selected from the group consisting of hydrogen; cyclopropyl; C$_{1-4}$alkyl optionally substituted with a substituent selected from the group consisting of fluoro and —CN; and C$_{2-4}$alkyl substituted with a substituent selected from the group consisting of —OR$^{1b}$ and —NR$^{2b}$R$^{2bb}$; wherein
R$^{1b}$, R$^{2b}$, and R$^{2bb}$ are each independently selected from the group consisting of hydrogen, C$_{1-4}$alkyl and cyclopropyl;
R$^{1B}$ is selected from the group consisting of hydrogen; halo; C$_{3-6}$cycloalkyl; C$_{1-4}$alkyl optionally substituted with a substituent selected from the group consisting of fluoro, hydroxy, and —CN; C$_{2-4}$alkyl substituted with a substituent selected from the group consisting of —OR$^{4B}$ and —NR$^{5B}$R$^{5BB}$; and C-linked 4- to 7-membered non-aromatic heterocyclyl containing at least one nitrogen, oxygen or sulfur atom; and R$^{1BB}$ is selected from the group consisting of hydrogen and methyl; or R$^{1B}$ and R$^{1BB}$ together with the carbon to which they are attached form a C$_{3-6}$cycloalkyl or a C-linked 4- to 7-membered non-aromatic heterocyclyl containing at least one nitrogen, oxygen or sulfur atom;
R$^{2B}$ is selected from the group consisting of hydrogen; —OR$^{6B}$; —NR$^{7B}$R$^{7BB}$; CF$_3$, C$_{1-4}$alkyl optionally substituted with a substituent selected from the group consisting of fluoro, —CN, —OR$^{4B}$, and —NR$^{5B}$R$^{5BB}$; and C-linked 4- to 7-membered non-aromatic heterocyclyl containing at least one nitrogen, oxygen or sulfur atom; wherein
R$^{4B}$, R$^{5B}$, R$^{5BB}$, R$^{6B}$, R$^{7B}$, and R$^{7BB}$ are each independently selected from the group consisting of hydrogen; C$_{1-4}$alkyl optionally substituted with a substituent selected from the group consisting of fluoro, —CN and —C(=O)NR$^{9B}$R$^{9BB}$; and C$_{2-4}$alkyl substituted with a substituent selected from the group consisting of —OR$^{10B}$ and —NR$^{11B}$R$^{11BB}$; wherein R$^{9B}$, R$^{9BB}$, R$^{10B}$, R$^{11B}$ and R$^{11BB}$ are each independently selected from the group consisting of hydrogen; C$_{1-4}$alkyl; and C-linked 4- to 7-membered non-aromatic heterocyclyl containing at least one nitrogen, oxygen or sulfur atom;

or (c) -L-R$^3$ is selected from the group consisting of —N(R$^C$)—COR$^{5C}$; and —N(R$^C$)—SO$_2$—R$^{13C}$ wherein R$^C$ is selected from the group consisting of hydrogen; cyclopropyl; C$_{1-4}$alkyl optionally substituted with a substituent selected from the group consisting of fluoro and —CN; and C$_{2-4}$alkyl substituted with a substituent selected from the group consisting of —OR$^{1c}$ and —NR$^{2c}$R$^{2cc}$;

R$^{5C}$ and R$^{13C}$ are each independently selected from the group consisting of hydrogen; Ar; Het$^1$; Het$^2$; Het$^3$; a 7- to 10-membered saturated spirocarbobicyclic system; and C$_{1-4}$alkyl optionally substituted with —NR$^{2c}$R$^{2cc}$, Ar, Het$^1$ or Het$^2$; wherein R$^{1c}$, R$^{2c}$, and R$^{2cc}$ are each independently selected from the group consisting of hydrogen and C$_{1-4}$alkyl;

or (d) L is selected from —N(R$^D$)—CR$^{1D}$R$^{1DD}$— and —N(R$^D$)—CR$^{1D}$R$^{1DD}$—CR$^{2D}$R$^{2DD}$—; wherein R$^D$ is selected from the group consisting of hydrogen; C$_{1-4}$alkyl optionally substituted with a substituent selected from the group consisting of fluoro and —CN; and C$_{2-4}$alkyl substituted with a substituent selected from —OR$^{1d}$ and —NR$^{2d}$R$^{2dd}$; wherein R$^{1d}$, R$^{2d}$ and R$^{2dd}$ are each independently selected from the group consisting of hydrogen and C$_{1-4}$alkyl;

R$^{1D}$, R$^{1DD}$, R$^{2D}$ and R$^{2DD}$ are each independently selected from the group consisting of hydrogen and C$_{1-4}$alkyl; and R$^3$ is selected from the group consisting of

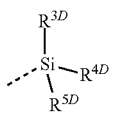

and

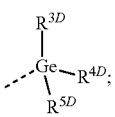

wherein

R$^{3D}$, R$^{4D}$, and R$^{5D}$ are each independently selected from the group consisting of C$_{1-6}$alkyl optionally substituted with —OH, —OC$_{1-6}$alkyl, or —NH$_2$ substituent;

or (e) -L-R$^3$ is

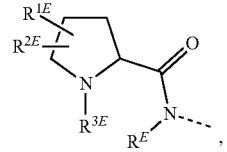

wherein

R$^E$ is selected from the group consisting of hydrogen and C$_{1-4}$alkyl;

R$^{1E}$ is selected from the group consisting of hydrogen, fluoro and C$_{1-4}$alkyl; and R$^{2E}$ is selected from the group consisting of fluoro, —OC$_{1-4}$alkyl, and C$_{1-4}$alkyl optionally substituted with 1, 2 or 3 fluoro substituents; or R$^{1E}$ and R$^{2E}$ are bound to the same carbon atom and together form a C$_{3-5}$cycloalkyl or a C-linked 4- to 6-membered heterocyclyl containing an oxygen atom; and R$^{3E}$ is selected from the group consisting of hydrogen; C$_{1-4}$alkyl optionally substituted with a fluoro or a —CN substituent; and C$_{2-4}$alkyl substituted with a substituent selected from the group consisting of —OR$^{4E}$ and —NR$^{5E}$R$^{5EE}$; wherein R$^{4E}$, R$^{5E}$ and R$^{5EE}$ are each independently selected from the group consisting of hydrogen; C$_{1-4}$alkyl optionally substituted with a substituent selected from the group consisting of fluoro, —CN, and —C(=O)NR$^{6E}$R$^{6EE}$; C$_{2-4}$alkyl substituted with a substituent selected from the group consisting of —OR$^{7E}$ and —NR$^{8E}$R$^{8EE}$; and C-linked 4- to 7-membered non-aromatic heterocyclyl containing at least one nitrogen, oxygen or sulfur atom; wherein R$^{6E}$, R$^{6EE}$, R$^{7E}$, R$^{8E}$ and R$^{8EE}$ are each independently selected from the group consisting of hydrogen and C$_{1-4}$alkyl;

or (f) -L-R$^3$ is a radical

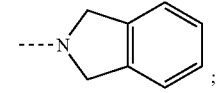

Ar is phenyl optionally substituted with one, two, or three substituents each independently selected from the group consisting of halo, —CN, —OR$^4$, —NR$^5$R$^{5'}$, —C(=O)NR$^5$R$^{5'}$, —S(=O)$_2$—NR$^5$R$^{5'}$, R$^{14}$, CF$_3$, and C$_{1-4}$alkyl optionally substituted with a substituent selected from the group consisting of fluoro, —CN, —OR$^6$, —NR$^7$R$^{7'}$, and —C(=O)NR$^8$R$^{8'}$;

Het$^1$ is a monocyclic heteroaryl selected from the group consisting of pyridyl, 4-, 5- or 6-pyrimidinyl, pyrazinyl, pyridazinyl, furanyl, thienyl, pyrrolyl, pyrazolyl, imidazolyl, 4- or 5-thiazolyl, isothiazolyl, and isoxazolyl; each of which may be optionally substituted with one, two, or three substituents each independently selected from the group consisting of halo, —CN, —OR$^4$, —NR$^5$R$^{5'}$, and C$_{1-4}$alkyl optionally substituted with a substituent selected from the group consisting of fluoro, —CN, —OR$^6$, Het$^2$, —NR$^7$R$^{7'}$, and —C(=O) NR$^8$R$^{8'}$; and Het² is a non-aromatic heterocyclyl optionally substituted with one, two, or three substituents each independently selected from the group consisting of halo, —CN, —C(=O)—C$_{1-6}$alkyl, —C(=O)Ar, —C(=O)Het¹, —C(=O)Het², —OR⁴, —NR⁵R⁵', and C$_{1-4}$alkyl optionally substituted with a substituent selected from the group consisting of fluoro, —CN, —OR⁶, —NR⁷R⁷', R¹² and —C(=O)NR⁸R⁸';
wherein
  R¹² is C-linked 4- to 7-membered non-aromatic heterocyclyl containing at least one nitrogen, oxygen or sulfur atom;
  R⁴, R⁵, R⁵', R⁶, R⁷, R⁷', R⁸ and R⁸' are each independently selected from the group consisting of hydrogen; —S(=O)$_2$—C$_{1-4}$alkyl; C$_{1-4}$alkyl optionally substituted with a substituent selected from the group consisting of fluoro, —C(=O)—C$_{1-4}$alkyl, —S(=O)$_2$—C$_{1-4}$alkyl, R¹¹'' and —C(=O)NR⁹R⁹'; and C$_{2-4}$alkyl substituted with a substituent selected from the group consisting of —OR¹⁰ and —NR¹¹R¹¹'; wherein
    R⁹, R⁹', R¹⁰, R¹¹, R¹¹' and R¹¹'' are each independently selected from the group consisting of hydrogen; C$_{1-4}$alkyl; and C-linked 4- to 7-membered non-aromatic heterocyclyl containing at least one nitrogen, oxygen or sulfur atom;
  R¹⁴ is a 5-membered monocyclic heteroaryl containing at least one nitrogen atom, and optionally 1, 2 or 3 additional heteroatoms each independently selected from nitrogen, oxygen and sulfur;
Het³ is selected from the group consisting of formula (b-1) and (b-2):

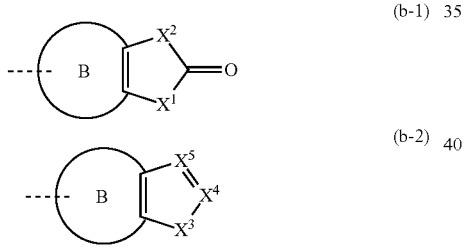

Ring B is phenyl;
X¹ represents CH$_2$, O or NH;
X² represents NH or O;
X³ represents NH or O;
X⁴ represents CH or N;
X⁵ represents CH or N;
wherein one C-atom or one N-atom in the 5-membered ring of (b-1) or (b-2), including suitable C-atoms and N-atoms in the definition of X¹, X², X³, X⁴ and X⁵, might be substituted with one or where possible two C$_{1-4}$alkyl groups optionally substituted with one, two or three halo atoms;
n1, n2, and m1 are each independently selected from 1 and 2;
m2 is 0 or 1.

3. The compound according to claim 1, wherein
R¹ is CF$_3$;
Y¹ is N;
R² is hydrogen;
Y² is CH$_2$;
A is a covalent bond or —CR$^{15a}$R$^{15b}$—;
R$^{15a}$ and R$^{15b}$ are hydrogen;

Q is hydrogen;
-L-R³ is selected from (a), (b), (c):
(a) -L-R³ is —NR⁴R¹⁴, wherein
  R⁴ is hydrogen;
  R¹⁴ is C$_{1-6}$alkyl;
or
(b) L is selected from the group consisting of —N(R$^B$)—, and —N(R$^B$)—CR$^{1B}$R$^{1BB}$—; and
  R³ is selected from the group consisting of Ar; Het¹; and Het³; wherein
    R$^B$ is hydrogen;
    R$^{1B}$ is hydrogen; and
    R$^{1BB}$ is selected from the group consisting of hydrogen and methyl;
or
(c) -L-R³ is selected from the group consisting of
  —N(R$^C$)—COR$^{5C}$; and
  —N(R$^C$)—SO$_2$—R$^{13C}$ wherein
  R$^C$ is selected from the group consisting of hydrogen and C$_{1-4}$alkyl;
  R$^{5C}$ and R$^{13C}$ are each independently selected from the group consisting of Ar; Het³; and C$_{1-4}$alkyl optionally substituted with Het²;
Ar is phenyl optionally substituted with one, two, or three substituents each independently selected from the group consisting of halo, —CN, —NR⁵R⁵', —C(=O)NR⁵R⁵', R¹⁴, CF$_3$, and C$_{1-4}$alkyl optionally substituted with CN substituent;
Het¹ is pyrazolyl optionally substituted with one, two, or three C$_{1-4}$alkyl substituents; and
Het² is a non-aromatic heterocyclyl;
wherein
  R⁵ and R⁵' are each independently selected from the group consisting of hydrogen; —S(=O)$_2$—C$_{1-4}$alkyl; and C$_{1-4}$alkyl;
  R¹⁴ is pyrazolyl, in particular pyrazolyl attached to the remainder of the molecule via a C-atom;
Het³ is selected from the group consisting of formula (b-1) and (b-2):

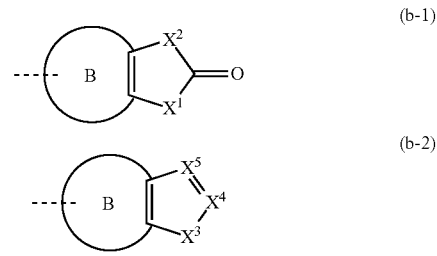

Ring B is phenyl;
X¹ represents O or NH;
X² represents NH;
X³ represents NH;
X⁴ represents N;
X⁵ represents CH;
n1, n2, and m1 are each independently selected from 1 and 2;
m2 is 0 or 1.

4. The compound according to claim 1, wherein
R¹ is CF$_3$;
Y¹ is N;
when Y¹ represents N, R² is selected from the group consisting of hydrogen, CH$_3$, —OCH$_3$, —NH$_2$, and —NH—CH$_3$;

$Y^2$ is $CH_2$;
$R^{15a}$ and $R^{15b}$ are hydrogen;
Q is hydrogen;
-L-$R^3$ is selected from (a), (b), (c), (d), (e), or (f):
(a) -L-$R^3$ is —$NR^A R^{14}$, wherein
$R^A$ is selected from the group consisting of hydrogen and $C_{1-4}$alkyl;
$R^{14}$ is $C_{1-6}$alkyl;
or
(b) L is selected from the group consisting of —$N(R^B)$—, and —$N(R^B)$—$CR^{1B}R^{1BB}$; and $R^3$ is selected from the group consisting of Ar; $Het^1$; $Het^2$; $Het^3$; and $R^{17}$; in particular $R^3$ is selected from the group consisting of Ar; $Het^1$; $Het^3$; and $R^{17}$; wherein
$R^B$ is selected from the group consisting of hydrogen and $C_{1-4}$alkyl;
$R^{1B}$ is selected from the group consisting of hydrogen and $C_{1-4}$alkyl; and
$R^{1BB}$ is selected from the group consisting of hydrogen and methyl; or $R^{1B}$ and $R^{1BB}$ together with the carbon to which they are attached form a $C_{3-6}$cycloalkyl;
or
(c) -L-$R^3$ is selected from the group consisting of —$N(R^C)$—$COR^{5C}$; and —$N(R^C)$—$SO_2$—$R^{13C}$ wherein
$R^C$ is selected from the group consisting of hydrogen and $C_{1-4}$alkyl;
$R^{5C}$ and $R^{13C}$ are each independently selected from the group consisting of Ar; and $C_{1-4}$alkyl optionally substituted with $Het^2$;
Ar is phenyl optionally substituted with one, two, or three substituents each independently selected from the group consisting of halo, —CN, —$OR^4$, —$NR^5R^{5'}$, —$C(=O)NR^5R^{5'}$, $Het^4$, —O-$Het^4$, —$C(=O)$—$Het^4$, —$S(=O)_2$—$Het^4$, —$S(=O)_2$—$NR^5R^{5'}$, —$S(=O)_2$—$C_{1-4}$alkyl, $R^{14}$, $CF_3$, $C_{3-5}$cycloalkyl optionally substituted with —CN, and $C_{1-4}$alkyl optionally substituted with one or two substituents each independently selected from the group consisting of $Het^4$, —CN, —$OR^6$, —$NR^7R^{7'}$, —$S(=O)_2$—$C_{1-4}$alkyl and —$C(=O)NR^8R^{8'}$;
$Het^1$ is a monocyclic heteroaryl selected from the group consisting of pyridyl, 2-, 4-, 5- or 6-pyrimidinyl, pyrazinyl, pyridazinyl, pyrazolyl, and imidazolyl; each of which may be optionally substituted with one, two, or three substituents each independently selected from the group consisting of —CN, —$OR^4$, —$C(=O)NR^5R^{5'}$, —$C(=O)$—$Het^4$, and $C_{1-4}$alkyl optionally substituted with —$C(=O)NR^8R^{8'}$; and
$Het^2$ is a non-aromatic heterocyclyl;
wherein
$R^4$, $R^5$, $R^{5'}$, $R^6$, $R^7$, $R^{7'}$, $R^8$ and $R^{8'}$ are each independently selected from the group consisting of hydrogen; —$C(=O)$—$C_{1-4}$alkyl; —$S(=O)_2$—$C_{1-4}$alkyl; $C_{1-4}$alkyl optionally substituted with a substituent selected from the group consisting of —CN, $R^{11'''}$ and $R^{16}$;
$C_{1-4}$alkyl substituted with three fluoro atoms; and
$C_{2-4}$alkyl substituted with a substituent selected from the group consisting of —$OR^{10}$ and —$NR^{11}R^{11'}$;
wherein
$R^{10}$, $R^{11}$, $R^{11'}$ and $R^{11'''}$ are each independently selected from the group consisting of hydrogen; $C_{1-4}$alkyl; —$S(=O)_2$—$C_{1-4}$alkyl; and C-linked 4- to 7-membered non-aromatic heterocyclyl containing at least one nitrogen, oxygen or sulfur atom, wherein said heterocyclyl is optionally substituted with one, two, or three substituents each independently selected from the group consisting of —$S(=O)_2$—$C_{1-4}$alkyl and $C_{1-4}$alkyl;
$R^{16}$ is N-linked 4- to 7-membered non-aromatic heterocyclyl containing at least one N-atom and optionally one additional heteroatom selected from nitrogen, oxygen and sulfur, wherein said heterocyclyl is optionally substituted with one, two, or three substituents each independently selected from the group consisting of —$S(=O)_2$—$C_{1-4}$alkyl;
$R^{14}$ is a 5-membered monocyclic heteroaryl containing at least one nitrogen atom, and optionally 1, 2 or 3 additional heteroatoms each independently selected from nitrogen, oxygen and sulfur;
$Het^4$ is a 4- to 7-membered non-aromatic heterocyclyl containing at least one nitrogen, oxygen or sulfur atom, wherein said heterocyclyl is optionally substituted with one, two, or three substituents each independently selected from the group consisting of —CN, oxo, —$C(=O)NR^5R^{5'}$, —O—$C_{1-4}$alkyl, —$S(=O)_2$—$C_{1-4}$alkyl, and $C_{1-4}$alkyl optionally substituted with —O—$C_{1-4}$alkyl;
$R^{17}$ is $C_{3-6}$cycloalkyl optionally substituted with one or more substituents selected from the group consisting of —$NR^5R^{5'}$.

5. The compound according to claim 1, wherein A is a covalent bond.

6. The compound according to claim 1, wherein A is —$CR^{15a}R^{15b}$—.

7. A pharmaceutical composition comprising a compound as claimed in claim 1 and a pharmaceutically acceptable carrier or diluent.

8. A process for preparing a pharmaceutical composition comprising mixing a pharmaceutically acceptable carrier with a therapeutically effective amount of a compound according to claim 1.

9. A method of slowing, interrupting or arresting the progression of disorders characterized by chromosomal translocations in MLL comprising administering to a subject in need thereof, a therapeutically effective amount of a compound as claimed in claim 1.

10. The method according to claim 9 wherein the disorder is cancer.

11. The method according to claim 10 wherein cancer is selected from leukemias, myeloma or a solid tumor cancer.

12. The method according to claim 11 wherein the leukemia is selected from acute leukemias, chronic leukemias, myeloid leukemias, myelogeneous leukemias, lymphoblastic leukemias, lymphocytic leukemias, Acute myelogeneous leukemias (AML), Chronic myelogenous leukemias (CML), Acute lymphoblastic leukemias (ALL), Chronic lymphocytic leukemias (CLL), T cell prolymphocytic leukemias (T-PLL), Large granular lymphocytic leukemia, Hairy cell leukemia (HCL), MLL-rearranged leukemias, MLL-PTD leukemias, MLL amplified leukemias, MLL-positive leukemias, and leukemias exhibiting HOX/MEIS1 gene expression signatures.

13. The method according to claim 11 wherein the solid tumor cancer is selected from prostate cancer, lung cancer, breast cancer, pancreatic cancer, colon cancer, liver cancer, melanoma or glioblastoma.

* * * * *

SEQUENCE LISTING

<160> NUMBER OF SEQ ID NOS: 3

<210> SEQ ID NO 1
<211> LENGTH: 616
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: MENIN protein sequence with His tag

```
<400> SEQUENCE: 1

Met Gly Leu Lys Ala Ala Gln Lys Thr Leu Phe Pro Leu Arg Ser Ile
1               5                   10                  15

Asp Asp Val Val Arg Leu Phe Ala Ala Glu Leu Gly Arg Glu Glu Pro
            20                  25                  30

Asp Leu Val Leu Leu Ser Leu Val Leu Gly Phe Val Glu His Phe Leu
            35                  40                  45

Ala Val Asn Arg Val Ile Pro Thr Asn Val Pro Glu Leu Thr Phe Gln
        50                  55                  60

Pro Ser Pro Ala Pro Asp Pro Pro Gly Gly Leu Thr Tyr Phe Pro Val
65                  70                  75                  80

Ala Asp Leu Ser Ile Ile Ala Ala Leu Tyr Ala Arg Phe Thr Ala Gln
                85                  90                  95

Ile Arg Gly Ala Val Asp Leu Ser Leu Tyr Pro Arg Glu Gly Gly Val
                100                 105                 110

Ser Ser Arg Glu Leu Val Lys Lys Val Ser Asp Val Ile Trp Asn Ser
            115                 120                 125

Leu Ser Arg Ser Tyr Phe Lys Asp Arg Ala His Ile Gln Ser Leu Phe
130                 135                 140

Ser Phe Ile Thr Gly Thr Lys Leu Asp Ser Ser Gly Val Ala Phe Ala
145                 150                 155                 160

Val Val Gly Ala Cys Gln Ala Leu Gly Leu Arg Asp Val His Leu Ala
                165                 170                 175

Leu Ser Glu Asp His Ala Trp Val Val Phe Gly Pro Asn Gly Glu Gln
            180                 185                 190

Thr Ala Glu Val Thr Trp His Gly Lys Gly Asn Glu Asp Arg Arg Gly
            195                 200                 205

Gln Thr Val Asn Ala Gly Val Ala Glu Arg Ser Trp Leu Tyr Leu Lys
        210                 215                 220

Gly Ser Tyr Met Arg Cys Asp Arg Lys Met Glu Val Ala Phe Met Val
225                 230                 235                 240

Cys Ala Ile Asn Pro Ser Ile Asp Leu His Thr Asp Ser Leu Glu Leu
                245                 250                 255

Leu Gln Leu Gln Gln Lys Leu Leu Trp Leu Leu Tyr Asp Leu Gly His
            260                 265                 270

Leu Glu Arg Tyr Pro Met Ala Leu Gly Asn Leu Ala Asp Leu Glu Glu
            275                 280                 285

Leu Glu Pro Thr Pro Gly Arg Pro Asp Pro Leu Thr Leu Tyr His Lys
            290                 295                 300

Gly Ile Ala Ser Ala Lys Thr Tyr Tyr Arg Asp Glu His Ile Tyr Pro
305                 310                 315                 320

Tyr Met Tyr Leu Ala Gly Tyr His Cys Arg Asn Arg Asn Val Arg Glu
                325                 330                 335

Ala Leu Gln Ala Trp Ala Asp Thr Ala Thr Val Ile Gln Asp Tyr Asn
            340                 345                 350

Tyr Cys Arg Glu Asp Glu Glu Ile Tyr Lys Glu Phe Phe Glu Val Ala
            355                 360                 365

Asn Asp Val Ile Pro Asn Leu Leu Lys Glu Ala Ala Ser Leu Leu Glu
            370                 375                 380

Ala Gly Glu Glu Arg Pro Gly Glu Gln Ser Gln Gly Thr Gln Ser Gln
385                 390                 395                 400

Gly Ser Ala Leu Gln Asp Pro Glu Cys Phe Ala His Leu Leu Arg Phe
```

```
                    405                 410                 415

Tyr Asp Gly Ile Cys Lys Trp Glu Glu Gly Ser Pro Thr Pro Val Leu
                420                 425                 430

His Val Gly Trp Ala Thr Phe Leu Val Gln Ser Leu Gly Arg Phe Glu
            435                 440                 445

Gly Gln Val Arg Gln Lys Val Arg Ile Val Ser Arg Glu Ala Glu Ala
        450                 455                 460

Ala Glu Ala Glu Glu Pro Trp Gly Glu Glu Ala Arg Glu Gly Arg Arg
465                 470                 475                 480

Arg Gly Pro Arg Arg Glu Ser Lys Pro Glu Glu Pro Pro Pro Lys
                485                 490                 495

Lys Pro Ala Leu Asp Lys Gly Leu Gly Thr Gly Gln Gly Ala Val Ser
                500                 505                 510

Gly Pro Pro Arg Lys Pro Pro Gly Thr Val Ala Gly Thr Ala Arg Gly
                515                 520                 525

Pro Glu Gly Gly Ser Thr Ala Gln Val Pro Ala Pro Ala Ala Ser Pro
    530                 535                 540

Pro Pro Glu Gly Pro Val Leu Thr Phe Gln Ser Glu Lys Met Lys Gly
545                 550                 555                 560

Met Lys Glu Leu Leu Val Ala Thr Lys Ile Asn Ser Ser Ala Ile Lys
                565                 570                 575

Leu Gln Leu Thr Ala Gln Ser Gln Val Gln Met Lys Lys Gln Lys Val
                580                 585                 590

Ser Thr Pro Ser Asp Tyr Thr Leu Ser Phe Leu Lys Arg Gln Arg Lys
            595                 600                 605

Gly Leu His His His His His His
    610                 615

<210> SEQ ID NO 2
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Beta-alanine

<400> SEQUENCE: 2

Ala Ser Ala Arg Trp Arg Phe Pro Ala Arg Pro Gly Thr
1               5                   10

<210> SEQ ID NO 3
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 3

His His His His His His
1               5
```